US010670605B2

(12) United States Patent
Cravatt et al.

(10) Patent No.: US 10,670,605 B2
(45) Date of Patent: Jun. 2, 2020

(54) CYSTEINE REACTIVE PROBES AND USES THEREOF

(71) Applicant: The Scripps Research Institute, La Jolla, CA (US)

(72) Inventors: Benjamin F. Cravatt, La Jolla, CA (US); Keriann M. Backus, La Jolla, CA (US); Bruno E. Correia, La Jolla, CA (US); Megan M. Blewett, San Diego, CA (US); John R. Teijaro, San Diego, CA (US)

(73) Assignee: THE SCRIPPS RESEARCH INSTITUTE, La Jolla, CA (US)

( * ) Notice: Subject to any disclaimer, the term of this patent is extended or adjusted under 35 U.S.C. 154(b) by 0 days.

(21) Appl. No.: 15/331,745

(22) Filed: Oct. 21, 2016

(65) Prior Publication Data

US 2017/0115303 A1    Apr. 27, 2017

Related U.S. Application Data

(60) Provisional application No. 62/345,710, filed on Jun. 3, 2016, provisional application No. 62/244,881, filed on Oct. 22, 2015.

(51) Int. Cl.
*G01N 33/68* (2006.01)
*C40B 60/00* (2006.01)
*C12N 9/04* (2006.01)
*C12N 9/10* (2006.01)
*C12N 9/64* (2006.01)
*G01N 33/50* (2006.01)

(52) U.S. Cl.
CPC ....... *G01N 33/6845* (2013.01); *C12N 9/0006* (2013.01); *C12N 9/1007* (2013.01); *C12N 9/6472* (2013.01); *C12Y 101/01042* (2013.01); *C12Y 201/01023* (2013.01); *C12Y 304/22061* (2013.01); *C12Y 304/22063* (2013.01); *G01N 33/5005* (2013.01); *G01N 33/5008* (2013.01); *G01N 33/6842* (2013.01)

(58) Field of Classification Search
CPC .................................................. G01N 33/68
USPC ......................................................... 506/13
See application file for complete search history.

(56) References Cited

U.S. PATENT DOCUMENTS

| 6,344,330 | B1 | 2/2002 | Ellman et al. |
| 8,778,302 | B2* | 7/2014 | Tai .......................... A61K 47/66 424/1.11 |
| 2009/0068107 | A1 | 3/2009 | Cravatt et al. |
| 2010/0021950 | A1 | 1/2010 | Lammert et al. |
| 2010/0179118 | A1* | 7/2010 | Ozawa ................. C07D 207/14 514/210.2 |
| 2010/0184661 | A1* | 7/2010 | Luo ................. A61K 47/48215 514/1.1 |
| 2011/0195527 | A1 | 8/2011 | O'Neill et al. |
| 2014/0357512 | A1 | 12/2014 | Yang et al. |
| 2015/0157686 | A1* | 6/2015 | Janssen-Heininger ...................... A61K 38/06 424/94.1 |
| 2016/0252509 | A1 | 9/2016 | Cravatt et al. |
| 2017/0115303 | A1* | 4/2017 | Cravatt .............. G01N 33/6845 |

FOREIGN PATENT DOCUMENTS

| WO | WO 0077184 A1 * | 12/2000 | ............. C07K 5/101 |
| WO | WO-0242773 A2 * | 5/2002 | ............. C40B 30/04 |
| WO | WO-2005118833 A2 | 12/2005 | |
| WO | WO-2015023724 A1 | 2/2015 | |
| WO | WO-2016029037 A1 | 2/2016 | |
| WO | WO-2017070611 A1 | 4/2017 | |
| WO | WO-2018136555 A2 | 7/2018 | |

OTHER PUBLICATIONS

Weerapana et al., Disparate Proteome Reactivity Profiles of Carbon Electrophiles, Nature Chemical Biology, 2008, 4(7), 405-407.*
Jacob et al., Control of Oxidative Posttranslational Cysteine Modifications: From Intricate Chemistry to Widespread Biological and Medical Applications, Chemical Research in Toxicology, 2012, 25, 588-604.*
Chalker et al., Chemical Modification of Proteins at Cysteine: Opportunities in Chemistry and Biology, Chem. Asian J., 2009, 4, 630-640.*
Bischoff et al., Amino Acids: Chemistry, Functionality and Selected Non-Enzymatic Post-Translational Modifications, Journal of Proteomics, 2012, 75, 2275-2296.*
Derakhshan et al., Unbiased Identification of Cyteine S-Nitrosylation Sites on Proteins, Nature Protocols, 2007, 2(7), 1685-1691.*
Barelier et al., Discovery of Fragment Molecules That Bind the Human Peroxiredoxin 5 Active Site, PLoS One, 2010, 5(3), 1-11. (Year: 2010).*
Scotcher et al., Identification of Two Reactive Cysteine Residues in the Tumor Suppressor Protein p53 Using Top-Down FTICR Mass Spectrometry, 2011, 22, 888-897. (Year: 2011).*
Erlanson et al., Tethering: Fragment-Based Drug Discovery, Annu. Rev. Biophys. Biomol. Structure, 2004, 33, 199-223. (Year: 2004).*
Deng et al., Proteome-Wide Quantification and Characterization of Oxidation-Sensitive Cysteines in Pathogenic Bacteria, Cell Host and Microbe, 2013, 13, 358-370. (Year: 2013).*
Ahmad et al., Structure Based Molecular Inhibition of Caspase-8 for Treatment of Multi-Neurodegenerative Disease Using Known Natural Compounds, Bioinformatics, 2014, 10(4), 191-195. (Year: 2014).*

(Continued)

*Primary Examiner* — Amy M Bunker
(74) *Attorney, Agent, or Firm* — Wilson Sonsini Goodrich & Rosati

(57) ABSTRACT

Disclosed herein are methods, compositions, probes, polypeptides, assays, and kits for identifying a cysteine containing protein as a binding target for a small molecule fragment. Also disclosed herein are methods, compositions, and probes for mapping a biologically active cysteine site on a protein and screening a small molecule fragment for interaction with a cysteine containing protein.

5 Claims, 62 Drawing Sheets

Specification includes a Sequence Listing.

(56) References Cited

OTHER PUBLICATIONS

Abegg et al. Proteome-Wide Profiling of Targets of Cysteine reactive Small molecules by Using Ethynyl Benziodoxolone Reagents. Angewandte Chemie International Edition 54:10852-10857 (2015).
Aldini et al. Identification of actin as a 15-deoxy-Delta12,14-prostaglandin J2 target in neuroblastoma cells: mass spectrometric, computational, and functional approaches to investigate the effect on cytoskeletal derangement. Biochemistry 46:2707-2718 (2007).
Bachovchin et al. Academic cross-fertilization by public screening yields a remarkable class of protein phosphatase methylesterase-1 inhibitors. PNAS USA 108:6811-6816 (2011).
Ban et al. Tyrosine bioconjugation through aqueous ene-type reactions: a click-like reaction for tyrosine. J Am Chem Soc 132:1523-1525 (2010).
Bennaars-Eiden et al. Covalent modification of epithelial fatty acid-binding protein by 4-hydroxynonenal in vitro and in vivo. Evidence for a role in antioxidant biology. J Biol Chem 277:50693-50702 (2002).
Bloem et al. Tissue distribution and functional expression of a cDNA encoding a novel mixed lineage kinase. J Mol Cell Cardiol 33:1739-1750 (2001).
Carbone et al. Inhibition of Hsp72-mediated protein refolding by 4-hydroxy-2-nonenal. Chem Res Toxicol 17:1459-1467 (2004).
Carbone et al. Modification of heat shock protein 90 by 4-hydroxynonenal in a rat model of chronic alcoholic liver disease. J Pharmacol Exp Ther 315:8-15 (2005).
Chipuk et al. Sphingolipid metabolism cooperates with BAK and BAX to promote the mitochondrial pathway of apoptosis. Cell 148:988-1000 (2012).
Codreanu et al. Global analysis of protein damage by the lipid electrophile 4-hydroxy-2-nonenal. Mol Cell Proteomics 8:670-680 (2009).
Cohen et al. Structural bioinformatics-based design of selective, irreversible kinase inhibitors. Science 308:1318-1321 (2005).
Deng et al. Proteome-wide Quantification and Characterization of Oxidation-Sensitive Cysteines in Pathogenic Bacteria. Cell Host Microbe 13:358-3¬70 (2013).
Doorn et al. Covalent modification of amino acid nucleophiles by the lipid peroxidation products 4-hydroxy-2-nonenal and 4-oxo-2-nonenal. Chem Res Toxicol 15:1445-1450 (2002).
Dubinina et al. Role of 4-hydroxy-trans-2-nonenal in cell functions. Biochemistry (Most) 75:1069-1087 (2010).
Forman. Reactive oxygen species and alpha,beta-unsaturated aldehydes as second messengers in signal transduction. Ann N Y Acad Sci 1203:35-44 (2010).
Frei et al. Fast and Highly Chemoselective Alkynylation of Thiols with Hypervalent Iodine Reagents Enabled through a Low Energy Barrier Concerted Mechanism. J Am Chem Soc 136:16563-16573 (2014).
Fritz et al. An overview of the chemistry and biology of reactive aldehydes. Free Radic Biol Med 59:85-91 (2012).
Fritz et al. Exploring the biology of lipid peroxidation-derived protein carbonylation. Chem Res Toxicol 24:1411-1419 (2011).
Fujishima et al. Ligand-directed acyl imidazole chemistry for labeling of membrane-bound proteins on live cells. J Am Chem Soc 134:3961-3964 (2012).
Giron et al. Cysteine Tagging for MS-based Proteomics. Mass spectrometry Reviews 30:366-395 (2011).
Gotoh et al. Identification and characterization of a novel MAP kinase kinase kinase, MLTK. J Biol Chem 276:4276-4286 (2001).
Gueraud et al. Chemistry and biochemistry of lipid peroxidation products. Free Radic Res 44:1098-1124 (2010).
Gushwa et al. Selective targeting of distinct active site nucleophiles by irreversible SRC-family kinase inhibitors. J Am Chem Soc 134:20214-20217 (2012).
Han et al. A comparative 'bottom up' proteomics strategy for the site-specific identification and quantification of protein modifications by electrophilic lipids. J Proteomics 75:5724-5733 (2012).

Hang et al. Exploring protein lipidation with chemical biology. Chem Rev 111:6341-6358 (2011).
Higdon et al. Methods for imaging and detecting modification of proteins by reactive lipid species. Free Radic Biol Med 47:201-212 (2009).
Huang et al. Crystal structure of an inactive Akt2 kinase domain. Structure 11:21-30 (2003).
Jacobs et al. Heat shock factor 1 attenuates 4-Hydroxynonenal mediated apoptosis: critical role for heat shock protein 70 induction and stabilization of Bcl-XL. J Biol Chem 282:33412-33420 (2007).
Jacobs et al. Systems analysis of protein modification and cellular responses induced by electrophile stress. Acc Chem Res. 43(5):673-683 (2010).
Keshet et al. The MAP kinase signaling cascades: a system of hundreds of components regulates a diverse array of physiological functions. Methods Mol Biol 661:3-38 (2010).
Kim et al. An azido-biotin reagent for use in the isolation of protein adducts of lipid-derived electrophiles by streptavidin catch and photorelease. Mol Cell Proteomics 8:2080-2089 (2009).
Knight et al. Features of selective kinase inhibitors. Chem Biol 12:621-637 (2005).
Kutuk et al. Apoptosis signalling by 4-hydroxynonenal: a role for JNK-c-Jun/AP-1 pathway. Redox Rep 12:30-34 (2007).
Leitner et al. Chemistry meets proteomics: the use of chemical tagging reactions for MS-based proteomics. Proteomics 6:5418-5434 (2006).
Leonard et al. Chemical 'omics' approaches for understanding protein cysteine oxidation in biology. Curr Opin Chem Biol 15:88-102 (2011).
Leonarduzzi et al. Signaling kinases modulated by 4-hydroxynonenal. Free Radic Biol Med 37:1694-1702 (2004).
Liu et al. Developing irreversible inhibitors of the protein kinase cysteinome. Chem Biol 20:146-159 (2013).
Lopachin et al. Molecular mechanisms of 4-hydroxy-2-nonenal and acrolein toxicity: nucleophilic targets and adduct formation. Chem Res Toxicol 22:1499-1508 (2009).
Marino et al. Proteomics: mapping reactive cysteines. Nat Chem Biol. 7(2):72-73 (2011).
Ngo et al. Mutant methionyl-tRNA synthetase from bacteria enables site-selective N-terminal labeling of proteins expressed in mammalian cells. PNAS USA 110:4992-4997 (2013).
Parola et al. HNE interacts directly with JNK isoforms in human hepatic stellate cells. J Clin Invest 102:1942-1950 (1998).
Patricelli et al. Functional interrogation of the kinome using nucleotide acyl phosphates. Biochemistry 46:350-358 (2007).
PCT/US2014/050828 International Preliminary Report on Patentability dated Feb. 25, 2016.
PCT/US2014/050828 International Search Report and Written Opinion dated Dec. 12, 2014.
PCT/US2016/058308 International Search Report and Written Opinion dated Jan. 17, 2017.
Perluigi et al. 4-Hydroxy-2-nonenal, a reactive product of lipid peroxidation, and neurodegenerative diseases: a toxic combination illuminated by redox proteomics studies. Antioxid Redox Signal 17:1590-1609 (2012).
Roe et al. Proteomic mapping of 4-hydroxynonenal protein modification sites by solid-phase hydrazide chemistry and mass spectrometry. Anal Chem 79:3747-3756 (2007).
Rostovtsev et al. A stepwise huisgen cycloaddition process: copper (i)-catalyzed regioselective "ligation" of azides and terminal alkynes. Angew. Chem. Int. Ed. Engl. 41(14):2596-2599 (2002).
Rudolph et al. Transduction of redox signaling by electrophileprotein reactions. Sci Signal 2:re7 (2009).
Shearn et al. Modification of Akt2 by 4-hydroxynonenal inhibits insulin-dependent Akt signaling in HepG2 cells. Biochemistry 50:3984-3996 (2011).
Shen et al. JNK signaling pathway is a key modulator in cell death mediated by reactive oxygen and nitrogen species. Free Radic Biol Med 40:928-939 (2006).
Simon et al. Determining target engagement in living systems. Nat Chem Biol 9(4):200-205 (2013).
Singh et al. The resurgence of covalent drugs. Nat Rev Drug Discov 10(4):307-317 (2011).

(56) References Cited

OTHER PUBLICATIONS

Speers et al. Activity-based protein profiling in vivo using a copper(i)-catalyzed azide-alkyne [3+2] cycloaddition. J Am Chem Soc. 125(16):4686-4687 (2003).
Surh et al. 15-Deoxy-$\Delta^{12,14}$-prostaglandin $J_2$, an electrophilic lipid mediator of anti-inflammatory and pro-resolving signaling. Biochem Pharmacol 82:1335-1351 (2011).
Tate. Recent advances in chemical proteomics: exploring the post-translational proteome. J Chem Biol 1:17-26 (2008).
Uchida. 4-Hydroxy-2-nonenal: a product and mediator of oxidative stress. Prog Lipid Res 42:318-343 (2003).
Vila et al. Identification of protein targets of 4-hydroxynonenal using click chemistry for ex vivo biotinylation of azido and alkynyl derivatives. Chem Res Toxicol. 21(2):432-444 (2008).
Wang et al. A chemoproteomic platform to quantitatively map targets of lipid-derived electrophiles. Nat Methods. 11(1):79-85 (2014).
Wang et al. Complete inhibition of anisomycin and UV radiation but not cytokine induced JNK and p38 activation by an aryl-substituted dihydropyrrolopyrazole quinoline and mixed lineage kinase 7 small interfering RNA. J Biol Chem 280:19298-19305 (2005).
Wang et al. Exploring post-translational arginine modification using chemically synthesized methylglyoxal hydroimidazolones (MG—Hs). J Am Chem Soc 134:8958-8967 (2012).
Weerapana et al. Disparate proteome reactivity profiles of carbon electrophiles. Nat Chem Biol 4:405-407 (2008).
Weerapana et al. Quantitative reactivity profiling predicts functional cysteines in proteomes. Nature 468:790-795 (2010).
Wong et al. Small molecule kinase inhibitors block the ZAK-dependent inflammatory effects of doxorubicin. Cancer Biol Ther. 14(1):56-63 (2013).
Yang et al. ZAK inhibits human lung cancer cell growth via ERK and JNK activation in an AP-1-dependent manner. Cancer Sci 101:1374-1381 (2010).
Yu et al. Effect of C-terminal truncations on MLK7 catalytic activity and JNK activation. Biochem Biophys Res Commun 310:452-457 (2003).
Zhou et al. A structure-guided approach to creating covalent FGFR inhibitors. Chem Biol 17:285-295 (2010).
Chalker et al. Chemical modification of proteins at cysteine: opportunities in chemistry and biology. Chem Asian J 4(5):630-640 (2009).
Pace et al. Diverse functional roles of reactive cysteines. ACS Chem Biol 8(2):283-296 (2013).
Kambe et al. Supporting Information—Mapping the Protein Interaction Landscape for Fully Functionalized Small-Molecule Probes in Human Cells. J Am Chem Soc 136(30):10777-10782 (2014).
PCT/US2018/14104 International Search Report and Written Opinion dated Jul. 26, 2018.
PCT/US2018/14104 Invitation to Pay Additional Fees dated May 31, 2018.
Bachovchin et al. The Pharmacological Landscape and Therapeutic Potential of Serine Hydrolases. Nature Reviews 11:52-68 (2012).
Long et al. The Metabolic Serine Hydrolases and Their Functions in Mammalian Physiology and Disease. Chemical Reviews 111:6022-6063 (2011).
U.S. Appl. No. 14/911,316 Office Action dated Jan. 12, 2018.
Backus et al. Proteome-wide covalent ligand discovery in native biological systems. Nature 534(7608):570-574 (2016).
Parker et al. Ligand and Target Discovery by Fragment-Based Screening in Human Cells. Cell 168(3):527-541 (2017).
PCT/US2018/014104 International Preliminary Report on Patentability dated Aug. 1, 2019.
U.S. Appl. No. 14/911,316 Office Action dated Mar. 27, 2019.

\* cited by examiner

Fragment electrophiles screened by isoTOP-ABPP

Fig. 3 (Cont.)
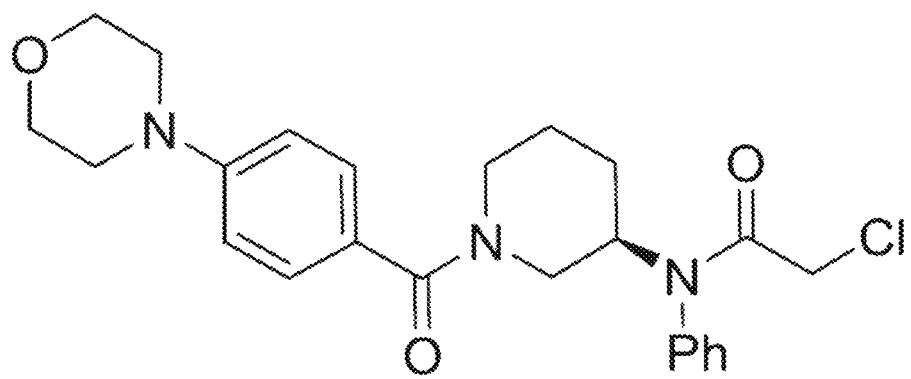
63 (R)
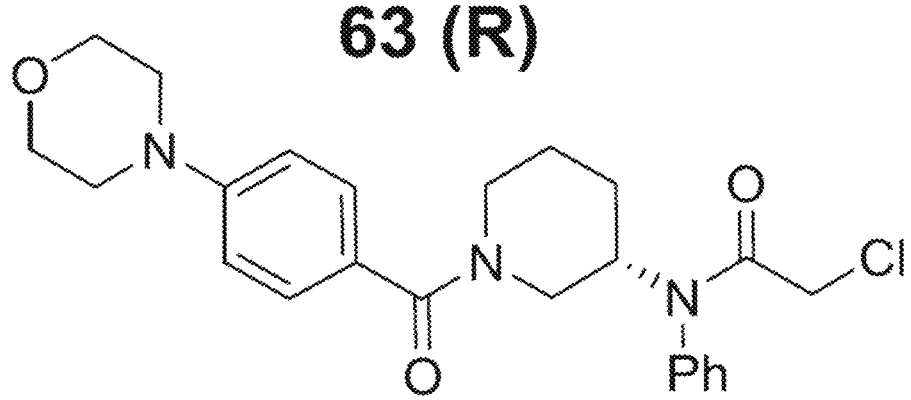
63 (S)

Fig. 6 (Cont.)
B
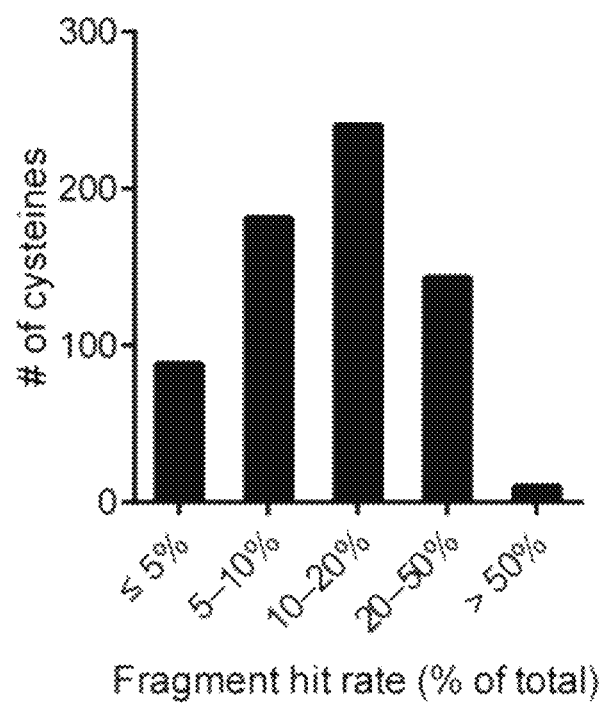
C
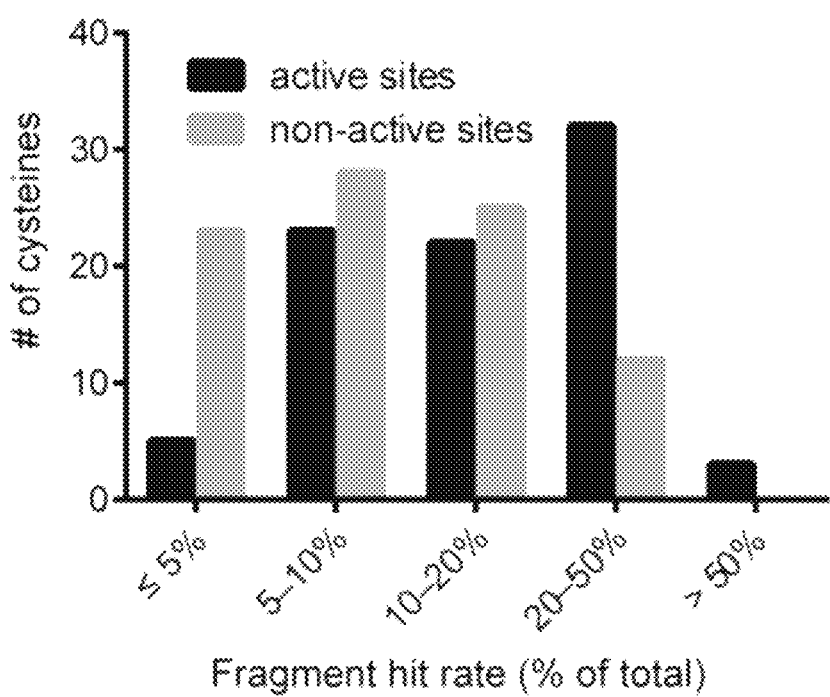

Fig. 6 (Cont.)
D
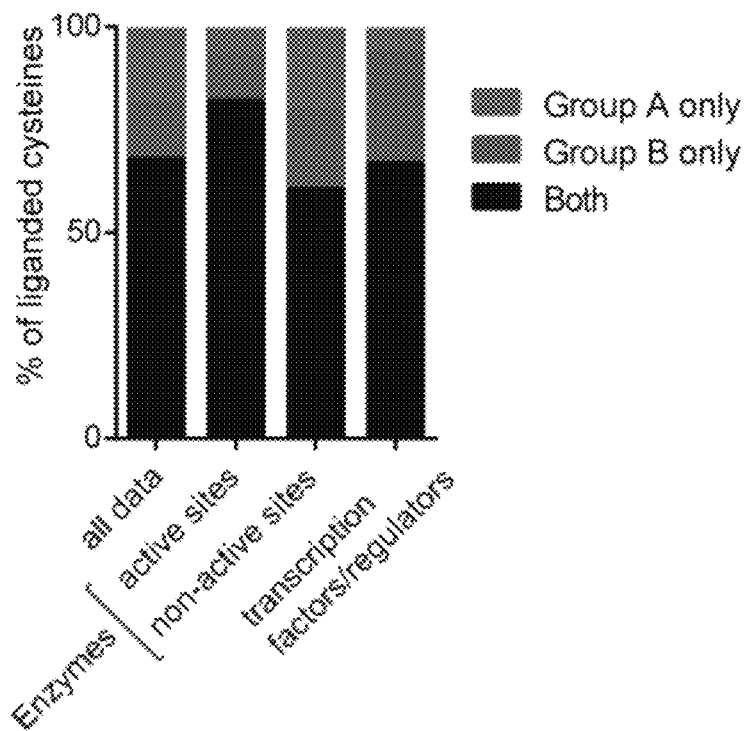
E
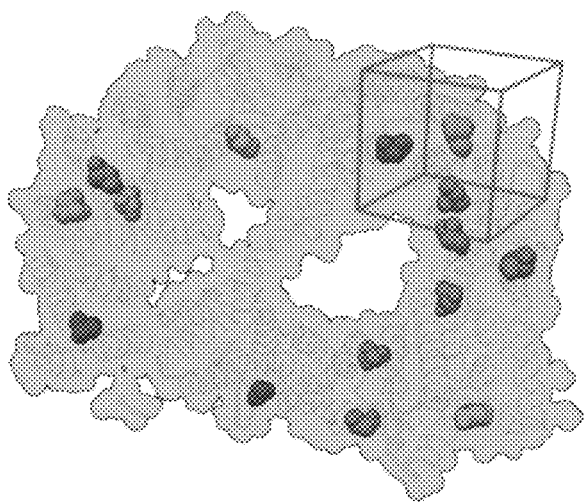
| XPO1 cysteine (events) | isoTOP-ABPP Liganded | isoTOP-ABPP Quantified | Docking prediction |
|---|---|---|---|
| Green (1) | + | + | Top result |
| Orange (4) | + (1) | + (4) | Ligandable |
| Blue (1) | – | + | Not ligandable |
| Red (2) | – | – | Ligandable |
| Gray (6) | – | – | Not ligandable |

Fig. 11 (Cont.)
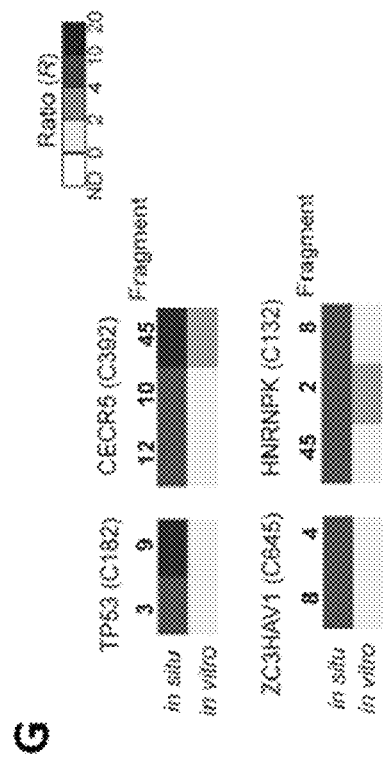
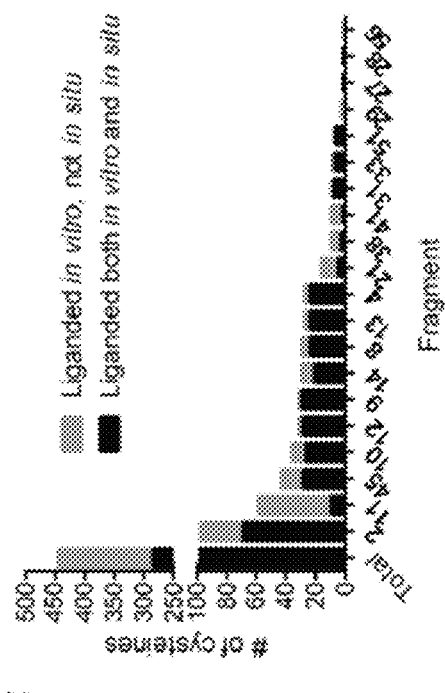

A

DMF-sensitive human cysteines
conserved in mice

Conserved DMF-sensitive human
cysteines also quantified and
sensitive to DMF in mice

```
PKCθ (human)   -------SNFDCG--SCQSCQGEAVNP
PKCθ (mouse)   -------SNFDCG--TCQACQGEAVNP
PKCδ (human)   -------NSYELG--SLQA-EDEANQP
PKCε (human)   AVSLKPTAWSLRHAVGPRPQTFLLDP
                        .  :.         :     :*
```

R$_{DMF}$  12.77

Time (hours)   1       2       4

R$_{DMF}$    2.24    2.92    4.21

$R_{MMF}$ 1.14

CYSTEINE REACTIVE PROBES AND USES THEREOF

CROSS-REFERENCE

This application claims the benefit of U.S. Provisional Application No. 62/345,710, filed on Jun. 3, 2016, and U.S. Provisional Application No. 62/244,881, filed on Oct. 22, 2015, each of which are incorporated herein by reference in their entireties.

STATEMENT AS TO FEDERALLY SPONSORED RESEARCH

The invention disclosed herein was made, at least in part, with U.S. government support under Grant Nos. CA087660, GM090294, GM108208, and GM069832 by the National Institutes of Health. Accordingly, the U.S. Government has certain rights in this invention.

SEQUENCE LISTING

The instant application contains a Sequence Listing which has been submitted electronically in ASCII format and is hereby incorporated by reference in its entirety. Said ASCII copy, created on Oct. 19, 2016, is named 48054-702_601_SL.txt and is 372,838 bytes in size.

BACKGROUND OF THE INVENTION

Protein function assignment has been benefited from genetic methods, such as target gene disruption, RNA interference, and genome editing technologies, which selectively disrupt the expression of proteins in native biological systems. Chemical probes offer a complementary way to perturb proteins that have the advantages of producing graded (dose-dependent) gain- (agonism) or loss- (antagonism) of-function effects that are introduced acutely and reversibly in cells and organisms. Small molecules present an alternative method to selectively modulate proteins and to serve as leads for the development of novel therapeutics.

SUMMARY OF THE INVENTION

Disclosed herein, in certain embodiments, is a method of identifying a cysteine containing protein as a binding target for a small molecule fragment, comprising: (a) obtaining a set of cysteine-reactive probe-protein complexes from a sample treated with a cysteine-reactive probe wherein the cysteine-reactive probe comprises a reactive moiety capable of forming a covalent bond with a cysteine residue located on the cysteine containing protein; (b) analyzing the set of cysteine-reactive probe-protein complexes by a proteomic analysis means; (c) based on step b), identifying a cysteine containing protein as the binding target for the small molecule fragment. In some embodiments, the method further comprises assigning a value to each of the cysteine containing protein from the set of cysteine-reactive probe-protein complexes for identifying a cysteine containing protein as the binding target for the small molecule fragment, wherein the value is determined based on the proteomic analysis means of step b). In some embodiments, the sample comprises a first cell solution and a second cell solution. In some embodiments, the method further comprises contacting the first cell solution with a small molecule fragment for an extended period of time prior to incubating the first cell solution with a first cysteine-reactive probe to generate a first group of cysteine-reactive probe-protein complexes. In some embodiments, the extended period of time is about 5, 10, 15, 20, 30, 60, 90, 120 minutes or longer. In some embodiments, the method further comprises contacting the second cell solution with a second cysteine-reactive probe to generate a second group of cysteine-reactive probe-protein complexes. In some embodiments, the first cysteine-reactive probe and the second cysteine-reactive probe are the same. In some embodiments, the first group and the second group of cysteine-reactive probe-protein complexes comprise the set of cysteine-reactive probe-protein complexes. In some embodiments, cells from the second cell solution are grown in a media (e.g., an isotopically enriched media). In some embodiments, cells from the first cell solution are grown in a media (e.g., an isotopically enriched media). In some embodiments, cells from both the first cell solution and the second cell solution are grown in two different isotopically enriched media so that cells from the first cell solution is distinguishable from cells obtained from the second cell solution. In other embodiments, cells from only one of the cell solutions (e.g., either the first cell solution or the second cell solution) are grown in an isotopically enriched media. In some embodiments, the method further comprises contacting the first cell solution with a first set of small molecule fragments and a complementing set of cysteine-reactive probes wherein each small molecule fragment competes with its complementing cysteine-reactive probe for binding with a cysteine residue, and wherein each small molecule fragment and each complementing cysteine-reactive probe are different within each respective set. In some embodiments, the method further comprises contacting the second cell solution with a second set of cysteine-reactive probes wherein the second set of cysteine-reactive probes is the same as the complementing set of cysteine-reactive probes, and wherein each cysteine-reactive probe is different within the set. In some embodiments, the first set of cysteine-reactive probes generates a third group of cysteine-reactive probe-protein complexes and the second set of cysteine-reactive probes generates a fourth group of cysteine-reactive probe-protein complexes. In some embodiments, the cysteine containing protein comprises a biologically active cysteine residue. In some embodiments, the biologically active cysteine site is a cysteine residue that is located about 10 Å or less to an active-site ligand or residue. In some embodiments, the cysteine residue that is located about 10 Å or less to the active-site ligand or residue is an active site cysteine. In some embodiments, the biologically active cysteine site is an active site cysteine. In some embodiments, the biologically active cysteine site is a cysteine residue that is located greater than 10 Å from an active-site ligand or residue. In some embodiments, the cysteine residue that is located greater than 10 Å from the active-site ligand or residue is a non-active site cysteine. In some embodiments, the biologically active cysteine site is a non-active site cysteine. In some embodiments, the small molecule fragment that covalently interacts with the biologically active cysteine impairs and/or inhibits activity of the cysteine containing protein. In some embodiments, the cysteine containing protein exists in an active form. In some embodiments, the small molecule fragment and/or the cysteine-reactive probe interact with the active form of the cysteine containing protein. In some embodiments, the cysteine containing protein exists in a pro-active form. In some embodiments, the small molecule fragment and/or the cysteine-reactive probe interact with the pro-active form of the cysteine containing protein. In some embodiments, the structural environment of the biologically active cysteine residue modulates the reactivity of the cysteine residue. In some embodiments, the structural environment is a hydrophobic environment or a hydrophilic environment. In some embodiments, the structural environment is a charged environment. In some embodiments, the structural environment is a nucleophilic environment. In some embodiments, the cysteine containing protein is an enzyme, a transporter, a receptor, a channel protein, an adaptor protein, a chaperone, a signaling protein, a plasma protein, transcription related protein, translation related protein, mitochondrial protein, or cytoskeleton related protein. In some embodiments, the cysteine containing protein is an enzyme, a transporter, a receptor, a channel protein, an adaptor protein, a chaperone, a signaling protein, transcription related protein, or translation related protein. In some embodiments, the enzyme comprises kinases, proteases, or deubiquitinating enzymes. In some embodiments, the protease is a cysteine protease. In some embodiments, the cysteine protease comprises caspases. In some embodiments, the signaling protein comprises vascular endothelial growth factor. In some embodiments, the signaling protein comprises a redox signaling protein. In some embodiments, the cysteine containing protein is a protein illustrated in Table 1. In some embodiments, the cysteine containing protein is a protein illustrated in Table 2. In some embodiments, the cysteine containing protein is a protein illustrated in Table 3. In some embodiments, the cysteine containing protein comprises a cysteine residue denoted in Table 3. In some embodiments, the cysteine containing protein is a protein illustrated in Table 8. In some embodiments, the cysteine containing protein is a protein illustrated in Table 9. In some embodiments, the cysteine containing protein is a protein illustrated in Table 10A, Table 10B, Table 10C, Table 10D or Table 10E. In some embodiments, the small molecule fragment is a small molecule fragment of Formula (I):

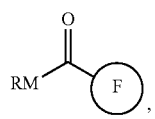

Formula (I)

wherein: RM is a reactive moiety selected from a Michael acceptor moiety, a leaving group moiety, or a moiety capable of forming a covalent bond with the thiol group of a cysteine residue; and F is a small molecule fragment moiety. In some embodiments, the Michael acceptor moiety comprises an alkene or an alkyne moiety. In some embodiments, F is obtained from a compound library. In some embodiments, the compound library comprises ChemBridge fragment library, Pyramid Platform Fragment-Based Drug Discovery, Maybridge fragment library, FRGx from AnalytiCon, TCI-Frag from AnCoreX, Bio Building Blocks from ASINEX, BioFocus 3D from Charles River, Fragments of Life (FOL) from Emerald Bio, Enamine Fragment Library, IOTA Diverse 1500, BIONET fragments library, Life Chemicals Fragments Collection, OTAVA fragment library, Prestwick fragment library, Selcia fragment library, TimTec fragment-based library, Allium from Vitas-M Laboratory, or Zenobia fragment library. In some embodiments, F is a small molecule fragment moiety illustrated in FIG. 3. In some embodiments, F further comprises a linker moiety that connects F to the carbonyl moiety. In some embodiments, the small molecule fragment is a small molecule fragment illustrated in FIG. 3. In some embodiments, the small molecule fragment is a specific inhibitor or a pan inhibitor. In some embodiments, the cysteine-reactive probe is a cysteine-reactive probe of Formula (II):

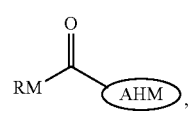

Formula (II)

wherein: RM is a reactive moiety selected from a Michael acceptor moiety, a leaving group moiety, or a moiety capable of forming a covalent bond to the thiol group of a cysteine residue; and AHM is an affinity handle moiety. In some embodiments, the Michael acceptor moiety comprises an alkene or an alkyne moiety. In some embodiments, the affinity handle moiety comprises an affinity handle and a binding moiety that facilitates covalent interaction of the cysteine-reactive probe to a cysteine residue of a cysteine-containing protein. In some embodiments, the binding moiety is a small molecule fragment obtained from a compound library. In some embodiments, the compound library comprises ChemBridge fragment library, Pyramid Platform Fragment-Based Drug Discovery, Maybridge fragment library, FRGx from AnalytiCon, TCI-Frag from AnCoreX, Bio Building Blocks from ASINEX, BioFocus 3D from Charles River, Fragments of Life (FOL) from Emerald Bio, Enamine Fragment Library, IOTA Diverse 1500, BIONET fragments library, Life Chemicals Fragments Collection, OTAVA fragment library, Prestwick fragment library, Selcia fragment library, TimTec fragment-based library, Allium from Vitas-M Laboratory, or Zenobia fragment library. In some embodiments, the affinity handle is a bioorthogonal affinity handle. In some embodiments, the affinity handle comprises a carbodiimide, N-hydroxysuccinimide (NHS) ester, imidoester, pentafluorophenyl ester, hydroxymethyl phosphine, maleimide, haloacetyl, pyridyl disulfide, thiosulfonate, vinylsulfone, hydrazide, alkoxyamine, alkyne, azide, or isocyanate group. In some embodiments, the affinity handle comprises an alkyne or an azide group. In some embodiments, the affinity handle is further conjugated to an affinity ligand. In some embodiments, the affinity ligand comprises a chromophore, a labeling group, or a combination thereof. In some embodiments, the chromophore comprises fluorochrome, non-fluorochrome chromophore, quencher, an absorption chromophore, fluorophore, organic dye, inorganic dye, metal chelate, or a fluorescent enzyme substrate. In some embodiments, the fluorophore comprises rhodamine, rhodol, fluorescein, thiofluorescein, aminofluorescein, carboxyfluorescein, chlorofluorescein, methylfluorescein, sulfofluorescein, aminorhodol, carboxyrhodol, chlororhodol, methylrhodol, sulforhodol, aminorhodamine, carboxyrhodamine, chlororhodamine, methylrhodamine, sulforhodamine, thiorhodamine, cyanine, indocarbocyanine, oxacarbocyanine, thiacarbocyanine, merocyanine, cyanine 2, cyanine 3, cyanine 3.5, cyanine 5, cyanine 5.5, cyanine 7, oxadiazole derivatives, pyridyloxazole, nitrobenzoxadiazole, benzoxadiazole, pyren derivatives, cascade blue, oxazine derivatives, Nile red, Nile blue, cresyl violet, oxazine 170, acridine derivatives, proflavin, acridine orange, acridine yellow, arylmethine derivatives, auramine, crystal violet, malachite green, tetrapyrrole derivatives, porphin, phtalocyanine, bilirubin 1-dimethylaminonaphthyl-5-sulfonate, 1-anilino-8-naphthalene sulfonate, 2-p-touidinyl-6-naphthalene sulfonate, 3-phenyl-7-isocyanatocoumarin, N-(p-(2-benzoxazolyl)phenyl)maleimide, stilbenes, pyrenes, 6-FAM (Fluorescein), 6-FAM (NHS Ester), 5(6)-FAM, 5-FAM, Fluorescein dT, 5-TAMRA-cadavarine, 2-aminoacridone, HEX, JOE (NHS Ester), MAX, TET, ROX, TAMRA, TARMA™ (NHS Ester), TEX 615, ATTO™ 488, ATTO™ 532, ATTO™ 550, ATTO™ 565, ATTO™ Rho101, ATTO™ 590, ATTO™ 633, ATTO™ 647N, TYE™ 563, TYE™ 665, or TYE™ 705. In some embodiments, the labeling group is biotin moiety, streptavidin moiety, bead, resin, a solid support, or a combination thereof. In some embodiments, the affinity handle moiety further comprises a chromophore. In some embodiments, the cysteine-reactive probe is a cysteine-reactive probe illustrated in FIG. 3. In some embodiments, the second cell solution further comprises a control. In some embodiments, the control is dimethyl sulfoxide (DMSO). In some embodiments, the proteomic analysis means comprises a mass spectroscopy method. In some embodiments, the mass spectroscopy method is a liquid-chromatography-mass spectrometry (LC-MS) method. In some embodiments, the method further comprises analyzing the results from the mass spectroscopy method by an algorithm for protein identification. In some embodiments, the algorithm combines the results from the mass spectroscopy method with a protein sequence database for protein identification. In some embodiments, the algorithm comprises ProLuCID algorithm, Probity, Scaffold, SEQUEST, or Mascot. In some embodiments, the mass spectroscopy method is a MALDI-TOF based method. In some embodiments, the value assigned to each of the cysteine containing protein is obtained from the mass spectroscopy analysis. In some embodiments, the value assigned to each of the cysteine containing protein is the area-under-the curve from a plot of signal intensity as a function of mass-to-charge ratio. In some embodiments, the identifying in step c) further comprises (i) locating a first value assigned to a cysteine containing protein from the first group of cysteine-reactive probe-protein complex and a second value of the same cysteine containing protein from the second group of cysteine-reactive probe-protein complex; and (ii) calculating a ratio between the two values assigned to the same cysteine containing protein. In some embodiments, the ratio of greater than 2 indicates that the cysteine containing protein is a candidate for interacting with the small molecule fragment. In some embodiments, the ratio of greater than 3 indicates that the cysteine containing protein is a candidate for interacting with the small molecule fragment. In some embodiments, the identifying in step c) further comprises calculating a percentage of inhibition of the cysteine-reactive probe to the cysteine containing protein. In some embodiments, the percentage of inhibition of greater than 50%, 60%, 70%, 80%, 90%, or at 100% indicates that the cysteine containing protein is a candidate for interacting with the small molecule fragment. In some embodiments, the cell is obtained from a tumor cell line. In some embodiments, the cell is obtained from a MDA-MB-231, Ramos, or Jurkat cell line. In some embodiments, the cell is obtained from a tumor sample. In some embodiments, the sample is a tissue sample. In some embodiments, the method is an in situ method. In some embodiments, the cysteine-reactive probe is not 4-hydroxynonenal or 15-deoxy-$\Delta$12,14-prostaglandin J2.

Disclosed herein, in certain embodiments, is a method of screening a small molecule fragment for interaction with a cysteine containing protein, comprising: (a) harvesting a set of cysteine-reactive probe-protein complexes from a sample treated with a cysteine-reactive probe wherein the cysteine-reactive probe comprises a reactive moiety capable of forming a covalent bond with a cysteine residue located on the cysteine containing protein; (b) analyzing the set of cysteine-reactive probe-protein complexes by a proteomic analysis means; and (c) based on step b), identifying the small molecule fragment as interacting with the cysteine containing protein. In some embodiments, the method further comprises assigning a value to each of the cysteine containing protein from the set of cysteine-reactive probe-protein complexes prior to identifying the small molecule fragment as interacting with the cysteine containing protein, wherein the value is determined based on the proteomic analysis means of step b). In some embodiments, the sample comprises a first cell solution and a second cell solution. In some embodiments, the method further comprises contacting the first cell solution with a small molecule fragment for an extended period of time prior to incubating the first cell solution with a first cysteine-reactive probe to generate a first group of cysteine-reactive probe-protein complexes. In some embodiments, the extended period of time is about 5, 10, 15, 20, 30, 60, 90, 120 minutes or longer. In some embodiments, the method further comprises contacting the second cell solution with a second cysteine-reactive probe to generate a second group of cysteine-reactive probe-protein complexes. In some embodiments, the first cysteine-reactive probe and the second cysteine-reactive probe are the same. In some embodiments, the first group and the second group of cysteine-reactive probe-protein complexes comprise the set of cysteine-reactive probe-protein complexes. In some embodiments, cells from the second cell solution are grown in a media (e.g., an isotopically enriched media). In some embodiments, cells from the first cell solution are grown in a media (e.g., an isotopically enriched media). In some embodiments, cells from both the first cell solution and the second cell solution are grown in two different isotopically enriched media so that cells from the first cell solution is distinguishable from cells obtained from the second cell solution. In other embodiments, cells from only one of the cell solutions (e.g., either the first cell solution or the second cell solution) are grown in an isotopically enriched media. In some embodiments, the method further comprises contacting the first cell solution with a first set of small molecule fragments and a complementing set of cysteine-reactive probes wherein each small molecule fragment competes with its complementing cysteine-reactive probe for binding with a cysteine residue, and wherein each small molecule fragment and each complementing cysteine-reactive probe are different within each respective set. In some embodiments, the method further comprises contacting the second cell solution with a second set of cysteine-reactive probes wherein the second set of cysteine-reactive probes is the same as the complementing set of cysteine-reactive probes, and wherein each cysteine-reactive probe is different within the set. In some embodiments, the first set of cysteine-reactive probes generates a third group of cysteine-reactive probe-protein complexes and the second set of cysteine-reactive probes generates a fourth group of cysteine-reactive probe-protein complexes. In some embodiments, the cysteine containing protein comprises a biologically active cysteine residue. In some embodiments, the biologically active cysteine site is a cysteine residue that is located about 10 Å or less to an active-site ligand or residue. In some embodiments, the cysteine residue that is located about 10 Å or less to the active-site ligand or residue is an active site cysteine. In some embodiments, the biologically active cysteine site is an active site cysteine. In some embodiments, the biologically active cysteine site is a cysteine residue that is located greater than 10 Å from an active-site ligand or residue. In some embodiments, the cysteine residue that is located greater than 10 Å from the active-site ligand or residue is a non-active site cysteine. In some embodiments, the biologically active cysteine site is a non-active site cysteine. In some embodiments, the small molecule fragment that covalently interacts with the biologically active cysteine impairs and/or inhibits activity of the cysteine containing protein. In some embodiments, the cysteine containing protein exists in an active form. In some embodiments, the small molecule fragment and/or the cysteine-reactive probe interact with the active form of the cysteine containing protein. In some embodiments, the cysteine containing protein exists in a pro-active form. In some embodiments, the small molecule fragment and/or the cysteine-reactive probe interact with the pro-active form of the cysteine containing protein. In some embodiments, the structural environment of the biologically active cysteine residue modulates the reactivity of the cysteine residue. In some embodiments, the structural environment is a hydrophobic environment or a hydrophilic environment. In some embodiments, the structural environment is a charged environment. In some embodiments, the structural environment is a nucleophilic environment. In some embodiments, the cysteine containing protein is selected from an enzyme, a transporter, a receptor, a channel protein, an adaptor protein, a chaperone, a signaling protein, a plasma protein, transcription related protein, translation related protein, mitochondrial protein, or cytoskeleton related protein. In some embodiments, the cysteine containing protein is selected from an enzyme, a transporter, a receptor, a channel protein, an adaptor protein, a chaperone, a signaling protein, transcription related protein, or translation related protein. In some embodiments, the enzyme comprises kinases, proteases, or deubiquitinating enzymes. In some embodiments, the protease is a cysteine protease. In some embodiments, the cysteine protease comprises caspases. In some embodiments, the signaling protein comprises vascular endothelial growth factor. In some embodiments, the signaling protein comprises a redox signaling protein. In some embodiments, the cysteine containing protein is selected from Table 1. In some embodiments, the cysteine containing protein is a protein illustrated in Table 2. In some embodiments, the cysteine containing protein is a protein illustrated in Table 3. In some embodiments, the cysteine containing protein comprises a cysteine residue denoted in Table 3. In some embodiments, the cysteine containing protein is a protein illustrated in Table 8. In some embodiments, the cysteine containing protein is a protein illustrated in Table 9. In some embodiments, the cysteine containing protein is a protein illustrated in Table 10A, Table 10B, Table 10C, Table 10D or Table 10E. In some embodiments, the cysteine containing protein is TIGAR, IMPDH2, IDH1, IDH2, BTK, ZAK, TGM2, Map2k7, XPO1, Casp5, Casp8, ERCC3, Park 7 (*Toxoplasma* DJ-1), GSTO1, ALDH2, CTSZ, STAT1, STAT3, SMAD2, RBPJ, FOXK1, IRF4, IRF8, GTF3C1, or TCERG1. In some embodiments, the small molecule fragment is a small molecule fragment of Formula (I):

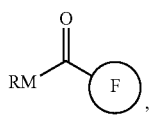

Formula (I)

wherein: RM is a reactive moiety selected from a Michael acceptor moiety, a leaving group moiety, or a moiety capable of forming a covalent bond with the thiol group of a cysteine residue; and F is a small molecule fragment moiety. In some embodiments, the Michael acceptor moiety comprises an alkene or an alkyne moiety. In some embodiments, F is obtained from a compound library. In some embodiments, the compound library comprises ChemBridge fragment library, Pyramid Platform Fragment-Based Drug Discovery, Maybridge fragment library, FRGx from AnalytiCon, TCI-Frag from AnCoreX, Bio Building Blocks from ASINEX, BioFocus 3D from Charles River, Fragments of Life (FOL) from Emerald Bio, Enamine Fragment Library, IOTA Diverse 1500, BIONET fragments library, Life Chemicals Fragments Collection, OTAVA fragment library, Prestwick fragment library, Selcia fragment library, TimTec fragment-based library, Allium from Vitas-M Laboratory, or Zenobia fragment library. In some embodiments, F is a small molecule fragment moiety illustrated in FIG. 3. In some embodiments, F further comprises a linker moiety that connects F to the carbonyl moiety. In some embodiments, the small molecule fragment is a small molecule fragment illustrated in FIG. 3. In some embodiments, the small molecule fragment is a specific inhibitor or a pan inhibitor. In some embodiments, the cysteine-reactive probe is a cysteine-reactive probe of Formula (II):

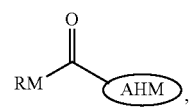

Formula (II)

wherein: RM is a reactive moiety selected from a Michael acceptor moiety, a leaving group moiety, or a moiety capable of forming a covalent bond to the thiol group of a cysteine residue; and AHM is an affinity handle moiety. In some embodiments, the Michael acceptor moiety comprises an alkene or an alkyne moiety. In some embodiments, the affinity handle moiety comprises an affinity handle and a binding moiety that facilitates covalent interaction of the cysteine-reactive probe to a cysteine residue of a cysteine-containing protein. In some embodiments, the binding moiety is a small molecule fragment obtained from a compound library. In some embodiments, the compound library comprises ChemBridge fragment library, Pyramid Platform Fragment-Based Drug Discovery, Maybridge fragment library, FRGx from AnalytiCon, TCI-Frag from AnCoreX, Bio Building Blocks from ASINEX, BioFocus 3D from Charles River, Fragments of Life (FOL) from Emerald Bio, Enamine Fragment Library, IOTA Diverse 1500, BIONET fragments library, Life Chemicals Fragments Collection, OTAVA fragment library, Prestwick fragment library, Selcia fragment library, TimTec fragment-based library, Allium from Vitas-M Laboratory, or Zenobia fragment library. In some embodiments, the affinity handle is a bioorthogonal affinity handle. In some embodiments, the affinity handle comprises a carbodiimide, N-hydroxysuccinimide (NHS) ester, imidoester, pentafluorophenyl ester, hydroxymethyl phosphine, maleimide, haloacetyl, pyridyl disulfide, thiosulfonate, vinylsulfone, hydrazide, alkoxyamine, alkyne, azide, or isocyanate group. In some embodiments, the affinity handle comprises an alkyne or an azide group. In some embodiments, the affinity handle is further conjugated to an affinity ligand. In some embodiments, the affinity ligand comprises a chromophore, a labeling group, or a combination thereof. In some embodiments, the chromophore comprises fluorochrome, non-fluorochrome chromophore, quencher, an absorption chromophore, fluorophore, organic dye, inorganic dye, metal chelate, or a fluorescent enzyme substrate. In some embodiments, the fluorophore comprises rhodamine, rhodol, fluorescein, thiofluorescein, aminofluorescein, carboxyfluorescein, chlorofluorescein, methylfluorescein, sulfofluorescein, aminorhodol, carboxyrhodol, chlororhodol, methylrhodol, sulforhodol; aminorhodamine, carboxyrhodamine, chlororhodamine, methylrhodamine, sulforhodamine, thiorhodamine, cyanine, indocarbocyanine, oxacarbocyanine, thiacarbocyanine, merocyanine, cyanine 2, cyanine 3, cyanine 3.5, cyanine 5, cyanine 5.5, cyanine 7, oxadiazole derivatives, pyridyloxazole, nitrobenzoxadiazole, benzoxadiazole, pyren derivatives, cascade blue, oxazine derivatives, Nile red, Nile blue, cresyl violet, oxazine 170, acridine derivatives, proflavin, acridine orange, acridine yellow, arylmethine derivatives, auramine, crystal violet, malachite green, tetrapyrrole derivatives, porphin, phtalocyanine, bilirubin 1-dimethylaminonaphthyl-5-sulfonate, 1-anilino-8-naphthalene sulfonate, 2-p-touidinyl-6-naphthalene sulfonate, 3-phenyl-7-isocyanatocoumarin, N-(p-(2-benzoxazolyl)phenyl)maleimide, stilbenes, pyrenes, 6-FAM (Fluorescein), 6-FAM (NHS Ester), 5(6)-FAM, 5-FAM, Fluorescein dT, 5-TAMRA-cadavarine, 2-aminoacridone, HEX, JOE (NHS Ester), MAX, TET, ROX, TAMRA, TARMA™ (NHS Ester), TEX 615, ATTO™ 488, ATTO™ 532, ATTO™ 550, ATTO™ 565, ATTO™ Rho101, ATTO™ 590, ATTO™ 633, ATTO™ 647N, TYE™ 563, TYE™ 665, or TYE™ 705. In some embodiments, the labeling group is biotin moiety, streptavidin moiety, bead, resin, a solid support, or a combination thereof. In some embodiments, the affinity handle moiety further comprises a chromophore. In some embodiments, the cysteine-reactive probe is a cysteine-reactive probe illustrated in FIG. 3. In some embodiments, the second cell solution further comprises a control. In some embodiments, the control is dimethyl sulfoxide (DMSO). In some embodiments, the proteomic analysis means comprises a mass spectroscopy method. In some embodiments, the mass spectroscopy method is a MALDI-TOF based method. In some embodiments, the mass spectroscopy method is a liquid-chromatography-mass spectrometry (LC-MS) method. In some embodiments, the method further comprises analyzing the results from the mass spectroscopy method by an algorithm for protein identification. In some embodiments, the algorithm combines the results from the mass spectroscopy method with a protein sequence database for protein identification. In some embodiments, the algorithm comprises ProLuCID algorithm, Probity, Scaffold, SEQUEST, or Mascot. In some embodiments, the value assigned to each of the cysteine containing protein is obtained from the mass spectroscopy analysis. In some embodiments, the value assigned to each of the cysteine containing protein is the area-under-the curve from a plot of signal intensity as a function of mass-to-charge ratio. In some embodiments, the identifying in step c) further comprises (i) locating a first value assigned to a cysteine containing protein from the first group of cysteine-reactive probe-protein complex and a second value of the same cysteine containing protein from the second group of cysteine-reactive probe-protein complex; and (ii) calculating a ratio between the two values assigned to the same cysteine containing protein. In some embodiments, the ratio of greater than 2 indicates that the cysteine containing protein is a candidate for interacting with the small molecule fragment. In some embodiments, the ratio of greater than 3 indicates that the cysteine containing protein is a candidate for interacting with the small molecule fragment. In some embodiments, the identifying in step c) further comprises calculating a percentage of inhibition of the cysteine-reactive probe to the cysteine containing protein. In some embodiments, the percentage of inhibition of greater than 50%, 60%, 70%, 80%, 90%, or at 100% indicates that the cysteine containing protein is a candidate for interacting with the small molecule fragment. In some embodiments, the cell is obtained from a tumor cell line. In some embodiments, the cell is obtained from a MDA-MB-231, Ramos, or Jurkat cell line. In some embodiments, the cell is obtained from a tumor sample. In some embodiments, the sample is a tissue sample. In some embodiments, the method is an in situ method.

Disclosed herein, in certain embodiments, is a method of mapping a biologically active cysteine site on a protein, comprising (a) harvesting a set of cysteine-reactive probe-protein complexes from a sample treated with a cysteine-reactive probe wherein the cysteine-reactive probe comprises a reactive moiety capable of forming a covalent bond with a cysteine residue located on the cysteine containing protein; (b) analyzing the set of cysteine-reactive probe-protein complexes by a proteomic analysis means; and (c) based on step b), mapping the biologically active cysteine site on the protein. In some embodiments, the sample comprises a first cell solution and a second cell solution. In some embodiments, the method further comprises contacting the first cell solution with a small molecule fragment for an extended period of time prior to incubating the first cell solution with a first cysteine-reactive probe to generate a first group of cysteine-reactive probe-protein complexes. In some embodiments, the extended period of time is about 5, 10, 15, 20, 30, 60, 90, 120 minutes or longer. In some embodiments, the method further comprises contacting the second cell solution with a second cysteine-reactive probe to generate a second group of cysteine-reactive probe-protein complexes. In some embodiments, the first cysteine-reactive probe and the second cysteine-reactive probe are the same. In some embodiments, the biologically active cysteine site is a cysteine residue that is located about 10 Å or less to an active-site ligand or residue. In some embodiments, the cysteine residue that is located about 10 Å or less to the active-site ligand or residue is an active site cysteine. In some embodiments, the biologically active cysteine site is an active site cysteine. In some embodiments, the biologically active cysteine site is a cysteine residue that is located greater than 10 Å from an active-site ligand or residue. In some embodiments, the cysteine residue that is located greater than 10 Å from the active-site ligand or residue is a non-active site cysteine. In some embodiments, the biologically active cysteine site is a non-active site cysteine. In some embodiments, the small molecule fragment that covalently interacts with the biologically active cysteine impairs and/or inhibits activity of the cysteine containing protein. In some embodiments, the cysteine containing protein exists in an active form. In some embodiments, the small molecule fragment and/or the cysteine-reactive probe interact with the active form of the cysteine containing protein. In some embodiments, the cysteine containing protein exists in a pro-active form. In some embodiments, the small molecule fragment and/or the cysteine-reactive probe interact with the pro-active form of the cysteine containing protein. In some embodiments, the structural environment of the biologically active cysteine residue modulates the reactivity of the cysteine residue. In some embodiments, the structural environment is a hydrophobic environment or a hydrophilic environment. In some embodiments, the structural environment is a charged environment. In some embodiments, the structural environment is a nucleophilic environment. In some embodiments, the protein is an enzyme, a transporter, a receptor, a channel protein, an adaptor protein, a chaperone, a signaling protein, a plasma protein, transcription related protein, translation related protein, mitochondrial protein, or cytoskeleton related protein. In some embodiments, the protein is an enzyme, a transporter, a receptor, a channel protein, an adaptor protein, a chaperone, a signaling protein, transcription related protein, or translation related protein. In some embodiments, the enzyme comprises kinases, proteases, or deubiquitinating enzymes. In some embodiments, the protease is a cysteine protease. In some embodiments, the cysteine protease comprises caspases. In some embodiments, the signaling protein comprises vascular endothelial growth factor. In some embodiments, the signaling protein comprises a redox signaling protein. In some embodiments, the protein is a protein illustrated in Table 1. In some embodiments, the cysteine containing protein is a protein illustrated in Table 2. In some embodiments, the cysteine containing protein is a protein illustrated in Table 3. In some embodiments, the cysteine containing protein comprises a cysteine residue denoted in Table 3. In some embodiments, the cysteine containing protein is a protein illustrated in Table 8. In some embodiments, the cysteine containing protein is a protein illustrated in Table 9. In some embodiments, the cysteine containing protein is a protein illustrated in Table 10A, Table 10B, Table 10C, Table 10D or Table 10E. In some embodiments, the small molecule fragment is a small molecule fragment of Formula (I):

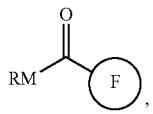

Formula (I)

wherein: RM is a reactive moiety selected from a Michael acceptor moiety, a leaving group moiety, or a moiety capable of forming a covalent bond with the thiol group of a cysteine residue; and F is a small molecule fragment moiety. In some embodiments, the Michael acceptor moiety comprises an alkene or an alkyne moiety. In some embodiments, F is obtained from a compound library. In some embodiments, the compound library comprises ChemBridge fragment library, Pyramid Platform Fragment-Based Drug Discovery, Maybridge fragment library, FRGx from AnalytiCon, TCI-Frag from AnCoreX, Bio Building Blocks from ASINEX, BioFocus 3D from Charles River, Fragments of Life (FOL) from Emerald Bio, Enamine Fragment Library, IOTA Diverse 1500, BIONET fragments library, Life Chemicals Fragments Collection, OTAVA fragment library, Prestwick fragment library, Selcia fragment library, TimTec fragment-based library, Allium from Vitas-M Laboratory, or Zenobia fragment library. In some embodiments, F is a small molecule fragment moiety illustrated in FIG. 3. In some embodiments, F further comprises a linker moiety that connects F to the carbonyl moiety. In some embodiments, the small molecule fragment is a small molecule fragment illustrated in FIG. 3. In some embodiments, the small molecule fragment is a specific inhibitor or a pan inhibitor. In some embodiments, the cysteine-reactive probe is a cysteine-reactive probe of Formula (II):

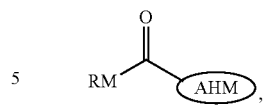

Formula (II)

wherein: RM is a reactive moiety selected from a Michael acceptor moiety, a leaving group moiety, or a moiety capable of forming a covalent bond to the thiol group of a cysteine residue; and AHM is an affinity handle moiety. In some embodiments, the Michael acceptor moiety comprises an alkene or an alkyne moiety. In some embodiments, the affinity handle moiety comprises an affinity handle and a binding moiety that facilitates covalent interaction of the cysteine-reactive probe to a cysteine residue of a cysteine-containing protein. In some embodiments, the binding moiety is a small molecule fragment obtained from a compound library. In some embodiments, the compound library comprises ChemBridge fragment library, Pyramid Platform Fragment-Based Drug Discovery, Maybridge fragment library, FRGx from AnalytiCon, TCI-Frag from AnCoreX, Bio Building Blocks from ASINEX, BioFocus 3D from Charles River, Fragments of Life (FOL) from Emerald Bio, Enamine Fragment Library, IOTA Diverse 1500, BIONET fragments library, Life Chemicals Fragments Collection, OTAVA fragment library, Prestwick fragment library, Selcia fragment library, TimTec fragment-based library, Allium from Vitas-M Laboratory, or Zenobia fragment library. In some embodiments, the affinity handle is a bioorthogonal affinity handle. In some embodiments, the affinity handle comprises a carbodiimide, N-hydroxysuccinimide (NHS) ester, imidoester, pentafluorophenyl ester, hydroxymethyl phosphine, maleimide, haloacetyl, pyridyl disulfide, thiosulfonate, vinylsulfone, hydrazide, alkoxyamine, alkyne, azide, or isocyanate group. In some embodiments, the affinity handle comprises an alkyne or an azide group. In some embodiments, the affinity handle is further conjugated to an affinity ligand. In some embodiments, the affinity ligand comprises a chromophore, a labeling group, or a combination thereof. In some embodiments, the chromophore comprises fluorochrome, non-fluorochrome chromophore, quencher, an absorption chromophore, fluorophore, organic dye, inorganic dye, metal chelate, or a fluorescent enzyme substrate. In some embodiments, the fluorophore comprises rhodamine, rhodol, fluorescein, thiofluorescein, aminofluorescein, carboxyfluorescein, chlorofluorescein, methylfluorescein, sulfofluorescein, aminorhodol, carboxyrhodol, chlororhodol, methylrhodol, sulforhodol; aminorhodamine, carboxyrhodamine, chlororhodamine, methylrhodamine, sulforhodamine, thiorhodamine, cyanine, indocarbocyanine, oxacarbocyanine, thiacarbocyanine, merocyanine, cyanine 2, cyanine 3, cyanine 3.5, cyanine 5, cyanine 5.5, cyanine 7, oxadiazole derivatives, pyridyloxazole, nitrobenzoxadiazole, benzoxadiazole, pyren derivatives, cascade blue, oxazine derivatives, Nile red, Nile blue, cresyl violet, oxazine 170, acridine derivatives, proflavin, acridine orange, acridine yellow, arylmethine derivatives, auramine, crystal violet, malachite green, tetrapyrrole derivatives, porphin, phtalocyanine, bilirubin 1-dimethylaminonaphthyl-5-sulfonate, 1-anilino-8-naphthalene sulfonate, 2-p-touidinyl-6-naphthalene sulfonate, 3-phenyl-7-isocyanatocoumarin, N-(p-(2-benzoxazolyl)phenyl)maleimide, stilbenes, pyrenes, 6-FAM (Fluorescein), 6-FAM (NHS Ester), 5(6)-FAM, 5-FAM, Fluorescein dT, 5-TAMRA-cadavarine, 2-aminoacridone, HEX, JOE (NHS Ester), MAX, TET, ROX, TAMRA, TARMA™ (NHS Ester), TEX 615, ATTO™ 488, ATTO™ 532, ATTO™ 550, ATTO™ 565, ATTO™ Rho101, ATTO™ 590, ATTO™ 633, ATTO™ 647N, TYE™ 563, TYE™ 665, or TYE™ 705. In some embodiments, the labeling group is biotin moiety, streptavidin moiety, bead, resin, a solid support, or a combination thereof. In some embodiments, the affinity handle moiety further comprises a chromophore. In some embodiments, the cysteine-reactive probe is a cysteine-reactive probe illustrated in FIG. 3. In some embodiments, the second cell solution further comprises a control. In some embodiments, the control is dimethyl sulfoxide (DMSO). In some embodiments, the proteomic analysis means comprises a mass spectroscopy method. In some embodiments, the mass spectroscopy method is a liquid-chromatography-mass spectrometry (LC-MS) method. In some embodiments, the method further comprises analyzing the results from the mass spectroscopy method by an algorithm for protein identification. In some embodiments, the algorithm combines the results from the mass spectroscopy method with a protein sequence database for protein identification. In some embodiments, the algorithm comprises ProLuCID algorithm, Probity, Scaffold, SEQUEST, or Mascot. In some embodiments, the mass spectroscopy method is a MALDI-TOF based method. In some embodiments, the cell is obtained from a tumor cell line. In some embodiments, the cell is obtained from a MDA-MB-231, Ramos, or Jurkat cell line. In some embodiments, the cell is obtained from a tumor sample. In some embodiments, the sample is a tissue sample. In some embodiments, the method is an in situ method.

Disclosed herein, in certain embodiments, is a composition comprising: a small molecule fragment of Formula (I):

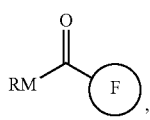

Formula (I)

wherein: RM is a reactive moiety selected from a Michael acceptor moiety, a leaving group moiety, or a moiety capable of forming a covalent bond with the thiol group of a cysteine residue; and F is a small molecule fragment moiety; and a cysteine containing protein wherein the cysteine containing protein is covalently bond to the small molecule fragment. In some embodiments, the Michael acceptor moiety comprises an alkene or an alkyne moiety. In some embodiments, F is obtained from a compound library. In some embodiments, F is a small molecule fragment moiety illustrated in FIG. 3. In some embodiments, F further comprises a linker moiety that connects F to the carbonyl moiety.

Disclosed herein, in certain embodiments, is a composition comprising: a cysteine-reactive probe of Formula (II):

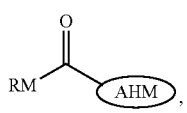

Formula (II)

wherein: RM is a reactive moiety selected from a Michael acceptor moiety, a leaving group moiety, or a moiety capable of forming a covalent bond to the thiol group of a cysteine residue; and AHM is an affinity handle moiety; and a cysteine containing protein wherein the cysteine containing protein is covalently bond to the cysteine-reactive probe. In some embodiments, the Michael acceptor moiety comprises an alkene or an alkyne moiety. In some embodiments, the affinity handle moiety comprises an affinity handle and a binding moiety that facilitates covalent interaction of the cysteine-reactive probe to a cysteine residue of a cysteine-containing protein. In some embodiments, the binding moiety is a small molecule fragment obtained from a compound library. In some embodiments, the affinity handle is a bioorthogonal affinity handle. In some embodiments, the affinity handle comprises a carbodiimide, N-hydroxysuccinimide (NHS) ester, imidoester, pentafluorophenyl ester, hydroxymethyl phosphine, maleimide, haloacetyl, pyridyl disulfide, thiosulfonate, vinylsulfone, hydrazide, alkoxyamine, alkyne, azide, or isocyanate group. In some embodiments, the affinity handle is further conjugated to an affinity ligand. In some embodiments, the affinity handle moiety further comprises a chromophore. In some embodiments, the cysteine-reactive probe is a cysteine-reactive probe illustrated in FIG. 3.

Disclosed herein, in certain embodiments, is a composition comprising: an isolated sample wherein the isolated sample is an isolated cell or a tissue sample; and a cysteine-reactive probe to be assayed for its ability to interact with a cysteine containing protein expressed in the isolated sample. In some embodiments, the composition further comprises contacting the isolated sample with a small molecule fragment for an extended period of time prior to incubating the isolated sample with the cysteine-reactive probe to generate a cysteine-reactive probe-protein complex. In some embodiments, the extended period of time is about 5, 10, 15, 20, 30, 60, 90, 120 minutes or longer.

Disclosed herein, in certain embodiments, is an isolated treated cell comprising a cysteine-reactive probe covalently attached to a cysteine containing protein. In some embodiments, the isolated treated cell further comprises a set of cysteine-reactive probes wherein each of the cysteine-reactive probes is covalently attached to a cysteine containing protein.

Disclosed herein, in certain embodiments, is an isolated treated cell comprising a small molecule fragment covalently attached to a cysteine containing protein. In some embodiments, the isolated treated cell further comprises a set of small molecule fragments wherein each of the small molecule fragments is covalently attached to a cysteine containing protein. In some embodiments, the isolated treated cell further comprises a cysteine-reactive probe. In some embodiments, the isolated treated cell further comprises a set of cysteine-reactive probes.

Disclosed herein, in certain embodiments, is an isolated treated population of cells comprising a set of cysteine-reactive probes covalently attached to cysteine containing proteins. Also disclosed herein, in certain embodiments, is an isolated treated population of cells comprising a set of small molecule fragments covalently attached to cysteine containing proteins. In some embodiments, the isolated treated population of cells further comprises a set of cysteine-reactive probes.

Disclosed herein, in certain embodiments, is an isolated and purified polypeptide comprising at least 90% sequence identity to at least seven contiguous amino acids of an amino acid sequence selected from Tables 1-3 or 8-9. In some embodiments, the isolated and purified polypeptide comprising at least 95% sequence identity to at least seven contiguous amino acids of an amino acid sequence selected from Tables 1-3 or 8-9. In some embodiments, the isolated and purified polypeptide comprising 100% sequence identity to at least seven contiguous amino acids of an amino acid sequence selected from Tables 1-3 or 8-9. In some embodiments, the isolated and purified polypeptide consisting 100% sequence identity to the full length of an amino acid sequence selected from Tables 1-3 or 8-9. In some embodiments, the isolated and purified polypeptide is at most 50 amino acids in length. A polypeptide probe for screening a small molecule fragment comprising an isolated and purified polypeptide described herein.

Further disclosed herein, in certain embodiments, is a nucleic acid encoding a polypeptide comprising at least 90% sequence identity at least seven contiguous amino acids of an amino acid sequence selected from Tables 1-3 or 8-9. In some embodiments, the nucleic acid encoding a polypeptide comprising at least 95% sequence identity at least seven contiguous amino acids of an amino acid sequence selected from Tables 1-3 or 8-9. In some embodiments, the nucleic acid encoding a polypeptide comprising 100% sequence identity at least seven contiguous amino acids of an amino acid sequence selected from Tables 1-3 or 8-9. In some embodiments, the nucleic acid encoding a polypeptide consisting 100% sequence identity to the full length of an amino acid sequence selected from Tables 1-3 or 8-9.

Disclosed herein, in certain embodiments, is a modified cysteine containing protein comprising a small molecule fragment having a covalent bond to a cysteine residue of a cysteine containing protein, wherein the small molecule fragment is a small molecule fragment of Formula (I):

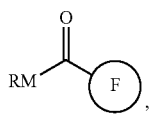

Formula (I)

wherein: RM is a reactive moiety selected from a Michael acceptor moiety, a leaving group moiety, or a moiety capable of forming a covalent bond with the thiol group of a cysteine residue; and F is a small molecule fragment moiety. In some embodiments, the cysteine containing protein is a protein illustrated in Table 1. In some embodiments, the cysteine containing protein is a protein illustrated in Table 2. In some embodiments, the cysteine containing protein is a protein illustrated in Table 3. In some embodiments, the cysteine containing protein comprises a cysteine residue denoted in Table 3. In some embodiments, the cysteine containing protein is a protein illustrated in Table 8. In some embodiments, the cysteine containing protein is a protein illustrated in Table 9. In some embodiments, the Michael acceptor moiety comprises an alkene or an alkyne moiety. In some embodiments, F is obtained from a compound library. In some embodiments, F is a small molecule fragment moiety illustrated in FIG. 3. In some embodiments, F further comprises a linker moiety that connects F to the carbonyl moiety. In some embodiments, the small molecule fragment binds irreversibly to the cysteine containing protein. In some embodiments, the small molecule fragment binds reversibly to the cysteine containing protein.

Disclosed herein, in certain embodiments, is a modified cysteine containing protein comprising a small molecule fragment having a covalent bond to a cysteine residue of a cysteine containing protein, wherein the small molecule fragment has a molecular weight of about 150 Dalton or higher. In some embodiments, the small molecule fragment has a molecular weight of about 175, 200, 225, 250, 275, 300, 350, 400, 450, 500, 550, 600, 650, 700, 750, 800, 850, 900, 950, 1000 Dalton, or higher. In some embodiments, the molecular weight of the small molecule fragment is prior to enrichment with a halogen, a nonmetal, or a transition metal. In some embodiments, the molecular weight of the small molecule fragment is calculated based on carbon and hydrogen atoms and optionally further based on nitrogen, oxygen and/or sulfur atoms. In some embodiments, the molecular weight of the small molecule fragment does not include the molecular weight of a halogen, a transition metal or a combination thereof. In some embodiments, the cysteine containing protein is about 20, 30, 35, 40, 45, 50, 55, 60, 65, 70, 75, 80, 85, 90, 95, 100, 150, 200, 250, 300, 350, 400, 450, 500, 600, 700, 800, 900, 1000 amino acid residues in length or more. In some embodiments, the cysteine containing protein is a protein illustrated in Table 1. In some embodiments, the cysteine containing protein is a protein illustrated in Table 2. In some embodiments, the cysteine containing protein is a protein illustrated in Table 3. In some embodiments, the cysteine containing protein comprises a cysteine residue denoted in Table 3. In some embodiments, the cysteine containing protein is a protein illustrated in Table 8. In some embodiments, the cysteine containing protein is a protein illustrated in Table 9. In some embodiments, the small molecule fragment is a small molecule fragment of Formula (I):

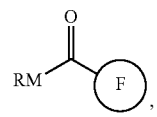

Formula (I)

wherein: RM is a reactive moiety selected from a Michael acceptor moiety, a leaving group moiety, or a moiety capable of forming a covalent bond with the thiol group of a cysteine residue; and F is a small molecule fragment moiety. In some embodiments, the small molecule fragment of Formula (I) has a molecular weight of about 150, 175, 200, 225, 250, 275, 300, 350, 400, 450, 500, 550, 600, 650, 700, 750, 800, 850, 900, 950, 1000 Dalton, or higher. In some embodiments, the Michael acceptor moiety comprises an alkene or an alkyne moiety. In some embodiments, F is obtained from a compound library. In some embodiments, F is a small molecule fragment moiety illustrated in FIG. 3. In some embodiments, F further comprises a linker moiety that connects F to the carbonyl moiety. In some embodiments, the small molecule fragment bond irreversibly to the cysteine containing protein. In some embodiments, the small molecule fragment bond reversibly to the cysteine containing protein.

Disclosed herein, in certain embodiments, is a cysteine containing protein-small molecule fragment complex produced by a process comprising contacting a cell solution with a small molecule fragment of Formula (I):

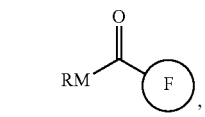

Formula (I)

wherein: RM is a reactive moiety selected from a Michael acceptor moiety, a leaving group moiety, or a moiety capable of forming a covalent bond with the thiol group of a cysteine residue; and F is a small molecule fragment moiety; and wherein the contacting time is between about 5 minutes and about 2 hours. In some embodiments, the Michael acceptor moiety comprises an alkene or an alkyne moiety. In some embodiments, F is obtained from a compound library. In some embodiments, F is a small molecule fragment moiety illustrated in FIG. 3. In some embodiments, F further comprises a linker moiety that connects F to the carbonyl moiety. In some embodiments, the small molecule fragment of Formula (I) has a molecular weight of about 150, 175, 200, 225, 250, 275, 300, 350, 400, 450, 500, 550, 600, 650, 700, 750, 800, 850, 900, 950, 1000 Dalton, or higher. In some embodiments, the cysteine containing protein is a protein illustrated in Table 1. In some embodiments, the cysteine containing protein is a protein illustrated in Table 2. In some embodiments, the cysteine containing protein is a protein illustrated in Table 3. In some embodiments, the cysteine containing protein comprises a cysteine residue denoted in Table 3. In some embodiments, the cysteine containing protein is a protein illustrated in Table 8. In some embodiments, the cysteine containing protein is a protein illustrated in Table 9. In some embodiments, the cysteine containing protein is a protein illustrated in Table 10A, Table 10B, Table 10C, Table 10D or Table 10E. In some embodiments, the small molecule fragment binds irreversibly to the cysteine containing protein. In some embodiments, the small molecule fragment binds reversibly to the cysteine containing protein.

Disclosed herein, in certain embodiments, is a modified cysteine containing protein comprising a cysteine-reactive probe having a covalent bond to a cysteine residue of a cysteine containing protein, wherein the cysteine-reactive probe is a cysteine-reactive probe of Formula (II):

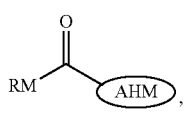

Formula (II)

wherein: RM is a reactive moiety selected from a Michael acceptor moiety, a leaving group moiety, or a moiety capable of forming a covalent bond to the thiol group of a cysteine residue; and AHM is an affinity handle moiety. In some embodiments, the cysteine containing protein is a protein illustrated in Table 1. In some embodiments, the cysteine containing protein is a protein illustrated in Table 2. In some embodiments, the cysteine containing protein is a protein illustrated in Table 8. In some embodiments, the cysteine containing protein is a protein illustrated in Table 9. In some embodiments, the cysteine containing protein is a protein illustrated in Table 10A, Table 10B, Table 10C, Table 10D or Table 10E. In some embodiments, the Michael acceptor moiety comprises an alkene or an alkyne moiety. In some embodiments, the affinity handle moiety comprises an affinity handle and a binding moiety that facilitates covalent interaction of the cysteine-reactive probe to a cysteine residue of a cysteine-containing protein. In some embodiments, the binding moiety is a small molecule fragment obtained from a compound library. In some embodiments, the affinity handle is a bioorthogonal affinity handle. In some embodiments, the affinity handle comprises a carbodiimide, N-hydroxysuccinimide (NHS) ester, imidoester, pentafluorophenyl ester, hydroxymethyl phosphine, maleimide, haloacetyl, pyridyl disulfide, thiosulfonate, vinylsulfone, hydrazide, alkoxyamine, alkyne, azide, or isocyanate group. In some embodiments, the affinity handle is further conjugated to an affinity ligand. In some embodiments, the affinity handle moiety further comprises a chromophore. In some embodiments, the cysteine-reactive probe is a cysteine-reactive probe illustrated in FIG. 3. In some embodiments, the cysteine-reactive probe binds irreversibly to the cysteine containing protein. In some embodiments, the cysteine-reactive probe binds reversibly to the cysteine containing protein.

Disclosed herein, in certain embodiments, is a cysteine-reactive probe of Formula (II):

Formula (II)

wherein: RM is a reactive moiety selected from a Michael acceptor moiety, a leaving group moiety, or a moiety capable of forming a covalent bond to the thiol group of a cysteine residue; and AHM is an affinity handle moiety. In some embodiments, the cysteine-reactive probe covalently binds to a cysteine residue on a cysteine containing protein. In some embodiments, cysteine containing protein is a protein illustrated in Table 1. In some embodiments, the cysteine containing protein is a protein illustrated in Table 2. In some embodiments, the cysteine containing protein is a protein illustrated in Table 3. In some embodiments, the cysteine containing protein comprises a cysteine residue denoted in Table 3. In some embodiments, the cysteine containing protein is a protein illustrated in Table 8. In some embodiments, the cysteine containing protein is a protein illustrated in Table 9. In some embodiments, the cysteine containing protein is a protein illustrated in Table 10A, Table 10B, Table 10C, Table 10D or Table 10E. In some embodiments, the cysteine-reactive probe binds irreversibly to the cysteine containing protein. In some embodiments, the cysteine-reactive probe binds reversibly to the cysteine containing protein.

Disclosed herein, in certain embodiments, is a compound capable of covalently binding to a cysteine containing protein identified, using the method comprising: (a) obtaining a set of cysteine-reactive probe-protein complexes from a sample wherein the cysteine-reactive probe comprises a reactive moiety capable of forming a covalent bond with a cysteine residue located on the cysteine containing protein; (b) analyzing the set of cysteine-reactive probe-protein complexes by a proteomic analysis means; (c) based on step b), identifying a cysteine containing protein as the binding target for the compound. In some embodiments, the compound is a small molecule fragment. In some embodiments, the small molecule fragment is a small molecule fragment of Formula (I):

Formula (I)

wherein: RM is a reactive moiety selected from a Michael acceptor moiety, a leaving group moiety, or a moiety capable of forming a covalent bond with the thiol group of a cysteine residue; and F is a small molecule fragment moiety. In some embodiments, the Michael acceptor moiety comprises an alkene or an alkyne moiety. In some embodiments, F is obtained from a compound library. In some embodiments, the compound library comprises ChemBridge fragment library, Pyramid Platform Fragment-Based Drug Discovery, Maybridge fragment library, FRGx from AnalytiCon, TCI-Frag from AnCoreX, Bio Building Blocks from ASINEX, BioFocus 3D from Charles River, Fragments of Life (FOL) from Emerald Bio, Enamine Fragment Library, IOTA Diverse 1500, BIONET fragments library, Life Chemicals Fragments Collection, OTAVA fragment library, Prestwick fragment library, Selcia fragment library, TimTec fragment-based library, Allium from Vitas-M Laboratory, or Zenobia fragment library. In some embodiments, F is a small molecule fragment moiety illustrated in FIG. 3. In some embodiments, F further comprises a linker moiety that connects F to the carbonyl moiety. In some embodiments, the small molecule fragment is a small molecule fragment illustrated in FIG. 3. In some embodiments, the small molecule fragment is a specific inhibitor or a pan inhibitor. In some embodiments, the cysteine containing protein comprises a biologically active cysteine residue. In some embodiments, the biologically active cysteine site is a cysteine residue that is located about 10 Å or less to an active-site ligand or residue. In some embodiments, the cysteine residue that is located about 10 Å or less to the active-site ligand or residue is an active site cysteine. In some embodiments, the biologically active cysteine site is an active site cysteine. In some embodiments, the biologically active cysteine site is a cysteine residue that is located greater than 10 Å from an active-site ligand or residue. In some embodiments, the cysteine residue that is located greater than 10 Å from the active-site ligand or residue is a non-active site cysteine. In some embodiments, the biologically active cysteine site is a non-active site cysteine. In some embodiments, the small molecule fragment that covalently interacts with the biologically active cysteine impairs and/or inhibits activity of the cysteine containing protein. In some embodiments, the cysteine containing protein exists in an active form. In some embodiments, the small molecule fragment and/or the cysteine-reactive probe interact with the active form of the cysteine containing protein. In some embodiments, the cysteine containing protein exists in a pro-active form. In some embodiments, the small molecule fragment and/or the cysteine-reactive probe interact with the pro-active form of the cysteine containing protein. In some embodiments, the structural environment of the biologically active cysteine residue modulates the reactivity of the cysteine residue. In some embodiments, the structural environment is a hydrophobic environment or a hydrophilic environment. In some embodiments, the structural environment is a charged environment. In some embodiments, the structural environment is a nucleophilic environment. In some embodiments, the cysteine containing protein is an enzyme, a transporter, a receptor, a channel protein, an adaptor protein, a chaperone, a signaling protein, a plasma protein, transcription related protein, translation related protein, mitochondrial protein, or cytoskeleton related protein. In some embodiments, the cysteine containing protein is an enzyme, a transporter, a receptor, a channel protein, an adaptor protein, a chaperone, a signaling protein, transcription related protein, or translation related protein. In some embodiments, the enzyme comprises kinases, proteases, or deubiquitinating enzymes.

In some embodiments, the protease is a cysteine protease. In some embodiments, the cysteine protease comprises caspases. In some embodiments, the signaling protein comprises vascular endothelial growth factor. In some embodiments, the signaling protein comprises a redox signaling protein. In some embodiments, the cysteine containing protein is a protein illustrated in Table 1. In some embodiments, the cysteine containing protein is a protein illustrated in Table 2. In some embodiments, the cysteine containing protein is a protein illustrated in Table 3. In some embodiments, the cysteine containing protein comprises a cysteine residue denoted in Table 3. In some embodiments, the cysteine containing protein is a protein illustrated in Table 8. In some embodiments, the cysteine containing protein is a protein illustrated in Table 9. In some embodiments, the cysteine containing protein is a protein illustrated in Table 10A, Table 10B, Table 10C, Table 10D or Table 10E.

Disclosed herein, in certain embodiments, is a derivative of a cysteine-containing protein having the structure of Formula (I),

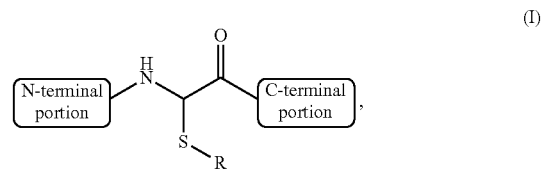

wherein, the derivation occurs at a cysteine residue; R is selected from:

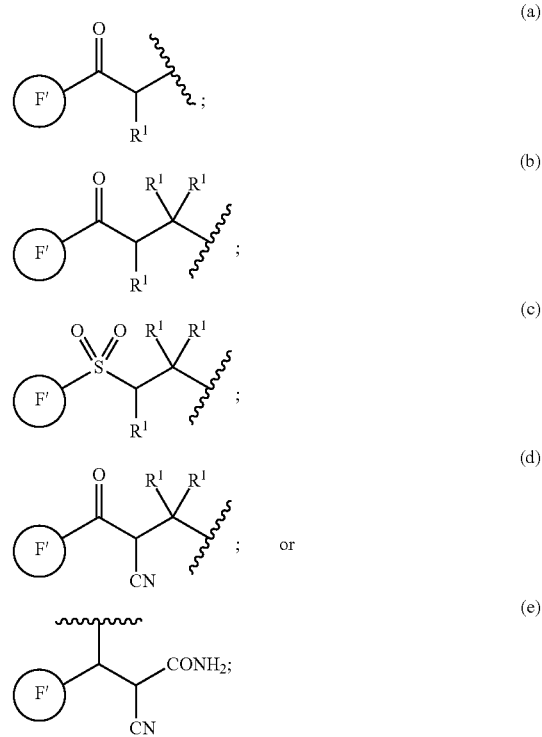

wherein $R^1$ is H, C1-C3 alkyl, or aryl; and F' is a small molecule fragment moiety. In some embodiments, F' has a molecular weight of about 175, 200, 225, 250, 275, 300, 350, 400, 450, 500, 550, 600, 650, 700, 750, 800, 850, 900, 950, 1000 Dalton, or higher. In some embodiments, the molecular weight of F' is prior to enrichment with a halogen, a nonmetal, or a transition metal. In some embodiments, the molecular weight of the small molecule fragment is calculated based on carbon and hydrogen atoms and optionally further based on nitrogen, oxygen and/or sulfur atoms. In some embodiments, the molecular weight of the small molecule fragment does not include the molecular weight of a halogen, a transition metal or a combination thereof. In some embodiments, F' is a small molecule fragment moiety illustrated in FIG. 3. In some embodiments, the cysteine containing protein is a cysteine containing protein described herein. In some embodiments, the cysteine containing protein is a protein illustrated in Tables 1, 2, 3, 8 or 9. In some embodiments, the cysteine containing protein is a protein illustrated in Table 1. In some embodiments, the cysteine containing protein is a protein illustrated in Table 2. In some embodiments, the cysteine containing protein is a protein illustrated in Table 3. In some embodiments, the cysteine containing protein is a protein illustrated in Table 8. In some embodiments, the cysteine containing protein is a protein illustrated in Table 9.

Disclosed herein, in certain embodiments, is a derivative of IDH1 protein having the structure of Formula (I),

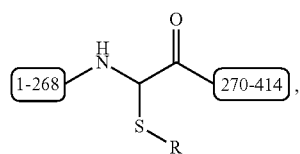
(I)

wherein, the derivation occurs at IDH1 cysteine residue position 269 based on SEQ ID NO: 1; R is selected from:

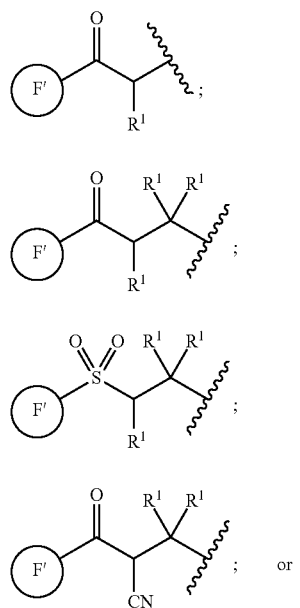

-continued

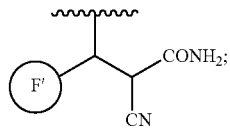
(e)

wherein $R^1$ is H, C1-C3 alkyl, or aryl; and F' is a small molecule fragment moiety. In some embodiments, F' has a molecular weight of about 175, 200, 225, 250, 275, 300, 350, 400, 450, 500, 550, 600, 650, 700, 750, 800, 850, 900, 950, 1000 Dalton, or higher. In some embodiments, the molecular weight of F' is prior to enrichment with a halogen, a nonmetal, or a transition metal. In some embodiments, the molecular weight of the small molecule fragment is calculated based on carbon and hydrogen atoms and optionally further based on nitrogen, oxygen and/or sulfur atoms. In some embodiments, the molecular weight of the small molecule fragment does not include the molecular weight of a halogen, a transition metal or a combination thereof. In some embodiments, F' is a small molecule fragment moiety illustrated in FIG. 3.

Disclosed herein, in certain embodiments, is a derivative of IDH2 protein having the structure of Formula (I),

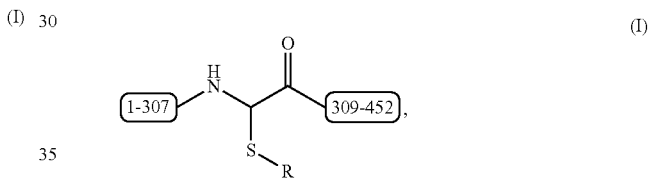
(I)

wherein the derivation occurs at IDH2 cysteine residue position 308 based on SEQ ID NO: 2; R is selected from:

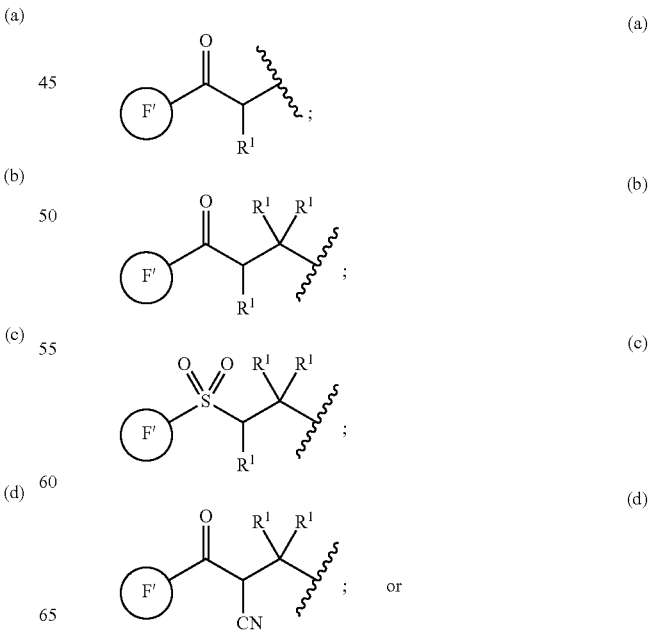

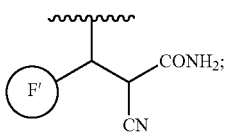

(e)

wherein R¹ is H, C1-C3 alkyl, or aryl; and F' is a small molecule fragment moiety. In some embodiments, F' has a molecular weight of about 175, 200, 225, 250, 275, 300, 350, 400, 450, 500, 550, 600, 650, 700, 750, 800, 850, 900, 950, 1000 Dalton, or higher. In some embodiments, the molecular weight of F' is prior to enrichment with a halogen, a nonmetal, or a transition metal. In some embodiments, the molecular weight of the small molecule fragment is calculated based on carbon and hydrogen atoms and optionally further based on nitrogen, oxygen and/or sulfur atoms. In some embodiments, the molecular weight of the small molecule fragment does not include the molecular weight of a halogen, a transition metal or a combination thereof. In some embodiments, F' is a small molecule fragment moiety illustrated in FIG. 3.

Disclosed herein, in certain embodiments, is a derivative of caspase-8 protein having the structure of Formula (I),

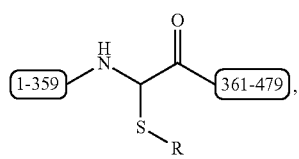

(I)

wherein the derivation occurs at caspase-8 cysteine residue position 360 based on SEQ ID NO: 3; R is selected from:

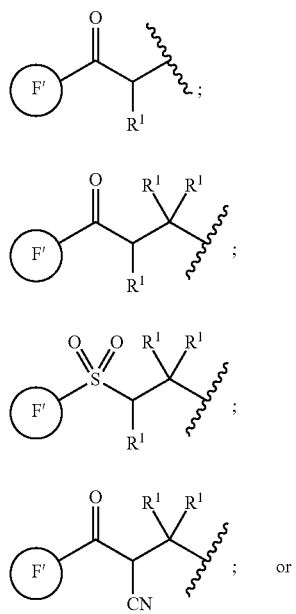

(a)

(b)

(c)

(d)

or

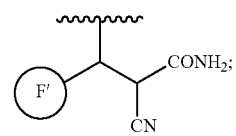

(e)

wherein R¹ is H, C1-C3 alkyl, or aryl; and F' is a small molecule fragment moiety. In some embodiments, F' has a molecular weight of about 175, 200, 225, 250, 275, 300, 350, 400, 450, 500, 550, 600, 650, 700, 750, 800, 850, 900, 950, 1000 Dalton, or higher. In some embodiments, the molecular weight of F' is prior to enrichment with a halogen, a nonmetal, or a transition metal. In some embodiments, the molecular weight of the small molecule fragment is calculated based on carbon and hydrogen atoms and optionally further based on nitrogen, oxygen and/or sulfur atoms. In some embodiments, the molecular weight of the small molecule fragment does not include the molecular weight of a halogen, a transition metal or a combination thereof. In some embodiments, F' is a small molecule fragment moiety illustrated in FIG. 3.

Disclosed herein, in certain embodiments, is a derivative of caspase-10 protein having the structure of Formula (I),

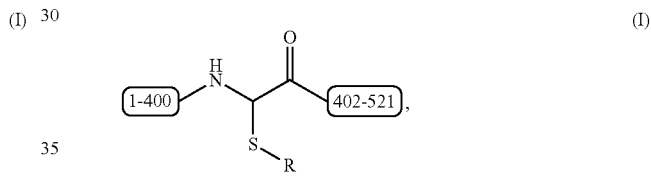

(I)

wherein the derivation occurs at caspase-10 cysteine residue position 401 based on SEQ ID NO: 4; R is selected from:

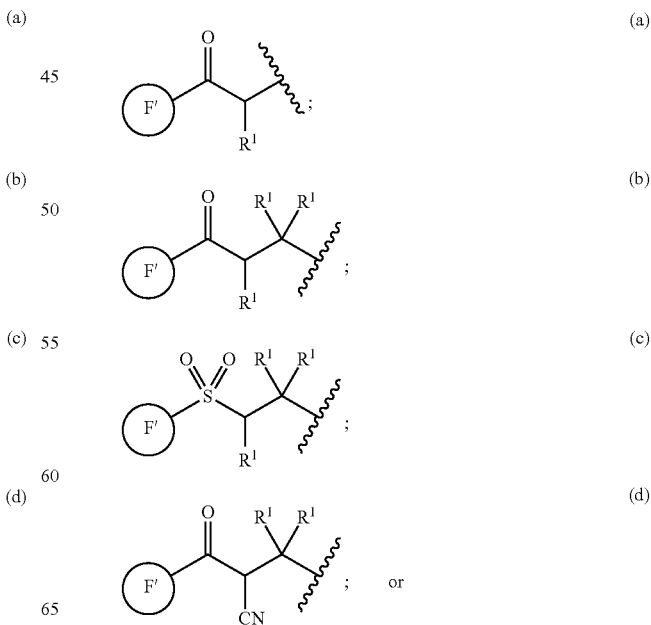

(a)

(b)

(c)

(d)

or (e)

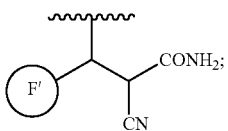

(e)

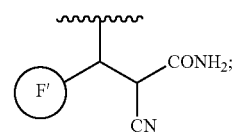

wherein R¹ is H, C1-C3 alkyl, or aryl; and F' is a small molecule fragment moiety. In some embodiments, F' has a molecular weight of about 175, 200, 225, 250, 275, 300, 350, 400, 450, 500, 550, 600, 650, 700, 750, 800, 850, 900, 950, 1000 Dalton, or higher. In some embodiments, the molecular weight of F' is prior to enrichment with a halogen, a nonmetal, or a transition metal. In some embodiments, the molecular weight of the small molecule fragment is calculated based on carbon and hydrogen atoms and optionally further based on nitrogen, oxygen and/or sulfur atoms. In some embodiments, the molecular weight of the small molecule fragment does not include the molecular weight of a halogen, a transition metal or a combination thereof. In some embodiments, F' is a small molecule fragment moiety illustrated in FIG. 3.

Disclosed herein, in certain embodiments, is a derivative of PRMT-1 protein having the structure of Formula (I),

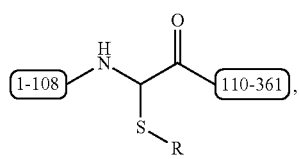

(I)

wherein the derivation occurs at PRMT-1 cysteine residue position 109 based on SEQ ID NO: 5; R is selected from:

wherein R¹ is H, C1-C3 alkyl, or aryl; and F' is a small molecule fragment moiety. In some embodiments, F' has a molecular weight of about 175, 200, 225, 250, 275, 300, 350, 400, 450, 500, 550, 600, 650, 700, 750, 800, 850, 900, 950, 1000 Dalton, or higher. In some embodiments, the molecular weight of F' is prior to enrichment with a halogen, a nonmetal, or a transition metal. In some embodiments, the molecular weight of the small molecule fragment is calculated based on carbon and hydrogen atoms and optionally further based on nitrogen, oxygen and/or sulfur atoms. In some embodiments, the molecular weight of the small molecule fragment does not include the molecular weight of a halogen, a transition metal or a combination thereof. In some embodiments, F' is a small molecule fragment moiety illustrated in FIG. 3.

Disclosed herein, in certain embodiments, is a derivative of ZAK protein having the structure of Formula (I),

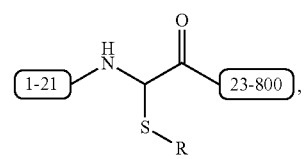

(I)

wherein the derivation occurs at ZAK cysteine residue position 22 based on SEQ ID NO: 6; R is selected from:

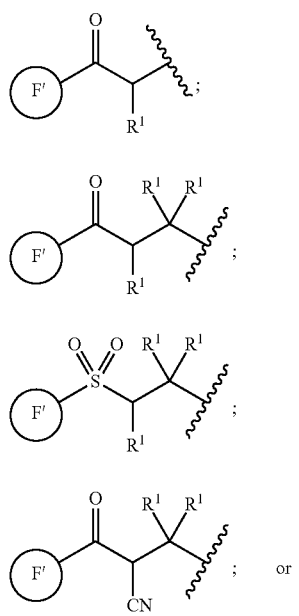

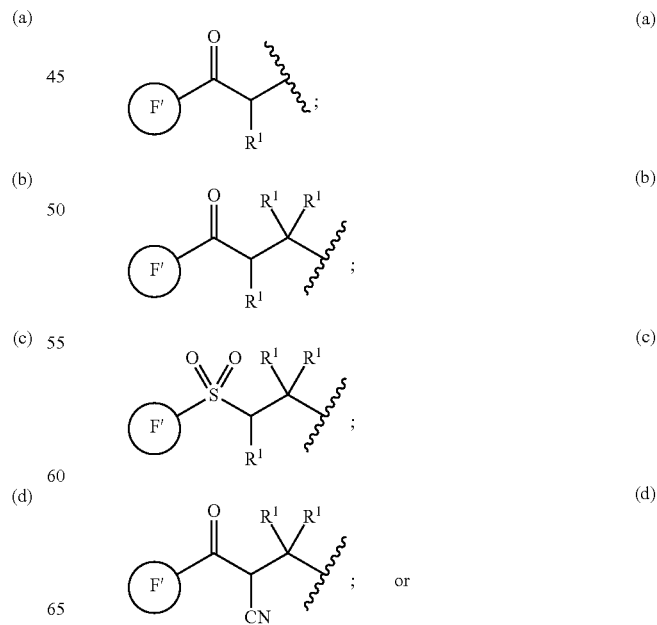

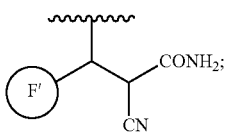
(e)

wherein $R^1$ is H, C1-C3 alkyl, or aryl; and F' is a small molecule fragment moiety. In some embodiments, F' has a molecular weight of about 175, 200, 225, 250, 275, 300, 350, 400, 450, 500, 550, 600, 650, 700, 750, 800, 850, 900, 950, 1000 Dalton, or higher. In some embodiments, the molecular weight of F' is prior to enrichment with a halogen, a nonmetal, or a transition metal. In some embodiments, the molecular weight of the small molecule fragment is calculated based on carbon and hydrogen atoms and optionally further based on nitrogen, oxygen and/or sulfur atoms. In some embodiments, the molecular weight of the small molecule fragment does not include the molecular weight of a halogen, a transition metal or a combination thereof. In some embodiments, F' is a small molecule fragment moiety illustrated in FIG. 3.

Disclosed herein, in certain embodiments, is a derivative of IMPDH2 protein having the structure of Formula (I),

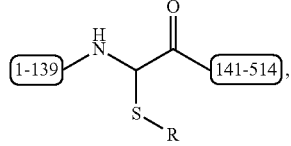
(I)

wherein the derivation occurs at IMPDH2 cysteine residue position 140 based on SEQ ID NO: 7; R is selected from:

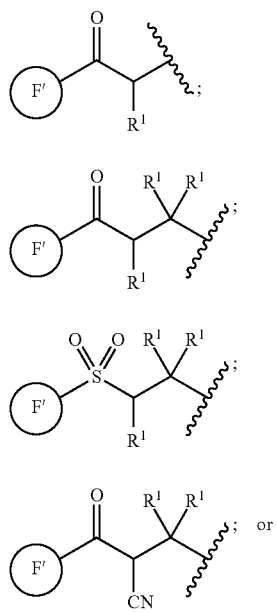

(a)

(b)

(c)

(d)

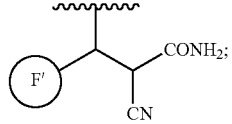
(e)

wherein $R^1$ is H, C1-C3 alkyl, or aryl; and F' is a small molecule fragment moiety. In some embodiments, F' has a molecular weight of about 175, 200, 225, 250, 275, 300, 350, 400, 450, 500, 550, 600, 650, 700, 750, 800, 850, 900, 950, 1000 Dalton, or higher. In some embodiments, the molecular weight of F' is prior to enrichment with a halogen, a nonmetal, or a transition metal. In some embodiments, the molecular weight of the small molecule fragment is calculated based on carbon and hydrogen atoms and optionally further based on nitrogen, oxygen and/or sulfur atoms. In some embodiments, the molecular weight of the small molecule fragment does not include the molecular weight of a halogen, a transition metal or a combination thereof. In some embodiments, F' is a small molecule fragment moiety illustrated in FIG. 3.

Disclosed herein, in certain embodiments, is a derivative of IMPDH2 protein having the structure of Formula (I),

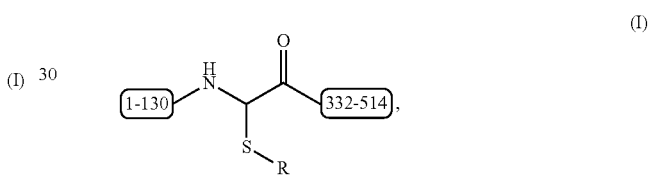
(I)

wherein the derivation occurs at IMPDH2 cysteine residue position 331 based on SEQ ID NO: 7; R is selected from:

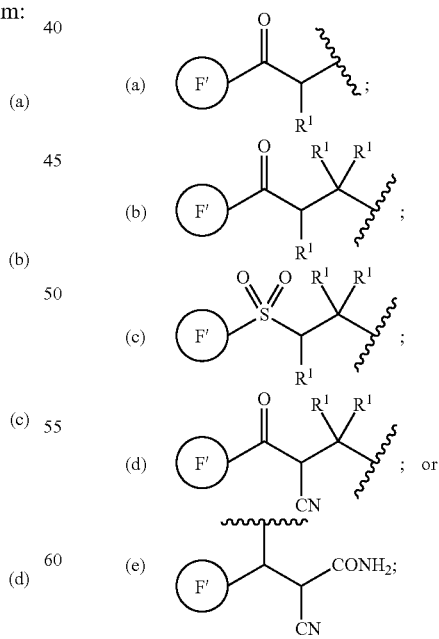

(a)

(b)

(c)

(d)

; or (e)

wherein $R^1$ is H, C1-C3 alkyl, or aryl; and F' is a small molecule fragment moiety. In some embodiments, F' has a molecular weight of about 175, 200, 225, 250, 275, 300, 350, 400, 450, 500, 550, 600, 650, 700, 750, 800, 850, 900, 950, 1000 Dalton, or higher. In some embodiments, the molecular weight of F' is prior to enrichment with a halogen, a nonmetal, or a transition metal. In some embodiments, the molecular weight of the small molecule fragment is calculated based on carbon and hydrogen atoms and optionally further based on nitrogen, oxygen and/or sulfur atoms. In some embodiments, the molecular weight of the small molecule fragment does not include the molecular weight of a halogen, a transition metal or a combination thereof. In some embodiments, F' is a small molecule fragment moiety illustrated in FIG. 3.

Disclosed herein, in certain embodiments, is a derivative of TIGAR protein having the structure of Formula (I),

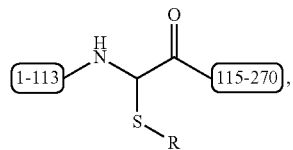

(I)

wherein the derivation occurs at TIGAR cysteine residue position 114 based on SEQ ID NO: 8; R is selected from:

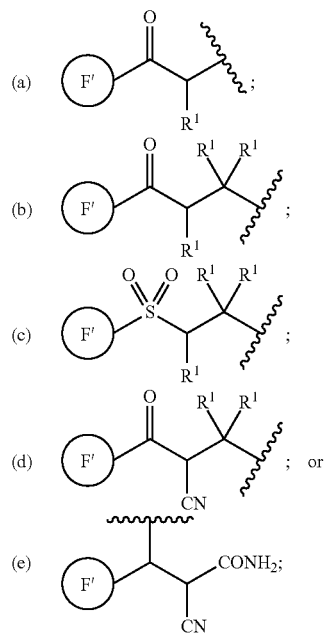

wherein $R^1$ is H, C1-C3 alkyl, or aryl; and F' is a small molecule fragment moiety. In some embodiments, F' has a molecular weight of about 175, 200, 225, 250, 275, 300, 350, 400, 450, 500, 550, 600, 650, 700, 750, 800, 850, 900, 950, 1000 Dalton, or higher. In some embodiments, the molecular weight of F' is prior to enrichment with a halogen, a nonmetal, or a transition metal. In some embodiments, the molecular weight of the small molecule fragment is calculated based on carbon and hydrogen atoms and optionally further based on nitrogen, oxygen and/or sulfur atoms. In some embodiments, the molecular weight of the small molecule fragment does not include the molecular weight of a halogen, a transition metal or a combination thereof. In some embodiments, F' is a small molecule fragment moiety illustrated in FIG. 3.

Disclosed herein, in certain embodiments, is a derivative of TIGAR protein having the structure of Formula (I),

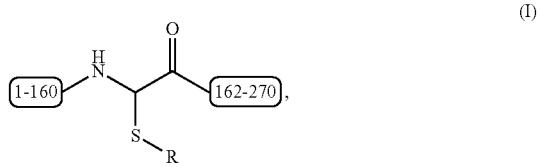

(I)

wherein the derivation occurs at TIGAR cysteine residue position 161 based on SEQ ID NO: 8; R is selected from:

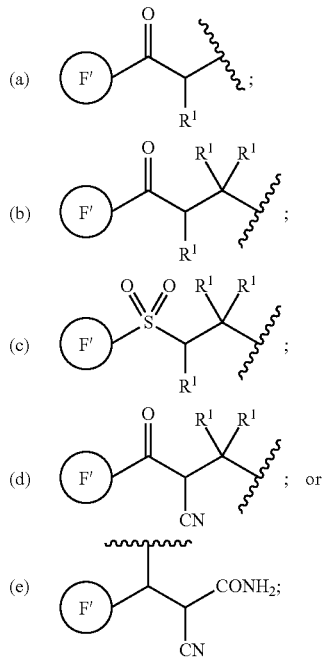

wherein $R^1$ is H, C1-C3 alkyl, or aryl; and F' is a small molecule fragment moiety. In some embodiments, F' has a molecular weight of about 175, 200, 225, 250, 275, 300, 350, 400, 450, 500, 550, 600, 650, 700, 750, 800, 850, 900, 950, 1000 Dalton, or higher. In some embodiments, the molecular weight of F' is prior to enrichment with a halogen, a nonmetal, or a transition metal. In some embodiments, the molecular weight of the small molecule fragment is calculated based on carbon and hydrogen atoms and optionally further based on nitrogen, oxygen and/or sulfur atoms. In some embodiments, the molecular weight of the small molecule fragment does not include the molecular weight of a halogen, a transition metal or a combination thereof. In some embodiments, F' is a small molecule fragment moiety illustrated in FIG. 3.

Disclosed herein, in certain embodiments, is a derivative of PKCθ protein having the structure of Formula (I),

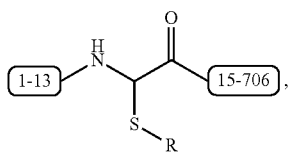

wherein the derivation occurs at PKCθ cysteine residue position 14 based on SEQ ID NO: 9; R is selected from:

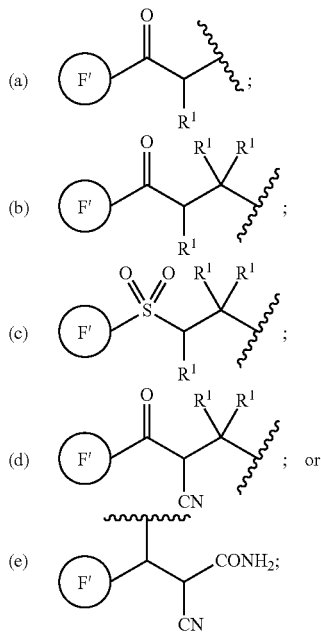

wherein $R^1$ is H, C1-C3 alkyl, or aryl; and F' is a small molecule fragment moiety. In some embodiments, F' has a molecular weight of about 175, 200, 225, 250, 275, 300, 350, 400, 450, 500, 550, 600, 650, 700, 750, 800, 850, 900, 950, 1000 Dalton, or higher. In some embodiments, the molecular weight of F' is prior to enrichment with a halogen, a nonmetal, or a transition metal. In some embodiments, the molecular weight of the small molecule fragment is calculated based on carbon and hydrogen atoms and optionally further based on nitrogen, oxygen and/or sulfur atoms. In some embodiments, the molecular weight of the small molecule fragment does not include the molecular weight of a halogen, a transition metal or a combination thereof. In some embodiments, F' is a small molecule fragment moiety illustrated in FIG. 3.

Disclosed herein, in certain embodiments, is a derivative of PKCθ protein having the structure of Formula (I),

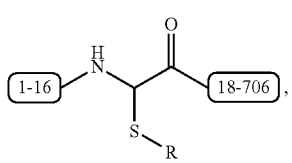

wherein the derivation occurs at PKCθ cysteine residue position 17 based on SEQ ID NO: 9; R is selected from:

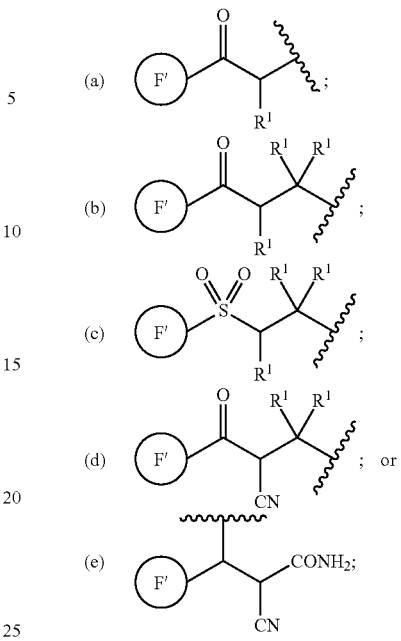

wherein $R^1$ is H, C1-C3 alkyl, or aryl; and F' is a small molecule fragment moiety. In some embodiments, F' has a molecular weight of about 175, 200, 225, 250, 275, 300, 350, 400, 450, 500, 550, 600, 650, 700, 750, 800, 850, 900, 950, 1000 Dalton, or higher. In some embodiments, the molecular weight of F' is prior to enrichment with a halogen, a nonmetal, or a transition metal. In some embodiments, the molecular weight of the small molecule fragment is calculated based on carbon and hydrogen atoms and optionally further based on nitrogen, oxygen and/or sulfur atoms. In some embodiments, the molecular weight of the small molecule fragment does not include the molecular weight of a halogen, a transition metal or a combination thereof. In some embodiments, F' is a small molecule fragment moiety illustrated in FIG. 3.

Disclosed herein, in certain embodiments, is a method of identifying a cysteine containing protein as a binding target for a small molecule fragment, comprising: (a) obtaining a set of cysteine-reactive probe-protein complexes from a sample comprising a first cell solution treated with a small molecule fragment and a cysteine reactive probe wherein the cysteine-reactive probe comprises a reactive moiety capable of forming a covalent bond with a cysteine residue located on the cysteine containing protein; (b) analyzing the set of cysteine-reactive probe-protein complexes by a proteomic analysis means; and (c) based on step b), identifying a cysteine containing protein as the binding target for the small molecule fragment. In some embodiments, the method further comprises determining a value of each of the cysteine containing protein from the set of cysteine-reactive probe-protein complexes for identifying a cysteine containing protein as the binding target for the small molecule fragment, wherein the value is determined based on the proteomic analysis means of step b). In some embodiments, the sample further comprises a second cell solution. In some embodiments, the method further comprises contacting the first cell solution with a small molecule fragment for an extended period of time prior to incubating the first cell solution with a first cysteine-reactive probe to generate a first group of cysteine-reactive probe-protein complexes. In some embodiments, the extended period of time is about 5, 10, 15, 20, 30, 60, 90, 120 minutes or longer. In some embodiments, the method further comprises contacting the second cell solution with a second cysteine-reactive probe to generate a second group of cysteine-reactive probe-protein complexes. In some embodiments, the first cysteine-reactive probe and the second cysteine-reactive probe are the same. In some embodiments, the first group and the second group of cysteine-reactive probe-protein complexes comprise the set of cysteine-reactive probe-protein complexes. In some embodiments, the cysteine containing protein is an enzyme, a transporter, a receptor, a channel protein, an adaptor protein, a chaperone, a signaling protein, a plasma protein, transcription related protein, translation related protein, mitochondrial protein, or cytoskeleton related protein. In some embodiments, the cysteine containing protein is a protein illustrated in Table 3. In some embodiments, the cysteine containing protein is a protein illustrated in Table 1, Table 2, Table 8, Table 9, Table 10A, Table 10B, Table 10C, Table 10D or Table 10E. In some embodiments, the small molecule fragment is a small molecule fragment of Formula (I):

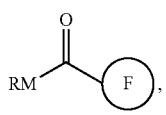

Formula (I)

wherein: RM is a reactive moiety selected from a Michael acceptor moiety, a leaving group moiety, or a moiety capable of forming a covalent bond with the thiol group of a cysteine residue; and F is a small molecule fragment moiety. In some embodiments, the Michael acceptor moiety comprises an alkene or an alkyne moiety. In some embodiments, F is obtained from a compound library. In some embodiments, the compound library comprises ChemBridge fragment library, Pyramid Platform Fragment-Based Drug Discovery, Maybridge fragment library, FRGx from AnalytiCon, TCI-Frag from AnCoreX, Bio Building Blocks from ASINEX, BioFocus 3D from Charles River, Fragments of Life (FOL) from Emerald Bio, Enamine Fragment Library, IOTA Diverse 1500, BIONET fragments library, Life Chemicals Fragments Collection, OTAVA fragment library, Prestwick fragment library, Selcia fragment library, TimTec fragment-based library, Allium from Vitas-M Laboratory, or Zenobia fragment library. In some embodiments, F is a small molecule fragment moiety illustrated in FIG. 3. In some embodiments, the cysteine-reactive probe is a cysteine-reactive probe of Formula (II):

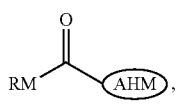

Formula (II)

wherein: RM is a reactive moiety selected from a Michael acceptor moiety, a leaving group moiety, or a moiety capable of forming a covalent bond to the thiol group of a cysteine residue; and AHM is an affinity handle moiety. In some embodiments, the Michael acceptor moiety comprises an alkene or an alkyne moiety. In some embodiments, the affinity handle moiety comprises an affinity handle and a binding moiety that facilitates covalent interaction of the cysteine-reactive probe to a cysteine residue of a cysteine-containing protein. In some embodiments, the binding moiety is a small molecule fragment obtained from a compound library. In some embodiments, the affinity handle comprises a carbodiimide, N-hydroxysuccinimide (NHS) ester, imidoester, pentafluorophenyl ester, hydroxymethyl phosphine, maleimide, haloacetyl, pyridyl disulfide, thiosulfonate, vinylsulfone, hydrazide, alkoxyamine, alkyne, azide, or isocyanate group. In some embodiments, the affinity handle is further conjugated to an affinity ligand. In some embodiments, the affinity ligand comprises a chromophore, a labeling group, or a combination thereof. In some embodiments, the chromophore comprises non-fluorochrome chromophore, quencher, an absorption chromophore, fluorophore, organic dye, inorganic dye, metal chelate, or a fluorescent enzyme substrate. In some embodiments, the labeling group is a biotin moiety, a streptavidin moiety, bead, resin, a solid support, or a combination thereof. In some embodiments, the cysteine-reactive probe is a cysteine-reactive probe illustrated in FIG. 3. In some embodiments, the proteomic analysis means comprises a mass spectroscopy method. In some embodiments, the identifying in step c) further comprises (i) locating a first value assigned to a cysteine containing protein from the first group of cysteine-reactive probe-protein complex and a second value of the same cysteine containing protein from the second group of cysteine-reactive probe-protein complex; and (ii) calculating a ratio between the two values assigned to the same cysteine containing protein. In some embodiments, the ratio of greater than 2 indicates that the cysteine containing protein is a candidate for interacting with the small molecule fragment. In some embodiments, the identifying in step c) further comprises calculating a percentage of inhibition of the cysteine-reactive probe to the cysteine containing protein. In some embodiments, the percentage of inhibition of greater than 50%, 60%, 70%, 80%, 90%, or at 100% indicates that the cysteine containing protein is a candidate for interacting with the small molecule fragment. In some embodiments, the method is an in situ method. In some embodiments, the cysteine-reactive probe is not 4-hydroxynonenal or 15-deoxy-Δ12,14-prostaglandin J2.

Disclosed herein, modified cysteine containing protein comprising a small molecule fragment having a covalent bond to a cysteine residue of a cysteine containing protein, wherein the small molecule fragment has a molecular weight of about 150 Dalton or higher. In some embodiments, the cysteine containing protein comprises a cysteine residue site denoted in Table 3. In some embodiments, the cysteine containing protein comprises a protein sequence illustrated in Table 1, Table 2, Table 8, Table 9, Table 10A, Table 10B, Table 10C, Table 10D or Table 10E. In some embodiments, the cysteine containing protein is about 20, 30, 35, 40, 45, 50, 55, 60, 65, 70, 75, 80, 85, 90, 95, 100, 150, 200, 250, 300, 350, 400, 450, 500, 600, 700, 800, 900, 1000 amino acid residues in length or more. In some embodiments, the cysteine residue of the modified cysteine containing protein has the structure SR, wherein R is selected from:

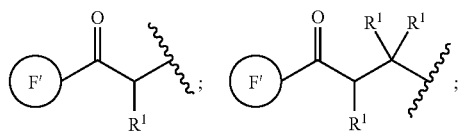

-continued

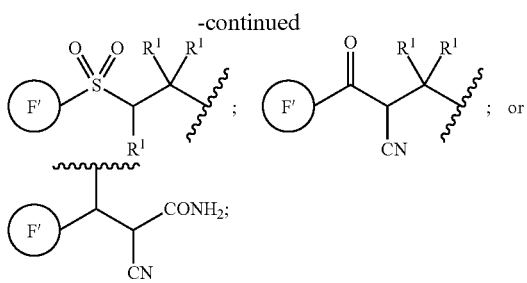

wherein $R^1$ is H, C1-C3 alkyl, or aryl; and F' is the small molecule fragment moiety. In some embodiments, the small molecule fragment has a molecular weight of about 175, 200, 225, 250, 275, 300, 350, 400, 450, 500, 550, 600, 650, 700, 750, 800, 850, 900, 950, 1000 Dalton, or higher. In some embodiments, the molecular weight of the small molecule fragment is calculated based on carbon and hydrogen atoms and optionally further based on nitrogen, oxygen and/or sulfur atoms. In some embodiments, the modified cysteine containing protein is selected from IDH2, caspase-8, caspase-10 or PRMT1. In some embodiments, IDH2 is modified at cysteine position 308. In some embodiments, caspase-8 is modified at cysteine position 360. In some embodiments, caspase-10 exist in the proform and is modified at cysteine position 401. In some embodiments, PRMT1 is modified at cysteine position 109. In some embodiments, the small molecule fragment is a small molecule fragment of Formula (I):

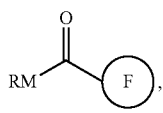

Formula (I)

wherein: RM is a reactive moiety selected from a Michael acceptor moiety, a leaving group moiety, or a moiety capable of forming a covalent bond with the thiol group of a cysteine residue; and F is a small molecule fragment moiety. In some embodiments, the Michael acceptor moiety comprises an alkene or an alkyne moiety. In some embodiments, F is obtained from a compound library. In some embodiments, F is a small molecule fragment moiety illustrated in FIG. 3. In some embodiments, F further comprises a linker moiety that connects F to the carbonyl moiety. In some embodiments, the small molecule fragment binds irreversibly to the cysteine containing protein. In some embodiments, the small molecule fragment binds reversibly to the cysteine containing protein.

Disclosed herein, in certain embodiments, is a method of screening a small molecule fragment for interaction with a cysteine containing protein, comprising: (a) harvesting a set of cysteine-reactive probe-protein complexes from a sample comprising a first cell solution treated with a small molecule fragment and a cysteine reactive probe wherein the cysteine-reactive probe comprises a reactive moiety capable of forming a covalent bond with a cysteine residue located on the cysteine containing protein; (b) analyzing the set of cysteine-reactive probe-protein complexes by a proteomic analysis means; and (c) based on step b), identifying the small molecule fragment as interacting with the cysteine containing protein. In some embodiments, the method further comprises determining a value of each of the cysteine containing protein from the set of cysteine-reactive probe-protein complexes prior to identifying the small molecule fragment as interacting with the cysteine containing protein, wherein the value is determined based on the proteomic analysis means of step b). In some embodiments, the cysteine containing protein is a protein illustrated in Table 3. In some embodiments, the cysteine containing protein is a protein illustrated in Table 1, Table 2, Table 8, Table 9, Table 10A, Table 10B, Table 10C, Table 10D or Table 10E.

BRIEF DESCRIPTION OF THE DRAWINGS

Various aspects of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 17A shows the fraction of cysteines predicted to be ligandable or unligandable by reactive docking that were quantified in isoTOP-ABPP experiments. FIG. 17B shows the fraction of cysteines predicted to be ligandable or unligandable by reactive docking that show heat-sensitive labeling by the IA-alkyne probe (R>3 native/heat denatured).

MLTK labeling by 59 was detected by CuAAC conjugation to a rhodamine-azide tag and analysis by SDS-PAGE and in-gel fluorescence scanning.

Figure 19:
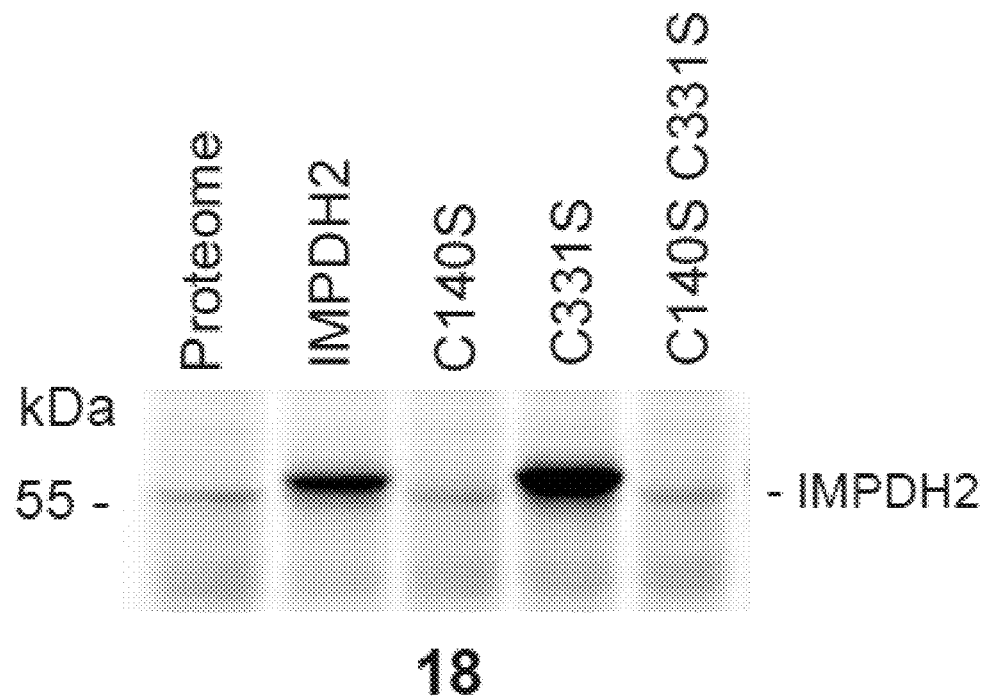

FIG. 19 shows click probe 18 (25 µM) labeled WT-IMPDH2 and C331S-IMPDH2, but not C140S-IMPDH2 (or C140S/C331S-IMPDH2). Labeling was detected by CuAAC conjugation to a rhodamine-azide reporter tag and analysis by SDS-PAGE and in-gel fluorescence scanning. Recombinant IMPDH2 WT and mutants were expressed and purified from E. coli and added to Jurkat lysates to a final concentration of 1 µM protein.

Figure 20:
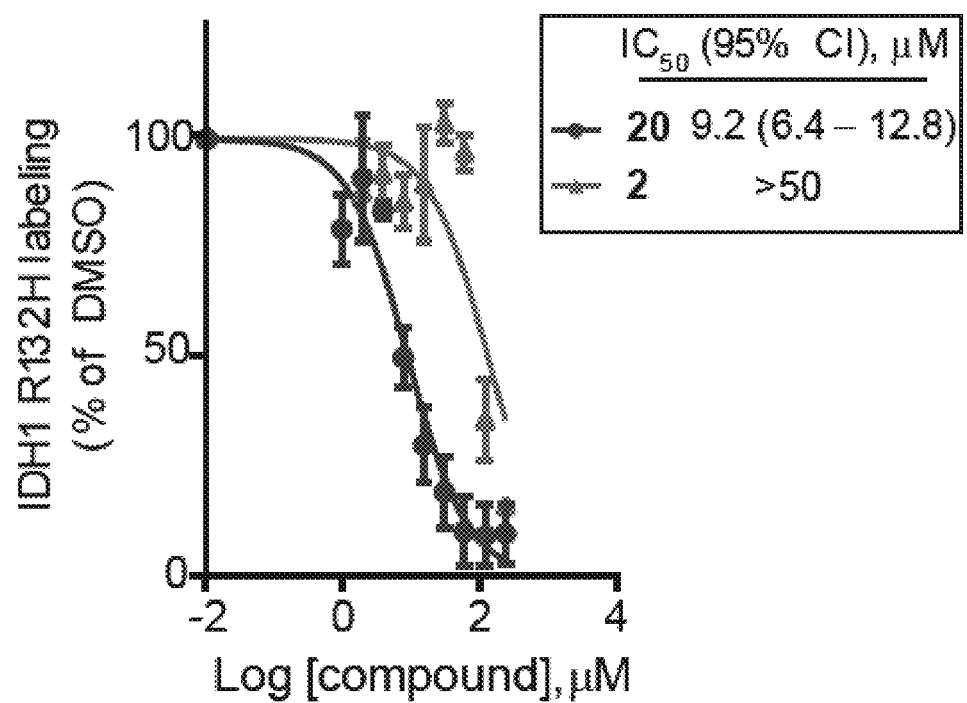

FIG. 20 shows the apparent $IC_{50}$ curve for blockade of IA rhodamine-labeling of R132H-IDH1 by 20.

Figure 21A:
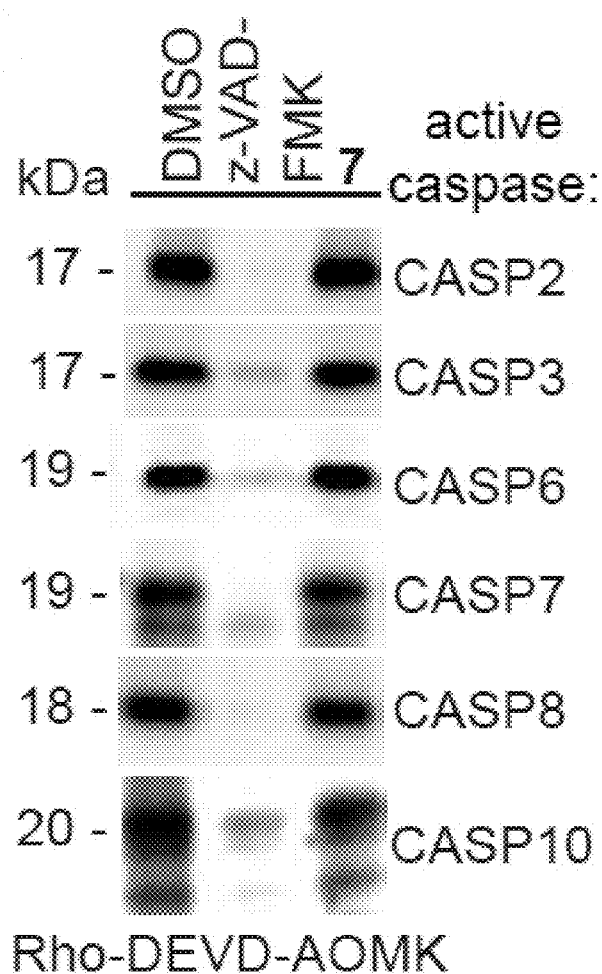
Figure 21B:
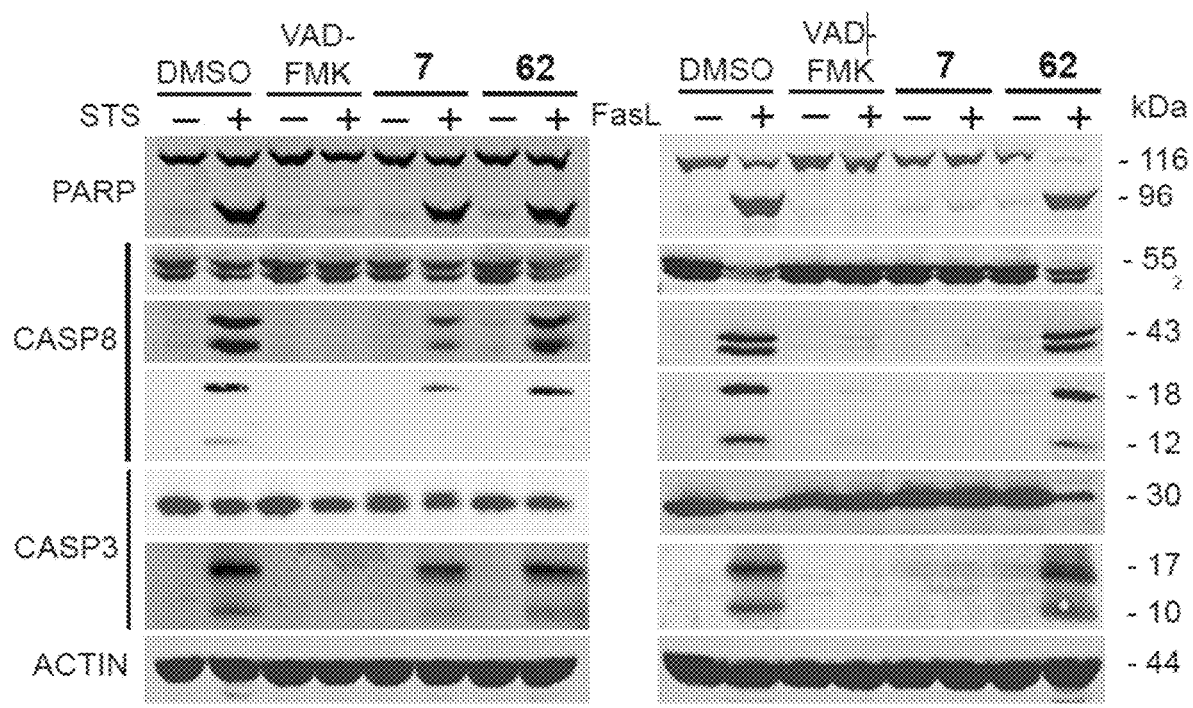
Figure 21C:
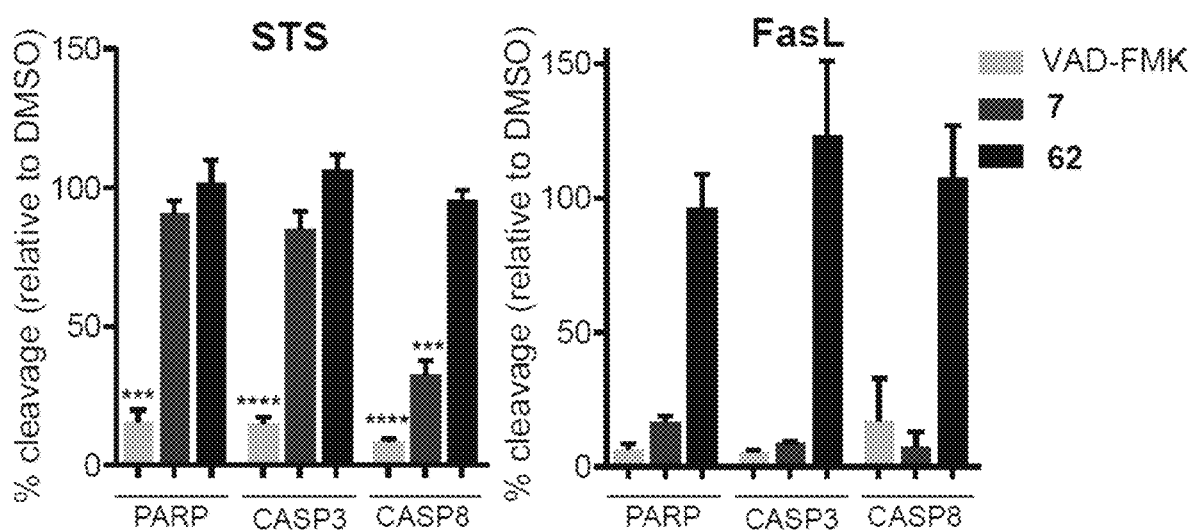

FIG. 21A-FIG. 21C show the activity of compounds 7 and 62 with respect to different recombinant caspases. FIG. 21A shows that 7 does not inhibit active caspases. Recombinant, active caspases were added to MDA-MD-231 lysate to a final concentration of 200 nM (CASP2, 3, 6, 7) or 1 µM (CASP8, 10), treated with z-VAD-FMK (25 µM) or 7 (50 µM), followed by labeling with the Rho-DEVD-AOMK probe ("DEVD" disclosed as SEQ ID NO: 857) (2 µM). FIG. 21B shows a western blot of the cleavage of PARP (96 kDa), CASP8 (p43/p41, p18), and CASP3 (p17). FIG. 21C shows that 7 protects Jurkat cells from extrinsic, but not intrinsic apoptosis. Cleavage of PARP, CASP8, and CASP3 detected by western blotting as shown in FIG. 21B was quantified for three (STS) or two (FasL) independent experiments. Cleavage products (PARP (96 kDa), CASP8 (p43/p41), CASP3 (p17)) were quantified for compound treatment and the % cleavage relative to DMSO treated samples was calculated. For FIG. 21C, STS data represent mean values±SEM for three independent experiments, and FasL data represent mean values±SD for two independent experiments. Statistical significance was calculated with unpaired students t-tests comparing active compounds (VAD-FMK and 7) to control compound 62; , $p<0.01$, *, $p<0.001$, ****, $p<0.0001$.

Figure 22:
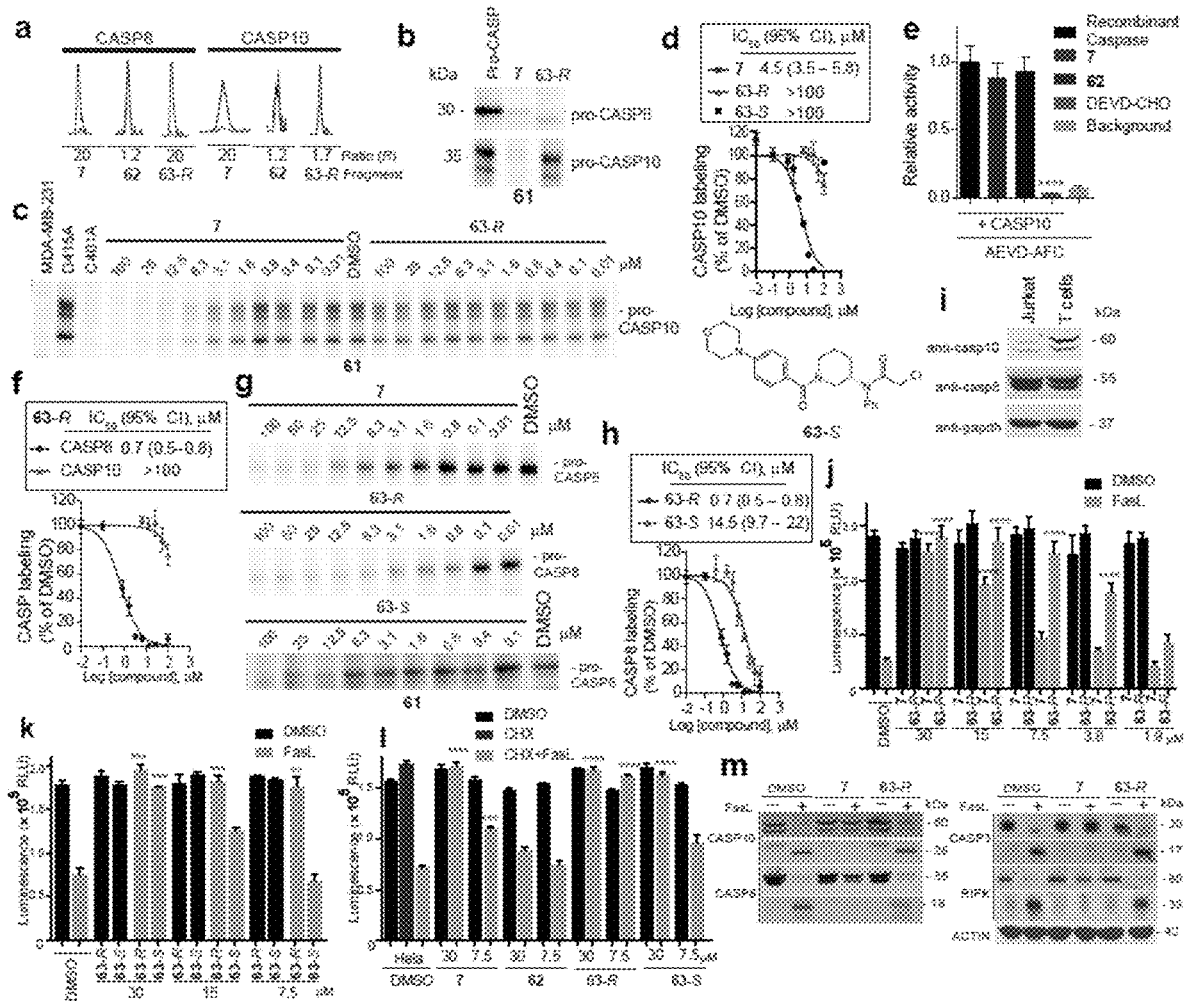

FIG. 22 shows that CASP10 is involved in intrinsic apoptosis in primary human T cells. A, Representative MS1 peptide signals showing R values for caspases detected by quantitative proteomics using probe 61. ABPP-SILAC experiments. Jurkat cells (10 million cells) were treated with either DMSO (heavy cells) or the indicated compounds (light cells) for 2 h followed by probe 61 (10 µM, 1 h). B, 7 competed 61-labeling of pro-CASP8 and CASP10, whereas 63-R selectively blocked probe labeling of pro-CASP8. C, 7, but not 63-R block probe labeling of pro-CASP10. Recombinant pro-CASP10 was added to MDA-MB-231 lysates to a final concentration of 300 nM, treated with the indicated compounds, and labeled with probe 61. Mutation of the catalytic cysteine C401A fully prevented labeling by 61. D, Apparent IC50 curve for blockade of 61-labeling of pro-CASP10 by 7, 63-R or 63-S. E, Neither 7 nor 63 (25 µM each) inhibited the activity of recombinant, purified active CASP10 (500 nM), which was assayed following addition of the protein to MDA-MB-231 lysate using fluorometric AEVD-AMC substrate ("AEVD" disclosed as SEQ ID NO: 859). DEVD-CHO ("DEVD" disclosed as SEQ ID NO: 857) (20 µM) inhibited the activity of CASP10. F, Apparent $IC_{50}$ curve for blockade of 61 labeling of pro-CASP8 and pro-CASP10 by 63-R. G, 63-R shows increased potency against pro-CASP8. Recombinant pro-CASP8 was added to MDA-MB-231 lysates to a final concentration of 300 nM, treated with the indicated compounds and labeled with probe 61. H, Apparent IC50 curve for blockade of 61 labeling of pro-CASP8 by 63-R compared with 63-S. The structure of 63-S is shown. I, CASP10 is more highly expressed in primary human T cells compared to Jurkat cells. Western blot analysis of full-length CASP10, CASP8 and GAPDH expression levels in Jurkat and T-cell lysates (2 mg/mL). J, Jurkat cells (150,000 cells/well) were incubated with 7 or 63-R at the indicated concentrations for 30 min prior to addition of staurosporine (2 µM) or SuperFasLigand™ (100 ng/mL). Cells were incubated for 4 h and viability was quantified with CellTiter-Glo®. K, Jurkat cells treated as in J, but with 63-R or 63-S. L, HeLa cells (20,000 cells/well) were seeded and 24 h later treated with the indicated compounds for 30 minutes prior to addition of SuperFasLigand™ (100 ng/mL) and cycloheximide (CHX, 2.5 ng/mL). Cells were incubated for 6 h and viability quantified with CTG. M, For T cells treated as in FIG. 14B cleavage of CASP10 (p22), CASP8 (p18), CASP3 (p17) and RIPK (33 kDa) was visualized by western blotting. For panels D-F, H, and J-K, data represent mean values±SEM for at least three independent experiments. Statistical significance was calculated with unpaired students t-tests comparing DMSO- to fragment-treated samples; , $p<0.01$, **, $p<0.0001$.

Figure 23A:
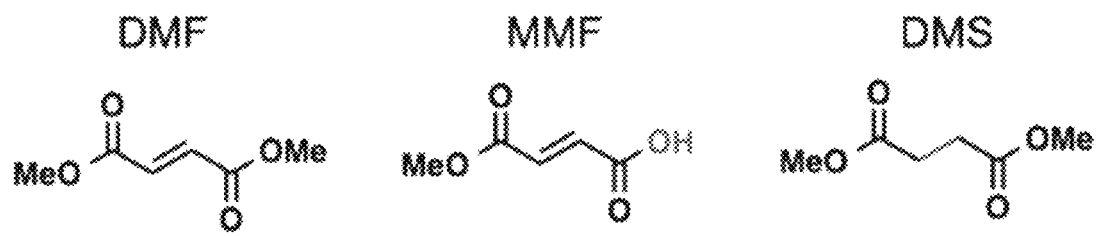
Figure 23B:
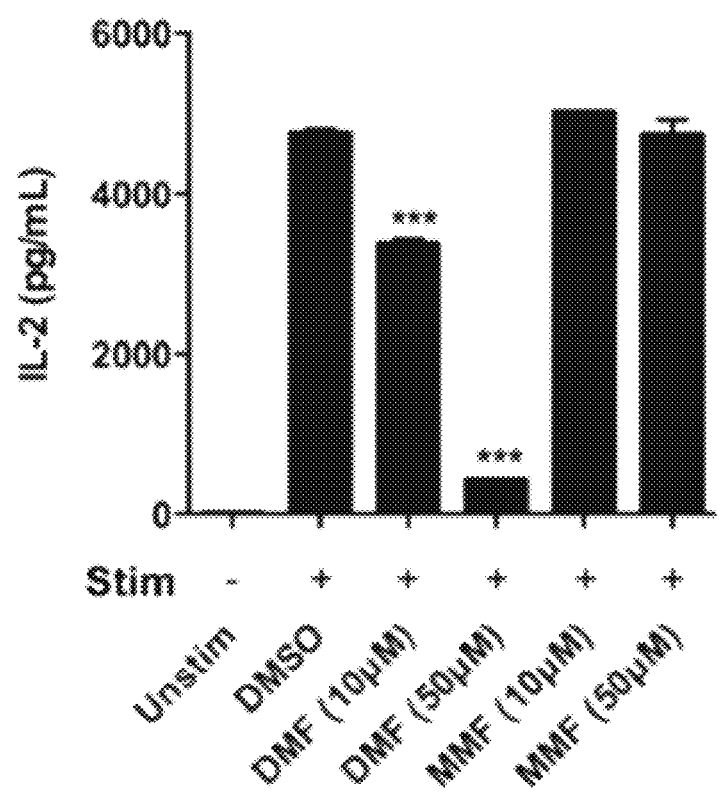
Figure 23C:
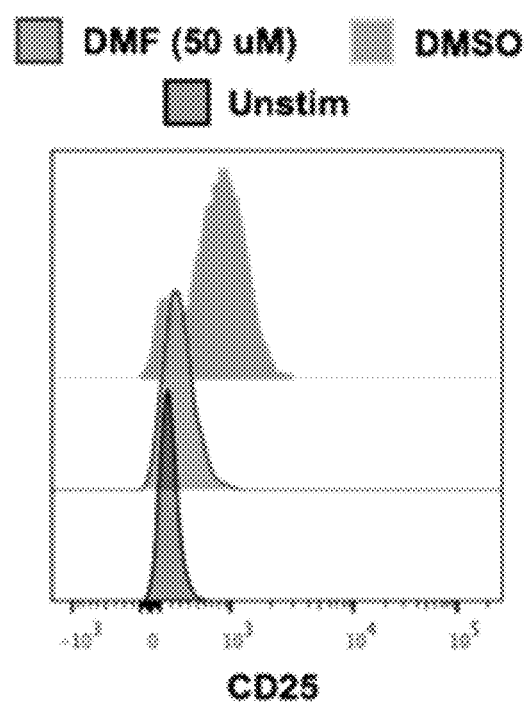
Figure 23D:
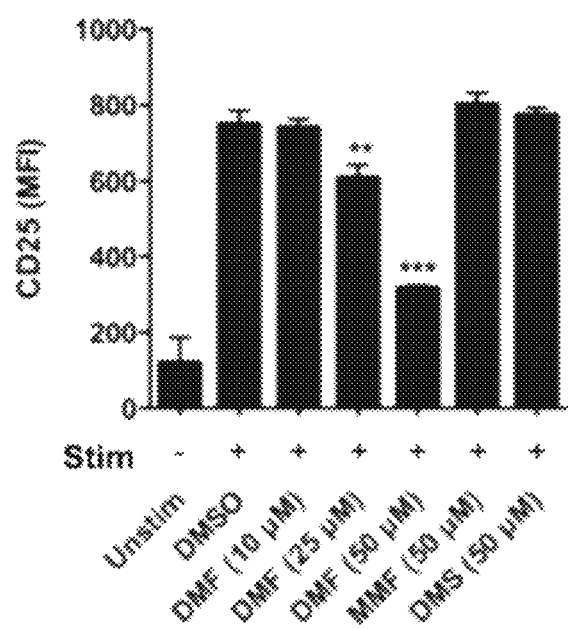
Figure 23E:
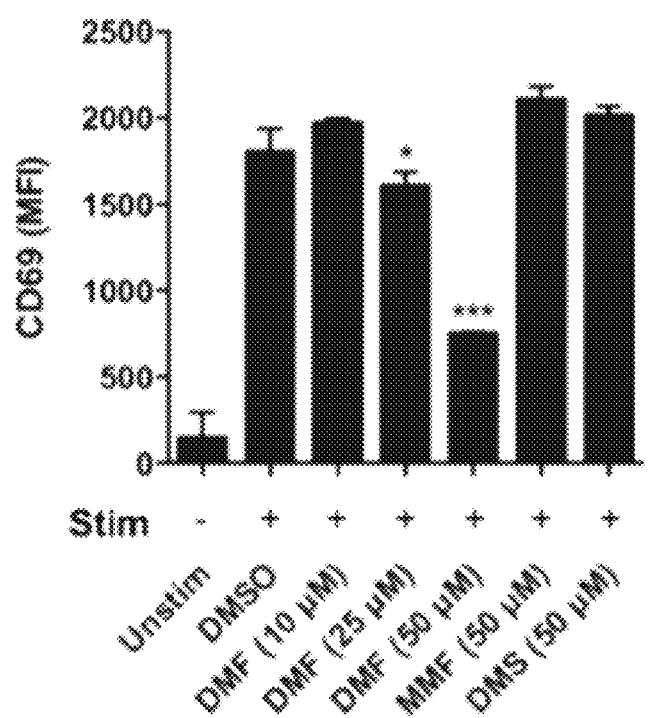
Figure 23F:
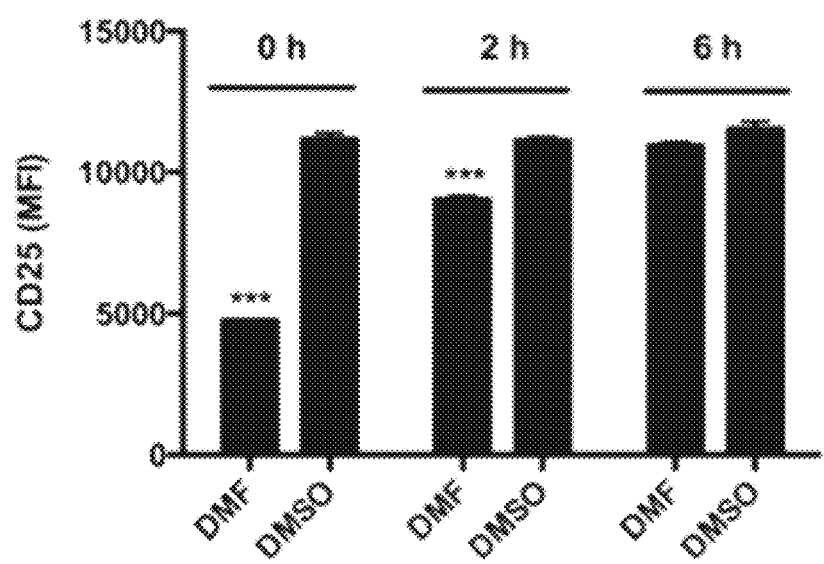

FIG. 23A-FIG. 23F exemplify DMF inhibits the activation of primary human T cells. FIG. 23A illustrates the chemical structures of DMF, MMF, and DMS. FIG. 23B-FIG. 23E illustrate bar graphs that exemplify IL-2 release (FIG. 23B), CD25 expression (FIG. 23C and FIG. 23D), and CD69 expression (FIG. 23E) in primary human T cells, either unstimulated (Unstim) or stimulated (Stim) with anti-CD3+anti-CD28 in the presence of DMSO or the indicated concentrations of DMF, MMF, and DMS for 8 hours. FIG. 23F illustrates a bar graph that exemplifies time course of DMF effects. T cells were stimulated with anti-CD3+anti-CD28 for the indicated periods of time before beginning DMF treatment. Cells were harvested 24 h after beginning T cell stimulation. Shown are data gated on CD4+ cells. Data represent mean±SE; n=4-6 experiments/group. *$p<0.05$, $p<0.01$, *$p<0.001$ in comparison to DMSO group.

Figure 24:
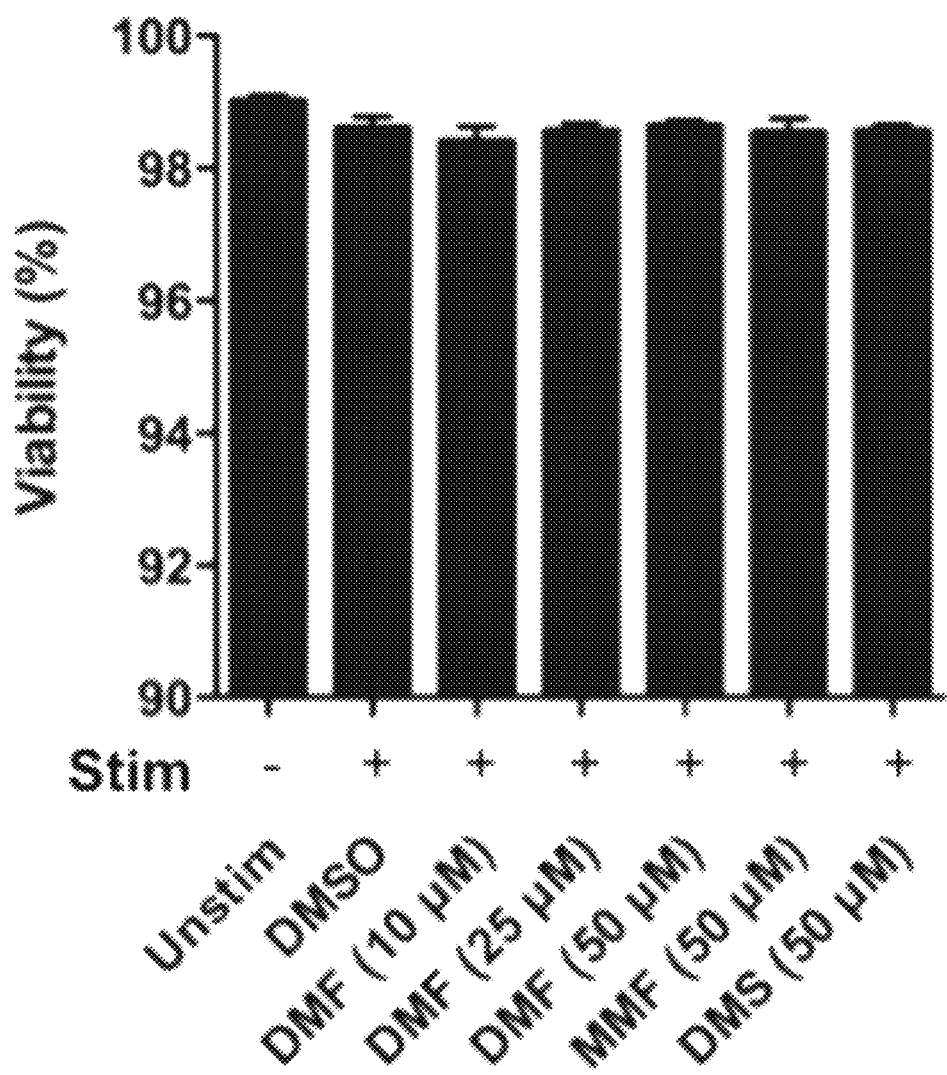

FIG. 24 illustrates a bar graph that exemplifies DMF does not affect T cell viability. Primary human T cells were stimulated with anti-CD3 and anti-CD28 antibodies as indicated and treated concomitantly with compound for 8 h. Cells were then stained with LIVE/DEAD fixable blue stain, and analyzed by flow cytometry. Shown are data gated on CD4+ cells. Data represent mean±SE for four experiments per group.

Figure 25A:
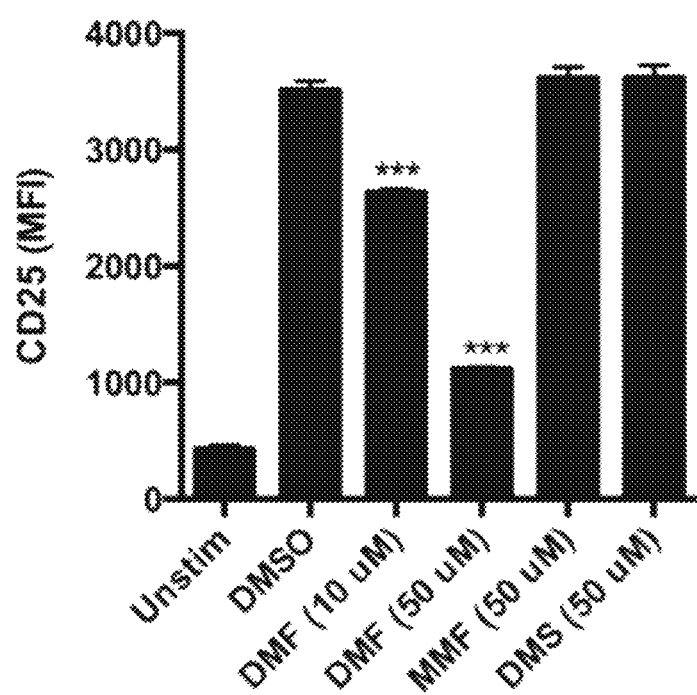
Figure 25B:
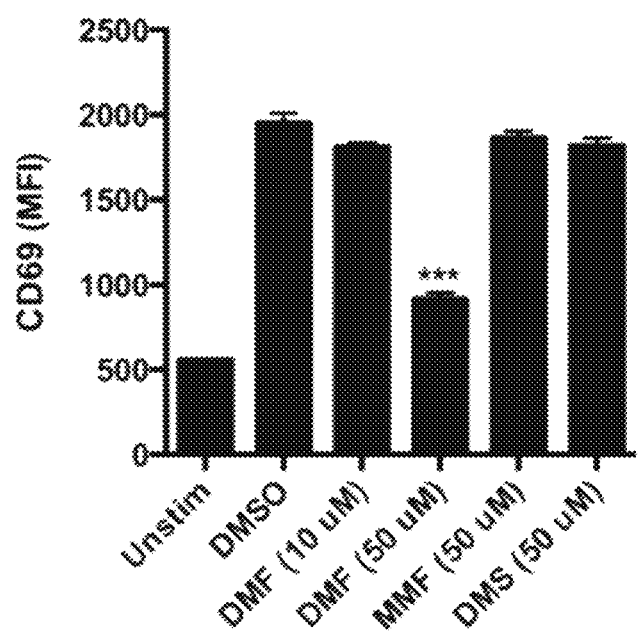

FIG. 25A-FIG. 25B illustrate bar graphs that exemplify DMF, but not MMF, inhibits the activation of primary mouse T cells. Splenic T cells were harvested from C57BL/6 mice and left either unstimulated (Unstim) or stimulated (Stim) with anti-CD3+anti-CD28 in the presence of DMSO or the indicated concentrations of DMF, MMF, and DMS for 8 h. Activation was assessed by measuring CD25 (FIG. 25A) and CD69 (FIG. 25B) expression. Data represent mean±SE for four experiments per group. ***$p<0.001$ in comparison to DMSO group.

Figure 26A:
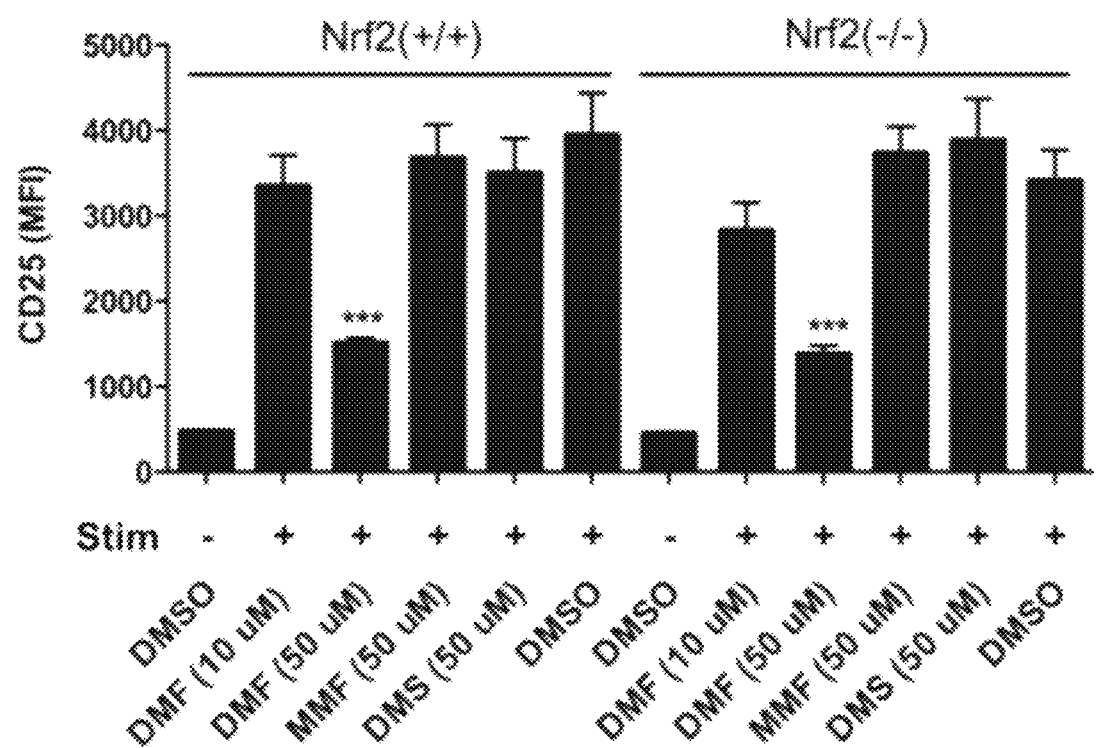
Figure 26B:
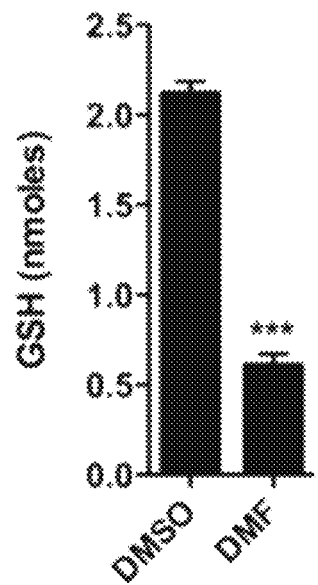
Figure 26C:
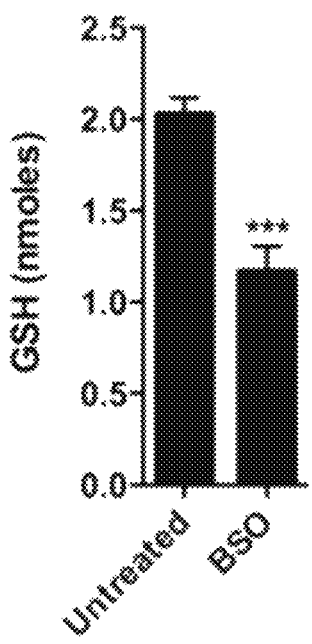
Figure 26D:
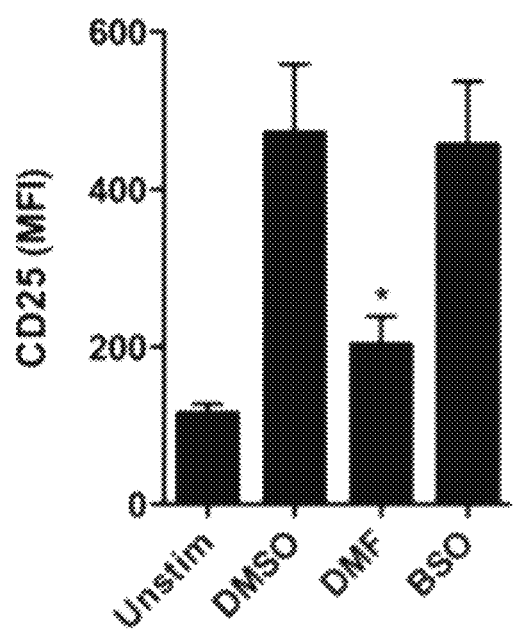

FIG. 26A-FIG. 26D illustrate bar graphs that exemplify inhibitory effects of DMF are equivalent in Nrf2(+/+) and (−/−) T cells and not caused by reductions in cellular GSH. FIG. 26A exemplifies CD25 expression in anti-CD3+anti-CD28-stimulated Nrf2(+/+) and (−/−) T cells. Splenic T cells were harvested from Nrf2(+/+) and (−/−) mice, then stimulated in the presence of indicated compounds for 24 h. FIG. 26B and FIG. 26C exemplify treatment with DMF or BSO causes significant reductions in GSH content of human T cells. Primary human T cells were stimulated with anti-CD3+anti-CD28 antibodies and treated with DMF (50 µM, 2 hours) or BSO (2.5 mM, 4 hours), after which intracellular GSH levels were measured. FIG. 26D exemplifies that BSO does not alter T cell activation. Primary human T cells were treated with DMSO, DMF (50 µM), or BSO (2.5 mM) and stimulated as indicated for 8 h, after which CD25 expression was measured. Data represent mean±SE for two biological replicates, with 3-4 technical replicates per biological replicate. *p<0.05, p<0.01. *p<0.001 in comparison to DMSO groups.

Figure 27A:
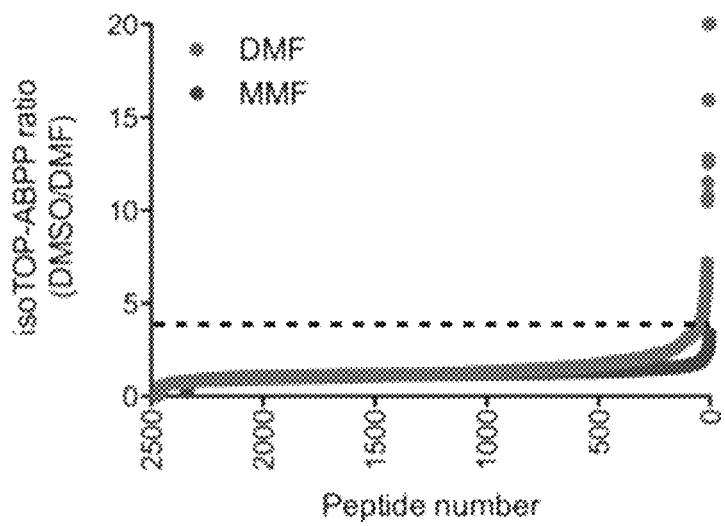
Figure 27B:
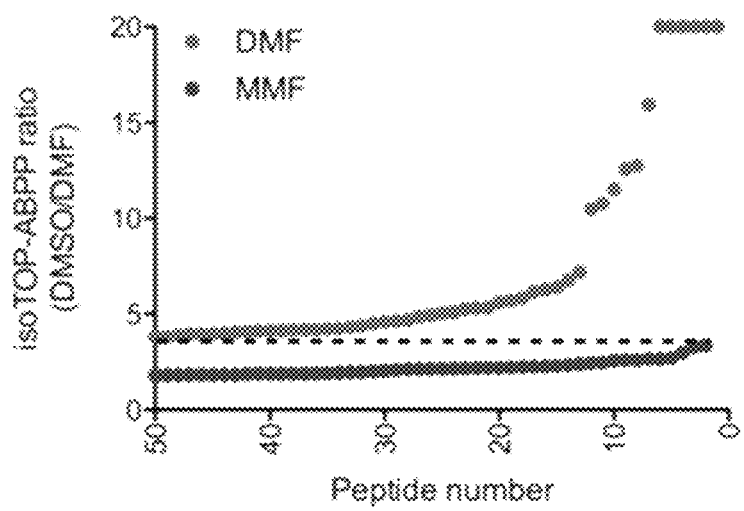
Figure 27C:
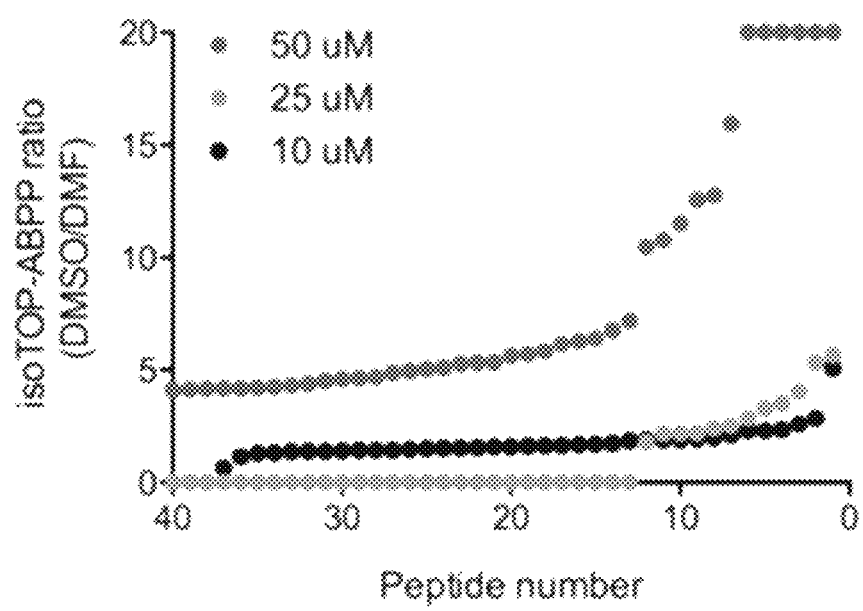
Figure 27D:
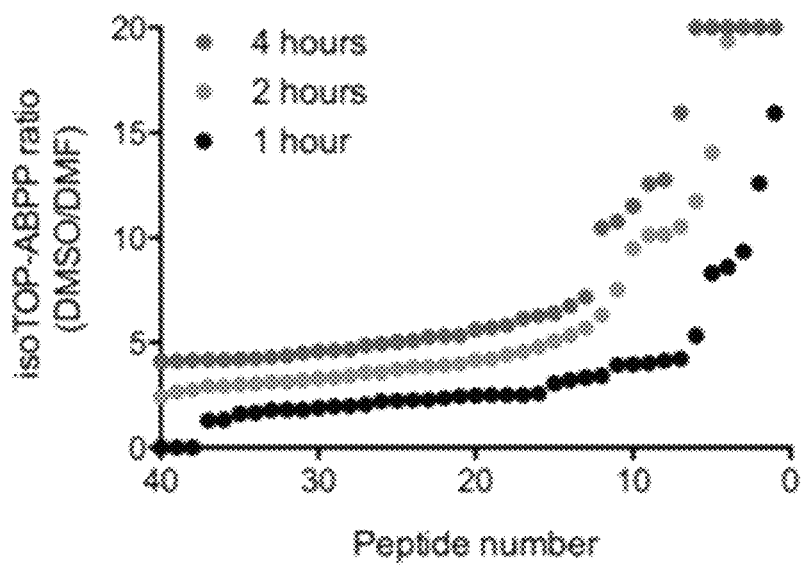
Figure 27E:
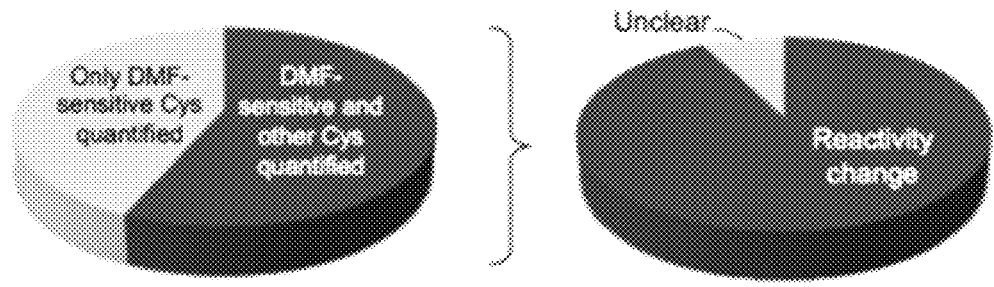
Figure 27F:
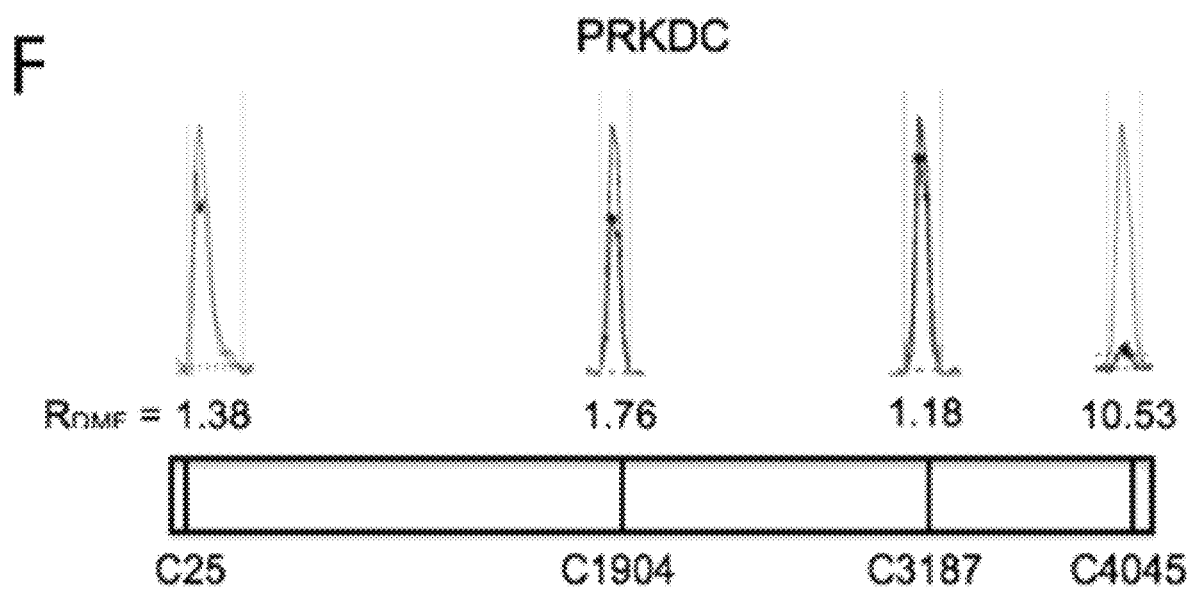

FIG. 27A-FIG. 27F exemplify isoTOP-ABPP of DMF-treated primary human T cells. FIG. 27A illustrates a graph that exemplifies isoTOP-ABPP ratios, or R values, for >2400 Cys residues in primary human T cells treated with DMSO or DMF or MMF (50 µM, 4 h). FIG. 27B illustrates a graph that exemplifies expanded profile for DMF-sensitive Cys residues (R values>4 for DMSO/DMF). For FIG. 27A and FIG. 27B, data represent aggregate quantified Cys residues from five biological replicates. For Cys residues quantified in more than one replicate, average ratios are reported. Dashed line designates R values>4, which was used to define DMF-sensitive Cys residues (>4-fold reductions in IA-alkyne reactivity in DMF-treated T cells). FIG. 27C and FIG. 27D illustrate graphs that exemplify concentration- and time-dependent profiles for DMF-sensitive Cys residues in T cells, respectively. For additional concentrations (10 and 25 µM) and time points (1 and 2 h), data represent aggregate quantified Cys residues from one-three isoTOP-ABPP experiments per group. FIG. 27E illustrates a chart which exemplifies fraction of proteins for which both a DMF-sensitive Cys residue and at least one additional Cys residue was quantified (Left) and, fraction of these proteins where additional Cys residue was clearly unchanged (Right) (R value<2.0 for DMSO/DMF). Unclear calls mark proteins with DMF-sensitive Cys residues where the R value for second Cys showed marginal evidence of potential change (R values between 2.0 and 3.9). FIG. 27F illustrates representative MS1 profiles for quantified Cys residues in PRKDC, one of which (C4045) shows sensitivity to DMF.

Figure 28A:
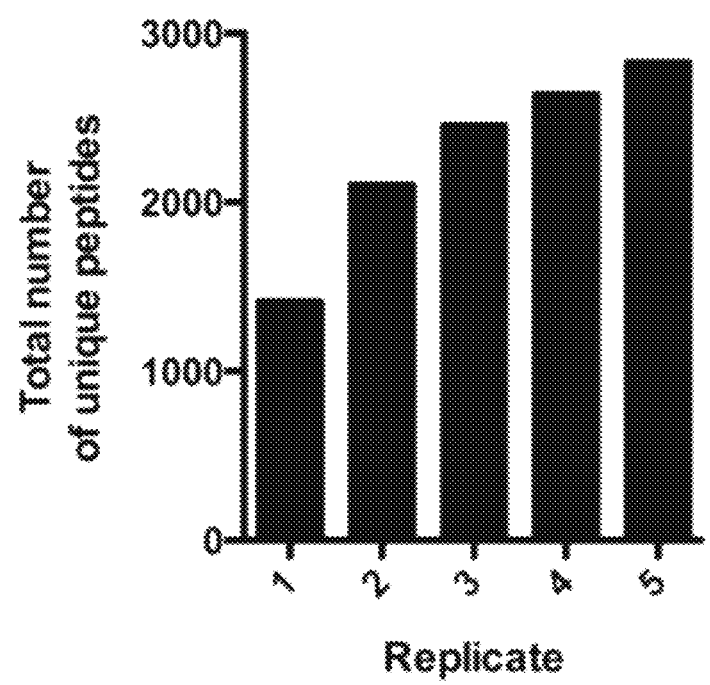
Figure 28B:
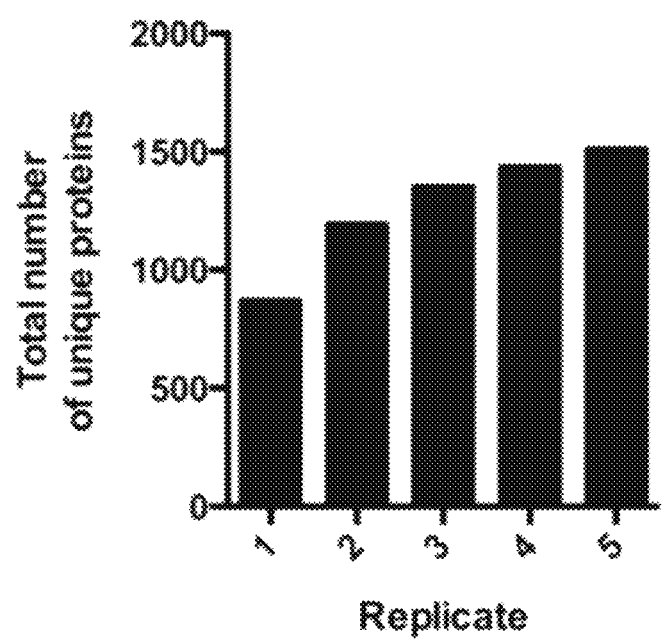

FIG. 28A-FIG. 28B illustrate bar graphs that exemplify the total number of unique quantified peptides (FIG. 28A) and proteins (FIG. 28B) begin to plateau after five biological replicates of the isoTOP-ABPP experiment in primary human T cells (treated with 50 uM DMF for 4 h).

Figure 29:
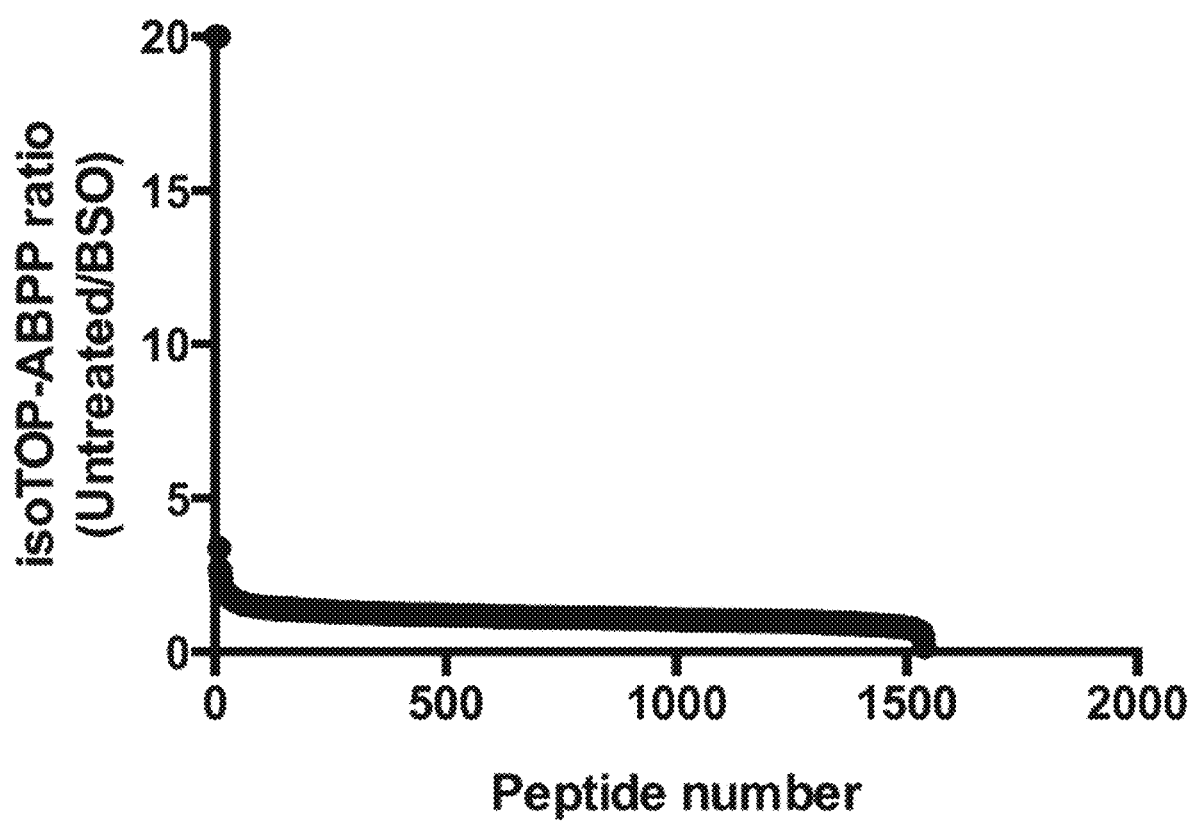

FIG. 29 illustrates a graph that exemplifies isoTOP-ABPP of BSO-treated primary human T cells. Cells were treated with 2.5 mM BSO for 4 hours. Data represent aggregate quantified Cys residues from two isoTOP-ABPP experiments per group.

Figure 30A:
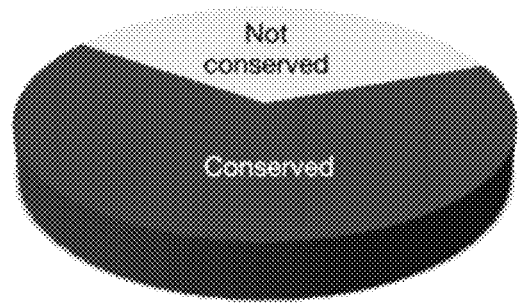
Figure 30B:
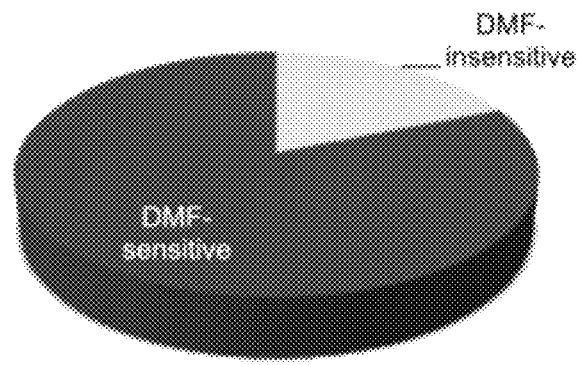
Figure 30C:
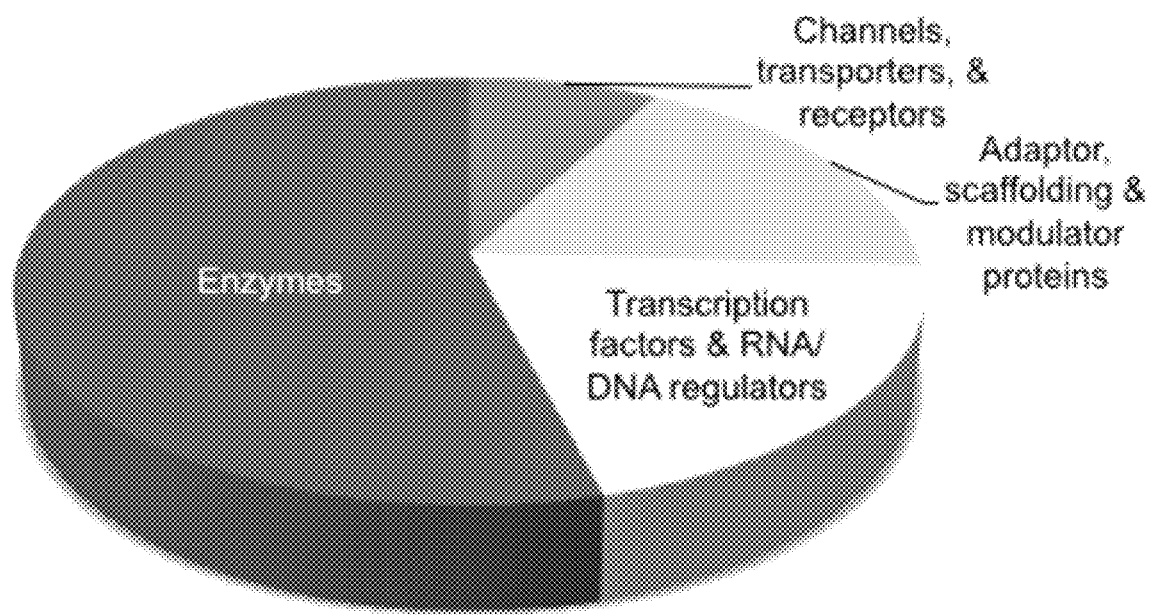

FIG. 30A-FIG. 30C exemplify conservation and functional analysis of DMF-sensitive cysteines. FIG. 30A exemplifies fraction of DMF-sensitive cysteines in the human T cell proteome that are conserved in mice. FIG. 30B exemplifies fraction of conserved DMF-sensitive Cys residues in human T cells that were quantified and also sensitive to DMF in mouse T cells. FIG. 30C exemplifies distribution of proteins harboring DMF-sensitive Cys residues by functional class.

Figure 31A:
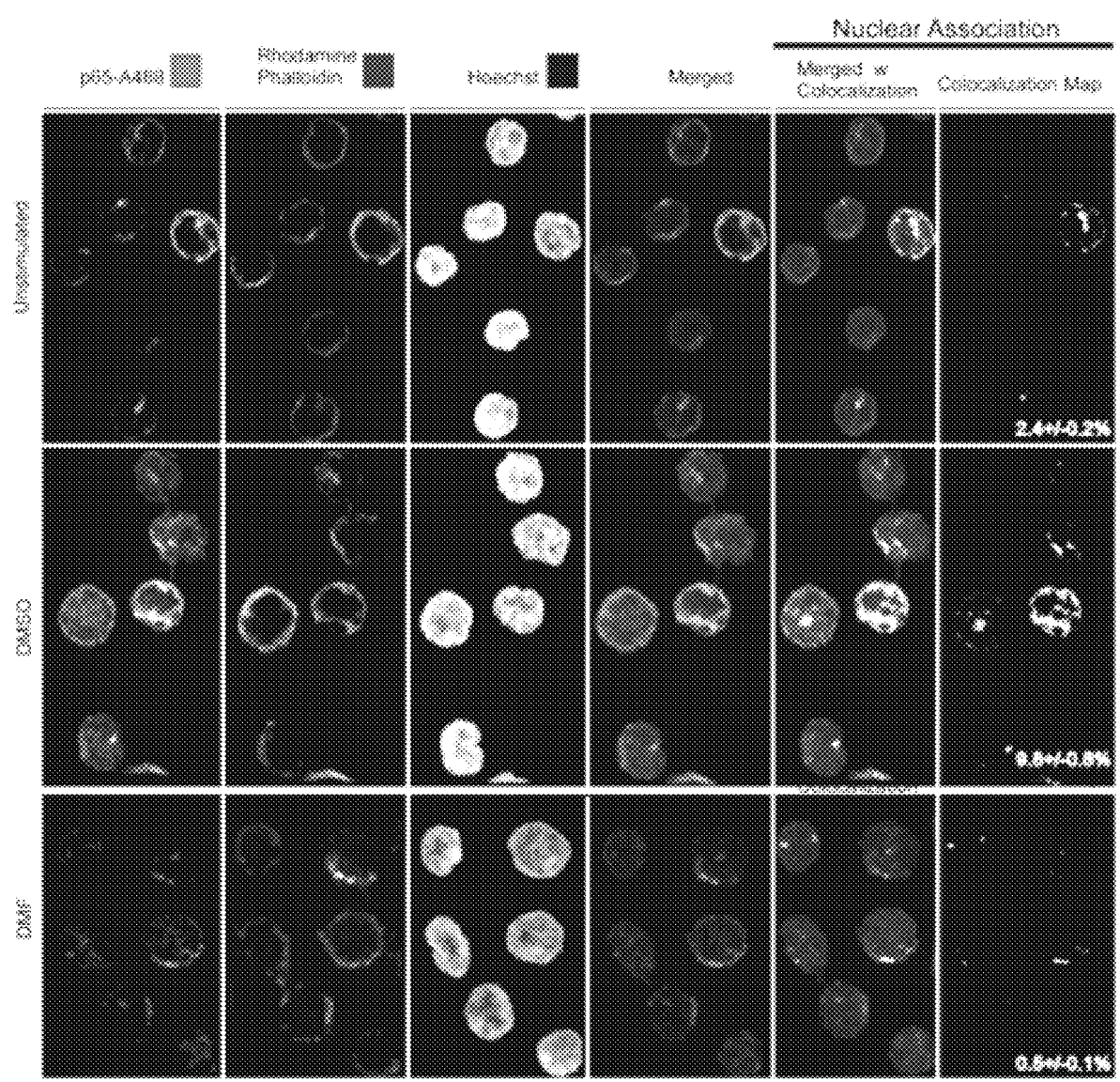
Figure 31B:
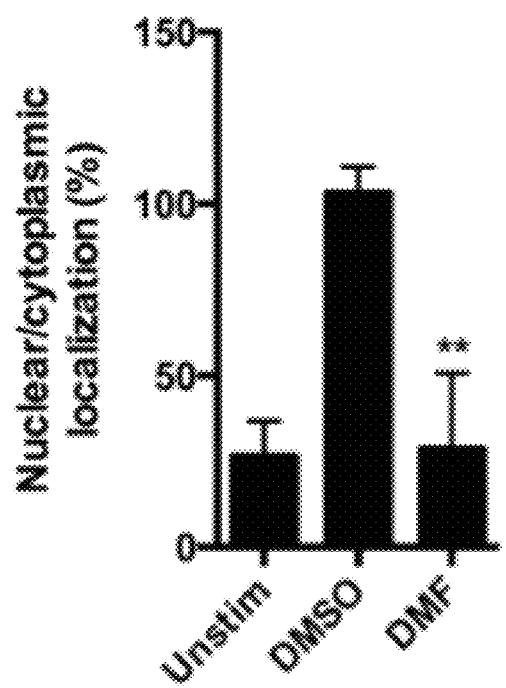
Figure 31C:
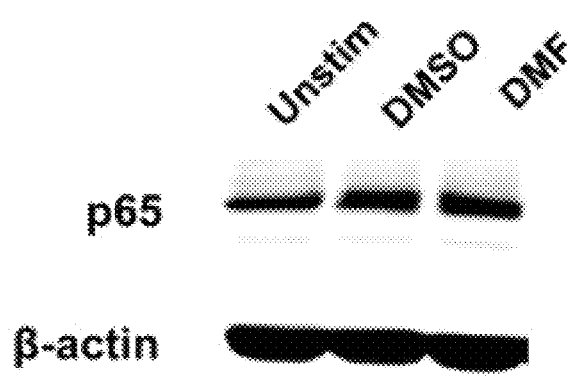

FIG. 31A-FIG. 31C exemplify DMF inhibits p65 translocation to the nucleus in primary human T cells. FIG. 31A exemplify Human T cells were either left unstimulated or stimulated with anti-CD3 and anti-CD28 antibodies and treated with DMSO or DMF (50 uM) for 1 h. FIG. 31B illustrates a bar graph that exemplifies ratio of nuclear to cytoplasmic localization of p65 for samples shown in FIG. 31A, as well as samples treated with MMF (50 uM) or DMS (50 uM). FIG. 31C exemplifies p65 levels in whole cell lysate.

Figures 32A, 32B:
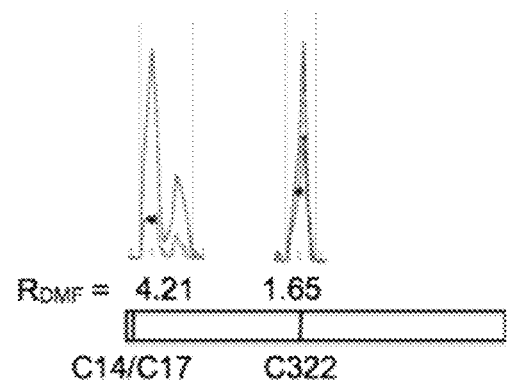
Figure 32C:
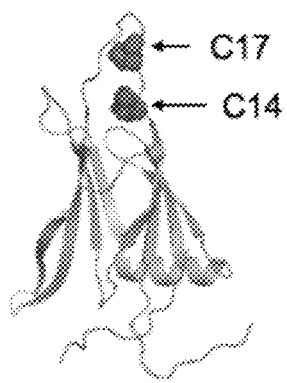
Figure 32D:
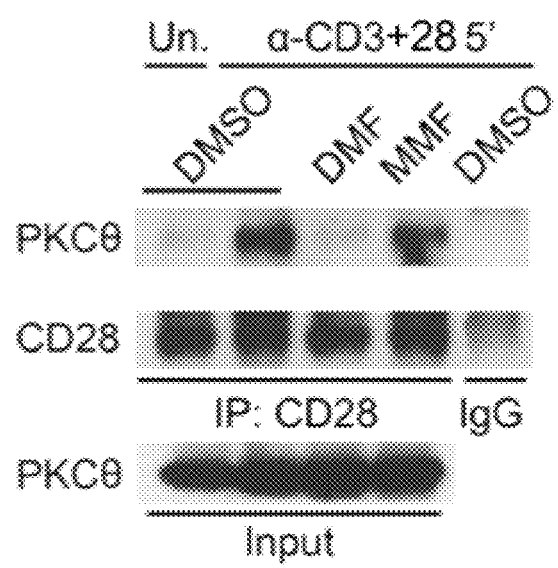
Figure 32E:
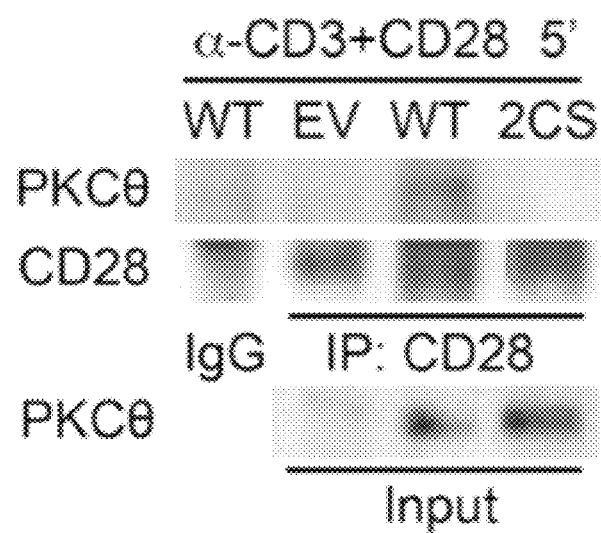
Figure 32F:
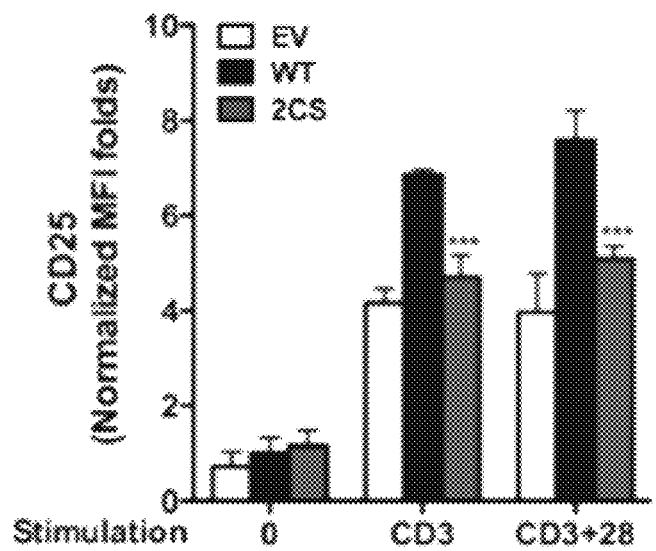
Figure 32G:
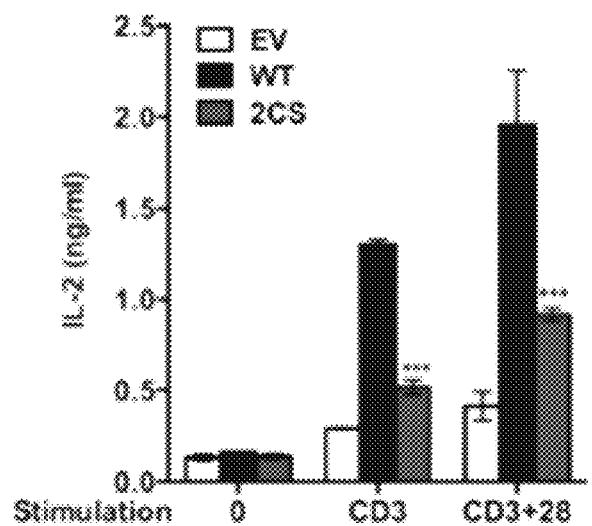

FIG. 32A-FIG. 32G exemplify DMF-sensitive C14/C17 residues in PKCθ are important for CD28 interactions and T cell activation. FIG. 32A illustrates representative MS1 profiles for DMF-sensitive (C14/C17) and -insensitive (C322) Cys residues in PKCθ. FIG. 32B exemplifies sequence conservation analysis of human and mouse PKCθ, human PKCδ, and human PKCε (SEQ ID NOS 865-868, respectively, in order of appearance). Shown in red are C14 and C17. FIG. 32C illustrates location of DMF-sensitive C14 and C17 residues in the C2 domain of PKCθ (PDB accession number 2ENJ). FIG. 32D exemplifies DMF, but not MMF, treatment blocks the association of PKCθ with CD28. Peripheral CD4+ T cells from C57BL/6 mice were pre-incubated with DMSO, DMF (50 µM), or MMF (50 µM), either left unstimulated or stimulated with anti-CD3+anti-CD28 for 5 min, then washed and lysed. Immunoprecipitations (IPs) were performed in the cell lysates with anti-CD28 or control IgG antibodies and IPs blotted for CD28 or PKCθ. FIG. 32E illustrates Co-IP of WT PKCθ and the C14S/C17S (2CS) PKCθ mutant with CD28. PKCθ(-/-) T cells were reconstituted with empty vector (EV), WT PKCθ, or the 2CS PKCθ mutant. FIG. 32F and FIG. 32 G illustrate PKCθ(-/-) T cells reconstituted with WT or 2CS PKCθ were assayed for activation potential by measuring CD25 expression (FIG. 32F) and IL-2 (FIG. 32G). For FIG. 32E-FIG. 32G, PKCθ(-/-) T cell cultures were pre-activated with plate-coated anti-CD3+anti-CD28 for 24 h before retroviral transduction with empty vector, WT PKCθ, or the 2CS PKCθ mutant. Cells were rested in culture medium without stimulation for 48 h, then re-stimulated with or without 1 µg/mL plate-coated anti-CD3(+28) overnight (FIG. 32F), for 48 h (FIG. 32G), or with soluble 10 µg/mL anti-CD3+anti-CD28 for 5 min prior to IP (FIG. 32D). For FIG. 32D and FIG. 32E, data are from a single experiment representative of three biological replicates. For FIG. 32F and FIG. 32G, data represent mean±SE for three biological replicates. ***p<0.001 in comparison to WT PKCθ group.

Figure 33A:
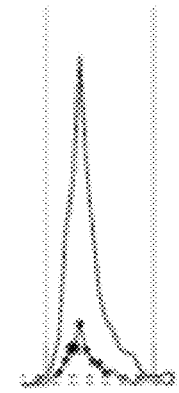
Figure 33B:
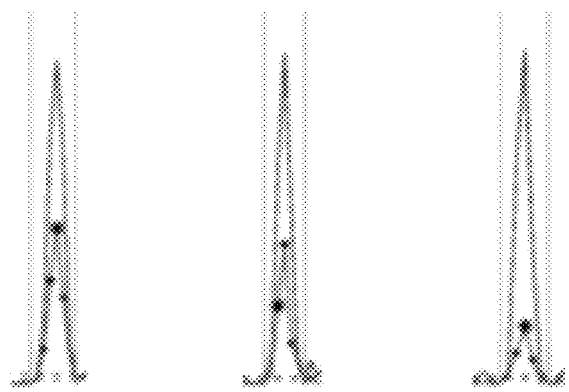
Figure 33C:
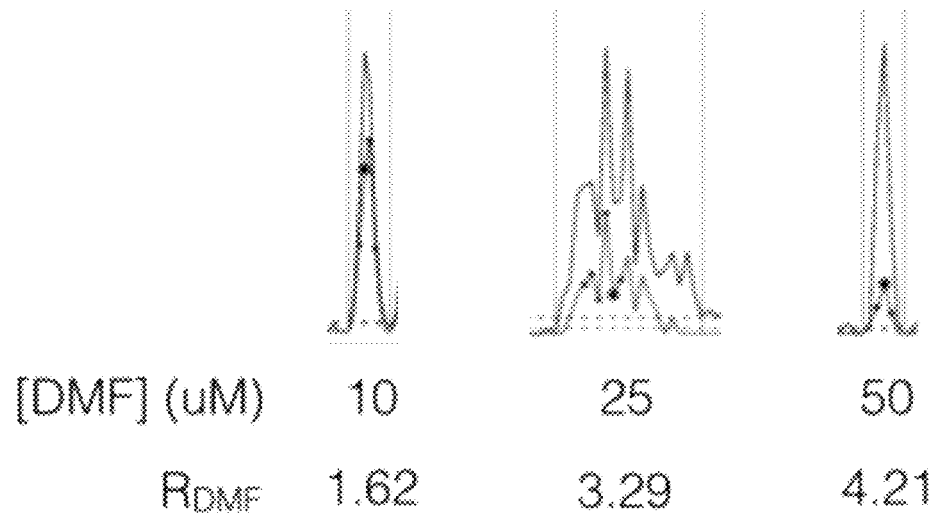
Figure 33D:
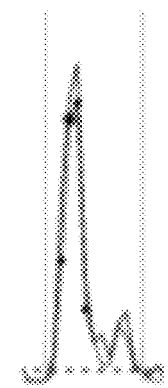

FIG. 33A-FIG. 33D exemplify DMF sensitivity of C14/C17 in PKCθ. FIG. 33A illustrates representative MS1 profile of C14/C17 of mouse PKCθ shows sensitivity to DMF (50 µM, 4 h) in isoTOP-ABPP experiments. FIG. 33B and FIG. 33C exemplify Time- and concentration-dependence of DMF sensitivity of C14/C17 in human PKCθ, respectively, as determined by isoTOP-ABPP experiments. FIG. 33D exemplifies C14/C17 of human PKCθ are insensitive to MMF treatment (50 µM MMF, 4 h).

Figure 34A:
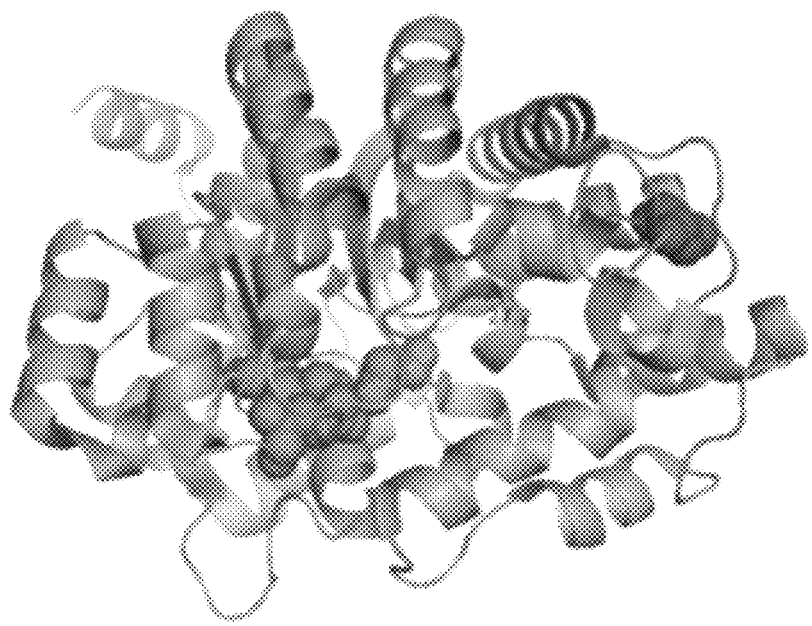
Figure 34B:

FIG. 34A-FIG. 34B exemplify DMF-sensitive Cys residue in ADA. FIG. 34A illustrates the DMF-sensitive Cys, C75 (magenta), is ~25 angstroms from the ADA active site (orange). FIG. 34B illustrates mutations in both residues neighboring C75 (G74 and R76 (blue)) have been associated with the severe combined immunodeficiency known as ADASCID (OMIM: 608958). PDB accession number: 3IAR.

DETAILED DESCRIPTION OF THE INVENTION

Cysteine containing proteins encompass a large repertoire of proteins that participate in numerous cellular functions such as mitogenesis, proliferation, apoptosis, gene regulation, and proteolysis. These proteins include enzymes, transporters, receptors, channel proteins, adaptor proteins, chaperones, signaling proteins, plasma proteins, transcription related proteins, translation related proteins, mitochondrial proteins, or cytoskeleton related proteins. Dysregulated expression of a cysteine containing protein, in many cases, is associated with or modulates a disease, such as an inflammatory related disease, a neurodegenerative disease, or cancer. As such, identification of a potential agonist/antagonist to a cysteine containing protein aids in improving the disease condition in a patient.

In some instances, potential constrains exist in drug screening due to the structurally complex compound and the inability of some of the structurally complexed compound to interact with the protein. As such, small molecule fragments are employed in some instances to serve as launching point for structure-guided elaboration of an initial interaction into a high-affinity drug. In some instances, one method of identifying a small molecule fragment that interacts with a cysteine containing protein is through monitoring their interaction under an in vitro environment. However in some cases, the in vitro environment does not mimic the native condition of the cysteine containing protein. In other cases, the in vitro environment lacks additional helper proteins to facilitate interaction with the small molecule fragment. Further still, in some instances, difficulties arise during the expression and/or purification stage of the cysteine-containing protein.

Described herein is another method of identifying small molecule fragments for interaction with a cysteine containing protein. In some instances, this method allows for mapping of small molecule fragments for interaction with a cysteine containing protein under native conditions, thereby allows for an accurate mapping of interaction with potential small molecule fragments. In some instances, this method also allows for identification of novel cysteine containing protein targets as this method eliminates the need of recombinant expression and purification.

In some embodiments, also described herein are compositions, cells, cell populations, assays, probes, and service related to the method of identifying a small molecule fragment for interaction with a cysteine containing protein.

General Methodology

Figure 1:
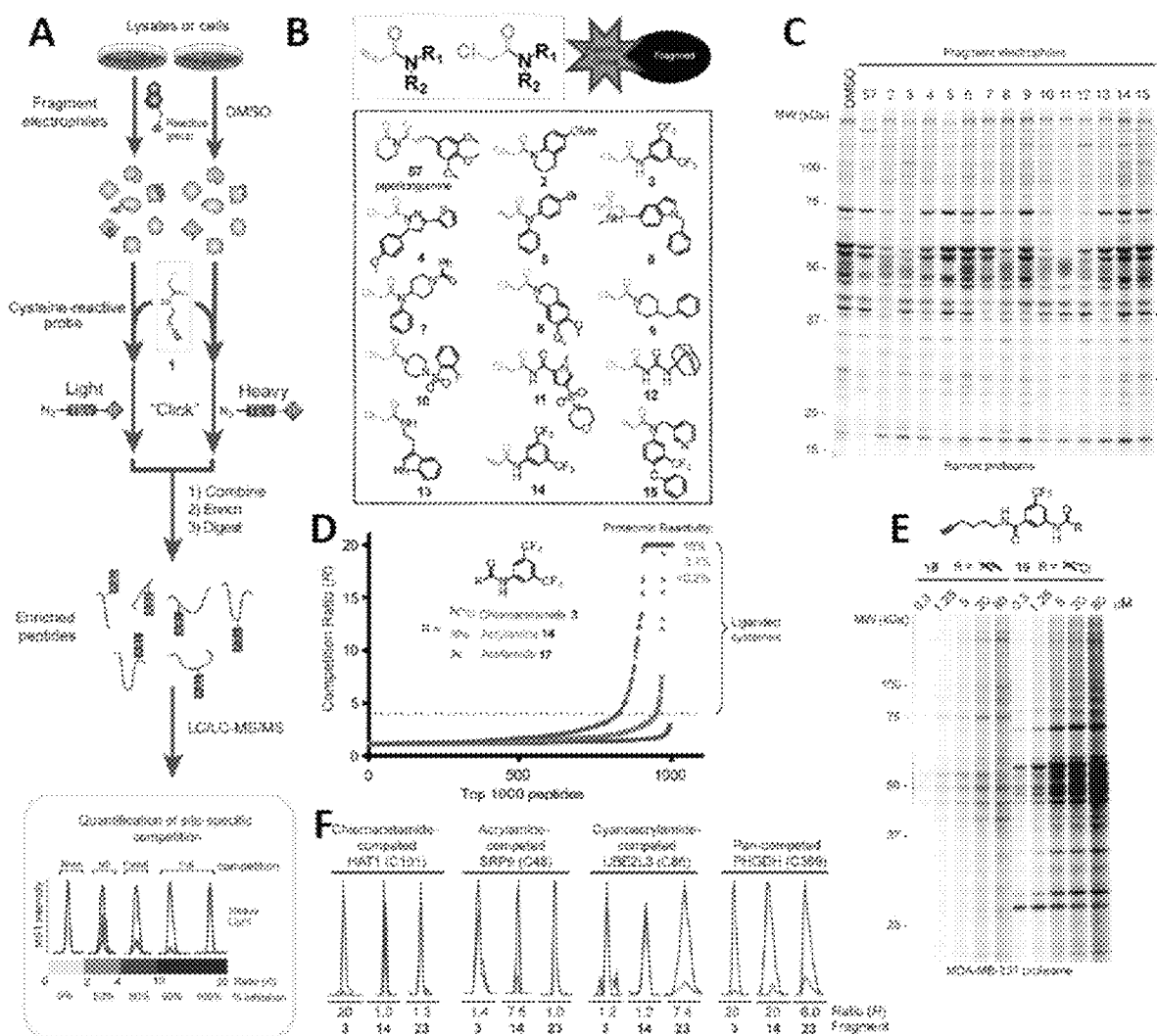
FIG. 1 illustrates proteome-wide screening of covalent fragments. A, General protocol for competitive isoTOP-ABPP. Cell lysate or intact cells are pre-treated with a fragment electrophile or DMSO and then reacted with an IA-alkyne probe 1. The fragment- and DMSO-treated samples are then conjugated to isotopically-differentiated TEV protease-cleavable biotin tags [light (red) and heavy (blue), respectively] by copper-mediated azide-alkyne cycloaddition (CuAAC or click) chemistry, mixed, and IA-labeled proteins enriched by streptavidin-conjugated beads and digested stepwise on-bead with trypsin and TEV to yield IA-labeled peptides for MS analysis. Competition ratios, or R values, are measured by dividing the MS1 ion peaks for IA-labeled peptides in DMSO-treated (heavy or blue) versus fragment-treated (light or red) samples. B, Representative members of the electrophilic fragment library, where the reactive (electrophilic) and binding groups are colored green and black, respectively. C, Initial analysis of the proteomic reactivity of fragments using an IA-rhodamine probe 16. Soluble proteome from Ramos cells was treated with the indicated fragments (500 µM each) for 1 h, followed by labeling with IA-rhodamine (1 µM, 1 h) and analysis by SDS-PAGE and in-gel fluorescence scanning. Several proteins were identified that show impaired reactivity with IA-rhodamine in the presence of one or more fragments (asterisks). Fluorescent gel shown in grayscale. D, Competitive isoTOP-ABPP analysis of fragment-cysteines interactions in the soluble proteome of MDA-MB-231 cells pre-treated with the following fragments (500 µM each): 3,5-di(trifluoromethyl)aniline chloroacetamide 3, acrylamide 14, and acetamide 17. Proteomic reactivity values, or liganded cysteine rates, for fragments were calculated as the percentage of total cysteines with R values ≥4 in DMSO/fragment (heavy/light) comparisons. E, Concentration-dependent labeling of MDA-MB-231 soluble proteomes with acrylamide 18 and chloroacetamide 19 click probes detected by CuACC with a rhodamine-azide tag and analysis by SDS-PAGE and in-gel fluorescence scanning. F, Representative MS1 peptide ion chromatograms from competitive isoTOP-ABPP experiments performed with fragments 3, 4, and 23 marking liganded cysteines selectively targeted by one of three fragments (or, in the case of PHGDH C369, by all three fragments).

In some embodiments, the methods described herein utilize a small molecule fragment and a cysteine-reactive probe for competitive interaction with a cysteine-containing protein. In some embodiments, the method is as described in FIG. 1A. FIG. 1A illustrates contacting a first cell solution with a small molecule fragment for an extended period of time prior to incubating the first cell solution with a first cysteine-reactive probe to generate a first group of cysteine-reactive probe-protein complexes. In some embodiments, the extended period of time is about 5, 10, 15, 20, 30, 60, 90, 120 minutes or longer. In some instances, the small molecule fragment competes with the first cysteine-reactive probe for interaction with a protein target. In some instances, the small molecule fragment or the cysteine-reactive probe form a covalent bond via a Michael's reaction with a cysteine residue of the cysteine containing protein. FIG. 1A further illustrates contacting a second cell solution with a second cysteine-reactive probe to generate a second group of cysteine-reactive probe-protein complexes. In some instances, the first cysteine-reactive probe and the second cysteine-reactive probe are the same.

In some embodiments, cells from the second cell solution are grown in an enriched media (e.g., an isotopically enriched media). In some cases, cells from the first cell solution are grown in an enriched media (e.g., an isotopically enriched media). In some instances, cells from both the first cell solution and the second cell solution are grown in two different enriched media (e.g., two different isotopically enriched media) so that a protein obtained from cells grown in the first cell solution is distinguishable from a protein obtained from cells grown in the second cell solution. In other embodiments, cells from only one of the cell solutions (e.g., either the first cell solution or the second cell solution) are grown in an enriched media (e.g., isotopically enriched media). In such cases, a protein obtained from the enriched cells (e.g., isotopically enriched cells) is distinguishable from a protein obtained from cells that have not been enriched (e.g., isotopically enriched).

As illustrated in FIG. 1A, in some instances the second cell solution is not treated with a small molecule fragment. In such cases, the second cell solution acts as a control.

In some instants, cells from the second cell solution are are further treated with a buffer. In some cases, the buffer is DMSO. In some cases, cells from the second cell solution are not treated with a small molecule fragment and the second cell solution acts as a control.

In some instances, a first group of cysteine-reactive probe-protein complexes and a second group of cysteine-reactive probe-protein complexes are harvested separately and combined to generate a set of cysteine-reactive probe-protein complexes which is further processed by a proteomic analysis means. In some cases, either the first group of cysteine-reactive probe-protein complexes or the second group of cysteine-reactive probe-protein complexes contain labeled proteins obtained from cells grown in an enriched media (e.g., isotopically enriched media). In some cases, both groups of cysteine-reactive probe-protein complexes contain labeled proteins obtained from cells grown in two different enriched media (e.g., two different isotopically enriched media). In other cases, either the first group of cysteine-reactive probe-protein complexes, the second group of cysteine-reactive probe-protein complexes, or both groups of cysteine-reactive probe-protein complexes contain labeled proteins in which the proteins have been labeled after harvesting from a cell.

In some instances, a first group of cysteine-reactive probe-protein complexes and a second group of cysteine-reactive probe-protein complexes are harvested separately and the proteins from one of the two groups of cysteine-reactive probe-protein complexes are subsequently labeled (e.g., by methylation). In some cases, first group of cysteine-reactive probe-protein complexes and a second group of cysteine-reactive probe-protein complexes are then combined and subjected to proteomic analysis means.

In other instances, a first group of cysteine-reactive probe-protein complexes and a second group of cysteine-reactive probe-protein complexes are harvested separately and both groups are subjected to proteomic analysis means. In some cases, data obtained from a protemoic analysis means is then combined for further analysis.

In some embodiments, the proteomic analysis means comprises a mass spectroscopy method. In some instances, the mass spectroscopy method is a liquid-chromatography-mass spectrometry (LC-MS) method. In some cases, the proteomic analysis means further comprise analyzing the results from the mass spectroscopy method by an algorithm for protein identification. In some cases, the algorithm combines the results from the mass spectroscopy method with a protein sequence database for protein identification. In some cases, the algorithm comprises ProLuCID algorithm, Probity, Scaffold, SEQUEST, or Mascot. In some cases, the mass spectroscopy method is a MALDI-TOF based method.

In some embodiments, a value is assigned to each of the cysteine binding protein from the cysteine-reactive probe-protein complexes after proteomic analysis, in which the value is determined from the proteomic analysis. In some cases, the value assigned to each of the cysteine containing protein is obtained from a mass spectroscopy analysis. In some instances, the value is an area-under-the curve from a plot of signal intensity as a function of mass-to-charge ratio. In some embodiments, a first value is assigned to a cysteine binding protein from the first group of cysteine-reactive probe-protein complex of the first cell solution and a second value of the same cysteine binding protein from the second group of cysteine-reactive probe-protein complex of the second cell solution. In some instances, a ratio is then calculated between the two values, the first value and the second value, and assigned to the same cysteine binding protein. In some instances, a ratio of greater than 2 indicates that the cysteine binding protein is a candidate for interacting with the small molecule fragment. In some instances, the ratio is greater than 2.5, 3, 3.5, 4, 4.5, 5, 6, 7, 8, 9, or 10. In some cases, the ratio is at most 20. In some instances, the same small molecule fragment interacts with a number of cysteine binding proteins in the presence of a cysteine-reactive probe. In some instances, the small molecule modulates the interaction of a cysteine-reactive probe with its cysteine binding protein partners. In some instances, the spectrum of ratios for a small molecule fragment with its interacting protein partners in the presence of a cysteine-reactive probe indicates the specificity of the small molecule fragment toward the protein. In some instances, the spectrum of ratio indicates whether the small molecule fragment is a specific inhibitor to a protein or a pan inhibitor.

In some embodiments, the cysteine containing protein identified by the above method comprises a biologically active cysteine residue. In some instances, the biologically active cysteine site is a cysteine residue that is located about 10 Å or less to an active-site ligand or residue. In some cases, the cysteine residue that is located about 10 Å or less to the active-site ligand or residue is an active site cysteine. In some cases, the biologically active cysteine site is an active site cysteine. In some embodiments, the biologically active cysteine site is a cysteine residue that is located greater than 10 Å from an active-site ligand or residue. In some cases, the cysteine residue that is located greater than 10 Å from the active-site ligand or residue is a non-active site cysteine. In some instances, the biologically active cysteine site is a non-active site cysteine.

In some embodiments, the small molecule fragment that covalently interacts with the biologically active cysteine impairs and/or inhibits activity of the cysteine containing protein. In some instances, the cysteine containing protein exists in an active form. In some embodiments, the small molecule fragment and/or the cysteine-reactive probe interact with the active form of the cysteine containing protein. In some instances, the cysteine containing protein exists in a pro-active form. In some embodiments, the small molecule fragment and/or the cysteine-reactive probe interact with the pro-active form of the cysteine containing protein.

In some embodiments, the structural environment of the biologically active cysteine residue modulates the reactivity of the cysteine residue. In some embodiments, the structural environment is a hydrophobic environment or a hydrophilic environment. In some embodiments, the structural environment is a charged environment. In some embodiments, the structural environment is a nucleophilic environment.

In some embodiments, the cysteine containing protein is an enzyme, a transporter, a receptor, a channel protein, an adaptor protein, a chaperone, a signaling protein, a plasma protein, transcription related protein, translation related protein, mitochondrial protein, or cytoskeleton related protein. In some instances, the cysteine containing protein is an enzyme, a transporter, a receptor, a channel protein, an adaptor protein, a chaperone, a signaling protein, transcription related protein, or translation related protein. In some embodiments, the cysteine containing protein is a protein illustrated in Tables 1, 2, 3, 8 or 9. In some instances, the cysteine residue of the cysteine-containing proteins illustrated in Tables 1, 2, 3, 8 or 9 is denoted by (*) in Tables 1, 2, 3, 8 or 9.

In some instances, a set of cysteine-reactive probes are added to the cell solutions. For example, a first set of cysteine-reactive probes are added to the first cell solution and a second set of cysteine-reactive probes are added to the second cell solution. In some cases, each cysteine-reactive probe is different within the set. In some instances, the first set of cysteine-reactive probes is the same as the second set of cysteine-reactive probes. In some cases, the first set of cysteine-reactive probes generate a third group of cysteine-reactive probe-protein complexes and the second set of cysteine-reactive probes generate a fourth group of cysteine-reactive probe-protein complexes. In some instances, the set of cysteine-reactive probes further facilitates identification of cysteine containing proteins.

In some embodiments, the sample is a cell sample. In other instances, the sample is a tissue sample.

In some instances, the method is an in-situ method.

Small Molecule Fragments

In some embodiments, the small molecule fragments described herein comprise non-naturally occurring molecules. In some instances, the non-naturally occurring molecules do not include natural and/or non-natural peptide fragments, or small molecules that are produced naturally within the body of a mammal.

In some embodiments, the small molecule fragments described herein comprise a molecule weight of about 100 Dalton or higher. In some embodiments, the small molecule fragments comprise a molecule weight of about 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 500, 550, 600, 650, 700, 750, 800, 850, 900, 950, 1000 Dalton, or higher. In some instances, the molecule weight of the small molecule fragments are between about 150 and about 500, about 150 and about 450, abut 150 and about 440, about 150 and about 430, about 150 and about 400, about 150 and about 350, about 150 and about 300, about 150 and about 250, about 170 and about 500, about 180 and about 450, about 190 and about 400, about 200 and about 350, about 130 and about 300, or about 120 and about 250 Dalton.

In some embodiments, the molecule weight of the small molecule fragments described herein is the molecule weight prior to enrichment with one or more elements selected from a halogen, a nonmetal, a transition metal, or a combination thereof. In some embodiments, the molecule weight of the small molecule fragments described herein is the molecule weight prior to enrichment with a halogen. In some embodiments, the molecule weight of the small molecule fragments described herein is the molecule weight prior to enrichment with a nonmetal. In some embodiments, the molecule weight of the small molecule fragments described herein is the molecule weight prior to enrichment with a transition metal. In some embodiments, the molecular weight of the small molecule fragment is calculated based on carbon and hydrogen atoms and optionally further based on nitrogen, oxygen and/or sulfur atoms.

In some embodiments, the molecular weight of the small molecule fragment does not include the molecular weight of a halogen, a transition metal or a combination thereof. In some cases, the molecular weight of the small molecule fragment does not include the molecular weight of a halogen, the molecular weight of the small molecule fragment does not include the molecular weight of a transition metal.

In some embodiments, the small molecule fragments described herein comprise micromolar or millimolar binding affinity. In some instances, the small molecule fragments comprise a binding affinity of about 1 µM, 10 µM, 100 µM, 500 µM, 1 mM, 10 mM, or higher.

In some embodiments, the small molecule fragments described herein has a high ligand efficiency (LE). Ligand efficiency is the measurement of the binding energy per atom of a ligand to its binding partner. In some instances, the ligand efficiency is defined as the ratio of the Gibbs free energy (ΔG) to the number of non-hydrogen atoms of the compound (N):

LE=(ΔG)/N.

In some cases, LE is also arranged as:

LE=1.4(-log IC$_{50}$)/N.

In some instances, the LE score is about 0.3 kcal mol$^{-1}$HA$^{-1}$, about 0.35 kcal mol$^{-1}$HA$^{-1}$, about 0.4 kcal mol$^{-1}$HA$^{-1}$, or higher.

In some embodiments, the small molecule fragments described herein are designed based on the Rule of 3. In some embodiments, the Rule of 3 comprises a non-polar solvent-polar solvent (e.g. octanol-water) partition coefficient log P of about 3 or less, a molecular mass of about 300 Daltons or less, about 3 hydrogen bond donors or less, about 3 hydrogen bond acceptors or less, and about 3 rotatable bonds or less.

In some embodiments, the small molecule fragments described herein comprises three cyclic rings or less.

In some embodiments, the small molecule fragments described herein binds to a cysteine residue of a polypeptide that is about 20 amino acid residues in length or more. In some instances, the small molecule fragments described herein binds to a cysteine residue of a polypeptide that is about 30, 35, 40, 45, 50, 55, 60, 65, 70, 75, 80, 85, 90, 95, 100, 150, 200, 250, 300, 350, 400, 450, 500, 600, 700, 800, 900, 1000 amino acid residues in length or more.

In some embodiments, the small molecule fragments described herein further comprise pharmacokinetic parameters that are unsuitable as a therapeutic agent for administration without further optimization of the small molecule fragments. In some instances, the pharmacokinetic parameters that are suitable as a therapeutic agent comprise parameters in accordance with FDA guideline, or in accordance with a guideline from an equivalent Food and Drug Administration outside of the United States. In some instances, the pharmacokinetic parameters comprise the peak plasma concentration (Cmax), the lowest concentration of a therapeutic agent (Cmin), volume of distribution, time to reach Cmax, elimination half-life, clearance, and the life. In some embodiments, the pharmacokinetic parameters of the small molecule fragments are outside of the parameters set by the FDA guideline, or by an equivalent Food and Drug Administration outside of the United States. In some instances, a skilled artisan understands in view of the pharmacokinetic parameters of the small molecule fragments described herein that these small molecule fragments are unsuited as therapeutic agents without further optimization.

In some embodiments, the small molecule fragments described herein comprise a reactive moiety which forms a covalent interaction with the thiol group of a cysteine residue of a cysteine containing protein, and an affinity handle moiety.

In some instances, a small molecule fragment described herein is a small molecule fragment of Formula (I):

Formula (I)

wherein:
RM is a reactive moiety selected from a Michael acceptor moiety, a leaving group moiety, or a moiety capable of forming a covalent bond with the thiol group of a cysteine residue; and F is a small molecule fragment moiety.

In some instances, the Michael acceptor moiety comprises an alkene or an alkyne moiety. In some cases, F is obtained from a compound library. In some cases, the compound library comprises ChemBridge fragment library, Pyramid Platform Fragment-Based Drug Discovery, Maybridge fragment library, FRGx from AnalytiCon, TCI-Frag from AnCoreX, Bio Building Blocks from ASINEX, BioFocus 3D from Charles River, Fragments of Life (FOL) from Emerald Bio, Enamine Fragment Library, IOTA Diverse 1500, BIONET fragments library, Life Chemicals Fragments Collection, OTAVA fragment library, Prestwick fragment library, Selcia fragment library, TimTec fragment-based library, Allium from Vitas-M Laboratory, or Zenobia fragment library.

In some embodiments, the small molecule fragment of Formula (I) does not contain a second binding site. In some instances, the small molecule fragment moiety does not bind to the protein. In some cases, the small molecule fragment moiety does not covalently bind to the protein. In some instances, the small molecule fragment moiety does not interact with a secondary binding site on the protein. In some instances, the secondary binding site is an active site such as an ATP binding site. In some cases, the active site is at least about 10, 15, 20, 25, 35, 40 Å, or more away from the biologically active cysteine residue. In some instances, the small molecule fragment moiety does not interact with an active site such as an ATP binding site.

Figure 3:
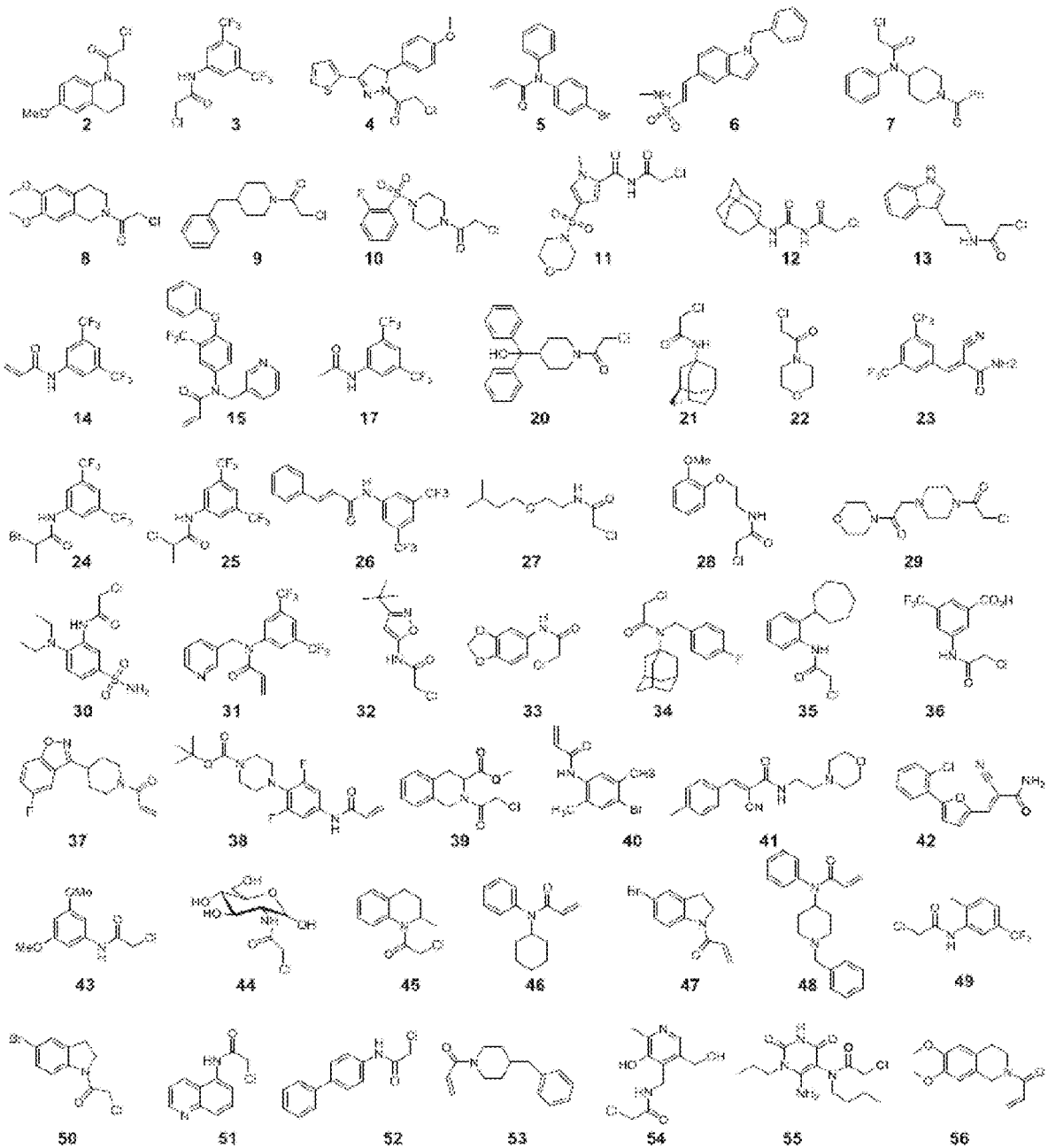
FIG. 3 shows composition of fragment electrophile library and structures of additional tool compounds, click probes, and fragments.
Figure 3:
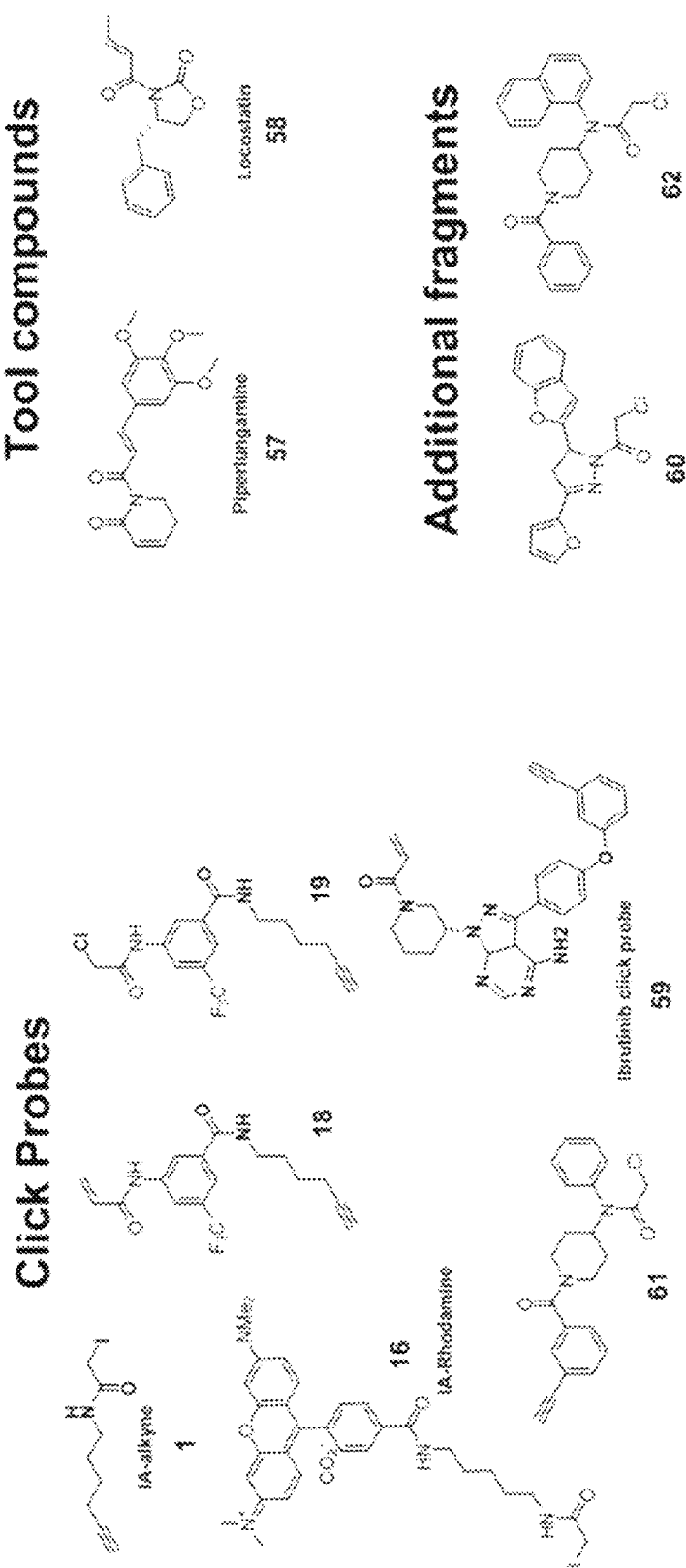

In some instances, F is a small molecule fragment moiety illustrated in FIG. 3. In some cases, F further comprises a linker moiety that connects F to the carbonyl moiety. In some cases, the small molecule fragment is a small molecule fragment illustrated in FIG. 3.

In some instances, F is a small molecule fragment moiety selected from: N-(4-bromophenyl)-N-phenylacrylamide, N-(1-benzoylpiperidin-4-yl)-2-chloro-N-phenylacetamide, 1-(4-benzylpiperidin-1-yl)-2-chloroethan-1-one, N-(2-(1H-indol-3-yl)ethyl)-2-chloroacetamide, N-(3,5-bis(trifluoromethyl)phenyl)acrylamide, N-(4-phenoxy-3-(trifluoromethyl)phenyl)-N-(pyridin-3-ylmethyl)acrylamide, N-(3,5-bis(trifluoromethyl)phenyl)acetamide, 2-chloro-1-(4-(hydroxydiphenylmethyl)piperidin-1-yl)ethan-1-one, (E)-3-(3,5-bis(trifluoromethyl)phenyl)-2-cyanoacrylamide, N-(3,5-bis(trifluoromethyl)phenyl)-2-bromopropanamide, N-(3,5-bis(trifluoromethyl)phenyl)-2-chloropropanamide, N-(3,5-bis(trifluoromethyl)phenyl)-N-(pyridin-3-ylmethyl) acrylamide, 3-(2-chloroacetamido)-5-(trifluoromethyl) benzoic acid, 1-(4-(5-fluorobenzisoxazol-3-yl)piperidin-1- yl)prop-2-en-1-one, tert-butyl 4-(4-acrylamido-2,6-difluorophenyl)piperazine-1-carboxylate, N-(4-bromo-2,5-dimethylphenyl)acrylamide, 2-Chloroacetamido-2-deoxy-α/β-D-glucopyranose, 2-chloro-1-(2-methyl-3,4-dihydroquinolin-1(2H)-yl)ethan-1-one, N-cyclohexyl-N-phenylacrylamide, 1-(5-bromoindolin-1-yl)prop-2-en-1-one, N-(1-benzylpiperidin-4-yl)-N-phenylacrylamide, 2-chloro-N-(2-methyl-5-(trifluoromethyl)phenyl)acetamide, 1-(5-bromoindolin-1-yl)-2-chloroethan-1-one, 2-chloro-N-(quinolin-5-yl)acetamide, 1-(4-benzylpiperidin-1-yl)prop-2-en-1-one, 2-chloro-N-((3-hydroxy-5-(hydroxymethyl)-2-methylpyridin-4-yl)methyl)acetamide, or 1-(6,7-dimethoxy-3,4-dihydroisoquinolin-2(1H)-yl)prop-2-en-1-one.

In some embodiments, the small molecule fragment of Formula (I) comprise a molecule weight of about 100, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 500, 550, 600, 650, 700, 750, 800, 850, 900, 950, 1000 Dalton, or higher. In some instances, the molecule weight of the small molecule fragment of Formula (I) is between about 150 and about 500, about 150 and about 450, abut 150 and about 440, about 150 and about 430, about 150 and about 400, about 150 and about 350, about 150 and about 300, about 150 and about 250, about 170 and about 500, about 180 and about 450, about 190 and about 400, about 200 and about 350, about 130 and about 300, or about 120 and about 250 Dalton.

In some embodiments, the molecule weight of the small molecule fragment of Formula (I) is the molecule weight prior to enrichment with one or more elements selected from a halogen, a nonmetal, a transition metal, or a combination thereof. In some embodiments, the molecule weight of the small molecule fragment of Formula (I) is the molecule weight prior to enrichment with a halogen. In some embodiments, the molecule weight of the small molecule fragment of Formula (I) is the molecule weight prior to enrichment with a nonmetal. In some embodiments, the molecule weight of the small molecule fragment of Formula (I) is the molecule weight prior to enrichment with a transition metal.

In some embodiments, the molecular weight of the small molecule fragment of Formula (I) does not include the molecular weight of a halogen, a transition metal or a combination thereof. In some embodiments, the molecular weight of the small molecule fragment of Formula (I) does not include the molecular weight of a halogen. In some embodiments, the molecular weight of the small molecule fragment of Formula (I) does not include the molecular weight of a transition metal.

In some instances, the small molecule fragment of Formula (I) comprises micromolar or millimolar binding affinity. In some instances, the small molecule fragment of Formula (I) comprises a binding affinity of about 1 μM, 10 μM, 100 μM, 500 μM, 1 mM, 10 mM, or higher.

In some cases, the small molecule fragment of Formula (I) has a LE score about 0.3 kcal mol$^{-1}$HA$^{-1}$, about 0.35 kcal mol$^{-1}$HA$^{-1}$, about 0.4 kcal mol$^{-1}$HA$^{-1}$, or higher In some embodiments, the small molecule fragment of Formula (I) follows the design parameters of Rule of 3. In some instances, the small molecule fragment of Formula (I) has a non-polar solvent-polar solvent (e.g. octanol-water) partition coefficient log P of about 3 or less, a molecular mass of about 300 Daltons or less, about 3 hydrogen bond donors or less, about 3 hydrogen bond acceptors or less, and about 3 rotatable bonds or less.

In some embodiments, the small molecule fragment of Formula (I) comprises three cyclic rings or less.

In some embodiments, the small molecule fragment of Formula (I) binds to a cysteine residue of a polypeptide (e.g., a cysteine containing protein) that is about 20 amino acid residues in length or more. In some instances, the small molecule fragments described herein binds to a cysteine residue of a polypeptide (e.g., a cysteine containing protein) that is about 30, 35, 40, 45, 50, 55, 60, 65, 70, 75, 80, 85, 90, 95, 100, 150, 200, 250, 300, 350, 400, 450, 500, 600, 700, 800, 900, 1000 amino acid residues in length or more.

In some instances, the small molecule fragment of Formula (I) has pharmacokinetic parameters outside of the parameters set by the FDA guideline, or by an equivalent Food and Drug Administration outside of the United States. In some instances, a skilled artisan understands in view of the pharmacokinetic parameters of the small molecule fragment of Formula (I) described herein that these small molecule fragment is unsuited as a therapeutic agent without further optimization.

In some embodiments, the small molecule fragment is a specific inhibitor or a pan inhibitor.

Cysteine-Reactive Probes

In some embodiments, a cysteine-reactive probe comprises a reactive moiety which forms a covalent interaction with the thiol group of a cysteine residue of a cysteine containing protein, and an affinity handle moiety.

In some embodiments, a cysteine-reactive probe is a cysteine-reactive probe of Formula (II):

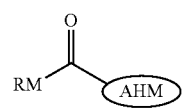

Formula (II)

wherein:
RM is a reactive moiety selected from a Michael acceptor moiety, a leaving group moiety, or a moiety capable of forming a covalent bond to the thiol group of a cysteine residue; and
AHM is an affinity handle moiety.

In some instances, the Michael acceptor moiety comprises an alkene or an alkyne moiety. In some cases, the affinity handle moiety comprises an affinity handle and a binding moiety that facilitates covalent interaction of the cysteine-reactive probe to a cysteine residue of a cysteine-containing protein. In some cases, the binding moiety is a small molecule fragment obtained from a compound library. In some instances, the compound library comprises ChemBridge fragment library, Pyramid Platform Fragment-Based Drug Discovery, Maybridge fragment library, FRGx from AnalytiCon, TCI-Frag from AnCoreX, Bio Building Blocks from ASINEX, BioFocus 3D from Charles River, Fragments of Life (FOL) from Emerald Bio, Enamine Fragment Library, IOTA Diverse 1500, BIONET fragments library, Life Chemicals Fragments Collection, OTAVA fragment library, Prestwick fragment library, Selcia fragment library, TimTec fragment-based library, Allium from Vitas-M Laboratory, or Zenobia fragment library.

In some embodiments, the affinity handle is a bioorthogonal affinity handle. In some embodiments, the affinity handle utilizes bioorthogonal chemistry. As used herein, bioorthogonal chemistry refers to any chemical reaction that occurs inside of a living system (e.g. a cell) without interfering with native biochemical processes.

In some cases, the affinity handle comprises a carbodiimide, N-hydroxysuccinimide (NHS) ester, imidoester, pentafluorophenyl ester, hydroxymethyl phosphine, maleimide, haloacetyl, pyridyl disulfide, thiosulfonate, vinylsulfone, hydrazide, alkoxyamine, alkyne, azide, or isocyanate group. In some cases, the affinity handle comprises an alkyne or an azide group.

In some instances, the affinity handle is an alkyne group. The term "alkyne group" as used in the context of an affinity handle refers to a group with a chemical formula of H—C≡C—R, $HC_2R$, $R_1$—C≡C—$R_2$, or $R_1C_2R_2$. In the context of the present chemical formula, R, $R_1$, and $R_2$ are independently a cysteine-reactive probe portion described herein, a linker, or a combination thereof. In some cases, the alkyne group is capable of being covalently linked in a chemical reaction with a molecule containing an azide. In some instances, the affinity handle is an azide group.

In some instances, the affinity handle (e.g. alkyne group or azide group) serve as nonnative and non-perturbed bioorthogonal chemical handles. In some instances, the affinity handle (e.g. alkyne group or azide group) is further derivatized through chemical reactions such as click chemistry. In some instances, the click chemistry is a copper(I)-catalyzed [3+2]-Huisgen 1,3-dipolar cyclo-addition of alkynes and azides leading to 1,2,3-triazoles. In other instances, the click chemistry is a copper free variant of the above reaction.

In some instances, the affinity handle further comprises a linker. In some instances, the linker bridges the affinity handle to the reactive moiety.

In some instances, the affinity handle is further conjugated to an affinity ligand. In some cases, the affinity ligand comprises a chromophore, a labeling group, or a combination thereof. In some embodiments, the chromophore comprises fluorochrome, non-fluorochrome chromophore, quencher, an absorption chromophore, fluorophore, organic dye, inorganic dye, metal chelate, or a fluorescent enzyme substrate. In some cases, the chromophore comprises non-fluorochrome chromophore, quencher, an absorption chromophore, fluorophore, organic dye, inorganic dye, metal chelate, or a fluorescent enzyme substrate. In other cases, the chromophore comprises a fluorophore.

In some embodiments, the fluorophore comprises rhodamine, rhodol, fluorescein, thiofluorescein, aminofluorescein, carboxyfluorescein, chlorofluorescein, methylfluorescein, sulfofluorescein, aminorhodol, carboxyrhodol, chlororhodol, methylrhodol, sulforhodol, aminorhodamine, carboxyrhodamine, chlororhodamine, methylrhodamine, sulforhodamine, thiorhodamine, cyanine, indocarbocyanine, oxacarbocyanine, thiacarbocyanine, merocyanine, cyanine 2, cyanine 3, cyanine 3.5, cyanine 5, cyanine 5.5, cyanine 7, oxadiazole derivatives, pyridyloxazole, nitrobenzoxadiazole, benzoxadiazole, pyren derivatives, cascade blue, oxazine derivatives, Nile red, Nile blue, cresyl violet, oxazine 170, acridine derivatives, proflavin, acridine orange, acridine yellow, arylmethine derivatives, auramine, crystal violet, malachite green, tetrapyrrole derivatives, porphin, phtalocyanine, bilirubin 1-dimethylaminonaphthyl-5-sulfonate, 1-anilino-8-naphthalene sulfonate, 2-p-touidinyl-6-naphthalene sulfonate, 3-phenyl-7-isocyanatocoumarin, N-(p-(2-benzoxazolyl)phenyl)maleimide, stilbenes, pyrenes, 6-FAM (Fluorescein), 6-FAM (NHS Ester), 5(6)-FAM, 5-FAM, Fluorescein dT, 5-TAMRA-cadavarine, 2-aminoacridone, HEX, JOE (NHS Ester), MAX, TET, ROX, TAMRA, TARMA™ (NHS Ester), TEX 615, ATTO™ 488, ATTO™ 532, ATTO™ 550, ATTO™ 565, ATTO™ Rho101, ATTO™ 590, ATTO™ 633, ATTO™ 647N, TYE™ 563, TYE™ 665, or TYE™ 705.

In some embodiments, the labeling group is a biotin moiety, a streptavidin moiety, bead, resin, a solid support, or a combination thereof. As used herein, a biotin moiety described herein comprises biotin and biotin derivatives. Exemplary biotin derivatives include, but are not limited by, desthiobiotin, biotin alkyne or biotin azide. In some instances, a biotin moiety described herein is desthiobiotin. In some cases, a biotin moiety described herein is d-Desthiobiotin.

In some instances, the labeling group is a biotin moiety. In some instances, the biotin moiety further comprises a linker such as a 5, 6, 7, 8, 9, 10, 11, 12, 13, 14, 15 or more residues in length. In some instances, the linker further comprises a cleavage site, such as a protease cleavage site. In some cases, the biotin moiety interacts with a streptavidin moiety. In some instances, the biotin moiety is further attached to a bead, such as a streptavidin-coupled bead. In some instances, the biotin moiety is further attached to a resin or a solid support, such as a streptavidin-coupled resin or a streptavidin-coupled solid support. In some instances, the solid support is a plate, a platform, a cover slide, a microfluidic channel, and the like.

In some embodiments, the affinity handle moiety further comprises a chromophore.

In some embodiments, the cysteine-reactive probe is a cysteine-reactive probe illustrated in FIG. 3. In some embodiments, the cysteine-reactive probe is a cysteine-reactive probe selected from: N-(hex-5-yn-1-yl)-2-iodoacetamide, Iodoacetamide-rhodamine, 3-acrylamido-N-(hex-5-yn-1-yl)-5-(trifluoromethyl)benzamide, 3-acrylamido-N-(hex-5-yn-1-yl)-5-(trifluoromethyl)benzamide, or 2-chloro-N-(1-(3-ethynylbenzoyl)piperidin-4-yl)-N-phenylacetamide.

Cysteine Containing Proteins

In some instances, the cysteine containing protein is a soluble protein or a membrane protein. In some instances, the cysteine containing protein is involved in one or more of a biological process such as protein transport, lipid metabolism, apoptosis, transcription, electron transport, mRNA processing, or host-virus interaction. In some instances, the cysteine containing protein is associated with one or more of diseases such as cancer or one or more disorders or conditions such as immune, metabolic, developmental, reproductive, neurological, psychiatric, renal, cardiovascular, or hematological disorders or conditions.

In some embodiments, the cysteine containing protein comprises a biologically active cysteine residue. In some embodiments, the cysteine containing protein comprises one or more cysteines in which at least one cysteine is a biologically active cysteine residue. In some cases, the biologically active cysteine site is a cysteine residue that is located about 10 Å or less to an active-site ligand or residue. In some cases, the cysteine residue that is located about 10 Å or less to the active-site ligand or residue is an active site cysteine. In other cases, the biologically active cysteine site is a cysteine residue that is located greater than 10 Å from an active-site ligand or residue. In some instances, the cysteine residue is located greater than 12 Å, 15 Å, 20 Å, 25 Å, 30 Å, 35 Å, 40 Å, 45 Å, or greater than 50 Å from an active-site ligand or residue. In some cases, the cysteine residue that is located greater than 10 Å from the active-site ligand or residue is a non-active site cysteine. In additional cases, the cysteine containing protein exists in an active form, or in a pro-active form.

In some embodiments, the cysteine containing protein comprises one or more functions of an enzyme, a transporter, a receptor, a channel protein, an adaptor protein, a chaperone, a signaling protein, a plasma protein, transcription related protein, translation related protein, mitochondrial protein, or cytoskeleton related protein. In some embodiments, the cysteine containing protein is an enzyme, a transporter, a receptor, a channel protein, an adaptor protein, a chaperone, a signaling protein, a plasma protein, transcription related protein, translation related protein, mitochondrial protein, or cytoskeleton related protein. In some instances, the cysteine containing protein has an uncategorized function.

In some embodiments, the cysteine containing protein is an enzyme. An enzyme is a protein molecule that accelerates or catalyzes chemical reaction. In some embodiments, non-limiting examples of enzymes include kinases, proteases, or deubiquitinating enzymes.

In some instances, exemplary kinases include tyrosine kinases such as the TEC family of kinases such as Tec, Bruton's tyrosine kinase (Btk), interleukin-2-indicible T-cell kinase (Itk) (or Emt/Tsk), Bmx, and Txk/Rlk; spleen tyrosine kinase (Syk) family such as SYK and Zeta-chain-associated protein kinase 70 (ZAP-70); Src kinases such as Src, Yes, Fyn, Fgr, Lck, Hck, Blk, Lyn, and Frk; JAK kinases such as Janus kinase 1 (JAK1), Janus kinase 2 (JAK2), Janus kinase 3 (JAK3), and Tyrosine kinase 2 (TYK2); or ErbB family of kinases such as Her1 (EGFR, ErbB1), Her2 (Neu, ErbB2), Her3 (ErbB3), and Her4 (ErbB4).

In some embodiments, the cysteine containing protein is a protease. In some embodiments, the protease is a cysteine protease. In some cases, the cysteine protease is a caspase. In some instances, the caspase is an initiator (apical) caspase. In some instances, the caspase is an effector (executioner) caspase. Exemplary caspase includes CASP2, CASP8, CASP9, CASP10, CASP3, CASP6, CASP7, CASP4, and CASP5. In some instances, the cysteine protease is a cathepsin. Exemplary cathepsin includes Cathepsin B, Cathepsin C, CathepsinF, Cathepsin H, Cathepsin K, Cathepsin L1, Cathepsin L2, Cathepsin O, Cathepsin S, Cathepsin W, or Cathepsin Z.

In some embodiments, the cysteine containing protein is a deubiquitinating enzyme (DUB). In some embodiments, exemplary deubiquitinating enzymes include cysteine proteases DUBs or metalloproteases. Exemplary cysteine protease DUBs include ubiquitin-specific protease (USP/UBP) such as USP1, USP2, USP3, USP4, USP5, USP6, USP7, USP8, USP9X, USP9Y, USP10, USP11, USP12, USP13, USP14, USP15, USP16, USP17, USP17L2, USP17L3, USP17L4, USP17L5, USP17L7, USP17L8, USP18, USP19, USP20, USP21, USP22, USP23, USP24, USP25, USP26, USP27X, USP28, USP29, USP30, USP31, USP32, USP33, USP34, USP35, USP36, USP37, USP38, USP39, USP40, USP41, USP42, USP43, USP44, USP45, or USP46; ovarian tumor (OTU) proteases such as OTUB1 and OTUB2; Machado-Josephin domain (MJD) proteases such as ATXN3 and ATXN3L; and ubiquitin C-terminal hydrolase (UCH) proteases such as BAP1, UCHL1, UCHL3, and UCHL5. Exemplary metalloproteases include the Jab1/Mov34/Mpr1 Pad1 N-terminal+(MPN+) (JAMM) domain proteases.

In some embodiments, exemplary cysteine containing proteins as enzymes include, but are not limited to, Glyceraldehyde-3-phosphate dehydrogenase (GAPDH), Protein arginine N-methyltransferase 1 (PRMT1), Peptidyl-prolyl cis-trans isomerase NIMA-interaction (PIN 1), Acetyl-CoA acetyltransferase (mitochondrial) (ACAT1), Glutathione S-transferase P (GSTP1), Elongation factor 2 (EEF2), Glutathione S-transferase omega-1 (GSTO1), Acetyl-CoA acetyltransferase (mitochondrial) (ACAT1), Protein disulfide-isomerase A4 (PDIA4), Prostaglandin E synthase 3 (PTGES3), Adenosine kinase (ADK), Elongation factor 2 (EEF2), Isoamyl acetate-hydrolyzing esterase 1 homolog (IAH1), Peroxiredoxin-5 (mitochondrial) (PRDX5), Inosine-5-monophosphate dehydrogenase 2 (IMPDH2), 3-hydroxyacyl-CoA dehydrogenase type-2 (HSD17B10), Omega-amidase NIT2 (NIT2), Aldose reductase (AKR1B1), Monofunctional C1-tetrahydrofolate synthase (mitochondrial) (MTHFD1L), Protein disulfide-isomerase A6 (PDIA6), Pyruvate kinase isozymes M1/M2 (PKM), 6-phosphogluconolactonase (PGLS), Acetyl-CoA acetyltransferase (mitochondrial) (ACAT1), ERO1-like protein alpha (ERO1L), Thioredoxin domain-containing protein 17 (TXNDC17), Protein disulfide-isomerase A4 (PDIA4), Protein disulfide-isomerase A3 (PDIA3), 3-ketoacyl-CoA thiolase (mitochondrial) (ACAA2), Dynamin-2 (DNM2), DNA replication licensing factor MCM3 (MCM3), Serine—tRNA ligase (cytoplasmic) (SARS), Fatty acid synthase (FASN), Acetyl-CoA acetyltransferase (mitochondrial) (ACAT1), Protein disulfide-isomerase (P4HB), Deoxycytidine kinase (DCK), Eukaryotic translation initiation factor 3 subunit (EIF3F), Protein disulfide-isomerase A6 (PDIA6), UDP-N-acetylglucosamine-peptide N-acetylglucosamine (OGT), Ketosamine-3-kinase (FN3KRP), Protein DJ-1 (PARK7), Phosphoglycolate phosphatase (PGP), DNA replication licensing factor MCM6 (MCM6), Fructose-2,6-bisphosphatase TIGAR (TIGAR), Cleavage and polyadenylation specificity factor subunit (CPSF3), Ubiquitin-conjugating enzyme E2 L3 (UBE2L3), Alanine—tRNA ligase, cytoplasmic (AARS), Mannose-1-phosphate guanyltransferase alpha (GMPPA), C-1-tetrahydrofolate synthase (cytoplasmic) (MTHFD1), Dynamin-1-like protein (DNM1L), Protein disulfide-isomerase A3 (PDIA3), Aspartyl aminopeptidase (DNPEP), Acetyl-CoA acetyltransferase (cytosolic) (ACAT2), Thioredoxin domain-containing protein 5 (TXNDC5), Thymidine kinase (cytosolic) (TK1), Inosine-5-monophosphate dehydrogenase 2 (IMPDH2), Ubiquitin carboxyl-terminal hydrolase isozyme L3 (UCHL3), Integrin-linked protein kinase (ILK), Cyclin-dependent kinase 2 (CDK2), Histone acetyltransferase type B catalytic subunit (HAT1), Enoyl-CoA delta isomerase 2 (mitochondrial) (ECI2), C-1-tetrahydrofolate synthase (cytoplasmic) (MTHFD1), Deoxycytidine kinase (DCK), Ubiquitin-like modifier-activating enzyme 6 (UBA6), Protein-L-isoaspartate(D-aspartate)O-methyltransferase (PCMT1), Monofunctional C1-tetrahydrofolate synthase (mitochondrial) (MTHFD1L), Thymidylate kinase (DTYMK), Protein ETHE (mitochondrial) (ETHE1), Arginine—tRNA ligase (cytoplasmic) (RARS), NEDD8-activating enzyme E1 catalytic subunit (UBA3), Dual specificity mitogen-activated protein kinase (MAP2K3), Ubiquitin-conjugating enzyme E2S (UBE2S), Amidophosphoribosyltransferase (PPAT), Succinate-semialdehyde dehydrogenase (mitochondrial) (ALDH5A1), CAD, Phosphoenolpyruvate carboxykinase (PCK2), 6-phosphofructokinase type C (PFKP), Acyl-CoA synthetase family member 2 (mitochondrial) (ACSF2), Multifunctional protein ADE2 (PAICS), Desumoylating isopeptidase 1 (DESI1), 6-phosphofructokinase type C (PFKP), V-type proton ATPase catalytic subunit A (ATP6V1A), 3-ketoacyl-CoA thiolase (peroxisomal) (ACAA1), Galactokinase (GALK), Thymidine kinase (cytosolic) (TK1), ATPase WRNIP1 (WRNIP1), Phosphoribosylformylglycinamidine synthase (PFAS), V-type proton ATPase catalytic subunit A (ATP6V1A), Thioredoxin domain-containing protein 5 (TXNDC5), 4-trimethylaminobutyraldehyde dehydrogenase (ALDH9A1), Dual specificity mitogen-activated protein kinase (MAP2K4), Calcineurin-like phosphoesterase domain-containing (CPPED1), Dual specificity protein phosphatase 12 (DUSP12), Phosphoribosylformylglycinamidine synthase (PFAS), Diphosphomevalonate decarboxylase (MVD), D-3-phosphoglycerate dehydrogenase (PHGDH), Cell cycle checkpoint control protein RAD9A (RAD9A), Peroxiredoxin-1 (PRDX1), Sorbitol dehydrogenase (SORD), Peroxiredoxin-4 (PRDX4), AMP deaminase 2 (AMPD2), Isocitrate dehydrogenase (IDH1), Pyruvate carboxylase (mitochondrial) (PC), Integrin-linked kinase-associated serine/threonine (ILKAP), Methylmalonate-semialdehyde dehydrogenase (ALDH6A1), 26S proteasome non-ATPase regulatory subunit 14 (PSMD14), Thymidylate kinase (DTYMK), 6-phosphofructo-2-kinase/fructose-2,6-bisphosphata (PFKFB2), Peroxiredoxin-5 (mitochondrial) (PRDX5), PDP1, Cathepsin B (CTSB), Transmembrane protease serine 12 (TMPRSS12), UDP-glucose 6-dehydrogenase (UGDH), Histidine triad nucleotide-binding protein 1 (HINT1), E3 ubiquitin-protein ligase UBR5 (UBR5), SAM domain and HD domain-containing protein 1 (SAMHD1), Probable tRNA threonylcarbamoyladenosine biosynthesis (OSGEP), Methylated-DNA—protein-cysteine methyltransferase (MGMT), Fatty acid synthase (FASN), Adenosine deaminase (ADA), Cyclin-dependent kinase 19 (CDK19), Serine/threonine-protein kinase 38 (STK38), Mitogen-activated protein kinase 9 (MAPK9), tRNA (adenine(58))-N(1))-methyltransferase catalytic (TRMT61A), Glyoxylate reductase/hydroxypyruvate reductase (GRHPR), Aldehyde dehydrogenase (mitochondrial) (ALDH2), Mitochondrial-processing peptidase subunit beta (PMPCB), 3-ketoacyl-CoA thiolase, peroxisomal (ACAA1), Lysophosphatidic acid phosphatase type 6 (ACP6), Ubiquitin/ISG15-conjugating enzyme E2 L6 (UBE2L6), Caspase-8 (CASP8), 2,5-phosphodiesterase 12 (PDE12), Thioredoxin domain-containing protein 12 (TXNDC12), Nitrilase homolog 1 (NIT1), ERO1-like protein alpha (ERO1L), SUMO-activating enzyme subunit 1 (SAE1), Leucine—tRNA ligase (cytoplasmic) (LARS), Protein-glutamine gamma-glutamyltransferase 2 (TGM2), Probable DNA dC-dU-editing enzyme APOBEC-3C (APOBEC3C), Double-stranded RNA-specific adenosine deaminase (ADAR), Isocitrate dehydrogenase (IDH2), Methylcrotonoyl-CoA carboxylase beta chain (mitochondrial) (MCCC2), Uridine phosphorylase 1 (UPP1), Glycogen phosphorylase (brain form) (PYGB), E3 ubiquitin-protein ligase UBR5 (UBR5), Procollagen-lysine, 2-oxoglutarate 5-dioxygenase 1 (PLOD1), Ubiquitin carboxyl-terminal hydrolase 48 (USP48), Aconitate hydratase (mitochondrial) (ACO2), GMP reductase 2 (GMPR2), Pyrroline-5-carboxylate reductase 1 (mitochondrial) (PYCR1), Cathepsin Z (CTSZ), E3 ubiquitin-protein ligase UBR2 (UBR2), Cysteine protease ATG4B (ATG4B), Serine/threonine-protein kinase Nek9 (NEK9), Lysine-specific demethylase 4B (KDM4B), Insulin-degrading enzyme (IDE), Dipeptidyl peptidase 9 (DPP9), Decaprenyl-diphosphate synthase subunit 2 (PDSS2), TFIIH basal transcription factor complex helicase (ERCC3), Methionine-R-sulfoxide reductase B2 (mitochondrial) (MSRB2), E3 ubiquitin-protein ligase BRE1B (RNF40), Thymidylate synthase (TYMS), Cyclin-dependent kinase 5 (CDK5), Bifunctional 3-phosphoadenosine 5-phosphosulfate (PAPSS2), Short/branched chain specific acyl-CoA dehydrogenase (ACADSB), Cathepsin D (CTSD), E3 ubiquitin-protein ligase HUWE1 (HUWE1), Calpain-2 catalytic subunit (CAPN2), Dual specificity mitogen-activated protein kinase (MAP2K7), Mitogen-activated protein kinase kinase kinase MLT (MLTK), Bleomycin hydrolase (BLMH), Probable ATP-dependent RNA helicase DDX59 (DDX59), Cystathionine gamma-lyase (CTH), S-adenosylmethionine synthase isoform type-2 (MAT2A), 6-phosphofructokinase type C (PFKP), Cytidine deaminase (CDA), DNA-directed RNA polymerase II subunit RPB2 (POLR2B), Protein disulfide-isomerase (P4HB), Procollagen-lysine,2-oxoglutarate 5-dioxygenase 3 (PLOD3), Nucleoside diphosphate-linked moiety X motif 8 (mitochondrial) (NUDT8), E3 ubiquitin-protein ligase HUWE1 (HUWE1), Methylated-DNA—protein-cysteine methyltransferase (MGMT), Nitrilase homolog 1 (NIT1), Interferon regulatory factor 2-binding protein 1 (IRF2BP1), Ubiquitin carboxyl-terminal hydrolase 16 (USP16), Glycylpeptide N-tetradecanoyltransferase 2 (NMT2), Cyclin-dependent kinase inhibitor 3 (CDKN3), Hydroxysteroid dehydrogenase-like protein 2 (HSDL2), Serine/threonine-protein kinase VRK1 (VRK1), Serine/threonine-protein kinase A-Raf (ARAF), ATP-citrate synthase (ACLY), Probable ribonuclease ZC3H12D (ZC3H12D), Peripheral plasma membrane protein CASK (CASK), DNA polymerase epsilon subunit 3 (POLE3), Aldehyde dehydrogenase X (mitochondrial) (ALDH1B1), UDP-N-acetylglucosamine transferase subunit ALG13 (ALG13), Protein disulfide-isomerase A4 (PDIA4), DNA polymerase alpha catalytic subunit (POLA1), Ethylmalonyl-CoA decarboxylase (ECHDC1), Protein-tyrosine kinase 2-beta (PTK2B), E3 SUMO-protein ligase RanBP2 (RANBP2), Legumain (LGMN), Non-specific lipid-transfer protein (SCP2), Long-chain-fatty-acid—CoA ligase 4 (ACSL4), Dual specificity protein phosphatase 12 (DUSP12), Oxidoreductase HTATIP2 (HTATIP2), Serine/threonine-protein kinase MRCK beta (CDC42BPB), Histone-lysine N-methyltransferase EZH2 (EZH2), Non-specific lipid-transfer protein (SCP2), Dual specificity mitogen-activated protein kinase (MAP2K7), Ubiquitin carboxyl-terminal hydrolase 28 (USP28), 6-phosphofructokinase (liver type) (PFKL), SWI/SNF-related matrix-associated actin-dependent (SMARCAD1), Protein phosphatase methylesterase 1 (PPME1), DNA replication licensing factor MCM5 (MCM5), 6-phosphofructo-2-kinase/fructose-2,6-bisphosphata (PFKFB4), Dehydrogenase/reductase SDR family member 11 (DHRS 11), Pyroglutamyl-peptidase 1 (PGPEP1), Probable E3 ubiquitin-protein ligase (MYCBP2), DNA fragmentation factor subunit beta (DFFB), Deubiquitinating protein VCIP135 (VCPIP1), Putative transferase CAF17 (mitochondrial) (IBA57), Calpain-7 (CAPN7), GDP-L-fucose synthase (TSTA3), Protein disulfide-isomerase A4 (PDIA4, Probable ATP-dependent RNA helicase DDX59 (DDX59), RNA exonuclease 4 (REXO4), PDK1, E3 SUMO-protein ligase (PIAS4), DNA (cytosine-5)-methyltransferase 1 (DNMT1), Alpha-aminoadipic semialdehyde dehydrogenase (ALDH7A1), Hydroxymethylglutaryl-CoA synthase (cytoplasmic) (HMGCS1), E3 ubiquitin-protein ligase (SMURF2), Aldehyde dehydrogenase X (mitochondrial) (ALDH1B1), Tyrosine-protein kinase (BTK), DNA repair protein RAD50 (RAD50), ATP-binding domain-containing protein 4 (ATPBD4), Nucleoside diphosphate kinase 3 (NME3), Interleukin-1 receptor-associated kinase 1 (IRAK1), Ribonuclease P/MRP protein subunit POP5 (POP5), Peptide-N(4)-(N-acetyl-beta-glucosaminyl)asparagin (NGLY1), Caspase-2 (CASP2), Ribosomal protein S6 kinase alpha-3 (RPS6KA3), E3 ubiquitin-protein ligase UBR1 (UBR1), Serine/threonine-protein kinase Chk2 (CHEK2), Phosphatidylinositol 3,4,5-trisphosphate 5-phospha (INPPL1), Histone acetyltransferase p300 (EP300), Creatine kinase U-type (mitochondrial) (CKMT1B), E3 ubiquitin-protein ligase TRIM33 (TRIM33), Cancer-related nucleoside-triphosphatase (NTPCR), Aconitate hydratase (mitochondrial) (ACO2), Ubiquitin carboxyl-terminal hydrolase 34 (USP34), Probable E3 ubiquitin-protein ligase HERC4 (HERC4), E3 ubiquitin-protein ligase HECTD1 (HECTD1), Peroxisomal 2,4-dienoyl-CoA reductase (DECR2), Helicase ARIP4 (RAD54L2), Ubiquitin-like modifier-activating enzyme 7 (UBA7), ER degradation-enhancing alpha-mannosidase-like 3 (EDEM3), Ubiquitin-conjugating enzyme E20 (UBE2O), Dual specificity mitogen-activated protein kinase (MAP2K7), Myotubularin-related protein 1 (MTMR1), Calcium-dependent phospholipase A2 (PLA2G5), Mitotic checkpoint serine/threonine-protein kinase (BUB1B), Putative transferase CAF17 (mitochondrial) (IBA57), Tyrosine-protein kinase ZAP-70 (ZAP70), E3 ubiquitin-protein ligase pellino homolog 1 (PELI1), Neuropathy target esterase (PNPLA6), Ribosomal protein S6 kinase alpha-3 (RPS6KA3), N6-adenosine-methyltransferase 70 kDa subunit (METTL3), Fructosamine-3-kinase (FN3K), Ubiquitin carboxyl-terminal hydrolase 22 (USP22), Rab3 GTPase-activating protein catalytic subunit (RAB3GAP1), Caspase-5 (CASP5), L-2-hydroxyglutarate dehydrogenase (mitochondrial) (L2HGDH), Saccharopine dehydrogenase-like oxidoreductase (SCCPDH), FLAD FAD synthase, Lysine-specific demethylase 3A (KDM3A), or Ubiquitin carboxyl-terminal hydrolase 34 (USP34).

In some embodiments, the cysteine containing protein is a signaling protein. In some instances, exemplary signaling protein includes vascular endothelial growth factor (VEGF) proteins or proteins involved in redox signaling. Exemplary VEGF proteins include VEGF-A, VEGF-B, VEGF-C, VEGF-D, and PGF. Exemplary proteins involved in redox signaling include redox-regulatory protein FAM213A.

In some embodiments, the cysteine containing protein is a transcription factor or regulator. Exemplary cysteine containing proteins as transcription factors and regulators include, but are not limited to, 40S ribosomal protein S3 (RPS3), Basic leucine zipper and W2 domain-containing protein (BZW1), Poly(rC)-binding protein 1 (PCBP1), 40S ribosomal protein S11 (RPS11), 40S ribosomal protein S4, X isoform (RPS4X), Signal recognition particle 9 kDa protein (SRP9), Non-POU domain-containing octamer-binding protein (NONO), N-alpha-acetyltransferase 15, NatA auxiliary subunit (NAA15), Cleavage stimulation factor subunit 2 (CSTF2), Lamina-associated polypeptide 2, isoform alpha (TMPO), Heterogeneous nuclear ribonucleoprotein R (HNRNPR), MMS19 nucleotide excision repair protein homolog (MMS19), SWI/SNF complex subunit SMARCC2 (SMARCC2), Enhancer of mRNA-decapping protein 3 (EDC3), H/ACA ribonucleoprotein complex subunit 2 (NHP2), WW domain-containing adapter protein with coiled-c (WAC), N-alpha-acetyltransferase 15 NatA auxiliary subunit (NAA15), 40S ribosomal protein S11 (RPS11), Signal transducer and activator of transcription 1 (STAT1), Mediator of RNA polymerase II transcription subunit (MED15), Lamina-associated polypeptide 2 (isoform alpha) (TMPO), MMS19 nucleotide excision repair protein homolog (MMS19), DNA mismatch repair protein Msh2 (MSH2), Recombining binding protein suppressor of hairless (RBPJ), Mediator of RNA polymerase II transcription subunit (MED17), Heterogeneous nuclear ribonucleoprotein U (HNRNPU), Transcription initiation factor IIA subunit 2 (GTF2A2), Chromatin accessibility complex protein 1 (CHRAC1), CDKN2A-interacting protein (CDKN2AIP), Zinc finger protein 217 (ZNF217), Signal transducer and activator of transcription 3 (STAT3), WD repeat and HMG-box DNA-binding protein 1 (WDHD1), Lamina-associated polypeptide 2 (isoform alpha) (TMPO), Lamina-associated polypeptide 2 (isoforms beta/gam) (TMPO), Interferon regulatory factor 4 (IRF4), Protein flightless-1 homolog (FLII), Heterogeneous nuclear ribonucleoprotein F (HNRNPF), Nucleus accumbens-associated protein 1 (NACC1), Transcription elongation regulator 1 (TCERG1), Protein HEXIM1 (HEXIM1), Enhancer of mRNA-decapping protein (EDC3), Zinc finger protein Aiolos (IKZF3), Transcription elongation factor SPT5 (SUPT5H), Forkhead box protein K1 (FOXK1), LIM domain-containing protein 1 (LIMD1), MMS19 nucleotide excision repair protein homolog (MMS19), Elongator complex protein 4 (ELP4), Ankyrin repeat and KH domain-containing protein 1 (ANKHD1), PML, Nuclear factor NF-kappa-B p100 subunit (NFKB2), Heterogeneous nuclear ribonucleoprotein L-like (HNRPLL), CCR4-NOT transcription complex subunit 3 (CNOT3), Constitutive coactivator of PPAR-gamma-like protein (FAM120A), Mediator of RNA polymerase II transcription subunit (MED15), 60S ribosomal protein L7 (RPL7), Interferon regulatory factor 8 (IRF8), COUP transcription factor 2 (NR2F2), Mediator of RNA polymerase II transcription subunit (MED1), tRNA (uracil-5-)-methyltransferase homolog A (TRMT2A), Transcription factor p65 (RELA), Exosome complex component RRP42 (EXOSC7), General transcription factor 3C polypeptide 1 (GTF3C1), Mothers against decapentaplegic homolog 2 (SMAD2), Ankyrin repeat domain-containing protein 17 (ANKRD17), MMS19 nucleotide excision repair protein homolog (MMS19), Death domain-associated protein 6 (DAXX), Zinc finger protein 318 (ZNF318), Thioredoxin-interacting protein (TXNIP), Glucocorticoid receptor (NR3C1), Iron-responsive element-binding protein 2 (IREB2), Zinc finger protein 295 (ZNF295), Polycomb protein SUZ12 (SUZ12), Cleavage stimulation factor subunit 2 tau variant (CSTF2T), C-myc promoter-binding protein (DENND4A), Pinin (PNN), Mediator of RNA polymerase II transcription subunit (MED9), POU domain, class 2, transcription factor 2 (POU2F2), Enhancer of mRNA-decapping protein 3 (EDC3), A-kinase anchor protein 1 (mitochondrial) (AKAP1), Transcription factor RelB (RELB), RNA polymerase II-associated protein 1 (RPAP1), Zinc finger protein 346 (ZNF346), Chromosome-associated kinesin KIF4A (KIF4A), Mediator of RNA polymerase II transcription subunit (MED12), Protein NPAT (NPAT), Leucine-rich PPR motif-containing protein (mitochondrial) (LRPPRC), AT-hook DNA-binding motif-containing protein 1 (AHDC1), Mediator of RNA polymerase II transcription subunit (MED12), Bromodomain-containing protein 8 (BRD8), Trinucleotide repeat-containing gene 6B protein (TNRC6B), Aryl hydrocarbon receptor nuclear translocator (ARNT), Activating transcription factor 7-interacting protein (ATF7IP), Glucocorticoid receptor (NR3C1), Chromosome transmission fidelity protein 18 homolog (CHTF18), or C-myc promoter-binding protein (DENND4A).

In some embodiments, the cysteine containing protein is a channel, transporter or receptor. Exemplary cysteine containing proteins as channels, transporters, or receptors include, but are not limited to, Chloride intracellular channel protein 4 (CLIC4), Exportin-1 (XPO1), Thioredoxin (TXN), Protein SEC13 homolog (SEC13), Chloride intracellular channel protein 1 (CLIC1), Guanine nucleotide-binding protein subunit beta-2 (GNB2L1), Sorting nexin-6 (SNX6), Conserved oligomeric Golgi complex subunit 3 (COG3), Nuclear cap-binding protein subunit 1 (NCBP1), Cytoplasmic dynein 1 light intermediate chain 1 (DYNC1L1), MOB-like protein phocein (MOB4), Programmed cell death 6-interacting protein (PDCD6IP), Glutaredoxin-1 (GLRX), ATP synthase subunit alpha (mitochondrial) (ATP5A1), Treacle protein (TCOF1), Dynactin subunit 1 (DCTN1), Importin-7 (IP07), Exportin-2 (CSE1L), ATP synthase subunit gamma (mitochondrial) (ATP5C1), Trafficking protein particle complex subunit 5 (TRAPPC5), Thioredoxin mitochondrial (TXN2), THO complex subunit 6 homolog (THOC6), Exportin-1 (XPO1), Nuclear pore complex protein Nup50 (NUP50), Treacle protein (TCOF1), Nuclear pore complex protein Nup93 (NUP93), Nuclear pore glycoprotein p62 (NUP62), Cytoplasmic dynein 1 heavy chain 1 (DYNC1H1), Thioredoxin-like protein 1 (TXNL1), Nuclear pore complex protein Nup214 (NUP214), Protein lin-7 homolog C (LIN7C), ADP-ribosylation factor-binding protein GGA2 (GGA2), Trafficking protein particle complex subunit 4 (TRAPPC4), Protein quaking (QKI), Perilipin-3 (PLIN3), Copper transport protein ATOX1 (ATOX1), Unconventional myosin-Ic (MYOIC), Nucleoporin NUP53 (NUP35), Vacuolar protein sorting-associated protein 18 homolog (VPS 18), Dedicator of cytokinesis protein 7 (DOCK7), Nucleoporin p54 (NUP54), Ras-related GTP-binding protein C (RRAGC), Arf-GAP with Rho-GAP domain (ANK repeat and PH domain) (ARAPI), Exportin-5 (XPOS5), Kinectin (KTN1), Chloride intracellular channel protein 6 (CLIC6), Voltage-gated potassium channel subunit beta-2 (KCNAB2), Exportin-5 (XPOS5), Ras-related GTP-binding protein C (RRAGC), Ribosome-binding protein 1 (RRBP1), Acyl-CoA-binding domain-containing protein 6 (ACBD6), Chloride intracellular channel protein 5 (CLIC5), Pleckstrin homology domain-containing family A member (PLEKHA2), ADP-ribosylation factor-like protein 3 (ARL3), Protein transport protein Sec24C (SEC24C), Voltage-dependent anion-selective channel protein (VDAC3), Programmed cell death 6-interacting protein (PDCD6IP), Chloride intracellular channel protein 3 (CLIC3), Multivesicular body subunit 12A (FAM125A), Eukaryotic translation initiation factor 4E transporter (EIF4ENIF1), NmrA-like family domain-containing protein 1 (NMRAL1), Nuclear pore complex protein Nup98-Nup96 (NUP98), Conserved oligomeric Golgi complex subunit 1 (COG1), Importin-4 (IP04), Pleckstrin homology domain-containing family A member (PLEKHA2), Cytoplasmic dynein 1 heavy chain 1 (DYNC1H1), DENN domain-containing protein 1C (DENND1C), Cytoplasmic dynein 1 heavy chain 1 (DYNC1H1), Protein ELYS (AHCTF1), Trafficking protein particle complex subunit 1 (TRAPPC1), Guanine nucleotide-binding protein-like 3 (GNL3), or Importin-13 (IPO13).

In some embodiments, the cysteine containing protein is a chaperone. Exemplary cysteine containing proteins as chaperones include, but are not limited to, 60 kDa heat shock protein (mitochondrial) (HSPD1), T-complex protein 1 subunit eta (CCT7), T-complex protein 1 subunit epsilon (CCTS5), Heat shock 70 kDa protein 4 (HSPA4), GrpE protein homolog 1 (mitochondrial) (GRPEL1), Tubulin-specific chaperone E (TBCE), Protein unc-45 homolog A (UNC45A), Serpin H1 (SERPINH1), Tubulin-specific chaperone D (TBCD), Peroxisomal biogenesis factor 19 (PEX19), BAG family molecular chaperone regulator 5 (BAGS), T-complex protein 1 subunit theta (CCT8), Protein canopy homolog 3 (CNPY3), DnaJ homolog subfamily C member 10 (DNAJC10), ATP-dependent Clp protease ATP-binding subunit clp (CLPX), or Midasin (MDN1).

In some embodiments, the cysteine containing protein is an adapter, scaffolding or modulator protein. Exemplary cysteine containing proteins as adapter, scaffolding, or modulator proteins include, but are not limited to, Proteasome activator complex subunit 1 (PSME1), TIP41-like protein (TIPRL), Crk-like protein (CRKL), Cofilin-1 (CFL 1), Condensin complex subunit 1 (NCAPD2), Translational activator GCN1 (GCN1L1), Serine/threonine-protein phosphatase 2A 56 kDa regulatory (PPP2R5D), UPF0539 protein C7orf59 (C7orf59), Protein diaphanous homolog 1 (DIAPH1), Protein asunder homolog (Asun), Ras GTPase-activating-like protein IQGAP1 (IQGAP1), Sister chromatid cohesion protein PDS5 homolog A (PDS5A), Reticulon-4 (RTN4), Proteasome activator complex subunit 4 (PSME4), Condensin complex subunit 2 (NCAPH), Sister chromatid cohesion protein PDS5 homolog A (PDS5A), cAMP-dependent protein kinase type I-alpha regulatory (PRKAR1A), Host cell factor 1 (HCFC1), Serine/threonine-protein phosphatase 4 regulatory (PPP4R2), Apoptotic chromatin condensation inducer in the nucleus (ACIN1), BRISC and BRCA1-A complex member 1 (BABAM1), Interferon-induced protein with tetratricopeptide (IFIT3), Ras association domain-containing protein 2 (RASSF2), Hsp70-binding protein 1 (HSPBP1), TBC1 domain family member 15 (TBC1D15), Dynamin-binding protein (DNMBP), Condensin complex subunit 1 (NCAPD2), Beta-2-syntrophin (SNTB2), Disks large homolog 1 (DLG1), TBC1 domain family member 13 (TBC1D13), Formin-binding protein 1-like (FNBPIL), Translational activator GCN1 (GCN1L1), GRB2-related adapter protein (GRAP), G2/mitotic-specific cyclin-B1 (CCNB1), Myotubularin-related protein 12 (MTMR12), Protein FADD (FADD), Translational activator GCN1 (GCN1L1), Wings apart-like protein homolog (WAPAL), cAMP-dependent protein kinase type II-beta regulatory (PRKAR2B), Malcavernin (CCM2), MPP1 55 kDa erythrocyte membrane protein, Actin filament-associated protein 1 (AFAP1), Tensin-3 (TNS3), tRNA methyltransferase 112 homolog (TRMT112), Symplekin (SYMPK), TBC1 domain family member 2A (TBC1D2), ATR-interacting protein (ATRIP), Ataxin-10 (ATXN10), Succinate dehydrogenase assembly factor 2 (mitochondrial) (SDHAF2), Formin-binding protein 1 (FNBP1), Myotubularin-related protein 12 (MTMR12), Interferon-induced protein with tetratricopeptide (IFIT3), Protein CBFA2T2 (CBFA2T2), Neutrophil cytosol factor 1 (NCF1), or Protein syndesmos (NUDT16L1).

In some embodiments, a cysteine containing protein comprises a protein illustrated in Tables 1-5 or Tables 7-9. In some instances, a cysteine containing protein comprises a protein illustrated in Table 1. In some embodiments, the cysteine containing protein comprises a cysteine residue denoted in Table 1. In some instances, a cysteine containing protein comprises a protein illustrated in Table 2. In some embodiments, the cysteine containing protein comprises a cysteine residue denoted in Table 2. In some instances, a cysteine containing protein comprises a protein illustrated in Table 3. In some embodiments, the cysteine containing protein comprises a cysteine residue denoted in Table 3. In some instances, a cysteine containing protein comprises a protein illustrated in Table 4. In some embodiments, the cysteine containing protein comprises a cysteine residue denoted in Table 4. In some instances, a cysteine containing protein comprises a protein illustrated in Table 5. In some embodiments, the cysteine containing protein comprises a cysteine residue denoted in Table 5. In some instances, a cysteine containing protein comprises a protein illustrated in Table 7. In some embodiments, the cysteine containing protein comprises a cysteine residue denoted in Table 7. In some instances, a cysteine containing protein comprises a protein illustrated in Table 8. In some embodiments, the cysteine containing protein comprises a cysteine residue denoted in Table 8. In some instances, a cysteine containing protein comprises a protein illustrated in Table 9. In some embodiments, the cysteine containing protein comprises a cysteine residue denoted in Table 9. In some instances, the cysteine containing protein is a modified protein, in which the protein is modified at a cysteine residue site by a small molecule fragment described herein, such as for example, by a small molecule fragment of Formula (I) described herein, a cysteine-reactive probe of Formula (II) described herein, or by a small molecule fragment illustrated in FIG. 3.

In some embodiments, described herein is a modified cysteine containing protein comprising a small molecule fragment having a covalent bond to a cysteine residue of a cysteine containing protein. In some instances, the cysteine containing protein is selected from Table 3. In some cases, one or more cysteine residues of each respective cysteine containing protein are denoted in Table 3. In some cases, a cysteine containing protein selected from Table 3 is modified by a small molecule fragment at at least one cysteine site denoted in Table 3 to generate a modified cysteine containing protein. In some cases, the cysteine containing protein is selected from AIP, PES1, IKBKB, XPO1, KDM4B, NR3C1, GSTP1, TNFAIP3, ACAT1, IRAK1, GNB2L1, IRF4, USP34, ZC3HAV1, USP7, PELI1, DCUN1D1, USP28, UBE2O, RRAGC, MLTK, USP22, KDM3A, or USP16. In some cases, the cysteine containing protein is selected from AIP, PES1, IKBKB, XPO1, GSTP1, ACAT1, IRAK1, IRF4, ZC3HAV1, USP7, PELI1, USP28, UBE2O, RRAGC, MLTK, USP22, KDM3A, or USP16. In some cases, the cysteine containing protein is selected from KDM4B, NR3C1, TNFAIP3, USP7 or USP22. In some cases, the cysteine containing protein is selected from GNB2L1 or USP34. In some cases, the cysteine containing protein is DCUN1D1. In some cases, the cysteine containing protein is selected from PES1, IKBKB, GSTP1, ACAT1, IRAK1, ZC3HAV1 or RRAGC. In some cases, the cysteine containing protein is selected from XPO1, GNB2L1, USP34, UBE2O, MLTK or USP22. In some cases, the cysteine containing protein is selected from KDM4B or NR3C1. In some cases, the cysteine containing protein is selected from TNFAIP3, USP7, USP28, KDM3A or USP16. In some cases, the cysteine containing protein is selected from IRF4, PELI1, DCUN1D1 or USP22. In some cases, the cysteine containing protein is AIP. In some cases, the cysteine containing protein is an enzyme and the enzyme is selected from IKBKB, KDM4B, GSTP1, TNFAIP3, ACAT1, IRAK1, USP34, USP7, PELI1, USP28, UBE2O, MLTK, USP22, KDM3A, or USP16. In some cases, the cysteine containing protein is a transcription factor or regulator and the transcription factor or regulator is selected from NR3C1, IRF4 or ZC3HAV1. In some cases, the cysteine containing protein is a channel, a transporter, or a receptor and the channel, transporter, or receptor is selected from GNB2L1 or RRAGC. In some cases, the cysteine containing protein is selected from AIP, PES1, XPO1 or DCUN1D1. In some cases, the cysteine containing protein is selected from PES1, CYR61, UBE2L6, XPO1, ADA, NR3C1, POU2F2, UCHL3, MGMT, ERCC3, ACAT1, STAT3, UBA7, CASP2, IDH2, LRBA, UBE2L3, RELB, IRF8, CASP8, PDIA6, PCK2, PFKFB4, PDE12, USP34, USP48, SMARCC2 or SAMHD1. In some cases, the cysteine containing protein is selected from PES1, CYR61, NR3C1, UCHL3, ERCC3, ACAT1, STAT3, CASP2, LRBA, UBE2L3, RELB, PDIA6, PCK2, PFKFB4, USP48 or SMARCC2. In some cases, the cysteine containing protein is selected from UBE2L6, POU2F2, MGMT, ACAT1, UBA7, CASP8, PDE12 or USP34. In some cases, the cysteine containing protein is selected from CYR61 or XPO1. In some cases, the cysteine containing protein is selected from ADA, MGMT, IDH2, IRF8 or SAMHD1. In some cases, the cysteine containing protein is selected from PES1, CYR61, XPO1, NR3C1 or SMARCC2. In some cases, the cysteine containing protein is selected from CYR61, UBE2L6, MGMT, ERCC3, ACAT1 or USP48. In some cases, the cysteine containing protein is selected from ADA, RELB or USP34. In some cases, the cysteine containing protein is selected from UCHL3, CASP2, IDH2, LRBA, CASP8, PCK2 or PDE12. In some cases, the cysteine containing protein is selected from MGMT, ACAT1, UBA7, UBE2L3 or IRF8. In some cases, the cysteine containing protein is selected from PFKFB4, ACAT1 or STAT3. In some cases, the cysteine containing protein is selected from POU2F2, PDIA6 or SAMHD1. In some cases, the cysteine containing protein is an enzyme and the enzyme is selected from UBE2L6, ADA, UCHL3, MGMT, ERCC3, ACAT1, UBA7, CASP2, IDH2, UBE2L3, CASP8, PDIA6, PCK2, PFKFB4, PDE12, USP34, USP48 or SAMHD1. In some cases, the cysteine containing protein is a transcription factor or a regulator and the transcription factor or regulator is selected from NR3C1, POU2F2, STAT3, RELB, IRF8 or SMARCC2. In some cases, the cysteine containing protein is selected from ZAP70, PRKCQ or PRMT1. In some cases, the cysteine containing protein is selected from ZAP70 or PRKCQ. In some cases, the cysteine containing protein is selected from CYR61, ZNF217, NCF1, IREB2, LRBA, CDK5, EP300, EZH2, UBE2S, VCPIP1, RRAGC or IRAK4. In some cases, the cysteine containing protein is selected from CYR61, ZNF217, IREB2, EP300, UBE2S, VCPIP1, RRAGC or IRAK4. In some cases, the cysteine containing protein is selected from NCF1, LRBA or CDK5. In some cases, the cysteine containing protein is EZH2. In some cases, the cysteine containing protein is selected from ZNF217, NCF1, CDK5, EP300 or IRAK4. In some cases, the cysteine containing protein is selected from CYR61, IREB2, LRBA or UBE2S. In some cases, the cysteine containing protein is selected from EZH2, VCPIP1 or RRAGC. In some cases, the cysteine containing protein is an enzyme and the enzyme is selected from CDK5, EP300, EZH2, UBE2S, VCPIP1 or IRAK4. In some cases, the cysteine containing protein is a transcription factor or a regulator and the transcription factor or regulator is selected from ZNF217 or IREB2. In some cases, the cysteine containing protein is an adapter, a scaffolding protein or a modulator protein and the adapter, scaffolding protein or the modulator protein is selected from NCF1. In some cases, the cysteine containing protein is a channel, a transporter or a receptor and the channel, transporter, or receptor is selected from RRAGC. In some cases, the cysteine containing protein is selected from CYR61 or LRBA. In some cases, the cysteine containing protein is about 20, 30, 35, 40, 45, 50, 55, 60, 65, 70, 75, 80, 85, 90, 95, 100, 150, 200, 250, 300, 350, 400, 450, 500, 600, 700, 800, 900, 1000 amino acid residues in length or more. In some cases, the cysteine residue of the modified cysteine containing protein has the structure SR, wherein R is selected from:

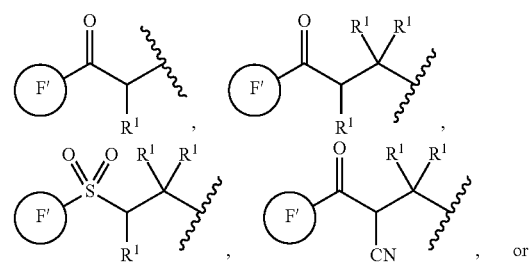

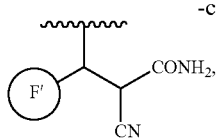

wherein $R^1$ is H, C1-C3 alkyl, or aryl; and F' is the small molecule fragment moiety. In some cases, the small molecule fragment has a molecular weight of about 175, 200, 225, 250, 275, 300, 350, 400, 450, 500, 550, 600, 650, 700, 750, 800, 850, 900, 950, 1000 Dalton, or higher. In some cases, the molecular weight of the small molecule fragment is prior to enrichment with a halogen, a nonmetal, or a transition metal. In some embodiments, the molecular weight of the small molecule fragment is calculated based on carbon and hydrogen atoms and optionally further based on nitrogen, oxygen and/or sulfur atoms. In some embodiments, the molecular weight of the small molecule fragment does not include the molecular weight of a halogen, a transition metal or a combination thereof. In some cases, the small molecule fragment is a small molecule fragment of Formula (I):

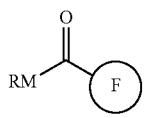

wherein RM is a reactive moiety selected from a Michael acceptor moiety, a leaving group moiety, or a moiety capable of forming a covalent bond with the thiol group of a cysteine residue; and F is a small molecule fragment moiety. In some cases, the Michael acceptor moiety comprises an alkene or an alkyne moiety. In some cases, F is obtained from a compound library. In some cases, F is a small molecule fragment moiety illustrated in FIG. 3. In some cases, F further comprises a linker moiety that connects F to the carbonyl moiety. In some cases, the small molecule fragment binds irreversibly to the cysteine containing protein. In some cases, the small molecule fragment binds reversibly to the cysteine containing protein.

In some embodiments, described herein is a modified cysteine containing protein comprising a small molecule fragment having a covalent bond to a cysteine residue of a cysteine containing protein, in which the cysteine containing protein is selected from Table 10A, enzymes. In some cases, one or more cysteine residues of each respective cysteine containing protein are denoted in Table 10A. In some cases, a cysteine containing protein selected from Table 10A is modified by a small molecule fragment at at least one cysteine site denoted in Table 10A to generate a modified cysteine containing protein. In some cases, the cysteine containing protein is about 20, 30, 35, 40, 45, 50, 55, 60, 65, 70, 75, 80, 85, 90, 95, 100, 150, 200, 250, 300, 350, 400, 450, 500, 600, 700, 800, 900, 1000 amino acid residues in length or more. In some cases, the cysteine residue of the modified cysteine containing protein has the structure SR, wherein R is selected from:

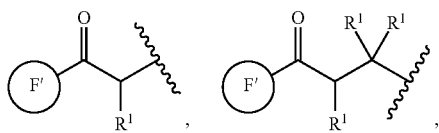

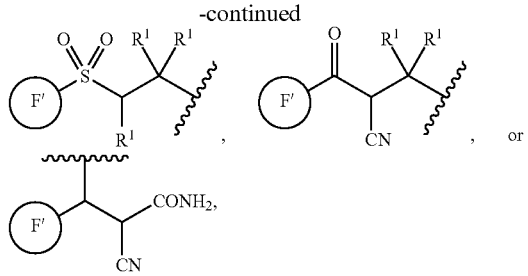

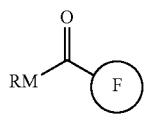

wherein $R^1$ is H, C1-C3 alkyl, or aryl; and F' is the small molecule fragment moiety. In some cases, the small molecule fragment has a molecular weight of about 175, 200, 225, 250, 275, 300, 350, 400, 450, 500, 550, 600, 650, 700, 750, 800, 850, 900, 950, 1000 Dalton, or higher. In some cases, the molecular weight of the small molecule fragment is prior to enrichment with a halogen, a nonmetal, or a transition metal. In some embodiments, the molecular weight of the small molecule fragment is calculated based on carbon and hydrogen atoms and optionally further based on nitrogen, oxygen and/or sulfur atoms. In some embodiments, the molecular weight of the small molecule fragment does not include the molecular weight of a halogen, a transition metal or a combination thereof. In some cases, the small molecule fragment is a small molecule fragment of Formula (I):

wherein RM is a reactive moiety selected from a Michael acceptor moiety, a leaving group moiety, or a moiety capable of forming a covalent bond with the thiol group of a cysteine residue; and F is a small molecule fragment moiety. In some cases, the Michael acceptor moiety comprises an alkene or an alkyne moiety. In some cases, F is obtained from a compound library. In some cases, F is a small molecule fragment moiety illustrated in FIG. 3. In some cases, F further comprises a linker moiety that connects F to the carbonyl moiety. In some cases, the small molecule fragment binds irreversibly to the cysteine containing protein. In some cases, the small molecule fragment binds reversibly to the cysteine containing protein.

In some embodiments, described herein is a modified cysteine containing protein comprising a small molecule fragment having a covalent bond to a cysteine residue of a cysteine containing protein, in which the cysteine containing protein is selected from Table 10B, transcription factors and regulators. In some cases, one or more cysteine residues of each respective cysteine containing protein are denoted in Table 10B. In some cases, a cysteine containing protein selected from Table 10B is modified by a small molecule fragment at at least one cysteine site denoted in Table 10B to generate a modified cysteine containing protein. In some cases, the cysteine containing protein is about 20, 30, 35, 40, 45, 50, 55, 60, 65, 70, 75, 80, 85, 90, 95, 100, 150, 200, 250, 300, 350, 400, 450, 500, 600, 700, 800, 900, 1000 amino acid residues in length or more. In some cases, the cysteine residue of the modified cysteine containing protein has the structure SR, wherein R is selected from:

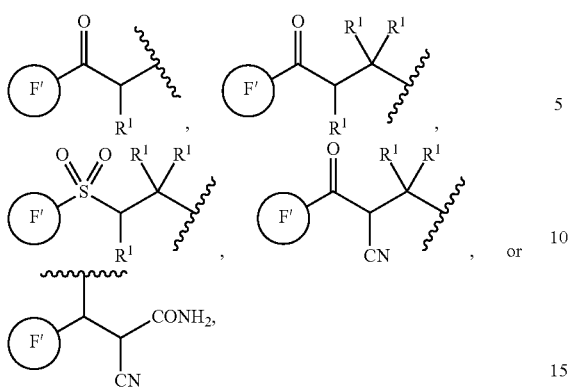

wherein $R^1$ is H, C1-C3 alkyl, or aryl; and F' is the small molecule fragment moiety. In some cases, the small molecule fragment has a molecular weight of about 175, 200, 225, 250, 275, 300, 350, 400, 450, 500, 550, 600, 650, 700, 750, 800, 850, 900, 950, 1000 Dalton, or higher. In some cases, the molecular weight of the small molecule fragment is prior to enrichment with a halogen, a nonmetal, or a transition metal. In some embodiments, the molecular weight of the small molecule fragment is calculated based on carbon and hydrogen atoms and optionally further based on nitrogen, oxygen and/or sulfur atoms. In some embodiments, the molecular weight of the small molecule fragment does not include the molecular weight of a halogen, a transition metal or a combination thereof. In some cases, the small molecule fragment is a small molecule fragment of Formula (I):

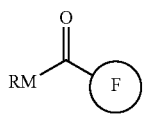

wherein RM is a reactive moiety selected from a Michael acceptor moiety, a leaving group moiety, or a moiety capable of forming a covalent bond with the thiol group of a cysteine residue; and F is a small molecule fragment moiety. In some cases, the Michael acceptor moiety comprises an alkene or an alkyne moiety. In some cases, F is obtained from a compound library. In some cases, F is a small molecule fragment moiety illustrated in FIG. 3. In some cases, F further comprises a linker moiety that connects F to the carbonyl moiety. In some cases, the small molecule fragment binds irreversibly to the cysteine containing protein. In some cases, the small molecule fragment binds reversibly to the cysteine containing protein.

In some embodiments, described herein is a modified cysteine containing protein comprising a small molecule fragment having a covalent bond to a cysteine residue of a cysteine containing protein, in which the cysteine containing protein is selected from Table 10C, channels, transporters or receptors. In some cases, one or more cysteine residues of each respective cysteine containing protein are denoted in Table 10C. In some cases, a cysteine containing protein selected from Table 10C is modified by a small molecule fragment at at least one cysteine site denoted in Table 10C to generate a modified cysteine containing protein. In some cases, the cysteine containing protein is about 20, 30, 35, 40, 45, 50, 55, 60, 65, 70, 75, 80, 85, 90, 95, 100, 150, 200, 250, 300, 350, 400, 450, 500, 600, 700, 800, 900, 1000 amino acid residues in length or more. In some cases, the cysteine residue of the modified cysteine containing protein has the structure SR, wherein R is selected from:

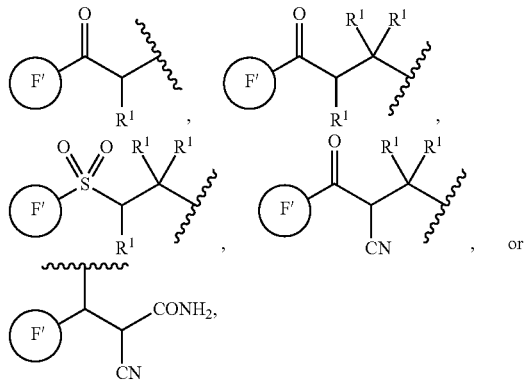

wherein $R^1$ is H, C1-C3 alkyl, or aryl; and F' is the small molecule fragment moiety. In some cases, the small molecule fragment has a molecular weight of about 175, 200, 225, 250, 275, 300, 350, 400, 450, 500, 550, 600, 650, 700, 750, 800, 850, 900, 950, 1000 Dalton, or higher. In some cases, the molecular weight of the small molecule fragment is prior to enrichment with a halogen, a nonmetal, or a transition metal. In some embodiments, the molecular weight of the small molecule fragment is calculated based on carbon and hydrogen atoms and optionally further based on nitrogen, oxygen and/or sulfur atoms. In some embodiments, the molecular weight of the small molecule fragment does not include the molecular weight of a halogen, a transition metal or a combination thereof. In some cases, the small molecule fragment is a small molecule fragment of Formula (I):

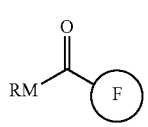

wherein RM is a reactive moiety selected from a Michael acceptor moiety, a leaving group moiety, or a moiety capable of forming a covalent bond with the thiol group of a cysteine residue; and F is a small molecule fragment moiety. In some cases, the Michael acceptor moiety comprises an alkene or an alkyne moiety. In some cases, F is obtained from a compound library. In some cases, F is a small molecule fragment moiety illustrated in FIG. 3. In some cases, F further comprises a linker moiety that connects F to the carbonyl moiety. In some cases, the small molecule fragment binds irreversibly to the cysteine containing protein. In some cases, the small molecule fragment binds reversibly to the cysteine containing protein.

In some embodiments, described herein is a modified cysteine containing protein comprising a small molecule fragment having a covalent bond to a cysteine residue of a cysteine containing protein, in which the cysteine containing protein is selected from Table 10D, adapter, scaffolding, or modulator proteins. In some cases, one or more cysteine residues of each respective cysteine containing protein are denoted in Table 10D. In some cases, a cysteine containing protein selected from Table 10D is modified by a small molecule fragment at at least one cysteine site denoted in Table 10D to generate a modified cysteine containing protein. In some cases, the cysteine containing protein is about 20, 30, 35, 40, 45, 50, 55, 60, 65, 70, 75, 80, 85, 90, 95, 100, 150, 200, 250, 300, 350, 400, 450, 500, 600, 700, 800, 900, 1000 amino acid residues in length or more. In some cases, the cysteine residue of the modified cysteine containing protein has the structure SR, wherein R is selected from:

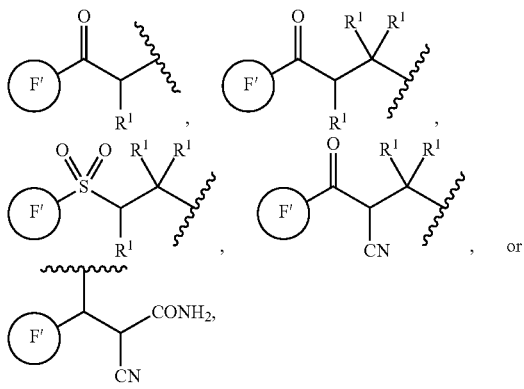

wherein $R^1$ is H, C1-C3 alkyl, or aryl; and F' is the small molecule fragment moiety. In some cases, the small molecule fragment has a molecular weight of about 175, 200, 225, 250, 275, 300, 350, 400, 450, 500, 550, 600, 650, 700, 750, 800, 850, 900, 950, 1000 Dalton, or higher. In some cases, the molecular weight of the small molecule fragment is prior to enrichment with a halogen, a nonmetal, or a transition metal. In some embodiments, the molecular weight of the small molecule fragment is calculated based on carbon and hydrogen atoms and optionally further based on nitrogen, oxygen and/or sulfur atoms. In some embodiments, the molecular weight of the small molecule fragment does not include the molecular weight of a halogen, a transition metal or a combination thereof. In some cases, the small molecule fragment is a small molecule fragment of Formula (I):

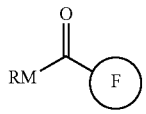

wherein RM is a reactive moiety selected from a Michael acceptor moiety, a leaving group moiety, or a moiety capable of forming a covalent bond with the thiol group of a cysteine residue; and F is a small molecule fragment moiety. In some cases, the Michael acceptor moiety comprises an alkene or an alkyne moiety. In some cases, F is obtained from a compound library. In some cases, F is a small molecule fragment moiety illustrated in FIG. 3. In some cases, F further comprises a linker moiety that connects F to the carbonyl moiety. In some cases, the small molecule fragment binds irreversibly to the cysteine containing protein. In some cases, the small molecule fragment binds reversibly to the cysteine containing protein.

In some embodiments, described herein is a modified cysteine containing protein comprising a small molecule fragment having a covalent bond to a cysteine residue of a cysteine containing protein, in which the cysteine containing protein is selected from Table 10E. In some cases, one or more cysteine residues of each respective cysteine containing protein are denoted in Table 10E. In some cases, a cysteine containing protein selected from Table 10E is modified by a small molecule fragment at at least one cysteine site denoted in Table 10E to generate a modified cysteine containing protein. In some cases, the cysteine containing protein is about 20, 30, 35, 40, 45, 50, 55, 60, 65, 70, 75, 80, 85, 90, 95, 100, 150, 200, 250, 300, 350, 400, 450, 500, 600, 700, 800, 900, 1000 amino acid residues in length or more. In some cases, the cysteine residue of the modified cysteine containing protein has the structure SR, wherein R is selected from:

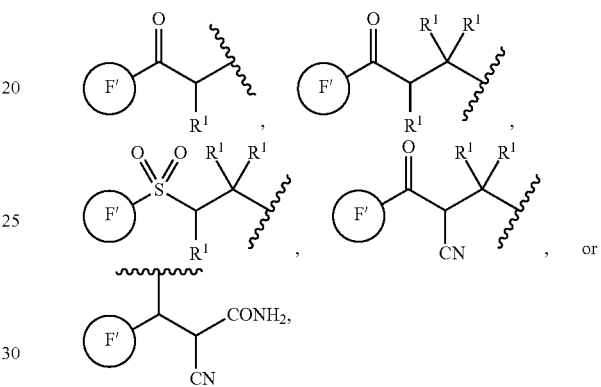

wherein $R^1$ is H, C1-C3 alkyl, or aryl; and F' is the small molecule fragment moiety. In some cases, the small molecule fragment has a molecular weight of about 175, 200, 225, 250, 275, 300, 350, 400, 450, 500, 550, 600, 650, 700, 750, 800, 850, 900, 950, 1000 Dalton, or higher. In some cases, the molecular weight of the small molecule fragment is prior to enrichment with a halogen, a nonmetal, or a transition metal. In some embodiments, the molecular weight of the small molecule fragment is calculated based on carbon and hydrogen atoms and optionally further based on nitrogen, oxygen and/or sulfur atoms. In some embodiments, the molecular weight of the small molecule fragment does not include the molecular weight of a halogen, a transition metal or a combination thereof. In some cases, the small molecule fragment is a small molecule fragment of Formula (I):

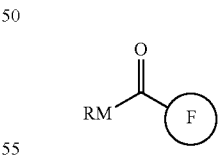

wherein RM is a reactive moiety selected from a Michael acceptor moiety, a leaving group moiety, or a moiety capable of forming a covalent bond with the thiol group of a cysteine residue; and F is a small molecule fragment moiety. In some cases, the Michael acceptor moiety comprises an alkene or an alkyne moiety. In some cases, F is obtained from a compound library. In some cases, F is a small molecule fragment moiety illustrated in FIG. 3. In some cases, F further comprises a linker moiety that connects F to the carbonyl moiety. In some cases, the small molecule fragment binds irreversibly to the cysteine containing protein. In some cases, the small molecule fragment binds reversibly to the cysteine containing protein.

In some embodiments, described herein is a modified cysteine containing protein comprising a small molecule fragment having a covalent bond to a cysteine residue of a cysteine containing protein, in which the cysteine containing protein comprises the motif $X_pC^*Z$, wherein $X_p$ is a polar residue, $C^*$ denotes the site of modification, and Z is any amino acid. In some cases, the cysteine containing protein is selected from Table 3. In some cases, the cysteine containing protein is selected from AIP, PES1, IKBKB, XPO1, KDM4B, NR3C1, GSTP1, TNFAIP3, ACAT1, IRAK1, GNB2L1, IRF4, USP34, ZC3HAV1, USP7, PELI1, DCUN1D1, USP28, UBE2O, RRAGC, MLTK, USP22, KDM3A, or USP16.

In some instances, described herein is a modified cysteine containing protein comprising a small molecule fragment having a covalent bond to a cysteine residue of a cysteine containing protein, in which the cysteine containing protein comprises the motif $X_pC^*X_n$, wherein $X_p$ is a polar residue, $C^*$ denotes the site of modification, and $X_n$ is a nonpolar residue. In some cases, the cysteine containing protein is selected from Table 3. In some cases, the cysteine containing protein is selected from AIP, PES1, IKBKB, XPO1, GSTP1, ACAT1, IRAK1, IRF4, ZC3HAV1, USP7, PELI1, USP28, UBE2O, RRAGC, MLTK, USP22, KDM3A, or USP16.

In some instances, described herein is a modified cysteine containing protein comprising a small molecule fragment having a covalent bond to a cysteine residue of a cysteine containing protein, in which the cysteine containing protein comprises the motif $X_pC^*X_p$, wherein $X_p$ is a polar residue and $C^*$ denotes the site of modification. In some cases, the cysteine containing protein is selected from Table 3. In some cases, the cysteine containing protein is selected from KDM4B, NR3C1, TNFAIP3, USP7 or USP22.

In some instances, described herein is a modified cysteine containing protein comprising a small molecule fragment having a covalent bond to a cysteine residue of a cysteine containing protein, in which the cysteine containing protein comprises the motif $X_pC^*X_b$, wherein $X_p$ is a polar residue, $C^*$ denotes the site of modification, and $X_b$ is a basic residue. In some cases, the cysteine containing protein is selected from Table 3. In some cases, the cysteine containing protein is selected from GNB2L1 or USP34.

In some instances, described herein is a modified cysteine containing protein comprising a small molecule fragment having a covalent bond to a cysteine residue of a cysteine containing protein, in which the cysteine containing protein comprises the motif $X_pC^*X_b$, wherein $X_p$ is a polar residue, $C^*$ denotes the site of modification, and $X_b$ is an acidic residue. In some cases, the cysteine containing protein is selected from Table 3. In some cases, the cysteine containing protein is DCUN1D1.

In some instances, described herein is a modified cysteine containing protein comprising a small molecule fragment having a covalent bond to a cysteine residue of a cysteine containing protein, in which the cysteine containing protein comprises the motif SC*Z, wherein C* denotes the site of modification, and Z is any amino acid. In some cases, the cysteine containing protein is selected from Table 3. In some cases, the cysteine containing protein is selected from PES1, IKBKB, GSTP1, ACAT1, IRAK1, ZC3HAV1 or RRAGC.

In some instances, described herein is a modified cysteine containing protein comprising a small molecule fragment having a covalent bond to a cysteine residue of a cysteine containing protein, in which the cysteine containing protein comprises the motif NC*Z, wherein C* denotes the site of modification, and Z is any amino acid. In some cases, the cysteine containing protein is selected from Table 3. In some cases, the cysteine containing protein is selected from XPO1, GNB2L1, USP34, UBE2O, MLTK or USP22.

In some instances, described herein is a modified cysteine containing protein comprising a small molecule fragment having a covalent bond to a cysteine residue of a cysteine containing protein, in which the cysteine containing protein comprises the motif YC*Z, wherein C* denotes the site of modification, and Z is any amino acid. In some cases, the cysteine containing protein is selected from Table 3. In some cases, the cysteine containing protein is selected from KDM4B or NR3C1.

In some instances, described herein is a modified cysteine containing protein comprising a small molecule fragment having a covalent bond to a cysteine residue of a cysteine containing protein, in which the cysteine containing protein comprises the motif TC*Z, wherein C* denotes the site of modification, and Z is any amino acid. In some cases, the cysteine containing protein is selected from Table 3. In some cases, the cysteine containing protein is selected from TNFAIP3, USP7, USP28, KDM3A or USP16.

In some instances, described herein is a modified cysteine containing protein comprising a small molecule fragment having a covalent bond to a cysteine residue of a cysteine containing protein, in which the cysteine containing protein comprises the motif QC*Z, wherein C* denotes the site of modification, and Z is any amino acid. In some cases, the cysteine containing protein is selected from Table 3. In some cases, the cysteine containing protein is selected from IRF4, PELI1, DCUN1D1 or USP22.

In some instances, described herein is a modified cysteine containing protein comprising a small molecule fragment having a covalent bond to a cysteine residue of a cysteine containing protein, in which the cysteine containing protein comprises the motif CC*Z, wherein C* denotes the site of modification, and Z is any amino acid. In some cases, the cysteine containing protein is selected from Table 3. In some cases, the cysteine containing protein is AIP.

In some instances, described herein is a modified cysteine containing protein comprising a small molecule fragment having a covalent bond to a cysteine residue of a cysteine containing protein, in which the cysteine containing protein is an enzyme and the enzyme comprises the motif $X_pC^*Z$, wherein $X_p$ is a polar residue, $C^*$ denotes the site of modification, and Z is any amino acid. In some cases, the cysteine containing protein is selected from Table 3. In some cases, the enzyme is selected from IKBKB, KDM4B, GSTP1, TNFAIP3, ACAT1, IRAK1, USP34, USP7, PELI1, USP28, UBE2O, MLTK, USP22, KDM3A, or USP16.

In some instances, described herein is a modified cysteine containing protein comprising a small molecule fragment having a covalent bond to a cysteine residue of a cysteine containing protein, in which the cysteine containing protein is a transcription factor or a regulator and the transcription factor or regulator comprises the motif $X_pC^*Z$, wherein $X_p$ is a polar residue, $C^*$ denotes the site of modification, and Z is any amino acid. In some cases, the cysteine containing protein is selected from Table 3. In some cases, the transcription factor or regulator is selected from NR3C1, IRF4 or ZC3HAV1.

In some instances, described herein is a modified cysteine containing protein comprising a small molecule fragment having a covalent bond to a cysteine residue of a cysteine containing protein, in which the cysteine containing protein is a channel, transporter or a receptor and the channel, transporter or receptor comprises the motif $X_pC^*Z$, wherein $X_p$ is a polar residue, C* denotes the site of modification, and Z is any amino acid. In some cases, the cysteine containing protein is selected from Table 3. In some cases, the channel, transporter, or receptor is selected from GNB2L1 or RRAGC.

In some instances, described herein is a modified cysteine containing protein comprising a small molecule fragment having a covalent bond to a cysteine residue of a cysteine containing protein, in which the cysteine containing protein comprises the motif $X_pC^*Z$, wherein $X_p$ is a polar residue, C* denotes the site of modification, and Z is any amino acid. In some cases, the cysteine containing protein is selected from Table 3. In some cases, the cysteine containing protein is selected from AIP, PES1, XPO1 or DCUN1D1.

In some instances, described herein is a modified cysteine containing protein comprising a small molecule fragment having a covalent bond to a cysteine residue of a cysteine containing protein, in which the cysteine containing protein comprises the motif $X_nC^*Z$, wherein $X_n$ is a nonpolar residue, C* denotes the site of modification, and Z is any amino acid. In some cases, the cysteine containing protein is selected from Table 3. In some cases, the cysteine containing protein is selected from PES1, CYR61, UBE2L6, XPO1, ADA, NR3C1, POU2F2, UCHL3, MGMT, ERCC3, ACAT1, STAT3, UBA7, CASP2, IDH2, LRBA, UBE2L3, RELB, IRF8, CASP8, PDIA6, PCK2, PFKFB4, PDE12, USP34, USP48, SMARCC2 or SAMHD1.

In some instances, described herein is a modified cysteine containing protein comprising a small molecule fragment having a covalent bond to a cysteine residue of a cysteine containing protein, in which the cysteine containing protein comprises the motif $X_nC^*X_n$, wherein $X_n$ is a nonpolar residue and C* denotes the site of modification. In some cases, the cysteine containing protein is selected from Table 3. In some cases, the cysteine containing protein is selected from PES1, CYR61, NR3C1, UCHL3, ERCC3, ACAT1, STAT3, CASP2, LRBA, UBE2L3, RELB, PDIA6, PCK2, PFKFB4, USP48 or SMARCC2.

In some instances, described herein is a modified cysteine containing protein comprising a small molecule fragment having a covalent bond to a cysteine residue of a cysteine containing protein, in which the cysteine containing protein comprises the motif $X_nC^*X_p$, wherein $X_n$ is a nonpolar residue, C* denotes the site of modification, and $X_p$ is a polar residue. In some cases, the cysteine containing protein is selected from Table 3. In some cases, the cysteine containing protein is selected from UBE2L6, POU2F2, MGMT, ACAT1, UBA7, CASP8, PDE12 or USP34.

In some instances, described herein is a modified cysteine containing protein comprising a small molecule fragment having a covalent bond to a cysteine residue of a cysteine containing protein, in which the cysteine containing protein comprises the motif $X_nC^*X_a$, wherein $X_n$ is a nonpolar residue, C* denotes the site of modification, and $X_b$ is an acidic residue. In some cases, the cysteine containing protein is selected from Table 3. In some cases, the cysteine containing protein is selected from CYR61 or XPO1.

In some instances, described herein is a modified cysteine containing protein comprising a small molecule fragment having a covalent bond to a cysteine residue of a cysteine containing protein, in which the cysteine containing protein comprises the motif $X_nC^*X_b$, wherein $X_n$ is a nonpolar residue, C* denotes the site of modification, and $X_b$ is a basic residue. In some cases, the cysteine containing protein is selected from Table 3. In some cases, the cysteine containing protein is selected from ADA, MGMT, IDH2, IRF8 or SAMHD1.

In some instances, described herein is a modified cysteine containing protein comprising a small molecule fragment having a covalent bond to a cysteine residue of a cysteine containing protein, in which the cysteine containing protein comprises the motif LC*Z, wherein C* denotes the site of modification, and Z is any amino acid. In some cases, the cysteine containing protein is selected from Table 3. In some cases, the cysteine containing protein is selected from PES1, CYR61, XPO1, NR3C1 or SMARCC2.

In some instances, described herein is a modified cysteine containing protein comprising a small molecule fragment having a covalent bond to a cysteine residue of a cysteine containing protein, in which the cysteine containing protein comprises the motif PC*Z, wherein C* denotes the site of modification, and Z is any amino acid. In some cases, the cysteine containing protein is selected from Table 3. In some cases, the cysteine containing protein is selected from CYR61, UBE2L6, MGMT, ERCC3, ACAT1 or USP48.

In some instances, described herein is a modified cysteine containing protein comprising a small molecule fragment having a covalent bond to a cysteine residue of a cysteine containing protein, in which the cysteine containing protein comprises the motif GC*Z, wherein C* denotes the site of modification, and Z is any amino acid. In some cases, the cysteine containing protein is selected from Table 3. In some cases, the cysteine containing protein is selected from ADA, RELB or USP34.

In some instances, described herein is a modified cysteine containing protein comprising a small molecule fragment having a covalent bond to a cysteine residue of a cysteine containing protein, in which the cysteine containing protein comprises the motif AC*Z, wherein C* denotes the site of modification, and Z is any amino acid. In some cases, the cysteine containing protein is selected from Table 3. In some cases, the cysteine containing protein is selected from UCHL3, CASP2, IDH2, LRBA, CASP8, PCK2 or PDE12.

In some instances, described herein is a modified cysteine containing protein comprising a small molecule fragment having a covalent bond to a cysteine residue of a cysteine containing protein, in which the cysteine containing protein comprises the motif VC*Z, wherein C* denotes the site of modification, and Z is any amino acid. In some cases, the cysteine containing protein is selected from Table 3. In some cases, the cysteine containing protein is selected from MGMT, ACAT1, UBA7, UBE2L3 or IRF8.

In some instances, described herein is a modified cysteine containing protein comprising a small molecule fragment having a covalent bond to a cysteine residue of a cysteine containing protein, in which the cysteine containing protein comprises the motif IC*Z, wherein C* denotes the site of modification, and Z is any amino acid. In some cases, the cysteine containing protein is selected from Table 3. In some cases, the cysteine containing protein is selected from PFKFB4, ACAT1 or STAT3.

In some instances, described herein is a modified cysteine containing protein comprising a small molecule fragment having a covalent bond to a cysteine residue of a cysteine containing protein, in which the cysteine containing protein comprises the motif $X_rC^*Z$, wherein $X_r$ denotes an aromatic residue, C* denotes the site of modification, and Z is any amino acid. In some cases, the cysteine containing protein is selected from Table 3. In some cases, the cysteine containing protein is selected from POU2F2, PDIA6 or SAMHD1.

In some instances, described herein is a modified cysteine containing protein comprising a small molecule fragment having a covalent bond to a cysteine residue of a cysteine containing protein, in which the cysteine containing protein is an enzyme and the enzyme comprises the motif $X_nC^*Z$, wherein $X_n$ is a nonpolar residue, $C^*$ denotes the site of modification, and Z is any amino acid. In some cases, the cysteine containing protein is selected from Table 3. In some cases, the enzyme is selected from UBE2L6, ADA, UCHL3, MGMT, ERCC3, ACAT1, UBA7, CASP2, IDH2, UBE2L3, CASP8, PDIA6, PCK2, PFKFB4, PDE12, USP34, USP48 or SAMHD1.

In some instances, described herein is a modified cysteine containing protein comprising a small molecule fragment having a covalent bond to a cysteine residue of a cysteine containing protein, in which the cysteine containing protein is a transcription factor or a regulator and the transcription factor or regulator comprises the motif $X_nC^*Z$, wherein $X_n$ is a nonpolar residue, $C^*$ denotes the site of modification, and Z is any amino acid. In some cases, the cysteine containing protein is selected from Table 3. In some cases, the transcription factor or regulator is selected from NR3C1, POU2F2, STAT3, RELB, IRF8 or SMARCC2.

In some instances, described herein is a modified cysteine containing protein comprising a small molecule fragment having a covalent bond to a cysteine residue of a cysteine containing protein, in which the cysteine containing protein comprises the motif $X_aC^*Z$, wherein $X_a$ is a nonpolar residue, $C^*$ denotes the site of modification, and Z is any amino acid. In some cases, the cysteine containing protein is selected from Table 3. In some cases, the cysteine containing protein is selected from PES1, CYR61, XPO1 or LRBA.

In some instances, described herein is a modified cysteine containing protein comprising a small molecule fragment having a covalent bond to a cysteine residue of a cysteine containing protein, in which the cysteine containing protein comprises the motif $X_aC^*Z$, wherein $X_a$ is an acidic residue, $C^*$ denotes the site of modification, and Z is any amino acid. In some cases, the cysteine containing protein is selected from Table 3. In some cases, the cysteine containing protein is selected from ZAP70, PRKCQ or PRMT1.

In some instances, described herein is a modified cysteine containing protein comprising a small molecule fragment having a covalent bond to a cysteine residue of a cysteine containing protein, in which the cysteine containing protein comprises the motif $EC^*Z$, wherein $C^*$ denotes the site of modification, and Z is any amino acid. In some cases, the cysteine containing protein is selected from Table 3. In some cases, the cysteine containing protein is selected from ZAP70 or PRKCQ.

In some instances, described herein is a modified cysteine containing protein comprising a small molecule fragment having a covalent bond to a cysteine residue of a cysteine containing protein, in which the cysteine containing protein comprises the motif $X_bC^*Z$, wherein $X_b$ is a basic residue, $C^*$ denotes the site of modification, and Z is any amino acid. In some cases, the cysteine containing protein is selected from Table 3. In some cases, the cysteine containing protein is selected from CYR61, ZNF217, NCF1, IREB2, LRBA, CDK5, EP300, EZH2, UBE2S, VCPIP1, RRAGC or IRAK4.

In some instances, described herein is a modified cysteine containing protein comprising a small molecule fragment having a covalent bond to a cysteine residue of a cysteine containing protein, in which the cysteine containing protein comprises the motif $X_bC^*X_n$, wherein $X_b$ is a basic residue, $C^*$ denotes the site of modification, and $X_n$ is a nonpolar residue. In some cases, the cysteine containing protein is selected from Table 3. In some cases, the cysteine containing protein is selected from CYR61, ZNF217, IREB2, EP300, UBE2S, VCPIP1, RRAGC or IRAK4.

In some instances, described herein is a modified cysteine containing protein comprising a small molecule fragment having a covalent bond to a cysteine residue of a cysteine containing protein, in which the cysteine containing protein comprises the motif $X_bC^*X_p$, wherein $X_b$ is a basic residue, $C^*$ denotes the site of modification, and $X_p$ is a polar residue. In some cases, the cysteine containing protein is selected from Table 3. In some cases, the cysteine containing protein is selected from NCF1, LRBA or CDK5.

In some instances, described herein is a modified cysteine containing protein comprising a small molecule fragment having a covalent bond to a cysteine residue of a cysteine containing protein, in which the cysteine containing protein comprises the motif $X_bC^*X_b$, wherein $X_b$ is a basic residue and $C^*$ denotes the site of modification. In some cases, the cysteine containing protein is selected from Table 3. In some cases, the cysteine containing protein is EZH2.

In some instances, described herein is a modified cysteine containing protein comprising a small molecule fragment having a covalent bond to a cysteine residue of a cysteine containing protein, in which the cysteine containing protein comprises the motif $RC^*Z$, wherein $C^*$ denotes the site of modification, and Z is any amino acid. In some cases, the cysteine containing protein is selected from Table 3. In some cases, the cysteine containing protein is selected from ZNF217, NCF1, CDK5, EP300 or IRAK4.

In some instances, described herein is a modified cysteine containing protein comprising a small molecule fragment having a covalent bond to a cysteine residue of a cysteine containing protein, in which the cysteine containing protein comprises the motif $KC^*Z$, wherein $C^*$ denotes the site of modification, and Z is any amino acid. In some cases, the cysteine containing protein is selected from Table 3. In some cases, the cysteine containing protein is selected from CYR61, IREB2, LRBA or UBE2S.

In some instances, described herein is a modified cysteine containing protein comprising a small molecule fragment having a covalent bond to a cysteine residue of a cysteine containing protein, in which the cysteine containing protein comprises the motif $HC^*Z$, wherein $C^*$ denotes the site of modification, and Z is any amino acid. In some cases, the cysteine containing protein is selected from Table 3. In some cases, the cysteine containing protein is selected from EZH2, VCPIP1 or RRAGC.

In some instances, described herein is a modified cysteine containing protein comprising a small molecule fragment having a covalent bond to a cysteine residue of a cysteine containing protein, in which the cysteine containing protein is an enzyme and the enzyme comprises the motif $X_bC^*Z$, wherein $X_b$ is a basic residue, $C^*$ denotes the site of modification, and Z is any amino acid. In some cases, the cysteine containing protein is selected from Table 3. In some cases, the enzyme is selected from CDK5, EP300, EZH2, UBE2S, VCPIP1 or IRAK4.

In some instances, described herein is a modified cysteine containing protein comprising a small molecule fragment having a covalent bond to a cysteine residue of a cysteine containing protein, in which the cysteine containing protein is a transcription factor or a regulator and the transcription factor or regulator comprises the motif $X_bC^*Z$, wherein $X_b$ is a basic residue, $C^*$ denotes the site of modification, and Z is any amino acid. In some cases, the cysteine containing protein is selected from Table 3. In some cases, the transcription factor or regulator is selected from ZNF217 or IREB2.

In some instances, described herein is a modified cysteine containing protein comprising a small molecule fragment having a covalent bond to a cysteine residue of a cysteine containing protein, in which the cysteine containing protein is an adapter, a scaffolding protein, or a modulator protein and the adapter, scaffolding protein or the modulator protein comprises the motif $X_bC^*Z$, wherein $X_b$ is a basic residue, $C^*$ denotes the site of modification, and Z is any amino acid. In some cases, the cysteine containing protein is selected from Table 3. In some cases, the adapter, scaffolding protein or the modulator protein is selected from NCF1.

In some instances, described herein is a modified cysteine containing protein comprising a small molecule fragment having a covalent bond to a cysteine residue of a cysteine containing protein, in which the cysteine containing protein is a channel, a transporter, or a receptor and the channel, transporter, or receptor comprises the motif $X_bC^*Z$, wherein $X_b$ is a basic residue, $C^*$ denotes the site of modification, and Z is any amino acid. In some cases, the cysteine containing protein is selected from Table 3. In some cases, the channel, transporter, or receptor is selected from RRAGC.

In some instances, described herein is a modified cysteine containing protein comprising a small molecule fragment having a covalent bond to a cysteine residue of a cysteine containing protein, in which the cysteine containing protein comprises the motif $X_bC^*Z$, wherein $X_b$ is a basic residue, $C^*$ denotes the site of modification, and Z is any amino acid. In some cases, the cysteine containing protein is selected from Table 3. In some cases, the cysteine containing protein is selected from CYR61 or LRBA.

In some cases, a cysteine containing protein described above comprises about 20, 30, 35, 40, 45, 50, 55, 60, 65, 70, 75, 80, 85, 90, 95, 100, 150, 200, 250, 300, 350, 400, 450, 500, 600, 700, 800, 900, 1000 amino acid residues in length or more.

In some cases, the cysteine residue of a modified cysteine containing protein described above has the structure SR, wherein R is selected from:

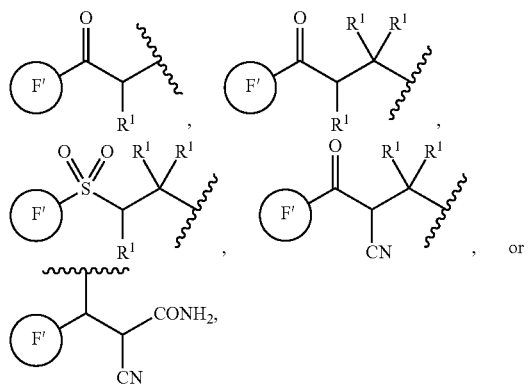

wherein $R^1$ is H, C1-C3 alkyl, or aryl; and F' is the small molecule fragment moiety. In some cases, the small molecule fragment has a molecular weight of about 175, 200, 225, 250, 275, 300, 350, 400, 450, 500, 550, 600, 650, 700, 750, 800, 850, 900, 950, 1000 Dalton, or higher. In some cases, the molecular weight of the small molecule fragment is prior to enrichment with a halogen, a nonmetal, or a transition metal. In some embodiments, the molecular weight of the small molecule fragment is calculated based on carbon and hydrogen atoms and optionally further based on nitrogen, oxygen and/or sulfur atoms. In some embodiments, the molecular weight of the small molecule fragment does not include the molecular weight of a halogen, a transition metal or a combination thereof. In some cases, the small molecule fragment is a small molecule fragment of Formula (I):

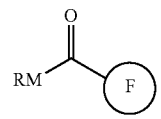

RM wherein RM is a reactive moiety selected from a Michael acceptor moiety, a leaving group moiety, or a moiety capable of forming a covalent bond with the thiol group of a cysteine residue; and F is a small molecule fragment moiety. In some cases, the Michael acceptor moiety comprises an alkene or an alkyne moiety. In some cases, F is obtained from a compound library. In some cases, F is a small molecule fragment moiety illustrated in FIG. 3. In some cases, F further comprises a linker moiety that connects F to the carbonyl moiety. In some cases, the small molecule fragment binds irreversibly to a cysteine containing protein described above. In some cases, the small molecule fragment binds reversibly to a cysteine containing protein described above.

Compositions, Cells, and Cell Populations

Disclosed herein also include compositions of a small molecule fragment conjugated to a cysteine containing protein, a cysteine-reactive probe conjugated to a cysteine containing protein, and treated sample compositions. In some embodiments, a composition described herein comprises a small molecule fragment of Formula (I):

Formula (I)

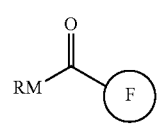

wherein:
RM is a reactive moiety selected from a Michael acceptor moiety, a leaving group moiety, or a moiety capable of forming a covalent bond with the thiol group of a cysteine residue; and
F is a small molecule fragment moiety; and
a cysteine containing protein wherein the cysteine containing protein is covalently bond to the small molecule fragment.

In some embodiments, also described herein is a composition that comprises a cysteine-reactive probe of Formula (II):

Formula (II)

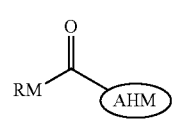

wherein:
RM is a reactive moiety selected from a Michael acceptor moiety, a leaving group moiety, or a moiety capable of forming a covalent bond to the thiol group of a cysteine residue; and AHM is an affinity handle moiety; and
a cysteine containing protein wherein the cysteine containing protein is covalently bond to the cysteine-reactive probe.

In some embodiments, also described herein is a composition that comprises an isolated sample wherein the isolated sample is an isolated cell or a tissue sample; and a cysteine-reactive probe to be assayed for its ability to interact with a cysteine containing protein expressed in the isolated sample.

Disclosed herein further include isolated treated cell and cell populations. In some embodiments, described herein is an isolated treated cell that comprises a cysteine-reactive probe covalently attached to a cysteine containing protein. In some instances, the isolated treated cell further comprises a set of cysteine-reactive probes wherein each of the cysteine-reactive probes is covalently attached to a cysteine containing protein.

In some embodiments, described herein is an isolated treated cell that comprises a small molecule fragment covalently attached to a cysteine containing protein. In some instances, the isolated treated cell further comprises a set of small molecule fragments wherein each of the small molecule fragment is covalently attached to a cysteine containing protein. In some instances, the isolated treated cell further comprises a cysteine-reactive probe. In some instances, the isolated treated cell further comprises a set of cysteine-reactive probes.

In some embodiments, also described herein is an isolated treated population of cells that comprises a set of cysteine-reactive probes covalently attached to cysteine containing proteins.

In some embodiments, further described herein is an isolated treated population of cells that comprises a set of small molecule fragments covalently attached to cysteine containing proteins. In some instances, the isolated treated population of cells further comprises a set of cysteine-reactive probes.

As disclosed elsewhere herein, the small molecule fragment is a small molecule fragment of Formula (I):

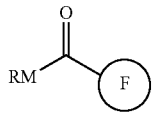

Formula (I)

wherein:
RM is a reactive moiety selected from a Michael acceptor moiety, a leaving group moiety, or a moiety capable of forming a covalent bond with the thiol group of a cysteine residue; and
F is a small molecule fragment moiety.

In some instances, the Michael acceptor moiety comprises an alkene or an alkyne moiety. In some cases, F is obtained from a compound library. In some embodiments, the compound library comprises ChemBridge fragment library, Pyramid Platform Fragment-Based Drug Discovery, Maybridge fragment library, FRGx from AnalytiCon, TCI-Frag from AnCoreX, Bio Building Blocks from ASINEX, BioFocus 3D from Charles River, Fragments of Life (FOL) from Emerald Bio, Enamine Fragment Library, IOTA Diverse 1500, BIONET fragments library, Life Chemicals Fragments Collection, OTAVA fragment library, Prestwick fragment library, Selcia fragment library, TimTec fragment-based library, Allium from Vitas-M Laboratory, or Zenobia fragment library. In some cases, F is a small molecule fragment moiety illustrated in FIG. 3. In some cases, F further comprises a linker moiety that connects F to the carbonyl moiety. In some embodiments, the small molecule fragment is a small molecule fragment illustrated in FIG. 3.

Also described elsewhere herein, the cysteine-reactive probe is a cysteine-reactive probe of Formula (II):

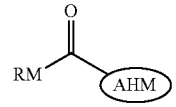

Formula (II)

wherein:
RM is a reactive moiety selected from a Michael acceptor moiety, a leaving group moiety, or a moiety capable of forming a covalent bond to the thiol group of a cysteine residue; and
AHM is an affinity handle moiety.

In some embodiments, the Michael acceptor moiety comprises an alkene or an alkyne moiety. In some instances, the affinity handle moiety comprises an affinity handle and a binding moiety that facilitates covalent interaction of the cysteine-reactive probe to a cysteine residue of a cysteine-containing protein. In some cases, the binding moiety is a small molecule fragment obtained from a compound library. In some cases, the compound library comprises ChemBridge fragment library, Pyramid Platform Fragment-Based Drug Discovery, Maybridge fragment library, FRGx from AnalytiCon, TCI-Frag from AnCoreX, Bio Building Blocks from ASINEX, BioFocus 3D from Charles River, Fragments of Life (FOL) from Emerald Bio, Enamine Fragment Library, IOTA Diverse 1500, BIONET fragments library, Life Chemicals Fragments Collection, OTAVA fragment library, Prestwick fragment library, Selcia fragment library, TimTec fragment-based library, Allium from Vitas-M Laboratory, or Zenobia fragment library.

In some instances, the affinity handle is a bioorthogonal affinity handle. In some cases, the affinity handle comprises a carbodiimide, N-hydroxysuccinimide (NHS) ester, imidoester, pentafluorophenyl ester, hydroxymethyl phosphine, maleimide, haloacetyl, pyridyl disulfide, thiosulfonate, vinylsulfone, hydrazide, alkoxyamine, alkyne, azide, or isocyanate group. In some cases, the affinity handle comprises an alkyne or an azide group. In some instances, the affinity handle is further conjugated to an affinity ligand. In some instances, the affinity ligand comprises a chromophore, a labeling group, or a combination thereof. In some cases, the chromophore comprises fluorochrome, non-fluorochrome chromophore, quencher, an absorption chromophore, fluorophore, organic dye, inorganic dye, metal chelate, or a fluorescent enzyme substrate. In some cases, the labeling group is biotin moiety, streptavidin moiety, bead, resin, a solid support, or a combination thereof. In some instances, the affinity handle moiety further comprises a chromophore. In some embodiments, the cysteine-reactive probe is a cysteine-reactive probe illustrated in FIG. 3.

Further described elsewhere herein, the cell or cell population is obtained from any mammal, such as human or non-human primates. In some embodiments, the cell or cell population is an epithelial cell, connective tissue cell, hormone secreting cell, a nerve cell, a skeletal muscle cell, a blood cell, or an immune system cell. In additional embodiments, the cell or cell population is cancerous or is obtained from a tumor site.

Polypeptides Comprising a Cysteine Interacting Site

Further disclosed herein are polypeptides that comprise one or more of the cysteine interacting sites identified by a method described herein. In some embodiments, described herein is an isolated and purified polypeptide that comprises at least 90% sequence identity to at least seven contiguous amino acids of an amino acid sequence selected from Tables 1-3 or 8-9. In some embodiments, the isolated and purified polypeptide comprises at least 91%, 92%, 93%, 94%, 95%, 96%, 97%, 98%, or 99% sequence identity to at least seven contiguous amino acids of an amino acid sequence selected from Tables 1-3 or 8-9. In some embodiments, the isolated and purified polypeptide comprises 100% sequence identity to at least seven contiguous amino acids of an amino acid sequence selected from Tables 1-3 or 8-9. In some instances, the isolated and purified polypeptide consists 100% sequence identity to the full length of an amino acid sequence selected from Tables 1-3 or 8-9. In some instances, the isolated and purified polypeptide is at most 50 amino acids in length.

In some embodiments, additionally described herein include nucleic acid encoding a polypeptide that comprises at least 90% sequence identity at least seven contiguous amino acids of an amino acid sequence selected from Tables 1-3 or 8-9. In some embodiments, the nucleic acid encoding a polypeptide comprises at least 91%, 92%, 93%, 94%, 95%, 96%, 97%, 98%, or 99% sequence identity at least seven contiguous amino acids of an amino acid sequence selected from Tables 1-3 or 8-9. In some embodiments, the nucleic acid encoding a polypeptide comprises 100% sequence identity at least seven contiguous amino acids of an amino acid sequence selected from Tables 1-3 or 8-9. In some embodiments, the nucleic acid encoding a polypeptide consists 100% sequence identity to the full length of an amino acid sequence selected from Tables 1-3 or 8-9.

In some embodiments, further disclosed herein include a method of mapping a biologically active cysteine site on a protein, which comprises harvesting a set of cysteine-reactive probe-protein complexes from a sample wherein the cysteine-reactive probe comprises a reactive moiety capable of forming a covalent bond with a cysteine residue located on the cysteine containing protein; analyzing the set of cysteine-reactive probe-protein complexes by a proteomic analysis means; and based on the previous step, mapping the biologically active cysteine site on the protein.

In some embodiments, the analyzing further comprises treating the set of cysteine-reactive probe-protein complexes with a protease to generate a set of protein fragments. The protease is a serine protease, a threonine protease, a cysteine protease, an aspartate protease, a glutamic acid protease, or a metalloprotease. In some instances, the protease is a serine protease. In some instances, the protease is trypsin. In some instances, cysteine-reactive probe-protein complex is further attached to a labeling group such as a biotin moiety. In some instances, the labeling group such as a biotin moiety further comprises a linker. In some instances, the linker is a peptide. In some instances, the peptide linker is about 7, 8, 9, 10, 11, 12, 13, 14, 15, 16, 17, 18, 19, 20 or more amino acid residues in length. In some instances, the peptide linker contains a cleavage site. A non-limiting list of cleavage sites includes Tobacco Etch Virus (TEV), thrombin (Thr), enterokinase (EKT), activated Factor X (Xa), or human Rhinovirus 3C protease (3C/PreScission). In some instances, the peptide linker contains a TEV protease cleavage site. In some instances, the TEV protease cleavage site comprises the following sequence Gly-Gln-Phe-Tyr-Leu-Asn-Glu (SEQ ID NO: 860). In some instances, the biotin moiety is further coupled to a bead (e.g. a streptavidin-coupled bead).

In some instances, the protein from the cysteine-reactive probe-protein complex attached to the bead (via a biotin moiety comprising a linker and attached to a streptavidin-coupled bead) is digested with trypsin, and the immobilized peptide or protein fragment is further separated and collected. In some instances, the collected peptide or protein fragment is then digested by a protease (e.g. TEV protease), and the treated protein fragment is then separated, and collected for analysis. In some instances, the analysis is a proteomic analysis as described above and elsewhere herein. In some instances, the sequence of the protein fragment is further determined. In some instances, the protein fragment correlates to a small molecule fragment binding site on the cysteine containing protein.

In some embodiments, the sequence of the protein fragment correlates to a sequence as illustrated in Tables 1-3 or 8-9. In some instances, the sequence as shown in Tables 1-3 or 8-9 correlate to a site on the full length protein as a drug binding site. In some instances, the sequence as shown in Tables 1-3 or 8-9 correlate to a drug binding site. In some instances, polypeptides comprising one or more of the sequences as shown in Tables 1-3 or 8-9 serve as probes for small molecule fragment screening.

In some instances after the generation of a polypeptide, the polypeptide is subjected to one or more rounds of purification steps to remove impurities. In some instances, the purification step is a chromatographic step utilizing separation methods such as affinity-based, size-exclusion based, ion-exchange based, or the like. In some cases, the polypeptide is at most 30%, 40%, 50%, 60%, 70%, 80%, 90%, 95%, 99%, 99.9%, or 100% pure or without the presence of impurities. In some cases, the polypeptide is at least 30%, 40%, 50%, 60%, 70%, 80%, 90%, 95%, 99%, 99.9%, or 100% pure or without the presence of impurities.

As described above, nucleic acid encoding a polypeptide that is derived from a cysteine containing protein is subjected to one or more rounds of purification steps to remove impurities. In some instances, the purification step is a chromatographic step utilizing separation methods such as affinity-based, size-exclusion based, ion-exchange based, or the like. In some cases, the nucleic acid is at most 30%, 40%, 50%, 60%, 70%, 80%, 90%, 95%, 99%, 99.9%, or 100% pure or without the presence of impurities. In some cases, the nucleic acid is at least 30%, 40%, 50%, 60%, 70%, 80%, 90%, 95%, 99%, 99.9%, or 100% pure or without the presence of impurities.

As used herein, a polypeptide includes natural amino acids, unnatural amino acids, or a combination thereof. In some instances, an amino acid residue refers to a molecule containing both an amino group and a carboxyl group. Suitable amino acids include, without limitation, both the D- and L-isomers of the naturally-occurring amino acids, as well as non-naturally occurring amino acids prepared by organic synthesis or other metabolic routes. The term amino acid, as used herein, includes, without limitation, α-amino acids, natural amino acids, non-natural amino acids, and amino acid analogs.

The term "α-amino acid" refers to a molecule containing both an amino group and a carboxyl group bound to a carbon which is designated the α-carbon.

The term "β-amino acid" refers to a molecule containing both an amino group and a carboxyl group in a β configuration.

"Naturally occurring amino acid" refers to any one of the twenty amino acids commonly found in peptides synthesized in nature, and known by the one letter abbreviations A, R, N, C, D, Q, E, G, H, I, L, K, M, F, P, S, T, W, Y and V.

The following table shows a summary of the properties of natural amino acids:

| Amino Acid | 3-Letter Code | 1-Letter Code | Side-chain Polarity | Side-chain charge (pH 7.4) | Hydropathy Index |
|---|---|---|---|---|---|
| Alanine | Ala | A | nonpolar | neutral | 1.8 |
| Arginine | Arg | R | polar | positive | −4.5 |
| Asparagine | Asn | N | polar | neutral | −3.5 |
| Aspartic acid | Asp | D | polar | negative | −1.5 |
| Cysteine | Cys | C | polar | neutral | 2.5 |
| Glutamic acid | Glu | E | polar | negative | −3.5 |
| Glutamine | Gln | Q | polar | neutral | −3.5 |
| Glycine | Gly | G | nonpolar | neutral | −0.4 |
| Histidine | His | H | polar | positive(10%) neutral(90%) | −3.2 |
| Isoleucine | Ile | I | nonpolar | neutral | 4.5 |
| Leucine | Leo | L | nonpolar | neutral | 3.8 |
| Lysine | Lys | K | polar | positive | −3.0 |
| Methionine | Met | M | nonpolar | neutral | 1.9 |
| Phenylalanine | Phe | F | nonpolar | neutral | 2.8 |
| Proline | Pro | P | nonpolar | neutral | −1.6 |
| Serine | Ser | S | polar | neutral | −0.8 |
| Threonine | Thr | T | polar | neutral | −0.7 |
| Tryptophan | Trp | W | nonpolar | neutral | −0.9 |
| Tyrosine | Tyr | Y | polar | neutral | −1.3 |
| Valine | Val | V | nonpolar | neutral | 4.2 |

"Hydrophobic amino acids" include small hydrophobic amino acids and large hydrophobic amino acids. "Small hydrophobic amino acid" are glycine, alanine, proline, and analogs thereof. "Large hydrophobic amino acids" are valine, leucine, isoleucine, phenylalanine, methionine, tryptophan, and analogs thereof. "Polar amino acids" are serine, threonine, asparagine, glutamine, cysteine, tyrosine, and analogs thereof. "Charged amino acids" are lysine, arginine, histidine, aspartate, glutamate, and analogs thereof. In some cases, aspartic acid and glutamic acid are referred to as acidic amino acids. In other cases, lysine, arginine and histinde are referred to as basic amino acids.

The term "amino acid analog" refers to a molecule which is structurally similar to an amino acid and which is substituted for an amino acid in the formation of a peptidomimetic macrocycle Amino acid analogs include, without limitation, β-amino acids and amino acids where the amino or carboxy group is substituted by a similarly reactive group (e.g., substitution of the primary amine with a secondary or tertiary amine, or substitution of the carboxy group with an ester).

The term "non-natural amino acid" refers to an amino acid which is not one of the twenty amino acids commonly found in peptides synthesized in nature, and known by the one letter abbreviations A, R, N, C, D, Q, E, G, H, I, L, K, M, F, P, S, T, W, Y and V.

In some instances, amino acid analogs include β-amino acid analogs. Examples of β-amino acid analogs include, but are not limited to, the following: cyclic β-amino acid analogs; β-alanine; (R)-β-phenylalanine; (R)-1,2,3,4-tetrahydro-isoquinoline-3-acetic acid; (R)-3-amino-4-(1-naphthyl)-butyric acid; (R)-3-amino-4-(2,4-dichlorophenyl) butyric acid; (R)-3-amino-4-(2-chlorophenyl)-butyric acid; (R)-3-amino-4-(2-cyanophenyl)-butyric acid; (R)-3-amino-4-(2-fluorophenyl)-butyric acid; (R)-3-amino-4-(2-furyl)-butyric acid; (R)-3-amino-4-(2-methylphenyl)-butyric acid; (R)-3-amino-4-(2-naphthyl)-butyric acid; (R)-3-amino-4-(2-thienyl)-butyric acid; (R)-3-amino-4-(2-trifluoromethylphenyl)-butyric acid; (R)-3-amino-4-(3,4-dichlorophenyl)bu- tyric acid; (R)-3-amino-4-(3,4-difluorophenyl)butyric acid; (R)-3-amino-4-(3-benzothienyl)-butyric acid; (R)-3-amino-4-(3-chlorophenyl)-butyric acid; (R)-3-amino-4-(3-cyanophenyl)-butyric acid; (R)-3-amino-4-(3-fluorophenyl)-butyric acid; (R)-3-amino-4-(3-methylphenyl)-butyric acid; (R)-3-amino-4-(3-pyridyl)-butyric acid; (R)-3-amino-4-(3-thienyl)-butyric acid; (R)-3-amino-4-(3-trifluoromethylphenyl)-butyric acid; (R)-3-amino-4-(4-bromophenyl)-butyric acid; (R)-3-amino-4-(4-chlorophenyl)-butyric acid; (R)-3-amino-4-(4-cyanophenyl)-butyric acid; (R)-3-amnino-4-(4-fluorophenyl)-butyric acid; (R)-3-amnino-4-(4-iodophenyl)-butyric acid; (R)-3-amnino-4-(4-methylphenyl)-butyric acid; (R)-3-amnino-4-(4-nitrophenyl)-butyric acid; (R)-3-amnino-4-(4-pyridyl)-butyric acid; (R)-3-amino-4-(4-trifluoromethylphenyl)-butyric acid; (R)-3-amnino-4-pentafluoro-phenylbutyric acid; (R)-3-amnino-5-hexenoic acid; (R)-3-amnino-5-hexynoic acid; (R)-3-amino-5-phenylpentanoic acid; (R)-3-amino-6-phenyl-5-hexenoic acid; (S)-1,2,3,4-tetrahydro-isoquinoline-3-acetic acid; (S)-3-amnino-4-(1-naphthyl)-butyric acid; (S)-3-amino-4-(2,4-dichlorophenyl)butyric acid; (S)-3-amino-4-(2-chlorophenyl)-butyric acid; (S)-3-amino-4-(2-cyanophenyl)-butyric acid; (S)-3-amino-4-(2-fluorophenyl)-butyric acid; (S)-3-amnino-4-(2-furyl)-butyric acid; (S)-3-amnino-4-(2-methylphenyl)-butyric acid; (S)-3-amnino-4-(2-naphthyl)-butyric acid; (S)-3-amino-4-(2-thienyl)-butyric acid; (S)-3-amino-4-(2-trifluoromethylphenyl)-butyric acid; (S)-3-amino-4-(3,4-dichlorophenyl)butyric acid; (S)-3-amnino-4-(3,4-difluorophenyl)-butyric acid; (S)-3-amnino-4-(3-benzothienyl)-butyric acid; (S)-3-amnino-4-(3-chlorophenyl)-butyric acid; (S)-3-amnino-4-(3-cyanophenyl)-butyric acid; (S)-3-amino-4-(3-fluorophenyl)-butyric acid; (S)-3-amnino-4-(3-methylphenyl)-butyric acid; (S)-3-amnino-4-(3-pyridyl)-butyric acid; (S)-3-amnino-4-(3-thienyl)-butyric acid; (S)-3-amnino-4-(3-trifluoromethylphenyl)-butyric acid; (S)-3-amnino-4-(4-bromophenyl)-butyric acid; (S)-3-amnino-4-(4-chlorophenyl) butyric acid; (S)-3-amnino-4-(4-cyanophenyl)-butyric acid; (S)-3-amino-4-(4-fluorophenyl) butyric acid; (S)-3-amnino-4-(4-iodophenyl)-butyric acid; (S)-3-amnino-4-(4-methylphenyl)-butyric acid; (S)-3-amnino-4-(4-nitrophenyl)-butyric acid; (S)-3-amnino-4-(4-pyridyl)-butyric acid; (S)-3-amino-4-(4-trifluoromethylphenyl)-butyric acid; (S)-3-amino-4-pentafluoro-phenylbutyric acid; (S)-3-amino-5-hexenoic acid; (S)-3-amino-5-hexynoic acid; (S)-3-amnino-5-phenylpentanoic acid; (S)-3-amnino-6-phenyl-5-hexenoic acid; 1,2,5,6-tetrahydropyridine-3-carboxylic acid; 1,2,5,6-tetrahydropyridine-4-carboxylic acid; 3-amino-3-(2-chlorophenyl)-propionic acid; 3-amnino-3-(2-thienyl)-propionic acid; 3-amino-3-(3-bromophenyl)-propionic acid; 3-amnino-3-(4-chlorophenyl)-propionic acid; 3-amnino-3-(4-methoxyphenyl)-propionic acid; 3-amino-4,4,4-trifluoro-butyric acid; 3-aminoadipic acid; D-β-phenylalanine; β-leucine; L-β-homoalanine; L-β-bomoaspartic acid γ-benzyl ester; L-β-homoglutamic acid δ-benzyl ester; L-D-homoisoleucine; L-β-homoleucine; L-β-homomethionine; L-β-homophenylalanine; L-β-homoproline; L-β-homotryptophan; L-β-homovaline; L-Nω-benzyloxycarbonyl-β-homolysine; Nω-L-β-homoarginine; O-benzyl-L-β-bomobydroxyproline; O-benzyl-L-β-homoserine; O-benzyl-L-β-bomotbreonine; O-benzyl-L-β-bomotyrosine; γ-trityl-L-β-bomoasparagine; (R)-β-phenylalanine; L-β-bomoaspartic acid 7-t-butyl ester; L-β-homoglutamnic acid δ-t-butyl ester; L-Nω-β-homolysine; Nδ-trityl-L-β-homoglutamiine; Nω-2,2,4,6,7-pentametbyl-dihydrobenzofuran-5-sulfonyl-L-3-bomoarginine; O-t-butyl-L-β-homohydroxy-proline; O-t-butyl-L-β-homoserine; O-t-butyl-L-β-homothreonine; O-t- butyl-L-β-homotyrosine; 2-aminocyclopentane carboxylic acid; and 2-aminocyclohexane carboxylic acid.

In some instances, amino acid analogs include analogs of alanine, valine, glycine or leucine. Examples of amino acid analogs of alanine, valine, glycine, and leucine include, but are not limited to, the following: α-methoxyglycine; α-allyl-L-alanine; α-aminoisobutyric acid; α-methyl-leucine; β-(1-naphthyl)-D-alanine; β-(1-naphthyl)-L-alanine; β-(2-naphthyl)-D-alanine; β-(2-naphthyl)-L-alanine; β-(2-pyridyl)-D-alanine; β-(2-pyridyl)-L-alanine; β-(2-thienyl)-D-alanine; β-(2-thienyl)-L-alanine; β-(3-benzothienyl)-D-alanine; β-(3-benzothienyl)-L-alanine; β-(3-pyridyl)-D-alanine; β-(3-pyridyl)-L-alanine; β-(4-pyridyl)-D-alanine; β-(4-pyridyl)-L-alanine; β-chloro-L-alanine; β-cyano-L-alanin; β-cyclohexyl-D-alanine; β-cyclohexyl-L-alanine; β-cyclopenten-1-yl-alanine; β-cyclopentyl-alanine; β-cyclopropyl-L-Ala-OH.dicyclohexylammonium salt; β-t-butyl-D-alanine; β-t-butyl-L-alanine; γ-aminobutyric acid; L-α,β-diaminopropionic acid; 2,4-dinitro-phenylglycine; 2,5-dihydro-D-phenylglycine; 2-amino-4,4,4-trifluorobutyric acid; 2-fluoro-phenylglycine; 3-amino-4,4,4-trifluoro-butyric acid; 3-fluoro-valine; 4,4,4-trifluoro-valine; 4,5-dehydro-L-leu-OH.dicyclohexylammonium salt; 4-fluoro-D-phenylglycine; 4-fluoro-L-phenylglycine; 4-hydroxy-D-phenylglycine; 5,5,5-trifluoro-leucine; 6-aminohexanoic acid; cyclopentyl-D-Gly-OH.dicyclohexylammonium salt; cyclopentyl-Gly-OH.dicyclohexylammonium salt; D-α,β-diaminopropionic acid; D-α-aminobutyric acid; D-α-t-butylglycine; D-(2-thienyl)glycine; D-(3-thienyl)glycine; D-2-aminocaproic acid; D-2-indanylglycine; D-allylglycine-dicyclohexylammonium salt; D-cyclohexylglycine; D-norvaline; D-phenylglycine; β-aminobutyric acid; β-aminoisobutyric acid; (2-bromophenyl)glycine; (2-methoxyphenyl)glycine; (2-methylphenyl)glycine; (2-thiazoyl)glycine; (2-thienyl)glycine; 2-amino-3-(dimethylamino)-propionic acid; L-α,β-diaminopropionic acid; L-α-aminobutyric acid; L-α-t-butylglycine; L-(3-thienyl) glycine; L-2-amino-3-(dimethylamino)-propionic acid; L-2-aminocaproic acid dicyclohexyl-ammonium salt; L-2-indanylglycine; L-allylglycine.dicyclohexyl ammonium salt; L-cyclohexylglycine; L-phenylglycine; L-propargylglycine; L-norvaline; N-α-aminomethyl-L-alanine; D-α,γ-diaminobutyric acid; L-α,γ-diaminobutyric acid; β-cyclopropyl-L-alanine; (N-β-(2,4-dinitrophenyl))-L-α,β-diaminopropionic acid; (N-β-1-(4,4-dimethyl-2,6-dioxocyclohex-1-ylidene)ethyl)-D-α,β-diaminopropionic acid; (N-β-1-(4,4-dimethyl-2,6-dioxocyclohex-1-ylidene)ethyl)-L-α,β-diaminopropionic acid; (N-β-4-methyltrityl)-L-α,β-diaminopropionic acid; (N-β-allyloxycarbonyl)-L-α,β-diaminopropionic acid; (N-γ-1-(4,4-dimethyl-2,6-dioxocyclohex-1-ylidene)ethyl)-D-α,γ-diaminobutyric acid; (N-γ-1-(4,4-dimethyl-2,6-dioxocyclohex-1-ylidene)ethyl)-L-α,γ-diaminobutyric acid; (N-γ-4-methyltrityl)-D-α,γ-diaminobutyric acid; (N-γ-4-methyltrityl)-L-α,γ-diaminobutyric acid; (N-γ-allyloxycarbonyl)-L-α,γ-diaminobutyric acid; D-α,γ-diaminobutyric acid; 4,5-dehydro-L-leucine; cyclopentyl-D-Gly-OH; cyclopentyl-Gly-OH; D-allylglycine; D-homocyclohexylalanine; L-1-pyrenylalanine; L-2-aminocaproic acid; L-allylglycine; L-homocyclohexylalanine; and N-(2-hydroxy-4-methoxy-Bzl)-Gly-OH.

In some instances, amino acid analogs include analogs of arginine or lysine. Examples of amino acid analogs of arginine and lysine include, but are not limited to, the following: citrulline; L-2-amino-3-guanidinopropionic acid; L-2-amino-3-ureidopropionic acid; L-citrulline; Lys(Me)$_2$-OH; Lys(N$_3$)—OH; Nδ-benzyloxycarbonyl-L-ornithine; Nω-nitro-D-arginine; Nω-nitro-L-arginine; α-methyl-ornithine; 2,6-diaminoheptanedioic acid; L-ornithine; (Nδ-1-(4,4-dimethyl-2,6-dioxo-cyclohex-1-ylidene)ethyl)-D-ornithine; (Nδ-1-(4,4-dimethyl-2,6-dioxo-cyclohex-1-ylidene) ethyl)-L-ornithine; (Nδ-4-methyltrityl)-D-ornithine; (Nδ-4-methyltrityl)-L-ornithine; D-ornithine; L-ornithine; Arg (MeXPbf)-OH; Arg(Me)$_2$-OH (asymmetrical); Arg(Me)2-OH (symmetrical); Lys(ivDde)-OH; Lys(Me)2-OH.HCl; Lys(Me3)-OH chloride; Nω-nitro-D-arginine; and Nω-nitro-L-arginine.

In some instances, amino acid analogs include analogs of aspartic or glutamic acids. Examples of amino acid analogs of aspartic and glutamic acids include, but are not limited to, the following: α-methyl-D-aspartic acid; α-methyl-glutamic acid; α-methyl-L-aspartic acid; γ-methylene-glutamic acid; (N-γ-ethyl)-L-glutamine; [N-α-(4-aminobenzoyl)]-L-glutamic acid; 2,6-diaminopimelic acid; L-α-aminosuberic acid; D-2-aminoadipic acid; D-α-aminosuberic acid; α-aminopimelic acid; iminodiacetic acid; L-2-aminoadipic acid; threo-β-methyl-aspartic acid; γ-carboxy-D-glutamic acid γ,γ-di-t-butyl ester; γ-carboxy-L-glutamic acid γ,γ-di-t-butyl ester; Glu(OAll)-OH; L-Asu(OtBu)-OH; and pyroglutamic acid.

In some instances, amino acid analogs include analogs of cysteine and methionine. Examples of amino acid analogs of cysteine and methionine include, but are not limited to, Cys(farnesyl)-OH, Cys(farnesyl)-OMe, α-methyl-methionine, Cys(2-hydroxyethyl)-OH, Cys(3-aminopropyl)-OH, 2-amino-4-(ethylthio)butyric acid, buthionine, buthionine-sulfoximine, ethionine, methionine methylsulfonium chloride, selenomethionine, cysteic acid, [2-(4-pyridyl)ethyl]-DL-penicillamine, [2-(4-pyridyl)ethyl]-L-cysteine, 4-methoxybenzyl-D-penicillamine, 4-methoxybenzyl-L-penicillamine, 4-methylbenzyl-D-penicillamine, 4-methylbenzyl-L-penicillamine, benzyl-D-cysteine, benzyl-L-cysteine, benzyl-DL-homocysteine, carbamoyl-L-cysteine, carboxyethyl-L-cysteine, carboxymethyl-L-cysteine, diphenylmethyl-L-cysteine, ethyl-L-cysteine, methyl-L-cysteine, t-butyl-D-cysteine, trityl-L-homocysteine, trityl-D-penicillamine, cystathionine, homocystine, L-homocystine, (2-aminoethyl)-L-cysteine, seleno-L-cystine, cystathionine, Cys(StBu)-OH, and acetamidomethyl-D-penicillamine.

In some instances, amino acid analogs include analogs of phenylalanine and tyrosine. Examples of amino acid analogs of phenylalanine and tyrosine include β-methyl-phenylalanine, β-hydroxyphenylalanine, α-methyl-3-methoxy-DL-phenylalanine, α-methyl-D-phenylalanine, α-methyl-L-phenylalanine, 1,2,3,4-tetrahydroisoquinoline-3-carboxylic acid, 2,4-dichloro-phenylalanine, 2-(trifluoromethyl)-D-phenylalanine, 2-(trifluoromethyl)-L-phenylalanine, 2-bromo-D-phenylalanine, 2-bromo-L-phenylalanine, 2-chloro-D-phenylalanine, 2-chloro-L-phenylalanine, 2-cyano-D-phenylalanine, 2-cyano-L-phenylalanine, 2-fluoro-D-phenylalanine, 2-fluoro-L-phenylalanine, 2-methyl-D-phenylalanine, 2-methyl-L-phenylalanine, 2-nitro-D-phenylalanine, 2-nitro-L-phenylalanine, 2;4;5-trihydroxy-phenylalanine, 3,4,5-trifluoro-D-phenylalanine, 3,4,5-trifluoro-L-phenylalanine, 3,4-dichloro-D-phenylalanine, 3,4-dichloro-L-phenylalanine, 3,4-difluoro-D-phenylalanine, 3,4-difluoro-L-phenylalanine, 3,4-dihydroxy-L-phenylalanine, 3,4-dimethoxy-L-phenylalanine, 3,5,3'-triiodo-L-thyronine, 3,5-diiodo-D-tyrosine, 3,5-diiodo-L-tyrosine, 3,5-diiodo-L-thyronine, 3-(trifluoromethyl)-D-phenylalanine, 3-(trifluoromethyl)-L-phenylalanine, 3-amino-L-tyrosine, 3-bromo-D-phenylalanine, 3-bromo-L-phenylalanine, 3-chloro-D-phenylalanine, 3-chloro-L-phenylalanine, 3-chloro-L-tyrosine, 3-cyano-D-phenylalanine, 3-cyano-L-phenylalanine, 3-fluoro-D-phenylalanine, 3-fluoro-L-phenylalanine, 3-fluoro-tyrosine, 3-iodo-D-phenylalanine, 3-iodo-L-phenylalanine, 3-iodo-L-tyrosine, 3-methoxy-L-tyrosine, 3-methyl-D-phenylalanine, 3-methyl-L-phenylalanine, 3-nitro-D-phenylalanine, 3-nitro-L-phenylalanine, 3-nitro-L-tyrosine, 4-(trifluoromethyl)-D-phenylalanine, 4-(trifluoromethyl)-L-phenylalanine, 4-amino-D-phenylalanine, 4-amino-L-phenylalanine, 4-benzoyl-D-phenylalanine, 4-benzoyl-L-phenylalanine, 4-bis(2-chloroethyl)amino-L-phenylalanine, 4-bromo-D-phenylalanine, 4-bromo-L-phenylalanine, 4-chloro-D-phenylalanine, 4-chloro-L-phenylalanine, 4-cyano-D-phenylalanine, 4-cyano-L-phenylalanine, 4-fluoro-D-phenylalanine, 4-fluoro-L-phenylalanine, 4-iodo-D-phenylalanine, 4-iodo-L-phenylalanine, homophenylalanine, thyroxine, 3,3-diphenylalanine, thyronine, ethyl-tyrosine, and methyl-tyrosine.

In some instances, amino acid analogs include analogs of proline. Examples of amino acid analogs of proline include, but are not limited to, 3,4-dehydro-proline, 4-fluoro-proline, cis-4-hydroxy-proline, thiazolidine-2-carboxylic acid, and trans-4-fluoro-proline.

In some instances, amino acid analogs include analogs of serine and threonine. Examples of amino acid analogs of serine and threonine include, but are not limited to, 3-amino-2-hydroxy-5-methylhexanoic acid, 2-amino-3-hydroxy-4-methylpentanoic acid, 2-amino-3-ethoxybutanoic acid, 2-amino-3-methoxybutanoic acid, 4-amino-3-hydroxy-6-methylheptanoic acid, 2-amino-3-benzyloxypropionic acid, 2-amino-3-benzyloxypropionic acid, 2-amino-3-ethoxypropionic acid, 4-amino-3-hydroxybutanoic acid, and α-methylserine.

In some instances, amino acid analogs include analogs of tryptophan. Examples of amino acid analogs of tryptophan include, but are not limited to, the following: α-methyl-tryptophan; β-(3-benzothienyl)-D-alanine; β-(3-benzothienyl)-L-alanine; 1-methyl-tryptophan; 4-methyl-tryptophan; 5-benzyloxy-tryptophan; 5-bromo-tryptophan; 5-chloro-tryptophan; 5-fluoro-tryptophan; 5-hydroxy-tryptophan; 5-hydroxy-L-tryptophan; 5-methoxy-tryptophan; 5-methoxy-L-tryptophan; 5-methyl-tryptophan; 6-bromo-tryptophan; 6-chloro-D-tryptophan; 6-chloro-tryptophan; 6-fluoro-tryptophan; 6-methyl-tryptophan; 7-benzyloxy-tryptophan; 7-bromo-tryptophan; 7-methyl-tryptophan; D-1,2,3,4-tetrahydro-norharman-3-carboxylic acid; 6-methoxy-1,2,3,4-tetrahydronorharman-1-carboxylic acid; 7-azatryptophan; L-1,2,3,4-tetrahydro-norharman-3-carboxylic acid; 5-methoxy-2-methyl-tryptophan; and 6-chloro-L-tryptophan.

In some instances, amino acid analogs are racemic. In some instances, the D isomer of the amino acid analog is used. In some cases, the L isomer of the amino acid analog is used. In some instances, the amino acid analog comprises chiral centers that are in the R or S configuration. Sometimes, the amino group(s) of a β-amino acid analog is substituted with a protecting group, e.g., tert-butyloxycarbonyl (BOC group), 9-fluorenylmethyloxycarbonyl (FMOC), tosyl, and the like. Sometimes, the carboxylic acid functional group of a β-amino acid analog is protected, e.g., as its ester derivative. In some cases, the salt of the amino acid analog is used.

In some embodiments, nucleic acid molecules refer to at least two nucleotides covalently linked together. In some instances, a nucleic acid described herein contains phosphodiester bonds, although in some cases, as outlined below (for example in the construction of primers and probes such as label probes), nucleic acid analogs are included that have alternate backbones, comprising, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwes et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphosphoroamidite linkages (see Eckstein, Oligonucleotides and Analogues: A Practical Approach. Oxford University Press), and peptide nucleic acid (also referred to herein as "PNA") backbones and linkages (see Egholm, J. Am. Chem. Soc. 114:1895 (1992); Meier et al., Chem. Int. Ed. Engl. 31:1008 (1992); Nielsen, Nature. 365:566 (1993); Carlsson et al., Nature 380:207 (1996), all of which are incorporated by reference). Other analog nucleic acids include those with bicyclic structures including locked nucleic acids (also referred to herein as "LNA"), Koshkin et al., J. Am. Chem. Soc. 120.13252 3 (1998); positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469,863; Kiedrowshi et al., Angew. Chem. Intl. Ed. English 30:423 (1991): Letsinger et al., J. Am. Chem. Soc. 110:4470 (1988); Letsinger et al., Nucleoside & amp; Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994): Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. (1995) pp 169 176). Several nucleic acid analogs are described in Rawls, C & E News Jun. 2, 1997 page 35. "Locked nucleic acids" are also included within the definition of nucleic acid analogs. LNAs are a class of nucleic acid analogues in which the ribose ring is "locked" by a methylene bridge connecting the 2'-O atom with the 4'-C atom. All of these references are hereby expressly incorporated by reference. In some instances, these modifications of the ribose-phosphate backbone are done to increase the stability and half-life of such molecules in physiological environments. For example, PNA:DNA and LNA-DNA hybrids exhibit higher stability and thus are used in some embodiments. The target nucleic acids are single stranded or double stranded, as specified, or contain portions of both double stranded or single stranded sequence. Depending on the application, the nucleic acids are DNA (including, e.g., genomic DNA, mitochondrial DNA, and cDNA), RNA (including. e.g., mRNA and rRNA) or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc.

Samples, Analytical Techniques, and Instrumentation

In certain embodiments, one or more of the methods disclosed herein comprise a sample. In some embodiments, the sample is a cell sample or a tissue sample. In some instances, the sample is a cell sample. In some embodiments, the sample for use with the methods described herein is obtained from cells of an animal. In some instances, the animal cell includes a cell from a marine invertebrate, fish, insects, amphibian, reptile, or mammal. In some instances, the mammalian cell is a primate, ape, equine, bovine, porcine, canine, feline, or rodent. In some instances, the mammal is a primate, ape, dog, cat, rabbit, ferret, or the like. In some cases, the rodent is a mouse, rat, hamster, gerbil, hamster, chinchilla, or guinea pig. In some embodiments, the bird cell is from a canary, parakeet or parrots. In some embodiments, the reptile cell is from a turtles, lizard or snake. In some cases, the fish cell is from a tropical fish. In some cases, the fish cell is from a zebrafish (e.g. *Danino rerio*). In some cases, the worm cell is from a nematode (e.g. *C. elegans*). In some cases, the amphibian cell is from a frog. In some embodiments, the arthropod cell is from a tarantula or hermit crab.

In some embodiments, the sample for use with the methods described herein is obtained from a mammalian cell. In some instances, the mammalian cell is an epithelial cell, connective tissue cell, hormone secreting cell, a nerve cell, a skeletal muscle cell, a blood cell, or an immune system cell.

Exemplary mammalian cells include, but are not limited to, 293A cell line, 293FT cell line, 293F cells, 293 H cells, HEK 293 cells, CHO DG44 cells, CHO-S cells, CHO-K1 cells, Expi293F™ cells, Flp-In™ T-REx™ 293 cell line, Flp-In™-293 cell line, Flp-In™-3T3 cell line, Flp-In™-BHK cell line, Flp-In™-CHO cell line, Flp-In™-CV-1 cell line, Flp-In™-Jurkat cell line, FreeStyle™ 293-F cells, FreeStyle™ CHO-S cells, GripTite™ 293 MSR cell line, GS-CHO cell line, HepaRG™ cells, T-REx™ Jurkat cell line, Per.C6 cells, T-REx™-293 cell line, T-REx™-CHO cell line, T-REx™-HeLa cell line, NC-HIMT cell line, and PC12 cell line.

In some instances, the sample for use with the methods described herein is obtained from cells of a tumor cell line. In some instances, the sample is obtained from cells of a solid tumor cell line. In some instances, the solid tumor cell line is a sarcoma cell line. In some instances, the solid tumor cell line is a carcinoma cell line. In some embodiments, the sarcoma cell line is obtained from a cell line of alveolar rhabdomyosarcoma, alveolar soft part sarcoma, ameloblastoma, angiosarcoma, chondrosarcoma, chordoma, clear cell sarcoma of soft tissue, dedifferentiated liposarcoma, desmoid, desmoplastic small round cell tumor, embryonal rhabdomyosarcoma, epithelioid fibrosarcoma, epithelioid hemangioendothelioma, epithelioid sarcoma, esthesioneuroblastoma, Ewing sarcoma, extrarenal rhabdoid tumor, extraskeletal myxoid chondrosarcoma, extraskeletal osteosarcoma, fibrosarcoma, giant cell tumor, hemangiopericytoma, infantile fibrosarcoma, inflammatory myofibroblastic tumor, Kaposi sarcoma, leiomyosarcoma of bone, liposarcoma, liposarcoma of bone, malignant fibrous histiocytoma (MFH), malignant fibrous histiocytoma (MFH) of bone, malignant mesenchymoma, malignant peripheral nerve sheath tumor, mesenchymal chondrosarcoma, myxofibrosarcoma, myxoid liposarcoma, myxoinflammatory fibroblastic sarcoma, neoplasms with perivascular epitheioid cell differentiation, osteosarcoma, parosteal osteosarcoma, neoplasm with perivascular epitheioid cell differentiation, periosteal osteosarcoma, pleomorphic liposarcoma, pleomorphic rhabdomyosarcoma, PNET/extraskeletal Ewing tumor, rhabdomyosarcoma, round cell liposarcoma, small cell osteosarcoma, solitary fibrous tumor, synovial sarcoma, telangiectatic osteosarcoma.

In some embodiments, the carcinoma cell line is obtained from a cell line of adenocarcinoma, squamous cell carcinoma, adenosquamous carcinoma, anaplastic carcinoma, large cell carcinoma, small cell carcinoma, anal cancer, appendix cancer, bile duct cancer (i.e., cholangiocarcinoma), bladder cancer, brain tumor, breast cancer, cervical cancer, colon cancer, cancer of Unknown Primary (CUP), esophageal cancer, eye cancer, fallopian tube cancer, gastroenterological cancer, kidney cancer, liver cancer, lung cancer, medulloblastoma, melanoma, oral cancer, ovarian cancer, pancreatic cancer, parathyroid disease, penile cancer, pituitary tumor, prostate cancer, rectal cancer, skin cancer, stomach cancer, testicular cancer, throat cancer, thyroid cancer, uterine cancer, vaginal cancer, or vulvar cancer.

In some instances, the sample is obtained from cells of a hematologic malignant cell line. In some instances, the hematologic malignant cell line is a T-cell cell line. In some instances, B-cell cell line. In some instances, the hematologic malignant cell line is obtained from a T-cell cell line of: peripheral T-cell lymphoma not otherwise specified (PTCL-NOS), anaplastic large cell lymphoma, angioimmunoblastic lymphoma, cutaneous T-cell lymphoma, adult T-cell leukemia/lymphoma (ATLL), blastic NK-cell lymphoma, enteropathy-type T-cell lymphoma, hematosplenic gamma-delta T-cell lymphoma, lymphoblastic lymphoma, nasal NK/T-cell lymphomas, or treatment-related T-cell lymphomas.

In some instances, the hematologic malignant cell line is obtained from a B-cell cell line of: acute lymphoblastic leukemia (ALL), acute myelogenous leukemia (AML), chronic myelogenous leukemia (CML), acute monocytic leukemia (AMoL), chronic lymphocytic leukemia (CLL), high-risk chronic lymphocytic leukemia (CLL), small lymphocytic lymphoma (SLL), high-risk small lymphocytic lymphoma (SLL), follicular lymphoma (FL), mantle cell lymphoma (MCL), Waldenstrom's macroglobulinemia, multiple myeloma, extranodal marginal zone B cell lymphoma, nodal marginal zone B cell lymphoma, Burkitt's lymphoma, non-Burkitt high grade B cell lymphoma, primary mediastinal B-cell lymphoma (PMBL), immunoblastic large cell lymphoma, precursor B-lymphoblastic lymphoma, B cell prolymphocytic leukemia, lymphoplasmacytic lymphoma, splenic marginal zone lymphoma, plasma cell myeloma, plasmacytoma, mediastinal (thymic) large B cell lymphoma, intravascular large B cell lymphoma, primary effusion lymphoma, or lymphomatoid granulomatosis.

In some embodiments, the sample for use with the methods described herein is obtained from a tumor cell line. Exemplary tumor cell line includes, but is not limited to, 600MPE, AU565, BT-20, BT-474, BT-483, BT-549, Evsa-T, Hs578T, MCF-7, MDA-MB-231, SkBr3, T-47D, HeLa, DU145, PC3, LNCaP, A549, H1299, NCI-H460, A2780, SKOV-3/Luc, Neuro2a, RKO, RKO-AS45-1, HT-29, SW1417, SW948, DLD-1, SW480, Capan-1, MC/9, B72.3, B25.2, B6.2, B38.1, DMS153, SU.86.86, SNU-182, SNU-423, SNU-449, SNU-475, SNU-387, Hs 817.T, LMH, LMH/2A, SNU-398, PLHC-1, HepG2/SF, OCI-Ly1, OCI-Ly2, OCI-Ly3, OCI-Ly4, OCI-Ly6, OCI-Ly7, OCI-Ly10, OCI-Ly18, OCI-Ly19, U2932, DB, HBL-1, RIVA, SUDHL2, TMD8, MEC1, MEC2, 8E5, CCRF-CEM, MOLT-3, TALL-104, AML-193, THP-1, BDCM, HL-60, Jurkat, RPMI 8226, MOLT-4, RS4, K-562, KASUMI-1, Daudi, GA-10, Raji, JeKo-1, NK-92, and Mino.

In some embodiments, the sample for use in the methods is from any tissue or fluid from an individual. Samples include, but are not limited to, tissue (e.g. connective tissue, muscle tissue, nervous tissue, or epithelial tissue), whole blood, dissociated bone marrow, bone marrow aspirate, pleural fluid, peritoneal fluid, central spinal fluid, abdominal fluid, pancreatic fluid, cerebrospinal fluid, brain fluid, ascites, pericardial fluid, urine, saliva, bronchial lavage, sweat, tears, ear flow, sputum, hydrocele fluid, semen, vaginal flow, milk, amniotic fluid, and secretions of respiratory, intestinal or genitourinary tract. In some embodiments, the sample is a tissue sample, such as a sample obtained from a biopsy or a tumor tissue sample. In some embodiments, the sample is a blood serum sample. In some embodiments, the sample is a blood cell sample containing one or more peripheral blood mononuclear cells (PBMCs). In some embodiments, the sample contains one or more circulating tumor cells (CTCs). In some embodiments, the sample contains one or more disseminated tumor cells (DTC, e.g., in a bone marrow aspirate sample).

In some embodiments, the samples are obtained from the individual by any suitable means of obtaining the sample using well-known and routine clinical methods. Procedures for obtaining tissue samples from an individual are well known. For example, procedures for drawing and processing tissue sample such as from a needle aspiration biopsy is well-known and is employed to obtain a sample for use in the methods provided. Typically, for collection of such a tissue sample, a thin hollow needle is inserted into a mass such as a tumor mass for sampling of cells that, after being stained, will be examined under a microscope.

Sample Preparation and Analysis

In some embodiments, the sample is a sample solution. In some instances, the sample solution comprises a solution such as a buffer (e.g. phosphate buffered saline) or a media. In some embodiments, the media is an isotopically labeled media. In some instances, the sample solution is a cell solution.

In some embodiments, the sample (e.g., cells or a cell solution) is incubated with a cysteine-reactive probe for analysis of protein cysteine-reactive probe interactions. In some instances, the sample (e.g., cells or a cell solution) is further incubated in the presence of a small molecule fragment prior to addition of the cysteine-reactive probe. In some instances, the sample is compared with a control. In some instances, the control comprises the cysteine-reactive probe but not the small molecule fragment. In some instances, a difference is observed between a set of cysteine-reactive probe protein interactions between the sample and the control. In some instances, the difference correlates to the interaction between the small molecule fragment and the cysteine containing proteins.

In some embodiments, the sample (e.g. cells or a cell solution) is further labeled for analysis of cysteine-reactive probe protein interactions. In some instances, the sample (e.g. cells or a cell solution) is labeled with an enriched media. In some cases, the sample (e.g. cells or a cell solution) is labeled with isotope-labeled amino acids, such as $^{13}C$ or $^{15}N$-labeled amino acids. In some cases, the labeled sample is further compared with a non-labeled sample to detect differences in cysteine-reactive probe protein interactions between the two samples. In some instances, this difference is a difference of a cysteine containing protein and its interaction with a small molecule fragment in the labeled sample versus the non-labeled sample. In some instances, the difference is an increase, decrease or a lack of protein cysteine-reactive probe interaction in the two samples. In some instances, the isotope-labeled method is termed SILAC, stable isotope labeling using amino acids in cell culture.

In some instances, the sample is divided into a first cell solution and a second cell solution. In some cases, the first cell solution is incubated with a small molecule fragment for an extended period of time prior to incubating the first cell solution with a first cysteine-reactive probe to generate a first group of cysteine-reactive probe-protein complexes. In some instances, the extended period of time is about 5, 10, 15, 20, 30, 60, 90, 120 minutes or longer. In some instances, the second cell solution comprises a second cysteine-reactive probe to generate a second group of cysteine-reactive probe-protein complexes. In some instances, the first cysteine-reactive probe and the second cysteine-reactive probe are the same. In some embodiments, cells from the second cell solution are further treated with a buffer, such as a control buffer, in which the buffer does not contain a small molecule fragment. In some embodiments, the control buffer comprises dimethyl sulfoxide (DMSO).

In some embodiments, the cysteine-reactive probe-protein complex is further conjugated to a chromophore, such as a fluorophore. In some instances, the cysteine-reactive probe-protein complex is separated and visualized utilizing an electrophoresis system, such as through a gel electrophoresis, or a capillary electrophoresis. Exemplary gel electrophoresis includes agarose based gels, polyacrylamide based gels, or starch based gels. In some instances, the cysteine-reactive probe-protein is subjected to a native electrophoresis condition. In some instances, the cysteine-reactive probe-protein is subjected to a denaturing electrophoresis condition.

In some instances, the cysteine-reactive probe-protein after harvesting is further fragmentized to generate protein fragments. In some instances, fragmentation is generated through mechanical stress, pressure, or chemical means. In some instances, the protein from the cysteine-reactive probe-protein complexes is fragmented by a chemical means. In some embodiments, the chemical means is a protease. Exemplary proteases include, but are not limited to, serine proteases such as chymotrypsin A, penicillin G acylase precursor, dipeptidase E, DmpA aminopeptidase, subtilisin, prolyl oligopeptidase, D-Ala-D-Ala peptidase C, signal peptidase I, cytomegalovirus assemblin, Lon-A peptidase, peptidase Clp, *Escherichia coli* phage KIF endosialidase CIMCD self-cleaving protein, nucleoporin 145, lactoferrin, murein tetrapeptidase LD-carboxypeptidase, or rhomboid-1; threonine proteases such as ornithine acetyltransferase; cysteine proteases such as TEV protease, amidophosphoribosyltransferase precursor, gamma-glutamyl hydrolase (*Rattus norvegicus*), hedgehog protein, DmpA aminopeptidase, papain, bromelain, cathepsin K, calpain, caspase-1, separase, adenain, pyroglutamyl-peptidase I, sortase A, hepatitis C virus peptidase 2, sindbis virus-type nsP2 peptidase, dipeptidyl-peptidase VI, or DeSI-1 peptidase; aspartate proteases such as beta-secretase 1 (BACE1), beta-secretase 2 (BACE2), cathepsin D, cathepsin E, chymosin, napsin-A, nepenthesin, pepsin, plasmepsin, presenilin, or renin; glutamic acid proteases such as AfuGprA; and metalloproteases such as peptidase_M48.

In some instances, the fragmentation is a random fragmentation. In some instances, the fragmentation generates specific lengths of protein fragments, or the shearing occurs at particular sequence of amino acid regions.

In some instances, the protein fragments are further analyzed by a proteomic method such as by liquid chromatography (LC) (e.g. high performance liquid chromatography), liquid chromatography-mass spectrometry (LC-MS), matrix-assisted laser desorption/ionization (MALDI-TOF), gas chromatography-mass spectrometry (GC-MS), capillary electrophoresis-mass spectrometry (CE-MS), or nuclear magnetic resonance imaging (NMR).

In some embodiments, the LC method is any suitable LC methods well known in the art, for separation of a sample into its individual parts. This separation occurs based on the interaction of the sample with the mobile and stationary phases. Since there are many stationary/mobile phase combinations that are employed when separating a mixture, there are several different types of chromatography that are classified based on the physical states of those phases. In some embodiments, the LC is further classified as normal-phase chromatography, reverse-phase chromatography, size-exclusion chromatography, ion-exchange chromatography, affinity chromatography, displacement chromatography, partition chromatography, flash chromatography, chiral chromatography, and aqueous normal-phase chromatography.

In some embodiments, the LC method is a high performance liquid chromatography (HPLC) method. In some embodiments, the HPLC method is further categorized as normal-phase chromatography, reverse-phase chromatography, size-exclusion chromatography, ion-exchange chromatography, affinity chromatography, displacement chromatography, partition chromatography, chiral chromatography, and aqueous normal-phase chromatography.

In some embodiments, the HPLC method of the present disclosure is performed by any standard techniques well known in the art. Exemplary HPLC methods include hydrophilic interaction liquid chromatography (HILIC), electrostatic repulsion-hydrophilic interaction liquid chromatography (ERLIC) and reverse phase liquid chromatography (RPLC).

In some embodiments, the LC is coupled to a mass spectroscopy as a LC-MS method. In some embodiments, the LC-MS method includes ultra-performance liquid chromatography-electrospray ionization quadrupole time-of-flight mass spectrometry (UPLC-ESI-QTOF-MS), ultra-performance liquid chromatography-electrospray ionization tandem mass spectrometry (UPLC-ESI-MS/MS), reverse phase liquid chromatography-mass spectrometry (RPLC-MS), hydrophilic interaction liquid chromatography-mass spectrometry (HILIC-MS), hydrophilic interaction liquid chromatography-triple quadrupole tandem mass spectrometry (HILIC-QQQ), electrostatic repulsion-hydrophilic interaction liquid chromatography-mass spectrometry (ER-LIC-MS), liquid chromatography time-of-flight mass spectrometry (LC-QTOF-MS), liquid chromatography-tandem mass spectrometry (LC-MS/MS), multidimensional liquid chromatography coupled with tandem mass spectrometry (LC/LC-MS/MS). In some instances, the LC-MS method is LC/LC-MS/MS. In some embodiments, the LC-MS methods of the present disclosure are performed by standard techniques well known in the art.

In some embodiments, the GC is coupled to a mass spectroscopy as a GC-MS method. In some embodiments, the GC-MS method includes two-dimensional gas chromatography time-of-flight mass spectrometry (GC*GC-TOFMS), gas chromatography time-of-flight mass spectrometry (GC-QTOF-MS) and gas chromatography-tandem mass spectrometry (GC-MS/MS).

In some embodiments, CE is coupled to a mass spectroscopy as a CE-MS method. In some embodiments, the CE-MS method includes capillary electrophoresis-negative electrospray ionization-mass spectrometry (CE-ESI-MS), capillary electrophoresis-negative electrospray ionization-quadrupole time of flight-mass spectrometry (CE-ESI-QTOF-MS) and capillary electrophoresis-quadrupole time of flight-mass spectrometry (CE-QTOF-MS).

In some embodiments, the nuclear magnetic resonance (NMR) method is any suitable method well known in the art for the detection of one or more cysteine binding proteins or protein fragments disclosed herein. In some embodiments, the NMR method includes one dimensional (1D) NMR methods, two dimensional (2D) NMR methods, solid state NMR methods and NMR chromatography. Exemplary ID NMR methods include $^1$Hydrogen, $^{13}$Carbon, $^{15}$Nitrogen, $^{17}$Oxygen, $^{19}$Fluorine, $^{31}$Phosphorus, $^{39}$Potassium, $^{23}$Sodium, $^{33}$Sulfur, $^{87}$Strontium, $^{27}$Aluminium, $^{43}$Calcium, $^{35}$Chlorine, $^{37}$Chlorine, $^{63}$Copper, $^{65}$Copper, $^{57}$Iron, $^{25}$Magnesium, $^{199}$Mercury or $^{67}$Zinc NMR method, distortionless enhancement by polarization transfer (DEPT) method, attached proton test (APT) method and ID-incredible natural abundance double quantum transition experiment (INADEQUATE) method. Exemplary 2D NMR methods include correlation spectroscopy (COSY), total correlation spectroscopy (TOCSY), 2D-INADEQUATE, 2D-adequate double quantum transfer experiment (ADEQUATE), nuclear overhauser effect spectroscopy (NOSEY), rotating-frame NOE spectroscopy (ROESY), heteronuclear multiple-quantum correlation spectroscopy (HMQC), heteronuclear single quantum coherence spectroscopy (HSQC), short range coupling and long range coupling methods. Exemplary solid state NMR method include solid state $^{13}$Carbon NMR, high resolution magic angle spinning (HR-MAS) and cross polarization magic angle spinning (CP-MAS) NMR methods. Exemplary NMR techniques include diffusion ordered spectroscopy (DOSY), DOSY-TOCSY and DOSY-HSQC.

In some embodiments, the protein fragments are analyzed by method as described in Weerapana et al., "Quantitative reactivity profiling predicts functional cysteines in proteomes," *Nature*, 468:790-795 (2010).

In some embodiments, the results from the mass spectroscopy method are analyzed by an algorithm for protein identification. In some embodiments, the algorithm combines the results from the mass spectroscopy method with a protein sequence database for protein identification. In some embodiments, the algorithm comprises ProLuCID algorithm, Probity, Scaffold, SEQUEST, or Mascot.

In some embodiments, a value is assigned to each of the protein from the cysteine-reactive probe-protein complex. In some embodiments, the value assigned to each of the protein from the cysteine-reactive probe-protein complex is obtained from the mass spectroscopy analysis. In some instances, the value is the area-under-the curve from a plot of signal intensity as a function of mass-to-charge ratio. In some embodiments, a first value is assigned to the protein obtained from the first cell solution and a second value is assigned to the same protein obtained from the second cell solution. In some instances, a ratio is calculated between the two values. In some instances, a ratio of greater than 2 indicates that the protein is a candidate for interacting with a drug or that the protein is a cysteine binding protein. In some instances, the ratio is greater than 2.5, 3, 3.5, 4, 4.5, 5, 6, 7, 8, 9, 10, 11, 12, 13, 14, 15, 16, 17, 18, 19, or 20. In some cases, the ratio is at most 20.

In some instances, the ratio is calculated based on averaged values. In some instances, the averaged value is an average of at least two, three, or four values of the protein from each cell solution, or that the protein is observed at least two, three, or four times in each cell solution and a value is assigned to each observed time. In some instances, the ratio further has a standard deviation of less than 12, 10, or 8.

In some instances, a value is not an averaged value. In some instances, the ratio is calculated based on value of a protein observed only once in a cell population. In some instances, the ratio is assigned with a value of 20.

In some embodiments, in the context of identifying a cysteine containing protein as a small fragment molecule binding target, a first ratio is obtained from two cell solutions in which both cell solutions have been incubated with a cysteine-reactive probe and the first cell solution is further incubated with a small molecule fragment. In some instances, the first ratio is further compared to a second ratio in which both cell solutions have been treated by cysteine-reactive probes in the absence of a small molecule fragment. In some instances, the first ratio is greater than 0.5, 1, 1.5, 2, 2.5, 3, 3.5, 4, 4.5, 5, 6, 7, 8, 9, 10, 11, 12, 13, 14, 15, 16, 17, 18, 19, or 20. In some instances, the second ratio is greater than 0.5, 1, 1.5, 2, 2.5, 3, 3.5, 4, 4.5, 5, 6, 7, 8, 9, 10, 11, 12, 13, 14, 15, 16, 17, 18, 19, or 20. In some instances, if the first ratio is greater than 2, 2.5, 3, 3.5, 4, 4.5, 5, 6, 7, 8, 9, 10, 11, 12, 13, 14, 15, 16, 17, 18, 19, or 20 and the second ratio is from about 0.5 to about 2, the two ratios indicate that a protein is a drug binding target.

In some embodiments, the value further enables calculating a percentage of inhibition of the cysteine-reactive probe to the cysteine containing protein. In some embodiments, the percentage of inhibition of greater than 50%, 60%, 70%, 80%, 90%, or at 100% indicates that the cysteine containing protein is a candidate for interacting with the small molecule fragment.

Kits/Article of Manufacture

Disclosed herein, in certain embodiments, are kits and articles of manufacture for use with one or more methods described herein. In some embodiments, described herein is a kit for identifying a cysteine containing protein as a small molecule fragment binding target. In some instances, also described herein is a kit for mapping binding sites on a cysteine containing protein. In some cases, described herein is a kit for identifying cysteine binding proteins. In some embodiments, also described herein is a kit for a high throughput screening of a small molecule fragment for interaction with a cysteine containing protein.

In some embodiments, such kit includes cysteine-reactive probes such as the cysteine-reactive probes described herein, test compounds such as small molecule fragments or libraries and/or controls, and reagents suitable for carrying out one or more of the methods described herein. In some instances, the kit further comprises samples, such as a cell sample, and suitable solutions such as buffers or media. In some embodiments, the kit further comprises recombinant proteins for use in one or more of the methods described herein. In some embodiments, additional components of the kit comprises a carrier, package, or container that is compartmentalized to receive one or more containers such as vials, tubes, and the like, each of the container(s) comprising one of the separate elements to be used in a method described herein. Suitable containers include, for example, bottles, vials, plates, syringes, and test tubes. In one embodiment, the containers are formed from a variety of materials such as glass or plastic.

The articles of manufacture provided herein contain packaging materials. Examples of pharmaceutical packaging materials include, but are not limited to, bottles, tubes, bags, containers, and any packaging material suitable for a selected formulation and intended mode of use.

For example, the container(s) include cysteine-reactive probes, test compounds, and one or more reagents for use in a method disclosed herein. Such kits optionally include an identifying description or label or instructions relating to its use in the methods described herein.

A kit typically includes labels listing contents and/or instructions for use, and package inserts with instructions for use. A set of instructions will also typically be included.

In one embodiment, a label is on or associated with the container. In one embodiment, a label is on a container when letters, numbers or other characters forming the label are attached, molded or etched into the container itself; a label is associated with a container when it is present within a receptacle or carrier that also holds the container, e.g., as a package insert. In one embodiment, a label is used to indicate that the contents are to be used for a specific therapeutic application. The label also indicates directions for use of the contents, such as in the methods described herein.

Services

In some embodiments, the methods provided herein also perform as a service. In some instances, a service provider obtain from the customer a plurality of small molecule fragment candidates for analysis with one or more of the cysteine-reactive probes for screening. In some embodiments, the service provider screens the small molecule fragment candidates using one or more of the methods described herein, and then provide the results to the customer. In some instances, the service provider provides the appropriate reagents to the customer for analysis utilizing one or more of the cysteine-reactive probes and one or more of the methods described herein. In some cases, the customer performs one or more of the methods described herein and then provide the results to the service provider for analysis. In some embodiments, the service provider then analyzes the results and provides the results to the customer. In some cases, the customer further analyze the results by interacting with software installed locally (at the customer's location) or remotely (e.g., on a server reachable through a network). Exemplary customers include pharmaceutical companies, clinical laboratories, physicians, patients, and the like. In some instances, a customer is any suitable customer or party with a need or desire to use the methods, systems, compositions, and kits described herein.

Digital Processing Device

In some embodiments, the methods described herein include a digital processing device, or use of the same. In further embodiments, the digital processing device includes one or more hardware central processing units (CPU) that carry out the device's functions. In still further embodiments, the digital processing device further comprises an operating system configured to perform executable instructions. In some embodiments, the digital processing device is optionally connected to a computer network. In further embodiments, the digital processing device is optionally connected to the Internet such that it accesses the World Wide Web. In still further embodiments, the digital processing device is optionally connected to a cloud computing infrastructure. In other embodiments, the digital processing device is optionally connected to an intranet. In other embodiments, the digital processing device is optionally connected to a data storage device.

In accordance with the description herein, suitable digital processing devices include, by are not limited to, server computers, desktop computers, laptop computers, notebook computers, subnotebook computers, netbook computers, netpad computers, set-top computers, media streaming devices, handheld computers, Internet appliances, mobile smartphones, tablet computers, personal digital assistants, video game consoles, and vehicles. Suitable tablet computers include those with booklet, slate, or convertible configurations.

In some embodiments, the digital processing device includes an operating system configured to perform executable instructions. The operating system is, for example, software, including programs and data, which manages the device's hardware and provides services for execution of applications. Suitable server operating systems include, by way of non-limiting examples, FreeBSD, OpenBSD, NetBSD®, Linux, Apple® Mac OS X Server®, Oracle® Solaris®, Windows Server®, and Novell®NetWare®. Suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing. Suitable mobile smart phone operating systems include, by way of non-limiting examples, Nokia® Symbian® OS, Apple® iOS®, Research In Motion® BlackBerry OS®, Google® Android®, Microsoft® Windows Phone®OS, Microsoft® Windows Mobile® OS, Linux®, and Palm® WebOS®. Suitable media streaming device operating systems include, by way of non-limiting examples, Apple TV®, Roku®, Boxee®, Google TV®, Google Chromecast®, Amazon Fire®, and Samsung® HomeSync®. Suitable video game console operating systems include, by way of non-limiting examples, Sony® PS3®, Sony® PS4®, Microsoft® Xbox 360®, Microsoft Xbox One, Nintendo® Wii®, Nintendo® Wii U®, and Ouya®.

In some embodiments, the device includes a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM). In other embodiments, the device is a storage device including, by way of non-limiting examples, CD-ROMs, DVDs, flash memory devices, magnetic disk drives, magnetic tapes drives, optical disk drives, and cloud computing based storage. In further embodiments, the storage and/or memory device is a combination of devices such as those disclosed herein.

In some embodiments, the digital processing device includes a display to send visual information to a user. In some embodiments, the display includes a cathode ray tube (CRT), a liquid crystal display (LCD), a thin film transistor liquid crystal display (TFT-LCD), an organic light emitting diode (OLED) display, a plasma display, a video projector, or a combination thereof.

In some embodiments, the digital processing device includes an input device to receive information from a user. In some embodiments, the input device is a keyboard. In some embodiments, the input device is a pointing device including, by way of non-limiting examples, a mouse, trackball, track pad, joystick, game controller, or stylus. In some embodiments, the input device is a touch screen or a multi-touch screen. In other embodiments, the input device is a microphone to capture voice or other sound input. In other embodiments, the input device is a video camera or other sensor to capture motion or visual input. In further embodiments, the input device is a Kinect™, Leap Motion™, or the like. In still further embodiments, the input device is a combination of devices such as those disclosed herein.

In some embodiments, the systems and methods disclosed herein include one or more non-transitory computer readable storage media encoded with a program including instructions executable by the operating system of an optionally networked digital processing device. In further embodiments, a computer readable storage medium is a tangible component of a digital processing device. In still further embodiments, a computer readable storage medium is optionally removable from a digital processing device. In some embodiments, a computer readable storage medium includes, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media.

In some embodiments, the systems and methods disclosed herein include at least one computer program, or use of the same. A computer program includes a sequence of instructions, executable in the digital processing device's CPU, written to perform a specified task. In some embodiments, computer readable instructions are implemented as program modules, such as functions, objects, Application Programming Interfaces (APIs), data structures, and the like, that perform particular tasks or implement particular abstract data types.

In some embodiments, the functionality of the computer readable instructions are combined or distributed as desired in various environments. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof.

In some embodiments, a computer program includes a web application. A web application, in various embodiments, utilizes one or more software frameworks and one or more database systems. In some embodiments, a web application is created upon a software framework such as Microsoft® .NET or Ruby on Rails (RoR). In some embodiments, a web application utilizes one or more database systems including, by way of non-limiting examples, relational, non-relational, object oriented, associative, and XML database systems. In further embodiments, suitable relational database systems include, by way of non-limiting examples, Microsoft® SQL Server, mySQL™, and Oracle®. A web application, in various embodiments, is written in one or more versions of one or more languages. In some embodiments, a web application is written in one or more markup languages, presentation definition languages, client-side scripting languages, server-side coding languages, database query languages, or combinations thereof. In some embodiments, a web application is written to some extent in a markup language such as Hypertext Markup Language (HTML), Extensible Hypertext Markup Language (XHTML), or eXtensible Markup Language (XML). In some embodiments, a web application is written to some extent in a presentation definition language such as Cascading Style Sheets (CSS). In some embodiments, a web application is written to some extent in a client-side scripting language such as Asynchronous Javascript and XML (AJAX), Flash® Actionscript, Javascript, or Silverlight®. In some embodiments, a web application is written to some extent in a server-side coding language such as Active Server Pages (ASP), ColdFusion®, Perl, Java™, JavaServer Pages (JSP), Hypertext Preprocessor (PHP), Python™, Ruby, Tcl, Smalltalk, WebDNA®, or Groovy. In some embodiments, a web application is written to some extent in a database query language such as Structured Query Language (SQL). In some embodiments, a web application integrates enterprise server products such as IBM® Lotus Domino®. In some embodiments, a web application includes a media player element. In various further embodiments, a media player element utilizes one or more of many suitable multimedia technologies including, by way of non-limiting examples, Adobe® Flash®, HTML 5, Apple® QuickTime®, Microsoft® Silverlight®, Java™, and Unity®.

In some embodiments, a computer program includes a mobile application provided to a mobile digital processing device. In some embodiments, the mobile application is provided to a mobile digital processing device at the time it is manufactured. In other embodiments, the mobile application is provided to a mobile digital processing device via the computer network described herein.

In view of the disclosure provided herein, a mobile application is created by techniques using hardware, languages, and development environments. Suitable programming languages include, by way of non-limiting examples, C, C++, C#, Objective-C, Java™, Javascript, Pascal, Object Pascal, Python™, Ruby, VB.NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator®, Celsius, Bedrock, Flash Lite, .NET Compact Framework, Rhomobile, and WorkLight Mobile Platform. Other development environments are available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

In some embodiments, commercial forums for distribution of mobile applications include, by way of non-limiting examples, Apple® App Store, Android™ Market, BlackBerry® App World, App Store for Palm devices, App Catalog for webOS, Windows® Marketplace for Mobile, Ovi Store for Nokia® devices, Samsung® Apps, and Nintendo® DSi Shop.

In some embodiments, a computer program includes a standalone application, which is a program that is run as an independent computer process, not an add-on to an existing process, e.g., not a plug-in. In some instances, standalone applications are compiled. A compiler is a computer program(s) that transforms source code written in a programming language into binary object code such as assembly language or machine code. Suitable compiled programming languages include, by way of non-limiting examples, C, C++, Objective-C, COBOL, Delphi, Eiffel, Java™, Lisp, Python™, Visual Basic, and VB .NET, or combinations thereof. Compilation is often performed, at least in part, to create an executable program. In some embodiments, a computer program includes one or more executable complied applications.

In some embodiments, the computer program includes a web browser plug-in. In computing, a plug-in is one or more software components that add specific functionality to a larger software application. Makers of software applications support plug-ins to enable third-party developers to create abilities which extend an application, to support easily adding new features, and to reduce the size of an application. When supported, plug-ins enable customizing the functionality of a software application. For example, plug-ins are commonly used in web browsers to play video, generate interactivity, scan for viruses, and display particular file types. In some instances, web browser plug-ins include Adobe® Flash® Player, Microsoft® Silverlight®, and Apple® QuickTime®. In some embodiments, the toolbar comprises one or more web browser extensions, add-ins, or add-ons. In some embodiments, the toolbar comprises one or more explorer bars, tool bands, or desk bands.

In view of the disclosure provided herein, plug-in frameworks are available that enable development of plug-ins in various programming languages, including, by way of non-limiting examples, C++, Delphi, Java™, PHP, Python™, and VB .NET, or combinations thereof.

Web browsers (also called Internet browsers) are software applications, designed for use with network-connected digital processing devices, for retrieving, presenting, and traversing information resources on the World Wide Web. Suitable web browsers include, by way of non-limiting examples, Microsoft® Internet Explorer®, Mozilla® Firefox®, Google® Chrome, Apple® Safari®, Opera Software® Opera®, and KDE Konqueror. In some embodiments, the web browser is a mobile web browser. Mobile web browsers (also called mircrobrowsers, mini-browsers, and wireless browsers) are designed for use on mobile digital processing devices including, by way of non-limiting examples, handheld computers, tablet computers, netbook computers, subnotebook computers, smartphones, music players, personal digital assistants (PDAs), and handheld video game systems. Suitable mobile web browsers include, by way of non-limiting examples, Google® Android® browser, RIM BlackBerry® Browser, Apple® Safari®, Palm® Blazer, Palm® WebOS® Browser, Mozilla® Firefox® for mobile, Microsoft® Internet Explorer® Mobile, Amazon® Kindle® Basic Web, Nokia® Browser, Opera Software® Opera® Mobile, and Sony® PSP™ browser.

In some embodiments, the systems and methods disclosed herein include software, server, and/or database modules, or use of the same. In view of the disclosure provided herein, software modules are created and implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

In some embodiments, the methods and systems disclosed herein include one or more databases, or use of the same. In view of the disclosure provided herein, databases are suitable for storage and retrieval of analytical information described elsewhere herein. In various embodiments, suitable databases include, by way of non-limiting examples, relational databases, non-relational databases, object oriented databases, object databases, entity-relationship model databases, associative databases, and XML databases. In some embodiments, a database is internet-based. In further embodiments, a database is web-based. In still further embodiments, a database is cloud computing-based. In other embodiments, a database is based on one or more local computer storage devices.

Server

Figure 2:
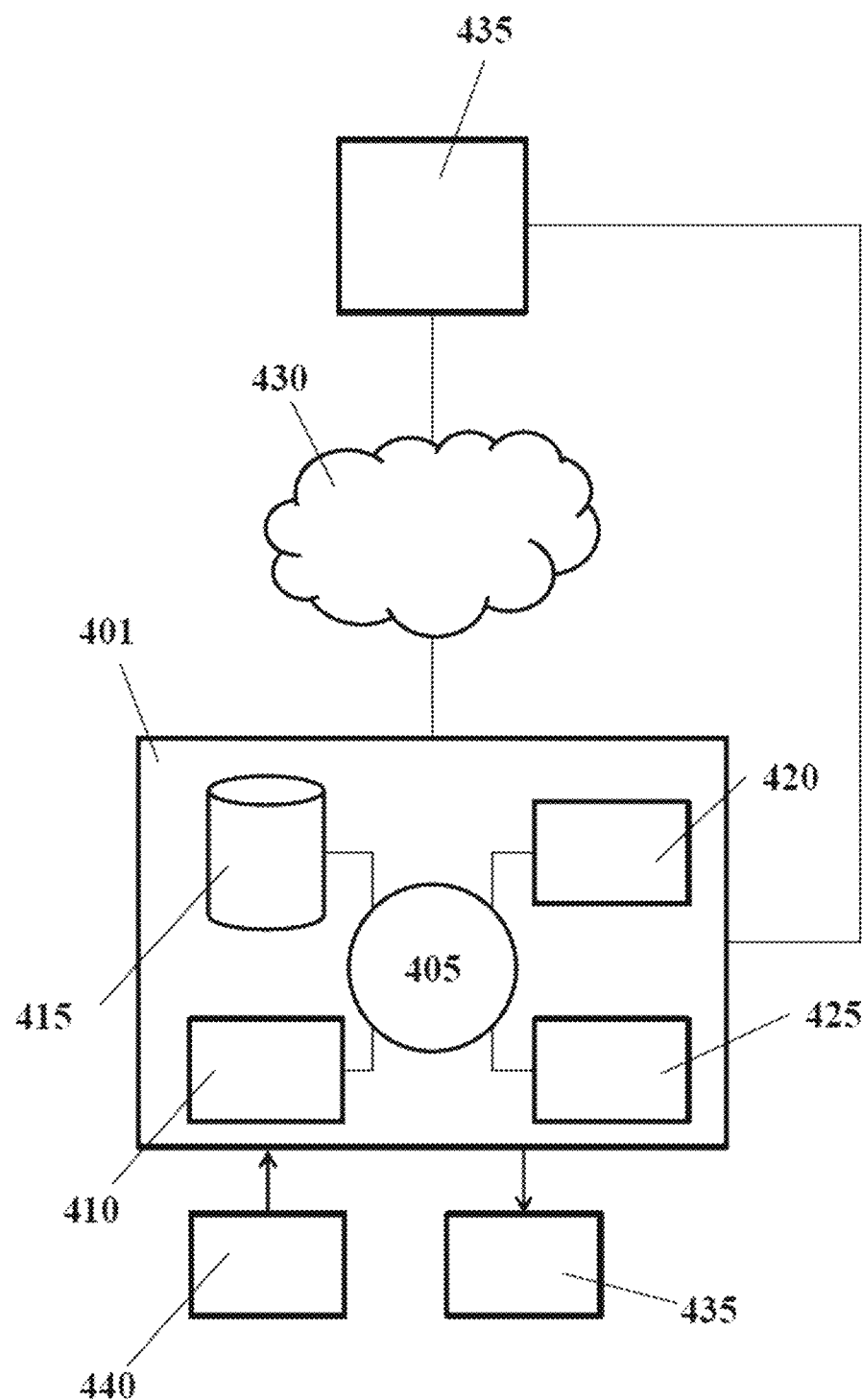
FIG. 2 illustrates a conceptual schematic of an exemplary computer server to be used for processing a method described herein.

In some embodiments, the methods provided herein are processed on a server or a computer server (FIG. 2). In some embodiments, the server 401 includes a central processing unit (CPU, also "processor") 405 which is a single core processor, a multi core processor, or plurality of processors for parallel processing. In some embodiments, a processor used as part of a control assembly is a microprocessor. In some embodiments, the server 401 also includes memory 410 (e.g. random access memory, read-only memory, flash memory); electronic storage unit 415 (e.g. hard disk); communications interface 420 (e.g. network adaptor) for communicating with one or more other systems; and peripheral devices 425 which includes cache, other memory, data storage, and/or electronic display adaptors. The memory 410, storage unit 415, interface 420, and peripheral devices 425 are in communication with the processor 405 through a communications bus (solid lines), such as a motherboard. In some embodiments, the storage unit 415 is a data storage unit for storing data. The server 401 is operatively coupled to a computer network ("network") 430 with the aid of the communications interface 420. In some embodiments, a processor with the aid of additional hardware is also operatively coupled to a network. In some embodiments, the network 430 is the Internet, an intranet and/or an extranet, an intranet and/or extranet that is in communication with the Internet, a telecommunication or data network. In some embodiments, the network 430 with the aid of the server 401, implements a peer-to-peer network, which enables devices coupled to the server 401 to behave as a client or a server. In some embodiments, the server is capable of transmitting and receiving computer-readable instructions (e.g., device/system operation protocols or parameters) or data (e.g., sensor measurements, raw data obtained from detecting metabolites, analysis of raw data obtained from detecting metabolites, interpretation of raw data obtained from detecting metabolites, etc.) via electronic signals transported through the network 430. Moreover, in some embodiments, a network is used, for example, to transmit or receive data across an international border.

In some embodiments, the server 401 is in communication with one or more output devices 435 such as a display or printer, and/or with one or more input devices 440 such as, for example, a keyboard, mouse, or joystick. In some embodiments, the display is a touch screen display, in which case it functions as both a display device and an input device. In some embodiments, different and/or additional input devices are present such an enunciator, a speaker, or a microphone. In some embodiments, the server uses any one of a variety of operating systems, such as for example, any one of several versions of Windows®, or of MacOS®, or of Unix®, or of Linux®.

In some embodiments, the storage unit 415 stores files or data associated with the operation of a device, systems or methods described herein.

In some embodiments, the server communicates with one or more remote computer systems through the network 430. In some embodiments, the one or more remote computer systems include, for example, personal computers, laptops, tablets, telephones, Smart phones, or personal digital assistants.

In some embodiments, a control assembly includes a single server 401. In other situations, the system includes multiple servers in communication with one another through an intranet, extranet and/or the Internet.

In some embodiments, the server 401 is adapted to store device operation parameters, protocols, methods described herein, and other information of potential relevance. In some embodiments, such information is stored on the storage unit 415 or the server 401 and such data is transmitted through a network.

Certain Terminology

Unless defined otherwise, all technical and scientific terms used herein have the same meaning as is commonly understood by one of skill in the art to which the claimed subject matter belongs. It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

As used herein, ranges and amounts can be expressed as "about" a particular value or range. About also includes the exact amount. Hence "about 5 µL" means "about 5 µL" and also "5 µL." Generally, the term "about" includes an amount that would be expected to be within experimental error.

The section headings used herein are for organizational purposes only and are not to be construed as limiting the subject matter described.

The term "protein", as used herein, encompasses a full-length cysteine containing protein, a full-length functional cysteine containing protein, a cysteine containing protein fragment, or a functionally active cysteine containing protein fragment. In some instances, a protein described herein is also referred to as an "isolated protein", or a protein that by virtue of its origin or source of derivation is not associated with naturally associated components that accompany it in its native state; is substantially free of other proteins from the same species; is expressed by a cell from a different species; or does not occur in nature.

The term "polypeptide", as used herein, refers to any polymeric chain of amino acids. The term "polypeptide" encompasses native or modified cysteine containing protein, cysteine containing protein fragments, or polypeptide analogs comprising non-native amino acid residues. In some instances, a polypeptide is monomeric. In other instances, a polypeptide is polymeric. In some instances, a polypeptide described herein is also referred to as an "isolated polypeptide", or a polypeptide that by virtue of its origin or source of derivation is not associated with naturally associated components that accompany it in its native state; is substantially free of other proteins from the same species; is expressed by a cell from a different species; or does not occur in nature.

As used herein, the terms "individual(s)", "subject(s)" and "patient(s)" mean any mammal. In some embodiments, the mammal is a human. In some embodiments, the mammal is a non-human. None of the terms require or are limited to situations characterized by the supervision (e.g. constant or intermittent) of a health care worker (e.g. a doctor, a registered nurse, a nurse practitioner, a physician's assistant, an orderly or a hospice worker).

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dode cyl, tetradecyl, hexadecyl, eicosyl, tetracosyl, and the like. It is understand that the alkyl group is acyclic. In some instances, the alkyl group is branched or unbranched. In some instances, the alkyl group is also substituted or unsubstituted. For example, the alkyl group is substituted with one or more groups including, but not limited to, alkyl, cycloalkyl, alkoxy, amino, ether, halide, hydroxy, nitro, silyl, sulfo-oxo, or thiol. A "lower alkyl" group is an alkyl group containing from one to six (e.g., from one to four) carbon atoms. In some instances, the term alkyl group is also a C1 alkyl, C1-C2 alkyl, C1-C3 alkyl, C1-C4 alkyl, C1-05 alkyl, C1-C6 alkyl, C1-C7 alkyl, C1-C8 alkyl, C1-C9 alkyl, C1-C10 alkyl, and the like up to and including a C1-C24 alkyl.

The term "aryl" as used herein is a group that contains any carbon-based aromatic group including, but not limited to, benzene, naphthalene, phenyl, biphenyl, anthracene, and the like. The aryl group can be substituted or unsubstituted. In some instances, the aryl group is substituted with one or more groups including, but not limited to, alkyl, cycloalkyl, alkoxy, alkenyl, cycloalkenyl, alkynyl, cycloalkynyl, aryl, heteroaryl, aldehyde, —NH$_2$, carboxylic acid, ester, ether, halide, hydroxy, ketone, azide, nitro, silyl, sulfo-oxo, or thiol. The term "biaryl" is a specific type of aryl group and is included in the definition of "aryl." In addition, the aryl group is optionally a single ring structure or comprises multiple ring structures that are either fused ring structures or attached via one or more bridging groups such as a carbon-carbon bond. For example, biaryl refers to two aryl groups that are bound together via a fused ring structure, as in naphthalene, or are attached via one or more carbon-carbon bonds, as in biphenyl.

EXAMPLES

These examples are provided for illustrative purposes only and not to limit the scope of the claims provided herein.

Example 1

Biological Methods
Preparation of Human Cancer Cell Line Proteomes

All cell lines were obtained from ATCC, were used with a low passage number and were grown at 37° C. with 5% CO$_2$. MDA-MB-231 cells and HEK-293T cells were grown in DMEM supplemented with 10% fetal bovine serum, penicillin, streptomycin and glutamine. Jurkat, Ramos and MUM2C cells were grown in RPMI-1640 medium supplemented with 10% fetal bovine serum, penicillin and streptomycin. For in vitro labeling, cells were grown to 100% confluence for MDA-MB-231 cells or until cell density reached 1.5 million cells/mL for Ramos and Jurkat cells. Cells were washed with cold PBS, scraped with cold PBS and cell pellets were isolated by centrifugation (1,400 g, 3 min, 4° C.), and stored at −80° C. until use. Cell pellets were lysed by sonication and fractionated (100,000 g, 45 min) to yield soluble and membrane fractions, which were then adjusted to a final protein concentration of 1.5 mg/mL for proteomics experiments and 1 mg/mL for gel-based ABPP experiments. The soluble lysate was prepared fresh from frozen pellets directly before each experiment. Protein concentration was determined using the Bio-Rad DC™ protein assay kit.

Screening of Fragment Electrophile Library by Gel-Based ABPP with IA-Rhodamine and Ac-Rho-DEVD-AMK ("DEVD" Disclosed as SEQ ID NO: 857)

25 μL of soluble proteome (1 mg/mL) was treated with fragment electrophiles (1 μL of 25× stock solution in DMSO) at ambient temperature for 1 h. IA-rhodamine (1 μL of 25 μM, final concentration=1 μM) was then added and allowed to react for an additional 1 h. The reactions were quenched with 8 μL of 4×SDS-PAGE loading buffer and the quenched samples analyzed by SDS-PAGE (10% polyacrylamide; 15 μL of sample/lane) and visualized by in-gel fluorescence using a flatbed fluorescent scanner (BioRad ChemiDocm MP or Hitachi FMBio IIe). To measure labeling of recombinant proteins expressed in E. coli, purified protein was added to soluble proteome to a final concentration of 1 μM (CASP8, PRMT1, IMPDH2), 2 μM (TIGAR, IDH1) or 4 μM (IDH1 R132H) and the proteomes were treated as detailed above. IDH1 labeling by IA-rhodamine is relatively better in MDA-MB-231 soluble proteome when compared with Ramos and Jurkat soluble proteome. Recombinant, active CASP8 in soluble proteome was labeled with Rho-DEVD-AOMK ("DEVD" disclosed as SEQ ID NO: 857) (1 μL of 50 μM, final concentration=2 μM), quenched and analyzed by SDS-PAGE on 14% polyacrylamide gels.

Gel-Based ABPP with Alkyne-Containing Click Probes

25 μL of soluble proteome (1 mg/mL) was labeled with the indicated concentration of 18 or 19 (1 μL of 25× stock solution in DMSO) for 1 h at ambient temperature followed by copper-mediated azide-alkyne cycloaddition (CuAAC) conjugation to rhodamine-azide. CuAAC was performed with 20 μM rhodamine-azide (50× stock in DMSO), 1 mM tris(2-carboxyethyl)phosphine hydrochloride (TCEP; fresh 50× stock in water, final concentration=1 mM), ligand (17× stock in DMSO:t-butanol 1:4, final concentration=100 μM) and 1 mM CuSO$_4$ (50× stock in water, final concentration=1 mM). Samples were allowed to react for 1 h at ambient temperature before quenching with 8 μL 4×SDS-PAGE loading buffer. Quenched reactions were analyzed by SDS-PAGE and visualized by in-gel fluorescence. For CASP8 and IMPDH2 25 μL of soluble proteomes containing IMPDH2 or Pro-CASP8 (1 μM each respectively) were treated with the indicated fragment for 1 h prior to incubation for 1 h with 18 (1 μl, of 625 μM, final concentration=25 μM) for IMPDH2 or 61 (1 μl, of 625 μM, final concentration=25 μM) for CASP8. For MLTK, HEK 293T cells stably overexpressing MTLK[2] were treated with the indicated fragment electrophiles for 1 h, followed by labeling with 59 (1 μl, of 125 μM, final concentration=5 μM) for 1 h. These were followed by CuAAC conjugation to rhodamine-azide and evaluation by SDS-PAGE as described above.

Determination of In Vitro IC$_{50}$ Values

25 μL of proteomes containing the indicated protein were treated with fragment electrophiles for 1 h at ambient temperature, labeled with the probes detailed above for 1 h, quenched, and analyzed by SDS-PAGE and in-gel fluorescence visualization (n=3). IA-rhodamine was used as the probe for C161S-TIGAR, C409S-CASP8 and PRMT1. 59 was used as a probe for MLTK. The soluble proteome containing IMPDH2 was treated with ATP for 15 min prior to incubation with 18 (1 µl, of 625 µM, final concentration=25 µM) for 1 h. MLTK and IMPDH2 were subjected to CuAAC conjugation to rhodamine-azide as detailed above. The percentage of labeling was determined by quantifying the integrated optical intensity of the bands, using ImageJ software. Nonlinear regression analysis was used to determine the IC50 values from a dose-response curve generated using GraphPad Prism 6.

isoTOP-ABPP Sample Preparation

For in situ labeling, MDA-MB-231 cells were grown to 95% confluence and Ramos cells were grown to 1 million cells/mL. The media in all samples was replaced with fresh media, containing 200 µM of the indicated fragments and the cells were incubated at 37° C. for 2 h, washed with cold PBS, scraped into cold PBS and harvested by centrifugation (see prior section on "Preparation of human cancer cell line proteomes").

Fragments 2, 3, 8, 9, 10, 12, 13, 14, 21, 27, 28, 29, 31, 33, 38, 45, 51 and 56 were screened at 200 µM in situ. Fragments 4 and 11 were screened at 100 µM in situ. Fragments 2, 3, 8, and 20 were tested at 50 µM in situ.

After in vitro or in situ fragment treatment, the samples were labeled for 1 h at ambient temperature with 100 µM iodoacetamide alkyne (IA-alkyne, 5 µL of 10 mM stock in DMSO). For direct labeling with 61, 61 (5 µL of 1 or 10 mM stocks in DMSO, final concentration=10 or 100 µM) was substituted for IA-alkyne. Samples were conjugated by CuAAC to either the light (fragment treated) or heavy (DMSO treated) TEV tags (10 µL of 5 mM stocks in DMSO, final concentration=100 µM), TCEP, TBTA ligand and $CuSO_4$ as detailed above. The samples were allowed to react for 1 h at which point the samples were centrifuged (16,000 g, 5 min, 4° C.). The resulting pellets were sonicated in ice-cold methanol (500 µL) and the resuspended light- and heavy-labeled samples were then combined and centrifuged (16,000 g, 5 min, 4° C.). The pellets were solubilized in PBS containing 1.2% SDS (1 mL) with sonication and heating (5 min, 95° C.) and any insoluble material was removed by an additional centrifugation step at ambient temperature (14, 000 g, 1 min).

For each sample, 100 µL of streptavidin-agarose beads slurry (Pierce) was washed in 10 mL PBS and then resuspended in 5 mL PBS. The SDS-solubilized proteins were added to the suspension of streptavidin-agarose beads and the bead mixture was rotated for 3 h at ambient temperature. After incubation, the beads were pelleted by centrifugation (1,400 g, 3 min) and were washed (2×10 mL PBS and 2×10 mL water).

The beads were transferred to eppendorf tubes with 1 mL PBS, centrifuged (1,400 g, 3 min), and resuspended in PBS containing 6 M urea (500 µL). To this was added 10 mM DTT (25 µL of a 200 mM stock in water) and the beads were incubated at 65° C. for 15 mins. 20 mM iodoacetamide (25 µL of a 400 mM stock in water) was then added and allowed to react at 37° C. for 30 mins with shaking. The bead mixture was diluted with 900 µL PBS, pelleted by centrifugation (1,400 g, 3 min), and resuspended in 200 µL PBS. To this was added 1 mM $CaCl_2$ (2 µL of a 200 mM stock in water) and trypsin (2 µg, Promega, sequencing grade) and the digestion was allowed to proceed overnight at 37° C. with shaking. The beads were separated from the digest with Micro Bio-Spin columns (Bio-Rad) by centrifugation (1,000 g, 1 min), washed (2×1 mL PBS and 2×1 mL water) and then transferred to fresh eppendorfs with 1 mL water. The washed beads were washed once further in 140 µL TEV buffer (50 mM Tris, pH 8, 0.5 mM EDTA, 1 mM DTT) and then resuspended in 140 µL TEV buffer. 5 µL TEV protease (80 µM) was added and the reactions were rotated overnight at 29° C. The TEV digest was separated from the beads with Micro Bio-Spin columns by centrifugation (1,400 g, 3 min) and the beads were washed once with water (100 µL). The samples were then acidified to a final concentration of 5% (v/v) formic acid and stored at −80° C. prior to analysis.

Liquid-Chromatography-Mass-Spectrometry (LC-MS) Analysis of isoTOP-ABPP Samples

TEV digests were pressure loaded onto a 250 µm (inner diameter) fused silica capillary column packed with C18 resin (Aqua 5 µm, Phenomenex). The samples were analyzed by multidimensional liquid chromatography tandem mass spectrometry (MudPIT), using an LTQ-Velos Orbitrap mass spectrometer (Thermo Scientific) coupled to an Agilent 1200-series quaternary pump. The peptides were eluted onto a biphasic column with a 5 µm tip (100 µm fused silica, packed with C18 (10 cm) and bulk strong cation exchange resin (3 cm, SCX, Phenomenex,)) in a 5-step MudPIT experiment, using 0%, 30%, 60%, 90%, and 100% salt bumps of 500 mM aqueous ammonium acetate and using a gradient of 5-100% buffer B in buffer A (buffer A: 95% water, 5% acetonitrile, 0.1% formic acid; buffer B: 5% water, 95% acetonitrile, 0.1% formic acid) as has been described in Weerapana et al. Nat Protoc 2:1414-1425 (2007). Data was collected in data-dependent acquisition mode with dynamic exclusion enabled (20 s, repeat of 2). One full MS (MS1) scan (400-1800 m/z) was followed by 30 MS2 scans (ITMS) of the nth most abundant ions.

Peptide and Protein Identification

The MS2 spectra data were extracted from the raw file using RAW Xtractor (version 1.9.9.2; available at http://fields.scripps.edu/downloads.php). MS2 spectra data were searched using the ProLuCID algorithm (publicly available at http://fields.scripps.edu/downloads.php) using a reverse concatenated, nonredundant variant of the Human UniProt database (release-2012_11). Cysteine residues were searched with a static modification for carboxyamidomethylation (+57.02146) and up to one differential modification for either the light or heavy TEV tags (+464.28595 or +470.29976 respectively). Peptides were required to have at least one tryptic terminus and to contain the TEV modification. ProLuCID data was filtered through DTASelect (version 2.0) to achieve a peptide false-positive rate below 1%.

R Value Calculation and Processing

The ratios of heavy/light for each unique peptide (DMSO/compound treated; isoTOP-ABPP ratios, R values) were quantified with in-house CIMAGE software, using default parameters (3 ms s per peak and signal to noise threshold 2.5). Site-specific engagement of electrophilic fragments was assessed by blockade of IA-alkyne probe labeling. For peptides that showed a ≥95% reduction in MS1 peak area from the fragment treated proteome (light TEV tag) when compared to the DMSO treated proteome (heavy TEV tag), a maximal ratio of 20 was assigned. Ratios for unique peptide entries were calculated for each experiment; overlapping peptides with the same modified cysteine (e.g. different charge states, MudPIT chromatographic steps or tryptic termini) were grouped together and the median ratio was reported as the final ratio (R). The peptide ratios reported by CIMAGE were further filtered to ensure the removal or correction of low quality ratios in each individual dataset. The quality filters applied were the following: removal of half tryptic peptides; for ratios with high standard deviations from the median (90% of the median or above) the lowest ratio was taken instead of the median; removal of peptides with R=20 and only a single ms2 event triggered during the elution of the parent ion; manual annotation of all the peptides with ratios of 20, removing any peptides with low-quality elution profiles that remained after the previous curation steps. Proteome reactivity values for individual fragments were computed as the percentage of the total quantified cysteine-containing peptides with R values≥4 (defined as liganded cysteines) for each replicate experiment and the final proteome reactivity value was calculated as the mean for all replicate experiments for each fragment from both MDA-MB-231 and Ramos cellular proteomes.

Cross-Data Processing

Biological replicates of the same compound and cell-line were averaged if the standard deviation was below 60% of the mean; otherwise the lowest value of the ratio set was taken. For peptides with multiple modified cysteines, the cysteine with the highest number of quantification events was kept and the remaining, redundant peptides were discarded. Peptides included in the aggregate dataset (those used for further bioinformatics and statistical analyses) were required to have been quantified in 3 experiments. Cysteines were categorized as liganded if they had at least two ratios R≥4 (hit fragments) and one ratio between 0.5 and 2 (control fragments). Although the majority (>75% of fragments) were profiled in at least two biological replicates, some data from single replicate MS experiments were included. Averaged filtered data for all fragments and representative individual filtered datasets are found in Tables 1-3.

In Situ Data Processing

R values were calculated and individual datasets were filtered as described above (R value calculation and processing). Two categories of hits in situ were defined: 1) cysteines liganded in situ that were also observed as hits in vitro and 2) cysteines that detected in vitro, but were only liganded in situ. For the first category, R values for the same cysteine containing peptide from in vitro and in situ experiments were compared and if both had ratios R≥4, the cysteine was considered ligandable in situ. To qualify for the second category, two ratios R≥4 for replicates of two different fragments were required to be detected in situ and at least one of these fragments must be quantified as a non-hit with R≤2 in vitro. Additionally, another cysteine from the same protein was required to be unliganded in situ (R≤2) by the same fragment to control for the possibility that changes in R values from changes in protein expression upon fragment treatment rather than from fragment competition.

Functional Annotation of Liganded Cysteines

Custom python scripts were used to compile functional annotations available in the UniProtKB/Swiss-Prot Protein Knowledge database (release-2012_11). Relevant Uniprot entries were mined for available functional annotations at the residue level, specifically for annotations regarding enzyme catalytic residues (active sites), disulfides (redox active and structural) and metal binding sites. Liganded proteins were queried against the Drugbank database (Version 4.2) and fractionated into DrugBank and non-Drugbank proteins. Functional keywords assigned at the protein level were collected from the Uniprot database and the Drugbank and non-drugbank categories were further classified into protein functional classes. Cysteine reactivity data was re-processed using ProLuCID as detailed above (Peptide and protein identification). Cysteines found in both the reactivity and ligandability datasets were sorted based on their reactivity values (lower ratio indicates higher reactivity). The moving average of the percentage of total liganded cysteines within each reactivity bin (step-size 50) was taken. Custom python scripts were developed to collect relevant NMR and X-ray structures from the RCSB Protein Data Bank (PDB). For proteins without available PDB structures, sequence alignments, performed with BLAST to proteins deposited in the PDB, were used to identify structural homologues. For annotation of active-site and non-active cysteines, enzymes with structures in the PDB were manually inspected to evaluate the location of the cysteine. Cysteines were considered to reside in enzyme active sites if they were within 10 Å of active-site ligand or residue(s). Cysteines outside of the 10 Å range were deemed non-active-site residues. Histograms of fragment hit-rates across high-coverage, ligandable cysteines, active-site and non-active site cysteines were calculated from the subset of ligandable cysteines quantified in 10 or more separate experiments. The fragment hit rate is reported as the percentage of the total quantification events with R≥4. For analyses of trends within the whole data, including histograms and heatmaps, a cell-line merged dataset was used where data from the MDA-MB-231 experiments was taken first and the Ramos data was used if there was no data from MDA-MB-231 experiments for a particular fragment and cysteine. Heatmaps were generated in R (version 3.1.3) using the heatmap.2 algorithm. Protein structures were rendered using Pymol.

GSH Reactivity

Glutathione (GSH) was diluted to a final concentration of 125 μM in assay buffer (100 mM Tris, pH 8.8, 10% ethanol as co solvent). In triplicate, to 100 μL of the GSH mixture in a clear 96 well plate (Costar® Corning®), the indicated electrophile (2 μL of a 50 mM stock solution in DMSO, final concentration=500 μM) was added and the reaction mixture was incubated at room temperature for 1 h. 5 μL of Ellman's reagent (100 mM stock in 1M NaOH, final concentration=5 mM) was added and the absorbance was measure at 440 nm on a plate reader (Tecan Infinite F500). The concentration of GSH remaining was calculated from a standard curve.

Reactive Cysteine Docking

In silico fragment library containing all chloroacetamide and acrylamide fragments from FIG. 3 was prepared using Open Babel library with custom Python scripts. Fragments were modeled in their reactive form (i.e., with explicit chloroacetamide and acrylamide warheads). 3D coordinates were generated from SMILES strings, calculating their protonation state at pH 7.4, and then minimizing them using MMF94s forcefield (50K iterations steepest descent; 90K conjugate gradient); for chiral molecules with undefined configuration, all enantiomers were generated, resulting in 53 total fragments For each protein, the UniProtKB ID was used to filter the PDB. Structures determined by X-ray crystallography were selected, privileging higher sequence coverage and structure resolution (See Table 5 for selected PDB IDs). When no human structures were available, the closest homologous organism available was selected (e.g. PRMT1:*R. norvegicus*). Protein structures were prepared following the standard AutoDock protocol. Waters, salts, and crystallographic additives were removed; AutoDockTools was used to add hydrogens, calculate Gasteiger-Marsili charges and generate PDBQT files.

MSMS reduced surface method was used to identify accessible cysteines. The protein volume was scanned using a probe radius of 1.5 Å; residues were considered accessible if they had at least one atom in contact with either external surfaces or internal cavities.

The fragment library was docked independently on each accessible cysteine using AutoDock 4.2. A grid box of 24.4×24.4×24.4 Å was centered on the geometric center of the residue; thiol hydrogen was removed from the sidechain, which was modeled as flexible during the docking; the rest of the structure was kept rigid. A custom 13-7 interaction potential was defined between the nucleophile sulfur and the reactive carbon in the ligands. The equilibrium distance ($r_{eq}$) was set to the length of the C—S covalent bond (1.8 Å); the potential well depth ($\varepsilon_{eq}$) varied between 1.0 and 0.175 to model to the reactivity of the different ligands. For each fragment, potential well depth was determined by dividing its proteomic reactivity percentage by 20, and the value for iodoacetamide was approximated as the maximum (2.5) for reference. The potential was implemented by modifying the force field table of AutoDock. Fragments were docked with no constraints, generating 100 poses using the default GA settings. For each fragment, the best docking score pose was analyzed: if the distance between the nucleophilic sulfur and the reactive carbon was ≤2.0 Å, the cysteine was considered covalently modified. If a residue was alkylated by at least one ligand, it was considered labeled. The docking score (i.e., negative binding energy) was calculated based on the estimated interaction energy of each fragment in its docked pose. The docking score of the best alkylating fragment defined the labeling score. The residue with the best labeling score was considered the most probable to be labeled.

Structural Modeling

IMPDH2 structure, including the Bateman domain, was modeled using I-TASSER.

Subcloning and Mutagenesis

Full length cDNAs encoding for IDH1 (Open Biosystems, Clone ID: 3880331) and IMPDH2 (Open Biosystems, Clone ID: 3447994) were subcloned into pET22b (+) (Novagen) with C-terminal His$_6$-affinity tag (SEQ ID NO: 861). Full length cDNA encoding for TIGAR (Origene, Sc320794) was subcloned into pET28a (+) (Novagen) with N-terminal His$_6$-affinity tag (SEQ ID NO: 861). Full length PRMT1 subcloned into pET45b (+) (Novagen) was previously generated by the Cravatt lab. Full-length human CASP3 (residues 1-277) and a truncated CASP8 (residues 217-479) without the CARD domain was subcloned into pET23b (Novagen) with C-terminal His$_6$-affinity tags (SEQ ID NO: 861). Cysteine mutants were generated using QuikChange site-directed mutagenesis, using primers containing the desired mutations and their respective compliments.

Recombinant Overexpression of TIGAR, IDH1, PRMT1 and IMPDH2

TIGAR, IDH1, PRMT1 and IMPDH2 were expressed in BL21(DE3) Chemically Competent Cells (NEB), grown on Terrific Broth supplemented with the desired antibiotic (50 µg/mL Kanamycin or 50 µg/mL Carbenicillin) to OD$_{600}$ of 0.8 and induced with 0.5 mM IPTG for 16 h at 18° C. Cells were immediately harvested and resuspended in 30 mL cold buffer A (25 mM Tris, pH 7.4, 200 mM NaCl, 10% glycerol, 1 mM BME), supplemented with lysozyme (Sigma), DNAase (NEB) and cOmplete protease inhibitor tablets (Roche), sonicated, and centrifuged (45,000 g, 30 min, 4° C.). The soluble fractions were collected and rotated for 1 h with 1 mL Ni-NTA slurry (Qiagen) at 4° C. The slurry was then transferred to a 50 mL volume, fritted column and collected by gravity flow. The resin was then washed with 100 mL buffer A containing 20 mM imidazole and eluted with 10 mL buffer A containing 200 mM imidazole. The eluant was concentrated to 2.5 mL (Amicon-Ultra-15, 10 kDa MW cutoff), buffer exchanged using PD10 columns (GE Amersham) into the storage buffer (50 mM HEPES, pH 7.4, 150 mM NaCl, 10% glycerol, 1 mM BME) and further concentrated (Amicon-Ultra-4, 10 kDa MW cutoff) to a final concentration of approximately 100 µM protein. Protein concentration was determined using the Bio-Rad DC™ protein assay kit. Protein purity was assayed by SDS-PAGE under reducing conditions and were >95% pure.

Recombinant CASP3, CASP8 and TEVprotease Expression

CASP3, CASP8, pro-CASP8 (D374A, D384A) and an N-terminal MBP fusion-His$_6$-TEV-Arg$_6$ protease construct pRK793 ("His$_6$" disclosed as SEQ ID NO: 861 and "Arg$_6$" disclosed as SEQ ID NO: 862) were expressed in E. coli BL21(DE3)pLysS cells (Stratagene). Cells were grown in 2×YT medium supplemented with 200 µg/ml ampicillin and 50 µg/ml chloramphenicol at 37° C. to an OD$_{600}$ of 0.8-1.0. Overexpression of caspase was induced with 0.2 mM IPTG at 30° C. for 4 h (CASP3) or at 12° C. overnight (CASP8) or with 0.5 mM IPTG at 30° C. for 4 h (TEV protease). Cells were immediately harvested and resuspended in ice cold buffer A (caspases: 100 mM Tris, pH 8.0, 100 mM NaCl; TEV protease: PBS) and subjected to 3 cycles of lysis by microfluidization (Microfluidics). The cell lysate was clarified by centrifugation (45,000 g, 30 min, 4° C.) and soluble fractions were loaded onto a 1 mL HisTrap HP Ni-NTA affinity column (GE Amersham) pre-equilibrated with buffer A and eluted with buffer A containing 200 mM imidazole. The eluted protein was immediately diluted two-fold with buffer B (20 mM Tris, pH 8.0) and purified by anion-exchange chromatography (HiTrap Q HP, GE Amersham) with a 30-column volume gradient to 50% of buffer B containing 1 M NaCl. The caspases were injected over a Superdex 200 16/60 gel filtration column (GE Amersham) and TEV protease over a Superdex 75 gel filtration column (GE Amersham) in buffer C (caspases: 20 mM Tris, pH 8.0, 50 mM NaCl; TEV protease: PBS, 10 mM DTT) to buffer exchange and to remove any remaining contaminants. Fractions containing the desired protein were pooled and concentrated to approximately 1 mg/mL (Millipore Ultrafree-15, 10 kDa MW cutoff). The purified proteins were immediately frozen and stored at −80° C. Protein concentrations were measured using both Bio-Rad colorimetric assay and A$_{280}$ absorbance in denaturing conditions. Protein purity was assayed by SDS-PAGE under reducing conditions and were >98% pure.

Retroviral Overexpression of Flag-Tagged IDH1 Proteins

R132H-IDH1, including an additional K345K silent mutation to remove an unwanted restriction site and GFP were subcloned into a modified pCLNCX retroviral vector. Retrovirus was prepared by taking 1.5 µg of each pCLNCX vector and 1.5 µg pCMV-VSV-G and 20 µL of Roche X-tremeGeneHP DNA transfection reagent to transfect HEK-293RTV cells. The medium was replaced after 1 day of transfection and the following day the culture supernatant was collected and filtered through 0.5 µM filter. 10 mL of the filtrate, containing the desired virus, was used to infect MUM2C cells in the presence of polybrene (8 µg/mL) for 48 h, at which point the infected cells were selected for in medium containing 100 µg/mL hygromycin for 7-10 days. Surviving cells were expanded and cultured in complete RPMI-1640 medium containing hygromycin.

IDH1 NADP Assay

Recombinant IDH1 and C269S-IDH1 (100 µM in storage buffer) were diluted 1:200 in MDA-MB-231 cellular proteome (1 mg/mL). To 25 µL of this mixture was added 1 µL of the indicated compound (25× stock solution in DMSO) and the lysates were incubated for 1 h at room temperature in clear 96 well plates (Corning® Costar®). 75 µL per well of a stock solution of NADP (13.3 mM) and isocitrate (13.3 mM) in IDH1 buffer (40 mM Tris, pH 7.4, 2 mM MgCl$_2$, 0.01% pluronic) was added immediately before measuring UV absorbance at 340 nm on a 96 well UV absorbance plate reader (TECAN). Absorbance was measured for 45 minutes and the relative activities were calculated from the change in absorbance for the linear portion of the curve.

IDH1 2-Hydroxyglutarate (2-HG) Formation Assay

MUM2C cells stably overexpressing IDH1 R132H were seeded 1.5×10$^6$ cells/150 mm dish. The following day the indicated compounds (50 mM stock solutions in DMSO) or DMSO were added to the cells to the final concentrations indicated and were allowed to incubate for 2 h. Control cells overexpressing GFP were treated in parallel. The cells were washed in ice-cold PBS and collected by scraping in ice-cold PBS and centrifugation (1,400 g, 3 min, 4° C.). The cell pellets were then resuspended in 100 µL ice-cold PBS followed by sonication and centrifugation at 16,000 g for 10 min. Lysates were then buffer exchanged into IDH1 buffer (40 mM Tris, pH 7.4, 2 mM MgCl$_2$) with 0.5 mL ZEBA spin desalting columns (Thermo Fisher, 89882). The protein concentrations were adjusted to 3.5 mg/mL and 25 µL of the lysate was mixed with 25 µL of the reaction mixture (2.5 mM NADPH and 2.5 mM α-ketoglutarate in IDH1 buffer) and the reaction was allowed to proceed for 4 h at which point the reaction mixtures were quenched with 50 µL cold methanol, followed by a centrifugation (16,000 g, 10 min, 4° C.). Formation of 2-HG was followed by targeted LC/MS analysis. The reaction mixture was separated with a Luna-NH$_2$ column (5 µm, 100 Å, 50×4.6 mm, Phenomenex) with a precolumn (NH$_2$, 4×3.0 mm) using a gradient of mobile phases A and B (mobile phase A: 100% CH$_3$CN, 0.1% formic acid; mobile phase B:95:5 (v/v) H$_2$O:CH$_3$CN, 50 mM NH$_4$OAc, 0.2% NH$_4$OH). The flow rate started at 0.1 mL/min, and the gradient consisted of 5 min 0% B, a linear increase to 100% B over 20 min at a flow rate of 0.4 mL/min, followed by an isocratic gradient of 100% B for 2 min at 0.5 mL/min before equilibrating for 3 min at 0% B at 0.4 mL/min (30 min total). For each run, the injection volume was 25 µL. MS analysis was performed on an Agilent G6410B tandem mass spectrometer with ESI source. The dwell time for 2-HG was set to 100 ms, and collision energy for 2-HG was set to 5. The capillary was set to 4 kV, and the fragmentor was set to 100 V. The drying gas temperature was 350° C., the drying gas flow rate was 11 L/min and the nebulizer pressure was 35 psi. The mass spectrometer was run in MRM mode, monitoring the transition of m/z from 146.7 to 129 for 2-HG (negative ionization mode). Treatments were conducted in triplicate. Background 2-HG production, calculated from the 'mock' GFP over expressing cells, was subtracted from the total 2-HG production.

TIGAR Activity Assay

TIGAR activity assay was conducted as described in Gerin et al. *The Biochemical Journal* 458:439-448 (2014). Formation of 3PG (3-phosphoglycerate) production from 23BPG (2,3-bisphosphoglycerate) was measured spectrophotometrically on a TECAN plate reader, measuring decrease in absorbance at 340 nm in clear, flat-bottom 96 well microplate (Corning® Costar®). 2 µL of recombinant TIGAR (10 mg/mL) was diluted into 1 mL dilution buffer (25 mM HEPES, pH 7.1, 25 mM KCl, 1 mM MgCl$_2$). 25 µL of diluted protein was incubated for 1 h with the indicated concentration of compound (1 µL, 25× stock in DMSO). Then 75 µL of assay mixture comprised of 25 mM HEPES (pH 7.1), 25 mM KCl, 1 mM MgCl$_2$, 0.5 mM NADH, 1 mM DTT, 1 mM 23BPG, 1 mM ATP-Mg, the equivalent of 1 µL each of rabbit muscle GAPDH (4000 units/mL, Sigma, G5537) and yeast PG kinase (6300 units/mL, Sigma, P7634) was added to the protein and decrease in absorbance was monitored at 340 nm. The background, calculated from samples lacking TIGAR, was subtracted from samples containing TIGAR. Experiments were performed in quadruplicate.

PRMT1 In Vitro Methylation Assays

PRMT1 assays were conducted as described in Weerapana et al. Nature 468:790-795 (2010). Recombinant human PRMT1 (0.85 µM, wild type or C101S mutant) in 25 µL methylation buffer (20 mM Tris, pH 8.0, 200 mM NaCl, 0.4 mM EDTA) was pre-incubated with indicated fragments for 1 h and methylation activity was monitored after addition of 1 mg of recombinant histone 4 (NEB, M2504S) and $^3$H-SAM (2 µCi). Reactions were further incubated for 60 min at ambient temperature and stopped with 4×SDS sample buffer. SDS-PAGE gels were fixed with 10% acetic acid/10% methanol (v/v), washed, and incubated with Amplify reagent (Amersham) before exposing to film at −80° C. for 3 days.

MLTK In Vitro Kinase Activity Assay

The kinase activity assay protocol was conducted as described in Wang et al. ACS Chemical biology 9:2194-2198 (2014). Kinase assay buffers, myelin basic protein (MBP) substrate and ATP stock solution were purchased from SignalChem. Radio-labeled [γ-$^{33}$P] ATP was purchased from PerkinElmer. 250 µL of HEK-293T soluble lysates (8 mg/mL), stably overexpressing WT, C22A or K45M MLTK were labeled for 1 h with 100 µM fragment or DMSO. The samples were then individually immunoprecipitated with 20 µL flag resin slurry per sample and then eluted with 15 µL 3×Flag-peptide. To each sample was added 5 µL of MBP and then 5 µL of [γ-$^{33}$P] ATP assay cocktail (250 µM, 167 µCi/mL) was added to initiate the kinase reaction. Each reaction mixture was incubated at ambient temperature for 30 min, and the reactions were terminated by spotting 25 µL of the reaction mixture onto individual precut phosphocellulose P81 paper. The spotted P81 strips were washed with 10 mL of 1% phosphoric acid (3×10 min). MLTK activity was measured by counting the radioactivity on the P81 paper in the presence of scintillation fluid in a scintillation counter. The background was determined from the K45M-inactive mutant MLTK activity level, which was subtracted from the WT and C22A samples. Relative activities for WT and C22A were normalized to their respective DMSO treated samples. Experiments were performed in triplicate.

CASP3 and CASP8 In Vitro Activity Assays

Caspase 3 and 8 assays were conducted with CASP8 activity assay kit (BioVision, K112-100) and Caspase 3 activity assay kit (Invitrogen, EnzChek® Caspase-3 Assay Kit), following the manufacturer's instructions. Briefly, recombinant Caspase 3 (10 µM) was added to soluble Ramos lysates (1 mg/mL) to a 100 nM final concentration of protease. Caspase 8 (30 µM) was added to soluble Ramos lysates to a 1 µM final concentration of protease. In triplicate, 50 µL lysate was treated with either DMSO, DEVD-CHO ("DEVD" disclosed as SEQ ID NO: 857) (20 µM) or the indicated compounds (100 µM) for 1 h, following which 50 µL of 2× reaction buffer containing 10 mM DTT and 5 µL substrate (4 mM stock in DMSO of IETD-AFC ("IETD" disclosed as SEQ ID NO: 858) for CASP8; 10 mM stock in DMSO of DEVD-AMC ("DEVD" disclosed as SEQ ID NO: 857) for CASP3) was added to each well and the samples were incubated at ambient temperature for 2 h. Caspase activity was measured from the increase in fluorescence (excitation 380 nm emission 460 nm). Experiments were performed in triplicate. Background was calculated from samples lacking the recombinant caspase.

Apoptosis Assays with Caspase 8 Inhibitors 4 mL of Jurkat cells in RPMI (1.5 million cells/mL) were treated with the indicated compound at 30 µM for 30 min (50 mM stock solution in DMSO). Z-VAD-FMK (EMD Millipore Biosciences, 627610) and was used at a final concentration of 100 µM. After pre-incubation, FASL (4 µL of 100 µg/µL stock solution of SuperFasLigandm in water, final concentration=100 ng/mL, Enzo life Sciences) or staurosporine (8 µL of 1 mM stock solution in DMSO, final concentration=2 µM, Fisher Scientific, 50664333). After 6 hours, cells were harvested by centrifugation, washed and lysed in cell lysis buffer (BioVision, 1067-100) and 40 µg of each sample were separated by SDS-Page on 14% polyacrylamide gels. The gels were transferred to nitrocellulose membranes and were immunoblotted overnight with the indicated antibodies. For measurements of cell viability, in quadruplicate for each condition, 150,000 cells (100 µL of 1.5 million cells/mL) were plated in Nunc™ MicroWell™ 96-Well Optical-Bottom Plates with Polymer Base (Fisher Scientific). Compounds, FASL and STS were used at the same concentrations indicated above with a 30 minute pre-incubation with compound, followed by 6 hours with either STS or FASL or DMSO. Cell viability was measured with CellTiter-Glo® Luminescent Cell Viability Assay (Promega) and was read on a Biotech Synergy 4 plate reader.

Western Blotting

For CASP8, CASP3 and PARP, cell pellets were resuspended in cell lysis buffer from (BioVision, 1067-100) with 1× cOmplete protease inhibitor (Roche) and allowed to incubate on ice for 30 min prior to centrifugation (10 min, 16,000 g). For all other proteins, cell pellets were resuspended in PBS and lysed with sonication prior to centrifugation (10 min, 16,000 g). The proteins were then resolved by SDS-PAGE and transferred to nitrocellulose membranes, blocked with 5% BSA in TBST and probed with the indicated antibodies. The primary antibodies and the dilutions used are as follows: anti-parp (Cell Signaling, 9532, 1:1000), anti-casp3 (Cell Signaling, 9662, 1:500), anti-casp8 (Cell Signaling, 9746, 1:500), anti-IDH1 (Cell Signaling, 1:500, 3997s), anti-actin (Cell Signaling, 3700, 1:3000), anti-gapdh (Santa Cruz, sc-32233, 1:2000) anti-flag (Sigma Aldrich, F1804, 1:3000). Blots were incubated with primary antibodies overnight at 4° C. with rocking and were then washed (3×5 min, TBST) and incubated with secondary antibodies (LICOR, IRDye® 800CW or IRDye® 800LT, 1:10,000) for 1 h at ambient temperature. Blots were further washed (3×5 min, TBST) and visualized on a LICOR Odyssey Scanner.

Statistical Analysis

Data are shown as mean±SEM. P values were calculated using unpaired, two-tailed Student's t-test. P values of <0.05 were considered significant.

Prediction Failures in Reactive Docking

Prediction failures were due to the approximations of the rigid model used with highly flexible/solvent exposed loop regions (STAT1:C255, PDB ID:1YVL; HAT1:C101, PDB ID:2POW; ZAP70:C117, PDB ID:4K2R), or with partially buried residues (SARS:C438, PDB ID:4187; PAICS:C374, PDB ID:2H31). In some embodiments, the simulation of some degree of flexibility (such as flexible side chains) improves the success rate. In some embodiments, the method was limited by availability and quality of crystallographic structures, when sequences were not fully resolved in available models (XPO1:C34, C1070, PDB ID:3GB8, FNBP1:C511, C555, C609, PDB ID:2EFL; IMPDH2:C140, PDB ID:1NF7), or when only orthologue sequences were available (PRMT1: R. Norvegicus, PDB ID:1ORI).

General Synthetic Methods

Chemicals and reagents were purchased from a variety of vendors, including Sigma Aldrich, Acros, Fisher, Fluka, Santa Cruz, CombiBlocks, BioBlocks, and Matrix Scientific, and were used without further purification, unless noted otherwise. Anhydrous solvents were obtained as commercially available pre-dried, oxygen-free formulations. Flash chromatography was carried out using 230-400 mesh silica gel. Preparative thin layer chromotography (PTLC) was carried out using glass backed PTLC plates 500-2000 µm thickness (Analtech). All reactions were monitored by thin layer chromatography carried out on 0.25 mm E. Merck silica gel plates (60F-254) and visualized with UV light, or by ninhydrin, ethanolic phosphomolybdic acid, iodine, p-anisaldehyde or potassium permanganate stain. NMR spectra were recorded on Varian INOVA-400, Bruker DRX-600 or Bruker DRX-500 spectrometers in the indicated solvent. Multiplicities are reported with the following abbreviations: s singlet; d doublet; t triplet; q quartet; p pentet; m multiplet; br broad. Chemical shifts were reported in ppm relative to TMS and J values were reported in Hz. Mass spectrometry data were collected on a HP1100 single-quadrupole instrument (ESI; low resolution) or an Agilent ESI-TOF instrument (HRMS).

In some embodiments, General Procedure A was used for the synthesis of one or more of the small molecule fragments and/or cysteine-reactive probes described herein. The amine was dissolved in anhydrous $CH_2Cl_2$ (0.2 M) and cooled to 0° C. To this, anhydrous pyridine (1.5 equiv.) was added in one portion, then chloroacetyl chloride (1.5 equiv.) dropwise and the reaction was monitored by TLC until complete disappearance of starting material and conversion to product was detected (typically 1 h). If the reaction did not proceed to completion, additional aliquots of pyridine (0.5 equiv.) and chloroacetyl chloride (0.5 equiv.) were added. The reaction was quenched with $H_2O$ (1 mL), diluted with $CH_2Cl_2$ (20 mL), and washed twice with saturated $NaHCO_3$ (100 mL). The organic layer was concentrated in vacuo and purified by preparatory thin layer or flash column chromatography to afford the desired product. In some embodiments, General Procedure A1 is similar to General Procedure A except triethylamine (3 equiv.) was used instead of pyridine. In some embodiments, General Procedure A2 is similar to General Procedure A except N-methylmorpholine (3 equiv.) was used instead of pyridine.

In some embodiments, General Procedure B was used for the synthesis of one or more of the small molecule fragments and/or cysteine-reactive probes described herein. The amine was dissolved in anhydrous $CH_2Cl_2$ (0.2 M) and cooled to 0° C. To this, triethylamine (TEA, 1.5 equiv.), was added in one portion, then acryloyl chloride (1.5 equiv.) dropwise, and the reaction was monitored by TLC until complete disappearance of starting material and conversion to product was detected (typically 1 h). If the reaction did not proceed to completion, additional aliquots of TEA (0.5 equiv.) and acryloyl chloride (0.5 equiv.) were added. The reaction was quenched with $H_2O$ (1 mL), diluted with $CH_2Cl_2$ (20 mL), and washed twice with saturated $NaHCO_3$ (100 mL). The organic layer was passed through a plug of silica, after which, the eluant was concentrated in vacuo and purified by preparatory thin layer or flash column chromatography to afford the desired product.

In some embodiments, General Procedure C was used for the synthesis of one or more of the small molecule fragments and/or cysteine-reactive probes described herein. Acryloyl chloride (80.4 µL, 1.0 mmol, 2 equiv.) was dissolved in anhydrous $CH_2Cl_2$ (4 mL) and cooled to 0° C. A solution of the amine (0.5 mmol, 1 equiv.) and N-methylmorpholine (0.16 mL, 1.5 mmol, 3 equiv.) in $CH_2Cl_2$ (2 mL) was then added dropwise. The reaction was stirred for 1 hr at 0° C. then allowed to warm up to room temperature slowly. After TLC analysis showed disappearance of starting material, or 6 h, whichever was sooner, the reaction was quenched with saturated aqueous $NaHCO_3$ (5 mL) and extracted with $CH_2Cl_2$ (3×10 mL). The combined organic layers were dried over anhydrous $Na_2SO_4$, concentrated in vacuo, and the residue obtained was purified by preparatory thin layer chromatography to afford the desired product.

Synthesis of Probes and Fragments
Purchased Fragments

The following electrophilic fragments were purchased from the indicated vendors. 2 (Santa Cruz Biotechnology sc-345083), 3 (Key Organics JS-092C), 4 (Sigma Aldrich T142433-10 mg), 6 (Toronto Research Chemicals M320600), 8 (Alfa Aesar H33763), 10 (Santa Cruz Biotechnology sc-345060), 11 (Santa Cruz Biotechnology sc-354895), 12 (Santa Cruz Biotechnology sc-354966), 21 (Santa Cruz Biotechnology, sc-279681), 22 (Sigma Aldrich 699357-5G), 26 (Sigma Aldrich T109959), 27 (Santa Cruz Biotechnology sc-342184), 28 (Santa Cruz Biotechnology sc-335173), 29 (Santa Cruz Biotechnology sc-348978), 30 (Santa Cruz Biotechnology sc-355362), 32 (Santa Cruz Biotechnology sc-354613), 33 (Sigma Aldrich R996505), 34 (Santa Cruz Biotechnology sc-355477), 35 (Santa Cruz Biotechnology sc-328985), 41 (Sigma Aldrich L469769), 42 (Sigma Aldrich R901946), 43 (Santa Cruz Biotechnology sc-307626), 52 (Enamine, EN300-08075), 55 (Santa Cruz Biotechnology sc-354880), 57 (VWR 100268-442), 58 (Enzo Life Sciences ALX-430-142-M005), 62 (WuXi Apptec).

Synthesis of Isotopically-Labeled TEV-Tags:

Isotopically-labeled heavy and light tags were synthesized with minor modifications to the procedure reported in Weerapana et al. *Nat Protoc* 2:1414-1425 (2007) and Weerapana et al. *Nature* 468:790-795 (2010). Fmoc-Rink-Amide-MBHA resin (EMD Biosciences; 0.5 M, 830 mg, 0.6 mmol/g loading) was deprotected with 4-methylpiperidine in DMF (50% v/v, 2×5 mL, 1 min). Fmoc-Lys($N_3$)—OH (Anaspec) (500 mg, 1.26 mmol, 1.26 equiv.) was coupled to the resin overnight at room temperature with DIEA (113 µl) and 2-(6-chloro-1H-benzotriazole-1-yl)-1, 1,3,3-tetramethylaminium hexafluorophosphate (HCTU; 1.3 mL of 0.5 M stock in DMF) followed by a second overnight coupling with Fmoc-Lys($N_3$)—OH (500 mg, 1.26 mmol, 1.26 equiv.), DIEA (113 µl), O-(7-azabenzotriazol-1-yl)-N,N,N',N'-tetramethyluronium hexafluorophosphate (HATU; 1.3 mL of 0.5 M stock in DMF). Unmodified resin was then capped (2×30 min) with $Ac_2O$ (400 µL) and DIEA (700 µL) in DMF after which the resin was washed with DMF (2×1 min). Deprotection with 4-methylpiperidine in DMF (50% v/v, 2×5 mL, 1 min) and coupling cycles (4 equiv. Fmoc-protected amino acid (EMD biosciences) in DMF) with HCTU (2 mL, 0.5 M in DMF) and DIEA (347.7 µL) were then repeated for the remaining amino acids. For the heavy TEV-tag, Fmoc-Valine-OH ($^{13}C_5C_{15}H_{21}{}^{15}NO_4$, $^{13}C_5$, 97-99%, $^{15}N$, 97-99%, Cambridge Isotope Laboratories, Inc.) was used. Reactions were monitored by ninhydrin stain and dual couplings were used for all steps that did not go to completion. Biotin (0.24 g, 2 equiv.) was coupled for two days at room temperature with NHS (0.1 g, 2 equiv.), DIC (0.16 g, 2 equiv.) and DIEA (0.175 g, 2 equiv.). The resin was then washed with DMF (5 mL, 2×1 min) followed by 1:1 $CH_2Cl_2$:MeOH (5 mL, 2×1 min), dried under a stream of nitrogen and transferred to a round-bottom flask. The peptides were cleaved for 90 minutes from the resin by treatment with 95:2.5:2.5 trifluoroacetic acid: water:triisopropylsilane. The resin was removed by filtration and the remaining solution was triturated with cold ether to provide either the light or heavy TEV-tag as a white solid. HPLC-MS revealed only minor impurities and the compounds were used without further purification. HRMS-ESI (m/z): calculated for $C_{83}H_{128}N_{23}O_{23}S$ [M+H]: (Light-TEV-Tag) 1846.9268; found: 1846.9187; calculated for $C_{78}{}^{13}C_5H_{128}N_{22}{}^{15}NO_{23}S$ [M+H]: (Heavy-TEV-Tag): 1852.9237; found: 1852.9309.

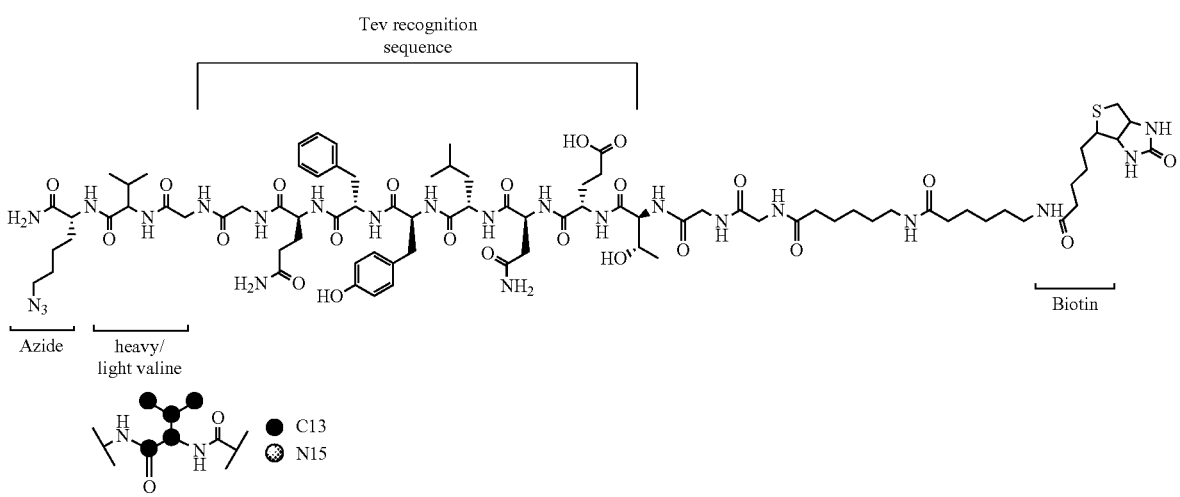 [SMILES: CC(C)C[C@H](NC(=O)[C@H](CC(N)=O)NC(=O)[C@H](CCC(=O)O)NC(=O)[C@@H](NC(=O)CNC(=O)CNC(=O)CCCCCNC(=O)CCCCCNC(=O)CCCCC1SCC2NC(=O)NC21)[C@H](C)O)C(=O)N[C@@H](Cc1ccc(O)cc1)C(=O)N[C@@H](Cc1ccccc1)C(=O)N[C@@H](CCC(N)=O)C(=O)NCC(=O)NCC(=O)NC(C(=O)N[C@H](CCCCN=[N+]=[N-])C(N)=O)C(C)C ; "N15" ; "C13" ; CC(C)NC(=O)C(NC(=O)C(C)C)C(C)C]

Synthesis of Probes and Fragments
Synthesis of 1

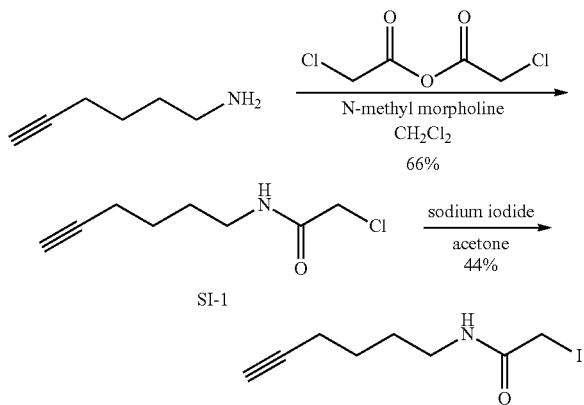

N-(hex-5-yn-1-yl)-2-chloroacetamide (SI-1)

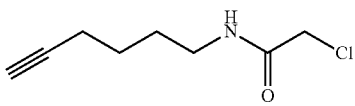

To a solution of 5-hexynylamine (63 mg, 0.65 mmol, 1.0 equiv.) in CH$_2$Cl$_2$ (3.2 mL, 0.2 M) at 0° C. was added N-methylmorpholine (215 µL, 3 equiv.) followed by chloroacetic anhydride portionwise (222 mg, 2 equiv.). The reaction was allowed to come to room temperature and then stirred overnight. The reaction was then diluted with ether (50 mL), washed with 1 M HCl, 1 M NaOH, then brine (20 mL each). The combined organic layers were dried over magnesium sulfate and concentrated to yield chloroacetamide SI-1 (74 mg, 66%). $^1$H NMR (400 MHz, Chloroform-d) δ 6.79 (s, 1H), 4.09 (d, J=1.1 Hz, 2H), 3.34 (q, J=6.8 Hz, 2H), 2.23 (td, J=6.9, 2.7 Hz, 2H), 1.98 (t, J=2.7 Hz, 1H), 1.75-1.62 (m, 4H), 1.62-1.51 (m, 2H).

N-(hex-5-yn-1-yl)-2-iodoacetamide (1)

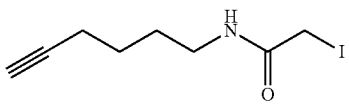

To a solution of chloroacetamide SI-1 (36.1 mg, 0.2 mmol) in acetone (1 mL, 0.2 M) was added sodium iodide (47 mg, 1.5 equiv.) and the reaction was stirred overnight. The next day the reaction was filtered through a plug of silica eluting with 20% ethyl acetate in hexanes, and the filtrate was concentrated to yield a 10:1 mixture of the desired iodoacetamide 1 and starting material. This mixture was re-subjected to the reaction conditions for one further day, at which point complete conversion was observed. The product was purified by silica gel chromatography, utilizing a gradient of 5 to 10 to 15 to 20% ethyl acetate in hexanes to yield the desired product (24 mg, 44%). In some embodiments, the reaction is performed with 2.5 equiv. of sodium iodide, in which case re-subjection is not necessary, and purification by PTLC is accomplished in 30% EtOAc/hexanes as eluent. $^1$H NMR (500 MHz, Chloroform-d) δ 6.16 (s, 1H), 3.69 (s, 2H), 3.30 (q, J=6.8 Hz, 2H), 2.23 (td, J=6.8, 2.6 Hz, 2H), 1.97 (t, J=2.6 Hz, 1H), 1.75-1.61 (m, 2H), 1.61-1.52 (m, 2H).

N-(4-bromophenyl)-N-phenylacrylamide (5)

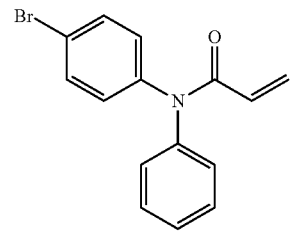 [SMILES: C=CC(=O)N(c1ccccc1)c1ccc(Br)cc1]

The title compound was synthesized according to General Procedure C from 4-bromophenylaniline (18.9 mg, 0.0762 mmol, 1 equiv.). Purification of the crude product by prep. TLC (30% EtOAc/hexanes) provided the title compound as a white solid (12.5 mg, 54%). $^1$H NMR (500 MHz, Chloroform-d) δ 7.47 (d, J=8.2 Hz, 2H), 7.39 (t, J=7.6 Hz, 2H), 7.32 (d, J=7.4 Hz, 1H), 7.21 (d, J=7.7 Hz, 2H), 7.12 (d, J=8.2 Hz, 2H), 6.48 (d, J=16.7 Hz, 1H), 6.17 (dd, J=16.8, 10.3 Hz, 1H), 5.65 (d, J=10.3 Hz, 1H); HRMS-ESI (m/z) calculated for C$_{15}$H$_{13}$BrNO [M+H]: 302.0175; found: 302.0176.

Synthesis of 7

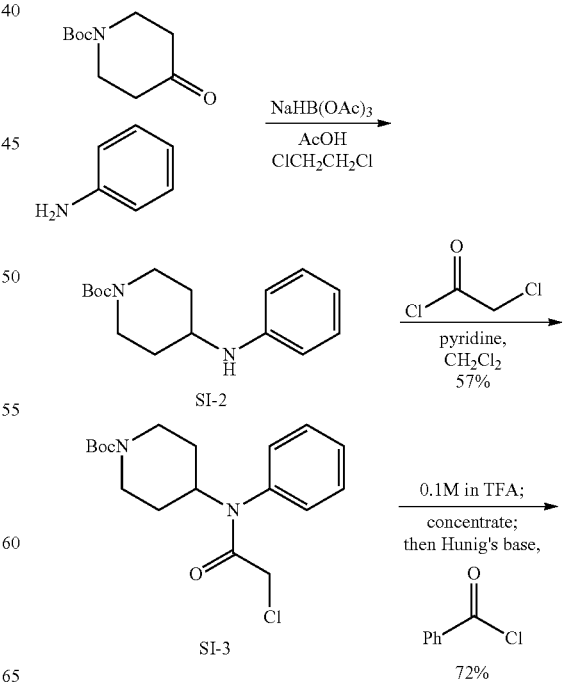

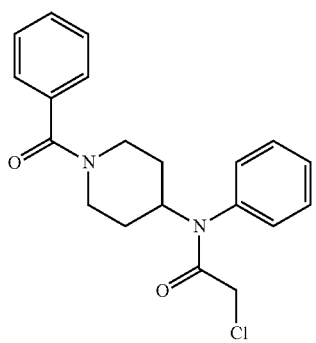

7 tert-butyl 4-(phenylamino)piperidine-1-carboxylate (SI-2)

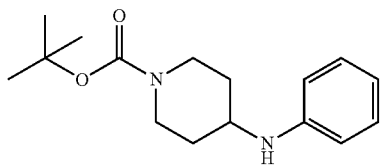 [SMILES: CC(C)(C)OC(=O)N1CCC(Nc2ccccc2)CC1]

SI-2 was prepared according to Thoma et al, *J. Med. Chem.* 47:1939-1955 (2004). $^1$H NMR (400 MHz, Chloroform-d) δ 7.24-7.12 (m, 2H), 6.75-6.68 (m, 1H), 6.66-6.58 (m, 2H), 3.88-3.81 (m, 1H), 3.44 (tt, J=10.4, 3.9 Hz, 2H), 3.00-2.88 (m, 2H), 2.10-1.99 (m, 2H), 1.48 (bs 9H), 1.41-1.27 (m, 2H).

tert-butyl 4-(2-chloro-N-phenylacetamido)piperidine-1-carboxylate (SI-3)

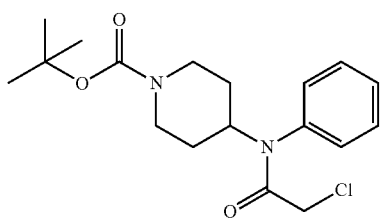 [SMILES: CC(C)(C)OC(=O)N1CCC(N(C(=O)CCl)c2ccccc2)CC1]

To a solution of aniline SI-2 (65 mg, 0.24 mmol) at 0° C. in CH$_2$C$_2$ (0.6 mL) was added pyridine (38 μL, 2 equiv.) followed by chloroacetyl chloride (37.4 μL, 2.0 equiv.) in CH$_2$Cl$_2$ (0.6 mL). The resulting solution was allowed to warm to room temperature and stirred overnight. The solution was then quenched with saturated aqueous sodium bicarbonate, extracted with Et$_2$O (3×10 mL). The combined organic layers were dried over magnesium sulfate, filtered and concentrated to give an off-white solid, which was used without further purification (47 mg, 57%). $^1$H NMR (400 MHz, Chloroform-d) δ 7.47-7.38 (m, 3H), 7.18-7.03 (m, 2H), 4.75-4.63 (m, 1H), 4.07 (s, 2H), 3.68 (s, 2H), 2.76 (s, 2H), 1.84-1.69 (m, 2H), 1.35 (s, 9H), 1.27-1.12 (m, 2H).

N-(1-benzoylpiperidin-4-yl)-2-chloro-N-phenylacetamide (7)

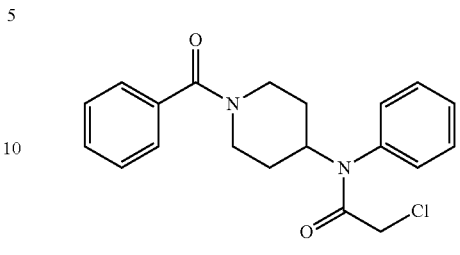

To neat SI-3 (47 mg, 0.128 mmol) was added trifluoroacetic acid (0.7 mL, final 0.2 M). The resulting solution was concentrated under a stream of nitrogen until no further evaporation was observed, providing the deprotected amine as its trifluoroacetate salt. This viscous gum was then treated with triethylamine in ethyl acetate (10% v/v, 2 mL; solution smokes upon addition). The resulting solution was concentrated to afford the free base, which contained only triethylammonium trifluoroacetate and the free amine by proton NMR. A stock solution was prepared by dissolving the resulting gum in CH$_2$Cl$_2$ (1.2 mL, ~0.1 M final).

The deprotected amine (0.3 mL of stock solution, 0.0319 mmol) was treated with Hunig's base (17.5 μL, 3 equiv.) and benzoyl chloride (7.6 μL, 2.0 equiv.). This solution was stirred overnight, quenched with saturated aqueous sodium bicarbonate, extracted with Et$_2$O (3×10 mL). The resulting solution was dried over magnesium sulfate, filtered and concentrated. The resulting oil was purified by silica gel chromatography (20% EtOAc/hexanes) to afford chloroacetamide 7 as a white solid (8.6 mg, 75%). $^1$H NMR (500 MHz, Chloroform-d) δ 7.55 (dd, J=5.5, 3.0 Hz, 3H), 7.50-7.32 (m, 5H), 7.21 (s, 2H), 4.92 (tt, J=12.3, 4.0 Hz, 1H), 4.87 (s, 1H), 3.87 (s, 1H), 3.78 (s, 2H), 3.21 (s, 1H), 2.97-2.90 (m, 1H), 2.01 (s, 1H), 1.90 (s, 1H), 1.45 (s, 1H), 1.36-1.26 (m, 1H); HRMS-ESI (m/z) calculated for C$_{20}$H$_{22}$ClN$_2$O$_2$[M+H]: 357.1364; found: 357.1362.

1-(4-benzylpiperidin-1-yl)-2-chloroethan-1-one (9)

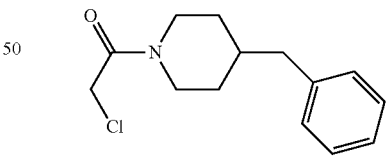

Following General Procedure A, starting from 4-benzylpiperidine (840 mg, 5.2 mmol, 1 equiv.), the desired compound was obtained after column chromatography as a yellow oil (1 g, 81%). Spectroscopic data matches those reported previously reported in Papadopoulou et al. *J. Med. Chem.* 55:5554-5565 (2012). $^1$H NMR (500 MHz, Chloroform-d) δ 7.42-7.14 (m, 5H), 4.61 (d, J=13.4 Hz, 1H), 4.14 (q, J=21.9, 11.5 Hz, 2H), 3.89 (d, J=13.5, 1H), 3.11 (td, J=13.1, 2.7 Hz, 1H), 2.69-2.57 (m, 3H), 1.92-1.75 (m, 3H), 1.40-1.21 (m, 2H); HRMS-ESI (m/z) calculated for C$_{14}$H$_{19}$ClNO [M+H]: 252.115; found: 252.115.

N-(2-(1H-indol-3-yl)ethyl)-2-chloroacetamide (13)

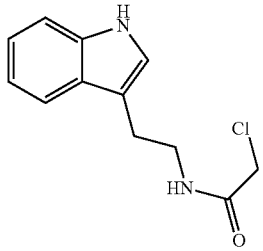 [SMILES: O=C(CCl)NCCc1c[nH]c2ccccc12]

Following General Procedure A, starting from tryptamine (400 mg, 2.5 mmol, 1 equiv.), the desired compound was obtained after column chromatography as a brownish solid (460 mg, 77%). $^1$H NMR (500 MHz, Chloroform-d) δ 8.55 (s, 1H), 7.70 (d, J=7.9 Hz, 1H), 7.45 (d, J=8.1 Hz, 1H), 7.30 (t, J=7.5 Hz, 1H), 7.23 (t, J=7.4 Hz, 1H), 7.10 (s, 1H), 6.84 (s, 1H), 4.08 (s, 2H), 3.72 (q, J=6.4 Hz, 2H), 3.10 (t, J=6.8 Hz, 2H); HRMS-ESI (m/z) calculated for $C_{12}H_{14}ClN_2O_2$ [M+H]: 237.0789; found: 237.0791.

N-(3,5-bis(trifluoromethyl)phenyl)acrylamide (14)

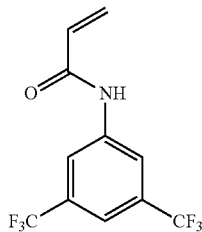

Following General Procedure B, starting from 3,5-bis(trifluoromethyl)aniline (1.16 g, 5 mmol, 1 equiv.), the desired compound was obtained after column chromatography as a white solid (1.05 g, 74%). $^1$H NMR (500 MHz, Chloroform-d) δ 8.33 (s, 1H), 8.18 (s, 2H), 7.68 (s, 1H), 6.57 (d, J=17.5 Hz, 1H), 6.38 (dd, J=16.9, 10.3 Hz, 1H), 5.93 (d, J=12.5 Hz, 1H); HRMS-ESI (m/z) calculated for $C_{11}H_8F_6NO_2$ [M+H]: 284.0505; found: 284.0504.

N-(4-phenoxy-3-(trifluoromethyl)phenyl)-N-(pyridin-3-ylmethyl)acrylamide (15)

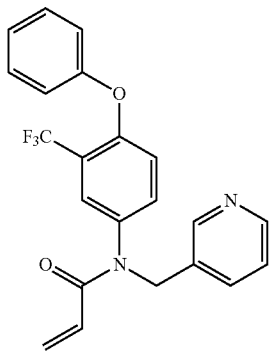 [SMILES: C=CC(=O)N(Cc1cccnc1)c1ccc(Oc2ccccc2)c(C(F)(F)F)c1]

4-phenoxy-3-(trifluoromethyl)aniline (260 mg, 1 mmol, 1 equiv.) (Combi-Blocks) was dissolved in TFA (5 mL). Following the reductive amination protocol reported by Boros et al. *J. Org. Chem* 74:3587-3590 (2009), the reaction mixture was cooled to 0° C. and to this sodium triacetoxyborohydride (STAB) (270 mg, 1.3 mmol, 1.3 equiv.) was added. 3-pyridinecarboxaldehyde (200 mg, 2 mmol, 2 equiv.) was dissolved in $CH_2Cl_2$ (5 mL) and slowly added to the reaction mixture. Upon complete conversion to product, the reaction was diluted with $CH_2Cl_2$ (20 mL) and washed with saturated sodium bicarbonate solution (3×20 mL) and the organic layer was dried then concentrated under reduced pressure. Without further purification the crude material was dissolved in anhydrous $CH_2Cl_2$ and subjected to General Procedure B. The resulting crude was purified by prep. TLC to give a white solid (31 mg, 10%). $^1$H NMR (500 MHz, Chloroform-d) δ 8.52 (d, J=3.5 Hz, 1H), 8.39 (s, 1H), 7.68 (d, J=7.8 Hz, 1H), 7.40 (t, J=7.7 Hz, 2H), 7.34 (s, 1H), 7.28-7.18 (m, 2H), 7.07 (d, J=8.2 Hz, 2H), 6.98 (d, J=7.5 Hz, 1H), 6.82 (d, J=8.8 Hz, 1H), 6.46 (d, J=16.8 Hz, 1H), 6.01 (dd, J=16.2, 10.7 Hz, 1H), 5.64 (d, J=10.3 Hz, 1H), 4.96 (s, 2H). HRMS-ESI (m/z) calculated for $C_{22}H_{18}F_3N_2O_2$ [M+H]: 399.1315; found: 399.1315.

Iodoacetamide-rhodamine (16)

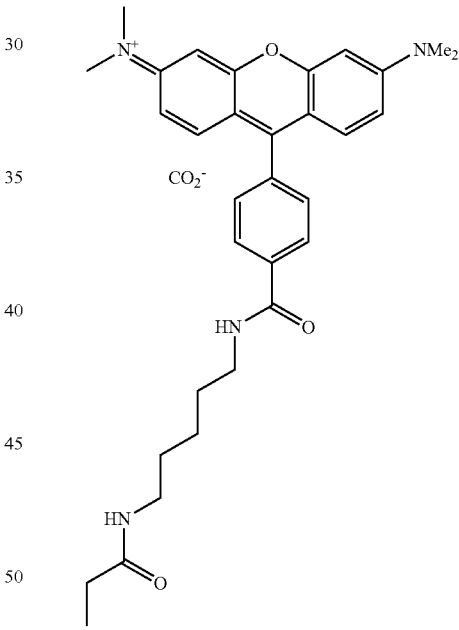

5-(and-6)-((N-(5-aminopentyl)amino)carbonyl)tetramethylrhodamine (tetramethylrhodamine cadaverine) mixed isomers (60 mg, 0.12 mmol, 1 equiv.) were dissolved in anhydrous DMF (500 µL) with sonication. To this was added DIPEA (60 µL, 0.34 mmol, 3 equiv.) and chloroacetyl chloride (10 µL, 0.13 mmol, 1 equiv., diluted 1:10 in DMF) and the reaction was stirred at room temperature for 20 min until complete conversion to the product was detected by TLC. The DMF was removed under a stream of nitrogen and the reaction mixture was separated by PTLC in MeOH:$CH_2Cl_2$:TEA (15:85:0.001). The chloroacetamide rhodamine was then eluted in MeOH:$CH_2Cl_2$ (15:85), concentrated under reduced pressure and redissolved in acetone (500 µL). NaI (150 mg, 1 mmol, 10 equiv.) was added to this and the reaction was stirred for 20 min at 50° C. until complete conversion to product was detected and the crude reaction mixture was purified by reverse phase HPLC on a C18 column and concentrated to yield the title compound as a purple solid that is a mixture of 5 and 6 carboxamide tetramethylrhodamine isomers (ratio ~6:1) (10 mg, 12%). $^1$H NMR (600 MHz, Methanol-$d_4$) δ 8.87 (t, J=4.8 Hz, 0.14H), 8.80-8.71 (m, 1H), 8.41 (dd, J=8.2, 1.1 Hz, 0.86H), 8.35 (br s, 1H), 8.27 (dt, J=7.9, 1.5 Hz, 0.164H), 8.20 (dt, J=8.2, 1.5 Hz, 0.86H), 7.81 (s, 0.86H), 7.53 (d, J=7.8 Hz, 0.14H), 7.18-7.11 (m, 2H), 7.07 (d, J=9.5 Hz, 2H), 7.00 (s, 2H), 3.68-3.62 (m, 2H), 3.46-3.37 (m, 2H), 3.31 (s, 12H, obscured by solvent) 3.21-3.12 (m, 2H), 1.81-1.21 (m, 6H); HRMS-ESI (m/z) calculated for $C_{32}H_{36}IN_4O_5$ [M+H]: 683.1725; found: 683.1716.

N-(3,5-bis(trifluoromethyl)phenyl)acetamide (17)

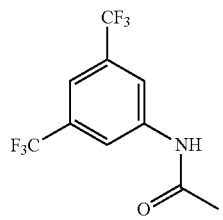 [SMILES: CC(=O)Nc1cc(C(F)(F)F)cc(C(F)(F)F)c1]

Following General Procedure A, starting with 3,5-bis (trifluoromethyl)aniline (327 mg, 1.42 mmol, 1 equiv.) and acetic anhydride (200 μL, 3 mmol, 2 equiv.), the title compound was obtained after PTLC as a white solid (302 mg, 78%). $^1$H NMR (500 MHz, Chloroform-d) δ 8.10 (s, 2H), 7.72 (s, 1H), 7.68 (s, 1H), 2.32 (d, J=0.9 Hz, 3H). HRMS-ESI (m/z) calculated for $CH_8F_6NO_2$ [M+H]: 284.0505; found: 284.0504.

Synthesis of 18 and 19

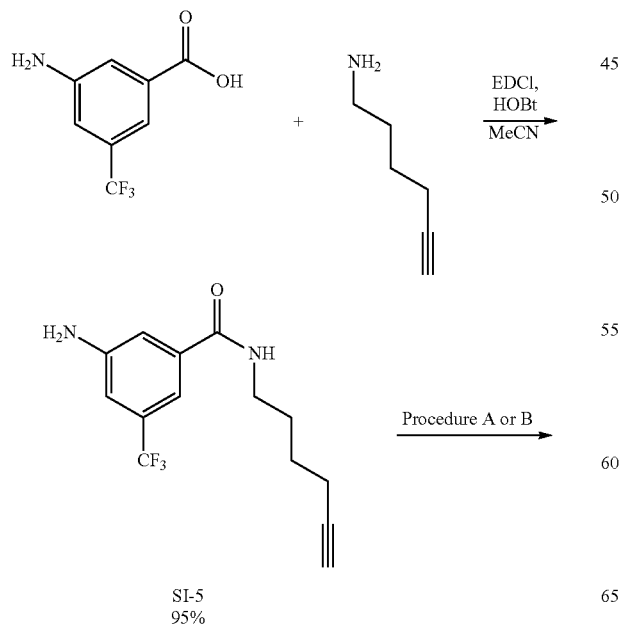

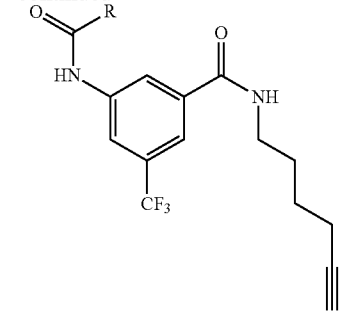

18 (70%), 19 (XX)

R = 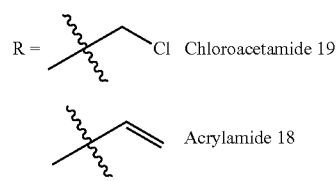

3-amino-N-(hex-5-yn-1-yl)-5-(trifluoromethyl)benzamide (SI-5)

To a solution of 3-amino-5-(trifluoromethyl)benzoic acid (74 mg, 0.36 mmol) in acetonitrile (3.6 mL, 0.1 M final) was added EDCI (83 mg, 1.2 equiv.) followed by hex-5-ynamine (35 mg, 1.0 equiv.) followed by 1-hydroxybenzotriazole hydrate (HOBt, 66.3 mg, 1.2 equiv.) and the resulting solution was stirred overnight. The reaction was diluted with ethyl acetate, washed with 1 M HCl twice and then brine. The organic layer was dried over magnesium sulfate and concentrated to yield aniline SI-5 (97.4 mg, 95%) as a white solid. $^1$H NMR (400 MHz, Chloroform-d) δ 7.29-7.22 (m, 2H), 6.98 (t, J=1.8 Hz, 1H), 6.38 (t, J=5.5 Hz, 1H), 4.08 (s, 2H), 3.46 (td, J=7.1, 5.7 Hz, 2H), 2.25 (td, J=6.9, 2.6 Hz, 2H), 1.99 (t, J=2.7 Hz, 1H), 1.81-1.55 (m, 4H).

3-acrylamido-N-(hex-5-yn-1-yl)-5-(trifluoromethyl)benzamide (18)

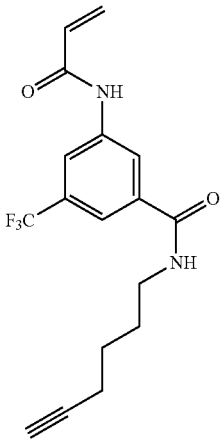 [SMILES: C#CCCCCNC(=O)c1cc(NC(=O)C=C)cc(C(F)(F)F)c1]

Following General Procedure B, starting with SI-5 (42 mg, 0.15 mmol, 1 equiv.), the title compound was obtained after column chromatography as a white solid (34 mg, 70%). $^1$H NMR (500 MHz, Chloroform-d) δ 8.94 (s, 1H), 8.24 (d, J=11.9 Hz, 2H), 7.71 (s, 1H), 6.87 (t, J=5.7 Hz, 1H), 6.55 (dd, J=17.4, 0.7 Hz, 1H), 6.43 (dd, J=16.9, 10.1 Hz, 1H), 5.88 (dd, J=10.1, 1.3 Hz, 1H), 3.56 (q, J=6.7 Hz, 2H), 2.33 (td, J=6.9, 2.7 Hz, 2H), 2.06 (t, J=2.7 Hz, 1H), 1.87 (p, J=7.3 Hz, 2H), 1.69 (p, J=7.8 Hz, 2H); HRMS-ESI (m/z) calculated for $C_{17}H_{18}F_3N_2O_2$ [M+H]: 339.1314; found 339.1313.

3-acrylamido-N-(hex-5-yn-1-yl)-5-(trifluoromethyl)benzamide (19)

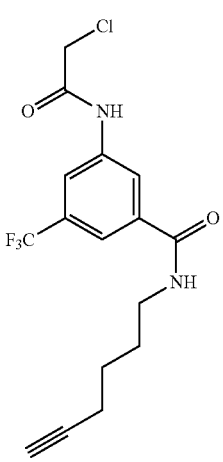 [SMILES: C#CCCCCNC(=O)c1cc(NC(=O)CCl)cc(C(F)(F)F)c1]

Synthesized according to General Procedure A2, starting from SI-5. $^1$H NMR (600 MHz, Chloroform-d) δ 8.57 (s, 1H), 8.16 (t, J=1.8 Hz, 1H), 8.05 (t, J=1.8 Hz, 1H), 7.79 (d, J=2.0 Hz, 1H), 6.38 (d, J=6.1 Hz, 1H), 4.23 (s, 2H), 3.51 (td, J=7.1, 5.7 Hz, 2H), 2.27 (td, J=6.9, 2.7 Hz, 2H), 2.00 (t, J=2.6 Hz, 1H), 1.82-1.74 (m, 2H), 1.71-1.59 (m, 2H); HRMS-ESI (m/z) calculated for $C_{16}H_{17}ClF_3N_2O_2$ [M+H]: 361.0925; found: 361.0925.

2-chloro-1-(4-(hydroxydiphenylmethyl)piperidin-1-yl)ethan-1-one (20)

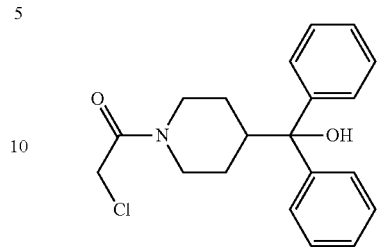

Following General Procedure A, starting with α,α-diphenyl-4-piperidinomethanol (800 mg, 3 mmol, 1 equiv.), the title compound was obtained after column chromatography as a white solid (637 mg, 61%). $^1$H NMR (500 MHz, Chloroform-d) δ 7.56 (d, J=7.6 Hz, 4H), 7.39 (q, J=7.1 Hz, 4H), 7.28 (q, J=6.8 Hz, 2H), 4.66 (d, J=13.3 Hz, 1H), 4.07 (dd, J=12.2, 4.2 Hz, 2H), 3.91 (d, J=13.4 Hz, 1H), 3.18 (t, J=12.9 Hz, 1H), 2.77-2.62 (m, 3H), 1.67 (t, J=12.5 Hz, 2H), 1.56 (q, J=11.8 Hz, 1H), 1.44 (q, J=12.4, 11.8 Hz, 1H); HRMS-ESI (m/z) calculated for $C_{20}H_{23}ClNO_2$ [M+H]: 344.1412; found: 344.1412.

(E)-3-(3,5-bis(trifluoromethyl)phenyl)-2-cyanoacrylamide (23)

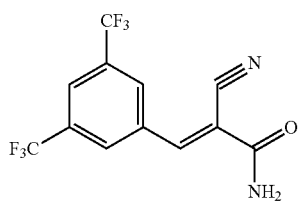 [SMILES: N#C/C(=C\c1cc(C(F)(F)F)cc(C(F)(F)F)c1)C(N)=O]

3,5-bis(trifluoromethyl)benzaldehyde (880 mg, 3.6 mmol, 1 equiv.) and 2-cyanoacetamide (460 mg, 5.5 mmol, 1.5 equiv.) were dissolved in MeOH (10 mL). To this was added piperidine (214 mg, 0.7 equiv.) and the reaction was stirred at room temperature for 30 minutes at which point starting material was consumed. After addition of an equivalent volume of water (10 mL), the precipitate was collected by filtration and washed with water/methanol (1:1) to yield the title compound as a white solid (534 mg, 47%); $^1$H NMR (400 MHz, Acetone-$d_6$) δ 8.78 (s, 2H), 8.61 (s, 1H), 8.41 (s, 1H), 7.57 (s, 1H), 7.42 (s, 1H); HRMS-ESI (m/z) calculated for $C_{12}H_7F_6N_2O_2$[M+H]: 309.0457; found: 309.0459.

N-(3,5-bis(trifluoromethyl)phenyl)-2-bromopropanamide (24)

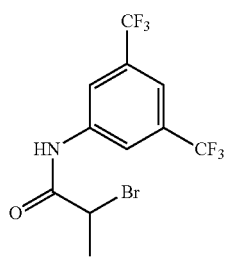 [SMILES: CC(Br)C(=O)Nc1cc(C(F)(F)F)cc(C(F)(F)F)c1]

Following General Procedure A1, starting with 3,5-bis(trifluoromethyl)aniline (250 mg, 1.1 mmol, 1 equiv.) and 2-bromopropionyl chloride (200 μL, 2 mmol, 1.8 equiv.) the title compound was obtained by PTLC as a white solid (130 mg, 35%). $^1$H NMR (500 MHz, Chloroform-d) δ 8.34 (s, 1H), 8.06 (s, 2H), 7.66 (s, 1H), 4.58 (q, J=7.0 Hz, 1H), 1.98 (d, J=7.0 Hz, 3H); HRMS-ESI (m/z) calculated for $C_{11}H_7BrF_6NO$ [M−H]: 361.9621; found: 361.9623.

N-(3,5-bis(trifluoromethyl)phenyl)-2-chloropropanamide (25)

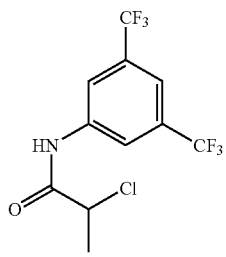 [SMILES: CC(Cl)C(=O)Nc1cc(C(F)(F)F)cc(C(F)(F)F)c1]

Following General Procedure A1, starting with 3,5-bis(trifluoromethyl)aniline (327 mg, 1.42 mmol, 1 equiv.) and 2-chloropropionyl chloride (200 μL, 2 mmol, 1.8 equiv.) the title compound was obtained by PTLC as a white solid (250 mg, 55%). $^1$H NMR (500 MHz, Chloroform-d) δ 8.61 (s, 1H), 8.16 (s, 2H), 7.75 (s, 1H), 4.67 (q, J=7.1 Hz, 1H), 1.93 (d, J=7.1 Hz, 3H); HRMS-ESI (m/z) calculated for $C_{11}H_7ClF_6NO$ [M−H]: 318.0126; found: 318.0126.

N-(3,5-bis(trifluoromethyl)phenyl)-N-(pyridin-3-ylmethyl)acrylamide (31)

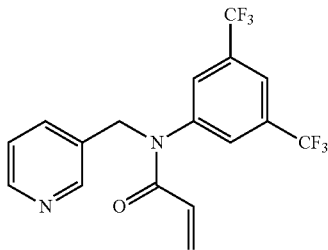 [SMILES: C=CC(=O)N(Cc1cccnc1)c1cc(C(F)(F)F)cc(C(F)(F)F)c1]

3,5-bis(trifluoromethyl)aniline (350 mg, 1.6 mmol, 1 equiv.) was dissolved in TFA (5 mL). The reaction mixture was cooled to 0° C. and to this sodium triacetoxyborohydride (STAB) (400 mg, 2 mmol, 1.3 equiv.) was added. 3-pyridinecarboxaldehyde (244 mg, 1.5 mmol, 1 equiv.) was dissolved in $CH_2Cl_2$ (5 mL) and slowly added to the reaction mixture dropwise over 10 minutes. Upon complete conversion to product, the reaction mixture was diluted with $CH_2Cl_2$ (20 mL) and washed with saturated sodium bicarbonate solution (3×20 mL) and the organic layer was dried then concentrated under reduced pressure. Without further purification the crude material was dissolved in anhydrous $CH_2Cl_2$ and subjected to General Procedure B. The resulting crude was purified by PTLC to give a white solid (10 mg, 2%). $^1$H NMR (500 MHz, Chloroform-d) δ 8.63 (d, J=3.8 Hz, 1H), 8.49 (s, 1H), 7.93 (s, 1H), 7.70 (d, J=7.7 Hz, 1H), 7.55 (s, 2H), 7.35 (dd, J=7.6, 5.3 Hz, 1H), 6.60 (dd, J=16.6, 1.6 Hz, 1H), 6.02 (dd, J=16.9, 10.2 Hz, 1H), 5.79 (dd, J=10.3, 1.6 Hz, 1H), 5.11 (s, 2H). HRMS-ESI (m/z) calculated for $C_{17}H_{13}F_6N_2O$ [M+H]: 375.0927; found: 375.0928.

3-(2-chloroacetamido)-5-(trifluoromethyl)benzoic acid (36)

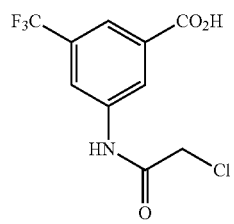 [SMILES: O=C(CCl)Nc1cc(C(=O)O)cc(C(F)(F)F)c1]

To a solution of 3-amino-5-(trifluoromethyl)benzoic acid (500 mg, 2.44 mmol) in 1.5 mL of dimethylacetamide (1.6 M) at 0° C. was added chloroacetyl chloride (214 μL, 2.69 mmol, 1.1 equiv.). The resulting solution was warmed to ambient temperature and stirred for 20 minutes, at which point ethyl acetate (40 mL) and water (30 mL) were added. The pH of the aqueous layer was adjusted to pH 10 via addition of 1 N NaOH, and the phases were separated. The aqueous layer was washed with 40 mL of ethyl acetate, then acidified by adding 1 N HCl. The product was extracted with ethyl acetate (40 mL), and the organic layer was washed with 1M HCl (2×40 mL), brine (40 mL), dried over magnesium sulfate and concentrated to provide the desired product (456 mg, 66%). $^1$H NMR (500 MHz, Chloroform-d) δ 8.31 (s, 1H), 8.27 (s, 1H), 8.14 (s, 1H), 4.13 (s, 2H); HRMS-ESI (m/z) calculated for $C_{10}H_8ClF_3NO_3$ [M+H]: 282.0139; found: 282.0141.

1-(4-(5-fluorobenzisoxazol-3-yl)piperidin-1-yl)prop-2-en-1-one (37)

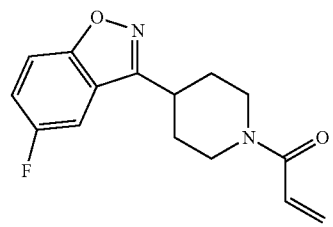 [SMILES: C=CC(=O)N1CCC(c2noc3ccc(F)cc23)CC1]

The title compound was obtained starting from 6-fluoro-3(4-piperidinyl)-1,2-benzisoxazole hydrochloride (53 mg, 0.2 mmol, 1 equiv.) according to General Procedure C as a colorless oil (49.1 mg, 87%). $^1$H NMR (400 MHz, Chloroform-d) δ 7.64 (dd, J=8.7, 5.1 Hz, 1H), 7.27 (dd, J=8.4, 2.3 Hz, 1H), 7.08 (td, J=8.9, 2.1 Hz, 1H), 6.64 (dd, J=16.8, 10.6 Hz, 1H), 6.32 (dd, J=16.9, 1.9 Hz, 1H), 5.73 (dd, J=10.6, 1.9 Hz, 1H), 4.70 (d, J=13.4 Hz, 1H), 4.15 (d, J=12.4 Hz, 1H), 3.53-3.13 (m, 2H), 2.99 (t, J=13.1 Hz, 1H), 2.25-2.07 (m, 2H), 2.00 (ddd, J=23.1, 14.2, 7.8 Hz, 2H); HRMS-ESI (m/z) calculated for $C_{15}H_{16}FN_2O$ [M+H]: 275.119; found: 275.119.

tert-butyl 4-(4-acrylamido-2,6-difluorophenyl)piperazine-1-carboxylate (38)

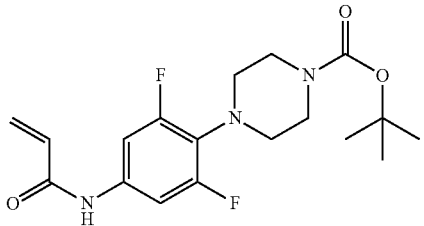 [SMILES: C=CC(=O)Nc1cc(F)c(N2CCN(C(=O)OC(C)(C)C)CC2)c(F)c1]

The title compound was obtained starting from tert-Butyl 4-(4-amino-2,6-difluorophenyl)piperazine-1-carboxylate according to General Procedure B. $^1$H NMR (400 MHz, Chloroform-d) δ 8.12 (s, 1H), 7.13 (d, J=10.4 Hz, 2H), 6.36 (d, J=16.9 Hz, 1H), 6.19 (dd, J=16.8, 10.2 Hz, 1H), 5.70 (d, J=10.2 Hz, 1H), 3.45 (t, J=4.7 Hz, 4H), 3.00 (t, J=3.7 Hz, 4H), 1.41 (s, 9H); HRMS-ESI (m/z) calculated for $C_{18}H_{24}F2N_3O_3$[M+H]: 368.178; found: 368.178.

N-(4-bromo-2,5-dimethylphenyl)acrylamide (40)

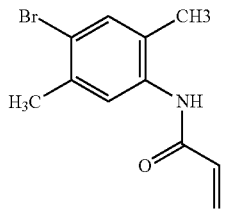

Following General Procedure B, starting from 4-bromo-2,5-dimethylaniline (900 mg, 4.5 mmol, 1 equiv.), the title compound was obtained after column chromatography and recrystallization from cold $CH_2Cl_2$ as a white solid (611 mg, 40%). $^1$H NMR (500 MHz, Chloroform-d) δ 7.87 (s, 1H), 7.43 (s, 1H), 7.16 (s, 1H), 6.50 (d, J=16.7 Hz, 1H), 6.35 (dd, J=16.4, 10.3 Hz, 1H), 5.86 (d, J=10.3 Hz, 1H), 2.42 (s, 3H), 2.28 (s, 3H); HRMS-ESI (m/z) calculated for $C_{11}H_{13}$BrNO [M+H]: 254.0175; found: 254.0175.

2-Chloroacetamido-2-deoxy-α/β-D-glucopyranose (44)

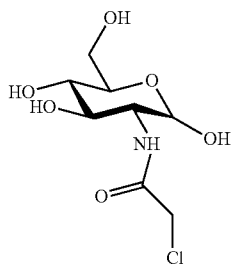

To a stirred solution of hexosamine hydrochloride (590 mg, 3.39 mmol, 1 equiv.) in anhydrous MeOH (200 mL) at room temperature was added sodium metal (60 mg, 2.6 mmol, 0.78 equiv.), TEA (400 μL, 5.7 mmol, 1.8 equiv.). Chloroacetic anhydride (1 g, 5.9 mmol, 1 equiv.) was then added and the mixture stirred for 6 h, monitoring for completeness by TLC. After which, the reaction mixture was concentrated in vacuo. The crude product then was purified by two rounds of column chromatography to afford the pure title product as a white solid (610 mg, 72%). $^1$H NMR (500 MHz, Methanol-$d_4$) 5.20 (d, J=3.7 Hz, 1Hα), 4.75 (d, J=8.3 Hz, 1Hβ), 4.19 (dd, J=20.2, 13.9 Hz, 2H), 4.19 (d, J=12.6 Hz, 1H), 3.95 (dd, J=10.6, 3.5 Hz, 1Hα), 3.83 (m, 3Hα, 3Hβ), 3.74 (d, J=5.1 Hz, 1Hβ), 3.70 (dd, J=11.4, 8.9 Hz, 1Hβ), 3.60 (dd, J=10.7, 9.5 Hz, 1Hβ), 3.46 (t, J=9.3 Hz, 1H), 3.42 (t, J=10.0 Hz, 1Hβ); HRMS-ESI (m/z) calculated for $C_8H_{15}$ClNO$_6$ [M+H]: 256.0582; found: 256.0582.

2-chloro-1-(2-methyl-3,4-dihydroquinolin-1(2H)-yl)ethan-1-one (45)

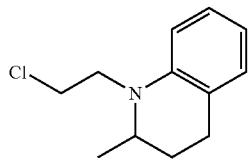

Chloroacetyl chloride (80.4 μL, 0.9 mmol, 1.7 equiv.) was dissolved in anhydrous $CH_2Cl_2$ (3 mL) and cooled to 0° C. A solution of 2-methyl-1,2,3,4-tetrahydroquinoline (80.1 mg, 0.544 mmol, 1 equiv.) and N-methylmorpholine (0.11 mL, 1.0 mmol, 1.8 equiv.) in $CH_2Cl_2$ (2 mL) was then added dropwise. After 6 h, the reaction was quenched with saturated aqueous NaHCO$_3$ (5 mL) and extracted with $CH_2Cl_2$ (3×10 mL). The combined organic layers were dried over anhydrous Na$_2$SO$_4$ and concentrated under reduced pressure. The resultant residue was purified by prep. TLC (30% EtOAc/hexanes), providing the title compound as an off-white solid (108.8 mg, 89%). $^1$H NMR (400 MHz, chloroform-d) δ 7.30-7.13 (m, 4H), 4.86-4.75 (m, 1H), 4.20 (d, J=12.5 Hz, 1H), 4.09 (d, J=12.5 Hz, 1H), 2.69-2.58 (m, 1H), 2.59-2.46 (m, 1H), 2.46-2.31 (m, 1H), 1.36-1.29 (m, 1H), 1.15 (d, J=6.5 Hz, 3H); HRMS-ESI (m/z) calculated for $C_{12}H_{15}$ClNO [M+H]: 224.0837; found: 224.0836.

N-cyclohexyl-N-phenylacrylamide (46)

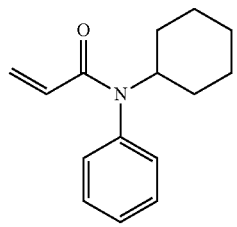 [SMILES: C=CC(=O)N(c1ccccc1)C1CCCCC1]

The title compound was synthesized according to General Procedure C from N-cyclohexylaniline (89.5 mg, 0.511 mmol, 1 equiv.). Purification of the crude product by flash column chromatography (10-20% EtOAc/hexanes) then prep. TLC (30% EtOAc/hexanes) provided the title compound as an off-white solid (53.1 mg, 45%). $^1$H NMR (400 MHz, chloroform-d) δ 7.42-7.33 (m, 3H), 7.10-7.06 (m, 2H), 6.31 (dd, J=16.7, 2.1 Hz, 1H), 5.77 (dd, J=16.7, 10.3

Hz, 1H), 5.41 (dd, J=10.4, 2.1 Hz, 1H), 4.65 (tt, J=12.2, 3.7 Hz, 1H), 1.85 (dt, J=11.2, 1.8 Hz, 2H), 1.75-1.68 (m, 2H), 1.61-1.53 (m, 1H), 1.40 (qt, J=13.3, 3.6 Hz, 2H), 1.07 (qd, J=12.4, 3.6 Hz, 2H), 0.91 (qt, J=13.1, 3.8 Hz, 1H); HRMS-ESI (m/z) calculated for $C_{15}H_{20}NO$ [M+H]: 230.1539; found: 230.1539.

1-(5-bromoindolin-1-yl)prop-2-en-1-one (47)

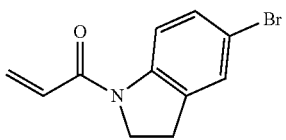

The title compound was synthesized according to General Procedure C from 5-bromoindoline (41.7 mg, 0.211 mmol, 1 equiv.), acryloyl chloride (32 μL, 0.40 mmol, 1.9 equiv.), and changing the base to pyridine (32 μL, 0.40 mmol, 1.9 equiv.). Purification of the crude product by re-precipitation from EtOAc provided the title compound as a white solid (67.8 mg, 64%). $^1$H NMR (400 MHz, chloroform-d) δ 8.16 (d, J=8.6 Hz, 1H), 7.33-7.25 (m, 2H), 6.60-6.42 (m, 2H), 5.84-5.76 (m, 1H), 4.15 (t, J=8.6 Hz, 2H), 3.17 (t, J=8.6 Hz, 2H); HRMS-ESI (m/z) calculated for $C_{11}H_{11}BrNO$ [M+H]: 252.0018; found: 252.0017.

N-(1-benzylpiperidin-4-yl)-N-phenylacrylamide (48)

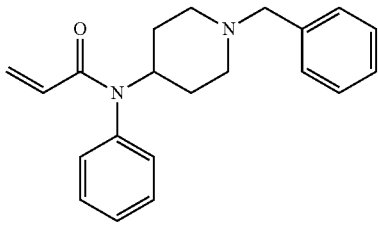 [SMILES: C=CC(=O)N(c1ccccc1)C1CCN(Cc2ccccc2)CC1]

The title compound was synthesized according to General Procedure C from 1-benzyl-N-phenylpiperidin-4-amine (30.0 mg, 0.113 mmol, 1 equiv.), acryloyl chloride (17 μL, 0.21 mmol, 1.9 equiv.), and changing the base to pyridine (17 μL, 0.21 mmol, 1.9 equiv.). Purification of the crude product by prep. TLC provided the title compound as a white solid (22.5 mg, 64%). $^1$H NMR (400 MHz, chloroform-d) δ 7.62-7.56 (m, 2H), 7.43-7.36 (m, 6H), 7.05 (d, J=6.2 Hz, 2H), 6.29 (dd, J=16.8, 2.1 Hz, 1H), 5.79 (dd, J=16.8, 10.3 Hz, 1H), 5.46 (dd, J=10.3, 2.1 Hz, 1H), 4.81-4.70 (m, 1H), 4.09 (s, 2H), 3.41 (d, J=12.0 Hz, 2H), 2.82 (q, J=11.5 Hz, 2H), 2.21 (q, J=11.9 Hz, 2H), 1.94 (d, J=14.2 Hz, 2H); HRMS-ESI (m/z) calculated for $C_{21}H_{25}N_2O$ [M+H]: 321.1961; found: 321.1962.

2-chloro-N-(2-methyl-5-(trifluoromethyl)phenyl) acetamide (49)

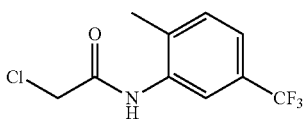 [SMILES: Cc1ccc(C(F)(F)F)cc1NC(=O)CCl]

The title compound was synthesized according to General Procedure A1 from 2-methyl-5-(trifluoromethyl)aniline (35.0 mg, 0.2 mmol, 1 equiv.). Purification of the crude product by prep. TLC (20% EtOAc/hexanes) provided the title compound as a white solid (48.2 mg, 95%). $^1$H NMR (600 MHz, chloroform-d) δ 8.31 (s, 1H), 8.25 (d, J=1.9 Hz, 1H), 7.37 (dd, J=7.9, 1.8 Hz, 1H), 7.32 (d, J=7.9 Hz, 1H), 4.25 (s, 2H), 2.36 (s, 3H); HRMS-ESI calculated for $C_{10}H_{10}ClF_3NO$ [M+H]: 252.0397; found: 252.0397.

1-(5-bromoindolin-1-yl)-2-chloroethan-1-one (50)

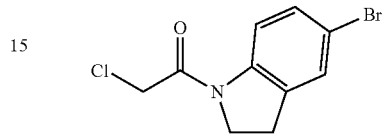

The title compound was synthesized according to General Procedure A1 from 5-bromoindoline (39.6 mg, 0.2 mmol, 1 equiv.). Purification of the crude product by prep. TLC (25% EtOAc/hexanes) provided the title compound as an off-white solid (48.6 mg, 89%). $^1$H NMR (600 MHz, CDCl$_3$) δ 8.07 (d, J=8.4 Hz, 1H), 7.32 (d, J=8.8 Hz, 2H), 4.17 (t, J=8.6 Hz, 2H), 4.14 (s, 2H), 3.22 (t, J=8.4 Hz, 2H); HRMS-ESI (m/z) calculated for $C_{10}H_{10}BrClNO$ [M+H]: 273.9629; found: 273.9629.

2-chloro-N-(quinolin-5-yl)acetamide (51)

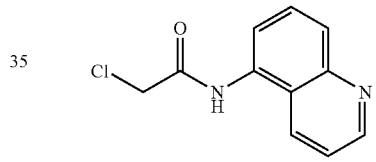

To a stirring suspension of 5-aminoquinoline (28.8 mg, 0.2 mmol, 1 equiv.) and potassium carbonate (82.9 mg, 0.6 mmol, 3 equiv.) in anhydrous CH$_2$Cl$_2$ (3 mL) at 0° C. was added chloroacetyl chloride (24 μL, 1.5 equiv.). The reaction was allowed to slowly warm up to room temperature. After 3 hours, the mixture was filtered, washed with EtOAc (10 mL) and CH$_2$Cl$_2$ (10 mL). The solid cake was then eluted with MeOH (20 mL) and the filtrate concentrated in vacuo. The residue was taken up in 10% MeOH/CH$_2$Cl$_2$ and passed through a pad of silica to provide the title compound as an off-white solid (42.6 mg, 82%). $^1$H NMR (500 MHz, CDCl$_3$) δ 8.96 (d, J=2.5 Hz, 1H), 8.71 (s, 1H), 8.20 (d, J=8.6 Hz, 1H), 8.04 (d, J=8.5 Hz, 1H), 7.94 (d, J=7.5 Hz, 1H), 7.74 (t, J=8.0 Hz, 1H), 7.48 (dd, J=8.5, 4.2 Hz, 1H), 4.35 (s, 2H); HRMS-ESI (m/z) calculated for $C_{11}H_9ClN_2O$ [M+H]: 221.0476; found: 221.0477.

1-(4-benzylpiperidin-1-yl)prop-2-en-1-one (53)

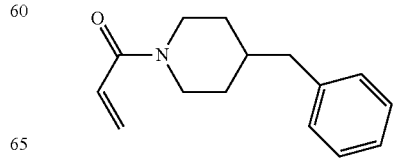

Following General Procedure B, starting from 4-benzylpiperidine (1 g, 5.7 mmol, 1 equiv.), the title compound was obtained after column chromatography as a yellow oil (748 mg, 57%). $^1$H NMR (500 MHz, Chloroform-d) δ 7.36 (t, J=7.4 Hz, 2H), 7.28 (t, J=7.4 Hz, 1H), 7.20 (d, J=7.1 Hz, 2H), 6.64 (dd, J=16.8, 10.6 Hz, 1H), 6.32 (dd, J=16.8, 1.9 Hz, 1H), 5.72 (dd, J=10.6, 1.9 Hz, 1H), 4.72 (d, J=12.7 Hz, 1H), 4.03 (d, J=13.0 Hz, 1H), 3.05 (t, J=12.7 Hz, 1H), 2.70-2.59 (m, 3H), 1.86 (ddp, J=14.6, 7.2, 3.5 Hz, 1H), 1.77 (m, 2H), 1.37-1.18 (m, 2H); HRMS-ESI (m/z) calculated for $C_{15}H_{20}ClNO$ [M+H]: 230.1539; found: 230.1539.

2-chloro-N-((3-hydroxy-5-(hydroxymethyl)-2-methylpyridin-4-yl)methyl)acetamide (54)

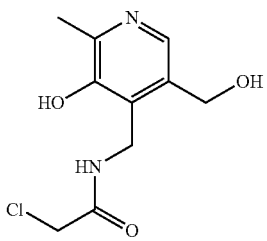 [SMILES: Cc1ncc(CO)c(CNC(=O)CCl)c1O]

To a stirred solution of pyridoxamine hydrochloride (150 mg, 0.64 mmol, 1 equiv.) in anhydrous MeOH (20 mL) at room temperature was added sodium metal (30 mg, 1.5 mmol, 2.3 equiv.), TEA (100 μL, 1 mmol, 1.6 equiv.). Chloroacetic anhydride (390 mg, 2.29 mmol, 3.5 equiv.) was added and the mixture stirred for 6 h, monitoring for completeness by TLC. After which, the reaction mixture was concentrated in vacuo. The crude product then was the purified by prep. TLC to afford the title compound as a white solid (46 mg, 30%). $^1$H NMR (500 MHz, Methanol-$d_4$) δ 7.97 (s, 1H), 4.81 (s, 2H), 4.61 (s, 2H), 4.17 (s, 3H), 4.06 (s, 1H), 3.35 (s, 1H), 2.52 (s, 3H); HRMS-ESI (m/z) calculated for $C_{10}H_{14}ClN_2O_3$[M+H]: 245.0687; found: 245.0688.

1-(6, 7-dimethoxy-3,4-dihydroisoquinolin-2(1H)-yl)prop-2-en-1-one (56)

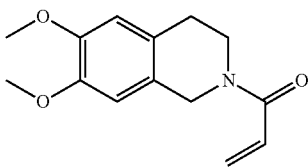 [SMILES: C=CC(=O)N1CCc2cc(OC)c(OC)cc2C1]

To a stirring suspension of the 6,7-dimethoxy-3,4-dihydroisoquinoline (1 g, 5.2 mmol, 1 equiv.) and TEA (1800 μL, 12.6 mmol, 2.5 equiv.) in anhydrous THF (10 mL) at 0° C. was added acryloyl chloride (1320 μL, 13.2 mmol, 2.6 equiv.) and the reaction was allowed to slowly warm up to room temperature. After 2 hours, the mixture was diluted with $CH_2Cl_2$ (2×50 mL) and washed with saturated brine (2×50 mL) and the combined organics were concentrated in vacuo. The residue was taken up in 10% MeOH/$CH_2Cl_2$ and purified by column chromatography to afford the title compound as a white solid (700 mg, 54%, mixture of E/Z isomers). $^1$H NMR (500 MHz, Chloroform-d) δ 6.63 (m, 3H), 6.29 (d, J=16.8 Hz, 1H), 5.69 (dd, J=10.6, 1.8 Hz, 1H), 4.69 (s, 1H [major]), 4.63 (s, 0.8H [minor]), 3.82 (s, 7H), 3.73 (t, J=5.6 Hz, 1H), 2.84-2.77 (m, 2H); HRMS-ESI (m/z) calculated for $C_{14}H_{18}NO_3$ [M+H]: 248.128; found: 248.1281.

2-chloro-N-(1-(3-ethynylbenzoyl)piperidin-4-yl)-N-phenylacetamide (61)

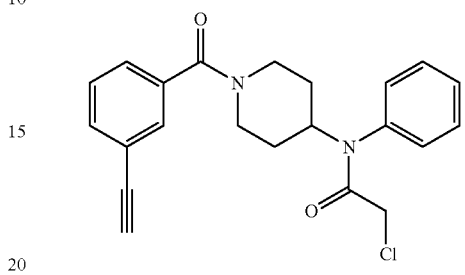

To an excess of neat SI-3 was added 0.7 mL of trifluoroacetic acid (0.2 M). The resulting solution was concentrated under a stream of nitrogen until no further evaporation was observed, providing the deprotected amine as its trifluoroacetate salt. The triflouroacetate amine salt (90.6 mg, 0.25 mmol) was taken up in DMF (0.5 mL, 0.5 M) and the resulting solution was cooled to 0° C. 3-ethynyl benzoic acid (44 mg, 1.2 equiv.), HATU (113 mg, 1.2 equiv.), and Hunig's base (86 μL, 2 equiv.) were sequentially added. The reaction was stirred for 2 hours at 0° C., diluted with $Et_2O$, and then washed with 1 M HCl. The organic layer was dried over magnesium sulfate, concentrated, and purified by flash chromatography (gradient from 40 to 70% ethyl acetate in hexanes) to provide the title compound (87 mg, 92%). $^1$H NMR (400 MHz, Chloroform-d) δ 7.51 (dd, J=9.5, 5.4 Hz, 4H), 7.43 (d, J=1.9 Hz, 1H), 7.39-7.25 (m, 2H), 7.14 (d, J=10.4 Hz, 2H), 4.86 (tt, J=15.1, 5.3 Hz, 2H), 3.72 (s, 3H), 3.19 (d, J=14.0 Hz, 1H), 3.11 (s, 1H), 2.86 (s, 1H), 1.90 (d, J=36.6 Hz, 2H), 1.38 (s, 1H), 1.24 (d, J=19.9 Hz, 1H); HRMS-ESI (m/z) calculated for $C_{22}H_{22}ClN_2O_2$[M+H]: 381.1364; found: 381.1363.

Global Profiling of Cysteine-Reactive Fragments in Native Populations

Cysteine is unique among protein-coding amino acids owing to its high nucleophilicity and sensitivity to oxidative modification. Cysteine residues perform catalytic functions in diverse enzyme classes and represent sites for post-translational regulation of proteins through disulfide bonding, iron-sulfur cluster formation, conversion to sulfinic and sulfonic acid, nitrosylation, S-glutathionylation and lipid modification. Using a quantitative chemical proteomic method termed isoTOP-ABPP (isotopic Tandem Orthogonal Proteolysis-Activity-Based Protein Profiling), global measurements of the intrinsic reactivity of cysteine residues was carried out and their sensitivity to modification by lipid-derived electrophiles was assessed. In order to determine whether isoTOP-ABPP was adapted to perform covalent FBLD in native biological systems, a cell preparation (lysate or intact cells) was pre-treated with DMSO or one member of a library of electrophilic small-molecule fragments and then exposed to a broad-spectrum cysteine-reactive probe iodoacetamide (IA)-alkyne 1 (FIG. 1A). Proteins harboring IA-alkyne-labeled cysteine residues from DMSO- and fragment-treated samples were conjugated by copper-mediated azide-alkyne cycloaddition (CuAAC or click) chemistry to isotopically differentiated azide-biotin tags (heavy and light, respectively), combined, enriched by streptavidin, and proteolytically digested on-bead to yield isotopic peptide pairs that were analyzed by LC-MS. Quantification of MS1 chromatographic peak ratios for peptide pairs identified fragment-competed Cys residues as those displaying high competition ratios, or R values, in DMSO/fragment comparisons.

A 50+ member fragment library was constructed with most compounds containing either a chloroacetamide or acrylamide electrophile (FIG. 1B and FIG. 3), which are well-characterized cysteine-reactive groups found in many chemical probes and some clinically approved drugs. These electrophiles were appended to structurally diverse small-molecule fragments (<300 Da) intended to serve as recognition elements that promote interactions with different subsets of the human proteome. The library also contained some additional electrophiles, such as cyanoacrylamides and vinylsulfonamides, and known bioactive electrophilic compounds (e.g., the anti-cancer agent piperlongumine and anti-migratory agent locostatin) (FIG. 1B, and FIG. 3). The electrophile library was screened at a high concentration (500 μM) comparable to the ligand concentrations used in typical FBLD experiments. A subset of the fragment library was initially assayed by competitive profiling in a human MDA-MB-231 breast cancer cell line proteome using an IA-rhodamine probe 16, which permitted facile SDS-PAGE detection of cysteine reactivity events. This experiment identified several proteins that showed reductions in IA-rhodamine labeling in the presence of one or more fragments (FIG. 1C, asterisks). Interestingly, the proteins exhibited distinct SARs across the test fragment set, indicating that the library recognition elements exert a strong influence over specific fragment-protein reactivity events.

Figure 4:
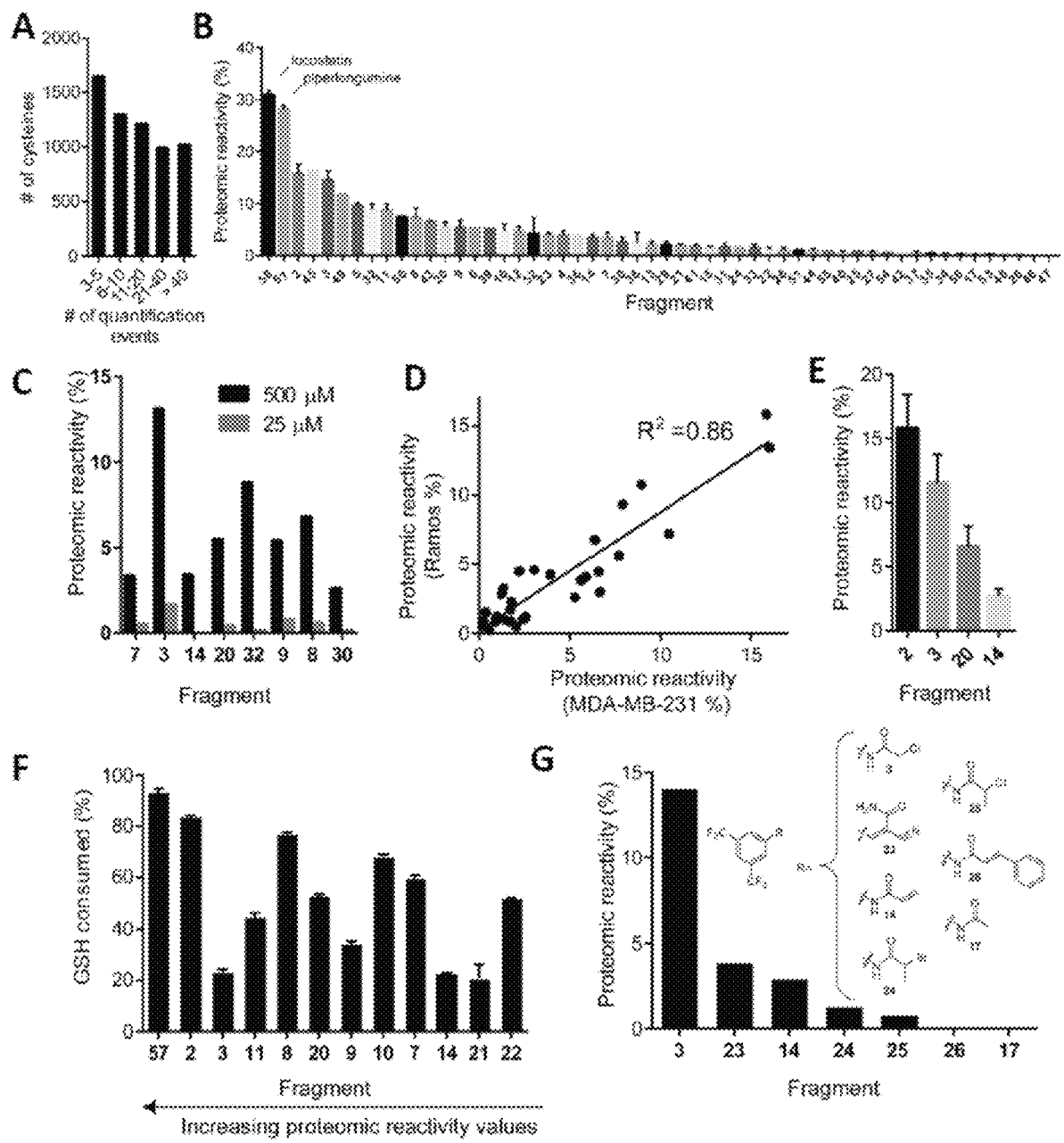
FIG. 4 illustrates analysis of proteomic reactivities of fragment electrophiles determined by competitive isoTOP-ABPP in human cell lysates. A, Frequency of quantification of all cysteines across the complete set of competitive isoTOP-ABPP experiments performed with fragment electrophiles. Note that cysteines were required to have been quantified in at least three isoTOP-ABPP data sets for interpretation. B, Rank order of proteomic reactivity values (or liganded cysteine rates) of fragments calculated as the percentage of all quantified cysteines with R values ≥4 for each fragment. The majority of fragments were evaluated in 2-4 replicate experiments in MDA-MB-231 and/or Ramos cell lysates, and their proteomic reactivity values are reported as mean±SEM values for the replicates. C, Comparison of the proteomic reactivities of representative fragments screened at 500 versus 25 µM in cell lysates. D, Comparison of proteomic reactivity values for fragments tested in both Ramos and MDA-MB-231 lysates. E, Mean±SEM data for proteomic reactivity values of representative fragments tested in at least three independent replicates. F, Relative GSH reactivity for representative fragment electrophiles. Consumption of GSH (125 µM) was measured using Ellman's reagent (5 mM) after 1 h incubation with the indicated fragments (500 µM). G, Proteomic reactivity values for fragments electrophiles (500 µM) possessing different electrophilic groups attached to a common binding element.

Competitive isoTOP-ABPP was used to globally map human proteins and the cysteine residues within these proteins that were targeted by fragment electrophiles. Each fragment was tested, in general, against two distinct human cancer cell proteomes (MDA-MB-231 and Ramos cells) and most fragments were screened in duplicate against at least one of these proteomes. On average, 927 cysteines were quantified per data set, and it was required that individual cysteines were quantified in at least three data sets for interpretation. Based on these criteria, more than 6157 cysteines from 2885 proteins were quantified in aggregate across all data sets with an average quantification frequency of 22 data sets per cysteine (FIG. 4A). Fragment-competed cysteine residues, or "liganded" cysteines, were defined as those showing ≥75% reductions in IA-alkyne labeling (R values≥4 for DMSO/fragment). To minimize the potential for false-positives, only cysteines that showed R values≥4 in two or more data sets and met additional criteria for data quality control were considered as targets of the fragment electrophiles. The proteomic reactivity values, or liganded cysteine rates, of individual fragments were then calculated as the percentage of liganded/total quantified cysteines in isoTOP-ABPP experiments performed on that fragment.

Most fragment electrophiles showed a tempered reactivity across the human proteome, with a median liganded cysteine rate of 3.8% for the library (FIG. 4B). Substantial differences in reactivity were, however, observed, with individual electrophiles showing liganded cysteine rates of <0.1% and others displaying rates >15% (FIG. 4B). That piperlongumine and locostatin fell into the latter category indicated the intrinsic proteomic reactivity of the fragment electrophiles did not, in general, exceed that of previously described electrophilic probes. A subset of fragments was also screened at lower concentrations (25-50 μM), which confirmed that their proteomic reactivities were concentration-dependent (FIG. 4C). The relative reactivity of fragment electrophiles was similar in MDA-MB-231 and Ramos cell proteomes (FIG. 4D), indicating that this parameter is an intrinsic property of the compounds. Fragments also showed consistent reactivity profiles when assayed in biological replicate experiments (FIG. 4E). Interestingly, it was found that the proteomic reactivity of fragment electrophiles was only marginally correlated with their glutathione adduction potential, which is a commonly used surrogate assay for measurements of proteinacious cysteine reactivity (FIG. 4F). These differences are attributed to the impact of the recognition element of fragment electrophiles on their interactions and, ultimately, reactivity with proteins.

A comparison of fragments 3, 14, 17, and 23-26 provided insights into the relative proteomic reactivity of different electrophilic groups coupled to a common recognition element (3,5-di(trifluoromethyl)phenyl group). Chloroacetamide 3 exhibited greater reactivity than acrylamide 14 (15% versus 3.4% liganded cysteines, respectively; FIG. 1D), with cyanoacrylamide 23 exhibiting similar reactivity to acrylamide 14 and other, more sterically congested electrophiles (24-26) showing reduced proteomic reactivity (FIG. 4G). Importantly, the non-electrophilic acetamide control fragment 17 showed negligible activity in competitive isoTOP-ABPP experiments (liganded cysteine rate <0.2%) (FIG. 1D), indicating that the vast majority of detected fragment-cysteine interactions reflected covalent reactions versus non-covalent binding events. Also in support of this conclusion, "clickable" alkyne analogues of 3 and 14 (compounds 19 and 18, respectively) exhibited different concentration-dependent proteome labeling profiles (19>18; FIG. 1E) that mirrored the respective liganded cysteine rates displayed by 3 and 14 in competitive isoTOP-ABPP experiments (3>14; FIG. 1D). Despite the greater overall proteomic reactivity of chloroacetamide 3 relative to acrylamide 14 and cyanoacrylamide 23, clear examples of cysteines were found that were preferentially liganded by the latter fragments (FIG. 1F).

In some instances, these findings demonstrate that the isoTOP-ABPP platform is one method for use to competitively profile fragment electrophiles against thousands of cysteine residues in native proteomes.

Cysteines Targeted by Fragment Electrophiles in Native Proteomes

Figure 5:
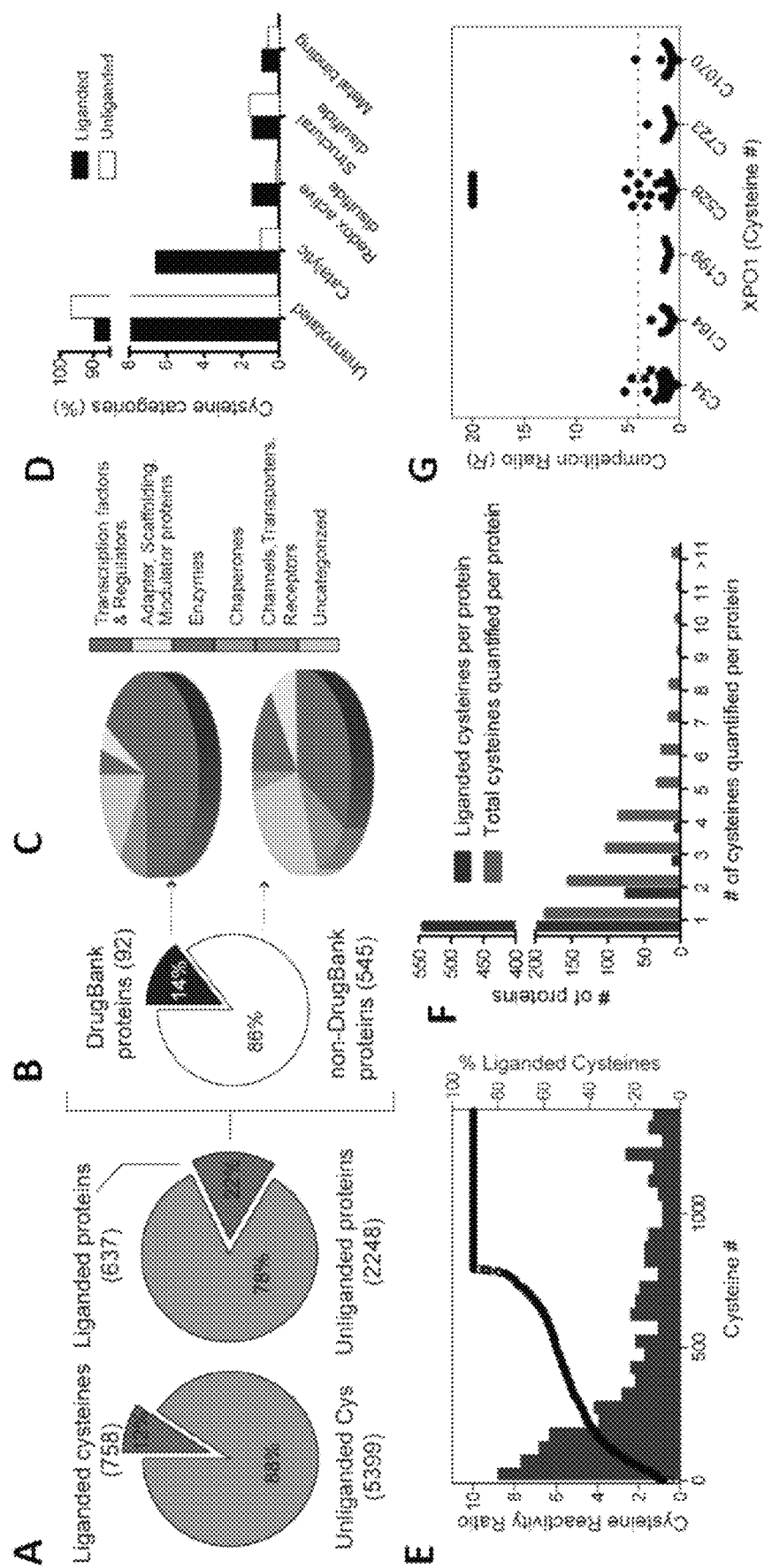
FIG. 5 illustrates analysis of cysteines and proteins liganded by fragment electrophiles. A, Fraction of total quantified cysteines and proteins that were liganded by fragment electrophiles in competitive isoTOP-ABPP experiments. B, Fraction of liganded proteins found in DrugBank. C, Functional classes of DrugBank and non-DrugBank proteins containing liganded cysteines. D, Functional categorization of liganded and unliganded cysteines based on residue annotations from the Uniprot database. E, Comparison of the ligandability of cysteines as a function of their intrinsic reactivity with the IA-alkyne probe. Cysteine reactivity values were taken from Weerapana, et al. *Nature* 468, 790-795 (2010), where lower ratios correspond to higher cysteine reactivity. Individual cysteines are plotted on the x-axis and were sorted by reactivity, which is shown on the left y-axis. A moving average with a step-size of 50 is shown in blue for the percentage of liganded cysteines within each reactivity bin (percent values shown on the right y-axis). F, Number of liganded and quantified cysteines per protein measured by isoTOP-ABPP. Respective average values of one and three for liganded and quantified cysteines per protein were measured by isoTOP-ABPP. G, R values for six cysteines in XPO1 quantified by isoTOP-ABPP, identifying C528 as the most liganded cysteine in this protein. Each point represents a distinct fragment-cysteine interaction quantified by isoTOP-ABPP.
Figure 7:
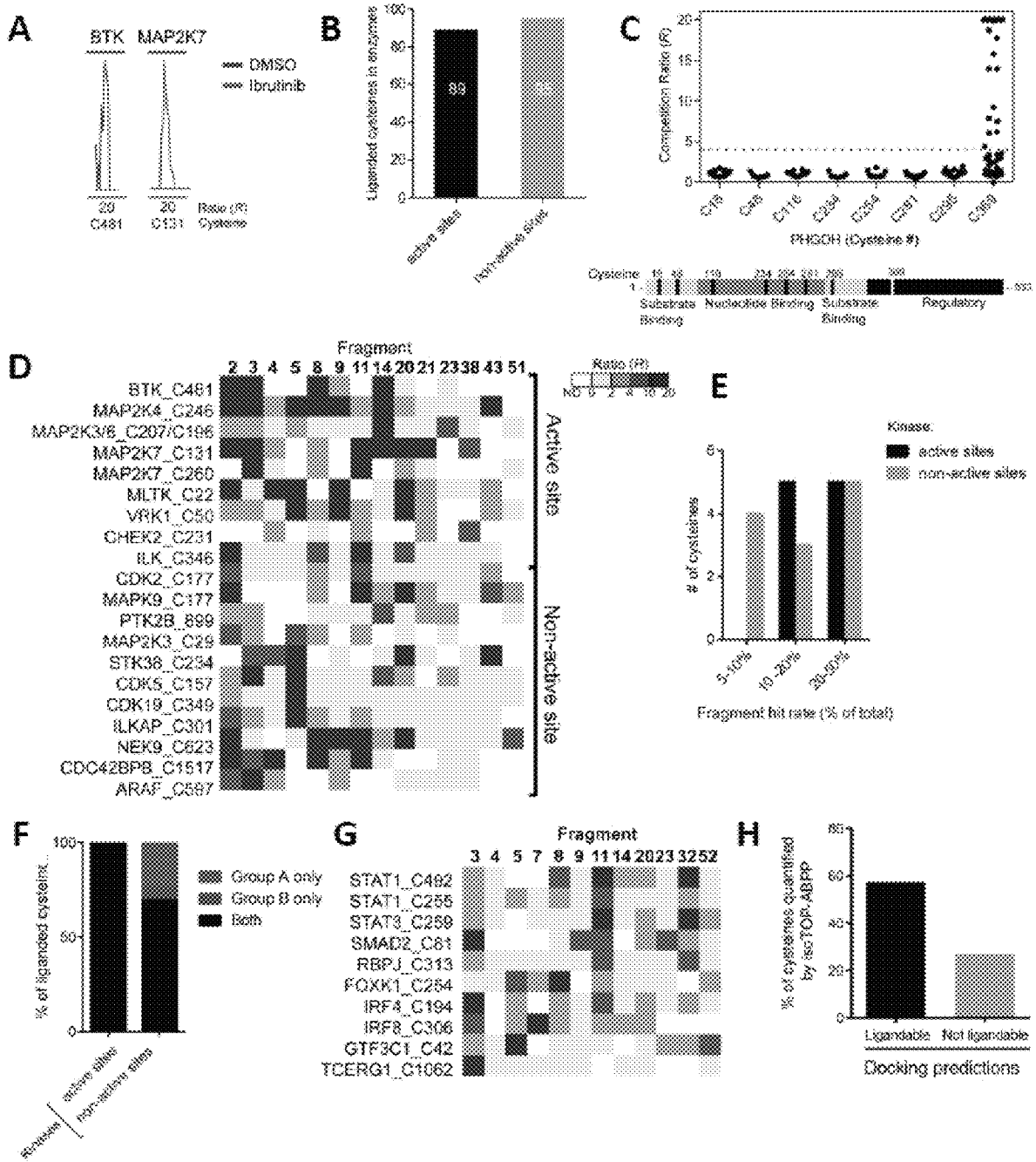
FIG. 7 illustrates analysis of cysteines liganded by fragment electrophiles in competitive isoTOP-ABPP experiments. A, Representative MS1 ion chromatograms for peptides containing C481 of BTK and C131 of MAP2K7, two cysteines known to be targeted by the anti-cancer drug ibrutinib. Ramos cells were treated with ibrutinib (1 µM, 1 h, red trace) or DMSO (blue trace) and evaluated by isoTOP-ABPP. B, Total number of liganded cysteines found in the active sites and non-active sites of enzymes for which X-ray and/or NMR structures have been reported (or reported for a close homologue of the enzyme). C, R values for eight cysteines in PHGDH quantified by isoTOP-ABPP, identifying a single liganded cysteine C369 that is targeted by several fragment electrophiles. Each point represents a distinct fragment-cysteine interaction quantified by isoTOP-ABPP. D, Heatmap showing representative fragment interactions for liganded cysteines found in the active sites and non-active sites of kinases. E, Histogram showing the fragment hit rate for active- and non-active site cysteines in kinases. F, The percentage of liganded cysteines in kinases that were targeted by only group A, only group B, or both group A and B compounds. G, Heatmap showing representative fragment interactions for liganded cysteines found in transcription factors/regulators. H, The fraction of cysteines predicted to be ligandable or not ligandable by reactive docking that were quantified in isoTOP-ABPP experiments.

Across all isoTOP-ABPP data sets combined, 758 liganded cysteines were identified on 637 distinct proteins, which corresponded to ~12 and 22% of the total quantified cysteines and proteins, respectively (FIG. 5A and Tables 1-3). Only a modest fraction of the proteins harboring liganded cysteines were found in the DrugBank database (15%; FIG. 5B), indicating the fragment electrophiles targeted many proteins that lack small-molecule probes. Among protein targets with known covalent ligands, the fragment electrophiles frequently targeted the same cysteine residues as these known ligands (Table 4); examples include the protein kinase BTK, in which electrophilic fragments targeted an active-site cysteine that also reacts with the cancer drug ibrutinib, and XPO1 and ERCC3, in which electrophilic fragments targeted conserved cysteines that are modified by bioactive natural products and candidate anti-cancer agents. In the case of BTK, it was confirmed that the interaction of ibrutinib with this kinase was detected by isoTOP-ABPP, which also identified a known ibrutinib off-target—MAP2K7—in Ramos cell lysates (FIG. 7A).

DrugBank proteins with liganded cysteines mostly originated from classes that are regarded as "druggable", including enzymes, channels, and transporters (FIG. 5C). Non-DrugBank proteins with liganded cysteines, on the other hand, showed a broader class distribution that included proteins, such as transcription factors and adaptor/scaffolding proteins, that are considered challenging to target with small-molecule ligands (FIG. 5C). Even among the enzymes targeted by fragment electrophiles, many examples were noted where the liganded cysteine was a non-active site residue (FIG. 7B). These data indicated that the cysteines modified by fragment electrophiles were not restricted to classical ligand-binding pockets on proteins. Also consistent with this premise, only ~6% of all of the liganded cysteines were functionally annotated as active-site residues (FIG. 5D). Active-site cysteines, as well as redox-active cysteines, were still, however, substantially enriched among the liganded cysteine group compared to unliganded cysteines quantified by isoTOP-ABPP (FIG. 5D). It had been previously found that active-site and redox-active cysteines also show, in general, greater intrinsic reactivity (as measured with the IA-alkyne probe) compared to other cysteines. While this heightened reactivity is a likely contributory factor to the ligandability of cysteines, as reflected in the high proportion of hyperreactive cysteines that were detected as targets of fragment electrophiles (FIG. 5E), liganded cysteines were also well-represented across a broad range of intrinsic reactivities (FIG. 5E). Finally, most proteins were found to harbor a single liganded cysteine among the several cysteines that were, on average, quantified per protein by isoTOP-ABPP (FIG. 5F). The nuclear export factor XPO1 and metabolic enzyme PHGDH provide compelling examples of the selectivity displayed by fragment electrophiles for individual cysteines within proteins (FIG. 5G and FIG. 7C). Among the six different XPO1 cysteine residues quantified by isoTOP-ABPP, a single cysteine, C528, was frequently targeted by fragment electrophiles (FIG. 5G), and this residue is also modified by electrophilic drugs in clinical development for cancer[40]. Similarly, among eight quantified cysteines in PHGDH, only C369, a non-active site residue, was targeted by electrophilic fragments (FIG. 7C).

Figure 6:
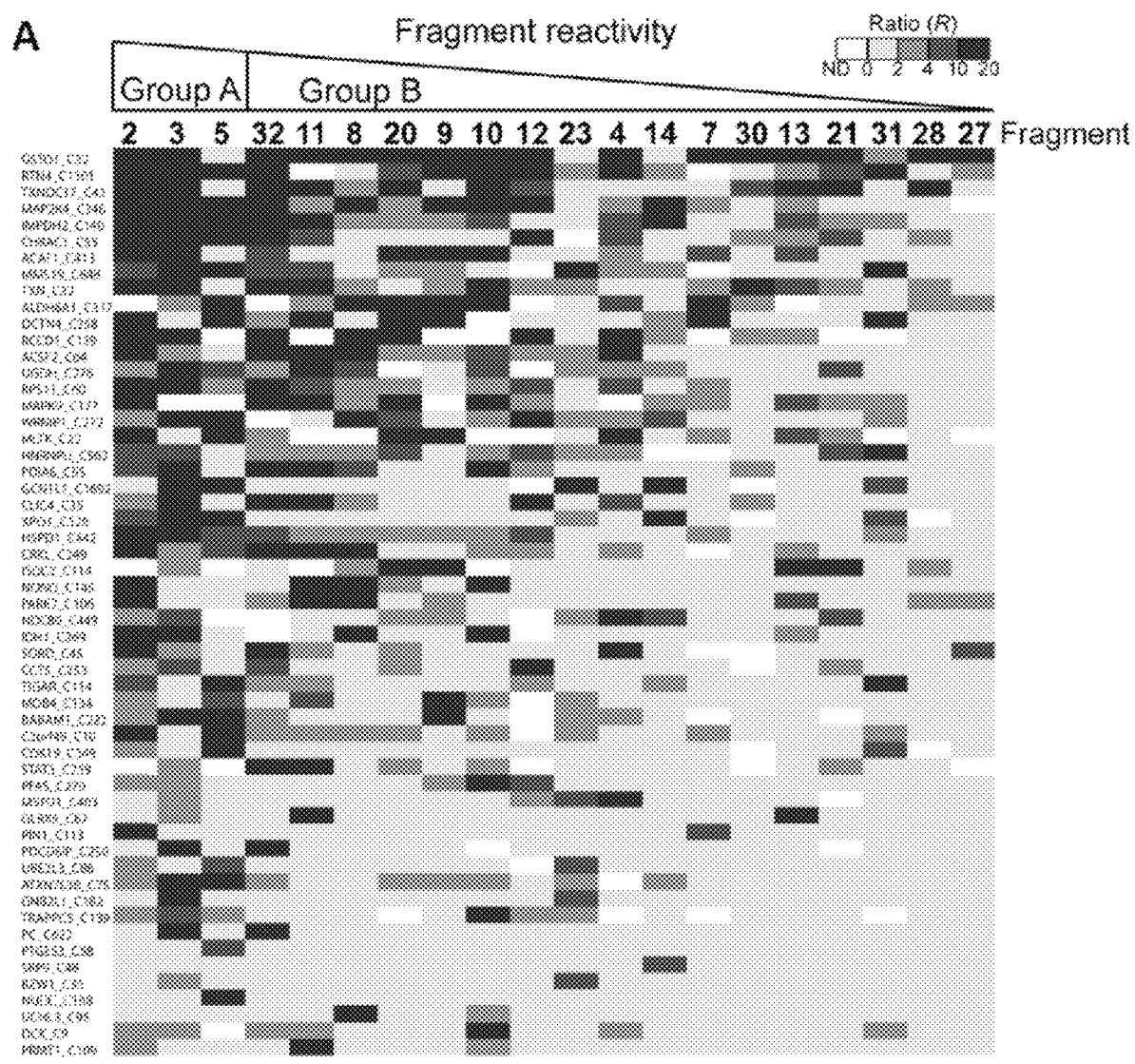
FIG. 6 illustrates analysis of fragment-cysteine interactions. A, Heatmap showing R values for representative cysteines and fragments organized by proteomic reactivity values (high to low, left to right) and percentage of fragment hits for individual cysteines (high to low, top to bottom). R values ≥4 designate fragment hits (colored medium and dark blue). White color designates fragment-cysteine interactions that were not detected (ND). B, C, Histograms depicting the percentage of fragments that are hits (R≥4) for all 768 liganded cysteines (B) or for liganded cysteines found in enzymes for which X-ray and/or NMR structures have been reported (or reported for a close homologue of the enzyme) (C). D, Percentage of liganded cysteines targeted only by group A (red) or B (blue) fragments or both group A and B fragments (black). Shown for all liganded cysteines, liganded cysteines in enzyme active and non-active sites, and liganded cysteines in transcription factors/regulators. For C, D, active-site cysteines were defined as those that reside <10 Å from established active-site residues and/or bound substrates/inhibitors in enzyme structures. E, Representative example of reactive docking predictions shown for XPO1 (PDB ID: 3GB8). All accessible cysteines were identified and reactive docking was conducted with all fragments from the library within a 25 Å docking cube centered on each accessible cysteine. Categories of XPO1 cysteines based on combined docking and isoTOP-ABPP results are shown. F, Success rate of reactive docking predictions for liganded cysteines identified by isoTOP-ABPP in 29 representative proteins.
Figure 6:
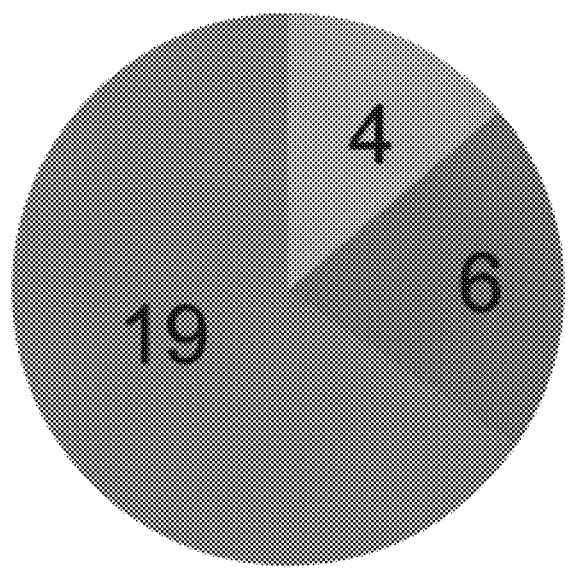
Figure 9:
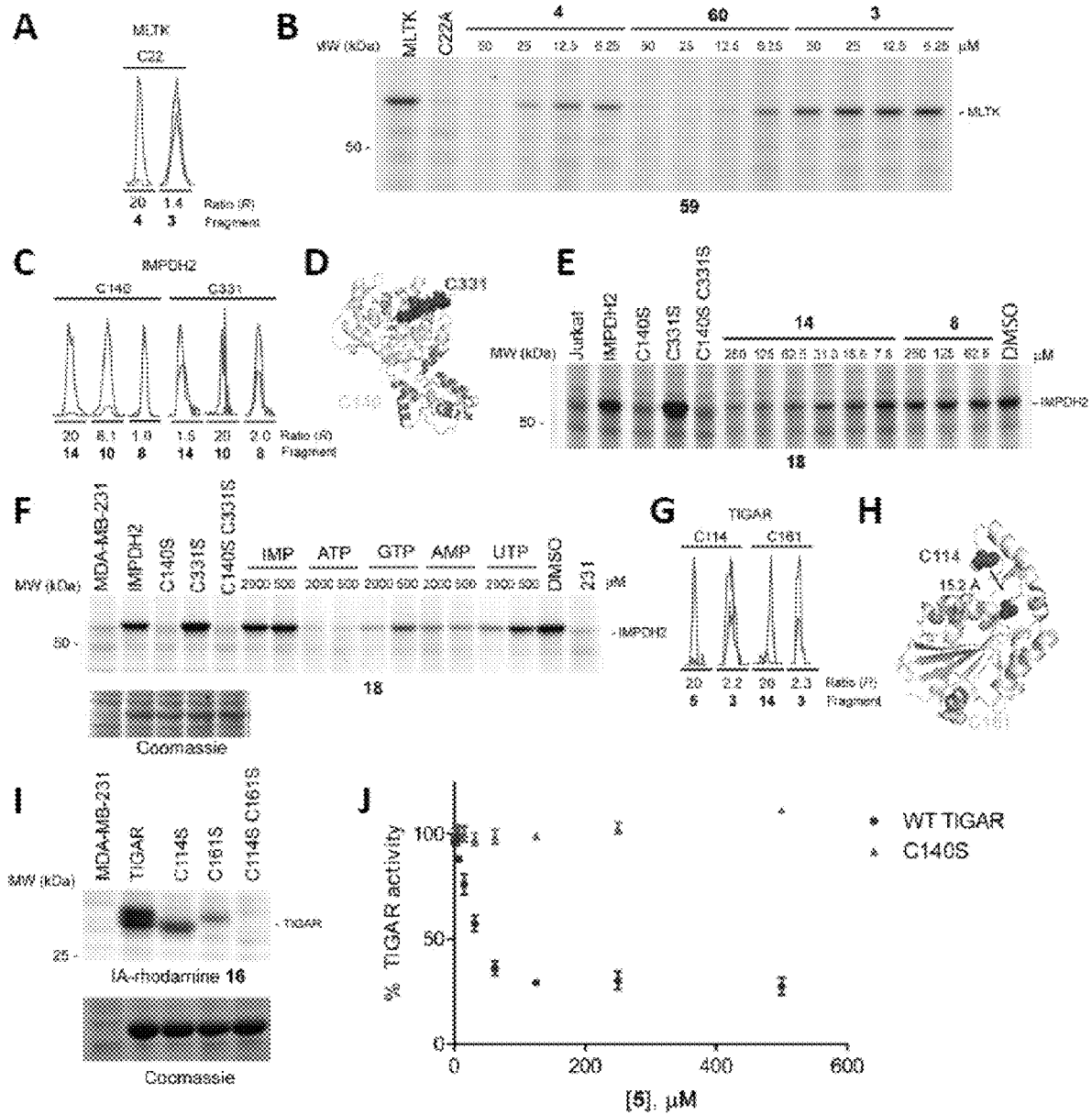
FIG. 9 illustrates confirmation and functional analysis of fragment-cysteine interactions. A, Representative MS1 ion chromatograms for the MLTK tryptic peptide containing liganded cysteine C22 quantified by isoTOP-ABPP in MDA-MB-231 lysates treated with fragment 4 or control fragment 3 (500 µM each). B, Lysates from HEK293T cells expressing WT- or C22A-MLTK treated with the indicated fragments and then an ibrutinib-derived activity probe 59 at 10 µM. MLTK labeling by 59 was detected by CuAAC conjugation to a rhodamine-azide tag and analysis by SDS-PAGE and in-gel fluorescence scanning. C, Representative MS1 ion chromatograms for IMPDH2 tryptic peptides containing the catalytic cysteine, C331, and Bateman domain cysteine, C140, quantified by isoTOP-ABPP in cell lysates treated with the indicated fragments (500 µM each). D, Structure of human IMPDH2 (PDB ID: 1NF7) (light grey) and its structurally unresolved Bateman domain modeled by ITASSER (dark grey) showing the positions of C331 (red spheres), Ribavirin Monophosphate and C2-Mycophenolic Adenine Dinucleotide (blue), and C140 (yellow spheres). E, Fragment reactivity with recombinant, purified IMPDH2 added to Jurkat lysates to a final concentration of 1 µM protein, where reactivity was detected in competition assays using the click probe 18 (25 µM; see FIG. 8H for structure of 18). Note that 18 reacted with WT- and C331S-IMPDH2, but not C140S or C140S/C331S-IMPDH2. F, Nucleotide competition of 18 (25 µM) labeling of WT-IMPDH2 added to cell lysates to a final concentration of 1 µM protein. G, Representative MS1 chromatograms for TIGAR tryptic peptides containing C114 and C161 quantified by isoTOP-ABPP in cell lysates treated with the indicated fragments (500 µM each). H, Crystal structure of TIGAR (PDB ID: 3DCY) showing C114 (red spheres), C161 (yellow spheres), and inorganic phosphate (blue). I, Labeling of recombinant, purified TIGAR and mutant proteins by the IA-rhodamine (2 µM) probe. TIGAR proteins were added to cell lysates, to a final concentration of 2 µM protein. J, Concentration-dependent inhibition of WT-TIGAR by 5. Note that the C140S-TIGAR mutant was not inhibited by 5. Data represent mean values±SEM for 4 replicate experiments at each concentration.
Figure 15:
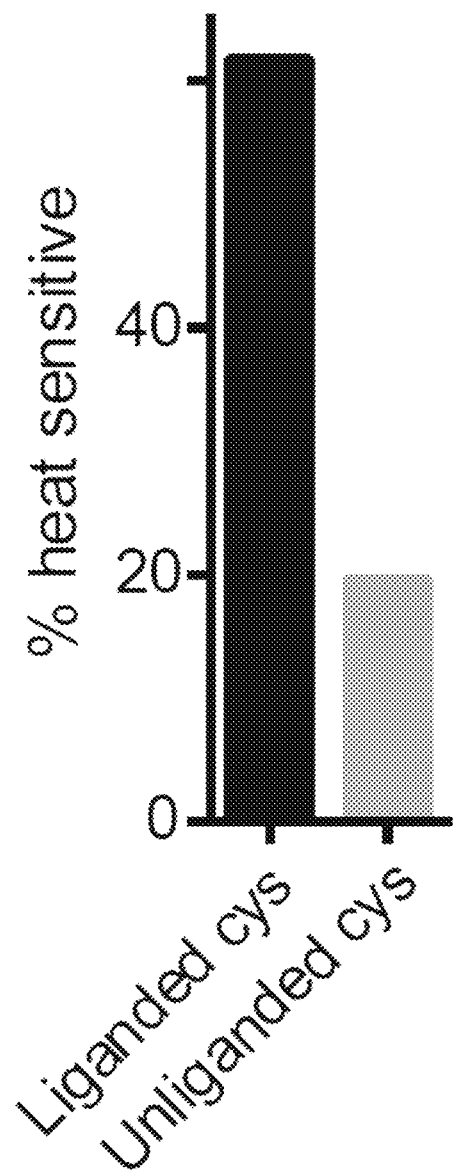
FIG. 15 illustrates a fraction of liganded (62%; 341 of 553 quantified cysteines) and unliganded (20%; 561 of 2870 quantified cysteines) cysteines that are sensitive to heat denaturation measured by IA-alkyne labeling (R>3 native/heat denatured).
Figure 16:
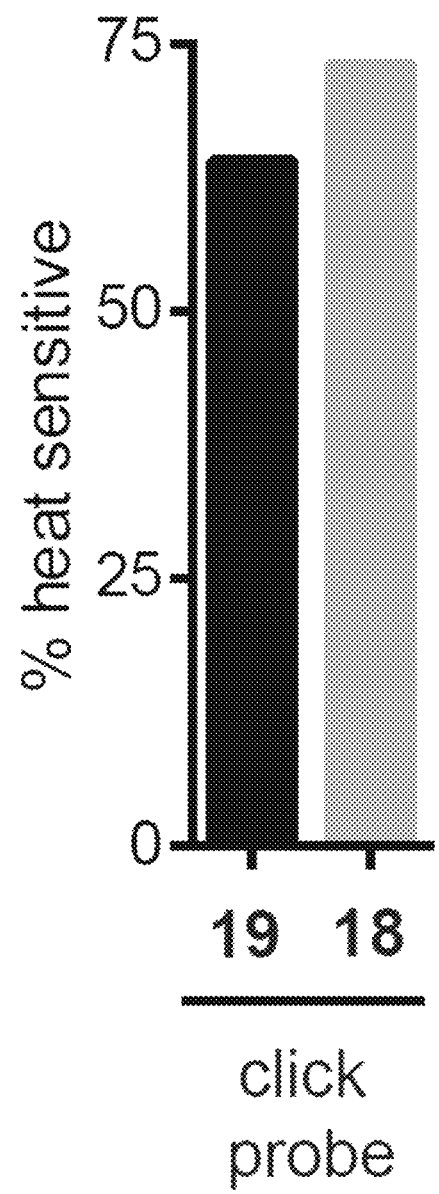
FIG. 16 shows a percentage of proteins identified by isoTOP-ABPP as liganded by fragments 3 and 14 and enriched by their corresponding click probes 19 and 18 that are sensitive to heat denaturation (64% (85 of 133 quantified protein targets) and 73% (19 of 26 quantified protein targets), respectively). Protein enrichment by 18 and 19 was measured by whole protein capture of isotopically-SILAC labeled MDA-MB-231 cells using quantitative (SILAC) proteomics.

Liganded cysteines displayed strikingly distinct SARs with the fragment electrophile library (FIG. 6A and Tables 1-3). While a handful of cysteines were targeted by a large number of fragments (>50%), most cysteines exhibited more restricted reactivity (FIG. 6A, B and Tables 1-3). The operational grouping of fragment electrophiles based on their relative proteomic reactivity values (group A, >10%; group B, <10%) revealed SAR features that emphasized both the recognition and reactivity components of cysteine-electrophile interactions. Certain cysteines, for instance, preferentially interacted with the less reactive (group B) fragments (e.g., GLRX5; MSTO1; SRP9; UCHL3; FIG. 6A), while others were mainly liganded by the most reactive (group A) fragments (e.g., ATXN7L3B; CRKL; C2ORF49; FIG. 6A), although, even in these cases, the interactions differed substantially across group A fragments. Liganded cysteines located in the active sites of proteins tended to show broader reactivity with the fragment electrophiles compared to other cysteines (FIG. 6C), possibly reflecting their greater ligandability, but clear SARs were observed for many non-active site cysteines and these residues were not disproportionately targeted by group A fragments (FIG. 6D). These principles applied across different protein classes and were well-exemplified in kinases, for which >20 liganded cysteines were identified that distributed near-evenly between active- and non-active-site residues (FIG. 7D-F). Even cysteines found in proteins considered challenging to drug, such as transcription factors/regulators, showed distinct SARs indicative of specific interactions involving both binding and reactivity (FIG. 6D and FIG. 9G). In addition, about greater than 60% of liganded cysteines, electrophile (IA-alkyne or fragment) reactivity was blocked by heat denaturation of the proteome, while about a fraction of unliganded cysteines (about 20%) showed decreased IA-alkyne labeling following heat denaturation (FIGS. 15 and 16). In some instances, these results shoed that the ligand-cysteine insteractions are specific in that they depend on both the binding groups of ligands and structured sites in protein.

Figure 17A:
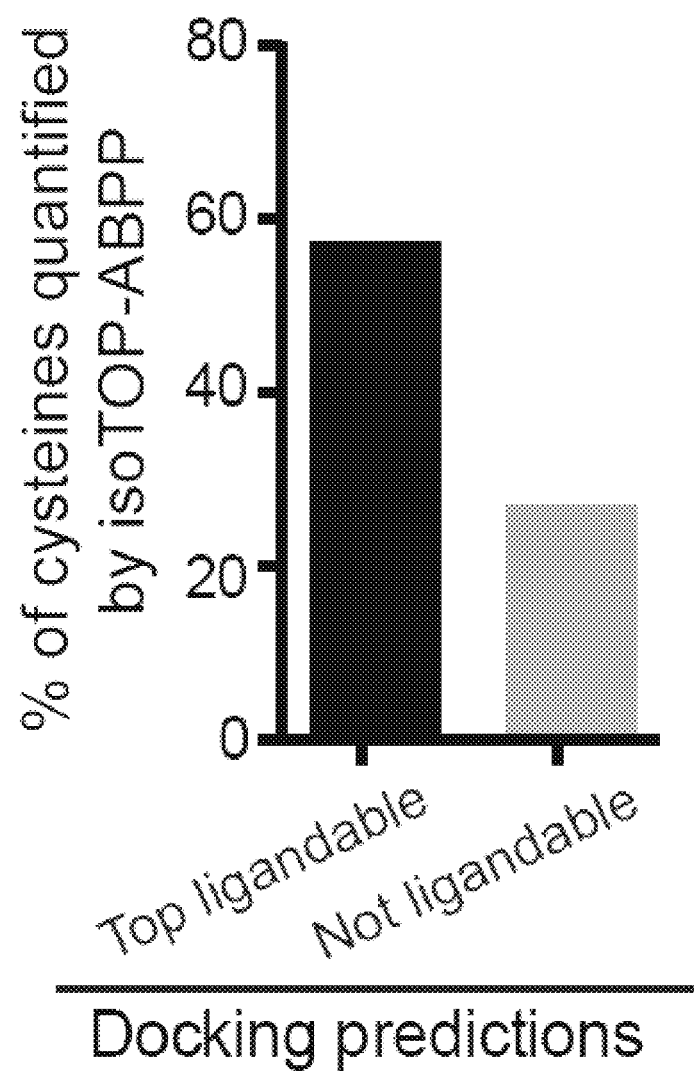
FIG. 17A-FIG. 17B illustrate exemplary fractions of cysteines predicted based on isoTOP-ABPP method or IA-alkyne probe.
Figure 17B:
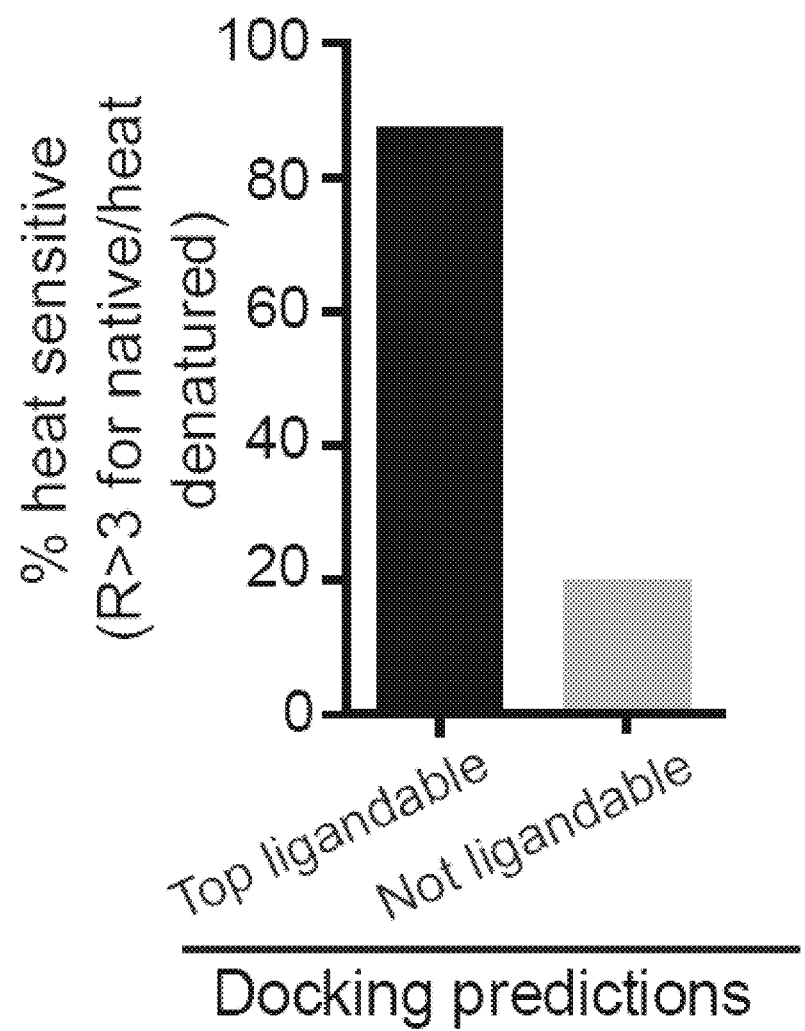

The availability of three-dimensional structures for a subset of proteins with liganded cysteines provided an opportunity to test whether docking predicts sites of fragment electrophile reactivity. Covalent docking programs have recently been introduced to discover ligands that target pre-specified cysteines in proteins; here, however, the aim was to computationally assess the relative ligandability of all cysteines within a protein and match these outputs to the data acquired in isoTOP-ABPP experiments. First, 29 representative protein targets were scanned and 99 solvent-accessible cysteines were identified. Then, the fragment electrophile library was docked on each residue independently using a modified potential to simulate non-covalent interactions preceding the alkylation event. In cases where the fragment electrophile bound favorably near a cysteine and the reactive group was within covalent bond distance of the cysteine, the cysteine was considered to be modified by the fragment. Docking scores were then calculated based on the estimated interaction energy of each fragment in its docked pose, and the ranking of these predictions matched the experimental data in 19 out of the 29 systems (i.e., cases where the top predicted ligandable cysteine matched the liganded cysteine determined by isoTOP-ABPP) (FIG. 6E, F and Table 5). In six out of the remaining 10 systems, the liganded cysteines were ranked second by reactive docking. In the remaining four systems, reactive docking failed to predict the liganded cysteine due to limitations in the docking scoring function or structural issues in the models used Notably, across the entire 29 proteins evaluated by reactive docking, it was found that cysteines predicted to be ligandable were much more likely to have been detected by isoTOP-ABPP compared to cysteines not predicted to be ligandable (FIG. 6E and FIG. 7H). It was also found that cysteines predicted to be ligandable were more likely to have been detected by isoTOP-ABPP and exhibited heat-sensitive IA-alkyne reactivity (FIG. 17A and FIG. 17B). These results indicate that reactive docking provides a good overall prediction of the ligandability of proteinaceous cysteines and suggest that IA-alkyne reactivity itself provides an independent experimental parameter useful for designating potentially ligandable cysteines in proteins.

Functional Analysis of Ligand-Cysteines Interactions

Figure 8:
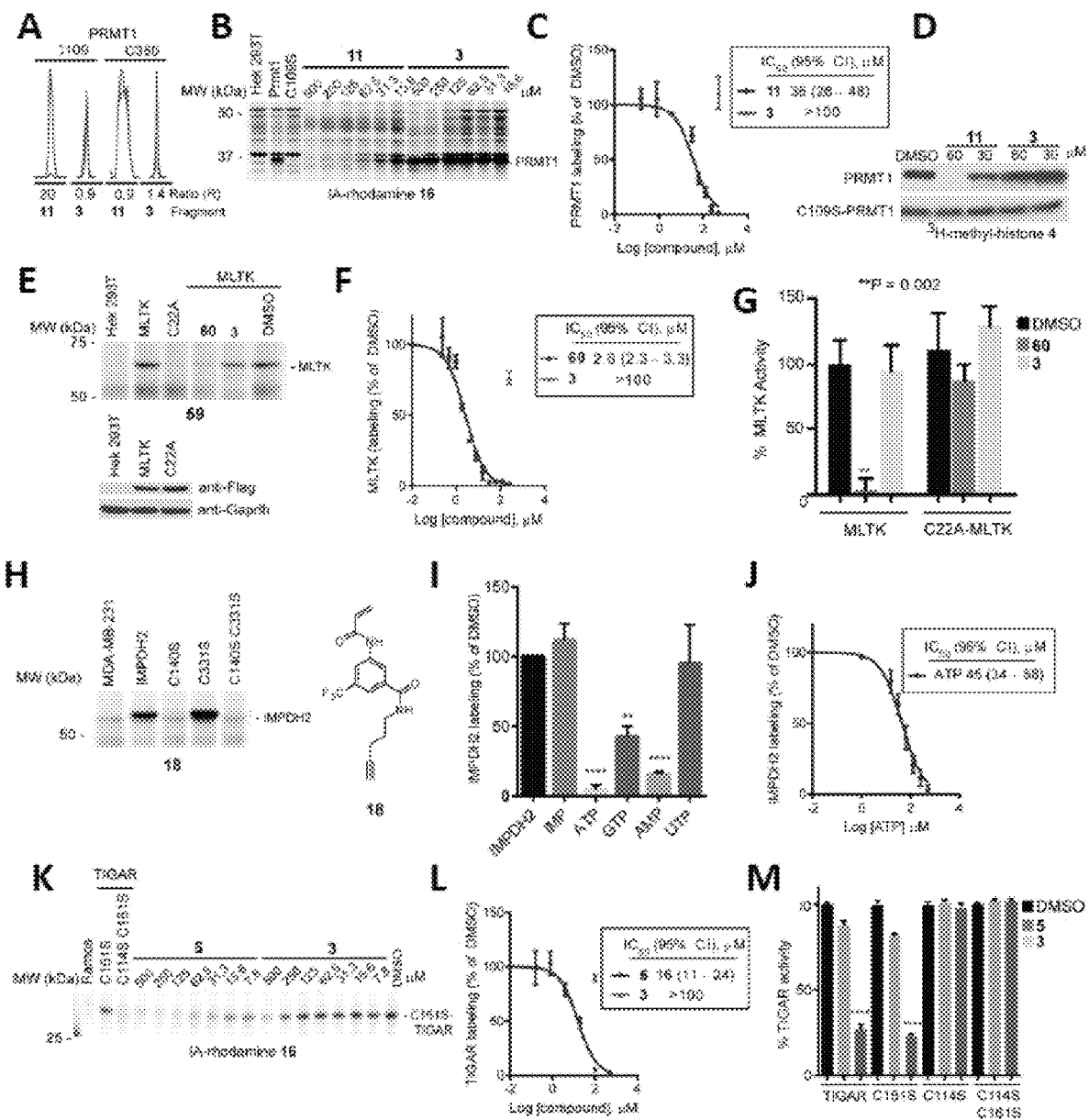
FIG. 8 illustrates confirmation and functional analysis of fragment-cysteine interactions. A, Representative MS1 chromatograms for the indicated Cys-containing peptides from PRMT1 quantified in competitive isoTOP-ABPP experiments of MDA-MB-231 cell lysates, showing blockade of IA-alkyne 1 labeling of C109 by fragment 11, but not control fragment 3. B, 11, but not 3 blocked IA-rhodamine (2 µM) labeling of recombinant, purified WT-PRMT1 (1 µM protein doped into HEK293T cell lysates). Note that a C109S-PRMT1 mutant did not react with IA-rhodamine. C, $IC_{50}$ curve for blockade of 16 labeling of PRMT1 by 11. CI, 95% confidence intervals. D, Effect of 11 and control fragment 3 on methylation of recombinant histone 4 by recombinant PRMT1. Shown is one representative experiment of three independent experiments that yielded similar results. E, 60, but not control fragment 3 (50 µM of each fragment) blocked labeling of recombinant MLTK (or ZAK) kinase by a previously reported ibrutinib-derived activity probe 59 (upper panel). A C22A-MLTK mutant did not react with the ibrutinib probe. Anti-FLAG blotting confirmed similar expression of WT- and C22A-MLTK proteins, which were expressed as FLAG-fusion proteins in HEK293T cells (lower panel). F, $IC_{50}$ curve for blockade of ibrutinib probe-labeling of MLTK by 60. G, 60, but not control fragment 3 (100 µM of each fragment) inhibited the kinase activity of WT-, but not C22A-MLTK. H, Click probe 18 (25 µM) labeled WT-IMPDH2 and C331S-IMPDH2, but not C140S-IMPDH2 (or C140S/C331S-IMPDH2). Labeling was detected by CuAAC conjugation to a rhodamine-azide reporter tag and analysis by SDS-PAGE and in-gel fluorescence scanning. Recombinant IMPDH2 WT and mutants were expressed and purified from E. coli and added to Jurkat lysates to a final concentration of 1 µM protein. I, Nucleotide competition profile for 18-labeling of recombinant WT-IMPDH2 (500 µM of each nucleotide). J, $IC_{50}$ curve for blockade of 18 labeling of IMPDH2 by ATP. K, 5, but not control fragment 3 blocked IA-rhodamine (2 µM) labeling of recombinant, purified C161S-TIGAR (2 µM protein doped into Ramos cell lysates). L, $IC_{50}$ curve for blockade of IA-rhodamine labeling of C161S-TIGAR by 5. M, 5, but not control fragment 3 (100 µM of each fragment) inhibited the catalytic activity of WT-TIGAR, C161S-TIGAR, but not C114S-TIGAR or C114S/C161S-TIGAR. For panels C, F, G, I, J, L, and M, data represent mean values±SEM for at least three independent experiments. Statistical significance was calculated with unpaired students t-tests comparing DMSO- to fragment-treated samples; , $p<0.01$, **, $p<0.0001$.

The next step was to confirm and determine the functional impact of ligand-cysteine interactions mapped by isoTOP-ABPP using recombinant proteins. Two proteins were selected for which the functional significance of the liganded cysteines had been previously demonstrated. The protein methyltransferase PRMT1 possesses a non-catalytic active-site cysteine (C109) that, when modified by electrophilic small molecules like 4-hydroxynonenal (HNE), results in the inhibition of PRMT1 activity[27]. Competitive isoTOP-ABPP revealed a very selective SAR for ligand engagement of C109 of PRMT1, with only three fragments (2, 11, and 51) blocking IA-alkyne labeling of this residue (FIG. 6A and FIG. 8A and Tables 1-3). Even though several additional cysteines in PRMT1 were quantified in isoTOP-ABPP experiments (none of which showed sensitivity to the tested fragment electrophiles; FIG. 8A and Tables 1-3), it was found that IA-rhodamine labeling of recombinant PRMT1 was blocked by mutating C109 to serine (FIG. 8B). These data are consistent with past studies indicating that C109 is the most reactive cysteine in PRMT1 and is selectively labeled by low concentrations of electrophilic probes. Using a convenient SDS-PAGE readout, it was confirmed that fragment 11 blocked IA-rhodamine labeling of PRMT1 with an $IC_{50}$ value of 36 µM, whereas control fragment 3 was inactive (FIG. 8B, C), despite displaying similar overall proteome reactivity to 11 (FIG. 4B). Pre-treatment with 11, but not 3, also inhibited PRMT1-catalyzed methylation of histone 4 in a C109-dependent manner (FIG. 8D). These data indicate that electrophilic ligands targeting C109 act as PRMT1 inhibitors.

Figure 18:
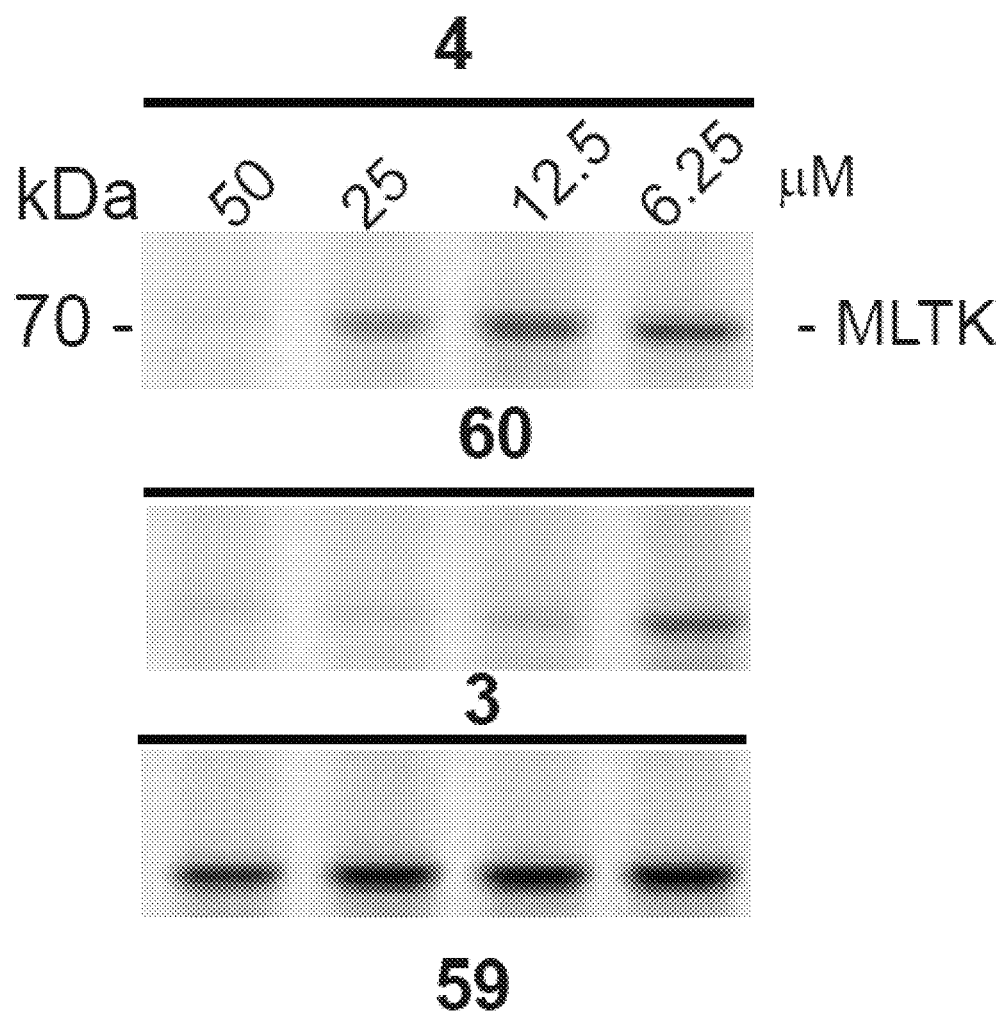
FIG. 18 shows lysates from HEK293T cells expressing WT or C22A-MLTK treated with the indicated fragments and then an ibrutinib-derived activity probe 59 at 10 µM.

MLTK, or ZAK, which is a MAP3 kinase that possesses an active site-proximal cysteine residue C22 that is modified by HNE to feedback-inhibit JNK pathways under conditions of oxidative stress, was then examined. MLTK has also recently been implicated as an oncogenic driver in gastric cancer and is an off-target for ibrutinib, which reacts with C22 of MLTK. Competitive isoTOP-ABPP experiments identified a subset of fragment electrophiles that blocked IA-alkyne labeling of C22 in MLTK (FIG. 9A and Tables 1-3). The SAR provided by isoTOP-ABPP was verified and extended by testing fragments for blockade of labeling of recombinant MLTK using an ibrutinib-derived activity probe (FIG. 8E and FIG. 9B), which identified the benzofuran fragment 60 as having good potency for inhibiting MLTK ($IC_{50}$ value of 2.6 µM) and 3 as an inactive control probe (FIGS. 8E, F and FIGS. 9A, B). Fragment 60, but not 3, also blocked the catalytic activity of MLTK using a substrate phosphorylation assay, and this inhibitory effect was not observed with a C22A-MLTK mutant (FIG. 8G and FIG. 18).

Next, proteins were evaluated that possessed previously uncharacterized liganded cysteines. IMPDH2, which is the rate-limiting enzyme in de novo synthesis of guanine nucleotides and regulates immune cell proliferation and cancer, contained two liganded cysteines—C140 and C331—that showed overlapping, but distinct SARs in competitive isoTOP-ABPP experiments (FIG. 9C, D; FIG. 19 and Tables 1-3). C331 serves as a catalytic nucleophile and active site-directed inhibitors of IMPDH2 have been described. C140, on the other hand, is found in a separate Bateman domain of IMPDH2, which serves as a module for allosteric regulation by sensing nucleotides (FIG. 9D) and has not been shown to react with electrophilic small molecules. Therefore focused was placed on the characterization of C140. It was first confirmed that fragment 14 directly labeled C140 of recombinant IMPDH2 by MS methods (Table 6). An alkyne analogue of 14 (18; FIG. 8H) was then synthesized, which provided a means to directly monitor ligand interactions at C140 by click chemistry conjugation to a rhodamine-azide tag and SDS-PAGE analysis. Click probe 18 labeled WT-IMPDH2 and a C331S-IMPDH2 mutant, but not the C140S or C140S/C331S mutants of this enzyme (FIG. 8H). Using this assay, it was confirmed that 14, but not control fragment 8, inhibited the labeling of IMPDH2 by 18 (FIG. 9E). IMPDH2 labeling by 18 was also inhibited by nucleotides ATP, AMP, and GTP, but not UTP or IMP (FIG. 8I and FIG. 9F). ATP blocked 18 labeling of IMPDH2 with an $IC_{50}$ value of 45 µM (FIG. 8J). Thus, covalent ligands targeting the Bateman domain of IMPDH2 serves not only as inhibitors, but also probes of nucleotide binding to this enzyme.

Two liganded cysteines—C114 and C161—were also identified in the p53-induced phosphatase TIGAR (FIG. 9G, H). In some instances, TIGAR acts as both a fructose-2,6-bisphosphatase and 2,3-bisphosphoglycerate phosphatase to shape the metabolic state of cancer cells and protect them from ROS-induced apoptosis. Inhibitors of TIGAR have not been described. C114 is found on the lid of the TIGAR active site, ~15 Å from the phosphate substrate binding site (FIG. 9H). C161 resides on the opposite side of the protein. Focus was placed on the characterization of fragment labeling of C114 given its proximity to the TIGAR active site. It was first confirmed that both C114 and C161 of recombinant TIGAR were labeled by the IA-rhodamine probe and this labeling was partly diminished in C114S and C161S single mutants and fully blocked in a C114S/C116S double mutant of TIGAR (FIG. 9I). It was also verified interactions of hit fragment 5 with C114 of TIGAR by LC-MS analysis (Table 6) and by showing that the fragment blocked IA-rhodamine labeling of a C161S-TIGAR mutant with an $IC_{50}$ value of 16 µM (FIG. 8K, L); in contrast, the control fragment 3 showed much lower potency (FIG. 8K, L). 5 also blocked the catalytic activity of WT- and C161S-, but not C114S- or C114S/C161S-TIGAR using a substrate assay (FIG. 8M). Control fragment 3 did not affect TIGAR catalytic activity (FIG. 8L). Inhibition of TIGAR substrate turnover by 5 plateaued at 70% (FIG. 9J), which indicates that the covalent ligand acts by an allosteric mechanism or does not extend fully into the active site of TIGAR to produce complete inhibition.

Electrophilic Ligands that Inhibit IDH1 Activity in Cancer Cells

Isocitrate dehydrogenase 1 (IDH1) and 2 (IDH2) are mutated in a number of human cancers to produce enzyme variants with a neomorphic catalytic activity that converts isocitrate to 2-hydroxyglutarate (2-HG). Increases in 2-HG inhibit α-ketoglutarate-dependent dioxygenases that function as tumor suppressors, in particular, by methylating DNA and proteins. Competitive isoTOP-ABPP experiments identified distinct subsets of ligands that targeted a conserved cysteine in IDH1 and IDH2 (C269 and C308, respectively; Tables 1-3). This cysteine is an active site-proximal residue that is 13 Å from the $NADP^+$ molecule in a crystal structure of IDH1 (FIG. 10A); glutathionylation of C308 has previously been shown to block IDH2 activity, but, to our knowledge, irreversible inhibitors of IDH enzymes have not been characterized.

Figure 10:
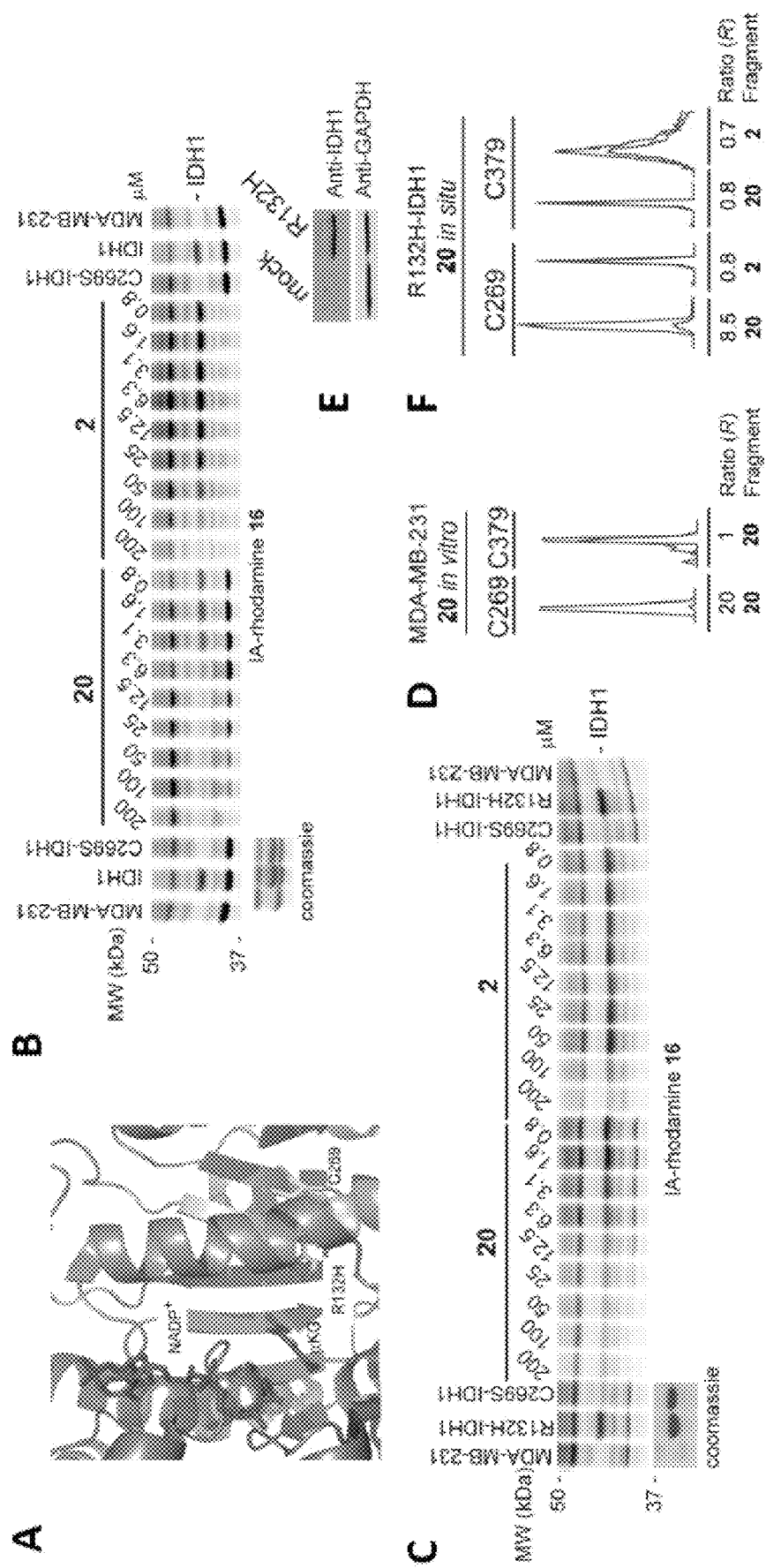
FIG. 10 illustrates in situ activity of fragment electrophiles. A, X-ray crystal structure of IDH1 (PDB ID: 3MAS) showing the position of C269 and the frequently mutated residue in cancer, R132. B, C, Reactivity of 20 and control fragment 2 with recombinant, purified WT-IDH1 (B) or R132H-IDH1 (C) added to cell lysates to a final concentration of 2 or 4 µM protein, respectively. Fragment reactivity was detected in competition assays using the IA-rhodamine probe (2 µM); note that the C269S-IDH1 mutant did not react with IA-rhodamine. D, Representative MS1 ion chromatograms for the IDH1 tryptic peptides containing liganded cysteine C269 and an unliganded cysteine C379 quantified by isoTOP-ABPP in MDA-MB-231 lysates treated with fragment 20 (25 µM). E, Western blot of MUM2C cells stably overexpressing GFP (mock) or R132H-IDH1 proteins. F, Representative MS1 chromatograms for the IDH1 tryptic peptides containing liganded cysteine C269 and an unliganded cysteine C379 quantified by isoTOP-ABPP in R132H-IDH-expressing MUM2C lysates treated with 20 or control fragment 2 (50 µM, 2 h, in situ).
Figure 11:
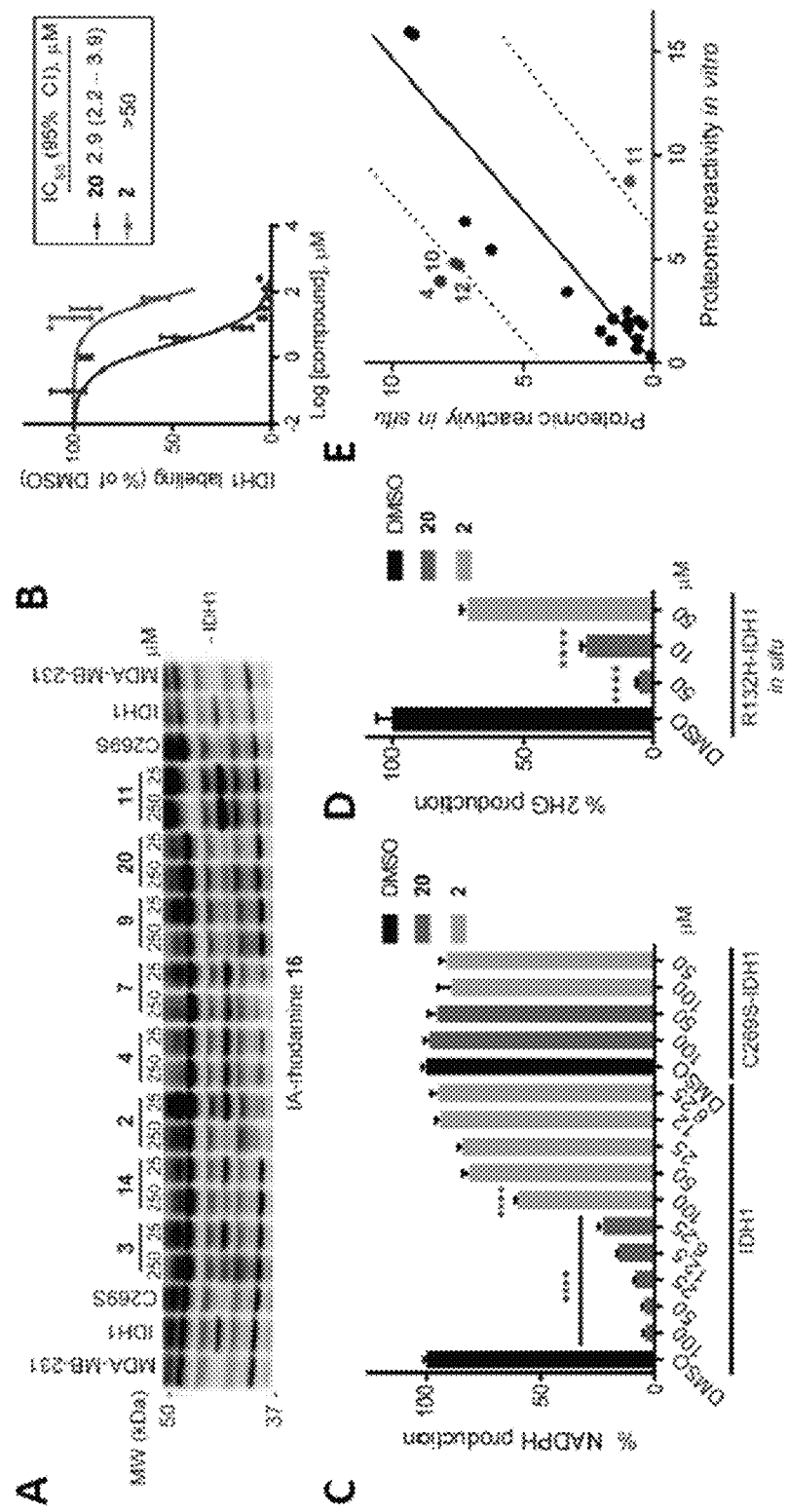
FIG. 11 illustrates in situ activity of fragment electrophiles. A, Blockade of 16 labeling of WT-IDH1 by representative fragment electrophiles. Recombinant, purified WT-IDH1 was added to MDA-MB-231 lysates at a final concentration of 2 µM, treated with fragments at the indicated concentrations, followed by IA-rhodamine probe 16 (2 µM) and analysis by SDS-PAGE and in-gel fluorescence scanning. Note that a C269S mutant of IDH1 did not label with IA-rhodamine 16. B, $IC_{50}$ curve for blockade of IA-rhodamine-labeling of IDH1 by 20. Note that the control fragment 2 showed much lower activity. C, 20, but not 2, inhibited IDH1-catalyzed oxidation of isocitrate to α-ketoglutarate (α-KG) as measured by an increase in NADPH production (340 nm absorbance). 20 did not inhibit the C269S-IDH1 mutant. D, 20 inhibited oncometabolite 2-hydroxyglutarate (2-HG) production by R132H-IDH1. MUM2C cells stably overexpressing the oncogenic R132H-IDH1 mutant or control GFP-expressing MUM2C cells were treated with the indicated fragments (2 h, in situ). Cells were harvested, lysed and IDH1-dependent production of 2-HG from α-KG and NADPH was measured by LC-MS and from which 2-HG production of GFP-expressing MUM2C cells was subtracted (GFP-expressing MUM2C cells produced <10% of the 2-HG generated by R132H-IDH1-expressing MUM2C cells). E, Proteomic reactivity values for individual fragments are comparable in vitro and in situ. One fragment (11) marked in red showed notably lower reactivity in situ versus in vitro. Reactivity values were calculated as in FIG. 1D. Dashed line mark 90% prediction intervals for the comparison of in vitro and in situ proteomic reactivity values for fragment electrophiles. Blue and red circles mark fragments that fall above (or just at) or below these prediction intervals, respectively. F, Fraction of cysteines liganded in vitro that is also liganded in situ. Shown are liganded cysteine numbers for individual fragments determined in vitro and the fraction of these cysteines that were liganded by the corresponding fragments in situ. G, Representative cysteines that were selectively targeted by fragments in situ, but not in vitro. For in situ-restricted fragment-cysteine interactions, a second cysteine in the parent protein was detected with an unchanging ratio (R~1), thus controlling for potential fragment-induced changes in protein expression. For panels B-D, data represent mean values±SEM for at least three independent experiments. Statistical significance was calculated with unpaired students t-tests comparing DMSO- to fragment-treated samples; ****, $p<0.0001$.

The functional significance of ligand interactions with IDH enzymes by recombinantly expressing wild type (WT) and a C269S mutant of IDH1 was explored. WT-, but not C269S-IDH1 reacted with the IA-rhodamine probe as detected by SDS-PAGE, and fragment electrophiles blocked this reaction with an SAR that mirrored that observed for endogenous IDH1 in competitive isoTOP-ABPP experiments (FIG. 11A and Tables 1-3). Fragment 20 inhibited IA-rhodamine labeling of WT-IDH1 with an $IC_{50}$ value of 2.9 µM (FIG. 11B and FIG. 10B) and showed similar activity with the R132H oncogenic mutant of IDH1 (FIG. 10C and FIG. 20). It was also confirmed by isoTOP-ABPP that 20 (25 µM) completely blocked IA-alkyne labeling of endogenous IDH1 in MDA-MD-231 proteomes (R value=20; FIG. 10D) and, by MS analysis, that 20 directly modifies C269 of IDH1 (Table 6). Fragment 2 showed much less activity against C269 of IDH1 ($IC_{50}$>50 µM; FIG. 11B and FIG. 10B) and was therefore selected as a control probe.

It was found that 20 blocked in a concentration-dependent manner the catalytic activity of WT-IDH1 (as measured by the reduction of NADP$^+$ to NADPH in the presence of isocitrate), but did not inhibit the activity of the C269S-IDH1 mutant (FIG. 11C). The in situ activity of 20 was also tested by generating a human cancer cell line that stably overexpressed R132H-IDH1 (FIG. 10E). The R132H-IDH1 cells were treated with fragments 20 and 2 for 2 h, lysed, and assayed ex situ for 2-HG production. 20 (50 µM) near-completely blocked 2-HG production by R132H cell lysates, while 2 (50 µM) only caused a slight decrease in this activity (FIG. 11D). Parallel competitive isoTOP-ABPP experiments confirmed that fragment 20, but not fragment 2 inhibited IA-alkyne labeling of C269 of IDH1 in situ (FIG. 10F).

Global Profiling of Cysteine-Reactive Fragments in Cells

Encouraged by the cellular activity of the IDH1 ligand 20, the capacity of fragment electrophiles to modify proteinaceous cysteines in situ was more broadly assessed. MDA-MB-231 and Ramos cells were treated with representative members of the fragment library (23 compounds tested in total; each compound tested at 200 µM, 2 h in situ treatment), and the cells were then harvested, lysed, and analyzed by isoTOP-ABPP. A handful of fragments were cytotoxic to cells and re-tested at lower (50 or 100 µM) concentrations. The tested fragments showed a broad range of in situ reactivities that generally matched their respective reactivities in vitro (FIG. 11E and Tables 1-3). Some fragments, however, showed somewhat greater reactivity in cells, while fragment 11 was notably devoid of activity in situ (FIG. 11E). These differences reflect the impact of transport and/or metabolic pathways on the cellular concentrations of fragment electrophiles. A substantial fraction (64%) of the liganded cysteines identified in cell lysates were also sensitive to the same electrophilic fragments in cells (FIG. 11F). A handful of fragment-cysteine interactions were also observed selectively in situ, but not in lysates, including C182 of p53 (TP53), a redox-regulated residue at the dimerization interface of the DNA binding domain$^{50}$ (FIG. 11G). In some instances, these liganded cysteines require an intact cellular environment to preserve their interactions with fragment electrophiles. Taken together, these findings indicate that the ligandability of cysteine residues is generally similar in lysates and cells, although exceptional cases underscore the importance of having the capability to perform ligand discovery experiments in situ.

Electrophilic Ligands that Target Pro-Caspase-8 and Block Extrinsic Apoptosis

Figure 12:
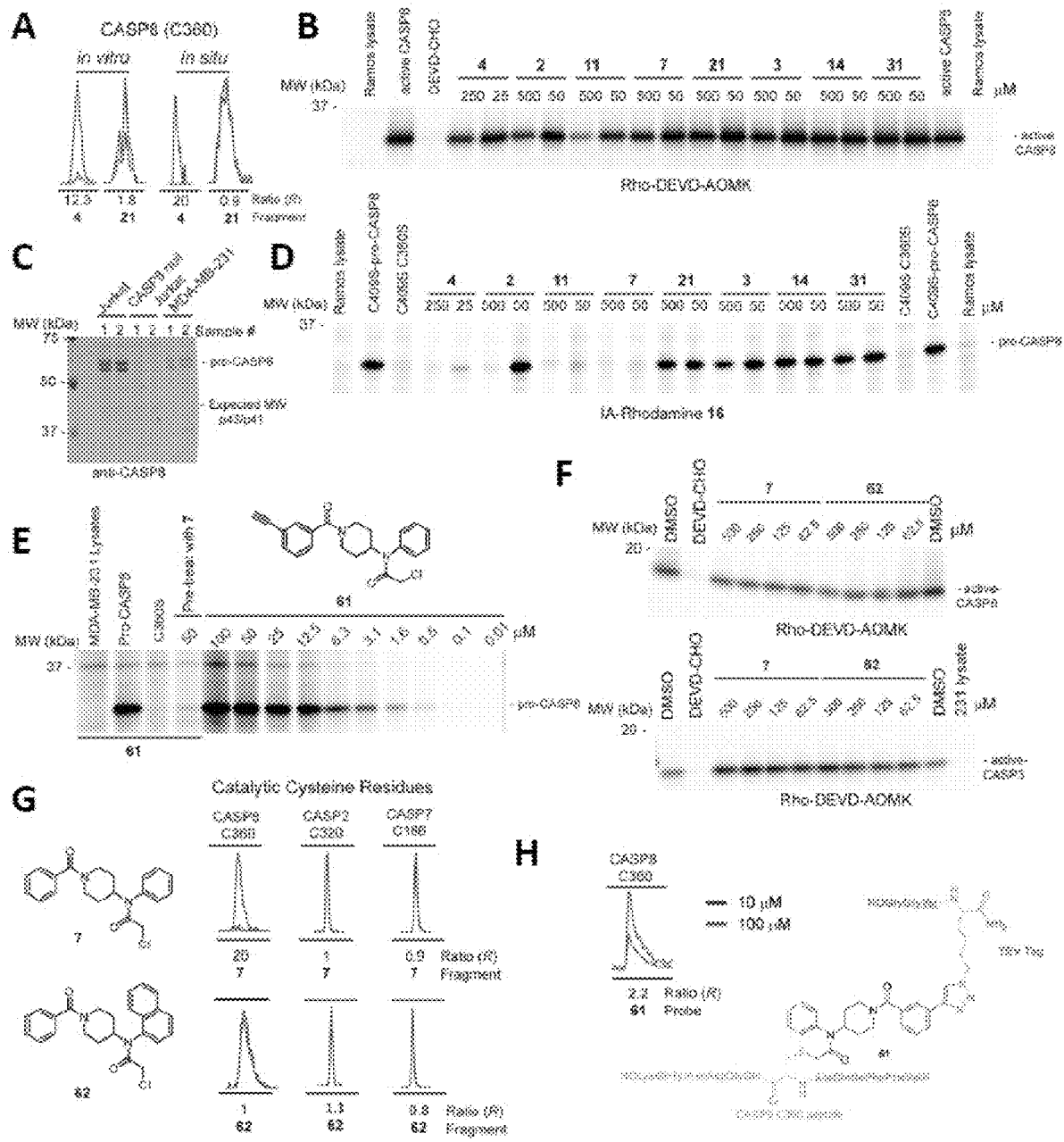
FIG. 12 illustrates fragment electrophiles that target pro-CASP8. A, Representative MS1 chromatograms for CASP8 tryptic peptide containing the catalytic cysteine C360 quantified by isoTOP-ABPP in cell lysates or cells treated with fragment 4 (250 µM, in vitro; 100 µM, in situ) and control fragment 21 (500 µM, in vitro; 200 µM, in situ). B, Fragment reactivity with recombinant, purified active CASP8 added to cell lysates, where reactivity was detected in competition assays using the caspase activity probe Rho-DEVD-AOMK probe ("DEVD" disclosed as SEQ ID NO: 857) (2 µM, 1 h). C, Western blot of proteomes from MDA-MB-231, Jurkat, and CASP8-null Jurkat proteomes showing that CASP8 was only found in the pro-enzyme form in these cells. D, Fragment reactivity with recombinant, purified pro-CASP8 (D374A, D384A, C409S) added to cell lysates to a final concentration of 1 µM protein, where reactivity was detected in competition assays with the IA-rhodamine probe (2 µM). Note that mutation of both cysteine-360 and cysteine-409 to serine prevented labeling of pro-CASP8 by IA-rhodamine. E, Concentration-dependent reactivity of click probe 61, with recombinant, purified pro-CASP8 (D374A, D384A) added to cell lysates to a final concentration of 1 µM protein. Note that pre-treatment with 7 blocked 61 reactivity with pro-CASP8 and mutation of C360 to serine prevented labeling of pro-CASP8 by 61 (25 µM). F, Fragments 7 and 62 did not block labeling by Rho-DEVD-AOMK ("DEVD" disclosed as SEQ ID NO: 857) (2 µM) of recombinant, purified active-CASP8 and active-CASP3 added to MDA-MB-231 cell lysates to a final concentration of 1 µM protein. G, Representative MS1 chromatograms for tryptic peptides containing the catalytic cysteines of CASP8 (C360), CASP2 (C320), and CASP7 (C186) quantified by isoTOP-ABPP in Jurkat cell lysates treated with 7 or 62 (50 µM, 1 h). H, Representative MS1 chromatograms for CASP8 tryptic peptide containing C360 quantified by isoTOP-ABPP in cell lysates treated with 10 versus 100 µM of 61. Structure of CASP8 C360 tryptic peptide adduct (blue) modified by 61 (black) and conjugated to TEV cleavable tag (red), where underline indicates site of isotopic modification. Figure discloses SEQ ID NO: 864.
Figure 13:
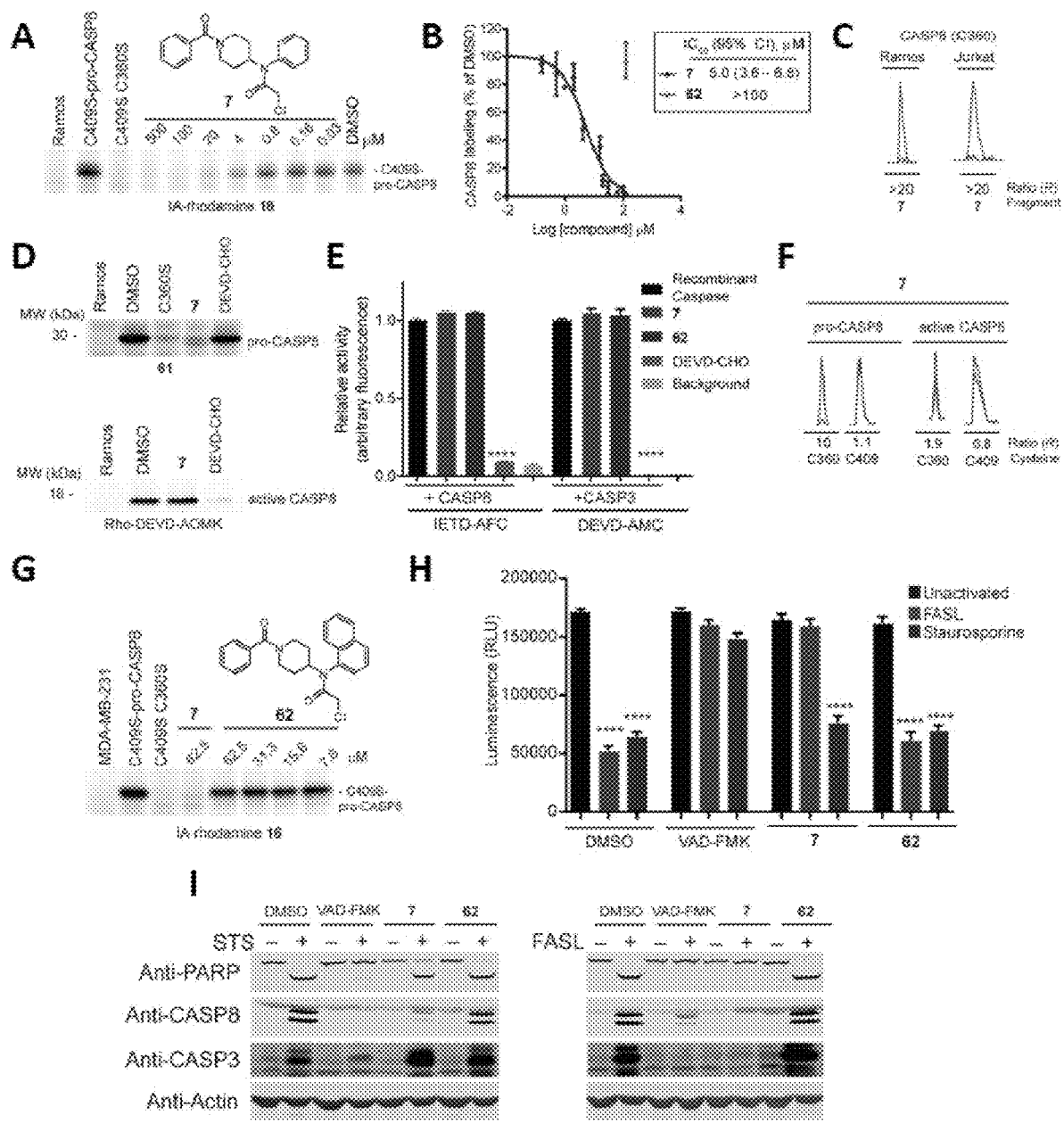
FIG. 13 illustrates fragment electrophiles that target pro-CASP8. A, 7 blocked IA-rhodamine 16 labeling of pro-CASP8. Experiments were performed with recombinant, purified pro-CASP8 (bearing a C409S mutation to eliminate IA-rhodamine labeling at this site) added to Ramos cell lysate at a final concentration of 1 µM and treated with the indicated concentrations of 7 followed by IA-rhodamine (2 µM). Note that a C360S/C409S-mutant of pro-CASP8 did not label with IA-rhodamine. B, $IC_{50}$ curve for blockade of IA-rhodamine labeling of pro-CASP8 (C409S) by 7. C, 7 (50 µM) fully competed IA-alkyne-labeling of C360 of endogenous CASP8 in cell lysates as measured by isoTOP-ABPP. Representative MS1 chromatograms are shown for the C360-containing peptide of CASP8. D, 7 selectively blocked probe labeling of pro-CASP8 compared to active CASP8. Recombinant pro- and active-CASP8 (added to Ramos cell lysates at a final concentration of 1 µM each) were treated with 7 (50 µM) or the established caspase inhibitor, Ac-DEVD-CHO ("DEVD" disclosed as SEQ ID NO: 857) (20 µM), for 1 h followed by labeling with the click probe 61 (25 µM) for pro-CASP8 and the Rho-DEVD-AOMK probe ("DEVD" disclosed as SEQ ID NO: 857) (2 µM) for active-CASP8. SDS-PAGE and in-gel fluorescence scanning revealed that 7 competes 61-labeling of pro-CASP8, but not Rho-DEVD-AOMK ("DEVD" disclosed as SEQ ID NO: 857) of active-CASP8, and, conversely, DEVD-CHO ("DEVD" disclosed as SEQ ID NO: 857) competed Rho-DEVD-AOMK ("DEVD" disclosed as SEQ ID NO: 857) labeling of active-CASP8, but not 61-labeling of pro-CASP8. E, Neither 7 nor control fragment 62 (100 µM each) inhibited the activity of recombinant, purified active CASP8 and CASP3, which were assayed following addition to Ramos cell lysate using DEVD-AMC and IETD-AFC substrates, respectively. DEVD-CHO ("DEVD" disclosed as SEQ ID NO: 857) (20 µM) inhibited the activity of both CASP8 and CASP3. F, 7 (30 µM) blocked IA-alkyne labeling of C360 of pro-CASP8, but not active-CASP8 as measured by isoTOP-ABPP. Recombinant pro- and active-CASP8 were added to Ramos lysates at 1 µM and then treated with 7 (30 µM) followed by isoTOP-ABPP. G, Substitution of a naphthylamine for the aniline portion of 7 furnishes a control fragment 62 that did not compete with IA-rhodamine labeling of C360 of pro-CASP8. H, 7, but not control fragment 62, blocked extrinsic, but not intrinsic apoptosis. Jurkat cells (1.5 million cells/mL) were incubated with 7 or 62 (30 µM) or the pan-caspase inhibitor VAD-FMK (100 µM) for 30 min prior to addition of staurosporine (2 µM) or SuperFasLigand™ (100 ng/mL). Cells were incubated for 6 hours and viability was quantified with CellTiter-Glo®. RLU-relative light unit. I, For cells treated as described in H, cleavage of PARP (89 kDa), CASP8 (p43/p41), and CASP3 (p19/p17) was visualized by western blot. For panels B, E, and H, data represent mean values±SEM for at least three independent experiments.

Several fragments targeted the catalytic cysteine nucleophile C360 of the protease caspase-8 (CASP8) in isoTOP-ABPP experiments performed in vitro and in situ (FIG. 12A and Tables 1-3). CASP8 plays important roles apoptosis, immune cell proliferation, and embryonic development, but selective, non-peptidic, and cell-active inhibitors for this protease are lacking. Representative fragment hits against recombinant, active CASP8 were screened using substrate and activity-based probe (Rho-DEVD-AOMK probe ("DEVD" disclosed as SEQ ID NO: 857)) assays and observed marginal to no inhibition with most fragments (FIG. 12B). Initially puzzled by this outcome, it was hypothesized that fragment labeling of CASP8 in isoTOP-ABPP experiments might reflect reaction with the inactive zymogen (pro-) rather than active form of this protease. Western blots confirmed that most, if not all of the CASP8 in MDA-MB-231 cell lysates existed in the pro-form (FIG. 12C). Next a recombinant form of pro-CASP8 was expressed with mutated cleavage sites (D374A and D384A) to prevent processing and activation. A non-catalytic cysteine C409S of pro-CASP8 was also mutated, which enabled detection of C360 labeling with IA-rhodamine by SDS-PAGE analysis (FIG. 13A). Several hit fragments detected in isoTOP-ABPP experiments completely blocked IA-rhodamine labeling of pro-CASP8 (FIG. 12D). Fragment 7 displayed the highest potency, with an IC$_{50}$ value of ~5 µM (FIG. 13A, B), which, when combined with the low overall proteome reactivity of this fragment (3%), designated it as suitable tool compound for further studies.

Fragment 7 (50 µM) fully blocked IA-alkyne labeling of C360 of CASP8 in isoTOP-ABPP experiments performed in both Ramos and Jurkat cell lysates (FIG. 13C). Next, a clickable analogue of 7 (61) was synthesized and it was found that this probe (25 µM) strongly labeled pro-CASP8, but not a C360S-pro-CASP8 mutant (FIG. 13D and FIG. 12E). 7 (50 µM) blocked labeling of pro-CASP8 by 61, but did not inhibit labeling of active CASP8 by the Rho-DEVD-AOMK probe ("DEVD" disclosed as SEQ ID NO: 857) developed to target active caspases (FIG. 13D and FIG. 12F). Conversely, the general caspase inhibitor Ac-DEVD-CHO ("DEVD" disclosed as SEQ ID NO: 857) (20 µM) blocked Rho-DEVD-AOMK ("DEVD" disclosed as SEQ ID NO: 857) labeling of active CASP8, but not 61 labeling of pro-CASP8 (FIG. 13D, FIG. 12F, and FIG. 21A). Similar results were obtained in substrate assays, where DEVD-CHO ("DEVD" disclosed as SEQ ID NO: 857), but not 7, blocked CASP8 activity (FIG. 13E). Cross-reactivity of 7 with other caspases was not observed, including recombinant, active CASP3 assayed with a substrate (FIG. 13E) or the Rho-DEVD-AOMK probe ("DEVD" disclosed as SEQ ID NO: 857) (FIG. 12F) or CASP2 and CASP7 in cell lysates measured by isoTOP-ABPP (FIG. 12G). Finally, to further verify that 7 preferentially reacts with pro-CASP8 over active CASP8 in complex biological systems, recombinant forms of these proteins were doped into MDA-MB-231 cell lysates followed by treatment with 7 (30 µM, 1 h) or DMSO and analysis by isoTOP-ABPP. 7 produced a near-complete blockade of IA-alkyne labeling of C360 for pro-CASP8 (R=10), but had little effect on IA-alkyne reaction with C360 of active CASP8 (R=1.9) (FIG. 13F).

Figure 14:
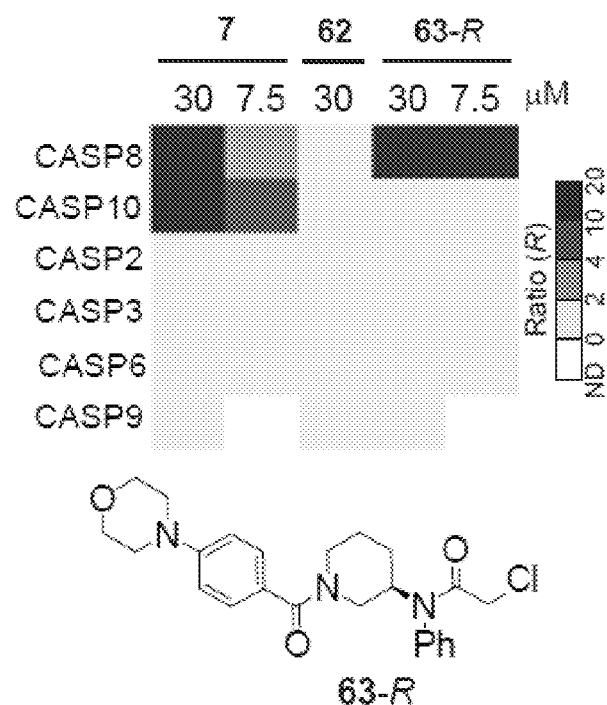
FIG. 14 shows electrohile compounds that target pro-CASP8 and pro-CASP10. Heatmap showing R values for caspases measured by quantitative proteomics in Jurkat cells treated with 7, 63-R, or 62 followed by probe 61 (10 µM, 1 h) (A). Comparison of effects of 7 and 63-R on FasL-induced apoptosis in Jurkat cells or anti-CD3, anti-CD28-activated primary human T cells (B). For B, data represent mean values±SEM for at least three independent experiments, and results are representative of multiple experiments performed with T cells from different human subjects. Statistical significance was calculated with unpaired students t-tests comparing DMSO- to fragment treated samples; ****, p<0.0001 and comparing Jurkat to T cells ####, p<0.0001.
Figure 14:
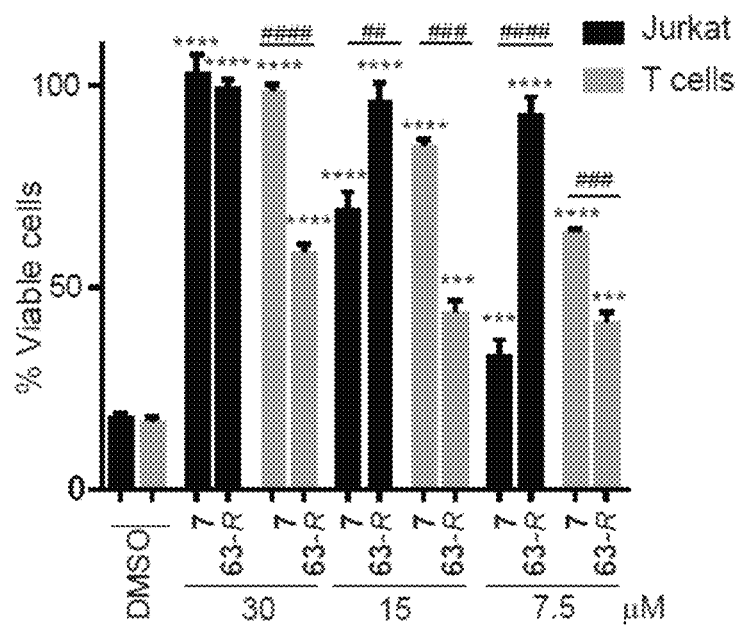

Treatment of Jurkat cell lysates with 10 or 100 µM of 61, followed by analysis of the combined samples by isoTOP-ABPP, confirmed direct labeling of C360 of CASP8 by 61 (FIG. 12H). The low R value observed for C360 in this analysis (R=2) indicated near complete labeling of this cysteine by 61 at 10 µM in cell lysates, consistent with the low µM IC$_{50}$ value displayed by the parent fragment 7 for inhibiting IA-rhodamine labeling of C360 of CASP8 (FIG. 13B). The effect of pro-CASP8 inhibition in cellular apoptosis assays was next to be evaluated. Because C360 is the catalytic nucleophile of CASP8, mutation of this residue was not possible to create a control protein for evaluating the pharmacological effects of 7 in cells. Instead, a structurally related inactive probe was developed for this purpose. It was found that bulky substituents placed on the aniline ring of 7 furnished compounds such as 62 that did not inhibit pro-CASP8 labeling by IA-rhodamine (FIG. 13B, G). It was confirmed that 62 also did not inhibit active CASP3 or CASP8 using substrate (FIG. 13E) and activity-probe (FIG. 12F) assays and was inactive against endogenous CASP8, CASP2, or CASP7 in Jurkat lysates as determined by isoTOP-ABPP (FIG. 12G). Based on these data, 62 was designed as a suitable inactive control probe for studying the inhibition of pro-CASP8 by 7. Jurkat cells were treated with 7 or 62 (30 µM, 30 min) prior to addition of FASL or staurosporine (STS) to induce extrinsic and instrinsic apoptosis, respectively. 7, but not 62, completely blocked FASL-induced apoptosis (FIG. 13H and FIG. 21B-C), as well as the proteolytic processing of CASP3, CASP8, and the apoptosis marker PARP (FIG. 13I). In contrast, 7 did not block STS-induced intrinsic apoptosis (FIG. 13H) or the cleavage of PARP and CASP3, although the compound did substantially inhibit cleavage of CASP8 in these cells (FIG. 13I). The non-selective caspase inhibitor VAD-FMK prevented both FASL- and STS-induced apoptosis and associated proteolytic processing events (FIG. 13H, I). Chemical proteomic experiments revealed that 7 fully inhibited CASP8, as well as the related initiator caspase CASP10 (but not other caspases, including CASP2, 3, 6, and 9) in Jurkat cells (FIG. 14A and FIG. 22A). It was confirmed that 7 blocked labeling of pro-CASP10 by 61 with an apparent IC50 value of 4.5 μM (FIG. 22B-D), but did not inhibit active CASP10 as measured by labeling with the Rho-DEVD-AOMK probe ("DEVD" disclosed as SEQ ID NO: 857) (FIG. 21A) or a substrate assay (FIG. 22E). As such, in some instances, 7 blocking CASP8 processing in both FASL- and STS-treated cells supports a model where CASP8 activation mainly occurs through auto-processing in either extrinsic or intrinsic apoptosis, but is only required for the former type of programmed cell death.

In some instances, the respective functions of CASP8 and CASP10 in extrinsic apoptosis and other cellular processes remain poorly understood in large part due to a lack of selective, non-peptidic, and cell-active inhibitors for these enzymes and the absence of animal models for CASP10 (which is not expressed in rodents). In some cases, the potency and selectivity of 7 was improved to address this issue. Conversion of the 4-piperidino moiety to a 3-piperidino group and addition of a p-morpholino substituent to the benzoyl ring of 7 furnished compound 63 that was separated by chiral chromatography into its two purified enantiomers, 63-R (FIG. 4c) and 63-S, the former of which showed substantially improved activity against CASP8 (apparent $IC_{50}$ value of 0.7 μM (95% CI, 0.5-0.8); FIG. 22F-H) and negligible cross-reactivity with CASP10 ($IC_{50}$ value>100 μM; FIG. 22C, D, F). 63-S was much less active against CASP8 (apparent $IC_{50}$ value of 15 μM; FIG. 22G, H) and also inactive against CASP10 (FIG. 14A). With dual CASP8/10 (7) and CASP8-selective (63-R) ligands in hand, we next set out to investigate the biological functions of these proteases.

The effects of caspase ligands in human T cells were evaluated, where both CASP8 and CASP10 are highly expressed (FIG. 22I) in Jurkat cells, which are a commonly studied immortalized human T cell line. It was found that 63-R fully blocked FasL-induced apoptosis in Jurkat cells and did so with greater potency than 7 (FIG. 14B and FIG. 22J) or 63-S (FIG. 22K). Similar results were obtained in HeLa cells, which express CASP8, but not CASP1026 (FIG. 22L). In contrast to these cell line results, FasL-induced apoptosis in primary human T cells showed substantial resistance to 63-R at all tested concentrations and instead was completely inhibited by the dual CASP8/10 ligand 7 (FIG. 14B). It was confirmed by chemical proteomics with probe 61 that 7 blocked both CASP8 and CASP10, while 63-R inhibited CASP8, but not CASP10, in primary human T cells and Jurkat cells (FIG. 14A). Consistent with these cell death results, 7, but not 63-R, prevented proteolytic processing of CASP3 and CASP10 in primary human T cells (FIG. 22M). In some instances, the processing of both CASP8 and the initiator caspase substrate RIP kinase were also preferentially inhibited by 7 versus 63-R (FIG. 22M, indicating that CASP10 also contribute to these proteolytic events in T cells, as has been suggested by biochemical studies.

Example 2

Dimethyl fumarate (DMF) is a drug used to treat autoimmune conditions, including multiple sclerosis and psoriasis. In some instances, the mechanism of action of DMF is unclear, but is proposed to involve covalent modification of proteins and/or serving as a pro-drug that is converted to monomethyl fumarate (MMF). Using an isoTOP-ABPP approach, the mechanism of action of DMF is examined.

Chemical Reagents

Assays were performed with the following reagents: dimethyl fumarate (DMF: 242926; Sigma Aldrich), monomethyl fumarate (MMF; 651419; Sigma Aldrich), dimethyl succinate (DMS; W239607; Sigma Aldrich), and buthionine sulfoximine (BSO: 14484; Caynman Chemical).

Isolation of Primary Human T Cells

All studies using samples from human volunteers follow protocols approved by the TSRI institutional review board. Blood from healthy donors (females aged 30-49) were obtained after informed consent. Peripheral blood mononuclear cells (PBMCs) were purified over Histopaque-1077 gradients (10771; Sigma) following the manufacturer's instructions. Briefly, blood (20×25 mL blood aliquots) were layered over Histopaque-1077 (12.5 mL) and the samples were then fractionated by centrifugation (2000 rpm, 20 min, 20° C., no brake). PBMC's were harvested from the Histopaque-plasma interface and washed twice with PBS. After that time, the T cells were isolated using an EasySep™ Human T Cell Isolation Kit (17951; STEMCELL) per the manufacturer's instructions.

Mice

C57BL/6J and $Nrf2^{-/-}$ mice (Stock No:017009; $Nfe2l2^{tm1Ywk}$: Jackson Labs) were bred and maintained in a closed breeding facility at The Scripps Research Institute and were 6-8 weeks old when used in experiments. All mice were used in accordance with guidelines from the Institutional Animal Care and Use Committee of The Scripps Research Institute.

For the PKCθ studies. C57BL/6 mice and $Prkcq^{-/-}$ mice were housed under specific pathogen-free conditions and used in accordance with a protocol approved by the La Jolla Institute for Allergy and Immunology Animal Care Committee.

Isolation of Primary Mouse T Cells

Spleens were harvested from female mice, perfused with collagenase, and incubated at 37° C. with 5% $CO_2$ for 30 min. After this time, the spleens were homogenized. Cells that passed through a 100 μm cell strainer were collected and washed with RPMI. T cells were isolated from the splenocytes using the EasySep™ Mouse T cell Isolation Kit (19851; STEMCELL) according to manufacturer's instructions.

For the PKCθ studies. $CD4^+$ T cells were isolated by anti-mouse CD4 magnetic particles (L3T4; BD IMag) and were cultured in RPMI-1640 medium (Gibco) supplemented with 10% (vol/vol) heat-inactivated FBS, 2 mM glutamine, 1 mM sodium pyruvate, 1 mM MEM nonessential amino acids, 100 U/mL each of penicillin G and streptomycin (Life Technologies) and recombinant IL-2 (100 U/mL, Biolegend).

T Cell Stimulation 96-well plates were coated with anti-CD3 (1:200; BioXcell) and anti-CD28 (1:500; 302933; BioLegend) in PBS (100 µL/well) overnight at 4° C. The plates were then washed twice with PBS and to each well was added 500,000 primary T cells in 100 µL of RPMI supplemented with 10% FBS, glutamine, and Pen-Strep. Cells were then treated with 100 µL of media containing compound at the indicated concentrations (final well volume of 200 µL). Cells were left at 37° C. in a 5% $CO_2$ incubator for the indicated periods of time and harvested by centrifugation (500 g, 8 min, 4° C.), followed by washing with PBS.

Cellular Analysis and Sorting by Flow Cytometry

Cells were transferred to a round bottom 96-well plate (0720095; Fisher Scientific), harvested by centrifugation (500 g, 3 min, 4° C.), washed with PBS, and stained with LIVE/DEAD fixable cell stain (L23105; ThermoFisher) according to the manufacturer's instructions. Briefly, one vial of LIVE/DEAD stain was resuspended in 50 uL of DMSO and added to 20 mL of PBS. To each well of the 96-well plate was added 200 µL of the stain, and the cells were incubated on ice for 30 min in the dark. After this time, cells were pelleted and washed once with PBS, then stained for cell surface antigens.

Flow cytometry analysis of cell surface antigens was performed with the following antibodies: Pacific Blue-conjugated anti-CD8 (1:25 dilution; clone RPA-T8; BD Biosciences), APC-conjugated anti-CD4 (1:25 dilution; clone RPA-T4; eBioscience), phycoerythrin-conjugated anti-CD25 (1:25 dilution; clone BC96; eBioscience or PC61; BioLegend (PKCθ studies)), FITC-conjugated anti-CD69 (1:25 dilution; clone FN50; eBioscience). All antibodies were diluted in 1% FBS in PBS, and 50 µL of the stain solution was added to each well. Cells were stained for 15 min on ice in the dark, after which cells were harvested by centrifugation (500 g, 3 min, 4° C.), washed with 1% FBS in PBS, and resuspended in 200 µL/well of 4% PFA in PBS. Flow cytometry acquisition was performed with BD FACSDivam-driven BD™ LSR II flow cytometer (Becton, Dickinson and Company). Data was then analyzed with FlowJo software (Treestar Inc.). Data represent mean±SE for four-five experiments per group.

Quantification of Secreted Cytokines by Enzyme-Linked Immunosorbent Assay (ELISA)

T cells were harvested and stimulated as described above. At the indicated time points, cell culture supernatants were collected and IL-2 levels were measured in clear microplates (991427; R&D Systems) according to the manufacturer's instructions (Human IL-2 DuoSet ELISA; DY202; R&D Systems). Plates were read in a Gemini SpectraMax 250 microplate reader set to 450 nm. Data represent mean±SE for four experiments per group.

For the PKCθ studies, aliquots of transduced $Prkcq^{-/-}$ $CD4+$ T cells (1×10$^6$) were stimulated for 48 h with anti-CD3 alone or anti-CD3 plus anti-CD28, and the concentration of IL-2 in culture supernatants was determined by enzyme-linked immunosorbent assay according to the manufacturer's instructions (BioLegend). Briefly, a 96-well plate (Corning Costar) was coated overnight at 4° C. with mAb to IL-2. Triplicates of IL-2 standards and supernatants from cultured cells were then added to the plate, followed by 2 h incubation at room temperature. A biotinylated polyclonal antibody to IL-2 was added to the plate, followed by incubation for 1 h at room temperature, and then Avidin-HRP was added, followed by incubation for 30 min at room temperature. The amount of bound avidin was then assessed with TMB peroxidase that was acidified by 2 N $H_2SO_4$. The absorbance of each well at 450 nm was then measured with a spectrophotometric plate reader (BioTek).

Quantification of Cellular Glutathione (GSH) Levels

Primary human T cells (2.5 million cells/mL, 20 mL per condition) were treated as indicated, harvested by centrifugation (500 g, 8 min, 4° C.), and washed twice with PBS. To the cell pellet was added 75 µL of lysis buffer. After vortexing, the samples were incubated on ice for 15 min, then harvested by centrifugation (16,000 g, 10 min, 4° C.). Protein concentrations were adjusted to at least 5 mg/mL and the assay performed according to manufacturer's instructions (Sigma-Aldrich, CS 1020). Data represent mean±SE for two biological replicates.

Protein Labeling and Click Chemistry

Cells were lysed by sonication and diluted to a concentration of 2 mg protein/mL. Protein concentrations were measured with the Bio-Rad DC™ protein assay reagents A and B (5000113, 5000114; Bio-Rad). 500 µL of proteome sample was treated with 100 µM of IA-alkyne probe using 10 µL of a 10 mM DMSO stock. The labeling reactions were incubated at room temperature for 1 h upon which time the samples were conjugated to isotopically-labeled TEV-cleavable tags (TEV tags) by copper-catalyzed azide-alkyne cycloaddition (CuACC or 'click chemistry'). 60 µL of heavy click chemistry reaction mixture was added to the DMSO-treated control sample and 60 µL of the light reaction mixture was added to the compound-treated sample. The click reaction mixture comprised TEV tags (10 µL of a 5 mM stock, light (fragment treated) or heavy (DMSO treated)), $CuSO_4$ (10 µL of a 50 mM stock in water), and TBTA (30 µL of a 1.7 mM stock in 4:1 tBuOH:DMSO). To this was added TCEP (10 µL of a 50 mM stock). The reaction was performed for 1 h at room temperature.

The light- and heavy-labeled samples were then centrifuged (16,000 g, 5 min, 4° C.) to harvest the precipitated proteins. The resulting pellets were resuspended in 500 µL of cold methanol by sonication and the heavy and light samples combined pairwise. Combined pellets were then washed with cold MeOH, after which the pellet was solubilized in PBS containing 1.2% SDS by sonication. The samples were heated at 90° C. for 5 min and subjected to streptavidin enrichment of probe-labeled proteins, sequential on-bead trypsin and TEV digestion, and liquid chromatography-tandem mass spectrometry (LC-MS/MS) according to the published isoTOP-ABPP protocols.

Peptide and Protein Identification

RAW Xtractor (version 1.9.9.2) was used to extract the MS2 spectra data from the raw files. MS2 data were searched against a reverse concatenated, nonredundant variant of the Human UniProt database (release-2012_11) using the ProLuCID algorithm. Cysteine residues were searched with a static modification for carboxyamidomethylation (+57.02146) and up to one differential modification for either the light or heavy TEV tags (+464.28595 or +470.29976, respectively). Peptides were required to have at least one tryptic terminus and to contain the TEV modification. ProLuCID data was filtered through DTASelect (version 2.0) to achieve a peptide false-positive rate below 1%.

R Value Calculation and Processing

The quantification of heavy/light ratios (isoTOP-ABPP ratios, R values) was performed by in-house CIMAGE software using default parameters (3 MS1's per peak and signal to noise threshold of 2.5). Site-specific engagement of electrophilic compounds was assessed by blockade of IA-alkyne probe labeling. For peptides that showed a=95% reduction in MS1 peak area from the compound-treated proteome (light TEV tag) when compared to the DMSO treated proteome (heavy TEV tag), a maximal ratio of 20 was assigned. Overlapping peptides with the same labeled cysteine (for example, same local sequence around the labeled cysteines but different charge states, MudPIT segment numbers, or tryptic termini) were grouped together, and the median ratio from each group was recorded as the R value of the peptide for that run.

Analysis of Cysteine Conservation

For each human protein containing a DMF-sensitive cysteine, the mouse homolog was identified and the human and mouse sequences aligned using the Align tool on UniProt.

Immunofluorescent Analysis of NF-kB Translocation

Primary human T cells were harvested and stimulated as described above (500,000 cells/well), with concomitant treatment with DMSO or DMF for 60 min. Cells were pelleted (500 g, 3 min, 4° C.), then each well was resuspended in 50 μL PBS and added to Poly-D-lysine coated coverslips (12 mm; 354087; Corning® BioCoat™). Cells were allowed to adhere to the coverslips for 30-60 min at 4° C. Coverslips were transferred to a 6 well plate and fixed with 4% PFA (157-4-100; Electron Microscopy Sciences) at room temperature for 10 min. After washing three times with PBS, cells were permeabilized with 0.1% Triton X-100 in PBS at room temperature for 10 min. Cells were washed three times with PBS, then placed cell-side-up on Parafilm. To each cover slip was added 150 μL of blocking buffer (2% BSA in PBS), and the slides were blocked for 30 min at room temperature.

The blocking buffer was aspirated, coverslips placed face down in 40 μL of antibody buffer (anti-human p65; p65Ab; FivePhoton Biochemicals; 1:500 dilution in blocking buffer), and allowed to stain overnight at 4° C. in a wet chamber. Cover slips were washed three times with PBS, then incubated with 150 μL of secondary antibody (anti-rabbit Alexa Fluor 488; A21441; Life Technologies; 1:200 dilution in PBS) for 2 h at room temperature. After washing three times with PBS, 150 μL of Hoechst counter stain was added (5 μg/mL in PBS) and coverslips were left at room temperature for 30-60 min. Cells were again washed with PBS three times, then stained with Alexa Fluor 555 Phalloidin red (8953S; Cell Signaling; 1:20 dilution in PBS). The coverslips were washed with PBS a final three times, then transferred to SuperFrost Plus slides (12-550-15, Fisherbrand) spotted with 10 μL of Prolong® Gold Antifade Mountant (P36934, ThermoFisher). The circumference of each coverslip was sealed with clear nail polish (72180; Electron Microscopy Sciences).

Images were acquired using a Zeiss 780 laser scanning confocal microscope with a 63× Objective (0.3 um image step size) and the automated stitching module to merged (10% overlap) and create a three dimensional multi-paneled mega image composite. The composite image was gathered as a z-series of at least 9 individual image panels that were auto-merged using zen software. The mega-image composite was projected into a maximum image projection in the zen software then analyzed using the colocalization modual in Zen (Zeiss Inc) and Image Pro Premier (Media Cybernetics). The Mander's Correlation Coefficients (MCC), specifically M1 and M2 between the various combination of fluorescent label (Rhodamine Phalloidin vs NFkB-P65 and Hoechst vs NFkB-p65) are calculated in ZEN (Zeiss inc) per cell and displayed as a percent. Each cell was outlined using the region of interest module and the software then calculated the M1 and M2 correlation coefficients between the two fluorophores and tabulated the results. The fluorescent signal dynamic range and threshold cutoff of real signal was defined by multiple background and secondary controls. Correlation coefficient values were compared using Image Pro Premier (IPP) (Media Cybernetics), where images were imported as raw calibrated czi files and analyzed using a similar module in IPP. Similar results were obtained with both platforms (not shown). Data represent mean±SE for two-three biological replicates.

Subcloning and Mutagenesis

QuikChange site-directed mutagenesis was performed on a pEF4 His A plasmid containing the full length human PKCθ (residues 1-707). The PKCθ insert was excised using BamHI and XhoI, then ligated into a pMIG vector.

PKCθ Retroviral Transduction and Stimulation

Platinum-E packaging cells were plated in a six-well plate in 2 mL RPMI-1640 medium plus 10% FBS. After 24 h, cells were transfected with empty pMIG vector or the appropriate PKCθ-expressing vector DNA (3 μg) with TransIT-LT1 transfection reagent (Mirus Bio). After overnight incubation, the medium was replaced and cultures were maintained for another 24 h. Retroviral supernatants were then collected and filtered, supplemented with 8 μg/mL of polybrene and used to infect CD4$^+$ T cells that had been pre-activated for 24 h with plate-bound monoclonal antibody to CD3 (8 μg/mL) and CD28 (8 μg/mL). After centrifuging plates for 1.5-2 h at 2.000 r.p.m., cell supernatants were replaced by fresh RPMI-1640 supplemented with 10% FBS and recombinant IL-2 (100 U/mL). Cells were incubated for another 24 h at 37° C. On day 3, cells were washed, moved to new plates and cultured in RPMI-1640 medium containing 10% FBS and recombinant IL-2 (100 U/mL) without stimulation for 2 additional days before restimulation with mAb to CD3 alone or plus mAb to CD28.

PKCθ Immunoprecipitation and Immunoblot Analysis

Cells were lysed in 1% (wt/vol) digitonin (D141. Sigma) lysis buffer (20 mM Tris-HCl, pH7.5, 150 mM NaCl, 5 mM EDTA) supplemented with protease inhibitors (10 μg/mL aprotinin, 10 μg/mL leupeptin and 1 mM PMSF) and phosphatase inhibitors (5 mM sodium pyrophosphate and 1 mM Na$_3$VO$_4$). Supernatants were incubated 2 h with 1 μg anti-CD28 mAb, and proteins were immunoprecipitated overnight at 4° C. with protein G-Sepharose beads (GE Healthcare). The immunoprecipitated proteins were resolved by SDS-PAGE, transferred onto a PVDF membrane and probed overnight at 4° C. with primary antibodies, followed by incubation for 1 h at room temperature with horseradish peroxidase (HRP)-conjugated secondary antibodies. Signals were visualized by enhanced chemiluminescence (ECL; GE Healthcare) and were exposed to X-ray film. Densitometry analysis was performed with ImageJ software. Immunoblotting antibodies to CD28 (C-20) and PKCθ (C-19) were obtained from Santa Cruz Biotechnology.

DMF, but not MMF, Inhibits T Cell Activation

Multiple sclerosis is an autoimmune disease with a prominent T cell component; as such, it was reasoned that DMF in some cases impact primary T cell activation. Consistent with this, previous reports have shown that DMF inhibits cytokine release from mouse splenocytes and promotes a Th2 phenotype via induction of IL-10-producing type II dendritic cells. The effects of DMF and MMF (FIG. 23A) were tested on cytokine release from primary human T cells activated with anti-CD3, anti-CD28 antibodies. Secretion of IL-2 was strongly inhibited by DMF, but not MMF (FIG. 23B). DMF, but not MMF or the non-electrophilic analogue dimethyl succinate (DMS, FIG. 23A) also blocked the expression of the early activation markers CD25 (FIG. 23C, D) and CD69 (FIG. 23E) in anti-CD3, anti-CD28-stimulated T cells. The blockade of T cell activation by DMF was concentration-dependent, with 10, 25 and 50 μM of the drug producing marginal/negligible, partial, and near-complete inhibition, respectively (FIG. 23B, D, E). In some instances, the effects of DMF on cytokine release and activation markers occurred at concentrations of the drug that did not impair T cell viability (FIG. 24). Similar results were obtained with primary splenic T cells from C57BL/6 mice, the activation of which was also suppressed by DMF, but not MMF or DMS (FIG. 25). Of note, the inhibitory effects of DMF were reduced if the drug was added two hours after anti-CD3, anti-CD28 stimulation and completely ablated if the drug was added six hours after stimulation (FIG. 23F), suggesting that DMF inhibits an early event(s) in the T cell activation pathway DMF Effects on T Cell Activation are Independent of Nrf2 and GSH DMF is thought to produce neuroprotective effects through activating the Nrf2-Keap1 pathway, but whether this pathway contributes to the immunomodulatory effects of DMF is unclear. A recent study showed that DMF inhibits pro-inflammatory cytokine release from primary mouse splenocytes and this effect was comparable in wild type and Nrf2(−/−) splenocytes (Gillard, et al., "DMF, but not other fumarates, inhibits NF-kappaB activity in vitro in an Nrf2-independent manner," *J. Neuroimmunol.* 283, 74-85 (2015)). Consistent with this, it was found that the activation of Nrf2(+/+) and (−/−) T cells was similarly sensitive to inhibition by DMF (FIG. 26A). In some instances. DMF also impair T cell activation through depleting glutathione (GSH), and, indeed, DMF-treated primary human T cells showed a significant decrease in cellular GSH content (FIG. 26B). Significant reductions in GSH were, however, also observed with the GSH synthesis inhibitor buthionine sulfoximine (BSO), which had no effect on T cell activation (FIG. 26C, D). In some cases, these data indicate that the blockade of T cell activation by DMF involves processes other than Nrf2 activation or GSH depletion.

Chemical Proteomic Discovery of DMF-Sensitive Cys Residues in T Cells

The inhibition of T cell activation by DMF, but not the non-electrophilic analogues MMF and DMS, pointed to a mechanism that involves covalent reactivity with one or more proteins important for T cell function. As such, a globally inventory of DMF-sensitive Cys residues in primary human and mouse T cells were examined using the quantitative chemical proteomic platform isoTOP-ABPP. In this method, DMF is evaluated for its ability to block the reactivity of proteinaceous Cys residues with the general electrophilic probe iodoacetamide-alkyne (IA-alkyne). Using isotopically differentiated azide-biotin tags (containing a TEV protease-cleavable linker), Cys residues are identified and comparatively quantified for their IA-reactivity in cells treated with DMF versus DMSO control. Primary advantages of the isoTOP-ABPP platform include: 1) the competing electrophile does not itself need to be chemically altered for target identification, which is particularly beneficial when studying very small compounds like DMF; and 2) isotopic labeling occurs late in the sample processing, which facilitates the quantitative analysis of primary cells and tissues that are not readily amenable to metabolic labeling.

The isoTOP-ABPP method was performed on primary human T cells treated with DMSO or DMF (50 µM, 4 h). Five independent replicates were performed, and the total aggregate number of unique quantified peptides and proteins began to plateau by the fourth and fifth replicate (FIG. 28), indicating that we approached maximal proteomic coverage of IA-reactive Cys residues in human T cells under the conditions employed. Of the more than 2400 quantified Cys residues, a small fraction (~40) showed substantial reductions (>four-fold; isoTOP-ABPP ratio (R value)>4) in IA-alkyne labeling in DMF-treated T cells (FIG. 27A, and Tables 7-9). Similar isoTOP-ABPP analyses revealed that none of the ~40 DMF-sensitive Cys residues were altered by MMF (50 µM, 4 h) or BSO (2.5 mM, 4 h) treatment, which, in general, affected the reactivity of very few Cys residues across the T cell proteome (FIG. 27A, B and FIG. 29, respectively). The Cys residues targeted by DMF exhibited concentration—(FIG. 27C and Tables 8-9) and time (FIG. 27D) dependent increases in DMF sensitivity, as revealed by isoTOP-ABPP experiments performed with human T cells treated with lower concentrations of DMF (10 and 25 µM, 4 h) or for shorter periods of time (50 µM DMF, 1 or 2 h). Of note, very few DMF-sensitive Cys residues were detected in T cells treated with 10 µM DMF, a concentration of the drug that also had limited impact T cell activation (FIG. 23B, D, E). These concentration- and time-dependent studies uncovered another ~10 DMFsensitive Cys residues that were not detected in the original 50 µM/4 h isoTOP-ABPP experiments, likely reflecting the stochastic nature of peptide discovery in data dependent MS experiments.

The possibility that some of the alterations in Cys reactivity following DMF treatment could reflect changes in protein expression was considered; however, multiple Cys residues were quantified by isoTOP-ABPP for the majority of proteins harboring DMF-sensitive Cys residues, and, in most of these cases, the additional quantified Cys residues were clearly unaffected by DMF treatment (FIG. 27E). The DNAactivated protein kinase PRKDC was shown as one representative example, for which IA-alkyne reactivity was quantified for several Cys residues, only one of which (C4045) was blocked by DMF (FIG. 27F). These results indicate that DMF directly impaired the IAalkyne reactivity of specific Cys residues rather than indirectly affecting protein expression in human T cells.

Conservation of DMF-Sensitive Cys Residues in Human and Mouse T Cells

Considering that DMF impaired the activation of both human and mouse T cells, it was surmised that at least a subset of Cys residues potentially important for mediating DMF action were conserved in humans and mice. Consistent with this, approximately two-thirds of the DMF-sensitive Cys residues discovered in human T cells are conserved in mice (FIG. 30A and Table 7). The isoTOP-ABPP experiments were performed on mouse T cells treated with DMF (50 µM, 4 h) and found that the vast majority (>80%) of the conserved, quantified Cys residues sensitive to DMF in human T cells were also blocked (R values>4) by this drug in mouse T cells (FIG. 30B and Tables 8-9). These results indicate that DMF targets a similar array of Cys residues in human and mouse T cells, pointing to a specific set of proteins as candidate sites of action for this electrophilic drug.

The proteins containing DMF-sensitive Cys residues, as a whole, originated from several functional classes, including enzymes, channels, transporters, scaffolding proteins, and transcriptional regulators (FIG. 30C). Among these proteins were several with important immune functions (Table 7). DMF-sensitive Cys residues were found, for instance, in multiple proteins that are either components or regulators of the NF-κB signaling pathway, including IκB kinase β (IKKβ or IKBKB), protein kinase C-θ (PKCθ or PRKCQ), and TNFAIP3 (Table 7). Consistent with these sites of DMF action and potentially others within the NF-κB pathway, it was found that DMF treatment blocked p65 nuclear translocation (FIG. 31), as has been shown in other cell types. DMF-sensitive Cys residues were also found in: 1) the adenosine deaminase enzyme ADA, deleterious mutations in which cause severe combined immunodeficiency in humans, 2) the transcription factors interferon regulatory factors-4 (IRF4) and -8 (IRF8), and 3) the immunomodulatory cytokine IL-16 (Table 7).

DMF Perturbs a CXXC Motif Critical for PKCθ-CD28 Interactions and T Cell Activation PKCθ is a key kinase involved in T cell signaling at the immunological synapse where engagement of the T cell receptor and CD28 co-receptor initiates activation of multiple downstream pathways, including NF-κB. T cells from PKCθ(−/−) mice are defective in early activation. The isoTOP-ABPP analysis identified two DMFsensitive Cys residues—C14 and C17—in human (FIG. 32A) and mouse (FIG. 33A) T cells, and these Cys residues showed time- and concentration-dependent increases in DMF sensitivity (FIG. 33B, C), but were not affected by MMF treatment (FIG. 33D). Because C14 and C17 are found on the same tryptic peptide, it was difficult to distinguish whether one or both residues was sensitive to DMF treatment, but, in certain isoTOP-ABPP experiments, this tryptic peptide appeared to migrate as two adjacent peaks, both of which showed DMF sensitivity (FIG. 32A), suggesting that the IA-alkyne reactivity of both C14 and C17 is blocked by DMF treatment. The isoTOP-ABPP experiments also identified a third Cys in PKCθ (C322) that was unaffected by DMF treatment (FIG. 32A), indicating that DMF caused reductions in C14/17 reactivity rather than changes in PKCθ expression. C14 and C17 form a CXXC motif found in the C2 domain of PKCθ, but not other PKC isoforms (FIG. 32B, C). The C2 domain of PKCθ was recently shown to bind phosphotyrosine-containing peptides and has been postulated to stabilize plasma membrane association of PKCθ at the immunological synapse. Upon TCR/CD28 stimulation, PKCθ is recruited to the immunological synapse where it interacts with the CD28 co-receptor by associating with the CD28 cytoplasmic tail. It was found that DMF, but not MMF, blocked the interaction between PKCθ and CD28 in mouse T cells (FIG. 32D). A retroviral transduction was used to reconstitute PKCθ(−/−) T cells with either WT- or a C14S/C17S-PKCθ mutant and found that the mutant protein failed to associate with CD28 (FIG. 32E). PKCθ(−/−) T cells reconstituted with the C14S/C17SPKCθ mutant also showed impaired expression of CD25 (FIG. 32F) and IL-2 release (FIG. 32G) compared to cells reconstituted with WT PKCθ following anti-CD3, anti-CD28 treatment. Taken together, these data indicate that the C14/C17 motif within the C2 domain of PKCθ regulates localization of this kinase to the immunological synapse, and disruption of this motif by DMF or genetic mutation impairs T cell activation.

Sensitive Cysteine Residue Sites in DMF Toward Probe ADA

The DMFsensitive Cys residue C75 is located between two amino acids—G74 and R76—that, when mutated in humans, contribute to an immunosuppressive phenotype. The amino acid 74-76 region of ADA is over 25 angstroms from the active site of the enzyme (FIG. 34), suggesting that it performs a non-catalytic function possibly perturbed by DMF reactivity. The DMF-sensitive Cys in IKBKB is located in the leucine-zipper domain and is distinct from another electrophile-sensitive Cys residue C179 found in the active site of this kinase.

Table 1 illustrates a list of liganded cysteines and their reactivity profiles with the fragment eletrophile library from isoTOP-ABPP experiments performed in cell lysates (in vitro). Table 1 further shows the accession number (or the protein identifier) of the protein.

TABLE 1A

| Identifier | Protein | SEQ ID NO: | 2_500 μM_ invitro_ 231 | 2_500 μM_ invitro_ ramos | 3_500 μM_ invitro_ 231 | 3_500 μM_ invitro_ ramos | 4_250 μM_ invitro_ 231 | 4_250 μM_ invitro_ ramos |
|---|---|---|---|---|---|---|---|---|
| Q99873_C109 | PRMT1 Protein arginine N-methyltransferase 1 | 17 | 3.1 | 12.6 | 1.3 | 1.8 | 1.1 | 0.2 |
| P24752_C119 | ACAT1 Acetyl-CoA acetyltransferase, mitochondrial | 22 | 3.9 | 3.2 | 2.1 | 5.3 | 1.8 | 0.2 |
| P09211_C48 | GSTP1 Glutathione S-transferase P | 25 | 3.1 | 1.6 | 2.9 | 1.7 | 3.2 | 0.5 |
| O14980_C34 | XPO1 Exportin-1 | 28 | 2.8 | 4.6 | 1.4 | 1.6 | 1.0 | 0.2 |
| P24752_C196 | ACAT1 Acetyl-CoA acetyltransferase, mitochondrial | 33 | 12.4 | 9.3 | 1.7 | 3.1 | 1.9 | 0.5 |
| Q15084_C55 | PDIA6 Protein disulfide-isomerase A6 | 51 | 6.3 | 7.1 | 17.9 | 14.9 | 1.3 | 1.2 |
| P24752_C413 | ACAT1 Acetyl-CoA acetyltransferase, mitochondrial | 56 | 18.1 | — | 15.3 | 20.0 | 3.3 | — |
| P63244_C182 | GNB2L1 Guanine nucleotide-binding protein subunit beta-2- | 85 | 1.2 | 1.2 | 20.0 | 4.7 | 0.9 | — |
| P24752_C126 | ACAT1 Acetyl-CoA acetyltransferase, mitochondrial | 89 | 20.0 | — | 2.6 | 2.4 | 2.1 | 1.2 |
| Q15084_C190 | PDIA6 Protein disulfide-isomerase A6 | 96 | — | 15.4 | 19.9 | 13.1 | 1.8 | 1.2 |
| Q8TAQ2_C145 | SMARCC2 SWI/SNF complex subunit SMARCC2 | 119 | 8.5 | 14.0 | 9.7 | 6.6 | 1.3 | — |
| P68036_C86 | UBE2L3 Ubiquitin-conjugating enzyme E2 L3 | 120 | 2.8 | 2.5 | 1.2 | 3.0 | 1.2 | — |
| P15374_C95 | UCHL3 Ubiquitin carboxyl-terminal hydrolase isozyme L3 | 146 | — | 1.8 | 1.7 | 1.4 | — | 0.9 |
| Q16763_C118 | UBE2S Ubiquitin-conjugating enzyme E2 S | 187 | 4.2 | 6.9 | 1.3 | 1.5 | 1.2 | — |
| Q16822_C306 | PCK2 Phosphoenolpyruvate carboxykinase | 192 | — | — | 10.6 | 0.9 | 2.2 | — |

TABLE 1A-continued

| | | | | | | | | |
|---|---|---|---|---|---|---|---|---|
| O14980_C528 | XPO1 Exportin-1 DLLGLCEQK K.DLLGLC*EQKR.G | 218 | 4.9 | 3.1 | 20.0 | 20.0 | 0.9 | 1.1 |
| O00170_C122 | AIP AH receptor-interacting protein | 240 | 12.5 | 6.7 | 7.0 | 3.1 | 2.5 | 0.3 |
| O75874_C269 | IDH1 Isocitrate dehydrogenase | 260 | 20.0 | — | 20.0 | 1.0 | 1.6 | 0.6 |
| O75362_C286 | ZNF217 Zinc finger protein 217 | 268 | 20.0 | 20.0 | 1.4 | — | 1.7 | — |
| P40763_C259 | STAT3 Signal transducer and activator of transcription 3 | 283 | — | — | 2.5 | 2.9 | 2.0 | 1.9 |
| Q9Y3Z3_C522 | SAMHD1 SAM domain and HD domain-containing protein 1 | 288 | — | 4.0 | 2.6 | — | 1.5 | — |
| P16455_C150 | MGMT Methylated-DNA-protein-cysteine methyltransferase | 291 | — | 20.0 | — | 17.1 | — | 6.9 |
| Q96GG9_C115 | DCUN1D1 DCN1-like protein 1 | 293 | — | 20.0 | — | 5.5 | — | — |
| P00813_C75 | ADA Adenosine deaminase | 296 | — | 7.3 | — | 1.5 | — | 0.1 |
| Q14790_C360 | CASP8 Caspase-8 | 335 | 9.8 | — | 3.3 | 2.3 | 12.3 | — |
| Q15306_C194 | IRF4 Interferon regulatory factor 4 | 338 | — | — | — | 20.0 | — | — |
| Q6L8Q7_C108 | PDE12 2,5-phosphodiesterase 12 | 339 | — | 5.1 | 3.6 | 1.8 | — | — |
| P48735_C308 | IDH2 Isocitrate dehydrogenase | 360 | 1.4 | — | 2.2 | — | 0.7 | — |
| Q86UV5_C39 | USP48 Ubiquitin carboxyl-terminal hydrolase 48 | 381 | — | 7.1 | 1.8 | 1.5 | 1.4 | 1.4 |
| P50851_C1704 | LRBA Lipopolysaccharide-responsive and beige-like ancho | 388 | — | 3.4 | — | 3.6 | — | 1.5 |
| O94953_C694 | KDM4B Lysine-specific demethylase 4B | 395 | 20.0 | 5.1 | 20.0 | 7.4 | 20.0 | — |
| P19447_C342 | ERCC3 TFIIH basal transcription factor complex helicase | 402 | 20.0 | — | 12.1 | — | 1.6 | 1.1 |
| Q00535_C157 | CDK5 Cyclin-dependent kinase 5 | 407 | — | 3.2 | — | 20.0 | — | 1.3 |
| Q9UPT9_C171 | USP22 Ubiquitin carboxyl-terminal hydrolase 22 | 413 | — | 7.1 | — | — | — | 4.0 |
| Q9HB90_C377 | RRAGC Ras-related GTP-binding protein C | 417 | 20.0 | — | 3.7 | — | 3.5 | — |
| P50851_C2675 | LRBA Lipopolysaccharide-responsive and beige-like ancho | 426 | — | 3.0 | — | 5.1 | 1.1 | — |
| Q9NYL2_C22 | MLTK Mitogen-activated protein kinase kinase kinase MLT | 430 | 20.0 | — | 1.8 | — | 20.0 | — |
| Q5T1V6_C414 | DDX59 Probable ATP-dependent RNA helicase DDX59 | 439 | 20.0 | 20.0 | — | 6.0 | — | — |
| Q9HB90_C358 | RRAGC Ras-related GTP-binding protein C | 452 | 20.0 | 20.0 | 1.2 | — | 1.5 | — |
| P16455_C145 | MGMT Methylated-DNA-protein-cysteine methyltransferase | 470 | — | 20.0 | — | 20.0 | — | 20.0 |
| Q9Y5T5_C205 | USP16 Ubiquitin carboxyl-terminal hydrolase 16 | 474 | 20.0 | — | — | 8.8 | — | 20.0 |
| Q02556_C306 | IRF8 Interferon regulatory factor 8 | 513 | — | — | — | 5.6 | — | — |
| Q15910_C503 | EZH2 Histone-lysine N-methyltransferase EZH2 | 557 | — | 2.8 | — | 2.0 | — | 1.5 |
| Q96RU2_C171 | USP28 Ubiquitin carboxyl-terminal hydrolase 28 | 569 | — | 1.1 | — | 1.7 | — | — |
| Q16877_C159 | PFKFB4 6-phosphofructo-2-kinase/fructose-2,6-bisphosphata | 582 | — | — | — | 12.9 | 1.4 | — |
| P04150_C302 | NR3C1 Glucocorticoid receptor | 600 | 2.3 | — | 7.6 | — | — | — |
| Q96JH7_C219 | VCPIP1 Deubiquitinating protein VCIP135 | 601 | — | 1.1 | 20.0 | 15.1 | — | — |
| P48200_C137 | IREB2 Iron-responsive element-binding protein 2 | 603 | — | 10.5 | — | — | — | — |
| O00622_C39 | CYR61 Protein CYR61 | 612 | — | — | 4.0 | — | 2.8 | — |
| Q5T1V6_C453 | DDX59 Probable ATP-dependent RNA helicase DDX59 | 620 | 20.0 | 20.0 | 20.0 | — | — | — |
| P51617_C608 | IRAK1 Interleukin-1 receptor-associated kinase 1 | 656 | — | 2.5 | — | 20.0 | — | — |
| P42575_C370 | CASP2 Caspase-2 | 661 | — | — | — | 7.4 | — | — |
| P09086_C346 | POU2F2 POU domain, class 2, transcription factor 2 | 663 | — | — | 1.7 | 5.5 | — | — |
| Q09472_C1738 | EP300 Histone acetyltransferase p300 | 676 | — | 12.7 | — | — | — | — |
| Q01201_C109 | RELB Transcription factor RelB | 681 | 20.0 | 20.0 | — | — | — | — |

TABLE 1A-continued

| Identifier | Protein | | | | | |
|---|---|---|---|---|---|---|
| Q70CQ2_C741 | USP34 Ubiquitin carboxyl-terminal hydrolase 34 | 688 | — | — | — | 3.2 | — | — |
| P41226_C599 | UBA7 Ubiquitin-like modifier-activating enzyme 7 | 702 | — | — | — | — | — | 20.0 |
| P14598_C378 | NCF1 Neutrophil cytosol factor 1 | 705 | — | 4.4 | — | 2.1 | — | 1.4 |
| Q9C0C9_C375 | UBE2O Ubiquitin-conjugating enzyme E2O | 707 | — | — | 9.8 | 4.1 | — | — |
| O00622_C134 | CYR61 Protein CYR61 | 713 | — | — | 20.0 | — | — | — |
| O00541_C361 | PES1 Pescadillo homolog | 718 | — | — | 1.5 | — | — | — |
| P43403_C117 | ZAP70 Tyrosine-protein kinase ZAP-70 | 726 | — | — | — | — | — | — |
| Q96FA3_C282 | PELI1 E3 ubiquitin-protein ligase pellino homolog 1 | 729 | — | — | — | — | — | — |
| Q9UPT9_C44 | USP22 Ubiquitin carboxyl-terminal hydrolase 22 | 737 | — | — | — | — | — | — |
| Q9Y4C1_C251 | KDM3A Lysine-specific demethylase 3A | 753 | — | — | 4.4 | 4.0 | — | — |
| Q70CQ2_C1090 | USP34 Ubiquitin carboxyl-terminal hydrolase 34 | 761 | — | — | — | 19.7 | — | — |
| O00622_C70 | CYR61 Protein CYR61 | 762 | — | — | 20.0 | — | — | — |
| P04150_C622 | NR3C1 Glucocorticoid receptor | 765 | — | — | 20.0 | — | — | — |

| Identifier | Protein | SEQ ID NO: | 2_500 uM_invitro_231 | 2_500 uM_invitro_ramos | 3_500 uM_invitro_231 | 3_500 uM_invitro_ramos | 4_250 uM_invitro_231 | 4_250 uM_invitro_ramos |
|---|---|---|---|---|---|---|---|---|
| Q99873_C109 | PRMT1 Protein arginine N-methyltransferase 1 | 17 | 3.1 | 12.6 | 1.3 | 1.8 | 1.1 | 0.2 |
| P24752_C119 | ACAT1 Acetyl-CoA acetyltransferase, mitochondrial | 22 | 3.9 | 3.2 | 2.1 | 5.3 | 1.8 | 0.2 |
| P09211_C48 | GSTP1 Glutathione S-transferase P | 25 | 3.1 | 1.6 | 2.9 | 1.7 | 3.2 | 0.5 |
| O14980_C34 | XPO1 Exportin-1 | 28 | 2.8 | 4.6 | 1.4 | 1.6 | 1.0 | 0.2 |
| P24752_C196 | ACAT1 Acetyl-CoA acetyltransferase, mitochondrial | 33 | 12.4 | 9.3 | 1.7 | 3.1 | 1.9 | 0.5 |
| Q15084_C55 | PDIA6 Protein disulfide-isomerase A6 | 51 | 6.3 | 7.1 | 17.9 | 14.9 | 1.3 | 1.2 |
| P24752_C413 | ACAT1 Acetyl-CoA acetyltransferase, mitochondrial | 56 | 18.1 | — | 15.3 | 20.0 | 3.3 | — |
| P63244_C182 | GNB2L1 Guanine nucleotide-binding protein subunit beta-2- | 85 | 1.2 | 1.2 | 20.0 | 4.7 | 0.9 | — |
| P24752_C126 | ACAT1 Acetyl-CoA acetyltransferase, mitochondrial | 89 | 20.0 | — | 2.6 | 2.4 | 2.1 | 1.2 |
| Q15084_C190 | PDIA6 Protein disulfide-isomerase A6 | 96 | — | 15.4 | 19.9 | 13.1 | 1.8 | 1.2 |
| Q8TAQ2_C145 | SMARCC2 SWI/SNF complex subunit SMARCC2 | 119 | 8.5 | 14.0 | 9.7 | 6.6 | 1.3 | — |
| P68036_C86 | UBE2L3 Ubiquitin-conjugating enzyme E2 L3 | 120 | 2.8 | 2.5 | 1.2 | 3.0 | 1.2 | — |
| P15374_C95 | UCHL3 Ubiquitin carboxyl-terminal hydrolase isozyme L3 | 146 | — | 1.8 | 1.7 | 1.4 | — | 0.9 |
| Q16763_C118 | UBE2S Ubiquitin-conjugating enzyme E2 S | 187 | 4.2 | 6.9 | 1.3 | 1.5 | 1.2 | — |
| Q16822_C306 | PCK2 Phosphoenolpyruvate carboxykinase | 192 | — | — | 10.6 | 0.9 | 2.2 | — |
| O14980_C528 | XPO1 Exportin-1 DLLGLCEQK K.DLLGLd*EQKR.G | 218 | 4.9 | 3.1 | 20.0 | 20.0 | 0.9 | 1.1 |
| O00170_C122 | AIP AH receptor-interacting protein | 240 | 12.5 | 6.7 | 7.0 | 3.1 | 2.5 | 0.3 |
| O75874-C269 | IDH1 Isocitrate dehydrogenase | 260 | 20.0 | — | 20.0 | 1.0 | 1.6 | 0.6 |

| Identifier | Protein | SEQ ID NO: | 2_500 μM_invitro_231 | 2_500 μM_invitro_ramos | 3_500 μM_invitro_231 | 3_500 μM_invitro_ramos | 4_250 μM_invitro_231 | 4_250 μM_invitro_ramos |
|---|---|---|---|---|---|---|---|---|
| O75362_C286 | ZNF217 Zinc finger protein 217 | 268 | 20.0 | 20.0 | 1.4 | — | 1.7 | — |
| P40763_C259 | STAT3 Signal transducer and activator of transcription 3 | 283 | — | — | 2.5 | 2.9 | 2.0 | 1.9 |
| Q9Y3Z3_C522 | SAMHD1 SAM domain and HD domain-containing protein 1 | 288 | — | 4.0 | 2.6 | — | 1.5 | — |

TABLE 1A-continued

| | | | | | | | | |
|---|---|---|---|---|---|---|---|---|
| P16455_C150 | MGMT Methylated-DNA-protein-cysteine methyltransferase | 291 | — | 20.0 | — | 17.1 | — | 6.9 |
| Q96GG9_C115 | DCUN1D1 DCN1-like protein 1 | 293 | — | 20.0 | — | 5.5 | — | — |
| P00813_C75 | ADA Adenosine deaminase | 296 | — | 7.3 | — | 1.5 | — | 0.1 |
| Q14790_C360 | CASP8 Caspase-8 | 335 | 9.8 | — | 3.3 | 2.3 | 12.3 | — |
| Q15306_C194 | IRF4 Interferon regulatory factor 4 | 338 | — | — | — | 20.0 | — | — |
| Q6L8Q7_C108 | PDE12 2,5-phosphodiesterase 12 | 339 | — | 5.1 | 3.6 | 1.8 | — | — |
| P48735_C308 | IDH2 Isocitrate dehydrogenase | 360 | 1.4 | — | 2.2 | — | 0.7 | — |
| Q86UV5_C39 | USP48 Ubiquitin carboxyl-terminal hydrolase 48 | 381 | — | 7.1 | 1.8 | 1.5 | 1.4 | 1.4 |
| P50851_C1704 | LRBA Lipopolysaccharide-responsive and beige-like ancho | 388 | — | 3.4 | — | 3.6 | — | 1.5 |
| O94953_C694 | KDM4B Lysine-specific demethylase 4B | 395 | 20.0 | 5.1 | 20.0 | 7.4 | 20.0 | — |
| P19447_C342 | ERCC3 TFIIH basal transcription factor complex helicase | 402 | 20.0 | — | 12.1 | — | 1.6 | 1.1 |
| Q00535_C157 | CDK5 Cyclin-dependent kinase 5 | 407 | — | 3.2 | — | 20.0 | — | 1.3 |
| Q9UPT9_C171 | USP22 Ubiquitin carboxyl-terminal hydrolase 22 | 413 | — | 7.1 | — | — | — | 4.0 |
| Q9HB90_C377 | RRAGC Ras-related GTP-binding protein C | 417 | 20.0 | — | 3.7 | — | 3.5 | — |
| P50851_C2675 | LRBA Lipopolysaccharide-responsive and beige-like ancho | 426 | — | 3.0 | — | 5.1 | 1.1 | — |
| Q9NYL2_C22 | MLTK Mitogen-activated protein kinase kinase kinase MLT | 430 | 20.0 | — | 1.8 | — | 20.0 | — |
| Q5T1V6_C414 | DDX59 Probable ATP-dependent RNA helicase DDX59 | 439 | 20.0 | 20.0 | — | 6.0 | — | — |
| Q9HB90_C358 | RRAGC Ras-related GTP-binding protein C | 452 | 20.0 | 20.0 | 1.2 | — | 1.5 | — |
| P16455_C145 | MGMT Methylated-DNA-protein-cysteine methyltransferase | 470 | — | 20.0 | — | 20.0 | — | 20.0 |
| Q9Y5T5_C205 | USP16 Ubiquitin carboxyl-terminal hydrolase 16 | 474 | 20.0 | — | — | 8.8 | — | 20.0 |
| Q02556_C306 | IRF8 Interferon regulatory factor 8 | 513 | — | — | — | 5.6 | — | — |
| Q15910_C503 | EZH2 Histone-lysine N-methyltransferase EZH2 | 557 | — | 2.8 | — | 2.0 | — | 1.5 |
| Q96RU2_C171 | USP28 Ubiquitin carboxyl-terminal hydrolase 28 | 569 | — | 1.1 | — | 1.7 | — | — |
| Q16877_C159 | PFKFB4 6-phosphofructo-2-kinase/fructose-2,6-bisphospha | 582 | — | — | — | 12.9 | 1.4 | — |
| P04150_C302 | NR3C1 Glucocorticoid receptor | 600 | 2.3 | — | 7.6 | — | — | — |
| Q96JH7_C219 | VCPIP1 Deubiquitinating protein VCIP135 | 601 | — | 1.1 | 20.0 | 15.1 | — | — |
| P48200_C137 | IREB2 Iron-responsive element-binding protein 2 | 603 | — | 10.5 | — | — | — | — |
| O00622_C39 | CYR61 Protein CYR61 | 612 | — | — | 4.0 | — | 2.8 | — |
| Q5T1V6_C453 | DDX59 Probable ATP-dependent RNA helicase DDX59 | 620 | 20.0 | 20.0 | 20.0 | — | — | — |
| P51617_C608 | IRAK1 Interleukin-1 receptor-associated kinase 1 | 656 | — | 2.5 | — | 20.0 | — | — |
| P42575_C370 | CASP2 Caspase-2 | 661 | — | — | — | 7.4 | — | — |
| P09086_C346 | POU2F2 POU domain, class 2, transcription factor 2 | 663 | — | — | 1.7 | 5.5 | — | — |
| Q09472_C1738 | EP300 Histone acetyltransferase p300 | 676 | — | 12.7 | — | — | — | — |
| Q01201_C109 | RELB Transcription factor RelB | 681 | 20.0 | 20.0 | — | — | — | — |
| Q70CQ2_C741 | USP34 Ubiquitin carboxyl-terminal hydrolase 34 | 688 | — | — | — | 3.2 | — | — |
| P41226_C599 | UBA7 Ubiquitin-like modifier-activating enzyme 7 | 702 | — | — | — | — | — | 20.0 |
| P14598_C378 | NCF1 Neutrophil cytosol factor 1 | 705 | — | 4.4 | — | 2.1 | — | 1.4 |
| Q9C0C9_C375 | UBE2O Ubiquitin-conjugating enzyme E2O | 707 | — | — | — | 9.8 | 4.1 | — |
| O00622_C134 | CYR61 Protein CYR61 | 713 | — | — | 20.0 | — | — | — |
| O00541_C361 | PES1 Pescadillo homolog | 718 | — | — | 1.5 | — | — | — |

TABLE 1A-continued

| | | | | | | | | |
|---|---|---|---|---|---|---|---|---|
| P43403_C117 | ZAP70 Tyrosine-protein kinase ZAP-70 | 726 | — | — | — | — | — | — |
| Q96FA3_C282 | PELI1 E3 ubiquitin-protein ligase pellino homolog 1 | 729 | — | — | — | — | — | — |
| Q9UPT9_C44 | USP22 Ubiquitin carboxyl-terminal hydrolase 22 | 737 | — | — | — | — | — | — |
| Q9Y4C1_C251 | KDM3A Lysine-specific demethylase 3A | 753 | — | — | 4.4 | 4.0 | — | — |
| Q70CQ2_C1090 | USP34 Ubiquitin carboxyl-terminal hydrolase 34 | 761 | — | — | — | 19.7 | — | — |
| O00622_C70 | CYR61 Protein CYR61 | 762 | — | — | 20.0 | — | — | — |
| P04150_C622 | NR3C1 Glucocorticoid receptor | 765 | — | — | 20.0 | — | — | — |

TABLE 1B

| Indentifier | 5_500 µM_invitro_231 | 5_500 µM_invitro_ramos | 6_500 µM_invitro_231 | 7_500 µM_invitro_231 | 7_500 µM_invitro_ramos | 8_500 µM_invitro_231 | 8_500 µM_invitro_ramos | 9_500 µM_invitro_231 | 9_500 µM_invitro_ramos | 10_500 µM_invitro_231 |
|---|---|---|---|---|---|---|---|---|---|---|
| Q99873_C109 | 0.9 | 1.3 | 1.1 | 1.1 | 1.1 | 1.2 | 1.2 | 1.0 | 1.5 | 2.3 |
| P24752_C119 | 1.8 | 2.4 | 1.1 | 2.3 | 2.0 | 1.8 | 0.7 | 2.2 | 3.1 | 1.5 |
| P09211_C48 | 2.2 | 2.4 | 1.2 | 1.8 | 0.9 | 2.6 | 2.0 | 2.3 | 1.4 | 1.4 |
| O14980_C34 | 1.1 | 1.2 | 1.2 | 1.7 | 1.8 | 2.4 | 1.5 | 1.2 | 1.1 | 1.2 |
| P24752_C196 | 1.5 | 2.2 | 1.0 | 1.9 | — | 2.7 | 1.5 | 3.1 | 2.1 | 2.5 |
| Q15084_C55 | 0.9 | 1.1 | 1.0 | 1.0 | — | 4.7 | 2.2 | 1.4 | 1.0 | 20.0 |
| P24752_C413 | 1.3 | — | 1.1 | 4.2 | — | 1.4 | 2.1 | 15.3 | — | 13.0 |
| P63244_C182 | 1.5 | 1.4 | 1.5 | 1.5 | — | 0.9 | 1.2 | 0.9 | 0.8 | 1.1 |
| P24752_C126 | 0.9 | 1.3 | 0.9 | 2.2 | — | 2.1 | 12.6 | 1.4 | — | 3.2 |
| Q15084_C190 | — | 1.7 | 1.1 | 1.0 | 1.2 | 20.0 | 2.7 | 2.0 | 1.3 | — |
| Q8TAQ2_C145 | — | 2.8 | — | 1.0 | — | 3.1 | 1.7 | 1.0 | 1.6 | 4.2 |
| P68036_C86 | — | 4.8 | 1.8 | 0.9 | — | 1.4 | 1.0 | 0.8 | 1.5 | 1.1 |
| P15374_C95 | 1.5 | 1.1 | 1.1 | 0.8 | — | 20.0 | 1.2 | 1.0 | 1.2 | 2.0 |
| Q16763_C118 | 2.8 | — | — | 1.5 | — | — | 1.1 | 0.8 | 1.0 | 1.7 |
| Q16822_C306 | 1.7 | — | — | 1.4 | — | 2.2 | 1.0 | 1.3 | — | 1.9 |
| O14980_C528 | 20.0 | — | 0.7 | 0.7 | — | 1.8 | — | 0.8 | 0.7 | 0.8 |
| O00170_C122 | — | — | — | — | — | — | 1.3 | — | 1.1 | — |
| O75874_C269 | — | 0.8 | — | 1.2 | — | 12.4 | — | — | 1.4 | 20.0 |
| O75362_C286 | — | — | 0.9 | 1.3 | — | 1.8 | — | 1.2 | — | 1.1 |
| P40763_C259 | — | — | 0.6 | 1.3 | 1.8 | 1.8 | 1.7 | 1.5 | 1.2 | 3.4 |
| QY93Z3_C522 | — | 5.4 | — | — | — | 1.8 | 1.1 | 1.0 | — | 1.8 |
| P16455_C150 | — | 9.6 | — | — | 20.0 | — | 15.8 | — | 4.0 | — |
| Q96GG9_C115 | — | — | — | — | 1.6 | — | 1.4 | — | 1.3 | 1.3 |
| P00813_C75 | — | 2.5 | — | — | 1.4 | — | 1.3 | 1.3 | 1.1 | — |
| Q14790_C360 | 1.0 | 1.3 | — | — | — | — | 1.4 | — | — | 2.8 |
| Q15306_C194 | — | 2.2 | — | — | — | — | 2.1 | — | 1.1 | — |
| Q6L8Q7_C108 | — | — | — | — | — | — | — | 1.3 | — | — |

TABLE 1B-continued

| Indentifier | 5_500 µM_ invitro_ 231 | 5_500 µM_ invitro_ ramos | 6_500 µM_ invitro_ 231 | 7_500 µM_ invitro_ 231 | 7_500 µM_ invitro_ ramos | 8_500 µM_ invitro_ 231 | 8_500 µM_ invitro_ ramos | 9_500 µM_ invitro_ 231 | 9_500 µM_ invitro_ ramos | 10_500 µM_ invitro_ 231 |
|---|---|---|---|---|---|---|---|---|---|---|
| P48735_C308 | 0.8 | — | — | 0.9 | — | 1.3 | — | 1.4 | — | 1.1 |
| Q86UV5_C39 | — | 1.2 | — | — | — | — | — | 0.8 | 0.9 | 2.5 |
| P50851_C1704 | — | 3.6 | — | 1.8 | 1.6 | — | 1.2 | 1.0 | 1.2 | — |
| O94953_C694 | — | — | 1.1 | — | — | 20.0 | 1.1 | 1.2 | 1.0 | — |
| P19447_C342 | — | 4.1 | 1.1 | 1.3 | 2.0 | 5.9 | — | 2.5 | — | 3.0 |
| Q00535_C157 | — | 20.0 | — | — | — | — | 1.3 | 1.2 | 0.8 | — |
| Q9UPT9_C171 | — | 20.0 | — | — | 3.2 | — | 2.3 | — | — | — |
| Q9HB90_C377 | — | — | — | — | — | 5.1 | — | 1.9 | — | — |
| P50851_C2675 | — | 20.0 | — | — | — | — | 1.1 | 1.5 | — | — |
| Q9NYL2_C22 | 20.0 | — | — | 3.1 | — | — | — | 20.0 | — | — |
| Q5T1V6_C414 | — | — | — | — | — | — | 2.0 | — | — | — |
| Q9HB90_C358 | — | — | 1.2 | — | — | — | — | 1.9 | — | — |
| P16455_C145 | — | 2.0 | — | — | — | — | 20.0 | — | 20.0 | — |
| Q9Y5T5_C205 | — | 1.1 | — | — | — | — | 20.0 | — | — | — |
| O00541_C272 | — | 12.3 | — | — | — | — | 1.6 | — | — | — |
| Q02556_C306 | — | 2.6 | — | — | 20.0 | — | 2.2 | — | 1.0 | — |
| Q15910_C503 | — | 20.0 | 1.8 | — | — | — | — | 1.1 | — | — |
| Q96RU2_C171 | — | — | 0.8 | — | — | 7.5 | — | 1.1 | — | 1.4 |
| Q16877_C159 | — | 20.0 | — | — | — | — | 1.0 | 1.5 | — | 1.2 |
| P04150_C302 | — | — | — | — | — | — | — | — | — | 4.1 |
| Q961H7_C219 | — | — | — | — | — | — | — | — | — | — |
| P48200_C137 | — | — | — | — | 2.2 | — | 1.6 | — | — | — |
| O00622_C39 | — | — | — | — | — | — | — | 2.0 | — | — |
| Q5T1V6_C453 | — | — | — | — | — | 20.0 | — | 2.1 | — | — |
| P51617_C608 | — | 10.1 | — | — | — | — | — | — | — | — |
| P42575_C370 | — | — | — | — | — | — | 2.0 | — | 1.2 | — |
| P09086_C346 | — | 4.6 | — | — | — | — | — | — | — | — |
| Q09472_C1738 | — | 20.0 | — | — | — | — | — | 1.5 | — | — |
| Q01201_C109 | — | — | — | — | — | — | — | — | — | — |
| Q70CQ2_C741 | — | — | — | — | — | — | — | — | — | — |
| P41226_C599 | — | — | — | — | — | — | — | — | — | — |
| P14598_C378 | — | 4.0 | — | — | — | — | 1.3 | — | — | — |
| Q9C0C9_C375 | — | — | — | — | — | — | — | — | — | — |
| O00622_C134 | — | — | — | — | — | — | — | 1.7 | — | 20.0 |
| O00541_C361 | — | — | — | — | — | — | — | 20.0 | — | — |
| P43403_C117 | — | — | — | — | — | 20.0 | — | — | — | 20.0 |

TABLE 1B-continued

| Identifier | 5_500 μM_ invitro_ 231 | 5_500 μM_ invitro_ ramos | 6_500 μM_ invitro_ 231 | 7_500 μM_ invitro_ 231 | 7_500 μM_ invitro_ ramos | 8_500 μM_ invitro_ 231 | 8_500 μM_ invitro_ ramos | 9_500 μM_ invitro_ 231 | 9_500 μM_ invitro_ ramos | 10_500 μM_ invitro_ 231 |
|---|---|---|---|---|---|---|---|---|---|---|
| Q96FA3_C282 | — | — | — | — | — | — | — | — | — | — |
| Q9UPT9_C44 | — | 20.0 | — | — | — | — | 1.5 | — | — | — |
| Q9Y4C1_C251 | — | — | — | — | — | — | — | — | — | — |
| Q70CQ2_C1090 | — | 20.0 | — | — | — | — | — | — | — | — |
| O00622_C70 | — | — | — | — | — | 20.0 | — | — | — | — |
| P04150_C622 | — | — | — | — | — | — | — | — | — | — |

TABLE 1C

| Identifier | 10_500 μM_ invitro_ ramos | 11_500 μM_ invitro_ 231 | 11_500 μM_ invitro_ ramos | 12_500 μM_ invitro_ 231 | 12_500 μM_ invitro_ ramos | 13_500 μM_ invitro_ 231 | 13_500 μM_ invitro_ ramos | 14_500 μM_ invitro_ 231 | 14_500 μM_ invitro_ ramos | 15_500 μM_ invitro_ 231 |
|---|---|---|---|---|---|---|---|---|---|---|
| Q99873_C109 | 1.3 | 20.0 | 20.0 | 1.4 | 1.3 | 1.0 | 0.9 | 0.8 | 1.4 | 0.9 |
| P24752_C119 | 1.4 | 1.2 | 0.9 | 1.0 | 0.7 | 1.2 | 0.6 | 1.2 | 1.8 | 1.0 |
| P09211_C48 | 0.8 | 1.7 | 1.1 | 2.9 | 1.1 | 1.5 | 1.2 | 3.2 | 2.1 | 2.5 |
| O14980_C34 | 0.7 | 1.2 | 1.0 | 1.2 | 0.7 | 0.9 | 0.7 | 1.1 | 1.5 | — |
| P24752_C196 | 1.7 | 1.5 | 1.3 | 1.2 | 0.9 | 1.6 | 1.7 | 1.1 | 1.4 | 0.9 |
| Q15084_C55 | — | 20.0 | 20.0 | 3.7 | 3.1 | 1.9 | 1.1 | 1.0 | 1.4 | 0.8 |
| P24752_C413 | 1.6 | 1.9 | 1.7 | 1.5 | 1.1 | 5.5 | 7.3 | 1.3 | 1.6 | 1.2 |
| P63244_C182 | 1.1 | 1.0 | 1.1 | 0.9 | 0.8 | 1.4 | 0.8 | 1.2 | 1.5 | — |
| P24752_C126 | 1.5 | 1.5 | — | 1.0 | 1.1 | 9.6 | 20.0 | 1.1 | 1.4 | 0.8 |
| Q15084_C190 | 3.3 | 20.0 | 20.0 | — | 20.0 | 1.5 | 1.3 | 1.1 | 1.8 | 0.9 |
| Q8TAQ2_C145 | — | 20.0 | — | 2.8 | 1.6 | — | 0.8 | 1.1 | 2.3 | — |
| P68036_C86 | 0.4 | — | 1.0 | — | — | 1.1 | 0.8 | 1.0 | 1.1 | — |
| P15374_C95 | — | 0.8 | 0.8 | — | 0.5 | — | 0.8 | 1.2 | 1.0 | — |
| Q16763_C118 | — | — | — | — | 0.6 | — | 0.7 | 0.7 | 1.2 | — |
| Q16822_C306 | 1.1 | 3.2 | 1.2 | 1.5 | 0.7 | 0.9 | 1.0 | — | 20.0 | — |
| O14980_C528 | — | 1.0 | 0.7 | 1.1 | — | — | 0.5 | 20.0 | 20.0 | 0.8 |
| O00170_C122 | 1.7 | — | 2.8 | — | 1.3 | — | 0.9 | — | 2.5 | — |
| O75874_C269 | — | 1.1 | 0.7 | — | — | 2.7 | — | 0.9 | 1.3 | — |
| O75362_C286 | — | 1.2 | 1.2 | 1.0 | — | 0.9 | 0.9 | 0.9 | — | — |
| P40763_C259 | — | 20.0 | 20.0 | — | — | — | 1.2 | 0.8 | 3.1 | — |
| Q9Y3Z3_C522 | — | 2.1 | — | — | — | 0.8 | — | 1.7 | 1.5 | — |
| P16455_C150 | 20.0 | — | 20.0 | — | 20.0 | — | 4.2 | 5.5 | 5.1 | — |
| Q96GG9_C115 | 1.0 | — | 0.9 | — | 0.6 | — | — | 1.1 | 1.6 | — |
| P00813_C75 | 1.0 | — | 7.5 | — | 0.7 | — | 0.9 | 1.5 | 1.7 | — |
| O14933_C98 | — | — | 3.4 | — | 1.3 | — | 1.0 | — | 2.8 | — |
| Q14790_C360 | 1.5 | 20.0 | 20.0 | — | — | — | — | 1.4 | 1.9 | — |

TABLE 1C-continued

| Identifier | 10_500 μM_ invitro_ ramos | 11_500 μM_ invitro_ 231 | 11_500 μM_ invitro_ ramos | 12_500 μM_ invitro_ 231 | 12_500 μM_ invitro_ ramos | 13_500 μM_ invitro_ 231 | 13_500 μM_ invitro_ ramos | 14_500 μM_ invitro_ 231 | 14_500 μM_ invitro_ ramos | 15_500 μM_ invitro_ 231 |
|---|---|---|---|---|---|---|---|---|---|---|
| Q15306_C194 | 2.5 | — | 4.3 | — | 3.7 | — | 1.1 | 1.3 | 2.2 | — |
| Q6L8Q7_C108 | — | 4.2 | — | — | 1.5 | — | 1.0 | 0.5 | 2.2 | 1.1 |
| P48735_C308 | — | 1.1 | — | 1.7 | — | 1.1 | — | 4.7 | — | — |
| Q86UV5_C39 | — | — | 1.0 | — | — | 0.8 | 0.6 | 0.8 | — | — |
| P50851_C1704 | 0.8 | — | 1.4 | — | — | 0.7 | 0.8 | 1.9 | 1.7 | — |
| O94953_C694 | 1.4 | — | 1.9 | — | — | 1.4 | 1.1 | — | 2.0 | — |
| P19447_C342 | — | 2.9 | 1.5 | 3.0 | — | 1.0 | — | 4.7 | — | — |
| Q00535_C157 | — | — | 1.3 | — | 1.0 | — | — | 6.1 | 2.3 | — |
| Q9UPT9_C171 | 3.8 | — | 8.2 | — | 4.1 | — | 0.8 | 4.0 | 4.0 | — |
| Q9HB90_C377 | — | — | 1.6 | — | — | 2.1 | — | — | 20.0 | — |
| P50851_C2675 | 1.3 | — | 1.3 | — | 1.5 | — | — | 1.9 | 2.9 | — |
| Q9NYL2_C22 | — | — | — | — | — | 5.2 | — | 1.6 | — | — |
| Q5T1V6_C414 | — | — | — | — | — | — | 1.2 | — | 4.0 | — |
| Q9HB90_C358 | — | — | — | — | — | 1.5 | — | 0.9 | 2.1 | 1.1 |
| P16455_C145 | — | — | 20.0 | — | — | — | 20.0 | 1.5 | 2.0 | — |
| Q9Y5T5_C205 | — | 20.0 | — | 2.2 | — | — | 3.3 | — | — | — |
| O00541_C272 | 2.2 | — | 4.2 | — | — | 1.7 | — | 2.6 | — | — |
| Q02556_C306 | 3.6 | — | 3.1 | — | — | — | 0.7 | 2.4 | 2.3 | — |
| Q15910_C503 | — | — | 1.3 | — | — | — | 0.8 | 0.6 | 1.9 | 0.8 |
| Q96RU2_C171 | — | 20.0 | — | — | — | — | 2.4 | 1.0 | — | — |
| Q16877_C159 | — | — | 0.6 | — | — | 0.9 | — | 2.3 | — | — |
| P04150_C302 | — | — | 1.5 | — | 1.3 | — | — | — | 2.2 | — |
| Q96JH7_C219 | — | — | — | — | — | — | — | 0.6 | 1.5 | — |
| P48200_C137 | 2.1 | — | 3.7 | — | — | — | — | 5.2 | — | — |
| O00622_C39 | — | 9.6 | — | — | — | 1.2 | — | 3.6 | — | — |
| Q5T1V6_C453 | — | 20.0 | — | — | — | — | 1.4 | 2.2 | — | — |
| P51617_C608 | — | — | 1.3 | — | — | — | — | — | — | — |
| P42575_C370 | 1.2 | — | 6.0 | — | — | — | — | — | — | — |
| P09086_C346 | — | — | 1.7 | — | — | — | 0.6 | — | — | — |
| Q09472_C1738 | — | — | — | — | — | — | 0.7 | 2.1 | — | — |
| Q01201_C109 | — | — | — | — | — | — | — | 1.7 | 2.4 | — |
| Q70CQ2_C741 | 0.9 | — | — | — | — | 0.8 | — | — | — | — |
| P41226_C599 | — | — | 1.9 | — | — | — | — | — | — | — |
| P14598_C378 | 1.1 | — | — | — | — | — | 0.7 | — | — | — |
| Q9C0C9_C375 | 0.8 | — | — | — | — | — | — | 2.8 | — | — |
| O00622_C134 | — | — | — | — | — | — | — | 0.7 | — | — |
| O00541_C361 | — | — | — | — | — | — | — | — | — | — |

TABLE 1C-continued

| Identifier | 10_500 μM_ invitro_ ramos | 11_500 μM_ invitro_ 231 | 11_500 μM_ invitro_ ramos | 12_500 μM_ invitro_ 231 | 12_500 μM_ invitro_ ramos | 13_500 μM_ invitro_ 231 | 13_500 μM_ invitro_ ramos | 14_500 μM_ invitro_ 231 | 14_500 μM_ invitro_ ramos | 15_500 μM_ invitro_ 231 |
|---|---|---|---|---|---|---|---|---|---|---|
| P43403_C117 | 20.0 | — | — | — | — | — | — | — | 1.3 | — |
| Q96FA3_C282 | — | — | — | — | — | — | — | 1.4 | — | — |
| Q9UPT9_C44 | — | — | — | — | — | — | — | — | — | — |
| Q9Y4C1_C251 | — | — | — | — | — | — | — | — | — | — |
| Q70CQ2_C1090 | — | — | — | — | — | — | — | — | — | — |
| O00622_C70 | — | — | — | — | — | — | — | — | — | — |
| P04150_C622 | — | 1.7 | — | — | — | — | — | — | — | — |

TABLE 1D

| Identifier | 15_500 µm_in-vitro_ramos | 27_500 µm_in-vitro_ramos_231 | 20_500 µm_in-vitro_ramos_231 | 20_500 µm_in-vitro_ramos | 21_500 µm_in-vitro_ramos_231 | 21_500 µm_in-vitro_ramos | 22_500 µm_in-vitro_ramos_231 | 22_500 µm_in-vitro_ramos | 23_500 µm_in-vitro_ramos_231 | 23_500 µm_in-vitro_ramos |
|---|---|---|---|---|---|---|---|---|---|---|
| Q99873_C109 | 1.2 | 0.7 | 1.9 | 2.2 | 1.1 | 1.5 | 1.0 | 1.0 | 0.8 | 1.0 |
| P24752_C119 | 1.2 | 0.9 | 3.6 | 2.6 | 0.9 | 1.1 | 1.0 | 0.8 | 1.7 | 2.0 |
| P09211_C48 | 1.3 | 1.3 | 2.5 | 1.1 | 1.1 | 1.3 | 0.9 | 0.7 | 0.8 | 0.9 |
| O14980_C34 | 1.2 | 0.9 | 1.0 | 1.2 | 0.9 | 1.2 | — | — | 3.4 | 5.3 |
| P24752_C196 | 1.6 | 0.9 | 3.7 | 2.9 | 1.0 | 1.1 | 0.7 | — | — | 1.8 |
| Q15084_C55 | 1.0 | 0.8 | 1.7 | 2.0 | 1.1 | 2.1 | 1.6 | 0.7 | 0.8 | 1.0 |
| P24752_C413 | 0.9 | 0.9 | 20.0 | 14.0 | 1.4 | 1.4 | 2.1 | 1.6 | 1.1 | 1.2 |
| P63244_C182 | 1.3 | 1.0 | 1.4 | 1.1 | 0.9 | 0.9 | 1.1 | 1.1 | 4.6 | — |
| P24752_C126 | — | 0.9 | 10.6 | 20.0 | 1.2 | 1.4 | 1.6 | 1.7 | 0.8 | 0.8 |
| Q15084_C190 | 1.2 | 0.9 | 2.1 | 2.1 | 1.1 | 2.3 | 2.4 | 4.2 | 0.8 | 1.1 |
| Q8TAQ2_C145 | 1.2 | 0.9 | 2.9 | 3.9 | 1.2 | — | 2.2 | 1.2 | 1.3 | — |
| P68036_C86 | 1.3 | 1.2 | 1.1 | 1.2 | 1.2 | 2.0 | — | 0.8 | 7.4 | 13.2 |
| P15374_C95 | 0.7 | 0.4 | 1.0 | 0.9 | 1.1 | — | — | 0.7 | 0.8 | 1.1 |
| Q16763_C118 | 1.2 | 0.8 | — | 2.9 | 0.9 | 2.0 | — | 0.9 | 1.6 | 2.4 |
| Q16822_C306 | — | 1.4 | 2.5 | 1.6 | 1.2 | — | — | — | 3.0 | — |
| O14980_C528 | 1.0 | 1.2 | 1.4 | 4.0 | 0.9 | 0.8 | — | — | — | 2.9 |
| O00170_C122 | 1.4 | 0.4 | — | 2.2 | 1.4 | — | 1.3 | 1.1 | — | 1.4 |
| O75874_C269 | 0.6 | 0.4 | — | 0.6 | 1.5 | — | 1.0 | — | 0.7 | 1.1 |
| O75362_C286 | — | 20.0 | 1.3 | — | 0.9 | — | — | — | 0.7 | — |
| P40763_C259 | 1.9 | 0.7 | 2.1 | 3.0 | — | 2.9 | 2.0 | — | 20.0 | 0.8 |
| Q9Y3Z3_C322 | 1.6 | 0.8 | — | 1.3 | — | 1.4 | — | 0.8 | 1.1 | — |
| P16455_C150 | 1.9 | 1.0 | — | 18.3 | — | 17.2 | — | 2.9 | — | 1.0 |
| Q96GG9_C115 | 0.8 | 1.1 | 1.2 | 1.2 | 1.0 | 1.0 | 1.0 | 0.8 | — | 20.0 |
| P00813_C75 | 1.1 | 1.1 | — | 1.5 | — | 1.3 | — | 1.3 | — | 1.1 |
| O14933_C98 | 1.3 | 1.2 | — | 3.9 | — | — | — | 2.0 | — | 1.2 |
| Q14790_C360 | — | 0.8 | 1.9 | 1.5 | 1.9 | 1.9 | — | — | 0.7 | 1.4 |
| Q15306_C194 | 2.2 | — | — | 3.0 | — | 1.7 | — | — | 1.4 | 1.9 |
| Q6L8Q7_C108 | — | 0.5 | 1.6 | — | 0.6 | — | 1.1 | 1.1 | 1.0 | — |
| P48735_C308 | — | 1.9 | 0.5 | — | 20.0 | — | — | — | — | 1.3 |
| Q86UV5_C39 | 0.7 | 0.8 | 1.1 | 1.8 | — | 1.2 | — | — | — | 3.4 |
| P50851_C1704 | 1.9 | — | 2.0 | 1.7 | — | 1.6 | — | — | — | 3.2 |
| O94953_C694 | — | 1.4 | 2.8 | 2.0 | — | 1.8 | — | — | — | — |
| P19447_C342 | 1.1 | 0.8 | 2.6 | — | 6.1 | — | — | — | 1.6 | 2.8 |
| Q00535_C157 | — | — | — | 2.0 | — | — | 1.7 | 0.9 | 5.1 | — |
| Q9UPT9_C171 | — | 1.0 | — | 20.0 | 1.4 | — | 1.1 | 1.1 | 1.5 | 2.6 |
| Q9HB90_C377 | — | — | — | — | 0.9 | 1.5 | 1.0 | 0.9 | — | — |
| P50851_C2675 | 1.6 | — | — | — | 2.0 | — | 1.7 | 1.1 | 1.4 | 1.4 |
| Q9NYL2_C22 | 1.0 | 1.1 | 20.0 | 3.1 | 1.2 | — | — | 1.3 | — | — |
| Q5T1V6_C414 | — | 0.8 | — | — | 1.2 | — | 1.6 | — | — | 1.0 |
| Q9HB90_C358 | — | 0.3 | — | — | — | 5.5 | — | — | — | 1.2 |
| P16455_C145 | 1.3 | — | — | — | 1.6 | — | — | 1.6 | — | 2.0 |
| Q9Y5T5_C205 | — | 1.6 | — | 20.0 | — | — | — | — | — | — |
| O00541_C272 | — | 1.1 | — | 2.1 | — | — | — | — | — | 2.0 |
| Q02556_C306 | 2.1 | — | — | — | — | — | — | — | — | 1.2 |
| Q15910_C503 | — | — | — | 2.4 | 1.1 | 1.2 | — | — | — | 1.0 |
| Q96RU2_C171 | — | 0.9 | — | 1.0 | — | — | — | 0.9 | — | 4.7 |
| Q16877_C159 | — | — | — | — | — | — | — | — | — | — |
| P04150_C302 | 0.9 | 1.3 | — | — | — | — | — | — | — | — |

TABLE 1D-continued

| | | | | | | | | |
|---|---|---|---|---|---|---|---|---|
| Q96JH7_C219 | 1.3 | 1.7 | — | — | — | — | — | — |
| P48200_C137 | 2.0 | 1.4 | — | — | — | — | — | 1.6 |
| O00622_C39 | — | 1.0 | — | — | — | — | 4.4 | — |
| Q5T1V6_C453 | — | — | — | — | — | — | — | — |
| P51617_C608 | — | 0.9 | 1.2 | — | — | — | — | 1.5 |
| P42575_C370 | 0.8 | — | 5.2 | — | — | — | — | 2.1 |
| P09086_C346 | — | — | — | 0.9 | — | — | — | 1.1 |
| Q09472_C1738 | — | 0.8 | 2.3 | — | — | — | — | — |
| Q01201_C109 | — | — | 3.2 | — | — | — | — | 1.3 |
| Q70CQ2_C741 | — | — | 1.7 | — | 1.7 | — | — | — |
| P41226_C599 | — | 0.7 | 12.2 | 2.8 | 2.5 | — | — | 3.2 |
| P14598_C378 | — | 0.7 | — | 1.1 | — | — | — | — |
| Q9C0C9_C375 | — | 1.5 | — | — | 2.4 | — | — | 1.4 |
| O00622_C134 | — | 0.6 | 20.0 | 20.0 | — | — | — | — |
| O00541_C361 | — | — | 20.0 | 20.0 | — | — | — | — |
| P43403_C117 | 20.0 | — | — | — | — | — | — | 1.1 |
| Q96FA3_C282 | — | 20.0 | — | — | — | — | — | — |
| Q9UPT9_C44 | — | — | — | — | — | — | — | — |
| Q9Y4C1_C251 | — | — | — | 0.7 | 0.7 | — | — | — |
| Q70CQ2_C1090 | — | — | 2.7 | — | 0.9 | — | — | — |
| O00622_C70 | — | 1.1 | — | — | — | — | — | — |
| P04150_C622 | — | — | — | — | — | — | — | — |

TABLE 1E

| Identifier | 24_500 µm_in-vitro_ramos | 25_500 µm_in-vitro_ramos_231 | 26_500 µm_in-vitro_ramos | 27_500 µm_in-vitro_ramos_231 | 27_500 µm_in-vitro_ramos | 28_500 µm_in-vitro_ramos_231 | 28_500 µm_in-vitro_ramos | 29_500 µm_in-vitro_ramos_231 | 29_500 µm_in-vitro_ramos | 30_500 µm_in-vitro_ramos |
|---|---|---|---|---|---|---|---|---|---|---|
| Q99873_C109 | 1.0 | 1.0 | 0.9 | 0.9 | 1.0 | 0.8 | 1.1 | 1.0 | 0.9 | 1.1 |
| P24752_C119 | 1.3 | 1.0 | 1.0 | 1.0 | 1.3 | 1.1 | 1.1 | 1.3 | 0.6 | 0.7 |
| P09211_C48 | 1.6 | 1.8 | 0.9 | 1.0 | 1.0 | 1.3 | 1.5 | 1.3 | 0.4 | 1.4 |
| O14980_C34 | 1.1 | 0.9 | 1.0 | 1.0 | 1.0 | 0.8 | 0.9 | 1.0 | 0.9 | 0.7 |
| P24752_C196 | 1.3 | 1.0 | 0.9 | 1.0 | 1.1 | 1.0 | 1.1 | 1.3 | 1.0 | 0.8 |
| Q15084_C55 | 1.2 | 1.0 | 0.9 | 1.1 | 1.2 | 1.2 | 1.5 | 1.3 | 1.3 | 2.2 |
| P24752_C413 | 1.1 | 1.2 | 0.9 | 0.8 | 1.3 | 1.2 | 1.4 | 1.3 | 0.7 | 1.1 |
| P63244_C182 | 2.6 | 0.9 | 1.0 | 1.0 | 1.1 | 1.0 | 1.1 | 1.0 | 1.2 | 1.2 |
| P24752_C126 | 1.1 | 1.0 | 0.9 | — | 1.3 | 1.7 | 1.6 | 1.2 | 0.8 | 1.1 |
| Q15084_C190 | 1.7 | — | 0.9 | — | 1.1 | 1.1 | 1.6 | 1.0 | — | 2.3 |
| Q8TAQ2_C145 | 5.4 | 1.5 | 0.7 | — | 1.2 | 1.4 | 1.2 | 0.9 | 1.5 | 1.1 |
| P68036_C86 | 1.1 | 0.8 | 0.8 | 0.9 | 1.0 | 1.1 | 0.9 | 0.9 | 1.0 | 0.7 |
| P15374_C95 | 1.2 | 1.0 | 0.9 | — | 0.9 | 1.0 | 0.8 | — | — | 0.7 |
| Q16763_C118 | — | 0.8 | — | 1.5 | 1.1 | 1.1 | — | 1.1 | 0.5 | 1.2 |
| Q16822_C306 | 20.0 | — | 0.9 | 0.9 | 0.8 | — | 1.2 | 1.0 | — | — |
| O14980_C528 | 1.3 | 1.0 | 0.9 | — | 1.0 | 0.9 | 1.0 | — | 1.3 | 1.1 |
| O00170_C122 | 0.9 | 1.0 | — | 1.0 | — | 1.1 | 1.0 | 0.8 | — | 0.7 |
| O75874_C269 | — | 20.0 | — | 0.9 | — | 1.0 | 1.0 | 0.9 | — | — |
| O75362_C286 | 1.7 | 0.9 | — | — | 0.9 | 1.0 | 1.1 | 1.5 | — | — |
| P40763_C259 | 1.1 | — | 0.9 | 1.0 | 2.3 | — | 1.7 | 1.5 | 1.3 | — |
| Q9Y3Z3_C322 | 4.0 | — | 0.9 | — | 1.0 | — | — | — | — | 0.7 |
| Q16455_C150 | 1.7 | — | 0.9 | — | 1.0 | — | — | — | — | — |
| Q96GG9_C115 | 1.2 | — | 0.8 | — | 1.0 | — | 0.9 | — | — | 1.3 |
| P00813_C75 | — | — | 1.0 | — | 1.0 | — | 1.2 | — | — | 2.0 |
| O114933_C98 | 1.4 | 1.0 | — | — | 1.2 | 1.1 | 1.0 | — | 1.2 | 1.1 |
| Q14790_C360 | 1.9 | — | 1.1 | — | 1.0 | 1.0 | 1.1 | — | — | 0.7 |
| Q15306_C194 | 1.4 | 0.8 | 1.1 | — | 1.0 | 1.0 | 1.2 | — | — | — |
| Q6L8Q7_C108 | — | 14.5 | — | — | 1.3 | 0.9 | — | 1.0 | — | 1.3 |
| P48735_C308 | 1.0 | 1.0 | — | 1.1 | — | — | 1.0 | 1.2 | — | — |
| Q86UV5_C39 | 1.3 | 0.8 | — | 1.0 | — | — | 1.3 | 0.8 | — | — |
| P50851_C1704 | — | — | — | 1.1 | 1.0 | 0.9 | 1.0 | — | — | — |
| O94953_C694 | — | — | 0.9 | — | 1.2 | 1.3 | — | — | — | 1.3 |
| P19447_C342 | — | 0.9 | — | — | — | 1.4 | — | — | — | — |
| Q00535_C157 | 3.1 | 1.1 | 0.9 | — | 1.0 | — | — | — | — | 1.4 |
| Q9UPT9_C171 | 1.5 | 1.0 | 1.0 | — | — | — | — | — | — | 0.9 |
| Q9HB90_C377 | 1.0 | — | 0.9 | — | 1.0 | 1.1 | 1.0 | — | — | 1.1 |
| P50851_C2675 | — | — | — | — | — | — | — | — | — | — |
| Q9NYL2_C22 | 1.7 | 0.8 | — | 1.0 | 20.0 | 20.0 | 20.0 | — | 20.0 | 1.0 |
| Q5T1V6_C414 | 0.9 | 0.9 | — | — | 0.9 | — | 1.6 | 1.2 | — | — |
| Q9HB90_C358 | 20.0 | — | — | — | — | — | — | — | — | — |
| P16455_C145 | 2.6 | — | — | — | — | — | — | — | — | — |
| Q9Y5T5_C205 | 1.2 | — | — | 1.1 | — | — | — | 0.9 | — | — |
| O00541_C272 | 1.3 | 0.8 | — | 1.2 | — | — | — | — | — | — |
| Q02556_C306 | — | — | — | 1.0 | — | — | — | 1.4 | — | — |
| Q15910_C503 | — | — | — | — | — | — | — | — | — | — |
| Q96RU2_C171 | — | — | — | — | — | — | — | — | — | — |
| Q16877_C159 | — | — | — | — | — | — | — | — | — | — |
| P04150_C302 | — | — | — | — | — | — | — | — | — | — |

TABLE 1E-continued

| | | | | | | | | |
|---|---|---|---|---|---|---|---|---|
| Q96IH7_C219 | 1.2 | — | — | — | — | — | — | — |
| P48200_C137 | — | 1.0 | — | — | — | — | — | — |
| O00622_C39 | 1.7 | 0.9 | — | 1.0 | — | — | — | — |
| Q5T1V6_C453 | 1.3 | — | — | — | — | — | — | — |
| P51617_C608 | 2.2 | — | — | — | — | — | — | — |
| P42575_C370 | 1.1 | 0.7 | — | 1.0 | — | 1.0 | — | — |
| P09086_C346 | — | 1.6 | — | — | — | — | — | — |
| Q09472_C1738 | 1.5 | — | — | — | — | — | — | 1.3 |
| Q01201_C109 | — | — | — | — | — | — | 1.1 | — |
| Q70CQ2_C741 | — | — | — | — | 1.3 | — | — | — |
| P41226_C599 | — | — | — | 2.0 | — | — | — | — |
| P14598_C378 | — | 1.0 | — | — | — | — | — | — |
| Q9C0C9_C375 | — | — | — | — | — | — | — | — |
| O00622_C134 | — | — | — | — | 1.2 | — | — | — |
| O00541_C361 | — | — | — | 2.0 | — | — | — | — |
| P43403_C117 | — | — | 0.5 | — | — | — | — | — |
| Q96FA3_C282 | — | — | — | — | — | — | 1.1 | — |
| Q9UPT9_C44 | 1.3 | — | — | — | — | — | 0.7 | — |
| Q9Y4C1_C251 | — | — | — | — | — | — | — | — |
| Q70CQ2_C1090 | — | — | — | — | — | — | — | — |
| O00622_C70 | — | — | — | — | — | — | — | — |
| P04150_C622 | — | — | — | — | — | — | — | — |

TABLE 1F?

| Identifier | 30_500 μm_in-vitro_ramos | 31_500 μm_in-vitro_ramos_231 | 31_500 μm_in-vitro_ramos | 32_500 μm_in-vitro_ramos_231 | 32_500 μm_in-vitro_ramos | 33_500 μm_in-vitro_ramos_231 | 33_500 μm_in-vitro_ramos | 34_500 μm_in-vitro_ramos_231 | 34_500 μm_in-vitro_ramos | 35_500 μm_in-vitro_ramos_231 |
|---|---|---|---|---|---|---|---|---|---|---|
| Q99873_C109 | 1.8 | 1.0 | 1.3 | 1.7 | 1.8 | 1.0 | 0.9 | 0.8 | 1.1 | 0.8 |
| P24752_C119 | 0.9 | 1.3 | 0.7 | 1.7 | 1.3 | 0.7 | 0.7 | 0.8 | 1.0 | 0.9 |
| P09211_C48 | 1.2 | 2.0 | 1.3 | 1.9 | 1.4 | 2.0 | 0.7 | 0.8 | 1.1 | 0.7 |
| O14980_C34 | 1.1 | 1.0 | 0.8 | 1.2 | 1.0 | 0.8 | 0.9 | 0.8 | 1.0 | 0.8 |
| P24752_C196 | 1.1 | 1.2 | 0.9 | 2.3 | 2.0 | 0.9 | 1.3 | 0.9 | 1.3 | 0.9 |
| Q15084_C55 | — | 1.6 | 1.1 | 20.0 | 20.0 | 3.3 | — | 0.9 | — | — |
| P24752_C413 | 1.9 | 1.3 | 1.0 | 6.8 | 4.1 | 1.3 | — | — | — | 0.9 |
| P63244_C182 | 1.6 | 1.1 | — | 1.9 | — | — | 1.1 | — | 1.1 | — |
| P24752_C126 | 1.6 | — | — | 7.3 | 8.6 | 4.3 | — | — | — | — |
| Q15084_C190 | — | 1.3 | 1.2 | 20.0 | 20.0 | 3.3 | 1.5 | 0.9 | — | 0.9 |
| Q8TAQ2_C145 | 1.5 | 1.1 | 0.9 | 20.0 | 20.0 | — | — | — | — | 0.9 |
| P68036_C86 | 1.5 | 1.3 | 1.3 | — | 0.9 | 1.5 | — | — | — | — |
| P15374_C95 | 1.0 | 1.7 | 0.7 | 1.1 | 1.0 | 0.9 | — | — | — | — |
| Q16763_C118 | 1.1 | 0.9 | 0.8 | 1.2 | 1.1 | — | — | — | — | — |
| Q16822_C306 | 1.1 | 1.9 | 1.2 | 3.2 | — | — | — | — | — | — |
| O14980_C528 | — | — | 3.2 | 1.7 | 1.2 | — | 1.0 | — | — | 0.9 |
| O00170_C122 | 2.0 | 5.2 | 0.6 | 3.7 | 1.9 | — | — | — | — | — |
| O75874_C269 | — | 0.4 | 0.7 | — | — | 1.2 | — | — | — | — |
| O75362_C286 | 2.1 | — | — | — | — | — | — | — | — | — |
| P40763_C259 | — | 1.7 | — | 10.2 | — | — | — | — | — | — |
| Q9Y3Z3_C322 | — | 1.5 | — | — | 1.8 | — | 1.9 | — | 1.4 | — |
| P16455_C150 | 5.1 | — | 2.8 | — | 20.0 | — | — | — | — | — |
| Q96GG9_C115 | 1.1 | — | 0.9 | — | 0.9 | — | — | — | 1.1 | — |
| P000813_C75 | 3.1 | — | 0.8 | — | 1.7 | — | 0.8 | 0.8 | — | — |
| O114933_C98 | 2.1 | — | — | 13.8 | 4.6 | — | 1.2 | — | — | — |
| Q14790_C360 | 5.2 | — | — | — | — | 3.1 | — | — | — | — |
| Q15306_C194 | 1.7 | 2.0 | 1.1 | — | 3.7 | — | 1.1 | — | — | — |
| Q6L8Q7_C108 | 1.6 | 1.3 | 1.1 | 2.5 | 1.9 | — | — | — | — | 0.8 |
| P48735_C308 | — | — | — | — | — | — | — | — | — | — |
| Q86UV5_C39 | — | — | 1.4 | — | 2.0 | — | — | — | — | — |
| P50851_C1704 | — | — | — | — | — | — | — | — | — | — |
| O94953_C694 | 2.3 | — | — | — | — | — | — | — | — | — |
| P19447_C342 | — | 2.1 | 1.1 | 1.7 | 1.7 | — | — | 0.7 | — | — |
| Q00535_C157 | 2.0 | 2.2 | — | — | 9.3 | 1.1 | — | — | — | — |
| Q9UPT9_C171 | — | — | — | 1.8 | 1.5 | — | — | 0.8 | — | — |
| Q9HB90_C377 | — | 2.3 | — | 2.1 | 1.1 | 3.7 | — | 0.6 | — | — |
| P50851_C2675 | 2.0 | — | 1.0 | 1.9 | 1.2 | — | — | — | — | — |
| Q9NYL2_C22 | — | — | — | — | 20.0 | — | — | — | 1.1 | — |
| Q5T1V6_C414 | — | — | — | — | — | 1.1 | — | — | — | — |
| Q9HB90_C358 | — | — | — | — | — | 1.4 | — | — | — | 0.8 |
| P16455_C145 | — | — | — | 1.7 | 1.7 | — | — | — | — | — |
| Q9Y5T5_C205 | 2.0 | — | — | 1.5 | — | — | — | — | 1.4 | — |
| O00541_C272 | — | — | — | — | — | — | — | — | — | — |
| Q02556_C306 | — | — | — | — | — | — | — | — | — | — |
| Q15910_C503 | — | — | — | — | — | — | — | — | — | — |
| Q96RU2_C171 | — | — | — | — | — | — | — | — | — | — |
| Q16877_C159 | — | — | — | — | — | — | — | — | — | — |
| P04150_C302 | — | — | — | — | — | — | — | — | — | — |

TABLE 1F-continued

| | | | | | | | | | |
|---|---|---|---|---|---|---|---|---|---|
| Q96IH7_C219 | — | — | — | 1.0 | — | — | — | — | — |
| P48200_C137 | — | 1.2 | — | — | — | — | — | — | — |
| O00622_C39 | — | 1.2 | — | — | — | — | — | — | — |
| Q5T1V6_C453 | — | — | — | — | 5.8 | — | — | — | — |
| P51617_C608 | 4.1 | — | — | — | — | 2.9 | — | — | — |
| P42575_C370 | — | — | — | 0.6 | — | — | — | — | — |
| P09086_C346 | — | — | — | — | — | — | — | — | — |
| Q09472_C1738 | — | — | — | — | — | — | — | — | — |
| Q01201_C109 | — | 4.2 | — | — | — | 20.0 | — | — | — |
| Q70CQ2_C741 | — | — | — | — | — | — | — | — | — |
| P41226_C599 | — | — | — | — | — | — | — | — | — |
| P14598_C378 | — | — | — | — | — | — | — | — | — |
| Q9C0C9_C375 | — | — | — | — | — | — | — | — | — |
| O00622_C134 | — | — | — | — | — | — | — | — | — |
| O00541_C361 | — | — | — | — | — | — | — | — | — |
| P43403_C117 | — | — | — | — | — | — | — | — | — |
| Q96FA3_C282 | 1.5 | — | — | — | — | — | — | — | — |
| Q9UPT9_C44 | 1.7 | — | — | — | — | — | — | — | — |
| Q9Y4C1_C251 | — | — | — | — | — | — | — | — | — |
| Q70CQ2_C1090 | — | — | — | — | — | — | — | — | — |
| O00622_C70 | — | — | — | — | — | — | — | — | — |
| P04150_C622 | — | 4.8 | — | — | — | — | — | — | — |

TABLE 1G

| Identifier | 35_500 μm_in-vitro_ramos | 36_500 μm_in-vitro_ramos_231 | 37_500 μm_in-vitro_ramos | 38_500 μm_in-vitro_ramos_231 | 38_500 μm_in-vitro_ramos | 39_500 μm_in-vitro_ramos_231 | 40_500 μm_in-vitro_ramos_231 | 40_500 μm_in-vitro_ramos | 41_500 μm_in-vitro_ramos_231 | 41_500 μm_in-vitro_ramos |
|---|---|---|---|---|---|---|---|---|---|---|
| Q99873_C109 | 1.0 | — | 1.0 | 0.9 | 1.4 | 1.5 | 0.8 | 1.3 | 0.9 | 0.9 |
| P24752_C119 | 1.0 | — | 0.8 | 1.0 | 1.7 | 1.7 | 0.8 | 0.9 | 1.0 | 0.8 |
| P09211_C48 | 1.3 | 1.6 | 1.2 | 1.9 | — | 2.0 | 1.6 | 1.6 | 1.3 | 0.9 |
| O14980_C34 | 1.3 | 1.3 | 0.9 | 1.0 | 1.3 | 1.3 | 0.8 | 1.1 | 3.1 | 2.0 |
| P24752_C196 | 1.4 | 1.5 | 1.0 | 1.0 | 1.3 | 3.0 | 0.8 | — | 1.3 | 1.0 |
| Q15084_C55 | — | — | 1.0 | 1.0 | 1.3 | 3.9 | 0.8 | — | 0.9 | 0.8 |
| P24752_C413 | 1.3 | 2.7 | 0.9 | 1.1 | 20.0 | 2.7 | 0.9 | 0.6 | — | 0.9 |
| P63244_C182 | 0.9 | 1.3 | 0.9 | 1.0 | — | 1.0 | 1.0 | — | 0.8 | 4.7 |
| Q15084_C126 | 10.4 | — | 0.9 | 1.0 | 1.4 | — | 0.9 | 1.7 | 1.0 | 0.9 |
| Q8TAQ2_C145 | — | — | 1.1 | 1.1 | — | 7.0 | 0.9 | 1.1 | 1.8 | 2.8 |
| P68036_C86 | — | — | — | 1.1 | 1.9 | 1.2 | 0.9 | 0.9 | 9.8 | 7.9 |
| P15374_C95 | — | — | — | — | 1.5 | 1.9 | 0.8 | 0.9 | 1.0 | 0.8 |
| Q16763_C118 | — | — | — | 2.7 | 12.5 | — | 0.9 | 0.8 | — | 3.4 |
| Q16822_C306 | 1.0 | — | 1.0 | 1.0 | 1.0 | 1.4 | — | — | 1.2 | 1.0 |
| O14980_C528 | 0.8 | — | 0.9 | 1.0 | — | — | — | — | 0.6 | — |
| O00170_C122 | — | — | — | 1.5 | 1.5 | — | — | — | 1.1 | 1.0 |
| O75874_C269 | — | 1.7 | 0.9 | 0.7 | 1.2 | 1.2 | — | 0.8 | — | 0.6 |
| P40763_C259 | — | — | 0.9 | 0.9 | 1.5 | 20.0 | — | 1.4 | 0.9 | — |
| Q9Y3Z3_C322 | 1.1 | — | 0.7 | — | — | 1.1 | 0.8 | 1.9 | 0.9 | 0.9 |
| Q16455_C150 | 1.3 | — | 1.0 | — | 1.8 | — | — | 0.9 | — | — |
| Q96GG9_C115 | 0.9 | — | 0.8 | 1.2 | 1.0 | — | — | 0.9 | 1.1 | 1.1 |
| P000813_C75 | 1.1 | — | 0.9 | — | 2.3 | — | — | 1.3 | 1.2 | 0.8 |
| O114933_C98 | — | — | — | 1.6 | 1.7 | — | — | 1.1 | 1.0 | 1.2 |
| Q14790_C360 | 1.3 | — | 1.0 | 1.0 | 4.1 | — | 0.8 | — | — | — |
| Q15306_C194 | 1.0 | — | 0.9 | — | 2.1 | — | — | — | 1.3 | — |
| Q6L8Q7_C108 | — | — | — | — | 6.8 | 3.2 | — | — | — | — |
| P48735_C308 | — | 1.3 | — | 0.9 | — | — | — | 1.6 | — | — |
| Q86UV5_C39 | 1.0 | — | 0.7 | 1.2 | 2.5 | — | — | — | 1.1 | 1.4 |
| P50851_C1704 | 1.1 | — | 1.0 | 3.7 | 2.4 | — | — | — | 1.5 | — |
| O94953_C694 | 1.1 | — | 1.1 | — | — | — | — | — | 3.0 | — |
| P19447_C342 | — | — | — | 1.3 | — | — | — | 1.4 | 1.1 | — |
| Q00535_C157 | — | — | — | 0.9 | — | — | — | 0.9 | 1.9 | 1.4 |
| Q9UPT9_C171 | 1.5 | — | — | 1.4 | — | — | — | — | 1.5 | — |
| Q9HB90_C377 | — | — | — | 1.0 | 1.8 | — | — | — | 1.1 | 1.0 |
| P50851_C2675 | 1.0 | — | 1.0 | — | — | — | — | 1.4 | 1.3 | — |
| Q9NYL2_C22 | — | — | — | 1.2 | — | — | — | 1.0 | 1.9 | 1.4 |
| Q5T1V6_C414 | 1.3 | — | 1.0 | 0.9 | 1.9 | — | — | — | — | — |
| Q9HB90_C358 | — | — | — | 1.1 | — | — | — | — | 0.8 | — |
| P16455_C145 | — | — | — | — | — | — | — | 1.0 | — | — |
| Q9Y5T5_C205 | 1.0 | — | 1.0 | 1.0 | — | — | 0.8 | 0.9 | — | 1.0 |
| O00541_C272 | 1.1 | — | — | — | — | — | — | 0.9 | — | — |
| Q02556_C306 | 1.2 | — | — | — | — | — | — | — | — | — |
| Q15910_C503 | — | — | — | — | — | — | — | — | — | — |
| Q96RU2_C171 | — | — | — | 3.3 | — | — | — | 1.2 | — | 1.4 |
| Q16877_C159 | — | — | — | — | — | — | — | — | — | — |
| P04150_C302 | 0.9 | — | 0.9 | — | — | — | — | — | — | — |

TABLE 1G-continued

| | | | | | | | |
|---|---|---|---|---|---|---|---|
| Q96IH7_C219 | — | — | — | — | — | — | — |
| P48200_C137 | 1.1 | — | 0.9 | — | 1.8 | 1.9 | — |
| O00622_C39 | — | — | — | 0.8 | — | 1.1 | — |
| Q5T1V6_C453 | — | — | — | — | — | — | 1.2 |
| P51617_C608 | — | — | — | — | — | — | 1.1 |
| P42575_C370 | — | — | 0.7 | — | 2.4 | 2.7 | — |
| P09086_C346 | — | — | — | — | — | — | — |
| Q09472_C1738 | — | — | — | — | — | — | — |
| Q01201_C109 | — | — | 1.1 | — | — | — | — |
| Q70CQ2_C741 | 1.2 | — | — | — | 4.1 | — | — |
| P41226_C599 | — | — | — | — | — | — | — |
| P14598_C378 | — | — | — | — | — | — | — |
| Q9C0C9_C375 | — | — | — | — | — | — | — |
| O00622_C134 | — | — | — | — | — | — | — |
| O00541_C361 | — | — | — | — | — | — | — |
| P43403_C117 | — | — | — | — | 7.0 | — | — |
| Q96FA3_C282 | — | — | — | — | — | — | — |
| Q9UPT9_C44 | — | — | — | — | — | — | 1.4 |
| Q9Y4C1_C251 | — | — | — | — | — | — | — |
| Q70CQ2_C1090 | — | — | — | — | — | — | — |
| O00622_C70 | — | — | — | — | — | — | — |
| P04150_C622 | — | — | — | — | — | — | — |

TABLE 1H

| Identifier | 42_500 μm_in-vitro_ramos | 43_500 μm_in-vitro_ramos_231 | 43_500 μm_in-vitro_ramos | 44_500 μm_in-vitro_ramos_231 | 45_500 μm_in-vitro_ramos_231 | 46_500 μm_in-vitro_ramos_231 | 47_500 μm_in-vitro_ramos_231 | 48_500 μm_in-vitro_ramos_231 | 49_500 μm_in-vitro_ramos_231 | 50_500 μm_in-vitro_ramos_231 |
|---|---|---|---|---|---|---|---|---|---|---|
| Q99873_C109 | 0.9 | 1.4 | 1.2 | 0.8 | 2.2 | 0.8 | 0.9 | 1.0 | 2.0 | 1.0 |
| P24752_C119 | 0.8 | 1.8 | 1.1 | 0.8 | 12.4 | 0.8 | 1.0 | 1.3 | 4.9 | 2.1 |
| P09211_C48 | 0.7 | 4.1 | 2.2 | 0.9 | 19.7 | 1.0 | 2.5 | 1.1 | — | 2.3 |
| O14980_C34 | 0.9 | 1.1 | — | 0.8 | 1.8 | 1.0 | 1.0 | 1.1 | 1.9 | 1.2 |
| P24752_C196 | 0.8 | 2.4 | 2.3 | 0.8 | 20.0 | 0.9 | 1.1 | 1.3 | 4.7 | 3.9 |
| Q15084_C55 | 0.9 | 20.0 | 20.0 | 1.0 | — | 0.8 | 0.9 | 1.0 | 12.8 | 1.3 |
| P24752_C413 | 0.7 | 15.9 | — | 0.8 | 20.0 | 1.1 | 1.1 | 1.1 | 2.6 | 9.2 |
| P63244_C182 | 0.8 | 0.9 | 0.9 | — | — | 0.8 | 0.9 | 1.1 | — | 0.8 |
| P24752_C126 | 0.8 | — | 20.0 | 0.8 | 20.0 | 0.9 | 1.0 | — | 20.0 | 20.0 |
| Q15084_C190 | 1.0 | 20.0 | — | 1.0 | 0.9 | 0.9 | 1.1 | — | 7.7 | — |
| Q8TAQ2_C145 | 0.8 | 20.0 | — | 1.0 | 20.0 | 1.0 | 1.5 | 1.1 | — | 2.8 |
| P68036_C86 | 0.9 | 1.1 | 1.7 | — | — | 1.2 | 2.0 | — | 1.9 | — |
| P15374_C95 | 0.8 | — | 20.0 | 0.8 | — | 1.0 | 1.0 | — | — | 1.3 |
| Q16763_C118 | 0.8 | 3.3 | 1.0 | 0.8 | 3.3 | 0.9 | — | — | — | 0.8 |
| Q16822_C306 | 0.8 | 4.6 | — | — | — | 0.7 | 1.0 | — | — | 2.7 |
| O14980_C528 | — | — | — | — | — | — | 2.2 | — | — | — |
| O00170_C122 | 0.8 | 2.1 | — | 0.8 | 20.0 | 0.6 | 0.9 | 1.0 | 4.8 | 2.3 |
| O75874_C269 | 1.0 | 0.8 | 2.1 | — | — | 0.9 | — | — | 1.0 | 20.0 |
| O75362_C286 | — | 1.9 | 1.2 | 0.8 | 20.0 | 1.2 | — | — | — | — |
| P40763_C259 | — | — | — | — | — | — | — | 1.4 | 3.0 | — |
| Q9Y3Z3_C522 | — | 2.2 | 20.0 | 0.8 | — | — | — | — | — | — |
| Q16455_C150 | — | — | — | — | — | — | — | — | — | — |
| Q96GG9_C115 | 0.9 | — | 1.2 | — | — | — | — | — | — | — |
| P000813_C75 | 0.8 | — | — | 2.0 | — | — | — | — | — | 1.5 |
| O114933_C98 | 1.0 | — | — | 0.7 | — | — | 1.6 | 1.1 | — | — |
| Q14790_C360 | — | — | 3.0 | — | — | — | — | — | — | — |
| Q15306_C194 | 1.2 | 2.9 | — | 0.8 | 20.0 | 1.0 | 1.2 | — | — | 1.8 |
| Q6L8Q7_C108 | — | — | — | 0.8 | — | 0.2 | — | — | — | 2.2 |
| P48735_C308 | — | — | — | — | — | 1.0 | — | — | 4.0 | — |
| Q86UV5_C39 | 0.9 | 20.0 | — | — | — | — | — | — | — | — |
| P50851_C1704 | 1.0 | — | 1.2 | — | — | — | — | — | — | — |
| O94953_C694 | — | — | 4.5 | — | — | — | — | 1.4 | — | — |
| P19447_C342 | — | — | — | — | — | — | — | — | — | — |
| Q00535_C157 | — | — | — | — | — | 1.1 | — | — | — | — |
| Q9UPT9_C171 | — | — | — | — | — | 1.0 | — | — | — | — |
| Q9HB90_C377 | — | — | 2.7 | — | — | — | — | — | — | — |
| P50851_C2675 | — | — | — | — | — | — | — | — | — | — |
| Q9NYL2_C22 | 0.9 | — | — | — | — | — | 1.5 | — | — | — |
| Q5T1V6_C414 | 1.5 | — | — | — | — | — | — | — | — | — |
| Q9HB90_C358 | 0.9 | 20.0 | — | — | — | — | — | — | — | — |
| P16455_C145 | — | — | — | — | — | 0.9 | — | — | — | — |
| Q9Y5T5_C205 | — | 1.5 | — | — | — | — | — | — | — | — |
| O00541_C272 | — | — | — | — | — | — | — | — | — | — |
| Q02556_C306 | — | — | — | — | — | — | — | — | — | — |
| Q15910_C503 | — | — | — | — | — | — | — | — | — | — |
| Q96RU2_C171 | — | — | — | — | — | — | — | — | — | — |
| Q16877_C159 | — | — | — | — | — | — | — | — | — | — |
| P04150_C302 | — | — | — | — | — | — | — | — | — | — |

TABLE 1H-continued

| | | | | | | | | | |
|---|---|---|---|---|---|---|---|---|---|
| Q96JH7_C219 | — | — | — | — | — | — | — | — | — |
| P48200_C137 | 1.0 | — | — | — | — | — | — | — | — |
| O00622_C39 | — | 20.0 | — | — | — | — | — | — | 2.3 |
| Q5T1V6_C453 | — | — | — | — | — | — | — | — | — |
| P51617_C608 | — | — | — | — | — | — | — | — | — |
| P42575_C370 | — | 2.2 | — | — | — | — | — | — | — |
| P09086_C346 | — | — | — | — | — | — | — | — | — |
| Q09472_C1738 | — | — | — | — | — | — | — | — | — |
| Q01201_C109 | — | — | — | — | — | — | — | — | — |
| Q70CQ2_C741 | — | — | 1.2 | — | — | — | — | — | — |
| P41226_C599 | — | — | — | — | — | — | — | — | — |
| P14598_C378 | — | — | — | — | — | — | — | — | — |
| Q9C0C9_C375 | — | — | 2.1 | — | — | — | — | — | — |
| O00622_C134 | — | — | — | — | — | — | — | — | — |
| O00541_C361 | — | — | — | — | — | — | — | — | — |
| P43403_C117 | — | — | — | — | — | — | — | — | — |
| Q96FA3_C282 | 1.2 | — | — | — | — | — | 1.9 | — | — |
| Q9UPT9_C44 | — | — | — | — | — | — | — | — | — |
| Q9Y4C1_C251 | — | — | — | — | — | — | — | — | — |
| Q70CQ2_C1090 | — | — | — | — | — | — | 1.0 | — | — |
| O00622_C70 | — | — | — | — | — | — | — | — | — |
| P04150_C622 | — | — | — | — | — | — | — | — | — |

TABLE 1I

| Identifier | 51_500 μm_in-vitro_ramos_231 | 51_500 μm_in-vitro_ramos | 52_500 μm_in-vitro_ramos_231 | 52_500 μm_in-vitro_ramos | 53_500 μm_in-vitro_ramos_231 | 53_500 μm_in-vitro_ramos | 54_500 μm_in-vitro_ramos_231 | 55_500 μm_in-vitro_ramos_231 | 56_500 μm_in-vitro_ramos_231 | 56_500 μm_in-vitro_ramos |
|---|---|---|---|---|---|---|---|---|---|---|
| Q99873_C109 | 0.9 | 9.5 | 0.9 | 1.3 | 0.9 | 1.1 | 1.2 | 1.0 | 1.0 | 1.1 |
| P24752_C119 | 0.8 | 0.9 | 1.4 | 0.8 | 0.9 | 0.7 | 1.0 | 0.9 | 1.0 | 1.2 |
| P09211_C48 | 1.1 | 1.0 | 1.0 | 1.9 | 2.3 | 1.2 | 1.3 | 1.4 | 1.9 | 1.9 |
| O14980_C34 | 0.9 | 1.0 | 1.0 | 1.1 | 0.9 | 1.0 | 1.1 | 0.9 | 0.9 | 0.9 |
| P24752_C196 | 1.1 | — | 1.3 | 1.5 | 1.2 | 0.9 | 1.1 | 1.0 | 1.1 | 1.0 |
| Q15084_C55 | 2.5 | 2.7 | 1.1 | 1.8 | 0.9 | 1.0 | 1.2 | 0.9 | 1.0 | 1.1 |
| P24752_C413 | 1.0 | 1.0 | 1.9 | 1.5 | 1.0 | — | 1.1 | 1.0 | 1.1 | 0.9 |
| P63244_C182 | 0.7 | 0.9 | 1.0 | — | — | 0.8 | — | 1.0 | 1.1 | — |
| P24752_C126 | 1.0 | 1.2 | 1.3 | 1.9 | — | — | — | — | 0.9 | — |
| Q15084_C190 | — | 5.6 | 1.0 | 1.9 | 1.0 | 1.0 | 1.1 | — | 0.9 | 1.1 |
| Q8TAQ2_C145 | — | 1.1 | 0.9 | 1.8 | — | 1.2 | 1.2 | — | 1.4 | 1.2 |
| P68036_C86 | — | 1.0 | 0.8 | 1.3 | 1.0 | 1.0 | — | 1.0 | 1.5 | 1.3 |
| P15374_C95 | — | 0.9 | 1.2 | — | — | 0.7 | — | — | 1.0 | 1.1 |
| Q16763_C118 | — | 0.9 | 1.2 | 1.6 | — | 0.8 | — | — | 1.2 | 1.1 |
| Q16822_C306 | — | 0.8 | 1.3 | — | — | — | — | — | 1.4 | — |
| O14980_C528 | 1.4 | 0.9 | 1.3 | 1.4 | 0.8 | 0.8 | — | — | 1.4 | 0.9 |
| O00170_C122 | — | — | — | — | — | 0.9 | — | — | 20.0 | — |
| O75874_C269 | 0.9 | 20.0 | 1.0 | — | 1.1 | — | 1.1 | — | 0.8 | — |
| P40763_C259 | — | — | 2.2 | — | — | 1.9 | 1.3 | 1.0 | 0.9 | — |
| Q9Y3Z3_C322 | — | — | 1.2 | — | — | 0.7 | — | — | 1.0 | 1.0 |
| P16455_C150 | — | 0.8 | — | 2.2 | 1.0 | 1.1 | 1.1 | — | 1.2 | 1.4 |
| Q96GG9_C115 | — | 1.0 | — | 1.0 | — | 0.9 | — | — | 1.4 | 1.0 |
| P000813_C75 | — | — | — | 1.2 | — | — | — | — | — | 0.9 |
| O114933_C98 | — | — | 1.4 | 1.4 | 1.0 | 1.0 | — | — | — | 1.1 |
| Q14790_C360 | — | — | — | — | — | — | 1.2 | — | — | — |
| Q15306_C194 | — | 1.4 | 1.4 | 1.4 | — | 1.0 | — | — | 1.0 | 1.5 |
| Q6L8Q7_C108 | — | — | 1.1 | 6.8 | — | 1.1 | — | — | — | — |
| P48735_C308 | — | — | — | — | 0.5 | — | — | — | 1.0 | — |
| Q86UV5_C39 | — | 1.8 | 0.9 | 1.1 | — | — | — | — | 1.0 | — |
| P50851_C1704 | — | 1.1 | — | 1.4 | — | — | — | — | — | — |
| O94953_C694 | — | 1.4 | 1.0 | — | — | — | — | — | 1.2 | 1.9 |
| P19447_C342 | 1.4 | — | — | — | 1.2 | 0.8 | — | — | 1.1 | — |
| Q00535_C157 | — | 1.0 | — | — | — | — | — | — | — | — |
| Q9UPT9_C171 | — | — | — | — | — | 1.1 | 1.1 | — | 1.2 | — |
| Q9HB90_C377 | 0.6 | — | — | — | — | — | — | — | — | — |
| P50851_C2675 | — | 0.9 | — | — | — | — | — | — | — | — |
| Q9NYL2_C22 | — | — | — | 1.4 | 0.8 | 0.6 | — | 1.2 | 1.1 | 1.0 |
| Q5T1V6_C414 | — | — | 1.1 | 6.8 | 1.1 | 1.0 | — | — | 1.0 | — |
| Q9HB90_C358 | — | — | — | — | — | — | — | — | 1.0 | 1.0 |
| P16455_C145 | — | 20.0 | — | 1.1 | — | — | — | — | — | — |
| Q9Y5T5_C205 | 1.7 | 3.2 | — | — | 1.1 | — | — | 1.0 | 1.1 | 0.9 |
| O00541_C272 | — | — | — | — | — | — | — | — | 1.1 | 1.0 |
| Q02556_C306 | — | 1.5 | — | — | — | — | — | — | — | — |
| Q15910_C503 | — | — | 0.9 | — | — | — | — | — | — | — |
| Q96RU2_C171 | — | — | — | — | — | — | — | — | — | — |
| Q16877_C159 | — | 1.1 | — | 1.8 | — | — | — | — | — | — |
| P04150_C302 | — | — | — | — | — | — | — | — | — | — |

TABLE 1I-continued

| | | | | | | | | |
|---|---|---|---|---|---|---|---|---|
| Q96IH7_C219 | | 2.3 | | | | | | |
| P48200_C137 | | | | | | | | |
| O00622_C39 | | | | | | | | |
| Q5T1V6_C453 | | 1.8 | | | | | | |
| P51617_C608 | | 1.1 | | 17.6 | | | | |
| P42575_C370 | | | | | | | | |
| P09086_C346 | | | | | | | | |
| Q09472_C1738 | | | 1.1 | | | | | |
| Q01201_C109 | | 1.6 | | | | | | |
| Q70CQ2_C741 | | 0.9 | | | | | | |
| P41226_C599 | | | | | | | | |
| P14598_C378 | | 0.8 | | | | | | |
| Q9C0C9_C375 | | | | | | | | |
| O00622_C134 | | | | | | | | |
| O00541_C361 | | | | | | | | |
| P43403_C117 | | | | | | | | |
| Q96FA3_C282 | | | | 20.0 | | | | |
| Q9UPT9_C44 | | | | | | | | |
| Q9Y4C1_C251 | | | | | | | | |
| Q70CQ2_C1090 | | | | | | | | |
| O00622_C70 | | | | | | | | 1.0 |
| P04150_C622 | | | | | | | | |

Table 2 illustrates a list of liganded cysteines and their reactivity profiles with the fragment electrophile library from isoTOP-ABPP experiments performed in situ. Table 2 further shows the accession number (or the protein identifier) of the protein.

TABLE 2A

| Identifier | Protein | SEQ ID NO: | 2_200 µM_in-situ_231 | 4_100 µM_in-situ_231 | 8_200 µM_in-situ_231 | 9_200 µM_in-situ_231 |
|---|---|---|---|---|---|---|
| P04406_C152 | GAPDH Glyceraldehyde-3-phosphate dehydrogenase | 16 | 20.0 | 1.6 | 1.1 | 1.7 |
| P61978_C132 | HNRNPK Heterogeneous nuclear ribonucleoprotein K | 768 | 5.0 | 3.8 | 4.2 | 1.4 |
| Q13526_C113 | PIN1 Peptidyl-prolyl cis-trans isomerase NIMA-interacting 1 | 19 | 20.0 | 3.4 | 2.6 | 3.3 |
| P24752_C119 | ACAT1 Acetyl-CoA acetyltransferase, mitochondrial | 22 | 2.6 | 3.0 | 5.5 | 3.8 |
| P24752_C413 | ACAT1 Acetyl-CoA acetyltransferase, mitochondrial | 56 | 20.0 | 4.5 | 20.0 | 19.5 |
| Q9NUY8_C283 | TBC1 domain family member 23 TBC1D23 | 101 | 4.1 | 2.1 | 4.9 | 2.1 |
| P13667_C206 | PDIA4 Protein disulfide-isomerase A4 | 36 | 2.6 | 6.8 | 15.2 | 1.1 |
| P12268_C140 | IMPDH2 Inosine-5-monophosphate dehydrogenase 2 | 45 | 1.3 | 1.0 | 0.9 | 1.2 |
| Q15365_C194 | PCBP1 Poly(rC)-binding protein 1 | 29 | 5.1 | 1.4 | 1.4 | 10.1 |
| Q9NVC6_C649 | MED17 Mediator of RNA polymerase II transcription subunit 17 | 211 | 7.7 | 1.7 | 3.2 | 2.2 |
| P42166_C561 | TMPO Lamina-associated polypeptide 2, isoform alpha | 88 | 8.3 | 20.0 | 4.6 | 3.7 |
| Q9Y696_C35 | CLIC4 Chloride intracellular channel protein 4 | 21 | 1.7 | 20.0 | 4.7 | 2.6 |
| P10599_C32 | TXN Thioredoxin | 34 | 7.9 | 3.3 | 5.9 | 20.0 |
| P31943_C267 | HNRNPH1 Heterogeneous nuclear ribonucleoprotein H | 769 | 3.8 | 6.0 | 5.3 | 2.1 |
| Q865X6_C67 | GLRX5 Glutaredoxin-related protein 5, mitochondrial | 26 | 1.1 | 1.4 | 1.0 | 5.1 |
| P15121_C299 | AKR1B1 Aldose reductase | 48 | 0.9 | 1.0 | 1.7 | 1.4 |
| P52597_C267 | HNRNPF Heterogeneous nuclear ribonucleoprotein F | 108 | 4.2 | 20.0 | — | 3.2 |
| Q9ULV4_C420 | CORO1C Coronin-1C | 770 | 3.0 | 1.3 | 4.6 | 2.0 |
| P62888_C92 | RPL30 60S ribosomal protein L30 | 100 | 1.0 | 2.7 | 1.5 | 1.3 |
| Q9NQR4_C153 | N1T2 Omega-amidase NIT2 | 47 | 13.1 | 0.7 | 20.0 | 20.0 |
| P42765_C92 | ACAA2 3-ketoacyl-CoA thiolase, mitochondrial | 71 | 20.0 | 3.7 | 20.0 | 4.3 |
| Q15084_C55 | PDIA6 Protein disulfide-isomerase A6 | 51 | 3.0 | 4.9 | 4.4 | 2.1 |
| Q96HE7_C241 | ERO1L ERO1-like protein alpha | 61 | 2.4 | 3.0 | 3.7 | — |
| Q99439_C164 | CNN2 Calponin-2 | 41 | — | 1.5 | 1.1 | 4.7 |
| P25205_C119 | MCM3 DNA replication licensing factor MCM3 | 74 | 3.5 | 4.3 | 3.5 | 1.9 |
| Q9NS86_C187 | LANCL2 LanC-like protein 2 | 203 | — | 1.6 | 6.1 | 15 |
| Q15233_C145 | NONO Non-POU domain-containing octamer-binding protein | 72 | — | 1.6 | 12.0 | 1.4 |
| Q9BRA2_C43 | TXNDC17 Thioredoxin domain-containing protein 17 | 62 | 15.5 | 3.5 | 20.0 | 20.0 |
| P35611_C68 | ADD1 Alpha-adducin | 771 | 5.8 | 4.3 | 2.4 | 4.3 |
| O75521_C380 | ECI2 Enoyl-CoA delta isomerase 2, mitochondrial | 155 | 0.6 | 1.6 | 0.8 | 0.7 |
| Q9BXW7_C392 | CECR5 Cat eye syndrome critical region protein 5 | 772 | 3.6 | 2.2 | 3.2 | 1.5 |
| P30101_C406 | PDIA3 Protein disulfide-isomerase A3 | 773 | 3.2 | 9.0 | 20.0 | 1.4 |
| Q96AB3_C114 | ISOC2 Isochorismatase domain-containing protein 2, mitochondria | 159 | 1.6 | 0.8 | 4.7 | — |
| P13667_C555 | PDIA4 Protein disulfide-isomerase A4 | 774 | 3.2 | 9.0 | 20.0 | 1.4 |
| Q09161_C44 | NCBP1 Nuclear cap-binding protein subunit 1 | 102 | 2.1 | 1.8 | 2.0 | — |
| P78417_C32 | GSTO1 Glutathione S-transferase omega-1 | 32 | — | 19.9 | 20.0 | — |
| Q9ULW0_C536 | TPX2 Targeting protein for Xklp2 | 437 | 20.0 | 20.0 | 20.0 | 5.7 |
| Q9NRG0_C55 | CHRAC1 Chromatin accessibility complex protein 1 | 252 | 20.0 | 20.0 | 7.4 | 2.9 |
| Q96T76_C848 | MMS19 nucleotide excision repair protein homolog | 114 | 3.9 | 20.0 | 1.7 | 20.0 |
| Q8TAQ2_C145 | SMARCC2 SWI/SNF complex subunit SMARCC2 | 775 | 4.6 | 3.1 | — | — |
| Q9BVC5_C10 | C2orf49 Ashwin | 168 | 2.7 | 3.3 | 4.5 | — |
| Q7Z2W4_C645 | ZC3HAV1 Zinc finger CCCH-type antiviral protein 1 | 776 | — | 4.4 | 5.1 | 3.0 |
| Q9BQ69_C186 | MACROD1 O-acetyl-ADP-ribose deacetylase MACROD1 | 777 | 4.8 | 1.8 | 5.0 | 1.2 |

TABLE 2A-continued

| Identifier | Protein | SEQ ID NO: | 2_200 µM_in-situ_231 | 4_100 µM_in-situ_231 | 8_200 µM_in-situ_231 | 9_200 µM_in-situ_231 |
|---|---|---|---|---|---|---|
| Q16831_C162 | UPP1 Uridine phosphorylase 1 | 364 | 1.2 | 1.0 | 20.0 | 7.7 |
| P30101_057 | PDIA3 Protein disulfide-isomerase A3 | 133 | 2.2 | 20.0 | 20.0 | — |
| P12268_C331 | IMPDH2 Inosine-5-monophosphate dehydrogenase 2 | 144 | 12.1 | 4.6 | — | 1.3 |
| O95571_C170 | ETHE1 Protein ETHE1, mitochondrial | 176 | 3.8 | 2.3 | 6.8 | 2.0 |
| O00299_C24 | CLIC1 Chloride intracellular channel protein 1 | 69 | 9.5 | 20.0 | 10.3 | 3.0 |
| O14879_C343 | IFIT3 Interferon-induced protein with tetratricopeptide | 308 | 7.6 | 6.6 | 2.1 | 17.2 |
| Q96CM8_C64 | ACSF2 Acyl-CoA synthetase family member 2, mitochondrial | 194 | 20.0 | 20.0 | 20.0 | — |
| P51946_C244 | CCNH Cyclin-H | 778 | 1.9 | 5.3 | — | — |
| P49588_C773 | AARS Alanine-tRNA ligase, cytoplasmic | 122 | — | 1.3 | 1.5 | 1.5 |
| O96RN5_C618 | MED15 Mediator of RNA polymerase II transcription subuni | 171 | 6.4 | 4.5 | 20.0 | |
| 015294_C758 | OGT UDP-N-acetylglucosamine peptide N-acetylglucosami | 104 | 2.6 | 6.4 | 2.4 | 2.1 |
| P46734_C207 | MAP2K3 Dual specificity mitogen-activated protein kinase | 184 | 0.8 | 0.6 | 0.8 | 3.3 |
| Q96S55_C272 | WRNIP1 ATPase WRNIP1 | 215 | 2.2 | 3.7 | 1.2 | 4.5 |
| O95229_C54 | ZWINT ZW10 interactor | 779 | 3.4 | 12.4 | 3.1 | 3.7 |
| O60610_C1227 | DIAPH1 Protein diaphanous homolog 1 | 780 | 2.2 | 1.6 | — | 1.5 |
| Q13428_C38 | TCOF1 Treacle protein | 150 | 3.3 | 2.8 | 2.0 | — |
| Q9Y277_C65 | VDAC3 Voltage-dependent anion-selective channel protein | 512 | 3.3 | 4.7 | 6.2 | — |
| P57764_C268 | GSDMD Gasdennin-D | 110 | 20.0 | 20.0 | 8.4 | — |
| Q9Y3A3_C134 | MOB4 MOB-like protein phocein | 121 | — | 1.2 | 1.6 | 20.0 |
| Q02252_C317 | ALDH6A1 Methylmalonate-semialdehyde dehydrogenase | 265 | 10.3 | 14.4 | — | — |
| Q9NYL9_C132 | TMOD3 Tropomodulin-3 | 130 | 2.2 | 0.8 | 0.9 | 7.6 |
| P83731_C6 | RPL24 60S ribosomal protein L24 | 147 | 2.4 | 0.7 | — | 4.3 |
| O95336_C32 | PGLS 6-phosphogluconolactonase | 55 | 14.9 | — | 20.0 | 6.7 |
| Q13155_C291 | AIMP2 Aminoacyl tRNA synthase complex-interacting multif | 83 | 20.0 | 20.0 | 2.4 | 1.9 |
| Q13418_C346 | ILK Integrin-linked protein kinase | 149 | 1.4 | 0.8 | — | 2.7 |
| A6NDU8_C179 | C5orf51 UPF0600 protein C5orf51 | 298 | 4.2 | 3.0 | — | 20.0 |
| Q9UKF0_C498 | CPSF3 Cleavage and polyadenylation specificity factor su | 118 | 6.2 | 3.5 | 20.0 | — |
| Q96F86_C413 | EDC3 Enhancer of mRNA-decapping protein 3 | 141 | 20.0 | 20.0 | — | — |
| P42224_C492 | STAT1 Signal transducer and activator of transcription 1 | 228 | 16.9 | — | — | 3.1 |
| P11216_C326 | PYGB Glycogen phosphorylase, brain form | 366 | — | 1.7 | 20.0 | 2.6 |
| P21980_C277 | TGM2 Protein-glutamine gamma-glutamyltransferase 2 | 356 | 0.7 | 0.5 | 0.7 | 2.3 |
| Q9HAV7_C124 | GRPEL1 GrpE protein homolog 1, mitochondrial | 206 | 3.2 | 1.7 | 2.2 | 4.7 |
| P24752_C126 | ACAT1 Acetyl-CoA acetyltransferase, mitochondrial | 89 | 9.1 | 2.8 | 4.5 | 14.1 |
| Q9NQ88_C161 | TIGAR Fructose-2,6-bisphosphatase TIGAR | 117 | 6.0 | — | — | 2.6 |
| Q13155_C23 | AIMP2 Aminoacyl tRNA synthase complex-interacting multifunctional protein 2 | 132 | — | 2.8 | 2.7 | — |
| Q9NQW6_C712 | ANLN Actin-binding protein anillin | 281 | — | 4.1 | 14.1 | 3.1 |
| P51649_C340 | ALDH5A1 Succinate-semialdehyde dehydrogenase, mitochondria | 189 | 1.9 | 1.0 | 2.7 | — |
| Q15021_C439 | NCAPD2 Condensin complex subunit 1 | 139 | — | 2.2 | 0.6 | 6.1 |
| Q5T0N5_C69 | FNBP1L Formin-binding protein 1-like | 418 | 20.0 | 20.0 | 3.6 | — |
| P38606_C138 | ATP6V1A V-type proton ATPase catalytic subunit A | 201 | — | 20.0 | 20.0 | 20.0 |
| Q9HCC0_C216 | MCCC2 Methylcrotonoyl-CoA carboxylase beta chain, mitoch | 363 | 4.6 | 5.9 | 3.9 | — |
| Q9NQC3_C1101 | RTN4 Reticulon-4 | 247 | 12.0 | 20.0 | — | 20.0 |
| P35754_C23 | GLRX Glutaredoxin-1 | 142 | — | 20.0 | — | — |
| Q99757_C90 | TXN2 Thioredoxin, mitochondrial | 208 | 10.1 | 3.6 | 4.5 | 20.0 |
| Q9Y3D0_C93 | FAM96B Mitotic spindle-associated MMXD complex subunit MIP18 | 179 | 20.0 | 20.0 | — | — |
| Q9UMS0_C213 | NFU1 iron-sulfur cluster scaffold homolog, mitochondrial | 394 | 7.4 | 4.4 | — | — |
| Q9NXV6_C516 | CDKN2AEP CDKN2A-interacting protein | 255 | 20.0 | — | — | 6.6 |
| Q96RS6_C376 | NUDCD1 NudC domain-containing protein 1 | 79 | — | 1.6 | — | 2.2 |
| Q14997_C1840 | PSME4 Proteasome activator complex subunit 4 | 257 | 2.8 | 20.0 | 20.0 | — |
| P50570_C27 | DNM2 Dynamin-2 | 73 | 4.6 | 2.2 | — | — |
| Q86YH6_C71 | PDSS2 Decaprenyl-diphosphate synthase subunit 2 | 401 | 20.0 | 20.0 | — | — |
| Q99497_C106 | PARK7 Protein DJ-1 | 109 | — | 0.9 | — | — |

TABLE 2A-continued

| Identifier | Protein | SEQ ID NO: | 2_200 μM_in-situ_231 | 4_100 μM_in-situ_231 | 8_200 μM_in-situ_231 | 9_200 μM_in-situ_231 |
|---|---|---|---|---|---|---|
| Q9UJW0_C258 | DCTN4 Dynactin subunit 4 | 103 | 4.0 | — | 20.0 | — |
| Q9BUH6_C180 | C9orf142 Uncharacterized protein C9orf142 | 348 | — | 1.2 | 6.6 | 2.8 |
| P24752_C196 | ACAT1 Acetyl-CoA acetyltransferase, mitochondrial | 33 | 20.0 | 3.5 | — | 5.8 |
| Q13162_C51 | PRDX4 Peroxiredoxin-4 | 781 | 4.6 | 1.2 | 1.4 | 3.3 |
| Q9BTA9_0553 | WAC WW domain-containing adapter protein with coiled-coil | 153 | 17.6 | 17.8 | 9.6 | — |
| P48643_C253 | CCT5 T-complex protein 1 subunit epsilon | 126 | — | 0.8 | 0.8 | — |
| O75362_C286 | ZNF217 Zinc finger protein 217 | 268 | 8.9 | — | — | — |
| O60825_C158 | PFKFB2 6-phosphofructo-2-kinase/fructose-2,6-bisphosphata | 272 | 0.7 | — | — | — |
| Q8NBS9_C350 | TXNDC5 Thioredoxin domain-containing protein 5 | 136 | — | 2.4 | — | 1.7 |
| Q9NYL2_C22 | MUTK Mitogen-activated protein kinase MLTK | 430 | 5.5 | 20.0 | 1.4 | 10.3 |
| P27707_C9 | DCK Deoxycytidine kinase | 93 | — | 1.4 | — | 4.9 |
| Q93009_C223 | USP7 Ubiquitin carboxyl-terminal hydrolase 7 | 782 | — | 6.8 | 20.0 | — |
| O14929_C101 | HAT1 Histone acetyltransferase type B catalytic subunit | 154 | — | — | — | 9.0 |
| Q9UPQ0_C140 | LIMCH1 LIM and calponin homology domains-containing protein | 783 | 20.0 | — | 20.0 | — |
| Q96NY7_C487 | CLIC6 Chloride intracellular channel protein 6 | 447 | — | 20.0 | 5.1 | 3.6 |
| Q9NQ88_C114 | TIGAR Fructose-2,6-bisphosphatase TIGAR | 143 | 2.8 | — | — | 1.9 |
| Q14790_C360 | CASP8 Caspase-8 | 335 | 20.0 | 20.0 | — | — |
| P04183_C230 | TK1 Thymidine kinase, cytosolic | 784 | 1.9 | 0.8 | — | 10.0 |
| P68366_C54 | TUBA4A Tubulin alpha-4A chain | 137 | 9.7 | 0.8 | 0.9 | — |
| Q13428_C1298 | TCOF1 Treacle protein | 785 | 4.7 | 5.6 | 20.0 | — |
| Q5MNZ6_C63 | WDR45L WD repeat domain phosphoinositide-interacting protein | 434 | — | 2.0 | 20.0 | — |
| O14980_0528 | XPO1 Exportin-1 | 786 | 20.0 | 1.9 | — | — |
| Q86W42_C35 | THOC6 THO complex subunit 6 homolog | 217 | — | — | — | 20.0 |
| Q9Y6G9_C51 | DYNC1LI1 Cytoplasmic dynein 1 light intermediate chain 1 | 107 | — | 3.5 | 4.1 | — |
| Q9NY27_C22 | PPP4R2 Serine/threonine-protein phosphatase 4 regulatory | 282 | 20.0 | 20.0 | — | — |
| Q8NFH5_C255 | NUP35 Nucleoporin NUP53 | 386 | 5.1 | 3.9 | — | — |
| Q9Y676_C128 | MRPS18B 28S ribosomal protein S18b, mitochondrial | 495 | 10.2 | 2.3 | 1.0 | — |
| P35658_C728 | NUP214 Nuclear pore complex protein Nup214 | 311 | 3.9 | 1.7 | — | — |
| Q9NTX5_C133 | ECHDC1 Ethylmalonyl-CoA decarboxylase | 532 | 1.5 | 1.7 | 2.0 | — |
| Q15118_C71 | PDK1 | 623 | 20.0 | 20.0 | 20.0 | — |
| Q00765_018 | REEP5 Receptor expression-enhancing protein 5 | 344 | — | 20.0 | 2.7 | — |
| P22307_C71 | SCP2 Non-specific lipid-transfer protein | 787 | 3.2 | 2.7 | 20.0 | — |
| O75521_C312 | ECI2 Enoyl-CoA delta isomerase 2, mitochondrial | 788 | 0.7 | 1.0 | 0.5 | 0.5 |
| P49189_C288 | ALDH9A1 4-trimethylaminobutyraldehyde dehydrogenase | 236 | — | — | — | 20.0 |
| Q5T440_C170 | IBA57 Putative transferase CAF17, mitochondrial | 608 | 14.0 | 1.5 | — | — |
| Q15084_C190 | PDIA6 Protein disulfide-isomerase A6 | 96 | — | 20.0 | 5.2 | — |
| Q96C19_C172 | EFHD2 EF-hand domain-containing protein D2 | 246 | — | 5.3 | — | 2.8 |
| P22061_C102 | PCMT1 Protein-L-isoaspartate(D-aspartate) O-methyltransferase | 163 | — | 2.8 | 4.5 | 1.2 |
| Q9NP73_C86 | ALG13 UDP-N-acetylglucosamine transferase subunit ALG13 | 528 | 20.0 | 20.0 | — | — |
| Q9BRF8_C54 | CPPED1 Calcineurin-like phosphoesterase domain-containing | 239 | — | 20.0 | — | 2.4 |
| Q6ICB0_C108 | DESI1 Desumoylating isopeptidase 1 | 197 | 20.0 | — | 20.0 | — |
| P29590_C389 | PML Protein PML | 304 | 15.6 | — | — | — |
| P07858_C211 | CTSB Cathepsin B | 323 | | 2.3 | — | 5.0 |
| Q9NX18_C83 | SDHAF2 Succinate dehydrogenase assembly factor 2, mitochondrial | 658 | 3.1 | 3.0 | — | — |
| P46109_0249 | CRKL Crk-like protein VPCAYDK K.RVPC*AYDK.T | 99 | 20.0 | — | — | 6.7 |
| P45984_C177 | MAPK9 Mitogen-activated protein kinase 9 | 302 | — | 12.0 | 20.0 | — |
| P19447_C342 | ERCC3 TFIIH basal transcription factor complex helicase | 402 | — | — | 12.4 | — |
| P42166_C341 | TMPO Lamina-associated polypeptide 2, isoform alpha | 175 | 10.4 | — | 4.4 | — |

TABLE 2A-continued

| Identifier | Protein | SEQ ID NO: | 2_200 μM_in-situ_231 | 4_100 μM_in-situ_231 | 8_200 μM_in-situ 231 | 9_200 μM_in-situ 231 |
|---|---|---|---|---|---|---|
| Q8N1F7_0522 | NUP93 Nuclear pore complex protein Nup93 | 275 | — | — | 20.0 | — |
| Q86UY8_C276 | NT5DC3 5-nucleotidase domain-containing protein 3 | 789 | 3.8 | — | — | — |
| Q8WWI1_C228 | LMO7 LIM domain only protein 7 | 504 | — | — | — | — |
| Q9NWA0_0139 | MED9 Mediator of RNA polymerase II transcription subunit | 654 | 4.3 | 14 | — | — |
| P09110_C381 | ACAA1 3-ketoacyl-CoA thiolase, peroxisomal | 205 | — | — | 0.8 | — |
| Q2NL82_C126 | TSR1 Pre-rRNA-processing protein TSR1 homolog | 233 | 20.0 | 13.8 | — | — |
| Q5JPI3_C308 | C3orf38 Uncharacterized protein C3orf38 | 544 | 2.9 | — | — | — |
| P23919_C163 | DTYMK Thymidylate kinase | 173 | — | 0.4 | 0.6 | — |
| Q96EB1_C218 | ELP4 Elongator complex protein 4 | 466 | — | 20.0 | — | 8.4 |
| Q96FX7_C209 | TRMT61A tRNA (adenine(58)-N(1))-methyltransferase catalytic | 313 | 20.0 | 2.4 | — | — |
| O14933_C98 | UBE2L6 Ubiquitin/ISG15-conjugating enzyme E2 L6 | 331 | — | 3.0 | — | — |
| Q29RF7_C242 | PDS5A Sister chromatid cohesion protein PDS5 homolog A | 232 | — | 3.0 | 1.0 | — |
| Q96T76_C819 | MMS19 MMS19 nucleotide excision repair protein homolog | 181 | — | — | — | — |
| P23919_C117 | DTYMK Thymidylate kinase | 267 | — | — | 0.4 | 7.3 |
| Q15149_C4574 | PLEC Plectin | 336 | — | 4.2 | — | 0.8 |
| Q96RP9_C153 | GFM1 Elongation factor G, mitochondrial | 524 | — | 1.0 | — | — |
| P04818_C199 | TYMS Thymidylate synthase | 406 | 20.0 | 20.0 | — | — |
| P27708_C73 | CAD CAD protein | 191 | 3.1 | — | 20.0 | — |
| P55265_C1224 | ADAR Double-stranded RNA-specific adenosine deaminase | 359 | 9.1 | — | — | — |
| Q9Y3D2_C105 | MSRB2 Methionine-R-sulfoxide reductase B2, mitochondrial | 403 | — | 20.0 | 20.0 | — |
| O00244_C12 | ATOX1 Copper transport protein ATOX1 | 365 | — | — | — | 4.7 |
| Q8WV74_C207 | NUDT8 Nucleoside diphosphate-linked moiety X motif 8, mitochondrial | 468 | 20.0 | 20.0 | 20.0 | — |
| Q9NRW3_C130 | APOBEC3C Probable DNA dC- dU-editing enzyme APOBEC-3C | 358 | 20.0 | 20.0 | — | — |
| P24468_C326 | NR2F2 COUP transcription factor 2 | 790 | 20.0 | 20.0 | 20.0 | — |
| P42166_C684 | TMPO Lamina-associated polypeptide 2, isoform alpha | 312 | — | — | 4.6 | — |
| Q96EY5_C231 | FAM125A Multivesicular body subunit 12A | 540 | 4.1 | 1.7 | — | 1.9 |
| P14635_C238 | CCNB1 G2/mitotic-specific cyclin-B1 | 448 | — | — | — | 3.7 |
| Q8NDH3_C81 | NPEPL1 Probable aminopeptidase NPEPL1 | 791 | 20.0 | 20.0 | 20.0 | — |
| Q9P0J1_C149 | PDP1 | 276 | 20.0 | — | — | — |
| Q96P48_C900 | ARAP1 Arf-GAP with Rho-GAP domain, ANK repeat and PH domain | 433 | 5.5 | — | — | — |
| Q96HE7_C37 | ERO1L ERO1-like protein alpha | 347 | — | 5.4 | — | 20.0 |
| Q07065_C100 | CKAP4 Cytoskeleton-associated protein 4 | 733 | — | — | — | 15.4 |
| Q9BRJ7_C88 | NUDT16L1 Protein syndesmos | 432 | 20.0 | 20.0 | — | — |
| O75439_C265 | PMPCB Mitochondrial-processing peptidase subunit beta | 320 | — | — | — | — |
| O43175_C369 | PHGDH D-3-phosphoglycerate dehydrogenase | 248 | 20.0 | — | — | — |
| Q9UNI6_C265 | DUSP12 Dual specificity protein phosphatase 12 | 241 | — | 0.8 | — | — |
| Q06203_C100 | PPAT Amidophosphoribosyltransferase | 188 | — | 1.7 | — | — |
| A0AVT1_C347 | UBA6 Ubiquitin-like modifier-activating enzyme 6 | 158 | — | 20.0 | — | 3.3 |
| Q86X76_C203 | NIT1 Nitrilase homolog 1 | 471 | — | 0.7 | — | — |
| Q6XZF7_C691 | DNMBP Dynamin-binding protein | 353 | — | 1.2 | — | 3.4 |
| Q15398_C129 | DLGAP5 Disks large-associated protein 5 | 167 | 20.0 | — | — | — |
| O75717_C773 | WDHD1 WD repeat and HMG-box DNA-binding protein 1 | 289 | — | — | 4.2 | — |
| Q01433_C107 | AMPD2 AMP deaminase 2 | 259 | 4.4 | 2.3 | 6.2 | 3.1 |
| Q8WVV9_C464 | HNRPLL Heterogeneous nuclear ribonucleoprotein L-like | 487 | — | — | — | — |
| O14733_C131 | MAP2K7 Dual specificity mitogen-activated protein kinase | 427 | — | — | — | — |
| Q14137_C404 | BOP1 Ribosome biogenesis protein BOP 1 | 535 | 20.0 | 1.2 | — | — |
| Q96RU2_C171 | USP28 Ubiquitin carboxyl-terminal hydrolase 28 | 569 | — | 20.0 | 1.2 | — |
| Q9Y679_C391 | AUP1 Ancient ubiquitous protein 1 | 564 | — | 20.0 | 20.0 | — |
| P51610_C1872 | HCFC1 Host cell factor 1 | 270 | 4.1 | — | — | — |
| P22307_C307 | SCP2 Non-specific lipid-transfer protein | 541 | 20.0 | 20.0 | 20.0 | — |
| Q9BTE3_C325 | MCMBP Mini-chromosome maintenance complex-binding protein | 792 | — | — | — | — |

TABLE 2A-continued

| Identifier | Protein | SEQ ID NO: | 2_200 μM_in-situ_231 | 4_100 μM_in-situ_231 | 8_200 μM_in-situ_231 | 9_200 μM_in-situ_231 |
|---|---|---|---|---|---|---|
| Q9HA64_C24 | FN3KRP Ketosamine-3-kinase | 106 | 6.3 | 20.0 | — | 20.0 |
| Q5TFE4_C119 | NT5DC1 5-nucleotidase domain-containing protein 1 | 75 | — | — | — | 20.0 |
| Q96N67_C2125 | DOCK7 Dedicator of cytokinesis protein 7 | 408 | — | 4.1 | 5.4 | — |
| P52948_C1312 | NUP98 Nuclear pore complex protein Nup98-Nup96 | 575 | — | — | — | — |
| Q5UIP0_C2298 | RIF1 Telomere-associated protein RIF1 | 607 | — | 20.0 | — | — |
| P51812_C436 | RPS6KA3 Ribosomal protein S6 kinase alpha-3 | 662 | — | — | — | 2.1 |
| Q92616_C1692 | GCN1L1 Translational activator GCN1 | 174 | 1.4 | — | — | — |
| QI5345_C297 | LRRC41 Leucine-rich repeat-containing protein 41 | 536 | — | — | — | — |
| Q9NPH0_C267 | ACP6 Lysophosphatidic acid phosphatase type 6 | 329 | — | 20.0 | 20.0 | — |
| P04183_C66 | TK1 Thymidine kinase, cytosolic | 138 | — | — | 2.3 | 7.0 |
| P42166_C629 | TMPO Lamina-associated polypeptide 2, isoform alpha | 793 | 4.4 | — | 1.7 | — |
| Q15013_C124 | MAD2L1BP MAD2L1-binding protein | 794 | — | 13.0 | 5.4 | — |
| Q9Y5Y2_C72 | NUBP2 Cytosolic Fe-S cluster assembly factor NUBP2 | 795 | 5.3 | — | — | 4.0 |
| O15446_C86 | CD3EAP DNA-directed RNA polymerase I subunit RPA34 | 796 | 3.9 | — | — | — |
| Q13630_C116 | TSTA3 GDP-L-fucose synthase | 797 | 20.0 | — | — | 1.9 |
| Q8IYQ7_C324 | THNSL1 Threonine synthase-like 1 | 628 | — | — | 20.0 | 1.6 |
| P05091_C319 | ALDH2 Aldehyde dehydrogenase, mitochondrial | 318 | — | 20.0 | — | — |
| Q29RF7_C532 | PDS5A Sister chromatid cohesion protein PDS5 homolog A | 261 | — | 20.0 | — | — |
| Q9Y570_C381 | PPME1 Protein phosphatase methylesterase 1 | 578 | 12.6 | 1.1 | — | 20.0 |
| Q14980_C961 | NUMA1 Nuclear mitotic apparatus protein 1 | 429 | — | — | — | — |
| P53384_C235 | NUBP1 Cytosolic Fe-S cluster assembly factor NUBP1 | 552 | — | 0.6 | 0.6 | 6.8 |
| Q15003_C418 | NCAPH Condensin complex subunit 2 | 258 | 20.0 | 20.0 | — | — |
| P53634_C258 | CTSC Dipeptidyl peptidase 1 | 798 | 0.9 | 1.2 | — | — |
| Q8NFF5_C499 | FLAD1 FAD synthase | 750 | 6.2 | — | — | — |
| Q9ULA0_C144 | DNPEP Aspartyl aminopeptidase | 134 | — | — | — | 2.1 |
| P22307_C94 | SCP2 Non-specific lipid-transfer protein | 559 | — | 20.0 | — | — |
| O15294_C620 | OGT UDP-N-acetylglucosamine-peptide N-acetylglucosamine | 279 | — | 20.0 | — | — |
| Q9Y5S2_C1517 | CDC42BPB Serine/threonine-protein kinase MRCK beta | 554 | 20.0 | 20.0 | — | — |
| Q8TD19_C623 | NEK9 Serine/threonine-protein kinase Nek9 | 393 | — | — | — | — |
| Q8N2W9_C326 | PIAS4 E3 SUMO-protein ligase PIAS4 | 625 | — | — | — | — |
| Q13158_C98 | FADD Protein FADD | 799 | 20.0 | — | — | — |
| Q9UKX7_C151 | NUP50 Nuclear pore complex protein Nup50 | 234 | 6.1 | — | — | — |
| Q6PCB5_C280 | RSBN1L Round spermatid basic protein 1-like protein | 519 | — | — | — | — |
| P10398_C597 | ARAF Serine/threonine-protein kinase A-Raf | 505 | — | — | — | 5.0 |
| Q9UL40_C68 | ZNF346 Zinc finger protein 346 | 706 | — | — | — | — |
| P46013_C903 | MKI67 Antigen KI-67 | 595 | 20.0 | — | — | — |
| Q16667_C39 | CDKN3 Cyclin-dependent kinase inhibitor 3 | 482 | — | 0.6 | — | — |
| O75150_C890 | RNF40 E3 ubiquitin-protein ligase BRE1B | 405 | | | | |
| Q00610_C870 | CLTC Clathrin heavy chain 1 | 113 | — | 2.1 | — | 2.8 |
| Q9Y5T5_C205 | USP16 Ubiquitin carboxyl-terminal hydrolase 16 | 474 | 7.9 | 20.0 | — | — |
| O95881_C66 | TXNDC12 Thioredoxin domain-containing protein 12 | 342 | — | — | — | — |
| Q7Z5K2_C160 | WAPAL Wings apart-like protein homolog | 800 | 20.0 | — | — | — |
| P42166_C518 | TMPO Lamina-associated polypeptide 2, isoform alpha | 801 | — | — | — | 3.4 |
| Q9Y2S7_C143 | POLDIP2 Polymerase delta-interacting protein 2 | 574 | — | — | — | 2.3 |
| E2QRD5_C183 | C15orf38-AP3S2 Protein C15orf38-AP3S2 | 581 | — | — | — | 4.9 |
| O95833_C22 | CLIC3 Chloride intracellular channel protein 3 | 531 | — | — | — | 20.0 |
| O94953_C694 | KDM4B Lysine-specific demethylase 4B | 395 | 20.0 | — | — | — |
| O00541_C272 | PES1 Pescadillo homolog | 511 | — | — | — | 5.0 |
| Q9NXJ5_C149 | PGPEPI Pyroglutamyl-peptidase 1 | 587 | — | 20.0 | | |
| Q8N5L8_C131 | RPP25L Ribonuclease P protein subunit p25-like protein | 670 | — | — | — | — |
| Q8IZ73_C246 | RPUSD2 RNA pseudouridylate synthase domain-containing protein | 441 | — | — | — | — |
| Q99798_C385 | ACO2 Aconitate hydratase, mitochondrial | 685 | 20.0 | 1.0 | — | — |
| Q9GZR2_C382 | REXO4 RNA exonuclease 4 | 621 | — | — | — | — |

TABLE 2A-continued

| Identifier | Protein | SEQ ID NO: | 2_200 µM_in-situ_231 | 4_100 µM_in-situ_231 | 8_200 µM_in-situ 231 | 9_200 µM_in-situ 231 |
|---|---|---|---|---|---|---|
| Q13613_C117 | MTMR1 Myotubularin-related protein 1 | 717 | — | — | — | — |
| Q9NUI1_C22 | DECR2 Peroxisomal 2,4-dienoyl-CoA reductase | 698 | — | — | — | — |
| Q02556_C306 | IRF8 Interferon regulatory factor 8 | 513 | — | — | — | — |
| Q9UPT9_C171 | USP22 Ubiquitin carboxyl-terminal hydrolase 22 | 802 | — | — | — | — |
| Q8N999_C302 | C12orf29 Uncharacterized protein C12orf29 | 484 | — | — | — | — |
| Q8IU81_C363 | IRF2BP1 Interferon regulatory factor 2-binding protein 1 | 803 | — | — | — | — |
| Q9C0I1_C152 | MTMR12 Myotubularin-related protein 12 | 671 | — | — | — | — |
| Q9P2X3_C195 | IMPACT Protein IMPACT | 678 | — | 20.0 | — | — |
| Q6QNY0_C168 | BL0C1S3 Biogenesis of lysosome-related organelles complex | 411 | — | — | | |
| Q15796_C81 | SMAD2 Mothers against decapentaplegic homolog 2 | 561 | 20.0 | — | — | — |
| Q9NZB2_C531 | FAM120A Constitutive coactivator of PPAR-gamma-like protein | 492 | — | — | — | — |
| Q9HB90_C377 | RRAGC Ras-related GTP-binding protein C | 417 | 3.3 | — | — | 4.3 |
| Q9BR61_C267 | ACBD6 Acyl-CoA-binding domain-containing protein 6 | 472 | — | — | — | — |
| P16455_C145 | MGMT Methylated-DNA protein-cysteine methyltransferase | 470 | — | — | — | — |
| Q86UV5_C39 | USP48 Ubiquitin carboxyl-terminal hydrolase 48 | 381 | 20.0 | — | — | — |
| A2A288_C367 | ZC3H12D Probable ribonuclease ZC3H12D | 515 | — | — | — | — |
| Q8NEC7_C140 | GSTCD Glutathione S-transferase C-terminal domain-containing protein | 602 | — | — | — | — |
| Q6PJG6_C673 | BRAT1 BRCA1-associated ATM activator 1 | 695 | — | — | — | — |
| Q13232_C158 | NME3 Nucleoside diphosphate kinase 3 | 653 | — | — | — | 2.7 |
| Q86X76_C165 | NIT1 Nitrilase homolog 1 | 345 | — | 0.9 | — | — |
| P42695_C541 | NCAPD3 Condensin-2 complex subunit D3 | 573 | — | — | — | — |
| P41226_C599 | UBA7 Ubiquitin-like modifier-activating enzyme 7 | 702 | — | — | — | — |
| Q99986_C50 | VRK1 Serine/threonine-protein kinase VRK1 | 497 | — | — | — | — |
| Q8WUM4_C90 | PDCD6IP Programmed cell death 6-interacting protein | 527 | — | — | — | — |
| P29590_C213 | PML Protein PML | 477 | — | — | — | — |
| Q9P0K7_C973 | RAI14 Ankycorbin | 638 | — | 8.7 | — | — |
| P53992_C78 | SEC24C Protein transport protein Sec24C | 498 | — | — | 5.4 | — |
| Q13867_C73 | BLMH Bleomycin hydrolase | 431 | — | — | — | 3.9 |
| Q8ND24_C655 | RNF214 RING finger protein 214 | 451 | 6.5 | — | — | 4.0 |
| Q96EK4_C48 | THAP11 TRAP domain-containing protein 11 | 538 | 7.9 | — | — | — |
| Q96IV0_C309 | NGLY1 Peptide-N(4)-(N-acetyl-beta-glucosaminyl)asparagin | 660 | — | — | — | — |
| Q5T1V6_C414 | DDX59 Probable ATP-dependent RNA helicase DDX59 | 439 | — | — | — | — |
| Q9UHQ1_C99 | NARF Nuclear prelamin A recognition factor | 740 | — | — | — | — |
| O43396_C34 | TXNL1 Thioredoxin-like protein 1 | 310 | — | — | — | — |
| Q8IV53_C174 | DENND1C DENN domain-containing protein 1C | 804 | — | — | — | — |
| Q8N9T8_C673 | KRI1 Protein KRI1 homolog | 563 | — | — | 5.3 | — |

TABLE 2B

| Identifier | 9_200 µM_insitu_ramos | 10_200 µM_insitu_231 | 10_200 µM_insitu_ramos | 11_100 µM_insitu_231 | 12_200 µM_insitu_231 | 13_200 µM_insitu_231 | 13_200 µM_insitu_ramos | 14_200 µM_insitu_231 | 14_200 µM_insitu_ramos | 21_200 µM_insitu_231 |
|---|---|---|---|---|---|---|---|---|---|---|
| P04406_C152 | 1.1 | 1.0 | 0.9 | 0.8 | 0.9 | 0.9 | 0.9 | 0.9 | 0.6 | 1.3 |
| P61978_C132 | 1.4 | 5.6 | 1.6 | 0.9 | 7.5 | 1.1 | 1.1 | 1.3 | 0.9 | 1.4 |
| Q13526_C113 | 1.3 | 2.0 | 1.3 | 0.7 | 0.6 | 0.9 | 1.0 | 0.8 | 1.0 | 0.7 |
| P24752_C119 | 4.3 | 4.5 | 1.5 | 1.2 | 4.1 | 2.1 | 2.8 | 1.0 | — | 1.6 |
| P24752_C413 | 20.0 | 7.8 | 2.2 | 1.2 | 9.9 | 3.5 | 20.0 | 0.9 | 0.8 | 1.5 |
| Q9NUY8_C283 | 1.5 | 2.0 | — | 1.1 | 2.9 | 1.1 | 1.1 | 0.8 | 0.6 | 0.8 |

TABLE 2B-continued

| Identifier | 9_200 μM_ insitu_ ramos | 10_200 μM_ insitu_ 231 | 10_200 μM_ insitu_ ramos | 11_100 μM_ insitu_ 231 | 12_200 μM_ insitu_ 231 | 13_200 μM_ insitu_ 231 | 13_200 μM_ insitu_ ramos | 14_200 μM_ insitu_ 231 | 14_200 μM_ insitu_ ramos | 21_200 μM_ insitu_ 231 |
|---|---|---|---|---|---|---|---|---|---|---|
| P13667_C206 | 1.4 | 3.8 | — | 4.1 | 16.6 | 1.1 | — | 1.0 | 0.7 | 0.8 |
| P12268_C140 | 1.1 | 0.7 | 0.9 | 0.6 | 1.2 | 0.7 | — | 10.3 | — | 0.6 |
| Q15365_C194 | 1.5 | 1.6 | 2.0 | 0.4 | 1.3 | 0.9 | 1.4 | 1.0 | — | 1.1 |
| Q9NVC6_C649 | 1.3 | 2.3 | 2.1 | 0.8 | 4.0 | 1.1 | 1.0 | 1.0 | 1.4 | 0.8 |
| P42166_C561 | 2.1 | 17.8 | — | 0.6 | 16.1 | 1.2 | 1.0 | 2.9 | — | 1.4 |
| Q9Y696_C35 | 1.6 | 2.7 | 1.6 | 1.9 | 20.0 | 2.3 | 3.2 | 0.7 | — | 1.1 |
| P10599_C32 | 2.1 | 3.8 | — | 13.0 | 20.0 | 7.9 | 4.1 | 3.1 | — | 3.9 |
| P31943_C267 | 1.5 | 4.8 | 2.5 | 0.9 | 5.0 | 1.1 | 1.2 | 1.3 | — | 1.5 |
| Q86SX6_C67 | 14.0 | 1.3 | 1.1 | 1.4 | 1.6 | 10.3 | 12.4 | 3.1 | — | 1.4 |
| P15121_C299 | 1.5 | 20.0 | — | 0.7 | 0.7 | — | 0.8 | 0.9 | — | 2.7 |
| P52597_C267 | 1.6 | 2.5 | 2.4 | 1.0 | 6.8 | 1.2 | 1.3 | 1.5 | — | 1.5 |
| Q9ULV4_C420 | 1.4 | 3.4 | — | 0.9 | 2.2 | 1.1 | 1.1 | 1.4 | — | 1.3 |
| P62888_C92 | 2.4 | 1.3 | 4.5 | 0.8 | 1.1 | 0.8 | 2.0 | 1.0 | — | 0.9 |
| Q9NQR4_C153 | 20.0 | 20.0 | — | 3.7 | 0.9 | 6.2 | 12.2 | 0.8 | — | 0.9 |
| P42765_C92 | 1.2 | 3.7 | 1.1 | — | 20.0 | — | 2.2 | 1.2 | 0.8 | 1.3 |
| Q15084_C55 | 1.4 | 3.1 | — | 4.3 | 15.4 | — | 1.5 | 1.0 | — | 0.9 |
| Q96HE7_C241 | 1.8 | 2.0 | — | 1.8 | 16.4 | 1.5 | 1.3 | 1.1 | — | 1.6 |
| Q99439_C164 | 1.3 | 1.2 | 1.3 | 0.6 | 0.9 | 0.9 | 1.3 | 0.9 | — | 0.9 |
| P25205_C119 | 1.8 | 2.3 | — | 0.7 | 1.0 | 1.1 | 1.3 | 1.2 | — | 1.1 |
| Q9NS86_C187 | 1.7 | 6.3 | — | 0.8 | 2.0 | 1.0 | 1.1 | 1.0 | 3.3 | 0.9 |
| Q15233_C145 | 1.4 | — | 2.2 | 1.2 | 2.4 | 1.0 | 1.1 | 1.0 | — | — |
| Q9BRA2_C43 | 5.4 | 20.0 | — | 17.7 | 20.0 | 20.0 | 5.2 | 1.4 | — | 16.0 |
| P35611_C68 | 2.3 | 1.9 | — | 0.9 | 3.6 | 1.1 | 1.0 | 1.6 | — | 0.8 |
| O75521_C380 | 1.1 | 4.8 | — | 0.8 | 1.9 | 1.0 | — | 1.1 | — | 1.8 |
| Q9BXW7_C392 | — | 20.0 | — | 1.1 | 5.1 | 2.0 | — | 1.6 | 1.1 | 1.6 |
| P30101_C406 | 1.6 | 3.3 | 1.4 | — | 20.0 | — | 2.0 | 1.1 | — | — |
| Q96AB3_C114 | 3.7 | 20.0 | — | 0.9 | 1.6 | 2.4 | — | 1.0 | — | 4.9 |
| P13667_C555 | 1.6 | 3.3 | 1.4 | — | 20.0 | — | 2.0 | 1.1 | — | — |
| Q09161_C44 | 1.4 | 12.4 | — | 1.1 | 4.7 | 1.0 | — | 2.0 | — | 1.3 |
| P78417_C32 | 20.0 | 20.0 | 20.0 | — | 20.0 | 20.0 | 20.0 | 1.7 | — | — |
| Q9ULW0_C536 | 1.6 | 17.6 | — | 1.4 | 20.0 | 1.5 | — | 1.5 | — | 0.9 |
| Q9NRG0_C55 | 2.5 | 2.7 | — | 1.1 | 20.0 | 1.2 | — | 1.7 | — | — |
| Q96T76_C848 | 1.8 | 2.5 | — | — | 20.0 | 0.6 | 1.5 | 5.0 | 20.0 | 0.7 |
| Q8TAQ2_C145 | 2.4 | — | 20.0 | 7.6 | — | 1.1 | — | 1.3 | — | 1.6 |
| Q9BVC5_C10 | 1.4 | 3.1 | — | 1.1 | 2.9 | 1.6 | — | 1.2 | — | 1.5 |
| Q7Z2W4_C645 | 1.3 | 3.8 | — | 1.0 | 3.3 | 1.3 | 0.9 | 1.4 | — | 0.9 |

TABLE 2B-continued

| Identifier | 9_200 μM_ insitu_ ramos | 10_200 μM_ insitu_ 231 | 10_200 μM_ insitu_ ramos | 11_100 μM_ insitu_ 231 | 12_200 μM_ insitu_ 231 | 13_200 μM_ insitu_ 231 | 13_200 μM_ insitu_ ramos | 14_200 μM_ insitu_ 231 | 14_200 μM_ insitu_ ramos | 21_200 μM_ insitu_ 231 |
|---|---|---|---|---|---|---|---|---|---|---|
| Q9BQ69_C186 | — | 2.4 | — | 1.0 | 2.7 | 1.4 | — | 1.1 | — | 1.4 |
| Q16831_C162 | — | 7.3 | — | 0.8 | 0.9 | 1.0 | — | 0.6 | — | 1.6 |
| P30101_C57 | 1.5 | 3.3 | — | 2.2 | 20.0 | — | 1.6 | 1.0 | — | 1.0 |
| P12268_C331 | 2.6 | — | 2.1 | 1.0 | — | — | 1.4 | 1.7 | — | 0.8 |
| O95571_C170 | 1.8 | 9.0 | — | 1.2 | 6.3 | 1.2 | 1.9 | 1.0 | — | 1.7 |
| O00299_C24 | 1.4 | 5.0 | — | 2.5 | 20.0 | — | 1.8 | 0.8 | — | 0.7 |
| O14879_C343 | — | 4.9 | — | 0.4 | 3.5 | 1.0 | — | 1.5 | — | 0.8 |
| Q96CM8_C64 | 20.0 | 20.0 | — | 1.5 | 17.9 | 1.4 | — | 1.5 | — | 2.0 |
| P51946_C244 | 2.0 | 1.7 | — | 1.3 | 1.3 | 1.0 | 1.2 | 1.6 | — | 1.4 |
| P49588_C773 | 2.0 | 2.1 | 1.7 | 0.9 | 0.9 | 0.8 | 1.1 | 1.0 | — | 1.1 |
| Q96RN5_C618 | — | — | — | 1.0 | 20.0 | 1.0 | 1.4 | 1.6 | — | 1.0 |
| O15294_C758 | — | 2.3 | — | 1.0 | 20.0 | 1.0 | — | 1.6 | 2.9 | 1.1 |
| P46734_C207 | 1.8 | 0.8 | — | 0.6 | 0.7 | 0.8 | — | 13.8 | — | 0.9 |
| Q96S55_C272 | 2.5 | 1.2 | — | — | 2.4 | 0.7 | — | 1.4 | — | 1.3 |
| O95229_C54 | — | 2.3 | — | 1.2 | 20.0 | 0.8 | 1.4 | 5.0 | 20.0 | 0.8 |
| O60610_C1227 | — | 1.5 | 1.4 | 0.9 | 0.8 | 0.7 | 0.9 | — | — | 20.0 |
| Q13428_C38 | 1.7 | 4.2 | — | 1.1 | 4.7 | 1.6 | — | 3.6 | — | 1.5 |
| Q9Y277_C65 | 0.8 | 3.3 | 2.5 | 1.4 | 3.9 | 1.0 | — | 1.7 | — | 2.9 |
| P57764_C268 | 4.9 | — | 2.2 | 0.7 | — | — | 1.5 | 1.6 | — | 0.7 |
| Q9Y3A3_C134 | 20.0 | 1.9 | — | 1.8 | 1.4 | — | 1.9 | 1.1 | — | — |
| Q02252_C317 | 2.6 | 1.5 | 0.7 | 0.9 | 3.2 | 1.3 | — | 1.1 | — | 1.5 |
| Q9NYL9_C132 | — | — | — | 0.5 | 0.6 | — | — | 0.5 | — | 1.4 |
| P83731_C6 | 1.3 | 0.4 | 2.0 | 0.5 | 0.3 | 0.7 | 1.0 | — | — | 1.0 |
| O95336_C32 | 2.6 | — | — | 0.9 | 20.0 | 1.6 | 2.2 | 3.2 | — | 0.9 |
| Q13155_C291 | — | 1.7 | — | 0.9 | 1.1 | — | — | 1.6 | — | 0.8 |
| Q13418_C346 | — | 1.1 | 8.3 | 0.6 | 0.6 | 0.7 | 2.1 | 0.8 | — | 0.5 |
| A6NDU8_C179 | 3.7 | 1.3 | — | 0.7 | — | 0.8 | — | 1.9 | — | 0.9 |
| Q9UKF6_C498 | 1.7 | 20.0 | 2.8 | 1.3 | 4.1 | — | 1.4 | 1.9 | — | 1.4 |
| Q96F86_C413 | 4.0 | 20.0 | 20.0 | 20.0 | — | 1.6 | 2.0 | 1.0 | — | 0.8 |
| P42224_C492 | — | 20.0 | — | 0.7 | 1.0 | 1.0 | — | 20.0 | — | 0.7 |
| P11216_C326 | — | 8.6 | — | 0.8 | 3.9 | 1.3 | — | 0.8 | — | 0.9 |
| P21980_C277 | — | 0.6 | — | 0.6 | 0.3 | 0.8 | — | 20.0 | — | 0.7 |
| Q9HAV7_C124 | 3.8 | 1.0 | — | 0.9 | 1.1 | — | — | 1.3 | — | 1.7 |
| P24752_C126 | 20.0 | 5.9 | — | 1.2 | 5.8 | — | — | 0.9 | — | 1.4 |
| Q9NQ88_C161 | 2.0 | 4.6 | 2.1 | 0.9 | — | 1.1 | 1.5 | 20.0 | — | 1.0 |
| Q13155_C23 | 1.6 | 2.3 | — | 1.2 | 1.6 | 0.9 | — | 1.1 | — | 0.9 |

TABLE 2B-continued

| Identifier | 9_200 µM_ insitu_ ramos | 10_200 µM_ insitu_ 231 | 10_200 µM_ insitu_ ramos | 11_100 µM_ insitu_ 231 | 12_200 µM_ insitu_ 231 | 13_200 µM_ insitu_ 231 | 13_200 µM_ insitu_ ramos | 14_200 µM_ insitu_ 231 | 14_200 µM_ insitu_ ramos | 21_200 µM_ insitu_ 231 |
|---|---|---|---|---|---|---|---|---|---|---|
| Q9NQW6_C712 | — | 11.2 | — | 0.9 | 16.7 | 1.3 | — | 2.1 | — | — |
| P51649_C340 | 1.5 | 13.4 | 20.0 | — | 20.0 | 1.1 | 1.3 | 0.7 | — | 1.2 |
| Q15021_C439 | — | 5.2 | — | 0.9 | 6.7 | — | — | 5.9 | — | 0.7 |
| Q5T0N5_C69 | — | 2.0 | — | 1.3 | 20.0 | 1.0 | — | 1.5 | — | 0.8 |
| P38606_C138 | — | 20.0 | — | 9.2 | 20.0 | 20.0 | — | 1.9 | — | 20.0 |
| Q9HCC0_C216 | 3.3 | 2.3 | — | 1.9 | 20.0 | — | 1.8 | 1.0 | — | 2.2 |
| Q9NQC3_C1101 | 20.0 | 20.0 | — | 1.1 | 20.0 | — | — | 20.0 | — | 2.1 |
| P35754_C23 | 5.7 | — | 13.0 | 20.0 | 20.0 | — | — | 0.7 | — | — |
| Q99757_C90 | — | — | — | 2.7 | 5.0 | — | — | 3.2 | — | 4.3 |
| Q9Y3D0_C93 | 2.1 | 2.1 | — | 0.9 | — | — | 1.4 | 2.7 | — | 0.5 |
| Q9UMS0_C213 | — | 20.0 | — | — | 20.0 | 1.6 | — | 3.5 | — | — |
| Q9NXV6_C516 | 13.8 | 7.7 | — | 1.0 | 3.3 | 2.4 | 1.6 | 1.4 | — | 0.8 |
| Q96RS6_C376 | 1.7 | 5.7 | — | 0.8 | 1.1 | 0.7 | 1.2 | 0.9 | 1.8 | 1.4 |
| Q14997_C1840 | — | 20.0 | — | — | 20.0 | 0.9 | 1.6 | — | 20.0 | 1.0 |
| P50570_C27 | 1.4 | 3.1 | — | 0.7 | 0.7 | — | 1.0 | 1.0 | — | 0.8 |
| Q86YH6_C71 | 6.6 | 20.0 | — | 1.0 | 20.0 | 1.2 | 1.8 | 20.0 | — | 2.1 |
| Q99497_C106 | 2.6 | 1.7 | — | 1.3 | 3.0 | — | 3.3 | 0.8 | — | — |
| Q9UJW0_C258 | 20.0 | 20.0 | 20.0 | 20.0 | 20.0 | — | 1.9 | 3.0 | — | — |
| Q9BUH6_C180 | — | 3.8 | — | — | 1.4 | 1.1 | — | 1.3 | — | — |
| P24752_C196 | 6.8 | 5.1 | 2.3 | 1.1 | 4.6 | — | — | 1.0 | — | 1.5 |
| Q13162_C51 | — | 2.0 | — | 0.9 | 1.0 | — | — | 0.9 | — | 1.7 |
| Q9BTA9_C553 | 2.1 | 20.0 | — | 1.7 | — | 1.4 | — | 1.7 | — | 2.8 |
| P48643_C253 | 1.1 | — | 0.9 | 0.6 | 5.1 | — | — | 0.8 | — | — |
| O75362_C286 | 1.8 | 2.6 | — | 1.0 | 20.0 | 1.1 | 20.0 | 1.4 | — | 1.1 |
| O60825_C158 | 1.8 | 0.7 | 1.2 | — | 0.8 | — | 0.9 | 1.5 | 14.2 | 1.4 |
| Q8NBS9_C350 | 1.8 | — | 1.4 | 3.4 | 9.4 | 1.3 | — | 1.0 | — | — |
| Q9NYL2_C22 | — | 1.2 | — | 0.7 | 0.7 | 1.3 | — | 0.9 | — | — |
| P27707_C9 | 1.5 | 1.9 | 1.7 | 0.5 | 1.4 | 1.0 | 1.3 | — | — | 1.3 |
| Q93009_C223 | 20.0 | 2.5 | — | 1.0 | 3.1 | — | 1.3 | 1.1 | — | 1.8 |
| O14929_C101 | — | 20.0 | — | 0.8 | 20.0 | 0.9 | 1.2 | 1.6 | 1.9 | 1.2 |
| Q9UPQ0_C140 | — | 3.9 | — | 1.0 | 1.9 | 1.1 | — | 4.6 | — | 0.8 |
| Q96NY7_C487 | — | 3.2 | — | 3.1 | 20.0 | 1.9 | — | 0.8 | — | 1.2 |
| Q9NQ88_C114 | 1.4 | 2.1 | — | 0.8 | — | 1.1 | 1.2 | 2.2 | 5.1 | 0.9 |
| Q14790_C360 | 3.2 | — | 5.8 | — | — | 1.2 | — | — | — | 0.9 |
| P04183_C230 | 2.0 | 1.3 | — | — | — | — | 0.7 | — | — | 0.7 |
| P68366_C54 | 1.8 | 7.9 | 2.8 | 0.3 | — | — | 1.3 | — | 5.1 | 0.8 |
| Q13428_C1298 | 2.5 | 5.9 | — | 0.8 | 20.0 | — | — | 3.0 | — | — |

TABLE 2B-continued

| Identifier | 9_200 µM_ insitu_ ramos | 10_200 µM_ insitu_ 231 | 10_200 µM_ insitu_ ramos | 11_100 µM_ insitu_ 231 | 12_200 µM_ insitu_ 231 | 13_200 µM_ insitu_ 231 | 13_200 µM_ insitu_ ramos | 14_200 µM_ insitu_ 231 | 14_200 µM_ insitu_ ramos | 21_200 µM_ insitu_ 231 |
|---|---|---|---|---|---|---|---|---|---|---|
| Q5MNZ6_C63 | 11.2 | 3.6 | — | 0.9 | 20.0 | 1.1 | — | 1.2 | — | 0.8 |
| O14980_C528 | 1.8 | 1.3 | 0.7 | 0.7 | — | 1.1 | 1.1 | 20.0 | — | 0.8 |
| Q86W42_C35 | 2.7 | — | — | 1.3 | — | — | — | 0.9 | — | — |
| Q9Y6G9_C51 | — | 4.9 | — | — | 6.5 | — | 1.5 | 2.1 | 4.3 | 0.6 |
| Q9NY27_C22 | 1.8 | — | 2.1 | 2.3 | 20.0 | — | 1.5 | 1.3 | — | — |
| Q8NFH5_C255 | 1.9 | 3.5 | — | 1.3 | 12.4 | 1.5 | — | 1.0 | — | 1.8 |
| Q9Y676_C128 | 1.3 | 2.9 | — | 0.8 | 1.4 | — | — | 1.2 | — | 1.5 |
| P35658_C728 | 4.2 | 20.0 | — | 0.8 | — | 1.0 | — | 1.2 | — | 1.3 |
| Q9NTX5_C133 | — | 1.6 | — | 1.0 | 1.2 | 1.1 | — | 1.0 | — | 1.1 |
| Q15118_C71 | — | 18.0 | 2.7 | 0.6 | — | 1.6 | — | 4.4 | — | 1.7 |
| Q00765_C18 | — | 4.2 | — | 0.8 | 20.0 | 1.2 | — | 20.0 | — | 0.7 |
| P22307_C71 | — | 8.3 | — | 2.0 | 3.7 | 4.9 | — | 1.1 | — | 8.3 |
| O75521_C312 | — | 5.0 | — | — | 4.2 | 0.7 | — | 1.4 | — | 1.6 |
| P49189_C288 | 20.0 | 20.0 | — | — | 1.8 | — | 12.0 | 0.9 | — | 1.0 |
| Q5T440_C170 | 2.4 | 5.7 | — | — | — | 1.2 | — | 1.2 | — | 1.6 |
| Q15084_C190 | 1.6 | 3.7 | — | — | 20.0 | — | — | 1.1 | — | — |
| Q96C19_C172 | — | 2.4 | — | 0.9 | 0.9 | 0.7 | — | 1.0 | — | — |
| P22061_C102 | 1.3 | 1.6 | — | 0.8 | 5.8 | 0.9 | — | 1.0 | — | — |
| Q9NP73_C86 | — | — | — | 0.7 | — | 0.9 | 1.4 | 1.1 | — | — |
| Q9BRF8_C54 | 1.9 | 3.8 | — | 1.0 | 1.2 | 1.4 | — | 0.9 | — | — |
| Q6ICB0_C108 | — | — | — | 0.7 | — | — | 4.0 | — | — | 0.6 |
| P29590_C389 | — | 7.9 | — | 0.5 | — | 1.3 | — | 1.2 | — | 20.0 |
| P07858_C211 | — | 7.4 | — | 1.1 | — | 1.6 | — | 1.0 | — | 2.6 |
| Q9NX18_C83 | — | 4.4 | — | 1.1 | 20.0 | — | — | 2.2 | — | 1.3 |
| P46109_C249 | 4.0 | 20.0 | — | — | 20.0 | — | 1.8 | 1.3 | — | 0.9 |
| P45984_C177 | 3.8 | 20.0 | — | 0.9 | 2.1 | — | — | 1.5 | — | — |
| P19447_C342 | 2.7 | 20.0 | — | 0.7 | 6.7 | 1.1 | — | 2.5 | — | 2.0 |
| P42166_C341 | 1.5 | — | — | 0.8 | — | 1.3 | 1.4 | 2.3 | — | 1.7 |
| Q8N1F7_C522 | 3.7 | — | — | — | 20.0 | — | 2.2 | 3.2 | 20.0 | — |
| Q86UY8_C276 | — | 5.8 | — | 1.4 | 20.0 | 1.5 | — | 2.8 | — | 1.8 |
| Q8WWI1_C228 | 1.4 | 17.2 | — | 1.3 | 20.0 | 2.0 | 1.0 | — | — | 1.1 |
| Q9NWA0_C139 | — | 2.9 | — | — | 20.0 | 1.1 | — | — | — | 1.5 |
| P09110_C381 | 0.9 | — | — | 0.8 | 4.5 | — | — | 1.0 | — | — |
| Q2NL82_C126 | — | 4.9 | — | — | 20.0 | — | — | 0.8 | — | 1.5 |
| Q5JPI3_C308 | 4.0 | — | — | 1.0 | — | 1.1 | 1.7 | 3.2 | — | 0.9 |
| P23919_C163 | 2.4 | — | — | 0.2 | — | — | — | 0.9 | — | — |
| Q96EB1_C218 | 3.7 | 1.1 | — | — | — | 1.2 | 1.7 | — | — | 0.7 |

TABLE 2B-continued

| Identifier | 9_200 µM_ insitu_ ramos | 10_200 µM_ insitu_ 231 | 10_200 µM_ insitu_ ramos | 11_100 µM_ insitu_ 231 | 12_200 µM_ insitu_ 231 | 13_200 µM_ insitu_ 231 | 13_200 µM_ insitu_ ramos | 14_200 µM_ insitu_ 231 | 14_200 µM_ insitu_ ramos | 21_200 µM_ insitu_ 231 |
|---|---|---|---|---|---|---|---|---|---|---|
| Q96FX7_C209 | 16.1 | — | — | — | 20.0 | 2.1 | 6.8 | 2.7 | — | 2.0 |
| O14933_C98 | 2.8 | 20.0 | 3.2 | — | — | — | — | 2.5 | — | 0.7 |
| Q29RF7_C242 | — | — | — | 0.9 | 12.9 | — | — | 1.8 | — | 0.9 |
| Q96T76_C819 | 4.0 | — | 3.0 | 0.8 | — | — | — | 3.4 | — | — |
| P23919_C117 | 1.4 | 0.4 | — | — | 0.2 | 0.6 | — | 1.2 | — | 0.9 |
| Q15149_C4574 | — | 2.2 | — | 1.1 | — | 1.4 | — | 1.2 | — | 1.0 |
| Q96RP9_C153 | 2.8 | 14.8 | — | — | 20.0 | — | 0.8 | 1.2 | — | 1.4 |
| P04818_C199 | 11.7 | 1.5 | — | — | — | — | — | — | — | — |
| P27708_C73 | 2.2 | — | — | — | — | — | 5.0 | 20.0 | 3.7 | 0.6 |
| P55265_C1224 | — | 10.7 | — | — | — | 1.9 | — | 4.2 | — | 2.2 |
| Q9Y3D2_C105 | — | 20.0 | — | 1.3 | 20.0 | — | — | 2.7 | — | — |
| O00244_C12 | 1.6 | 2.1 | — | 0.7 | — | 1.5 | — | 0.7 | — | 0.7 |
| Q8WV74_C207 | 20.0 | — | 20.0 | — | — | 13.1 | — | 20.0 | — | — |
| Q9NRW3_C130 | 6.2 | — | — | — | — | — | — | — | 1.4 | 1.3 |
| P24468_C326 | — | 20.0 | — | 0.9 | — | — | — | 4.9 | — | 1.1 |
| P42166_C684 | — | 5.2 | — | 0.7 | — | 1.2 | — | 3.1 | — | — |
| Q96EY5_C231 | 2.1 | — | — | 0.7 | — | — | — | — | — | 0.7 |
| P14635_C238 | 2.1 | 6.7 | — | 0.7 | — | 1.3 | 1.5 | 2.6 | — | — |
| Q8NDH3_C81 | — | 5.7 | — | — | 20.0 | — | — | 1.4 | — | 1.6 |
| Q9P0J1_C149 | — | 18.0 | — | 1.4 | 18.5 | — | — | 1.3 | — | — |
| Q96P48_C900 | — | 1.8 | — | — | 1.9 | 1.2 | — | — | — | 0.7 |
| Q96HE7_C37 | — | — | — | — | — | — | 1.4 | 1.4 | — | — |
| Q07065_C100 | — | — | — | 1.0 | 20.0 | 1.6 | — | 11.2 | — | 2.2 |
| Q9BRJ7_C88 | 4.0 | 20.0 | — | — | — | — | — | — | — | — |
| O75439_C265 | 1.7 | — | 2.1 | 1.0 | — | — | — | 20.0 | — | — |
| O43175_C369 | 2.0 | — | 2.4 | — | — | — | 2.0 | — | 20.0 | 1.0 |
| Q9UNI6_C265 | — | 1.2 | — | — | 1.2 | — | — | 0.7 | — | — |
| Q06203_C100 | 2.9 | — | 20.0 | — | — | — | 2.0 | — | — | — |
| A0AVT1_C347 | 2.6 | — | 20.0 | 1.6 | — | 1.3 | — | — | — | — |
| Q86X76_C203 | 20.0 | — | — | 0.8 | 3.9 | — | — | 0.7 | — | 0.8 |
| Q6XZF7_C691 | 10.0 | 20.0 | 20.0 | — | — | 1.6 | — | — | — | 0.8 |
| Q15398_C129 | — | — | — | 0.6 | — | — | — | — | — | — |
| O75717_C773 | — | 2.2 | — | 1.2 | — | 1.1 | — | 1.7 | — | — |
| Q01433_C107 | 1.4 | — | — | 0.6 | — | — | — | — | — | — |
| Q8WVV9_C464 | — | — | — | 0.9 | 20.0 | — | — | 2.2 | — | 1.4 |
| O14733_C131 | — | 1.8 | — | — | 1.7 | — | 1.6 | — | 20.0 | 0.7 |
| Q14137_C404 | 2.1 | 20.0 | — | — | — | 1.1 | — | — | — | 1.1 |

TABLE 2B-continued

| Identifier | 9_200 µM_ insitu_ ramos | 10_200 µM_ insitu_ 231 | 10_200 µM_ insitu_ ramos | 11_100 µM_ insitu_ 231 | 12_200 µM_ insitu_ 231 | 13_200 µM_ insitu_ 231 | 13_200 µM_ insitu_ ramos | 14_200 µM_ insitu_ 231 | 14_200 µM_ insitu_ ramos | 21_200 µM_ insitu_ 231 |
|---|---|---|---|---|---|---|---|---|---|---|
| Q96RU2_C171 | — | — | — | 2.2 | 20.0 | — | — | 1.3 | — | — |
| Q9Y679_C391 | — | — | — | 3.0 | — | — | — | — | — | 1.5 |
| P51610_C1872 | 1.0 | 1.5 | — | 0.5 | — | 1.0 | — | 1.1 | — | — |
| P22307_C307 | — | — | — | 2.9 | 20.0 | — | — | 0.9 | — | 20.0 |
| Q9BTE3_C325 | 5.4 | — | — | — | — | — | — | 5.7 | — | — |
| Q9HA64_C24 | 1.6 | — | — | — | — | — | — | 1.7 | — | 0.6 |
| Q5TFE4_C119 | 20.0 | — | 20.0 | — | — | — | 1.7 | 3.8 | — | 1.2 |
| Q96N67_C2125 | — | — | — | — | — | — | — | 1.8 | — | — |
| P52948_C1312 | — | 20.0 | — | — | 20.0 | 1.2 | — | 1.7 | — | 1.1 |
| Q5UIP0_C2298 | — | 20.0 | — | 1.3 | — | — | — | 20.0 | — | 0.9 |
| P51812_C436 | 1.8 | — | — | 0.5 | 1.4 | 1.0 | — | 0.6 | — | — |
| Q92616_C1692 | — | — | — | — | — | — | 0.9 | 20.0 | — | — |
| Q15345_C297 | — | — | — | 1.1 | — | 1.6 | — | 5.8 | — | 1.1 |
| Q9NPH0_C267 | 2.6 | 13.4 | — | — | — | — | — | 1.2 | — | — |
| P04183_C66 | 1.8 | — | — | 0.6 | — | 1.0 | — | — | — | — |
| P42166_C629 | — | 2.5 | — | 0.6 | — | 1.0 | — | 20.0 | — | 1.6 |
| Q15013_C124 | — | — | — | 1.0 | — | — | — | 1.4 | — | — |
| Q9Y5Y2_C72 | 1.3 | 1.3 | — | 0.5 | — | — | 1.5 | — | — | — |
| O15446_C86 | — | 4.7 | — | — | 3.3 | 1.3 | — | 1.0 | — | 1.7 |
| Q13630_C116 | 1.6 | 20.0 | — | — | — | — | 1.2 | — | — | 0.8 |
| Q8IYQ7_C324 | — | 5.3 | — | — | — | 1.3 | — | 1.6 | — | 2.0 |
| P05091_C319 | 20.0 | — | — | — | 20.0 | — | — | 3.3 | — | — |
| Q29RF7_C532 | — | 20.0 | — | — | — | — | 2.0 | 2.5 | — | — |
| Q9Y570_C381 | — | 4.7 | — | — | — | 0.9 | — | — | — | — |
| Q14980_C961 | — | — | — | — | 20.0 | 2.2 | — | — | — | 3.7 |
| P53384_C235 | — | — | — | — | 0.5 | — | — | — | — | — |
| Q15003_C418 | 2.5 | — | — | 1.6 | — | — | — | — | — | — |
| P53634_C258 | — | 5.5 | — | — | 13.4 | 1.6 | — | 1.9 | — | 2.8 |
| Q8NFF5_C499 | 12.1 | — | — | 16 | — | — | — | 20.0 | — | — |
| Q9ULA0_C144 | 1.3 | 5.2 | — | — | — | — | — | — | — | — |
| P22307_C94 | — | — | — | 3.3 | 20.0 | — | — | 1.0 | — | — |
| O15294_C620 | — | — | 12.0 | — | — | — | — | 1.0 | — | — |
| Q9Y5S2_C1517 | — | — | — | 1.2 | — | — | — | 0.9 | — | — |
| Q8TD19_C623 | 20.0 | — | — | — | — | — | 20.0 | — | — | 0.8 |
| Q8N2W9_C326 | 2.6 | 4.5 | — | — | — | — | 20.0 | — | — | 1.0 |
| Q13158_C98 | — | — | — | — | — | 1.6 | — | — | — | — |

TABLE 2B-continued

| Identifier | 9_200 µM_ insitu_ ramos | 10_200 µM_ insitu_ 231 | 10_200 µM_ insitu_ ramos | 11_100 µM_ insitu_ 231 | 12_200 µM_ insitu_ 231 | 13_200 µM_ insitu_ 231 | 13_200 µM_ insitu_ ramos | 14_200 µM_ insitu_ 231 | 14_200 µM_ insitu_ ramos | 21_200 µM_ insitu_ 231 |
|---|---|---|---|---|---|---|---|---|---|---|
| Q9UKX7_C151 | 1.8 | — | — | 1.0 | 6.7 | — | — | 1.8 | — | — |
| Q6PCB5_C280 | 2.5 | — | — | — | 20.0 | — | 0.8 | 20.0 | — | — |
| P10398_C597 | 1.3 | 1.4 | — | — | — | — | 1.0 | — | — | 0.7 |
| Q9UL40_C68 | 20.0 | — | — | — | 20.0 | — | 20.0 | 20.0 | — | — |
| P46013_C903 | — | — | — | — | — | — | — | — | — | — |
| Q16667_C39 | 4.5 | 2.3 | — | — | — | — | 1.2 | — | — | 0.8 |
| O75150_C890 | — | — | 4.2 | — | 1.1 | — | — | — | 1.1 | — |
| Q00610_C870 | — | — | — | — | 0.9 | 1.7 | — | — | 20.0 | — |
| Q9Y5T5_C205 | — | — | — | — | — | — | 20.0 | — | — | 0.9 |
| O95881_C66 | 20.0 | — | — | — | 20.0 | 20.0 | — | 1.3 | — | — |
| Q7Z5K2_C160 | — | 20.0 | — | 1.0 | — | — | — | 2.4 | — | — |
| P42166_C518 | 1.3 | 4.2 | — | 0.8 | — | — | — | — | — | 1.4 |
| Q9Y2S7_C143 | — | 13.9 | — | — | — | — | — | 1.3 | — | — |
| E2QRD5_C183 | — | — | — | 0.9 | — | — | — | — | — | 0.8 |
| O95833_C22 | — | — | — | — | — | — | — | 0.8 | — | 1.0 |
| O94953_C694 | 4.2 | — | 3.9 | — | — | — | 1.5 | — | — | — |
| O00541_C272 | — | — | — | 1.0 | — | 1.4 | — | 3.8 | — | — |
| Q9NXJ5_C149 | 20.0 | — | 11.0 | — | 3.9 | — | 20.0 | — | — | — |
| Q8N5L8_C131 | — | — | — | — | — | 1.2 | — | 1.3 | — | 0.8 |
| Q8IZ73_C246 | 6.5 | — | — | — | — | — | — | — | — | 1.8 |
| Q99798_C385 | — | 0.7 | — | — | — | — | — | — | — | 2.0 |
| Q9GZR2_C382 | 1.0 | — | — | — | 20.0 | — | 0.9 | 1.2 | — | — |
| Q13613_C117 | 4.3 | — | — | — | — | — | — | 1.0 | 1.7 | 0.9 |
| Q9NUI1_C22 | — | — | — | 2.1 | — | — | — | 1.1 | — | — |
| Q02556_C306 | 5.5 | — | — | — | — | — | 1.5 | — | — | — |
| Q9UPT9_C171 | 4.4 | — | 9.3 | 0.8 | — | — | 3.2 | — | — | — |
| Q8N999_C302 | 20.0 | — | — | — | — | — | — | — | — | — |
| Q8IU81_C363 | — | 5.9 | — | — | — | — | — | — | — | — |
| Q9C0I1_C152 | — | — | — | — | 20.0 | — | 6.5 | — | — | 0.7 |
| Q9P2X3_C195 | — | — | — | — | — | — | — | 1.6 | — | — |
| Q6QNY0_C168 | 4.6 | — | — | — | — | — | 1.2 | — | — | — |
| Q15796_C81 | 5.6 | — | — | — | — | — | — | — | — | 1.3 |
| Q9NZB2_C531 | — | — | — | — | 20.0 | — | — | — | — | 1.6 |
| Q9HB90_C377 | 20.0 | — | — | — | — | — | — | 1.1 | — | — |
| Q9BR61_C267 | — | — | — | — | — | 1.1 | — | — | 6.9 | — |
| P16455_C145 | 20.0 | — | 20.0 | — | — | — | — | — | — | — |
| Q86UV5_C39 | — | — | — | — | — | — | — | — | 1.4 | — |

TABLE 2B-continued

| Identifier | 9_200 μM_ insitu_ ramos | 10_200 μM_ insitu_ 231 | 10_200 μM_ insitu_ ramos | 11_100 μM_ insitu_ 231 | 12_200 μM_ insitu_ 231 | 13_200 μM_ insitu_ 231 | 13_200 μM_ insitu_ ramos | 14_200 μM_ insitu_ 231 | 14_200 μM_ insitu_ ramos | 21_200 μM_ insitu_ 231 |
|---|---|---|---|---|---|---|---|---|---|---|
| A2A288_C367 | 5.2 | — | — | — | — | — | — | — | — | — |
| Q8NEC7_C140 | — | — | — | — | — | 1.8 | 20.0 | — | — | — |
| Q6PJG6_C673 | — | — | — | — | — | — | — | — | — | — |
| Q13232_C158 | — | — | — | — | — | — | — | — | — | — |
| Q86X76_C165 | 20.0 | — | — | — | — | — | — | — | 0.8 | — |
| P42695_C541 | — | 20.0 | 6.5 | — | — | — | — | — | — | 2.3 |
| P41226_C599 | 20.0 | 8.0 | — | — | — | — | — | — | — | 1.0 |
| Q99986_C50 | — | — | 0.7 | — | — | — | — | 1.6 | — | — |
| Q8WUM4_C90 | 5.0 | — | — | — | — | — | — | 1.0 | — | — |
| P29590_C213 | 4.5 | — | — | — | — | — | — | — | — | — |
| Q9P0K7_C973 | — | — | — | 0.8 | — | — | — | — | — | — |
| P53992_C78 | — | — | — | — | — | 0.7 | — | — | — | — |
| Q13867_C73 | — | 4.2 | — | — | — | — | — | — | — | — |
| Q8ND24_C655 | — | — | — | — | — | — | — | — | — | — |
| Q96EK4_C48 | 2.3 | — | — | — | — | — | — | — | — | — |
| Q96IV0_C309 | 6.8 | — | — | — | — | — | — | — | — | — |
| Q5T1V6_C414 | 3.7 | 11.3 | — | — | — | — | — | — | — | — |
| Q9UHQ1_C99 | 20.0 | — | — | — | — | — | 20.0 | — | — | — |
| O43396_C34 | — | — | — | — | — | — | — | 7.3 | — | — |
| Q8IV53_C174 | — | — | 5.0 | — | — | — | — | — | — | — |
| Q8N9T8_C673 | — | — | — | — | — | — | — | — | — | — |

TABLE 2C

| Identifier | 27_200 μM_ insitu_ 231 | 28_200 μM_ insitu_ 231 | 29_200 μM_ insitu_ ramos | 31_200 μM_ insitu_ 231 | 31_200 μM_ insitu_ ramos | 33_200 μM_ insitu_ 231 | 38_200 μM_ insitu_ 231 | 41_200 μM_ insitu_ 231 | 45_200 μM_ insitu_ 231 | 51_200 μM_ insitu_ 231 | 56_200 μM_ insitu_ 231 |
|---|---|---|---|---|---|---|---|---|---|---|---|
| P04406_C152 | 0.5 | 0.8 | 1.2 | 0.8 | 1.0 | 1.1 | 0.9 | 0.6 | 20.0 | 1.0 | 0.9 |
| P61978_C132 | 0.9 | 1.0 | 1.2 | 0.9 | 1.1 | 1.3 | 1.0 | 0.9 | 9.3 | 1.2 | 0.8 |
| Q13526_C113 | 0.5 | 0.7 | 1.0 | 0.6 | 1.1 | 1.2 | 1.0 | 0.6 | 10.0 | 1.4 | — |
| P24752_C119 | 1.6 | 1.0 | 1.2 | 0.6 | 0.7 | 2.3 | 1.2 | 1.9 | 12.4 | 0.7 | 0.8 |
| P24752_C413 | 1.9 | 1.0 | 1.2 | 1.0 | — | 20.0 | 1.1 | 0.9 | 20.0 | 1.1 | 0.7 |
| Q9NUY8_C283 | 0.6 | 0.7 | 1.3 | 0.6 | — | 1.6 | 1.0 | 0.7 | 2.7 | 2.1 | 0.9 |
| P13667_C206 | 1.0 | 1.3 | 1.4 | 0.8 | 1.1 | 2.7 | 0.9 | 1.0 | 1.9 | 5.3 | 0.8 |
| P12268_C140 | 0.5 | 0.6 | 1.6 | 0.6 | 1.0 | 1.4 | 1.2 | 0.7 | 1.9 | 1.0 | 1.1 |
| Q15365_C194 | 0.5 | — | 1.0 | 0.7 | 1.6 | 2.2 | 15 | 0.3 | 1.5 | 0.6 | 1.2 |
| Q9NVC6_C649 | 1.3 | 1.1 | 1.6 | 0.8 | — | 1.2 | 1.2 | 0.8 | 20.0 | — | 0.8 |
| P42166_C561 | 0.8 | 1.1 | 0.9 | 1.3 | 2.5 | 2.9 | 20.0 | 0.7 | 20.0 | 1.3 | 1.1 |

TABLE 2C-continued

| Identifier | 27_200 µM_ insitu_ 231 | 28_200 µM_ insitu_ 231 | 29_200 µM_ insitu_ ramos | 31_200 µM_ insitu_ 231 | 31_200 µM_ insitu_ ramos | 33_200 µM_ insitu_ 231 | 38_200 µM_ insitu_ 231 | 41_200 µM_ insitu_ 231 | 45_200 µM_ insitu_ 231 | 51_200 µM_ insitu_ 231 | 56_200 µM_ insitu_ 231 |
|---|---|---|---|---|---|---|---|---|---|---|---|
| Q9Y696_C35 | 1.0 | 2.7 | 1.0 | 0.6 | — | 8.9 | 1.0 | 0.6 | 1.4 | 2.6 | 0.9 |
| P10599_C32 | 2.5 | 20.0 | 1.9 | 1.2 | 1.7 | 20.0 | 2.1 | 0.4 | 5.7 | 13.9 | 1.5 |
| P31943_C267 | 1.1 | — | 1.4 | 0.7 | 0.9 | 1.3 | 1.2 | 1.0 | 3.6 | 1.3 | 0.8 |
| Q86SX6_C67 | 1.5 | — | 1.2 | — | 0.7 | 1.0 | 1.0 | 1.0 | 9.1 | 1.0 | 0.8 |
| P15121_C299 | 0.5 | 0.8 | 1.1 | 0.8 | 1.3 | 0.7 | 1.0 | 0.9 | 1.0 | 0.9 | 0.9 |
| P52597_C267 | 1.0 | — | 1.2 | 1.2 | 1.3 | 1.6 | 1.8 | 0.8 | 4.1 | 1.3 | 0.9 |
| Q9ULV4_C420 | 0.8 | 0.7 | — | 0.8 | 1.1 | 1.6 | 1.4 | 0.8 | 3.2 | 1.1 | 1.0 |
| P62888_C92 | 0.6 | 0.9 | 2.0 | — | — | 1.1 | 3.2 | 0.8 | 2.2 | 0.9 | 0.9 |
| Q9NQR4_C153 | 1.3 | — | — | 0.6 | 1.4 | 1.0 | 1.1 | 0.7 | 2.0 | 0.6 | 0.8 |
| P42765_C92 | 1.2 | — | 0.9 | 0.8 | 1.2 | 1.3 | 0.9 | 1.1 | 15.1 | 1.1 | — |
| Q15084_C55 | 1.2 | 1.4 | 1.0 | 0.7 | — | 3.7 | 0.8 | 0.9 | 2.0 | 5.0 | 0.8 |
| Q96HE7_C241 | 0.9 | 1.1 | 1.3 | 0.7 | — | 2.3 | 1.6 | 0.7 | 2.1 | 1.7 | 0.9 |
| Q99439_C164 | — | 0.9 | 1.0 | 0.7 | 1.3 | 1.5 | 1.5 | 0.4 | 1.8 | — | 1.2 |
| P25205_C119 | 1.0 | — | 1.3 | 0.5 | — | 1.2 | 0.9 | 0.9 | 6.2 | 2.6 | 1.0 |
| Q9NS86_C187 | 0.4 | — | 1.7 | 0.5 | — | 1.5 | 2.0 | 0.6 | 3.1 | 2.0 | 1.2 |
| Q15233_C145 | 1.2 | 1.1 | — | 0.7 | 0.8 | 1.3 | 0.9 | 1.1 | 3.7 | 1.6 | 0.8 |
| Q9BRA2_C43 | 20.0 | — | 2.3 | 0.6 | — | 20.0 | 1.1 | 0.6 | 8.0 | — | 3.9 |
| P35611_C68 | 0.9 | 1.7 | — | — | — | 1.6 | 1.4 | 0.9 | 20.0 | 1.0 | 0.8 |
| O75521_C380 | 1.6 | 0.8 | 1.2 | — | — | 0.7 | 0.9 | 1.1 | 1.2 | 1.0 | 1.1 |
| Q9BXW7_C392 | 1.3 | 1.0 | 1.5 | — | — | 1.1 | 0.8 | 1.0 | 4.9 | 1.1 | 0.8 |
| P30101_C406 | 1.2 | — | 1.5 | 0.8 | 1.1 | — | 0.8 | 1.0 | 2.6 | 6.0 | 0.7 |
| Q96AB3_C114 | 1.0 | 0.8 | 1.1 | 0.7 | — | 0.9 | 1.2 | 0.7 | 3.1 | 0.8 | — |
| P13667_C555 | 1.2 | — | 1.5 | 0.8 | 1.1 | — | 0.8 | 1.0 | 2.6 | 6.0 | 0.7 |
| Q09161_C44 | 0.8 | — | 1.1 | 0.6 | — | 1.1 | 1.2 | 0.8 | 2.5 | 1.2 | 1.0 |
| P78417_C32 | 20.0 | 20.0 | 20.0 | 0.8 | 2.6 | 20.0 | 1.0 | 0.3 | 1.9 | — | 1.3 |
| Q9ULW0_C536 | 1.1 | 1.0 | 1.8 | — | — | 2.2 | 1.2 | 1.2 | 20.0 | 1.4 | — |
| Q9NRG0_C55 | 0.9 | — | 1.5 | — | 1.6 | 1.1 | 1.0 | 0.9 | 20.0 | 1.1 | 1.0 |
| Q96T76_C848 | 0.5 | 0.8 | 1.0 | 20.0 | — | — | — | 0.7 | 20.0 | — | 1.4 |
| Q8TAQ2_C145 | 2.1 | 0.9 | 2.7 | 0.8 | 1.1 | 1.3 | 1.3 | 1.2 | 2.9 | 1.2 | 0.8 |
| Q9BVC5_C10 | 1.1 | 0.9 | 1.8 | — | — | 1.3 | 0.9 | 1.0 | 3.4 | 1.0 | 0.8 |
| Q7Z2W4_C645 | 0.8 | — | 1.6 | — | — | 2.1 | 0.9 | 0.9 | 4.6 | 1.6 | 0.9 |
| Q9BQ69_C186 | 2.4 | — | 1.5 | 0.5 | — | 0.9 | 3.6 | 1.2 | 3.3 | 1.2 | 0.8 |
| Q16831_C162 | 0.5 | 0.7 | — | — | — | 1.3 | 1.4 | 0.8 | 1.3 | 1.1 | 1.1 |
| P30101_C57 | 1.1 | 1.6 | 1.2 | 0.9 | — | — | 0.9 | 1.3 | 2.6 | — | 0.7 |
| P12268_C331 | 0.7 | 0.8 | 1.3 | 1.0 | 1.1 | 1.5 | 1.3 | 0.8 | 4.1 | — | — |
| O95571_C170 | 1.1 | — | 1.5 | — | — | 1.2 | — | 1.1 | 3.1 | — | 0.8 |
| O00299_C24 | 0.7 | — | 1.1 | 0.6 | — | 8.4 | 1.0 | 0.6 | — | — | 0.9 |

TABLE 2C-continued

| Identifier | 27_200 μM_ insitu_ 231 | 28_200 μM_ insitu_ 231 | 29_200 μM_ insitu_ ramos | 31_200 μM_ insitu_ 231 | 31_200 μM_ insitu_ ramos | 33_200 μM_ insitu_ 231 | 38_200 μM_ insitu_ 231 | 41_200 μM_ insitu_ 231 | 45_200 μM_ insitu_ 231 | 51_200 μM_ insitu_ 231 | 56_200 μM_ insitu_ 231 |
|---|---|---|---|---|---|---|---|---|---|---|---|
| O14879_C343 | 0.4 | 0.7 | — | 0.9 | — | 2.4 | — | 0.3 | 4.0 | 1.3 | 1.2 |
| Q96CM8_C64 | 1.8 | — | 2.3 | 0.8 | — | 2.3 | 1.1 | 0.8 | 20.0 | — | 0.8 |
| P51946_C244 | 1.1 | — | 1.1 | — | — | 0.9 | 1.0 | 1.2 | 2.4 | 0.7 | 1.0 |
| P49588_C773 | 0.6 | — | 1.1 | — | 1.2 | — | 0.7 | 0.7 | 10.1 | — | — |
| Q96RN5_C618 | 0.8 | 0.7 | 1.3 | 0.9 | — | 2.0 | 1.4 | — | 20.0 | 2.1 | 0.8 |
| O15294_C758 | 1.0 | 1.0 | — | — | — | 1.2 | — | 0.9 | 2.9 | 1.1 | 1.0 |
| P46734_C207 | 0.8 | — | — | — | — | 1.2 | 1.5 | 0.7 | 1.5 | 0.7 | 1.3 |
| Q96S55_C272 | 0.9 | 0.5 | — | — | — | 1.2 | 1.3 | 0.8 | 2.5 | 0.9 | 0.9 |
| O95229_C54 | 0.5 | 0.7 | 1.2 | — | — | — | — | 0.6 | — | 1.0 | 1.0 |
| O60610_C1227 | 0.5 | — | 1.6 | 0.6 | 1.2 | — | 0.3 | 0.6 | 3.0 | — | 1.2 |
| Q13428_C38 | 1.3 | 1.0 | 1.5 | — | — | — | 1.1 | 1.1 | 2.8 | 1.1 | 0.8 |
| Q9Y277_C65 | 1.6 | 1.2 | — | — | 1.0 | — | 20.0 | 1.4 | — | — | 0.9 |
| P57764_C268 | 0.6 | — | 1.1 | — | 3.1 | — | 1.8 | 0.6 | 20.0 | 1.8 | 0.8 |
| Q9Y3A3_C134 | — | — | 1.2 | 1.0 | 1.8 | 1.2 | 1.0 | 0.9 | 2.3 | — | 0.9 |
| Q02252_C317 | 2.0 | 1.1 | 1.2 | — | — | 2.3 | 2.4 | 0.8 | 2.6 | — | — |
| Q9NYL9_C132 | 0.6 | 0.7 | 0.9 | 0.7 | 0.7 | — | 2.6 | 0.3 | 0.9 | 0.8 | — |
| P83731_C6 | 0.4 | — | 1.6 | — | — | 1.6 | 2.1 | 0.3 | 1.2 | — | — |
| O95336_C32 | 0.5 | — | 3.0 | — | 1.7 | 2.3 | 2.8 | 0.6 | — | — | 0.9 |
| Q13155_C291 | 0.7 | 0.9 | — | 0.8 | — | — | 1.7 | 0.7 | 7.3 | 1.1 | 1.1 |
| Q13418_C346 | 0.6 | — | — | 0.6 | — | 1.4 | 1.0 | 0.6 | — | 0.8 | — |
| A6NDU8_C179 | 0.7 | 0.8 | 1.0 | — | — | 7.4 | 1.4 | 0.6 | 20.0 | — | 1.2 |
| Q9UKF6_C498 | 1.5 | — | 2.3 | — | — | 1.6 | — | 1.0 | 20.0 | — | 1.0 |
| Q96F86_C413 | 0.7 | — | 1.9 | — | 1.3 | 3.0 | — | — | 20.0 | 20.0 | 1.2 |
| P42224_C492 | — | 0.8 | 3.8 | 0.8 | 1.9 | 1.3 | — | 0.6 | 20.0 | 2.4 | 1.2 |
| P11216_C326 | 0.7 | — | — | 0.5 | — | 1.6 | 1.2 | 0.7 | 5.3 | 0.8 | — |
| P21980_C277 | 0.6 | 0.4 | — | — | — | — | 1.4 | 0.6 | 1.1 | 1.0 | — |
| Q9HAV7_C124 | 0.6 | — | 1.0 | — | — | — | 1.0 | 0.6 | 2.1 | — | 0.7 |
| P24752_C126 | — | 1.2 | 1.2 | 0.7 | — | 20.0 | — | 0.8 | — | — | 0.8 |
| Q9NQ88_C161 | 0.6 | — | 1.3 | 1.0 | 2.6 | — | — | — | 20.0 | — | 1.4 |
| Q13155_C23 | 0.7 | — | 1.6 | — | — | 1.4 | 1.4 | — | 4.4 | 1.2 | 0.9 |
| Q9NQW6_C712 | 1.0 | 0.9 | — | 0.7 | — | 1.5 | 1.5 | 0.7 | 5.9 | — | 1.0 |
| P51649_C340 | 0.9 | — | 1.0 | — | 1.0 | 0.9 | — | — | 2.4 | — | — |
| Q15021_C439 | 0.6 | 0.9 | 1.4 | 20.0 | — | — | 1.1 | 0.8 | — | 1.1 | 1.2 |
| Q5T0N5_C69 | 0.6 | — | — | — | — | 2.6 | 1.5 | 0.6 | 5.4 | 1.7 | 1.0 |
| P38606_C138 | 4.6 | — | — | — | 1.7 | 20.0 | 2.1 | 0.8 | — | 10.6 | 1.1 |
| Q9HCC0_C216 | 1.0 | — | — | — | 1.0 | — | 1.0 | 7.0 | 0.9 | 0.7 |

TABLE 2C-continued

| Identifier | 27_200 μM_ insitu_ 231 | 28_200 μM_ insitu_ 231 | 29_200 μM_ insitu_ ramos | 31_200 μM_ insitu_ 231 | 31_200 μM_ insitu_ ramos | 33_200 μM_ insitu_ 231 | 38_200 μM_ insitu_ 231 | 41_200 μM_ insitu_ 231 | 45_200 μM_ insitu_ 231 | 51_200 μM_ insitu_ 231 | 56_200 μM_ insitu_ 231 |
|---|---|---|---|---|---|---|---|---|---|---|---|
| Q9NQC3_C1101 | 1.4 | — | — | 12.8 | — | 2.1 | 20.0 | 1.0 | — | 1.2 | 0.8 |
| P35754_C23 | 0.7 | 1.4 | — | 0.6 | 1.1 | 20.0 | 0.9 | 0.5 | 16.3 | — | 0.9 |
| Q99757_C90 | 6.3 | — | 1.6 | 1.4 | — | — | 3.6 | 0.5 | 6.7 | 5.0 | — |
| Q9Y3D0_C93 | 0.7 | 0.8 | 1.0 | — | — | — | 2.4 | 0.6 | 20.0 | 20.0 | — |
| Q9UMS0_C213 | 1.3 | — | 2.0 | 1.5 | — | 1.9 | 3.5 | 0.9 | 7.1 | 1.8 | 0.7 |
| Q9NXV6_C516 | 1.4 | — | 1.1 | — | — | 1.4 | 1.8 | 0.9 | — | — | — |
| Q96RS6_C376 | — | — | 1.3 | 0.8 | — | — | 1.3 | 0.7 | — | — | — |
| Q14997_C1840 | 20.0 | 0.9 | — | — | 1.2 | — | 20.0 | 0.9 | — | 20.0 | — |
| P50570_C27 | 0.5 | — | 1.0 | — | — | — | 0.9 | 0.5 | 15.4 | 1.1 | — |
| Q86YH6_C71 | 1.3 | — | 1.1 | — | — | — | — | 0.9 | 20.0 | — | 1.0 |
| Q99497_C106 | 0.9 | 1.0 | — | 0.8 | 1.0 | — | 1.1 | 0.6 | 20.0 | 1.4 | — |
| Q9UJW0_C258 | 0.8 | — | 20.0 | — | — | — | — | 0.7 | 2.7 | 1.1 | 1.3 |
| Q9BUH6_C180 | — | 1.1 | 1.5 | 0.8 | — | 1.4 | 1.4 | 0.6 | 5.5 | — | 1.3 |
| P24752_C196 | — | — | 1.1 | — | — | 3.4 | 1.0 | 0.9 | — | — | 0.8 |
| Q13162_C51 | 0.9 | — | — | — | 1.3 | 1.7 | 2.4 | — | 2.3 | — | 1.0 |
| Q9BTA9_C553 | — | — | 1.1 | — | — | 1.1 | 1.0 | 19.1 | 1.2 | 0.9 | |
| P48643_C253 | — | 0.8 | — | 0.5 | 1.0 | — | 1.1 | 0.8 | 1.2 | 0.8 | 0.9 |
| O75362_C286 | 1.0 | 0.9 | 1.0 | — | — | — | — | 1.0 | 20.0 | — | 0.9 |
| O60825_C158 | — | — | 0.9 | — | 1,3 | — | — | 0.7 | 1.3 | 0.9 | 1.2 |
| Q8NBS9_C350 | 1.1 | 1.1 | — | 0.8 | — | 2.6 | — | 0.9 | 2.1 | — | 0.8 |
| Q9NYL2_C22 | 0.7 | — | 1.2 | — | — | 1.5 | — | 0.6 | 2.3 | — | 1.0 |
| P27707_C9 | — | — | 1.2 | — | 1.2 | 1.9 | 1.8 | 0.4 | — | — | — |
| Q93009_C223 | 1.1 | 1.0 | 1.0 | — | — | — | 0,8 | — | 20.0 | 1.0 | — |
| O14929_C101 | — | — | 1.0 | — | — | 1.3 | 1.1 | 0.6 | 20.0 | — | — |
| Q9UPQ0_C140 | 0.7 | — | — | — | — | 2.5 | 2.5 | 0.5 | 20.0 | — | 1.1 |
| Q96NY7_C487 | — | — | — | 0.5 | — | 14.9 | — | 0.4 | 1.8 | — | 1.3 |
| Q9NQ88_C114 | 0.4 | — | 0.9 | — | — | — | — | 0.6 | 4.6 | — | — |
| Q14790_C360 | 0.4 | — | 1.6 | 0.5 | — | 3.2 | 1.0 | 0.5 | 20.0 | — | 1.2 |
| P04183_C230 | — | — | 1.2 | — | 2.1 | 1.6 | 2.8 | 0.6 | 2.0 | 0.7 | — |
| P68366_C54 | 0.3 | — | 1.0 | — | 1.1 | — | 2.0 | — | — | — | — |
| Q13428_C1298 | 1.0 | 0.9 | — | — | 2.2 | — | 2.0 | 1.0 | 4.7 | — | — |
| Q5MNZ6_C63 | — | 1.7 | — | — | — | 1.6 | — | 0.8 | 2.6 | — | 0.7 |
| O14980_C528 | — | — | 1.1 | — | — | — | 2.1 | 0.9 | — | 1.1 | — |
| Q86W42_C35 | 1.3 | 1.3 | — | 0.5 | — | 1.6 | 0.8 | 1.1 | 20.0 | 1.4 | 0.7 |
| Q9Y6G9_C51 | 0.6 | 0.7 | — | — | 1.6 | 1.8 | — | 0.7 | — | — | — |
| Q9NY27_C22 | — | — | 1.7 | — | — | — | 1.0 | 0.8 | 20.0 | 2.2 | — |
| Q8NFH5_C255 | — | — | 1.6 | — | — | — | 1.1 | 0.8 | 5.5 | — | — |

TABLE 2C-continued

| Identifier | 27_200 µM_ insitu_ 231 | 28_200 µM_ insitu_ 231 | 29_200 µM_ insitu_ ramos | 31_200 µM_ insitu_ 231 | 31_200 µM_ insitu_ ramos | 33_200 µM_ insitu_ 231 | 38_200 µM_ insitu_ 231 | 41_200 µM_ insitu_ 231 | 45_200 µM_ insitu_ 231 | 51_200 µM_ insitu_ 231 | 56_200 µM_ insitu_ 231 |
|---|---|---|---|---|---|---|---|---|---|---|---|
| Q9Y676_C128 | 1.0 | — | — | — | — | — | 1.0 | — | 2.0 | 1.0 | — |
| P35658_C728 | — | — | 1.7 | 0.7 | — | 6.4 | — | 1.1 | 3.1 | — | — |
| Q9NTX5_C133 | 1.5 | — | — | — | — | 1.0 | — | — | 4.2 | — | 0.9 |
| Q15118_C71 | 1.5 | — | 1.8 | — | — | — | 1.3 | — | 20.0 | — | — |
| Q00765_C18 | 1.1 | — | 1.4 | — | — | 1.1 | — | — | 20.0 | — | 0.9 |
| P22307_C71 | 20.0 | — | — | — | — | — | — | 1.2 | 16.8 | 5.6 | — |
| O75521_C312 | 1.1 | — | — | — | — | — | 1.1 | — | 0.7 | — | 0.9 |
| P49189_C288 | — | — | — | — | — | 20.0 | 0.7 | 0.8 | 20.0 | — | 0.9 |
| Q5T440_C170 | — | — | 1.3 | — | — | 2.5 | — | 0.7 | 3.5 | — | 1.0 |
| Q15084_C190 | 1.0 | — | 1.0 | 1.0 | — | — | 1.0 | 0.9 | 2.8 | — | — |
| Q96C19_C172 | — | — | 1.2 | 1.6 | — | — | 0.7 | 0.5 | — | 1.2 | — |
| P22061_C102 | 2.2 | — | 1.2 | — | — | — | — | 0.7 | — | — | — |
| Q9NP73_C86 | 0.4 | — | 2.0 | — | — | — | 1.3 | 0.5 | 20.0 | 1.3 | — |
| Q9BRF8_C54 | — | — | 1.5 | — | — | 1.8 | — | 0.7 | 20.0 | — | — |
| Q6ICB0_C108 | 1.9 | — | 1.0 | 1.2 | 1.3 | — | 1.1 | — | 3.1 | 1.1 | — |
| P29590_C389 | 0.5 | — | — | 1.1 | — | — | 2.2 | 0.4 | 3.4 | 0.9 | — |
| P07858_C211 | 0.8 | — | — | — | — | 2.2 | 1.8 | 0.4 | 2.4 | — | — |
| Q9NX18_C83 | 1.5 | — | 1.9 | — | — | — | — | — | 3.7 | 1.0 | 0.7 |
| P46109_C249 | — | — | 4.2 | — | — | — | 1.6 | — | 20.0 | — | 0.8 |
| P45984_C177 | 0.5 | — | 1.7 | — | — | 2.0 | — | 0.5 | — | — | 1.1 |
| P19447_C342 | — | — | — | — | — | — | 1.0 | 0.7 | 5.9 | — | 0.7 |
| P42166_C341 | 0.6 | — | — | — | 2.0 | — | — | 0.5 | — | 1.2 | — |
| Q8N1F7_C522 | — | — | 1.7 | — | 3.6 | 1.7 | 1.7 | 0.8 | 20.0 | — | — |
| Q86UY8_C276 | 1.7 | — | — | — | — | 0.8 | — | 1.7 | 2.1 | 1.2 | — |
| Q8WWI1_C228 | 0.8 | — | 1.0 | — | — | — | — | 0.8 | 20.0 | — | — |
| Q9NWA0_C139 | 1.3 | — | 0.7 | — | — | 1.6 | — | 0.8 | — | — | 1.1 |
| P09110_C381 | — | 0.8 | — | 0.7 | — | — | 0.8 | 0.9 | 1.2 | — | 0.8 |
| Q2NL82_C126 | 0.4 | — | — | — | — | — | 0.9 | 0.8 | 20.0 | 1.9 | — |
| Q5JPI3_C308 | 0.7 | — | 1.3 | — | — | — | — | 0.7 | — | — | 0.7 |
| P23919_C163 | 0.2 | 0.4 | — | — | 1.0 | — | 5.7 | 0.2 | — | — | 0.9 |
| Q96EB1_C218 | 0.6 | — | 1.1 | — | — | — | 1.3 | — | 20.0 | — | — |
| Q96FX7_C209 | — | — | — | — | — | — | 1.0 | — | 20.0 | — | 0.9 |
| O14933_C98 | — | — | 2.4 | — | 1.9 | — | 1.6 | 0.5 | 20.0 | — | — |
| Q29RF7_C242 | 0.9 | 1.0 | — | — | — | — | 1.0 | — | — | 1.8 | 1.0 |
| Q96T76_C819 | 0.5 | — | — | 20.0 | 20.0 | — | 4.6 | 0.6 | 20.0 | — | 0.9 |
| P23919_C117 | — | — | 1.6 | — | — | 2.5 | 4.4 | — | — | — | — |
| Q15149_C4574 | 1.3 | — | — | — | — | 1.4 | — | 0.9 | — | — | 1.0 |

TABLE 2C-continued

| Identifier | 27_200 µM_ insitu_ 231 | 28_200 µM_ insitu_ 231 | 29_200 µM_ insitu_ ramos | 31_200 µM_ insitu_ 231 | 31_200 µM_ insitu_ ramos | 33_200 µM_ insitu_ 231 | 38_200 µM_ insitu_ 231 | 41_200 µM_ insitu_ 231 | 45_200 µM_ insitu_ 231 | 51_200 µM_ insitu_ 231 | 56_200 µM_ insitu_ 231 |
|---|---|---|---|---|---|---|---|---|---|---|---|
| Q96RP9_C153 | 1.6 | — | 1.2 | — | — | — | — | 1.1 | — | — | — |
| P04818_C199 | 0.5 | — | 2.5 | — | — | — | 20.0 | 0.7 | 20.0 | 20.0 | — |
| P27708_C73 | 0.5 | — | 1.8 | — | — | — | — | 0.7 | — | — | — |
| P55265_C1224 | 1.4 | — | 1.8 | — | — | 1.6 | — | — | 20.0 | 1.3 | — |
| Q9Y3D2_C105 | 1.5 | — | — | — | — | — | 1.6 | 1.2 | 20.0 | — | — |
| O00244_C12 | 0.4 | — | 1.4 | — | — | 1.8 | — | — | — | — | — |
| Q8WV74_C207 | 2.2 | — | — | — | — | — | — | 0.9 | 20.0 | — | — |
| Q9NRW3_C130 | 1.3 | — | 13.3 | — | — | — | — | 0.9 | 20.0 | — | 0.9 |
| P24468_C326 | 1.2 | — | — | — | — | — | — | 0.8 | 20.0 | — | — |
| P42166_C684 | — | — | — | — | 3.3 | — | 3.0 | — | 6.8 | 1.2 | 1.1 |
| Q96EY5_C231 | 0.6 | — | 1.1 | — | — | 1.2 | 1.8 | — | — | — | — |
| P14635_C238 | — | — | — | — | — | 1.2 | 1.8 | 0.5 | — | — | — |
| Q8NDH3_C81 | — | — | — | 1.0 | — | — | 2.0 | — | — | — | 1.0 |
| Q9P0J1_C149 | — | — | 1.0 | — | — | — | 0.9 | 20.0 | — | 0.8 | — |
| Q96P48_C900 | — | — | 1.1 | 1.1 | — | 1.7 | — | 0.5 | — | — | — |
| Q96HE7_C37 | — | — | 2.1 | 0.6 | — | — | 3.4 | 0.4 | 20.0 | — | — |
| Q07065_C100 | — | — | — | — | — | 1.7 | — | 1.0 | 20.0 | — | — |
| Q9BRJ7_C88 | — | 1.7 | — | 2.9 | — | — | 0.4 | — | 1.6 | 1.0 | — |
| O75439_C265 | 1.6 | 0.6 | — | 1.0 | 1.4 | — | — | 1.3 | — | — | — |
| O43175_C369 | — | — | 1.1 | 20.0 | 20.0 | — | — | — | — | — | — |
| Q9UNI6_C265 | 0.6 | 0.8 | — | — | — | — | 1.0 | 1.0 | 7.5 | — | — |
| Q06203_C100 | 0.8 | — | 1.6 | 0.6 | 1.2 | — | 1.2 | — | — | — | — |
| A0AVT1_C347 | 0.8 | — | — | — | 1.9 | — | — | 0.6 | — | — | — |
| Q86X76_C203 | — | — | — | — | — | — | — | 1.3 | 20.0 | — | 0.8 |
| Q6XZF7_C691 | — | — | 2.3 | — | 2.5 | — | — | — | — | — | — |
| Q15398_C129 | 0.5 | — | 1.2 | — | 2.4 | 1.3 | 1.4 | — | — | 7.4 | 1.3 |
| O75717_C773 | — | — | — | — | — | — | 2.3 | 1.0 | 3.6 | — | 0.9 |
| Q01433_C107 | 0.4 | — | — | 0.7 | — | — | — | 0.5 | — | — | — |
| Q8WVV9_C464 | — | — | — | — | — | 2.2 | 1.5 | — | 20.0 | 3.2 | — |
| O14733_C131 | — | — | 1.0 | — | — | — | 20.0 | 0.8 | — | — | — |
| Q14137_C404 | 0.6 | — | 1.5 | — | — | — | — | — | — | — | — |
| Q96RU2_C171 | 1.1 | 1.1 | — | — | — | — | 0.8 | — | — | — | — |
| Q9Y679_C391 | 1.2 | — | — | — | — | — | — | — | 20.0 | 20.0 | 0.7 |
| P51610_C1872 | — | — | — | — | — | — | 1.3 | 0.5 | — | — | — |
| P22307_C307 | — | — | — | — | — | — | — | 1.1 | — | — | — |
| Q9BTE3_C325 | — | 1.0 | — | 1.9 | 3.5 | — | 2.2 | 0.6 | 20.0 | — | — |
| Q9HA64_C24 | — | — | — | — | — | — | 1.7 | — | — | — | 1.0 |

TABLE 2C-continued

| Identifier | 27_200 µM_ insitu_ 231 | 28_200 µM_ insitu_ 231 | 29_200 µM_ insitu_ ramos | 31_200 µM_ insitu_ 231 | 31_200 µM_ insitu_ ramos | 33_200 µM_ insitu_ 231 | 38_200 µM_ insitu_ 231 | 41_200 µM_ insitu_ 231 | 45_200 µM_ insitu_ 231 | 51_200 µM_ insitu_ 231 | 56_200 µM_ insitu_ 231 |
|---|---|---|---|---|---|---|---|---|---|---|---|
| Q5TFE4_C119 | — | — | — | 3.1 | — | — | — | 0.5 | — | — | — |
| Q96N67_C2125 | 0.9 | — | — | 0.8 | — | — | 1.5 | 0.7 | — | — | 0.9 |
| P52948_C1312 | 1.3 | — | — | — | — | 1.8 | 1.3 | — | — | — | — |
| Q5UIP0_C2298 | — | — | — | — | — | 3.4 | — | — | — | — | — |
| P51812_C436 | — | — | 1.3 | — | — | — | — | 4.5 | — | — | — |
| Q92616_C1692 | 0.5 | — | — | 0.6 | 2.0 | 1.2 | — | 0.7 | — | — | — |
| Q15345_C297 | — | — | — | 0.9 | — | 1.9 | 1.4 | 0.8 | — | — | — |
| Q9NPH0_C267 | 1.3 | — | 2.1 | — | — | — | — | — | 20.0 | — | — |
| P04183_C66 | — | — | 1.6 | 0.7 | — | — | — | 0.4 | — | — | — |
| P42166_C629 | — | — | 1.6 | — | — | — | — | — | — | — | — |
| Q15013_C124 | 1.0 | 1.0 | — | — | — | — | — | — | 20.0 | 1.2 | — |
| Q9Y5Y2_C72 | — | — | 1.1 | — | — | — | 1.7 | — | — | — | — |
| O15446_C86 | — | — | — | — | — | 1.6 | — | — | 4.6 | — | — |
| Q13630_C116 | — | — | — | — | — | — | — | — | 20.0 | — | — |
| Q8IYQ7_C324 | — | — | — | — | — | 1.4 | — | — | — | — | — |
| P05091_C319 | — | — | 10.5 | — | — | — | — | 0.9 | 20.0 | — | — |
| Q29RF7_C532 | — | — | — | 5.1 | 8.1 | — | — | 0.8 | — | — | — |
| Q9Y570_C381 | — | — | 1.2 | — | — | — | — | 0.2 | — | — | — |
| Q14980_C961 | 2.4 | — | — | 1.1 | — | 4.8 | 2.6 | — | — | — | — |
| P53384_C235 | — | — | — | 0.7 | — | — | 2.0 | 0.2 | — | — | — |
| Q15003_C418 | — | — | 1.4 | — | — | — | — | — | 20.0 | — | 1.3 |
| P53634_C258 | — | — | — | — | — | — | — | — | — | — | — |
| Q8NFF5_C499 | — | — | 3.4 | — | — | — | — | — | — | — | 1.3 |
| Q9ULA0_C144 | — | — | 1.3 | — | — | — | — | 0.8 | — | — | 0.9 |
| P22307_C94 | — | 20.0 | — | — | — | — | — | — | 20.0 | — | — |
| O15294_C620 | — | — | 2.6 | 1.1 | — | — | — | 1.0 | — | — | — |
| Q9Y5S2_C1517 | — | — | — | — | — | — | — | 0.4 | 20.0 | — | — |
| Q8TD19_C623 | — | — | — | 0.7 | 1.4 | — | — | 0.6 | — | — | — |
| Q8N2W9_C326 | — | — | — | — | — | — | 0.9 | 0.8 | — | — | — |
| Q13158_C98 | 0.6 | — | 1.3 | 0.9 | — | — | 1.5 | — | — | — | — |
| Q9UKX7_C151 | — | — | — | — | — | — | — | 0.8 | — | — | — |
| Q6PCB5_C280 | 1.0 | — | 1.4 | — | — | — | — | — | — | — | — |
| P10398_C597 | — | — | 1.2 | — | — | — | — | — | — | — | — |
| Q9UL40_C68 | 1.9 | — | 2.4 | — | — | — | — | — | — | — | — |
| P46013_C903 | — | — | 1.6 | — | — | — | 1.1 | 1.0 | 20.0 | 1.1 | — |
| Q16667_C39 | — | — | 1.7 | — | — | — | — | — | — | — | — |
| O75150_C890 | 1.2 | — | — | 0.7 | — | — | — | 1.3 | — | — | — |

TABLE 2C-continued

| Identifier | 27_200 μM_ insitu_ 231 | 28_200 μM_ insitu_ 231 | 29_200 μM_ insitu_ ramos | 31_200 μM_ insitu_ 231 | 31_200 μM_ insitu_ ramos | 33_200 μM_ insitu_ 231 | 38_200 μM_ insitu_ 231 | 41_200 μM_ insitu_ 231 | 45_200 μM_ insitu_ 231 | 51_200 μM_ insitu_ 231 | 56_200 μM_ insitu_ 231 |
|---|---|---|---|---|---|---|---|---|---|---|---|
| Q00610_C870 | — | — | — | — | — | — | 20.0 | — | — | — | — |
| Q9Y5T5_C205 | 1.2 | — | — | — | — | — | 1.5 | — | — | — | — |
| O95881_C66 | — | — | — | — | — | — | 1.0 | 1.0 | — | — | — |
| Q7Z5K2_C160 | — | — | 0.7 | — | — | — | — | 1.0 | — | — | — |
| P42166_C518 | — | — | — | — | — | — | 2.2 | — | — | — | — |
| Q9Y2S7_C143 | — | — | — | — | — | — | — | — | 1.2 | — | 0.8 |
| E2QRD5_C183 | — | — | — | 0.8 | — | — | — | — | 0.5 | — | — |
| O95833_C22 | — | — | — | 0.5 | — | — | — | — | 13.8 | — | — |
| O94953_C694 | — | — | 1.1 | — | — | — | — | — | — | — | — |
| O00541_C272 | — | — | — | — | — | — | — | — | 0.9 | — | — |
| Q9NXJ5_C149 | — | — | — | — | — | — | — | — | — | — | — |
| Q8N5L8_C131 | — | — | — | — | — | 1.7 | — | — | 7.3 | — | — |
| Q8IZ73_C246 | — | — | — | 0.4 | 1.0 | — | 1.7 | — | — | — | — |
| Q99798_C385 | — | — | — | — | — | — | — | 0.1 | — | — | — |
| Q9GZR2_C382 | — | — | — | — | — | — | — | — | 20.0 | — | — |
| Q13613_C117 | — | — | 1.5 | — | — | — | — | — | — | — | — |
| Q9NUI1_C22 | — | — | — | 0.7 | — | — | — | — | 17.0 | — | — |
| Q02556_C306 | — | — | 1.4 | — | 2.0 | — | — | — | — | — | — |
| Q9UPT9_C171 | — | — | — | — | — | — | — | — | — | — | — |
| Q8N999_C302 | — | 0.6 | — | — | — | — | — | 0.3 | 20.0 | — | — |
| Q8IU81_C363 | — | — | — | 0.7 | — | — | 1.3 | — | 1.7 | — | — |
| Q9C0I1_C152 | — | — | 4.6 | — | — | — | — | — | — | — | — |
| Q9P2X3_C195 | — | — | — | 0.5 | — | — | — | — | 20.0 | — | — |
| Q6QNY0_C168 | — | — | 1.6 | — | — | — | 1.0 | — | — | — | — |
| Q15796_C81 | — | — | 1.3 | — | — | — | — | — | — | — | — |
| Q9NZB2_C531 | — | — | — | — | — | 2.4 | — | — | — | — | 0.6 |
| Q9HB90_C377 | — | — | — | — | — | — | — | — | — | — | — |
| Q9BR61_C267 | — | — | 2.5 | — | — | — | — | — | 0.5 | — | — |
| P16455_C145 | — | — | — | — | 1.2 | — | — | — | — | — | — |
| Q86UV5_C39 | — | — | — | — | 1.3 | — | — | — | — | — | — |
| A2A288_C367 | — | — | 1.3 | — | 1.9 | — | — | — | — | — | — |
| Q8NEC7_C140 | — | — | — | — | — | — | — | — | 20.0 | — | — |
| Q6PJG6_C673 | — | — | 4.6 | — | 20.0 | — | — | — | — | — | 0.9 |
| Q13232_C158 | — | — | 1.5 | — | — | — | — | — | 8.8 | — | — |
| Q86X76_C165 | — | — | — | — | — | — | — | — | — | — | — |
| P42695_C541 | — | — | — | — | — | — | — | — | — | — | — |
| P41226_C599 | — | — | — | — | — | — | — | — | — | — | — |

TABLE 2C-continued

| Identifier | 27_200 μM_ insitu_ 231 | 28_200 μM_ insitu_ 231 | 29_200 μM_ insitu_ ramos | 31_200 μM_ insitu_ 231 | 31_200 μM_ insitu_ ramos | 33_200 μM_ insitu_ 231 | 38_200 μM_ insitu_ 231 | 41_200 μM_ insitu_ 231 | 45_200 μM_ insitu_ 231 | 51_200 μM_ insitu_ 231 | 56_200 μM_ insitu_ 231 |
|---|---|---|---|---|---|---|---|---|---|---|---|
| Q99986_C50 | — | — | — | — | — | — | — | — | 4.1 | — | — |
| Q8WUM4_C90 | 0.6 | — | — | — | — | — | — | — | — | — | — |
| P29590_C213 | 0.8 | — | — | — | — | — | — | — | — | — | — |
| Q9P0K7_C973 | — | — | — | — | — | — | — | — | — | — | — |
| P53992_C78 | — | — | — | — | — | — | — | — | — | — | — |
| Q13867_C73 | — | — | — | — | — | — | — | — | — | — | — |
| Q8ND24_C655 | — | — | — | — | — | — | — | — | — | — | — |
| Q96EK4_C48 | — | — | — | — | — | — | — | — | — | — | — |
| Q96IV0_C309 | — | — | 3.0 | — | — | — | — | — | — | — | — |
| Q5T1V6_C414 | — | — | — | — | — | — | — | — | — | — | — |
| Q9UHQ1_C99 | — | — | — | — | — | — | — | — | — | — | — |
| O43396_C34 | — | — | — | — | — | — | — | — | — | — | — |
| Q8IV53_C174 | — | — | — | — | — | — | — | — | — | — | — |
| Q8N9T8_C673 | — | — | — | — | — | — | — | — | — | — | — |

TABLE 3 illustrates a list of cysteine containing proteins and potential cysteine site of conjugation.

| Identifier | Protein Name | Cysteine Location | Protein Class |
|---|---|---|---|
| O00170 | AIP AH receptor-interacting protein | C122 | Uncategorized |
| O00541 | PES1 Pescadillo homolog | C272; C361 | Uncategorized |
| O00622 | CYR61 Protein CYR61 | C39; C70; C134 | Uncategorized |
| O14920 | IKBKB Inhibitor of nuclear factor kappa-B kinase subunit | C464 | Enzyme |
| O14933 | UBE2L6 Ubiquitin/ISG15-conjugating enzyme E2 L6 PCTK | C98 | Enzyme |
| O14980 | XPO1 Exportin-1 | C34; C528; C1070 | Uncategorized |
| O75362 | ZNF217 Zinc finger protein 217 | C286 | Transcription factors and regulators |
| O94953 | KDM4B Lysine-specific demethylase 4B | C694 | Enzyme |
| P00813 | ADA Adenosine deaminase | C75 | Enzyme |
| P04150 | NR3C1 Glucocorticoid receptor | C302; C622 | Transcription factors and regulators |
| P09086 | POU2F2 POU domain, class 2, transcription factor 2 | C346 | Transcription factors and regulators |
| P09211 | GSTP1 Glutathione S-transferase P | C48 | Enzyme |
| P14598 | NCF1 Neutrophil cytosol factor 1 | C378 | Adapter, scaffolding, modulator proteins |
| P15374 | UCHL3 Ubiquitin carboxyl-terminal hydrolase isozyme L3 | C95 | Enzyme |
| P16455 | MGMT Methylated-DNA--protein-cysteine methyltransferase | C145; C150 | Enzyme |
| P17812 | CTP synthase 1 | C491 | Enzyme |
| P19447 | ERCC3 TFIIH basal transcription factor complex helicase | C342 | Enzyme |
| P21580 | TNFAIP3 Tumor necrosis factor alpha-induced protein 3 | C54 | Enzyme |
| P24752 | ACAT1 Acetyl-CoA acetyltransferase, mitochondrial | C119; C126; C196; C413 | Enzyme |
| P40261 | Nicotinamide N-methyltransferase | C165 | Enzyme |

TABLE 3-continued illustrates a list of cysteine containing proteins and potential cysteine site of conjugation.

| Identifier | Protein Name | Cysteine Location | Protein Class |
|---|---|---|---|
| P40763 | STAT3 Signal transducer and activator of transcription 3 | C259 | Transcription factors and regulators |
| P41226 | UBA7 Ubiquitin-like modifier-activating enzyme 7 | C599 | Enzyme |
| P42575 | CASP2 Caspase-2 | C370 | Enzyme |
| P43403 | ZAP70 Tyrosine-protein kinase ZAP-70 | C117 | Enzyme |
| P48200 | IREB2 Iron-responsive element-binding protein 2 | C137 | Transcription factors and regulators |
| P48735 | IDH2 Isocitrate dehydrogenase | C308 | Enzyme |
| P50851 | LRBA Lipopolysaccharide-responsive and beige-like anchor protein | C1704; C2675 | Uncategorized |
| P51617 | IRAK1 Interleukin-1 receptor-associated kinase 1 | C608 | Enzyme |
| P61081 | NEDD8-conjugating enzyme Ubc12 | C47 | Enzyme |
| P61088 | Ubiquitin-conjugating enzyme E2 N | C87 | Enzyme |
| P63244 | GNB2L1 Guanine nucleotide-binding protein subunit beta-2-like 1 | C182 | Channels, Transporters, Receptors |
| P68036 | UBE2L3 Ubiquitin-conjugating enzyme E2 L3 | C86 | Enzyme |
| Q00535 | CDK5 Cyclin-dependent kinase 5 | C157 | Enzyme |
| Q01201 | RELB Transcription factor RelB | C109 | Transcription factors and regulators |
| Q02556 | IRF8 Interferon regulatory factor 8 | C306 | Transcription factors and regulators |
| Q04759 | PRKCQ Protein kinase C theta type | C14; C17 | Enzyme |
| Q06124 | Tyrosine-protein phosphatase non-receptor type 11 | C573 | Enzyme |
| Q09472 | EP300 Histone acetyltransferase p300 | C1738 | Enzyme |
| Q14790 | CASP8 Caspase-8 | C360 | Enzyme |
| Q15084 | PDIA6 Protein disulfide-isomerase A6 | C55; C58; C190; C193 | Enzyme |
| Q15306 | IRF4 Interferon regulatory factor 4 | C194 | Transcription factors and regulators |
| Q15910 | EZH2 Histone-lysine N-methyltransferase EZH2 | C503 | Enzyme |
| Q16186 | Proteasomal ubiquitin receptor ADRM1 | C88 | Channels, Transporters, Receptors |
| Q16763 | UBE2S Ubiquitin-conjugating enzyme E2 S | C118 | Enzyme |
| Q16822 | PCK2 Phosphoenolpyruvate carboxykinase | C306 | Enzyme |
| Q16875 | 6-phosphofructo-2-kinase/fructose-2,6-bisphosphatase 3 | C155 | Enzyme |
| Q16877 | PFKFB4 6-phosphofructo-2-kinase/fructose-2,6-bisphosphata | C159 | Enzyme |
| Q6L8Q7 | PDE12 2,5-phosphodiesterase 12 | C108 | Enzyme |
| Q7OCQ2 | USP34 Ubiquitin carboxyl-terminal hydrolase 34 | C741; C1090 | Enzyme |
| Q7Z2W4 | ZC3HAV1 Zinc finger CCCH-type antiviral protein 1 | C645 | Transcription factors and regulators |
| Q86UV5 | USP48 Ubiquitin carboxyl-terminal hydrolase 48 | C39 | Enzyme |
| Q8TAQ2 | SMARCC2 SWI/SNF complex subunit SMARCC2 | C145 | Transcription factors and regulators |
| Q92851 | Caspase-10 | C401 | Enzyme |
| Q93009 | USP7 Ubiquitin carboxyl-terminal hydrolase 7 | C223; C315 | Enzyme |
| Q96FA3 | PELI1 E3 ubiquitin-protein ligase pellino homolog 1 | C282 | Enzyme |
| Q96GG9 | DCUN1D1 DCN1-like protein 1 | C115 | Uncategorized |
| Q96JH7 | VCPIP1 Deubiquitinating protein VCIP135 | C219 | Enzyme |
| Q96RU2 | USP28 Ubiquitin carboxyl-terminal hydrolase 28 | C171; C733 | Enzyme |
| Q99873 | PRMT1 Protein arginine N-methyltransferase 1 | C109 | Enzyme |
| Q9C0C9 | UBE2O Ubiquitin-conjugating enzyme E2 O | C375 | Enzyme |
| Q9HB90 | RRAGC Ras-related GTP-binding protein C | C358; C377 | Channels, transporters, and receptors |

TABLE 3-continued illustrates a list of cysteine containing proteins and potential cysteine site of conjugation.

| Identifier | Protein Name | Cysteine Location | Protein Class |
|---|---|---|---|
| Q9NRW4 | Dual specificity protein phosphatase 22 | C124 | Enzyme |
| Q9NWZ3 | IRAK4 Interleukin-1 receptor-associated kinase 4 | C13 | Enzyme |
| Q9NYL2 | MLTK Mitogen-activated protein kinase kinase kinase MLT | C22 | Enzyme |
| Q9UPT9 | USP22 Ubiquitin carboxyl-terminal hydrolase 22 | C44; C171 | Enzyme |
| Q9Y3Z3 | SAMHD1 SAM domain and HD domain-containing protein 1 | C522 | Enzyme |
| Q9Y4C1 | KDM3A Lysine-specific demethylase 3A | C251 | Enzyme |
| Q9Y5T5 | USP16 Ubiquitin carboxyl-terminal hydrolase 16 | C205 | Enzyme |

Table 4 shows representative cysteines with known covalent ligands targeted by fragment electrophiles in isoTOP-ABPP experiments.

| Protein | Liganded cysteine | Fragment(s) | Other cysteines quantified by isoTOP-ABPP | Previous covalent inhibitor(s) | Cysteine location |
|---|---|---|---|---|---|
| BTK | C481 | 2, 3, 14, 31 | C145, C337 | Ibrutinib | Active site |
| TGM2 | C277 | 12, 14, 32 | C10, C27, C230, C269, C290, C336, C370, C524, C545, C620 | 18d | Active Site |
| Map2k7 | C131 | 2, 3, 11, 14, 20, 21, 38 | C260, C280 | Ibrutinib | Active Site |
| XPO1 | C528 | 2, 3, 5, 14, 24, 31, 43, 56 | C34, C119, C164, C199, C327, C498, C723, C1070 | KPT-330 | Non-active site |
| Casp5 | C315 | 3, 50 | — | Z-WEHD-CHO/FMK ("WEHD" disclosed as SEQ ID NO: 863) | Active Site |
| Casp8 | C360 | 2, 4, 11 | C236, C409 | Z-VAD-FMK, CV8/9-AOMK | Active Site |
| ERCC3 | C342 | 2, 3, 5, 8, 14, 21 | — | Triptolide | Active Site |
| Park 7 (Toxoplasma DJ-1) | C106 | 2, 9, 8, 11, 13, 43, 45, 50, 52 | C46, C53 | WRR-086 | Active Site |
| GSTO1 | C32 | 2-13, 16, 18-22, 33, 27-30, 32-34, 36, 39, 43, 49, 50, 52, 54, 55 | C90, C192, C237 | KT53 | Active Site |
| ALDH2 | C319 | 3, 8-10,12, 27, 28, 32, 39, 40, 43, 49, 50 | C66, C179, C386, C472 | Disulfiram | Active Site |
| CTSZ | C92 | 4, 11, 20, 28, 32 | C89, C126, C132, C154, C170, C173, C179, C214 | Cy5DCG04 | Active Site |

Table 5 shows Reactive docking results for liganded cysteines.

| Protein | PDB ID: | Most ligandable cysteine by docking | Cysteine location | Most ligandable cysteine by isoTOP-ABPP | Match |
|---|---|---|---|---|---|
| Aldh2 | 1O05 | C319 | Active site | C319 | Yes |
| BTK | 1K2P | C481 | Active site | C481 | Yes |
| CASP8 | 1QTN | C360 | Active Site | C360 | Yes |
| CCNB1 | 2JGZ | C238 | Non-active site | C238 | Yes |
| CDKN3 | 1FQ1 | C39 | Non-active site | C39 | Yes |
| CLIC4 | 2AEH | C35 | Non-active site | C35 | Yes |
| DTYMK | 1E2G | C163 | Non-active site | C163 | Yes |
| IDH1 | 3MAP | C269 | Non-active site | C269 | Yes |
| IMPDH2 | 1NF7 | C331 | Active site | C331, C140 | Yes |

| Protein | PDB ID: | Most ligandable cysteine by docking | Cysteine location | Most ligandable cysteine by isoTOP-ABPP | Match |
|---|---|---|---|---|---|
| GLRX5 | 2WUL | C67 | Active site | C67 | Yes |
| GSTO1 | 1EEM | C32 | Active site | C32 | Yes |
| NME3 | 1ZS6 | C158 | Non-active site | C158 | Yes |
| PKM | 4JPG | C423 | Non-active site | C423 | Yes |
| SRC | 2SRC | C277 | Active Site | C277 | Yes |
| TIGAR | 3DCY | C114 | Non-active site | C114, C161 | Yes |
| TXNDC | 1WOU | C43 | Active site | C43 | Yes |
| UGDH | 3ITK | C276 | Active site | C276 | Yes |
| UPP1 | 3EUF | C162 | Non-active site | C162 | Yes |
| XPO1 | 3GB8 | C528 | Non-active site | C528 | Yes |
| CDK5 | 1UNG | C157 | Non-active site | C269 | Second |
| EDC3 | 3D3K | C311 | Non-active site | C137, C413, C499 | Second |
| NR2F2 | 3CJW | C213 | Non-active site | C326, C213 (in situ) | Second |
| PDCD6IP | 2R02 | C231 | Non-active site | C90 | Second |
| PRMT1 | 1ORI | C285 | Active site | C109 | Second |
| UBE2S | 1ZDN | C118 | Non-active site | C95 | Second |
| FNBP1 | 2EFL | C145 | Non-active site | C70 | No |
| HAT1 | 2P0W | C120 | Non-active site | C101 | No |
| MAPK9 | 3NPC | C163 | Active site | C177 | No |
| STAT1 | 1YVL | C543 | Non-active site | C492, C255 | No |

Table 6 shows site of fragment labeling for recombinant proteins. The underlines portion indicates the fragment-modified cysteines.

| Protein | Cysteine | Fragment # | Peptide | SEQ ID NO: | M + H calculated (m/z) | M + H observed (m/z) | Charge |
|---|---|---|---|---|---|---|---|
| IMPDH2 | C140 | 14 | R.HGFCGIPITDTGR.M | 45 | 715.86 | 715.86 | 2 |
| TIGAR | C114 | 5 | R.EECPVFTPPGGETLDQVK.M | 143 | 1123.97 | 1123.97 | 2 |
| CASP8 | C360 | 7 | K.VFFIQACQGDNYQK.G | 335 | 660.98 | 660.98 | 3 |
| IDH1 | C269 | 20 | K.SEGGFIWACK.N | 260 | 702.84 | 702.84 | 2 |

TABLE 7 illustrates a list of DMF-sensitive Cys residues in human T cells, defined as Cys residues that showed R values (DMSO/DMF) >4 in isoTOP-ABPP experiments comparing DMSO- versus DMF-treated T cells.

| Name | Full name | Protein function | Residue | Conserved in mice | Role in immunology |
|---|---|---|---|---|---|
| ADA | Adenosine deaminase | Adenosine deaminase | C75 | yes | Positive regulator of T cell co-activation |
| AGFG2 | Arf-GAP domain and FG repeat-containing protein 2 | GTPase activator | C39 | yes | Unknown |
| AIP | AH receptor-interacting protein | Transcription factor binding | C122 | yes | Unknown |
| CRKL | Crk-like protein | Poly(A) RNA binding | C249 | yes | Unknown |
| FLII | Protein flightless-1 homolog | Actin binding | C46 | yes | Unknown |
| GAK | Cyclin-G-associated kinase | Serine/threonine protein kinase | C87 | yes | Unknown |
| HUWE1 | E3 ubiquitin-protein ligase HUWE1 | E3 ubiquitin-protein ligase | C3372 | yes | Unknown |
| IKBKB | Inhibitor of nuclear factor kappa-B kinase subunit | Serine kinase | C464 | yes | Phosphorylates IkB-α in NF-κB pathway |
| IL16 | Pro-interleukin-16 | Cytokine | C1004 | yes | Influences migration of CD4+ lymphocytes |
| IRF4 | Interferon regulatory factor 4 | DNA binding | C194 | yes | Regulates dendritic cell and B cell development, as well as T/B cell differentiation |
| IRF8 | Interferon regulatory factor 8 | DNA binding | C306 | yes | Plays a negative regulatory role in immune cells. Binds to upstream regulatory region of MHC class I |

TABLE 7-continued illustrates a list of DMF-sensitive Cys residues in human T cells, defined as Cys residues that showed R values (DMSO/DMF) >4 in isoTOP-ABPP experiments comparing DMSO- versus DMF-treated T cells.

| Name | Full name | Protein function | Residue | Conserved in mice | Role in immunology |
|---|---|---|---|---|---|
| | | | | | genes. Regulates the development and differentiation of myeloid cells. |
| KIAA0528 | Uncharacterized protein | Calcium-dependent phospholipid binding | C993 | yes | Unknown |
| LAS1L | Ribosomal biogenesis protein | Poly(A) RNA binding | C456 | yes | Unknown |
| MARS2 | Methionine--tRNA ligase, mitochondrial | Methionine-tRNA ligase | C425 | yes | Unknown |
| MAT2A | S-adenosylmethionine synthase isoform type-2 | Methionine adenosyltransferase | C56 | yes | Unknown |
| MAT2A | S-adenosylmethionine synthase isoform type-2 | Methionine adenosyltransferase | C104 | yes | Unknown |
| MTCH2 | Mitochondrial carrier homolog 2 | Induces mitochondrial depolarization | C296 | yes | Unknown |
| PGP | Phosphoglycolate phosphatase | Phosphatase | C297 | yes | Unknown |
| PML | Protein Promyelocytic leukemia | RNA/DNA binding | C479 | yes | Modulates TGF-beta signaling, induced by interferon to promote antiviral responses |
| PRKCQ | Protein kinase C theta type | Serine/threonine protein kinase | C14 | yes | Promotes TCR signaling through activation of NF-κB and other transcription factors |
| PYGB | Glycogen phosphorylase, brain form | Phosphorylase | C326 | yes | Unknown |
| RARS | Arginine--tRNA ligase, cytoplasmic | tRNA binding | C32 | yes | Unknown |
| SON | Protein SON | RNA/DNA binding | C92 | yes | Unknown |
| SYNE2 | Nesprin-2 | Actin binding | C553 | yes | Unknown |
| TDRKH | Tudor and KH domain-containing protein | RNA binding | C109 | yes | Unknown |
| THNSL1 | Threonine synthase-like 1 | Threonine synthase | C324 | yes | Unknown |
| THOC1 | THO complex subunit 1 | RNA/DNA binding | C49 | yes | Unknown |
| TNFAIP3 | Tumor necrosis factor alpha-induced protein 3 | Ubiquitin-specific protease | C54 | yes | Inhibits NF-κB signaling upon TCR-mediated T cell activation |
| UBR4 | E3 ubiquitin-protein ligase | Ubiquitin ligase | C2554 | yes | Unknown |
| USP7 | Ubiquitin carboxyl-terminal hydrolase 7 | Ubiquitin-specific protease | C315 | yes | Deubiquitinates FOXP3, increasing Treg suppressive capacity |
| VDAC3 | Voltage-dependent anion-selective channel protein | Mitochondrial outer membrane channel | C65 | yes | Unknown |
| VDAC3 | Voltage-dependent anion-selective channel protein | Voltage-gated anion channel | C36 | yes | Unknown |
| ZC3HAV1 | Zinc finger CCCH-type antiviral protein 1 | Poly(A) RNA binding | C645 | yes | Inhibits viral replication |
| ZNF346 | Zinc finger protein 346 | RNA binding | C68 | yes | Unknown |
| AARS | Alanine--tRNA ligase, cytoplasmic | Alanine-tRNA ligase | C773 | no | Unknown |

TABLE 7-continued illustrates a list of DMF-sensitive Cys residues in human T cells, defined as Cys residues that showed R values (DMSO/DMF) >4 in isoTOP-ABPP experiments comparing DMSO- versus DMF-treated T cells.

| Name | Full name | Protein function | Residue | Conserved in mice | Role in immunology |
|---|---|---|---|---|---|
| APOBEC3C | Probable DNA dC-dU-editing enzyme | Cytidine deaminase | C130 | no | Inhibits retrovirus replication |
| BCL2A1 | Bcl-2-related protein A1 | Scaffolding protein | C55 | no | Expression induced by inflammatory cytokines |
| BCL2A1 | Bcl-2-related protein A1 | Scaffolding protein | C19 | no | Unknown |
| CHRAC1 | Chromatin accessibility complex protein 1 | Chromatin remodeling | C55 | no | Unknown |
| DCXR | L-xylulose reductase | Xylulose reductase | C244 | no | Unknown |
| GHDC | GH3 domain-containing protein | Uncharacterized | C502 | no | Unknown |
| IRAK4 | Interleukin-1 receptor-associated kinase 4 | Serine/threonine protein kinase | C13 | no | Helps initiate innate immune response by promoting ubiquitination of IRAK1 upon TLR activation. Also implicated in T cell activation |
| NADSYN1 | Glutamine-dependent NAD(+) synthetase | NAD(+) synthase | C428 | no | Unknown |
| PGLS | 6-phospho-gluconolactonase | Hydrolysis of 6-phosphoglucono-lactone | C32 | no | Unknown |
| PRKDC | DNA-dependent protein kinase catalytic subunit | Serine/threonine protein kinase | C4045 | no | Regulates DNA damage response, involved in V(D)J recombination |
| PUSL1 | tRNA pseudouridine synthase-like 1 | Pseudouridine synthase | C292 | no | Unknown |
| RIN3 | Ras and Rab interactor 3 | GTPase activator | C942 | no | Unknown |
| SCLY | Selenocysteine lyase | Selenocysteine lyase | C22 | no | Unknown |
| SPCS2 | Signal peptidase complex subunit 2 | Peptidase | C17 | no | Unknown |
| TRNT1 | CCA tRNA nucleotidyl-transferase 1, mitochondrial | tRNA binding | C373 | no | Mutations lead to B-cell immunodeficiency as well as progressive reductions in T and NK cells (OMIM number 616084) |
| TUBGCP3 | Gamma-tubulin complex component 3 | Gamma-tubulin binding | C194 | no | Unknown |
| UBE2L6 | Ubiquitin/ISG 15-conjugating enzyme E2 L6 | Ubiquitin-conjugating enzyme | C98 | no | Acts as an E2 enzyme for an IFN-induced ubiquitin-like protein |

TABLE 8 illustrates an exemplary list of DMF sensitive cysteine-containing proteins in human T cell targets. Table 8 further shows the accession number (or the protein identifier) of the protein.

| Identifier | Protein Name | SEQ ID NO: | DMF_ 50 µM_4h | DMF_ 50 µM_2h | DMF_ 50 µM_1h | DMF_ 25 µM_4h | DMF_ 10 µM_4h | DMF_ 50 µM_4h |
|---|---|---|---|---|---|---|---|---|
| Q9NRW3_C130 | APOBEC3C Probable DNA dC-dU-editing enzyme APOBEC-3C | 805 | 20 | 20 | 8.6 | — | 1.92 | 1.48 |

TABLE 8-continued illustrates an exemplary list of DMF sensitive cysteine-containing proteins in human T cell targets. Table 8 further shows the accession number (or the protein identifier) of the protein.

| Identifier | Protein Name | SEQ ID NO: | DMF_ 50 μM_4h | DMF_ 50 μM_2h | DMF_ 50 μM_1h | DMF_ 25 μM_4h | DMF_ 10 μM_4h | DMF_ 50 μM_4h |
|---|---|---|---|---|---|---|---|---|
| Q9NWZ3_C13 | IRAK4 Interleukin-1 receptor-associated kinase 4 | 806 | 20 | — | 8.3 | — | — | 1.48 |
| Q9Y2W6_C109 | TDRKH Tudor and KH domain-containing protein | 807 | 20 | 20 | 4 | — | 2.34 | 1.36 |
| Q6IA69_C428 | NADSYN1 Glutamine-dependent NAD(+) synthetase | 808 | 20 | 2.31 | 1.81 | — | 1.43 | 1.33 |
| O14920_C464 | IKBKB Inhibitor of nuclear factor kappa-B kinase subunit | 809 | 20 | 10.12 | 3.96 | — | 2.59 | — |
| P00813_C75 | ADA Adenosine deaminase | 810 | 20 | 5.08 | 2.51 | — | 2.29 | — |
| Q9Y277_C65 | VDAC3 Voltage-dependent anion-selective channel protein | 811 | 15.94 | 7.53 | 3.35 | 5.64 | 1.73 | 1.39 |
| P49588_C773 | AARS Alanine--tRNA ligase, cytoplasmic | 812 | 12.75 | 10.16 | 9.34 | — | 2.84 | 1.24 |
| O14933_C98 | UBE2L6 Ubiquitin/ISG15-conjugating enzyme E2 L6 | 813 | 12.55 | 2.92 | 2.44 | — | 1.49 | 1.7 |
| O95336_C32 | PGLS 6-phosphogluconolactonase | 814 | 11.51 | 9.49 | 3.42 | 5.32 | 1.9 | 1.26 |
| A6NDG6_C297 | PGP Phosphoglycolate phosphatase | 815 | 10.77 | 4.21 | 3.06 | — | — | 1.52 |
| Q7Z6Z7_C3372 | HUWE1 E3 ubiquitin-protein ligase HUWE1 | 816 | 10.48 | 4.43 | 2.28 | — | 1.58 | 1.2 |
| Q16548_C55 | BCL2A1 Bcl-2-related protein A1 | 817 | 7.18 | — | — | — | — | 0.97 |
| P11216_C326 | PYGB Glycogen phosphorylase, brain form | 818 | 6.76 | 3.73 | 2.47 | 3.53 | 1.65 | 1.29 |
| O95081_C39 | AGFG2 Arf-GAP domain and FG repeat-containing protein 2 | 819 | 6.39 | 3.85 | — | — | 1.42 | 1.24 |
| Q7Z2W4_C645 | ZC3HAV1 Zinc finger CCCH-type antiviral protein 1 | 820 | 6.28 | 3.13 | 2.36 | 2.52 | 1.46 | 1.3 |
| O00170_C122 | AIP AH receptor-interacting protein | 821 | 6.14 | 3.05 | — | — | — | 1.24 |
| Q96Q11_C373 | TRNT1 CCA tRNA nucleotidyltransferase 1, mitochondrial | 822 | 5.83 | 2.66 | 1.97 | — | — | 1.29 |
| Q8TB24_C942 | RIN3 Ras and Rab interactor 3 | 823 | 5.7 | 3 | — | — | — | 1.23 |
| Q9Y4W2_C456 | LAS1L Ribosomal biogenesis protein LAS1L | 824 | 5.61 | 3.42 | 1.8 | — | 1.29 | 1.14 |
| Q02556_C306 | IRF8 Interferon regulatory factor 8 | 825 | 5.32 | — | 1.66 | — | 1.9 | — |
| Q96GW9_C425 | MARS2 Methionine--tRNA ligase, mitochondrial .A | 826 | 5.3 | 4.16 | 2.23 | 2.86 | 1.84 | 1.3 |
| Q15306_C194 | IRF4 Interferon regulatory factor 4 | 827 | 5.25 | 3.13 | 1.32 | 1.78 | 1.69 | 1.33 |
| Q15005_C17 | SPCS2 Signal peptidase complex subunit 2 | 828 | 5.09 | 3.86 | 2.25 | 2.41 | 1.42 | 1.32 |
| P54136_C32 | RARS Arginine--tRNA ligase, cytoplasmic | 829 | 5.02 | 3.58 | 2.58 | 4.03 | 0.62 | 1.78 |
| Q960W5_C194 | TUBGCP3 Gamma-tubulin complex component 3 | 830 | 4.94 | 2.44 | — | — | — | — |
| P46109_C249 | CRKL Crk-like protein | 831 | 4.86 | 3.21 | 2.21 | — | 1.38 | 1.27 |
| Q8N0Z8_C292 | PUSL1 tRNA pseudouridine synthase-like 1 | 832 | 4.68 | — | — | — | — | 1.36 |
| Q5T4S7_C2554 | UBR4 E3 ubiquitin-protein ligase UBR4 | 833 | 4.63 | 2.1 | 1.6 | — | 1.52 | 1.2 |
| Q9UL40_C68 | ZNF346 Zinc finger protein 346 | 834 | 4.6 | 3.91 | 2.5 | 1.98 | 1.26 |
| Q13045_C46 | FLU Protein flightless-1 homolog | 835 | 4.5 | 3.57 | 2.05 | — | 1.55 | 1.27 |
| Q86YS7_C993 | KIAA0528 Uncharacterized protein KIAA0528 | 836 | 4.38 | — | — | — | 1.4 | 1.4 |
| Q9Y6C9_C296 | MTCH2 Mitochondrial carrier homolog 2 | 837 | 4.3 | 2.44 | 1.81 | — | 1.68 | 1.35 |
| Q7Z4W1_C244 | DCXR L-xylulose reductase | 838 | 4.24 | 2.76 | 1.29 | — | 2.3 | — |
| Q04759_C14 | PRKCQ Protein kinase C theta type | 839 | 4.21 | 2.92 | — | 3.29 | 1.62 | 1.14 |
| P18583_C92 | SON Protein SON | 840 | 4.17 | 6.31 | 2.5 | — | — | 1.31 |
| P31153_C56 | MAT2A S-adenosylmethionine synthase isoform type-2 | 841 | 4.17 | — | — | — | — | — |

TABLE 8-continued illustrates an exemplary list of DMF sensitive cysteine-containing proteins in human T cell targets. Table 8 further shows the accession number (or the protein identifier) of the protein.

| Identifier | Protein Name | SEQ ID NO: | DMF_ 50 μM_4h | DMF_ 50 μM_2h | DMF_ 50 μM_1h | DMF_ 25 μM_4h | DMF_ 10 μM_4h | DMF_ 50 μM_4h |
|---|---|---|---|---|---|---|---|---|
| Q16548_C19 | BCL2A1 Bcl-2-related protein A1 | 842 | 4.16 | 2.09 | — | 2.19 | 1,15 | 1.28 |
| Q14005_C1004 | IL16 Pro-interleukin-16 | 843 | 4.13 | 3.32 | 1.95 | — | 1.37 | 1.31 |
| P31153_C104 | MAT2A S-adenosylmethionine synthase isoform type-2 | 844 | 4.11 | — | — | — | 1.5 | 1.31 |
| Q9Y277_C36 | VDAC3 Voltage-dependent anion-selective channel protein | 845 | 4.11 | 3.98 | 3.21 | — | — | 1.18 |
| Q8WXH0_C553 | SYNE2 Nesprin-2 | 846 | 4.05 | 3.29 | — | — | 1.61 | — |
| Q96115_C22 | SCLY Selenocysteine lyase | 847 | 4.04 | 2.16 | 1.9 | 2.16 | 1.31 | 1.27 |
| P29590_C479 | PML Protein PML | 848 | — | 4.57 | — | 2.17 | 2.1 | 1.27 |
| Q8IYQ7_C324 | THNSL1 Threonine synthase-like 1 | 849 | — | 19.36 | 15.93 | — | — | 1.4 |
| Q93009_C315 | USP7 Ubiquitin carboxyl-terminal hydrolase 7 | 850 | — | 14.06 | 5.33 | — | 1.9 | 1.4 |
| P21580_C54 | TNFAIP3 Tumor necrosis factor alpha-induced protein 3 | 851 | — | 5.34 | — | — | 1.58 | — |
| O14976_C87 | GAK Cyclin-G-associated kinase | 852 | — | 4.79 | — | — | 1.36 | — |
| Q96FV9_C49 | THOC1 THO complex subunit 1 | 853 | — | 5.7 | 3.93 | — | — | 0.97 |
| P78527_C4045 | PRKDC DNA-dependent protein kinase catalytic subunit | 854 | — | 10.53 | 4.14 | — | — | 1.23 |
| Q9NRG0_C55 | CHRAC1 Chromatin accessibility complex protein 1 | 855 | — | 11.72 | 12.59 | — | 5.07 | 1.27 |
| Q8N2G8_C502 | GHDC GH3 domain-containing protein | 856 | — | 20 | 4.23 | — | — | — |

TABLE 9 illustrates the full protein sequence of exemplary cysteine-containing proteins described herein. The cysteine residue of interest is denoted with (*).

| Protein Identifier (Accession No.) | Protein Name | Cysteine Residue Number | Sequence | SEQ ID NO: |
|---|---|---|---|---|
| O75874 | Isocitrate dehydrogenase 1 (IDH1) | C269 | MSKKISGGSV VEMQGDEMTR IIWELIKEKL IFPYVELDLH SYDLGIENRD ATNDQVTKDA AEAIKKHNVG VKCATITPDE KRVEEFKLKQ MWKSPNGTIR NILGGTVFRE AIICKNIPRL VSGWVKPIII GRHAYGDQYR ATDFVVPGPG KVEITYTPSD GTQKVTYLVH NFEEGGGVAM GMYNQDKSIE DFAHSSFQMA LSKGWPLYLS TKNTILKKYD GRFKDIFQEI YDKQYKSQFE AQKIWYEHRL IDDMVAQAMK SEGGFIWAC*K NYDGDVQSDS VAQGYGSLGM MTSVLVCPDG KTVEAEAAHG TVTRHYRMYQ KGQETSTNPI ASIFAWTRGL AHRAKLDNNK ELAFFANALE EVSIETIEAG FMTKDLAACI KGLPNVQRSD YLNTFEFMDK LGENLKIKLA QAKL | 1 |
| P48735 | Isocitrate dehydrogenase 2 (IDH2) | C308 | MAGYLRVVRS LCRASGSRPA WAPAALTAPT SQEQPRRHYA DKRIKVAKPV VEMDGDEMTR IIWQFIKEKL ILPHVDIQLK YFDLGLPNRD QTDDQVTIDS ALATQKYSVA VKCATITPDE ARVEEFKLKK MWKSPNGTIR NILGGTVFRE PIICKNIPRL VPGWTKPITI GRHAGDQYK ATDFVADRAG TFKMVFTPKD GSGVKEWEVY NFPAGGVGMG MYNTDESISG FAHSCFQYAI QKKWPLYMST KNTILKAYDG RFKDIFQEIF DKHYKTDFDK NKIWYEHRLI DDMVAQVLKS SGGFVWAC*KN YDGDVQSDIL AQGFGSLGLM TSVLVCPDGK TIEAEAAHGT VTRHYREHQK | 2 |

TABLE 9-continued illustrates the full protein sequence of exemplary cysteine-containing proteins described herein. The cysteine residue of interest is denoted with (*).

| Protein Identifier (Accession No.) | Protein Name | Cysteine Residue Number | Sequence | SEQ ID NO: |
|---|---|---|---|---|
| | | | GRPTSTNPIA SIFAWTRGLE HRGKLDGNQD LIRFAQMLEK VCVETVESGA MTKDLAGCIH GLSNVKLNEH FLNTTDFLDT IKSNLDRALG RQ | |
| Q14790 | CASP8 | C360 | MDFSRNLYDI GEQLDSEDLA SLKFLSLDYI PQRKQEPIKD ALMLFQRLQE KRMLEESNLS FLKELLFRIN RLDLLITYLN TRKEEMEREL QTPGRAQISA YRVMLYQISE EVSRSELRSF KFLLQEEISK CKLDDDMNLL DIFIEMEKRV ILGEGKLDIL KRVCAQINKS LLKIINDYEE FSKERSSSLE GSPDEFSNGE ELCGVMTISD SPREQDSESQ TLDKVYQMKS KPRGYCLIIN NHNFAKAREK VPKLHSIRDR NGTHLDAGAL TTTFEELHFE IKPHDDCTVE QIYEILKIYQ LMDHSNMDCF ICCILSHGDK GIIYGTDGQE APIYELTSQF TGLKCPSLAG KPKVFFIQAC* QGDNYQKGIP VETDSEEQPY LEMDLSSPQT RYIPDEADFL LGMATVNNCV SYRNPAEGTW YIQSLCQSLR ERCPRGDDIL TILTEVNYEV SNKDDKKNMG KQMPQPTFTL RKKLVFPSD | 3 |
| Q92851 | CASP10 | C401 | MKSQGQHWYS SSDKNCKVSF REKLLIIDSN LGVQDVENLK FLCIGLVPNK KLEKSSSASD VFEHLLAEDL LSEEDPFFLA ELLYIIRQKK LLQHLNCTKE EVERLLPTRQ RVSLFRNLLY ELSEGIDSEN LKDMIFLLKD SLPKTEMTSL SFLAFLEKQG KIDEDNLTCL EDLCKTVVPK LLRNIEKYKR EKAIQIVTPP VDKEAESYQG EEELVSQTDV KTFLEALPQE SWQNKHAGSN GNRATNGAPS LVSRGMQGAS ANTLNSETST KRAAVYRMNR NHRGLCVIVN NHSFTSLKDR QGTHKDAEIL SHVFQWLGFT VHIHNNVTKV EMEMVLQKQK CNPAHADGDC FVFCILTHGR FGAVYSSDEA LIPIREIMSH FTALQCPRLA EKPKLFFIQA C*QGEEIQPSV SIEADALNPE QAPTSLQDSI PAEADFLLGL ATVPGYVSFR HVEEGSWYIQ SLCNHLKKLV PRMLKFLEKT MEIRGRKRTV WGAKQISATS LPTAISAQTP RPPMRRWSSV S | 4 |
| Q99873 | PRMT1 | C109 | MENFVATLAN GMSLQPPLEE VSCGQAESSE KPNAEDMTSK DYYFDSYAHF GIHEEMLKDE VRTLTYRNSM FHNRHLFKDK VVLDVGSGTG ILCMFAAKAG ARKVIGIEC*S SISDYAVKIV KANKLDHVVT IIKGKVEEVE LPVEKVDIII SEWMGYCLFY ESMLNTVLYA RDKWLAPDGL IFPDRATLYV TAIEDRQYKD YKIHWWENVY GFDMSCIKDV AIKEPLVDVV DPKQLVTNAC LIKEVDIYTV KVEDLTFTSP FCLQVKRNDY VHALVAYFNI EFTRCHKRTG FSTSPESPYT HWKQTVFYME DYLTVKTGEE IFGTIGMRPN AKNNRDLDFT IDLDFKGQLC ELSCSTDYRM R | 5 |
| Q9NYL2 | MAP3 kinase MLTK (or ZAK) | C22 | MSSLGASFVQ IKFDDLQFFE NC*GGGSFGSV YRAKWISQDK EVAVKKLLKI EKEAEILSVL SHRNIIQFYG VILEPPNYGI VTEYASLGSL YDYINSNRSE EMDMDHIMTW ATDVAKGMHY LHMEAPVKVI HRDLKSRNVV IAADGVLKIC DFGASRPHNH TTHMSLVGTF PWMAPEVIQS LPVSETCDTY SYGVVLWEML TREVPFKGLE GLQVAWLVVE KNERLTIPSS CPRSFAELLH QCWEADAKKR PSFKQIISIL ESMSNDTSLP DKCNSFLHNK AEWRCEIEAT LERLKKLERD LSFKEQELKE RERRLKMWEQ KLTEQSNTPL LPSFEIGAWT EDDVYCWVQQ LVRKGDSSAE MSVYASLFKE NNITGKRLLL LEEEDLKDMG IVSKGHIIHF KSAIEKLTHD YINLFHFPPL IKDSGGEPEE NEEKIVNLEL VFGFHLKPGT | 6 |

TABLE 9-continued illustrates the full protein sequence of exemplary cysteine-containing proteins described herein. The cysteine residue of interest is denoted with (*).

| Protein Identifier (Accession No.) | Protein Name | Cysteine Residue Number | Sequence | SEQ ID NO: |
|---|---|---|---|---|
| | | | GPQDCKWKMY MEMDGDEIAI TYIKDVTFNT NLPDAEILKM TKPPFVMEKW IVGIAKSQTV ECTVTYESDV RTPKSTKHVH SIQWSRTKPQ DEVKAVQLAI QTLFTNSDGN PGSRSDSSAD CQWLDTLRMR QIASNTSLQR SQSNPILGSP FFSHFDGQDS YAAAVRRPQV PIKYQQITPV NQSRSSSPTQ YGLTKNFSSL HLNSRDSGFS SGNTDTSSER GRYSDRSRNK YGRGSISLNS SPRGRYSGKS QHSTPSRGRY PGKFYRVSQS ALNPHQSPDF KRSPRDLHQP NTIPGMPLHP ETDSRASEED SKVSEGGWTK VEYRKKPHRP SPAKTNKERA RGDHRGWRNF | |
| P12268 | IMPDH2 | C140, C331 | MADYLISGGT SYVPDDGLTA QQLFNCGDGL TYNDFLILPG YIDFTADQVD LTSALTKKIT LKTPLVSSPM DVTEAGMAI AMALTGGIGF IHHNCTPEFQ ANEVRKVKKY EQGFITDPVV LSPKDRVRDV FEAKARHGFC* GIPITDTGRM GSRLVGIISS RDIDFLKEEE HDCFLEEIMT KREDLVVAPA GITLKEANEI LQRSKKGKLP IVNEDDELVA IIARTDLKKN RDYPLASKDA KKQLLCGAAI GTHEDDKYRL DLLAQAGVDV VVLDSSQGNS IFQINMIKYI KDKYPNLQVI GGNVVTAAQA KNLIDAGVDA LRVGMGSGSI C*ITQEVLACG RPQATAVYKV SEYARRFGVP VIADGGIQNV GHIAKALALG ASTVMMGSLL AATTEAPGEY FFSDGIRLKK YRGMGSLDAM DKHLSSQNRY FSEADKIKVA QGVSGAVQDK GSIHKFVPYL IAGIQHSCQD IGAKSLTQVR AMMYSGELKF EKRTSSAQVE GGVHSLHSYE KRLF | 7 |
| Q9NQ88 | TIGAR | C114, C161 | MARFALTVVR HGETRFNKEK IIQGQGVDEP LSETGFKQAA AAGIFLNNVK FTHAFSSDLM RTKQTMHGIL ERSKFCKDMT VKYDSRLRER KYGVVEGKAL SELRAMAKAA REEC*PVFTPP GGETLDQVKM RGIDFFEFLC QLILKEADQK EQFSQGSPSN C*LETSLAEIF PLGKNHSSKV NSDSGIPGLA ASVLVVSHGA YMRSLFDYFL TDLKCSLPAT LSRSELMSVT PNTGMSLFII NFEEGREVKP TVQCICMNLQ DHLNGLTETR | 8 |
| Q04759 | PKCθ | C14, C17 | MSPFLRIGLS NFDC*GSC*QSC QGEAVNPYCA VLVKEYVESE NGQMYIQKKP TMYPPWDSTF DAHINKGRVM QIIVKGKNVD LISETTVELY SLAERCRKNN GKTEIWLELK PQGRMLMNAR YFLEMSDTKD MNEFETEGFF ALHQRRGAIK QAKVHHVKCH EFTATFFPQP TFCSVCHEFV WGLNKQGYQC RQCNAAIHKK CIDKVIAKCT GSAINSRETM FHKERFKIDM PHRFKVYNYK SPTFCEHCGT LLWGLARQGL KCDACGMNVH HRCQTKVANL CGINQKLMAE ALAMIESTQQ ARCLRDTEQI FREGPVEIGL PCSIKNEARP PCLPTPGKRE PQGISWESPL DEVDKMCHLP EPELNKERPS LQIKLKIEDF ILHKMLGKGS FGKVFLAEFK KTNQFFAIKA LKKDVVLMDD DVECTMVEKR VLSLAWEHPF LTHMFCTFQT KENLFFVMEY LNGGDLMYHI QSCHKFDLSR ATFYAAEIIL GLQFLHSKGI VYRDLKLDNI LLDKDGHIKI ADFGMCKENM LGDAKTNTFC GTPDYIAPEI LLGQKYNHSV DWWSFGVLLY EMLIGQSPFH GQDEEELFHS IRMDNPFYPR WLEKEAKDLL VKLFVREPEK RLGVRGDIRQ HPLFREINWE ELERKEIDPP FRPKVKSPFD CSNFDKEFLN EKPRLSFADR ALINSMDQNM FRNFSFMNPG MERLIS | 9 |

Table 10A-Table 10E illustrate a list of cysteine containing proteins and potential cysteine site of conjugation separated by protein class. Table 10A illustrates cysteine containing enzymes and potential cysteine conjugation site. Table 10B shows a list of cysteine containing transcription factors and regulators. Table 10C shows an exemplary list of cysteine containing channels, transcporters and receptors. Table 10D illustrates an exemplary cysteine containing adapter, scaffolding, and modulator protein. Table 10E provides an exemplary list of uncategorized cysteine containing proteins.

TABLE 10A

| Identifier | Protein Name | Cysteine Location | Protein Class |
|---|---|---|---|
| O14920 | IKBKB Inhibitor of nuclear factor kappa-B kinase subunit | C464 | Enzyme |
| O14933 | UBE2L6 Ubiquitin/ISG15-conjugating enzyme E2 L6 PCTK | C98 | Enzyme |
| O94953 | KDM4B Lysine-specific demethylase 4B | C694 | Enzyme |
| P00813 | ADA Adenosine deaminase | C75 | Enzyme |
| P09211 | GSTP1 Glutathione S-transferase P | C48 | Enzyme |
| P15374 | UCHL3 Ubiquitin carboxyl-terminal hydrolase isozyme L3 | C95 | Enzyme |
| P16455 | MGMT Methylated-DNA--protein-cysteine methyltransferase | C145; C150 | Enzyme |
| P17812 | CTP synthase 1 | C491 | Enzyme |
| P19447 | ERCC3 TFIIH basal transcription factor complex helicase | C342 | Enzyme |
| P21580 | TNFAIP3 Tumor necrosis factor alpha-induced protein 3 | C54 | Enzyme |
| P24752 | ACAT1 Acetyl-CoA acetyltransferase, mitochondrial | C119; C126; C196; C413 | Enzyme |
| P40261 | Nicotinamide N-methyltransferase | C165 | Enzyme |
| P41226 | UBA7 Ubiquitin-like modifier-activating enzyme 7 | C599 | Enzyme |
| P42575 | CASP2 Caspase-2 | C370 | Enzyme |
| P43403 | ZAP70 Tyrosine-protein kinase ZAP-70 | C117 | Enzyme |
| P48735 | IDH2 Isocitrate dehydrogenase | C308 | Enzyme |
| P51617 | IRAK1 Interleukin-1 receptor-associated kinase 1 | C608 | Enzyme |
| P61081 | NEDD8-conjugating enzyme Ubc12 | C47 | Enzyme |
| P61088 | Ubiquitin-conjugating enzyme E2 N | C87 | Enzyme |
| P68036 | UBE2L3 Ubiquitin-conjugating enzyme E2 L3 | C86 | Enzyme |
| Q00535 | CDK5 Cyclin-dependent kinase 5 | C157 | Enzyme |
| Q04759 | PRKCQ Protein kinase C theta type | C14; C17 | Enzyme |
| Q06124 | Tyrosine-protein phosphatase non-receptor type 11 | C573 | Enzyme |
| Q09472 | EP300 Histone acetyltransferase p300 | C1738 | Enzyme |
| Q14790 | CASP8 Caspase-8 | C360 | Enzyme |
| Q15084 | PDIA6 Protein disulfide-isomerase A6 | C55; C58; C190; C193 | Enzyme |
| Q15910 | EZH2 Histone-lysine N-methyltransferase EZH2 | C503 | Enzyme |
| Q16763 | UBE2S Ubiquitin-conjugating enzyme E2 S | C118 | Enzyme |
| Q16822 | PCK2 Phosphoenolpyruvate carboxykinase | C306 | Enzyme |
| Q16875 | 6-phosphofructo-2-kinase/fructose-2,6-bisphosphatase 3 | C155 | Enzyme |
| Q16877 | PFKFB4 6-phosphofructo-2-kinase/fructose-2,6-bisphosphata | C159 | Enzyme |
| Q6L8Q7 | PDE12 2,5-phosphodiesterase 12 | C108 | Enzyme |
| Q70CQ2 | USP34 Ubiquitin carboxyl-terminal hydrolase 34 | C741; C1090 | Enzyme |
| Q86UV5 | USP48 Ubiquitin carboxyl-terminal hydrolase 48 | C39 | Enzyme |
| Q92851 | Caspase-10 | C401 | Enzyme |
| Q93009 | USP7 Ubiquitin carboxyl-terminal hydrolase 7 | C223; C315 | Enzyme |
| Q96FA3 | PELI1 E3 ubiquitin-protein ligase pellino homolog 1 | C282 | Enzyme |
| Q96JH7 | VCPIP1 Deubiquitinating protein VCIP135 | C219 | Enzyme |
| Q96RU2 | USP28 Ubiquitin carboxyl-terminal hydrolase 28 | C171; C733 | Enzyme |
| Q99873 | PRMT1 Protein arginine N-methyltransferase 1 | C109 | Enzyme |
| Q9C0C9 | UBE2O Ubiquitin-conjugating enzyme E2 O | C375 | Enzyme |
| Q9NRW4 | Dual specificity protein phosphatase 22 | C124 | Enzyme |
| Q9NWZ3 | IRAK4 Interleukin-1 receptor-associated kinase 4 | C13 | Enzyme |
| Q9NYL2 | MLTK Mitogen-activated protein kinase kinase kinase MLT | C22 | Enzyme |
| Q9UPT9 | USP22 Ubiquitin carboxyl-terminal hydrolase 22 | C44; C171 | Enzyme |
| Q9Y3Z3 | SAMHD1 SAM domain and HD domain-containing protein 1 | C522 | Enzyme |
| Q9Y4C1 | KDM3A Lysine-specific demethylase 3A | C251 | Enzyme |
| Q9Y5T5 | USP16 Ubiquitin carboxyl-terminal hydrolase 16 | C205 | Enzyme |

TABLE 10B

| Identifier | Protein Name | Cysteine Location | Protein Class |
|---|---|---|---|
| O75362 | ZNF217 Zinc finger protein 217 | C286 | Transcription factors and regulators |
| P04150 | NR3C1 Glucocorticoid receptor | C302; C622 | Transcription factors and regulators |
| P09086 | POU2F2 POU domain, class 2, transcription factor 2 | C346 | Transcription factors and regulators |
| P40763 | STAT3 Signal transducer and activator of transcription 3 | C259 | Transcription factors and regulators |
| P48200 | IREB2 Iron-responsive element-binding protein 2 | C137 | Transcription factors and regulators |
| Q01201 | RELB Transcription factor RelB | C109 | Transcription factors and regulators |
| Q02556 | IRF8 Interferon regulatory factor 8 | C306 | Transcription factors and regulators |
| Q15306 | IRF4 Interferon regulatory factor 4 | C194 | Transcription factors and regulators |
| Q7Z2W4 | ZC3HAV1 Zinc finger CCCH-type antiviral protein 1 | C645 | Transcription factors and regulators |
| Q8TAQ2 | SMARCC2 SWI/SNF complex subunit SMARCC2 | C145 | Transcription factors and regulators |

TABLE 10C

| Identifier | Protein Name | Cysteine Location | Protein Class |
|---|---|---|---|
| P63244 | GNB2L1 Guanine nucleotide-binding protein subunit beta-2-like 1 | C182 | Channels, Transporters, Receptors |
| Q16186 | Proteasomal ubiquitin receptor ADRM1 | C88 | Channels, Transporters, Receptors |
| Q9HB90 | RRAGC Ras-related GTP-binding protein C | C358; C377 | Channels, transporters, and receptors |

TABLE 10D

| Identifier | Protein Name | Cysteine Location | Protein Class |
|---|---|---|---|
| P14598 | NCF1 Neutrophil cytosol factor 1 | C378 | Adapter, scaffolding, modulator proteins |

TABLE 10E

| Identifier | Protein Name | Cysteine Location | Protein Class |
|---|---|---|---|
| O00170 | AIP AH receptor-interacting protein | C122 | Uncategorized |
| O00541 | PES1 Pescadillo homolog | C272; C361 | Uncategorized |
| O00622 | CYR61 Protein CYR61 | C39; C70; C134 | Uncategorized |
| O14980 | XPO1 Exportin-1 | C34; C528; C1070 | Uncategorized |
| P50851 | LRBA Lipopolysaccharide-responsive and beige-like anchor protein | C1704; C2675 | Uncategorized |
| Q96GG9 | DCUN1D1 DCN1-like protein 1 | C115 | Uncategorized |

The examples and embodiments described herein are for illustrative purposes only and various modifications or changes suggested to persons skilled in the art are to be included within the spirit and purview of this application and scope of the appended claims.

What is claimed is:

1. A modified pro-caspase 8 (pro-CASP8) protein comprising a non-naturally occurring small molecule fragment having a covalent bond to Cys360 of the pro-CASP8 protein, wherein:

the pro-CASP8 protein comprises SEQ ID NO: 3;

the pro-CASP8 protein has a structure of Formula (I):

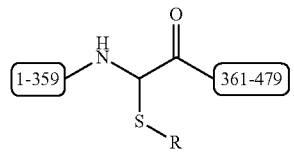

Formula (I)

wherein:

S is the sulfur atom of Cys360, and

R is

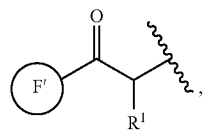

wherein $R^1$ is H; and

F' is selected from the group consisting of

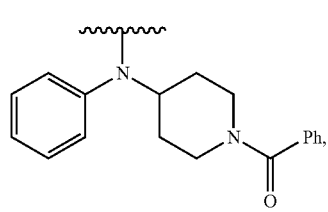

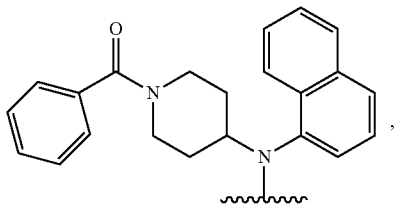

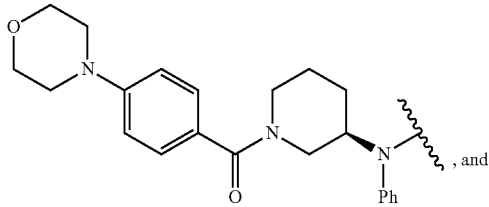

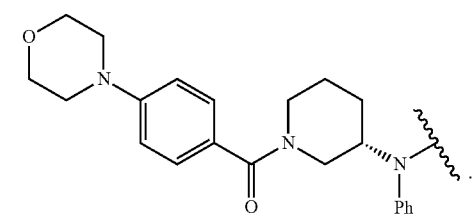

2. The modified pro-CASP8 protein of claim 1, wherein the small molecule fragment binds irreversilby to Cys360— of the pro-CASP8 protein.

3. The modified pro-CASP8 protein of claim 1, wherein the small molecule fragment binds reversibly to Cys360 of the pro-CASP8 protein.

4. The modified pro-CASP8 protein of claim 1, wherein F' is selected from the group consisting of 717
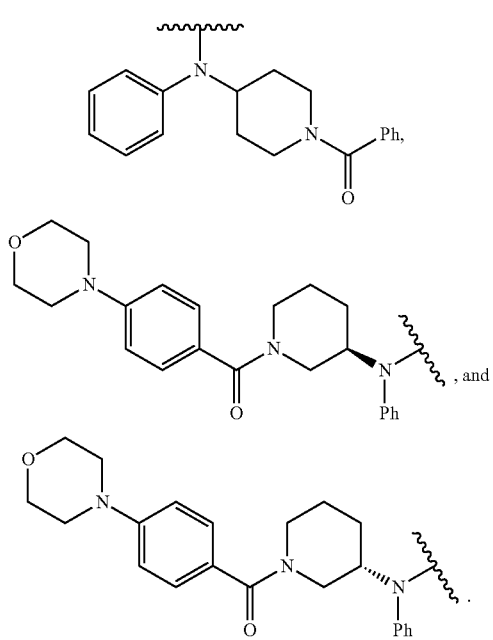, and
718
5. The modified pro-CASP8 protein of claim 1, wherein F' is selected from the group consisting of
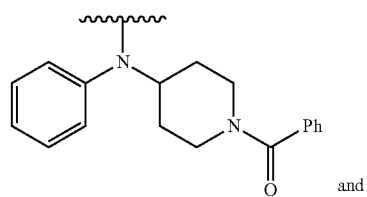 and
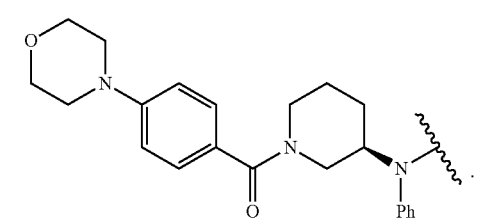.
* * * * *

UNITED STATES PATENT AND TRADEMARK OFFICE
CERTIFICATE OF CORRECTION

PATENT NO. : 10,670,605 B2
APPLICATION NO. : 15/331745
DATED : June 2, 2020
INVENTOR(S) : Cravatt et al.

It is certified that error appears in the above-identified patent and that said Letters Patent is hereby corrected as shown below:

In the Specification

Column 1, at Line 12, please replace the paragraph with the following replacement paragraph:
-- STATEMENT OF GOVERNMENT LICENSE RIGHTS
This invention was made with government support under grant numbers CA087660, GM090294, GM108208, and GM069832 awarded by the National Institutes of Health. The government has certain rights in the invention. --

Signed and Sealed this
First Day of December, 2020

Andrei Iancu
*Director of the United States Patent and Trademark Office*

SEQUENCE LISTING

<160> NUMBER OF SEQ ID NOS: 868

<210> SEQ ID NO 1
<211> LENGTH: 414
<212> TYPE: PRT
<213> ORGANISM: Homo sapiens
<220> FEATURE:
<223> OTHER INFORMATION: Isocitrate dehydrogenase 1 (IDH1);
      O75874 C269
<220> FEATURE:
<221> NAME/KEY: MOD_RES
<222> LOCATION: (269)..(269)
<223> OTHER INFORMATION: Site of chemical conjugation

<400> SEQUENCE: 1

```
Met Ser Lys Lys Ile Ser Gly Gly Ser Val Val Glu Met Gln Gly Asp
1               5                   10                  15

Glu Met Thr Arg Ile Ile Trp Glu Leu Ile Lys Glu Lys Leu Ile Phe
            20                  25                  30

Pro Tyr Val Glu Leu Asp Leu His Ser Tyr Asp Leu Gly Ile Glu Asn
        35                  40                  45

Arg Asp Ala Thr Asn Asp Gln Val Thr Lys Asp Ala Ala Glu Ala Ile
    50                  55                  60

Lys Lys His Asn Val Gly Val Lys Cys Ala Thr Ile Thr Pro Asp Glu
65                  70                  75                  80

Lys Arg Val Glu Glu Phe Lys Leu Lys Gln Met Trp Lys Ser Pro Asn
                85                  90                  95

Gly Thr Ile Arg Asn Ile Leu Gly Gly Thr Val Phe Arg Glu Ala Ile
            100                 105                 110

Ile Cys Lys Asn Ile Pro Arg Leu Val Ser Gly Trp Val Lys Pro Ile
        115                 120                 125

Ile Ile Gly Arg His Ala Tyr Gly Asp Gln Tyr Arg Ala Thr Asp Phe
    130                 135                 140

Val Val Pro Gly Pro Gly Lys Val Glu Ile Thr Tyr Thr Pro Ser Asp
145                 150                 155                 160

Gly Thr Gln Lys Val Thr Tyr Leu Val His Asn Phe Glu Glu Gly Gly
                165                 170                 175

Gly Val Ala Met Gly Met Tyr Asn Gln Asp Lys Ser Ile Glu Asp Phe
            180                 185                 190

Ala His Ser Ser Phe Gln Met Ala Leu Ser Lys Gly Trp Pro Leu Tyr
        195                 200                 205

Leu Ser Thr Lys Asn Thr Ile Leu Lys Lys Tyr Asp Gly Arg Phe Lys
    210                 215                 220

Asp Ile Phe Gln Glu Ile Tyr Asp Lys Gln Tyr Lys Ser Gln Phe Glu
225                 230                 235                 240

Ala Gln Lys Ile Trp Tyr Glu His Arg Leu Ile Asp Asp Met Val Ala
                245                 250                 255

Gln Ala Met Lys Ser Glu Gly Gly Phe Ile Trp Ala Cys Lys Asn Tyr
            260                 265                 270

Asp Gly Asp Val Gln Ser Asp Ser Val Ala Gln Gly Tyr Gly Ser Leu
        275                 280                 285

Gly Met Met Thr Ser Val Leu Val Cys Pro Asp Gly Lys Thr Val Glu
```

```
            290                 295                 300
Ala Glu Ala Ala His Gly Thr Val Thr Arg His Tyr Arg Met Tyr Gln
305                 310                 315                 320

Lys Gly Gln Glu Thr Ser Thr Asn Pro Ile Ala Ser Ile Phe Ala Trp
                325                 330                 335

Thr Arg Gly Leu Ala His Arg Ala Lys Leu Asp Asn Asn Lys Glu Leu
                340                 345                 350

Ala Phe Phe Ala Asn Ala Leu Glu Glu Val Ser Ile Glu Thr Ile Glu
                355                 360                 365

Ala Gly Phe Met Thr Lys Asp Leu Ala Ala Cys Ile Lys Gly Leu Pro
                370                 375                 380

Asn Val Gln Arg Ser Asp Tyr Leu Asn Thr Phe Glu Phe Met Asp Lys
385                 390                 395                 400

Leu Gly Glu Asn Leu Lys Ile Lys Leu Ala Gln Ala Lys Leu
                405                 410

<210> SEQ ID NO 2
<211> LENGTH: 452
<212> TYPE: PRT
<213> ORGANISM: Homo sapiens
<220> FEATURE:
<223> OTHER INFORMATION: Isocitrate dehydrogenase 2 (IDH2);
      P48735 C308
<220> FEATURE:
<221> NAME/KEY: MOD_RES
<222> LOCATION: (308)..(308)
<223> OTHER INFORMATION: Site of chemical conjugation

<400> SEQUENCE: 2

Met Ala Gly Tyr Leu Arg Val Val Arg Ser Leu Cys Arg Ala Ser Gly
1               5                   10                  15

Ser Arg Pro Ala Trp Ala Pro Ala Ala Leu Thr Ala Pro Thr Ser Gln
                20                  25                  30

Glu Gln Pro Arg Arg His Tyr Ala Asp Lys Arg Ile Lys Val Ala Lys
            35                  40                  45

Pro Val Val Glu Met Asp Gly Asp Glu Met Thr Arg Ile Ile Trp Gln
        50                  55                  60

Phe Ile Lys Glu Lys Leu Ile Leu Pro His Val Asp Ile Gln Leu Lys
65                  70                  75                  80

Tyr Phe Asp Leu Gly Leu Pro Asn Arg Asp Gln Thr Asp Asp Gln Val
                85                  90                  95

Thr Ile Asp Ser Ala Leu Ala Thr Gln Lys Tyr Ser Val Ala Val Lys
            100                 105                 110

Cys Ala Thr Ile Thr Pro Asp Glu Ala Arg Val Glu Glu Phe Lys Leu
        115                 120                 125

Lys Lys Met Trp Lys Ser Pro Asn Gly Thr Ile Arg Asn Ile Leu Gly
130                 135                 140

Gly Thr Val Phe Arg Glu Pro Ile Ile Cys Lys Asn Ile Pro Arg Leu
145                 150                 155                 160

Val Pro Gly Trp Thr Lys Pro Ile Thr Ile Gly Arg His Ala His Gly
                165                 170                 175

Asp Gln Tyr Lys Ala Thr Asp Phe Val Ala Asp Arg Ala Gly Thr Phe
            180                 185                 190

Lys Met Val Phe Thr Pro Lys Asp Gly Ser Gly Val Lys Glu Trp Glu
        195                 200                 205

Val Tyr Asn Phe Pro Ala Gly Gly Val Gly Met Gly Met Tyr Asn Thr
210                 215                 220
```

```
Asp Glu Ser Ile Ser Gly Phe Ala His Ser Cys Phe Gln Tyr Ala Ile
225                 230                 235                 240

Gln Lys Lys Trp Pro Leu Tyr Met Ser Thr Lys Asn Thr Ile Leu Lys
            245                 250                 255

Ala Tyr Asp Gly Arg Phe Lys Asp Ile Phe Gln Glu Ile Phe Asp Lys
        260                 265                 270

His Tyr Lys Thr Asp Phe Asp Lys Asn Lys Ile Trp Tyr Glu His Arg
    275                 280                 285

Leu Ile Asp Asp Met Val Ala Gln Val Leu Lys Ser Ser Gly Gly Phe
290                 295                 300

Val Trp Ala Cys Lys Asn Tyr Asp Gly Asp Val Gln Ser Asp Ile Leu
305                 310                 315                 320

Ala Gln Gly Phe Gly Ser Leu Gly Leu Met Thr Ser Val Leu Val Cys
            325                 330                 335

Pro Asp Gly Lys Thr Ile Glu Ala Glu Ala Ala His Gly Thr Val Thr
        340                 345                 350

Arg His Tyr Arg Glu His Gln Lys Gly Arg Pro Thr Ser Thr Asn Pro
    355                 360                 365

Ile Ala Ser Ile Phe Ala Trp Thr Arg Gly Leu Glu His Arg Gly Lys
370                 375                 380

Leu Asp Gly Asn Gln Asp Leu Ile Arg Phe Ala Gln Met Leu Glu Lys
385                 390                 395                 400

Val Cys Val Glu Thr Val Glu Ser Gly Ala Met Thr Lys Asp Leu Ala
            405                 410                 415

Gly Cys Ile His Gly Leu Ser Asn Val Lys Leu Asn Glu His Phe Leu
        420                 425                 430

Asn Thr Thr Asp Phe Leu Asp Thr Ile Lys Ser Asn Leu Asp Arg Ala
    435                 440                 445

Leu Gly Arg Gln
    450

<210> SEQ ID NO 3
<211> LENGTH: 479
<212> TYPE: PRT
<213> ORGANISM: Homo sapiens
<220> FEATURE:
<223> OTHER INFORMATION: CASP8;
      Q14790 C360
<220> FEATURE:
<221> NAME/KEY: MOD_RES
<222> LOCATION: (360)..(360)
<223> OTHER INFORMATION: Site of chemical conjugation

<400> SEQUENCE: 3

Met Asp Phe Ser Arg Asn Leu Tyr Asp Ile Gly Glu Gln Leu Asp Ser
1               5                   10                  15

Glu Asp Leu Ala Ser Leu Lys Phe Leu Ser Leu Asp Tyr Ile Pro Gln
            20                  25                  30

Arg Lys Gln Glu Pro Ile Lys Asp Ala Leu Met Leu Phe Gln Arg Leu
        35                  40                  45

Gln Glu Lys Arg Met Leu Glu Glu Ser Asn Leu Ser Phe Leu Lys Glu
    50                  55                  60

Leu Leu Phe Arg Ile Asn Arg Leu Asp Leu Leu Ile Thr Tyr Leu Asn
65                  70                  75                  80

Thr Arg Lys Glu Glu Met Glu Arg Glu Leu Gln Thr Pro Gly Arg Ala
            85                  90                  95
```

-continued

Gln Ile Ser Ala Tyr Arg Val Met Leu Tyr Gln Ile Ser Glu Val
            100                 105                 110

Ser Arg Ser Glu Leu Arg Ser Phe Lys Phe Leu Leu Gln Glu Glu Ile
    115                 120                 125

Ser Lys Cys Lys Leu Asp Asp Met Asn Leu Leu Asp Ile Phe Ile
130                 135                 140

Glu Met Glu Lys Arg Val Ile Leu Gly Glu Gly Lys Leu Asp Ile Leu
145                 150                 155                 160

Lys Arg Val Cys Ala Gln Ile Asn Lys Ser Leu Leu Lys Ile Ile Asn
                165                 170                 175

Asp Tyr Glu Glu Phe Ser Lys Glu Arg Ser Ser Leu Glu Gly Ser
            180                 185                 190

Pro Asp Glu Phe Ser Asn Gly Glu Glu Leu Cys Gly Val Met Thr Ile
            195                 200                 205

Ser Asp Ser Pro Arg Glu Gln Asp Ser Glu Ser Gln Thr Leu Asp Lys
210                 215                 220

Val Tyr Gln Met Lys Ser Lys Pro Arg Gly Tyr Cys Leu Ile Ile Asn
225                 230                 235                 240

Asn His Asn Phe Ala Lys Ala Arg Glu Lys Val Pro Lys Leu His Ser
                245                 250                 255

Ile Arg Asp Arg Asn Gly Thr His Leu Asp Ala Gly Ala Leu Thr Thr
                260                 265                 270

Thr Phe Glu Glu Leu His Phe Glu Ile Lys Pro His Asp Asp Cys Thr
            275                 280                 285

Val Glu Gln Ile Tyr Glu Ile Leu Lys Ile Tyr Gln Leu Met Asp His
            290                 295                 300

Ser Asn Met Asp Cys Phe Ile Cys Cys Ile Leu Ser His Gly Asp Lys
305                 310                 315                 320

Gly Ile Ile Tyr Gly Thr Asp Gly Gln Glu Ala Pro Ile Tyr Glu Leu
                325                 330                 335

Thr Ser Gln Phe Thr Gly Leu Lys Cys Pro Ser Leu Ala Gly Lys Pro
            340                 345                 350

Lys Val Phe Phe Ile Gln Ala Cys Gln Gly Asp Asn Tyr Gln Lys Gly
            355                 360                 365

Ile Pro Val Glu Thr Asp Ser Glu Glu Gln Pro Tyr Leu Glu Met Asp
370                 375                 380

Leu Ser Ser Pro Gln Thr Arg Tyr Ile Pro Asp Glu Ala Asp Phe Leu
385                 390                 395                 400

Leu Gly Met Ala Thr Val Asn Asn Cys Val Ser Tyr Arg Asn Pro Ala
                405                 410                 415

Glu Gly Thr Trp Tyr Ile Gln Ser Leu Cys Gln Ser Leu Arg Glu Arg
            420                 425                 430

Cys Pro Arg Gly Asp Asp Ile Leu Thr Ile Leu Thr Glu Val Asn Tyr
            435                 440                 445

Glu Val Ser Asn Lys Asp Asp Lys Lys Asn Met Gly Lys Gln Met Pro
            450                 455                 460

Gln Pro Thr Phe Thr Leu Arg Lys Lys Leu Val Phe Pro Ser Asp
465                 470                 475

<210> SEQ ID NO 4
<211> LENGTH: 521
<212> TYPE: PRT
<213> ORGANISM: Homo sapiens
<220> FEATURE:
<223> OTHER INFORMATION: CASP10;

Q92851_C401
<220> FEATURE:
<221> NAME/KEY: MOD_RES
<222> LOCATION: (401)..(401)
<223> OTHER INFORMATION: Site of chemical conjugation

<400> SEQUENCE: 4

Met Lys Ser Gln Gly Gln His Trp Tyr Ser Ser Asp Lys Asn Cys
1               5                   10                  15

Lys Val Ser Phe Arg Glu Lys Leu Leu Ile Ile Asp Ser Asn Leu Gly
            20                  25                  30

Val Gln Asp Val Glu Asn Leu Lys Phe Leu Cys Ile Gly Leu Val Pro
        35                  40                  45

Asn Lys Lys Leu Glu Lys Ser Ser Ala Ser Asp Val Phe Glu His
50                  55                  60

Leu Leu Ala Glu Asp Leu Leu Ser Glu Glu Asp Pro Phe Phe Leu Ala
65                  70                  75                  80

Glu Leu Leu Tyr Ile Ile Arg Gln Lys Lys Leu Leu Gln His Leu Asn
                85                  90                  95

Cys Thr Lys Glu Glu Val Glu Arg Leu Leu Pro Thr Arg Gln Arg Val
            100                 105                 110

Ser Leu Phe Arg Asn Leu Leu Tyr Glu Leu Ser Glu Gly Ile Asp Ser
        115                 120                 125

Glu Asn Leu Lys Asp Met Ile Phe Leu Leu Lys Asp Ser Leu Pro Lys
130                 135                 140

Thr Glu Met Thr Ser Leu Ser Phe Leu Ala Phe Leu Glu Lys Gln Gly
145                 150                 155                 160

Lys Ile Asp Glu Asp Asn Leu Thr Cys Leu Glu Asp Leu Cys Lys Thr
            165                 170                 175

Val Val Pro Lys Leu Leu Arg Asn Ile Glu Lys Tyr Lys Arg Glu Lys
        180                 185                 190

Ala Ile Gln Ile Val Thr Pro Pro Val Asp Lys Glu Ala Glu Ser Tyr
    195                 200                 205

Gln Gly Glu Glu Glu Leu Val Ser Gln Thr Asp Val Lys Thr Phe Leu
210                 215                 220

Glu Ala Leu Pro Gln Glu Ser Trp Gln Asn Lys His Ala Gly Ser Asn
225                 230                 235                 240

Gly Asn Arg Ala Thr Asn Gly Ala Pro Ser Leu Val Ser Arg Gly Met
            245                 250                 255

Gln Gly Ala Ser Ala Asn Thr Leu Asn Ser Glu Thr Ser Thr Lys Arg
        260                 265                 270

Ala Ala Val Tyr Arg Met Asn Arg Asn His Arg Gly Leu Cys Val Ile
    275                 280                 285

Val Asn Asn His Ser Phe Thr Ser Leu Lys Asp Arg Gln Gly Thr His
290                 295                 300

Lys Asp Ala Glu Ile Leu Ser His Val Phe Gln Trp Leu Gly Phe Thr
305                 310                 315                 320

Val His Ile His Asn Asn Val Thr Lys Val Glu Met Glu Met Val Leu
            325                 330                 335

Gln Lys Gln Lys Cys Asn Pro Ala His Ala Asp Gly Asp Cys Phe Val
        340                 345                 350

Phe Cys Ile Leu Thr His Gly Arg Phe Gly Ala Val Tyr Ser Ser Asp
    355                 360                 365

Glu Ala Leu Ile Pro Ile Arg Glu Ile Met Ser His Phe Thr Ala Leu
370                 375                 380

-continued

```
Gln Cys Pro Arg Leu Ala Glu Lys Pro Lys Leu Phe Phe Ile Gln Ala
385                 390                 395                 400

Cys Gln Gly Glu Glu Ile Gln Pro Ser Val Ser Ile Glu Ala Asp Ala
                405                 410                 415

Leu Asn Pro Glu Gln Ala Pro Thr Ser Leu Gln Asp Ser Ile Pro Ala
            420                 425                 430

Glu Ala Asp Phe Leu Leu Gly Leu Ala Thr Val Pro Gly Tyr Val Ser
        435                 440                 445

Phe Arg His Val Glu Glu Gly Ser Trp Tyr Ile Gln Ser Leu Cys Asn
    450                 455                 460

His Leu Lys Lys Leu Val Pro Arg Met Leu Lys Phe Leu Glu Lys Thr
465                 470                 475                 480

Met Glu Ile Arg Gly Arg Lys Arg Thr Val Trp Gly Ala Lys Gln Ile
                485                 490                 495

Ser Ala Thr Ser Leu Pro Thr Ala Ile Ser Ala Gln Thr Pro Arg Pro
                500                 505                 510

Pro Met Arg Arg Trp Ser Ser Val Ser
            515                 520

<210> SEQ ID NO 5
<211> LENGTH: 361
<212> TYPE: PRT
<213> ORGANISM: Homo sapiens
<220> FEATURE:
<223> OTHER INFORMATION: PRMT1;
      Q99873 C109
<220> FEATURE:
<221> NAME/KEY: MOD_RES
<222> LOCATION: (109)..(109)
<223> OTHER INFORMATION: Site of chemical conjugation

<400> SEQUENCE: 5

Met Glu Asn Phe Val Ala Thr Leu Ala Asn Gly Met Ser Leu Gln Pro
1               5                   10                  15

Pro Leu Glu Glu Val Ser Cys Gly Gln Ala Glu Ser Ser Glu Lys Pro
            20                  25                  30

Asn Ala Glu Asp Met Thr Ser Lys Asp Tyr Tyr Phe Asp Ser Tyr Ala
        35                  40                  45

His Phe Gly Ile His Glu Glu Met Leu Lys Asp Glu Val Arg Thr Leu
    50                  55                  60

Thr Tyr Arg Asn Ser Met Phe His Asn Arg His Leu Phe Lys Asp Lys
65                  70                  75                  80

Val Val Leu Asp Val Gly Ser Gly Thr Gly Ile Leu Cys Met Phe Ala
                85                  90                  95

Ala Lys Ala Gly Ala Arg Lys Val Ile Gly Ile Glu Cys Ser Ser Ile
            100                 105                 110

Ser Asp Tyr Ala Val Lys Ile Val Lys Ala Asn Lys Leu Asp His Val
        115                 120                 125

Val Thr Ile Ile Lys Gly Lys Val Glu Glu Val Glu Leu Pro Val Glu
    130                 135                 140

Lys Val Asp Ile Ile Ile Ser Glu Trp Met Gly Tyr Cys Leu Phe Tyr
145                 150                 155                 160

Glu Ser Met Leu Asn Thr Val Leu Tyr Ala Arg Asp Lys Trp Leu Ala
                165                 170                 175

Pro Asp Gly Leu Ile Phe Pro Asp Arg Ala Thr Leu Tyr Val Thr Ala
            180                 185                 190
```

-continued

```
Ile Glu Asp Arg Gln Tyr Lys Asp Tyr Lys Ile His Trp Glu Asn
            195                 200                 205

Val Tyr Gly Phe Asp Met Ser Cys Ile Lys Asp Val Ala Ile Lys Glu
    210                 215                 220

Pro Leu Val Asp Val Val Asp Pro Lys Gln Leu Val Thr Asn Ala Cys
225                 230                 235                 240

Leu Ile Lys Glu Val Asp Ile Tyr Thr Val Lys Val Glu Asp Leu Thr
            245                 250                 255

Phe Thr Ser Pro Phe Cys Leu Gln Val Lys Arg Asn Asp Tyr Val His
            260                 265                 270

Ala Leu Val Ala Tyr Phe Asn Ile Glu Phe Thr Arg Cys His Lys Arg
            275                 280                 285

Thr Gly Phe Ser Thr Ser Pro Glu Ser Pro Tyr Thr His Trp Lys Gln
            290                 295                 300

Thr Val Phe Tyr Met Glu Asp Tyr Leu Thr Val Lys Thr Gly Glu Glu
305                 310                 315                 320

Ile Phe Gly Thr Ile Gly Met Arg Pro Asn Ala Lys Asn Asn Arg Asp
            325                 330                 335

Leu Asp Phe Thr Ile Asp Leu Asp Phe Lys Gly Gln Leu Cys Glu Leu
            340                 345                 350

Ser Cys Ser Thr Asp Tyr Arg Met Arg
            355                 360

<210> SEQ ID NO 6
<211> LENGTH: 800
<212> TYPE: PRT
<213> ORGANISM: Homo sapiens
<220> FEATURE:
<223> OTHER INFORMATION: MAP3 kinase MLTK (or ZAK);
      Q9NYL2 C22
<220> FEATURE:
<221> NAME/KEY: MOD_RES
<222> LOCATION: (22)..(22)
<223> OTHER INFORMATION: Site of chemical conjugation

<400> SEQUENCE: 6

Met Ser Ser Leu Gly Ala Ser Phe Val Gln Ile Lys Phe Asp Asp Leu
1               5                   10                  15

Gln Phe Phe Glu Asn Cys Gly Gly Gly Ser Phe Gly Ser Val Tyr Arg
            20                  25                  30

Ala Lys Trp Ile Ser Gln Asp Lys Glu Val Ala Val Lys Lys Leu Leu
            35                  40                  45

Lys Ile Glu Lys Glu Ala Glu Ile Leu Ser Val Leu Ser His Arg Asn
    50                  55                  60

Ile Ile Gln Phe Tyr Gly Val Ile Leu Glu Pro Pro Asn Tyr Gly Ile
65                  70                  75                  80

Val Thr Glu Tyr Ala Ser Leu Gly Ser Leu Tyr Asp Tyr Ile Asn Ser
                85                  90                  95

Asn Arg Ser Glu Glu Met Asp Met Asp His Ile Met Thr Trp Ala Thr
            100                 105                 110

Asp Val Ala Lys Gly Met His Tyr Leu His Met Glu Ala Pro Val Lys
            115                 120                 125

Val Ile His Arg Asp Leu Lys Ser Arg Asn Val Val Ile Ala Ala Asp
            130                 135                 140

Gly Val Leu Lys Ile Cys Asp Phe Gly Ala Ser Arg Phe His Asn His
145                 150                 155                 160

Thr Thr His Met Ser Leu Val Gly Thr Phe Pro Trp Met Ala Pro Glu
```

```
                165                 170                 175
Val Ile Gln Ser Leu Pro Val Ser Glu Thr Cys Asp Thr Tyr Ser Tyr
                180                 185                 190

Gly Val Val Leu Trp Glu Met Leu Thr Arg Glu Val Pro Phe Lys Gly
                195                 200                 205

Leu Glu Gly Leu Gln Val Ala Trp Leu Val Val Lys Asn Glu Arg
210                 215                 220

Leu Thr Ile Pro Ser Ser Cys Pro Arg Ser Phe Ala Glu Leu Leu His
225                 230                 235                 240

Gln Cys Trp Glu Ala Asp Ala Lys Lys Arg Pro Ser Phe Lys Gln Ile
                245                 250                 255

Ile Ser Ile Leu Glu Ser Met Ser Asn Asp Thr Ser Leu Pro Asp Lys
                260                 265                 270

Cys Asn Ser Phe Leu His Asn Lys Ala Glu Trp Arg Cys Glu Ile Glu
                275                 280                 285

Ala Thr Leu Glu Arg Leu Lys Lys Leu Glu Arg Asp Leu Ser Phe Lys
                290                 295                 300

Glu Gln Glu Leu Lys Glu Arg Glu Arg Arg Leu Lys Met Trp Glu Gln
305                 310                 315                 320

Lys Leu Thr Glu Gln Ser Asn Thr Pro Leu Leu Pro Ser Phe Glu Ile
                325                 330                 335

Gly Ala Trp Thr Glu Asp Asp Val Tyr Cys Trp Val Gln Gln Leu Val
                340                 345                 350

Arg Lys Gly Asp Ser Ser Ala Glu Met Ser Val Tyr Ala Ser Leu Phe
                355                 360                 365

Lys Glu Asn Asn Ile Thr Gly Lys Arg Leu Leu Leu Glu Glu Glu
                370                 375                 380

Asp Leu Lys Asp Met Gly Ile Val Ser Lys Gly His Ile Ile His Phe
385                 390                 395                 400

Lys Ser Ala Ile Glu Lys Leu Thr His Asp Tyr Ile Asn Leu Phe His
                405                 410                 415

Phe Pro Pro Leu Ile Lys Asp Ser Gly Gly Glu Pro Glu Glu Asn Glu
                420                 425                 430

Glu Lys Ile Val Asn Leu Glu Leu Val Phe Gly Phe His Leu Lys Pro
                435                 440                 445

Gly Thr Gly Pro Gln Asp Cys Lys Trp Lys Met Tyr Met Glu Met Asp
                450                 455                 460

Gly Asp Glu Ile Ala Ile Thr Tyr Ile Lys Asp Val Thr Phe Asn Thr
465                 470                 475                 480

Asn Leu Pro Asp Ala Glu Ile Leu Lys Met Thr Lys Pro Pro Phe Val
                485                 490                 495

Met Glu Lys Trp Ile Val Gly Ile Ala Lys Ser Gln Thr Val Glu Cys
                500                 505                 510

Thr Val Thr Tyr Glu Ser Asp Val Arg Thr Pro Lys Ser Thr Lys His
                515                 520                 525

Val His Ser Ile Gln Trp Ser Arg Thr Lys Pro Gln Asp Glu Val Lys
                530                 535                 540

Ala Val Gln Leu Ala Ile Gln Thr Leu Phe Thr Asn Ser Asp Gly Asn
545                 550                 555                 560

Pro Gly Ser Arg Ser Asp Ser Ser Ala Asp Cys Gln Trp Leu Asp Thr
                565                 570                 575

Leu Arg Met Arg Gln Ile Ala Ser Asn Thr Ser Leu Gln Arg Ser Gln
                580                 585                 590
```

-continued

Ser Asn Pro Ile Leu Gly Ser Pro Phe Phe Ser His Phe Asp Gly Gln
          595                 600                 605

Asp Ser Tyr Ala Ala Val Arg Arg Pro Gln Val Pro Ile Lys Tyr
610                 615                 620

Gln Gln Ile Thr Pro Val Asn Gln Ser Arg Ser Ser Pro Thr Gln
625                 630                 635                 640

Tyr Gly Leu Thr Lys Asn Phe Ser Ser Leu His Leu Asn Ser Arg Asp
                  645                 650                 655

Ser Gly Phe Ser Ser Gly Asn Thr Asp Thr Ser Ser Glu Arg Gly Arg
              660                 665                 670

Tyr Ser Asp Arg Ser Arg Asn Lys Tyr Gly Arg Gly Ser Ile Ser Leu
              675                 680                 685

Asn Ser Ser Pro Arg Gly Arg Tyr Ser Gly Lys Ser Gln His Ser Thr
              690                 695                 700

Pro Ser Arg Gly Arg Tyr Pro Gly Lys Phe Tyr Arg Val Ser Gln Ser
705                 710                 715                 720

Ala Leu Asn Pro His Gln Ser Pro Asp Phe Lys Arg Ser Pro Arg Asp
                  725                 730                 735

Leu His Gln Pro Asn Thr Ile Pro Gly Met Pro Leu His Pro Glu Thr
              740                 745                 750

Asp Ser Arg Ala Ser Glu Glu Asp Ser Lys Val Ser Glu Gly Gly Trp
              755                 760                 765

Thr Lys Val Glu Tyr Arg Lys Lys Pro His Arg Pro Ser Pro Ala Lys
              770                 775                 780

Thr Asn Lys Glu Arg Ala Arg Gly Asp His Arg Gly Trp Arg Asn Phe
785                 790                 795                 800

<210> SEQ ID NO 7
<211> LENGTH: 514
<212> TYPE: PRT
<213> ORGANISM: Homo sapiens
<220> FEATURE:
<223> OTHER INFORMATION: IMPDH2;
      P12268 C140, C331
<220> FEATURE:
<221> NAME/KEY: MOD_RES
<222> LOCATION: (140)..(140)
<223> OTHER INFORMATION: Site of chemical conjugation
<220> FEATURE:
<221> NAME/KEY: MOD_RES
<222> LOCATION: (331)..(331)
<223> OTHER INFORMATION: Site of chemical conjugation

<400> SEQUENCE: 7

Met Ala Asp Tyr Leu Ile Ser Gly Gly Thr Ser Tyr Val Pro Asp Asp
1               5                   10                  15

Gly Leu Thr Ala Gln Gln Leu Phe Asn Cys Gly Asp Gly Leu Thr Tyr
              20                  25                  30

Asn Asp Phe Leu Ile Leu Pro Gly Tyr Ile Asp Phe Thr Ala Asp Gln
              35                  40                  45

Val Asp Leu Thr Ser Ala Leu Thr Lys Lys Ile Thr Leu Lys Thr Pro
50                  55                  60

Leu Val Ser Ser Pro Met Asp Thr Val Thr Glu Ala Gly Met Ala Ile
65                  70                  75                  80

Ala Met Ala Leu Thr Gly Gly Ile Gly Phe Ile His His Asn Cys Thr
                  85                  90                  95

Pro Glu Phe Gln Ala Asn Glu Val Arg Lys Val Lys Lys Tyr Glu Gln
              100                 105                 110

```
Gly Phe Ile Thr Asp Pro Val Leu Ser Pro Lys Asp Arg Val Arg
            115                 120                 125

Asp Val Phe Glu Ala Lys Ala Arg His Gly Phe Cys Gly Ile Pro Ile
130                 135                 140

Thr Asp Thr Gly Arg Met Gly Ser Arg Leu Val Gly Ile Ile Ser Ser
145                 150                 155                 160

Arg Asp Ile Asp Phe Leu Lys Glu Glu His Asp Cys Phe Leu Glu
                165                 170                 175

Glu Ile Met Thr Lys Arg Glu Asp Leu Val Val Ala Pro Ala Gly Ile
            180                 185                 190

Thr Leu Lys Glu Ala Asn Glu Ile Leu Gln Arg Ser Lys Lys Gly Lys
            195                 200                 205

Leu Pro Ile Val Asn Glu Asp Glu Leu Val Ala Ile Ile Ala Arg
            210                 215                 220

Thr Asp Leu Lys Lys Asn Arg Asp Tyr Pro Leu Ala Ser Lys Asp Ala
225                 230                 235                 240

Lys Lys Gln Leu Leu Cys Gly Ala Ala Ile Gly Thr His Glu Asp Asp
                245                 250                 255

Lys Tyr Arg Leu Asp Leu Leu Ala Gln Ala Gly Val Asp Val Val
            260                 265                 270

Leu Asp Ser Ser Gln Gly Asn Ser Ile Phe Gln Ile Asn Met Ile Lys
            275                 280                 285

Tyr Ile Lys Asp Lys Tyr Pro Asn Leu Gln Val Ile Gly Gly Asn Val
            290                 295                 300

Val Thr Ala Ala Gln Ala Lys Asn Leu Ile Asp Ala Gly Val Asp Ala
305                 310                 315                 320

Leu Arg Val Gly Met Gly Ser Gly Ser Ile Cys Ile Thr Gln Glu Val
                325                 330                 335

Leu Ala Cys Gly Arg Pro Gln Ala Thr Ala Val Tyr Lys Val Ser Glu
                340                 345                 350

Tyr Ala Arg Arg Phe Gly Val Pro Val Ile Ala Asp Gly Gly Ile Gln
            355                 360                 365

Asn Val Gly His Ile Ala Lys Ala Leu Ala Leu Gly Ala Ser Thr Val
            370                 375                 380

Met Met Gly Ser Leu Leu Ala Ala Thr Thr Glu Ala Pro Gly Glu Tyr
385                 390                 395                 400

Phe Phe Ser Asp Gly Ile Arg Leu Lys Lys Tyr Arg Gly Met Gly Ser
                405                 410                 415

Leu Asp Ala Met Asp Lys His Leu Ser Ser Gln Asn Arg Tyr Phe Ser
                420                 425                 430

Glu Ala Asp Lys Ile Lys Val Ala Gln Gly Val Ser Gly Ala Val Gln
            435                 440                 445

Asp Lys Gly Ser Ile His Lys Phe Val Pro Tyr Leu Ile Ala Gly Ile
450                 455                 460

Gln His Ser Cys Gln Asp Ile Gly Ala Lys Ser Leu Thr Gln Val Arg
465                 470                 475                 480

Ala Met Met Tyr Ser Gly Glu Leu Lys Phe Glu Lys Arg Thr Ser Ser
                485                 490                 495

Ala Gln Val Glu Gly Gly Val His Ser Leu His Ser Tyr Glu Lys Arg
            500                 505                 510

Leu Phe
```

-continued

```
<210> SEQ ID NO 8
<211> LENGTH: 270
<212> TYPE: PRT
<213> ORGANISM: Homo sapiens
<220> FEATURE:
<223> OTHER INFORMATION: TIGAR;
      Q9NQ88 C114, C161
<220> FEATURE:
<221> NAME/KEY: MOD_RES
<222> LOCATION: (114)..(114)
<223> OTHER INFORMATION: Site of chemical conjugation
<220> FEATURE:
<221> NAME/KEY: MOD_RES
<222> LOCATION: (161)..(161)
<223> OTHER INFORMATION: Site of chemical conjugation

<400> SEQUENCE: 8

Met Ala Arg Phe Ala Leu Thr Val Val Arg His Gly Glu Thr Arg Phe
1               5                   10                  15

Asn Lys Glu Lys Ile Ile Gln Gly Gln Gly Val Asp Glu Pro Leu Ser
            20                  25                  30

Glu Thr Gly Phe Lys Gln Ala Ala Ala Gly Ile Phe Leu Asn Asn
        35                  40                  45

Val Lys Phe Thr His Ala Phe Ser Ser Asp Leu Met Arg Thr Lys Gln
50                  55                  60

Thr Met His Gly Ile Leu Glu Arg Ser Lys Phe Cys Lys Asp Met Thr
65                  70                  75                  80

Val Lys Tyr Asp Ser Arg Leu Arg Glu Arg Lys Tyr Gly Val Val Glu
                85                  90                  95

Gly Lys Ala Leu Ser Glu Leu Arg Ala Met Ala Lys Ala Ala Arg Glu
            100                 105                 110

Glu Cys Pro Val Phe Thr Pro Pro Gly Gly Glu Thr Leu Asp Gln Val
        115                 120                 125

Lys Met Arg Gly Ile Asp Phe Phe Glu Phe Leu Cys Gln Leu Ile Leu
130                 135                 140

Lys Glu Ala Asp Gln Lys Glu Gln Phe Ser Gln Gly Ser Pro Ser Asn
145                 150                 155                 160

Cys Leu Glu Thr Ser Leu Ala Glu Ile Phe Pro Leu Gly Lys Asn His
                165                 170                 175

Ser Ser Lys Val Asn Ser Asp Ser Gly Ile Pro Gly Leu Ala Ala Ser
            180                 185                 190

Val Leu Val Val Ser His Gly Ala Tyr Met Arg Ser Leu Phe Asp Tyr
        195                 200                 205

Phe Leu Thr Asp Leu Lys Cys Ser Leu Pro Ala Thr Leu Ser Arg Ser
210                 215                 220

Glu Leu Met Ser Val Thr Pro Asn Thr Gly Met Ser Leu Phe Ile Ile
225                 230                 235                 240

Asn Phe Glu Glu Gly Arg Glu Val Lys Pro Thr Val Gln Cys Ile Cys
                245                 250                 255

Met Asn Leu Gln Asp His Leu Asn Gly Leu Thr Glu Thr Arg
            260                 265                 270

<210> SEQ ID NO 9
<211> LENGTH: 706
<212> TYPE: PRT
<213> ORGANISM: Homo sapiens
<220> FEATURE:
<223> OTHER INFORMATION: PKCtheta;
      Q04759 C14, C17
<220> FEATURE:
<221> NAME/KEY: MOD_RES
```

```
<222> LOCATION: (14)..(14)
<223> OTHER INFORMATION: Site of chemical conjugation
<220> FEATURE:
<221> NAME/KEY: MOD_RES
<222> LOCATION: (17)..(17)
<223> OTHER INFORMATION: Site of chemical conjugation

<400> SEQUENCE: 9

Met Ser Pro Phe Leu Arg Ile Gly Leu Ser Asn Phe Asp Cys Gly Ser
1               5                   10                  15

Cys Gln Ser Cys Gln Gly Glu Ala Val Asn Pro Tyr Cys Ala Val Leu
            20                  25                  30

Val Lys Glu Tyr Val Glu Ser Glu Asn Gly Gln Met Tyr Ile Gln Lys
        35                  40                  45

Lys Pro Thr Met Tyr Pro Pro Trp Asp Ser Thr Phe Asp Ala His Ile
    50                  55                  60

Asn Lys Gly Arg Val Met Gln Ile Ile Val Lys Gly Lys Asn Val Asp
65                  70                  75                  80

Leu Ile Ser Glu Thr Thr Val Glu Leu Tyr Ser Leu Ala Glu Arg Cys
                85                  90                  95

Arg Lys Asn Asn Gly Lys Thr Glu Ile Trp Leu Glu Leu Lys Pro Gln
            100                 105                 110

Gly Arg Met Leu Met Asn Ala Arg Tyr Phe Leu Glu Met Ser Asp Thr
        115                 120                 125

Lys Asp Met Asn Glu Phe Glu Thr Glu Gly Phe Phe Ala Leu His Gln
    130                 135                 140

Arg Arg Gly Ala Ile Lys Gln Ala Lys Val His His Val Lys Cys His
145                 150                 155                 160

Glu Phe Thr Ala Thr Phe Phe Pro Gln Pro Thr Phe Cys Ser Val Cys
                165                 170                 175

His Glu Phe Val Trp Gly Leu Asn Lys Gln Gly Tyr Gln Cys Arg Gln
            180                 185                 190

Cys Asn Ala Ala Ile His Lys Lys Cys Ile Asp Lys Val Ile Ala Lys
        195                 200                 205

Cys Thr Gly Ser Ala Ile Asn Ser Arg Glu Thr Met Phe His Lys Glu
    210                 215                 220

Arg Phe Lys Ile Asp Met Pro His Arg Phe Lys Val Tyr Asn Tyr Lys
225                 230                 235                 240

Ser Pro Thr Phe Cys Glu His Cys Gly Thr Leu Leu Trp Gly Leu Ala
                245                 250                 255

Arg Gln Gly Leu Lys Cys Asp Ala Cys Gly Met Asn Val His His Arg
            260                 265                 270

Cys Gln Thr Lys Val Ala Asn Leu Cys Gly Ile Asn Gln Lys Leu Met
        275                 280                 285

Ala Glu Ala Leu Ala Met Ile Glu Ser Thr Gln Gln Ala Arg Cys Leu
    290                 295                 300

Arg Asp Thr Glu Gln Ile Phe Arg Glu Gly Pro Val Glu Ile Gly Leu
305                 310                 315                 320

Pro Cys Ser Ile Lys Asn Glu Ala Arg Pro Pro Cys Leu Pro Thr Pro
                325                 330                 335

Gly Lys Arg Glu Pro Gln Gly Ile Ser Trp Glu Ser Pro Leu Asp Glu
            340                 345                 350

Val Asp Lys Met Cys His Leu Pro Glu Pro Glu Leu Asn Lys Glu Arg
        355                 360                 365

Pro Ser Leu Gln Ile Lys Leu Lys Ile Glu Asp Phe Ile Leu His Lys
```

```
                370             375             380
Met Leu Gly Lys Gly Ser Phe Gly Lys Val Phe Leu Ala Glu Phe Lys
385                 390                 395                 400

Lys Thr Asn Gln Phe Phe Ala Ile Lys Ala Leu Lys Lys Asp Val Val
            405                 410                 415

Leu Met Asp Asp Asp Val Glu Cys Thr Met Val Glu Lys Arg Val Leu
        420                 425                 430

Ser Leu Ala Trp Glu His Pro Phe Leu Thr His Met Phe Cys Thr Phe
    435                 440                 445

Gln Thr Lys Glu Asn Leu Phe Phe Val Met Glu Tyr Leu Asn Gly Gly
450                 455                 460

Asp Leu Met Tyr His Ile Gln Ser Cys His Lys Phe Asp Leu Ser Arg
465                 470                 475                 480

Ala Thr Phe Tyr Ala Ala Glu Ile Ile Leu Gly Leu Gln Phe Leu His
                485                 490                 495

Ser Lys Gly Ile Val Tyr Arg Asp Leu Lys Leu Asp Asn Ile Leu Leu
            500                 505                 510

Asp Lys Asp Gly His Ile Lys Ile Ala Asp Phe Gly Met Cys Lys Glu
        515                 520                 525

Asn Met Leu Gly Asp Ala Lys Thr Asn Thr Phe Cys Gly Thr Pro Asp
530                 535                 540

Tyr Ile Ala Pro Glu Ile Leu Leu Gly Gln Lys Tyr Asn His Ser Val
545                 550                 555                 560

Asp Trp Trp Ser Phe Gly Val Leu Leu Tyr Glu Met Leu Ile Gly Gln
                565                 570                 575

Ser Pro Phe His Gly Gln Asp Glu Glu Glu Leu Phe His Ser Ile Arg
            580                 585                 590

Met Asp Asn Pro Phe Tyr Pro Arg Trp Leu Glu Lys Glu Ala Lys Asp
        595                 600                 605

Leu Leu Val Lys Leu Phe Val Arg Glu Pro Glu Lys Arg Leu Gly Val
610                 615                 620

Arg Gly Asp Ile Arg Gln His Pro Leu Phe Arg Glu Ile Asn Trp Glu
625                 630                 635                 640

Glu Leu Glu Arg Lys Glu Ile Asp Pro Pro Phe Arg Pro Lys Val Lys
                645                 650                 655

Ser Pro Phe Asp Cys Ser Asn Phe Asp Lys Glu Phe Leu Asn Glu Lys
            660                 665                 670

Pro Arg Leu Ser Phe Ala Asp Arg Ala Leu Ile Asn Ser Met Asp Gln
        675                 680                 685

Asn Met Phe Arg Asn Phe Ser Phe Met Asn Pro Gly Met Glu Arg Leu
690                 695                 700

Ile Ser
705

<210> SEQ ID NO 10
<211> LENGTH: 14
<212> TYPE: PRT
<213> ORGANISM: Homo sapiens
<220> FEATURE:
<223> OTHER INFORMATION: RPS3 40S ribosomal protein S3;
      P23396_C97
<220> FEATURE:
<221> NAME/KEY: MOD_RES
<222> LOCATION: (4)..(4)
<223> OTHER INFORMATION: Site of chemical conjugation

<400> SEQUENCE: 10
```

```
Arg Gly Leu Cys Ala Ile Ala Gln Ala Glu Ser Leu Arg Tyr
1               5                   10

<210> SEQ ID NO 11
<211> LENGTH: 26
<212> TYPE: PRT
<213> ORGANISM: Homo sapiens
<220> FEATURE:
<223> OTHER INFORMATION: TUBA4A Tubulin alpha-4A chain;
      P68366_C295
<220> FEATURE:
<221> NAME/KEY: MOD_RES
<222> LOCATION: (16)..(16)
<223> OTHER INFORMATION: Site of chemical conjugation

<400> SEQUENCE: 11

Lys Ala Tyr His Glu Gln Leu Ser Val Ala Glu Ile Thr Asn Ala Cys
1               5                   10                  15

Phe Glu Pro Ala Asn Gln Met Val Lys Cys
            20                  25

<210> SEQ ID NO 12
<211> LENGTH: 16
<212> TYPE: PRT
<213> ORGANISM: Homo sapiens
<220> FEATURE:
<223> OTHER INFORMATION: TUBA4A Tubulin alpha-4A chain;
      P68366_C347
<220> FEATURE:
<221> NAME/KEY: MOD_RES
<222> LOCATION: (10)..(10)
<223> OTHER INFORMATION: Site of chemical conjugation

<400> SEQUENCE: 12

Lys Arg Ser Ile Gln Phe Val Asp Trp Cys Pro Thr Gly Phe Lys Val
1               5                   10                  15

<210> SEQ ID NO 13
<211> LENGTH: 16
<212> TYPE: PRT
<213> ORGANISM: Homo sapiens
<220> FEATURE:
<223> OTHER INFORMATION: TUBA1A Tubulin alpha-1A chain;
      Q71U36_C347
<220> FEATURE:
<221> NAME/KEY: MOD_RES
<222> LOCATION: (10)..(10)
<223> OTHER INFORMATION: Site of chemical conjugation

<400> SEQUENCE: 13

Lys Arg Thr Ile Gln Phe Val Asp Trp Cys Pro Thr Gly Phe Lys Val
1               5                   10                  15

<210> SEQ ID NO 14
<211> LENGTH: 19
<212> TYPE: PRT
<213> ORGANISM: Homo sapiens
<220> FEATURE:
<223> OTHER INFORMATION: TUBA1A Tubulin alpha-1A chain;
      Q71U36_C376
<220> FEATURE:
<221> NAME/KEY: MOD_RES
<222> LOCATION: (4)..(4)
<223> OTHER INFORMATION: Site of chemical conjugation

<400> SEQUENCE: 14

Arg Ala Val Cys Met Leu Ser Asn Thr Thr Ala Ile Ala Glu Ala Trp
1               5                   10                  15
```

Ala Arg Leu

<210> SEQ ID NO 15
<211> LENGTH: 30
<212> TYPE: PRT
<213> ORGANISM: Homo sapiens
<220> FEATURE:
<223> OTHER INFORMATION: BZW1 Basic leucine zipper and W2 domain-
      containing prot; Q7L1Q6_C35
<220> FEATURE:
<221> NAME/KEY: MOD_RES
<222> LOCATION: (12)..(12)
<223> OTHER INFORMATION: Site of chemical conjugation

<400> SEQUENCE: 15

Lys Glu Arg Phe Asp Pro Thr Gln Phe Gln Asp Cys Ile Ile Gln Gly
1               5                   10                  15

Leu Thr Glu Thr Gly Thr Asp Leu Glu Ala Val Ala Lys Phe
            20                  25                  30

<210> SEQ ID NO 16
<211> LENGTH: 19
<212> TYPE: PRT
<213> ORGANISM: Homo sapiens
<220> FEATURE:
<223> OTHER INFORMATION: GAPDH Glyceraldehyde-3-phosphate dehydrogenase;
      P04406_C152
<220> FEATURE:
<221> NAME/KEY: MOD_RES
<222> LOCATION: (8)..(8)
<223> OTHER INFORMATION: Site of chemical conjugation

<400> SEQUENCE: 16

Lys Ile Ile Ser Asn Ala Ser Cys Thr Thr Asn Cys Leu Ala Pro Leu
1               5                   10                  15

Ala Lys Val

<210> SEQ ID NO 17
<211> LENGTH: 17
<212> TYPE: PRT
<213> ORGANISM: Homo sapiens
<220> FEATURE:
<223> OTHER INFORMATION: PRMT1 Protein arginine N-methyltransferase 1;
      Q99873_C109
<220> FEATURE:
<221> NAME/KEY: MOD_RES
<222> LOCATION: (7)..(7)
<223> OTHER INFORMATION: Site of chemical conjugation

<400> SEQUENCE: 17

Lys Val Ile Gly Ile Glu Cys Ser Ser Ile Ser Asp Tyr Ala Val Lys
1               5                   10                  15

Ile

<210> SEQ ID NO 18
<211> LENGTH: 16
<212> TYPE: PRT
<213> ORGANISM: Homo sapiens
<220> FEATURE:
<223> OTHER INFORMATION: PCBP1 Poly(rC)-binding protein 1;
      Q15365_C109
<220> FEATURE:
<221> NAME/KEY: MOD_RES
<222> LOCATION: (9)..(9)
<223> OTHER INFORMATION: Site of chemical conjugation

<400> SEQUENCE: 18

Arg Leu Val Val Pro Ala Thr Gln Cys Gly Ser Leu Ile Gly Lys Gly

<210> SEQ ID NO 19
<211> LENGTH: 24
<212> TYPE: PRT
<213> ORGANISM: Homo sapiens
<220> FEATURE:
<223> OTHER INFORMATION: PIN1 Peptidyl-prolyl cis-trans isomerase NIMA-
      interacti; Q13526_C113
<220> FEATURE:
<221> NAME/KEY: MOD_RES
<222> LOCATION: (19)..(19)
<223> OTHER INFORMATION: Site of chemical conjugation

<400> SEQUENCE: 19

Lys Ile Lys Ser Gly Glu Glu Asp Phe Glu Ser Leu Ala Ser Gln Phe
1               5                   10                  15

Ser Asp Cys Ser Ser Ala Lys Ala
            20

<210> SEQ ID NO 20
<211> LENGTH: 21
<212> TYPE: PRT
<213> ORGANISM: Homo sapiens
<220> FEATURE:
<223> OTHER INFORMATION: NUDC Nuclear migration protein nudC;
      Q9Y266_C188
<220> FEATURE:
<221> NAME/KEY: MOD_RES
<222> LOCATION: (16)..(16)
<223> OTHER INFORMATION: Site of chemical conjugation

<400> SEQUENCE: 20

Arg Trp Thr Gln Thr Leu Ser Glu Leu Asp Leu Ala Val Pro Phe Cys
1               5                   10                  15

Val Asn Phe Arg Leu
            20

<210> SEQ ID NO 21
<211> LENGTH: 18
<212> TYPE: PRT
<213> ORGANISM: Homo sapiens
<220> FEATURE:
<223> OTHER INFORMATION: CLIC4 Chloride intracellular channel protein 4;
      Q9Y696_C35
<220> FEATURE:
<221> NAME/KEY: MOD_RES
<222> LOCATION: (12)..(12)
<223> OTHER INFORMATION: Site of chemical conjugation

<400> SEQUENCE: 21

Lys Ala Gly Ser Asp Gly Glu Ser Ile Gly Asn Cys Pro Phe Ser Gln
1               5                   10                  15

Arg Leu

<210> SEQ ID NO 22
<211> LENGTH: 21
<212> TYPE: PRT
<213> ORGANISM: Homo sapiens
<220> FEATURE:
<223> OTHER INFORMATION: ACAT1 Acetyl-CoA acetyltransferase,
      mitochondrial; P24752_C119
<220> FEATURE:
<221> NAME/KEY: MOD_RES
<222> LOCATION: (15)..(15)
<223> OTHER INFORMATION: Site of chemical conjugation

<400> SEQUENCE: 22

-continued

```
Arg Gln Ala Val Leu Gly Ala Gly Leu Pro Ile Ser Thr Pro Cys Thr
1               5                   10                  15

Thr Ile Asn Lys Val
            20

<210> SEQ ID NO 23
<211> LENGTH: 19
<212> TYPE: PRT
<213> ORGANISM: Homo sapiens
<220> FEATURE:
<223> OTHER INFORMATION: HSPD1 60 kDa heat shock protein, mitochondrial;
      P10809_C442
<220> FEATURE:
<221> NAME/KEY: MOD_RES
<222> LOCATION: (14)..(14)
<223> OTHER INFORMATION: Site of chemical conjugation

<400> SEQUENCE: 23

Arg Ala Ala Val Glu Glu Gly Ile Val Leu Gly Gly Gly Cys Ala Leu
1               5                   10                  15

Leu Arg Cys

<210> SEQ ID NO 24
<211> LENGTH: 11
<212> TYPE: PRT
<213> ORGANISM: Homo sapiens
<220> FEATURE:
<223> OTHER INFORMATION: TUBA4A Tubulin alpha-4A chain;
      P68366_C315
<220> FEATURE:
<221> NAME/KEY: MOD_RES
<222> LOCATION: (5)..(5)
<223> OTHER INFORMATION: Site of chemical conjugation

<400> SEQUENCE: 24

Lys Tyr Met Ala Cys Cys Leu Leu Tyr Arg Gly
1               5                   10

<210> SEQ ID NO 25
<211> LENGTH: 12
<212> TYPE: PRT
<213> ORGANISM: Homo sapiens
<220> FEATURE:
<223> OTHER INFORMATION: GSTP1 Glutathione S-transferase P;
      P09211_C48
<220> FEATURE:
<221> NAME/KEY: MOD_RES
<222> LOCATION: (4)..(4)
<223> OTHER INFORMATION: Site of chemical conjugation

<400> SEQUENCE: 25

Lys Ala Ser Cys Leu Tyr Gly Gln Leu Pro Lys Phe
1               5                   10

<210> SEQ ID NO 26
<211> LENGTH: 21
<212> TYPE: PRT
<213> ORGANISM: Homo sapiens
<220> FEATURE:
<223> OTHER INFORMATION: GLRX5 Glutaredoxin-related protein 5,
      mitochondrial; Q86SX6_C67
<220> FEATURE:
<221> NAME/KEY: MOD_RES
<222> LOCATION: (9)..(9)
<223> OTHER INFORMATION: Site of chemical conjugation

<400> SEQUENCE: 26

Lys Gly Thr Pro Glu Gln Pro Gln Cys Gly Phe Ser Asn Ala Val Val
1               5                   10                  15
```

-continued

```
Gln Ile Leu Arg Leu
            20

<210> SEQ ID NO 27
<211> LENGTH: 12
<212> TYPE: PRT
<213> ORGANISM: Homo sapiens
<220> FEATURE:
<223> OTHER INFORMATION: EEF2 Elongation factor 2;
      P13639_C41
<220> FEATURE:
<221> NAME/KEY: MOD_RES
<222> LOCATION: (10)..(10)
<223> OTHER INFORMATION: Site of chemical conjugation

<400> SEQUENCE: 27

Lys Ser Thr Leu Thr Asp Ser Leu Val Cys Lys Ala
1               5                   10

<210> SEQ ID NO 28
<211> LENGTH: 24
<212> TYPE: PRT
<213> ORGANISM: Homo sapiens
<220> FEATURE:
<223> OTHER INFORMATION: XPO1 Exportin-1;
      O14980_C34
<220> FEATURE:
<221> NAME/KEY: MOD_RES
<222> LOCATION: (13)..(13)
<223> OTHER INFORMATION: Site of chemical conjugation

<400> SEQUENCE: 28

Lys Leu Asp Ile Asn Leu Leu Asp Asn Val Val Asn Cys Leu Tyr His
1               5                   10                  15

Gly Glu Gly Ala Gln Gln Arg Met
            20

<210> SEQ ID NO 29
<211> LENGTH: 25
<212> TYPE: PRT
<213> ORGANISM: Homo sapiens
<220> FEATURE:
<223> OTHER INFORMATION: PCBP1 Poly(rC)-binding protein 1;
      Q15365_C194
<220> FEATURE:
<221> NAME/KEY: MOD_RES
<222> LOCATION: (18)..(18)
<223> OTHER INFORMATION: Site of chemical conjugation

<400> SEQUENCE: 29

Arg Val Met Thr Ile Pro Tyr Gln Pro Met Pro Ala Ser Ser Pro Val
1               5                   10                  15

Ile Cys Ala Gly Gly Gln Asp Arg Cys
            20                  25

<210> SEQ ID NO 30
<211> LENGTH: 29
<212> TYPE: PRT
<213> ORGANISM: Homo sapiens
<220> FEATURE:
<223> OTHER INFORMATION: CCT7 T-complex protein 1 subunit eta;
      Q99832_C29
<220> FEATURE:
<221> NAME/KEY: MOD_RES
<222> LOCATION: (20)..(20)
<223> OTHER INFORMATION: Site of chemical conjugation

<400> SEQUENCE: 30
```

Lys Glu Gly Thr Asp Ser Ser Gln Gly Ile Pro Gln Leu Val Ser Asn
1               5                   10                  15

Ile Ser Ala Cys Gln Val Ile Ala Glu Ala Val Arg Thr
            20                  25

<210> SEQ ID NO 31
<211> LENGTH: 12
<212> TYPE: PRT
<213> ORGANISM: Homo sapiens
<220> FEATURE:
<223> OTHER INFORMATION: RPS11 40S ribosomal protein S11;
      P62280_C60
<220> FEATURE:
<221> NAME/KEY: MOD_RES
<222> LOCATION: (2)..(2)
<223> OTHER INFORMATION: Site of chemical conjugation

<400> SEQUENCE: 31

Lys Cys Pro Phe Thr Gly Asn Val Ser Ile Arg Gly
1               5                   10

<210> SEQ ID NO 32
<211> LENGTH: 9
<212> TYPE: PRT
<213> ORGANISM: Homo sapiens
<220> FEATURE:
<223> OTHER INFORMATION: GSTO1 Glutathione S-transferase omega-1;
      P78417_C32
<220> FEATURE:
<221> NAME/KEY: MOD_RES
<222> LOCATION: (3)..(3)
<223> OTHER INFORMATION: Site of chemical conjugation

<400> SEQUENCE: 32

Arg Phe Cys Pro Phe Ala Glu Arg Thr
1               5

<210> SEQ ID NO 33
<211> LENGTH: 14
<212> TYPE: PRT
<213> ORGANISM: Homo sapiens
<220> FEATURE:
<223> OTHER INFORMATION: ACAT1 Acetyl-CoA acetyltransferase,
      mitochondrial; P24752_C196
<220> FEATURE:
<221> NAME/KEY: MOD_RES
<222> LOCATION: (7)..(7)
<223> OTHER INFORMATION: Site of chemical conjugation

<400> SEQUENCE: 33

Lys Ile His Met Gly Ser Cys Ala Glu Asn Thr Ala Lys Lys
1               5                   10

<210> SEQ ID NO 34
<211> LENGTH: 17
<212> TYPE: PRT
<213> ORGANISM: Homo sapiens
<220> FEATURE:
<223> OTHER INFORMATION: TXN Thioredoxin;
      P10599_C32
<220> FEATURE:
<221> NAME/KEY: MOD_RES
<222> LOCATION: (12)..(12)
<223> OTHER INFORMATION: Site of chemical conjugation

<400> SEQUENCE: 34

Lys Leu Val Val Val Asp Phe Ser Ala Thr Trp Cys Gly Pro Cys Lys
1               5                   10                  15

Met

```
<210> SEQ ID NO 35
<211> LENGTH: 18
<212> TYPE: PRT
<213> ORGANISM: Homo sapiens
<220> FEATURE:
<223> OTHER INFORMATION: CCT8 T-complex protein 1 subunit theta;
      P50990_C244
<220> FEATURE:
<221> NAME/KEY: MOD_RES
<222> LOCATION: (7)..(7)
<223> OTHER INFORMATION: Site of chemical conjugation

<400> SEQUENCE: 35

Lys Ile Ala Val Tyr Ser Cys Pro Phe Asp Gly Met Ile Thr Glu Thr
1               5                   10                  15

Lys Gly

<210> SEQ ID NO 36
<211> LENGTH: 28
<212> TYPE: PRT
<213> ORGANISM: Homo sapiens
<220> FEATURE:
<223> OTHER INFORMATION: PDIA4 Protein disulfide-isomerase A4;
      P13667_C206
<220> FEATURE:
<221> NAME/KEY: MOD_RES
<222> LOCATION: (23)..(23)
<223> OTHER INFORMATION: Site of chemical conjugation

<400> SEQUENCE: 36

Lys Glu Asn Phe Asp Glu Val Val Asn Asp Ala Asp Ile Ile Leu Val
1               5                   10                  15

Glu Phe Tyr Ala Pro Trp Cys Gly His Cys Lys Lys
            20                  25

<210> SEQ ID NO 37
<211> LENGTH: 13
<212> TYPE: PRT
<213> ORGANISM: Homo sapiens
<220> FEATURE:
<223> OTHER INFORMATION: SEC13 Protein SEC13 homolog;
      P55735_C187
<220> FEATURE:
<221> NAME/KEY: MOD_RES
<222> LOCATION: (7)..(7)
<223> OTHER INFORMATION: Site of chemical conjugation

<400> SEQUENCE: 37

Arg Phe Ala Ser Gly Gly Cys Asp Asn Leu Ile Lys Leu
1               5                   10

<210> SEQ ID NO 38
<211> LENGTH: 19
<212> TYPE: PRT
<213> ORGANISM: Homo sapiens
<220> FEATURE:
<223> OTHER INFORMATION: PTGES3 Prostaglandin E synthase 3;
      Q15185_C58
<220> FEATURE:
<221> NAME/KEY: MOD_RES
<222> LOCATION: (11)..(11)
<223> OTHER INFORMATION: Site of chemical conjugation

<400> SEQUENCE: 38

Lys His Leu Asn Glu Ile Asp Leu Phe His Cys Ile Asp Pro Asn Asp
1               5                   10                  15

Ser Lys His
```

```
<210> SEQ ID NO 39
<211> LENGTH: 13
<212> TYPE: PRT
<213> ORGANISM: Homo sapiens
<220> FEATURE:
<223> OTHER INFORMATION: ADK Adenosine kinase;
      P55263_C353
<220> FEATURE:
<221> NAME/KEY: MOD_RES
<222> LOCATION: (4)..(4)
<223> OTHER INFORMATION: Site of chemical conjugation

<400> SEQUENCE: 39

Arg Thr Gly Cys Thr Phe Pro Glu Lys Pro Asp Phe His
1               5                   10

<210> SEQ ID NO 40
<211> LENGTH: 10
<212> TYPE: PRT
<213> ORGANISM: Homo sapiens
<220> FEATURE:
<223> OTHER INFORMATION: RPS5 40S ribosomal protein S5;
      P46782_C66
<220> FEATURE:
<221> NAME/KEY: MOD_RES
<222> LOCATION: (4)..(4)
<223> OTHER INFORMATION: Site of chemical conjugation

<400> SEQUENCE: 40

Lys Ala Gln Cys Pro Ile Val Glu Arg Leu
1               5                   10

<210> SEQ ID NO 41
<211> LENGTH: 16
<212> TYPE: PRT
<213> ORGANISM: Homo sapiens
<220> FEATURE:
<223> OTHER INFORMATION: CNN2 Calponin-2;
      Q99439_C164
<220> FEATURE:
<221> NAME/KEY: MOD_RES
<222> LOCATION: (5)..(5)
<223> OTHER INFORMATION: Site of chemical conjugation

<400> SEQUENCE: 41

Lys Ala Gly Gln Cys Val Ile Gly Leu Gln Met Gly Thr Asn Lys Cys
1               5                   10                  15

<210> SEQ ID NO 42
<211> LENGTH: 26
<212> TYPE: PRT
<213> ORGANISM: Homo sapiens
<220> FEATURE:
<223> OTHER INFORMATION: EEF2 Elongation factor 2;
      P13639_C136
<220> FEATURE:
<221> NAME/KEY: MOD_RES
<222> LOCATION: (17)..(17)
<223> OTHER INFORMATION: Site of chemical conjugation

<400> SEQUENCE: 42

Arg Val Thr Asp Gly Ala Leu Val Val Asp Cys Val Ser Gly Val
1               5                   10                  15

Cys Val Gln Thr Glu Thr Val Leu Arg Gln
            20                  25

<210> SEQ ID NO 43
<211> LENGTH: 26
```

```
<212> TYPE: PRT
<213> ORGANISM: Homo sapiens
<220> FEATURE:
<223> OTHER INFORMATION: IAH1 Isoamyl acetate-hydrolyzing esterase 1
      homolog; Q2TAA2_C137
<220> FEATURE:
<221> NAME/KEY: MOD_RES
<222> LOCATION: (11)..(11)
<223> OTHER INFORMATION: Site of chemical conjugation

<400> SEQUENCE: 43

Arg Val Ile Leu Ile Thr Pro Thr Pro Leu Cys Glu Thr Ala Trp Glu
1               5                   10                  15

Glu Gln Cys Ile Ile Gln Gly Cys Lys Leu
            20                  25

<210> SEQ ID NO 44
<211> LENGTH: 24
<212> TYPE: PRT
<213> ORGANISM: Homo sapiens
<220> FEATURE:
<223> OTHER INFORMATION: PRDX5 Peroxiredoxin-5, mitochondrial;
      P30044_C204
<220> FEATURE:
<221> NAME/KEY: MOD_RES
<222> LOCATION: (14)..(14)
<223> OTHER INFORMATION: Site of chemical conjugation

<400> SEQUENCE: 44

Lys Ala Leu Asn Val Glu Pro Asp Gly Thr Gly Leu Thr Cys Ser Leu
1               5                   10                  15

Ala Pro Asn Ile Ile Ser Gln Leu
            20

<210> SEQ ID NO 45
<211> LENGTH: 15
<212> TYPE: PRT
<213> ORGANISM: Homo sapiens
<220> FEATURE:
<223> OTHER INFORMATION: IMPDH2 Inosine-5-monophosphate dehydrogenase 2;
      P12268_C140
<220> FEATURE:
<221> NAME/KEY: MOD_RES
<222> LOCATION: (5)..(5)
<223> OTHER INFORMATION: Site of chemical conjugation

<400> SEQUENCE: 45

Arg His Gly Phe Cys Gly Ile Pro Ile Thr Asp Thr Gly Arg Met
1               5                   10                  15

<210> SEQ ID NO 46
<211> LENGTH: 16
<212> TYPE: PRT
<213> ORGANISM: Homo sapiens
<220> FEATURE:
<223> OTHER INFORMATION: HSD17B10 3-hydroxyacyl-CoA dehydrogenase
      type-2; Q99714_C214
<220> FEATURE:
<221> NAME/KEY: MOD_RES
<222> LOCATION: (3)..(3)
<223> OTHER INFORMATION: Site of chemical conjugation

<400> SEQUENCE: 46

Lys Val Cys Asn Phe Leu Ala Ser Gln Val Pro Phe Pro Ser Arg Leu
1               5                   10                  15

<210> SEQ ID NO 47
<211> LENGTH: 12
<212> TYPE: PRT
```

```
<213> ORGANISM: Homo sapiens
<220> FEATURE:
<223> OTHER INFORMATION: NIT2 Omega-amidase NIT2;
      Q9NQR4_C153
<220> FEATURE:
<221> NAME/KEY: MOD_RES
<222> LOCATION: (7)..(7)
<223> OTHER INFORMATION: Site of chemical conjugation

<400> SEQUENCE: 47

Arg Val Gly Leu Gly Ile Cys Tyr Asp Met Arg Phe
1               5                  10

<210> SEQ ID NO 48
<211> LENGTH: 13
<212> TYPE: PRT
<213> ORGANISM: Homo sapiens
<220> FEATURE:
<223> OTHER INFORMATION: AKR1B1 Aldose reductase;
      P15121_C299
<220> FEATURE:
<221> NAME/KEY: MOD_RES
<222> LOCATION: (3)..(3)
<223> OTHER INFORMATION: Site of chemical conjugation

<400> SEQUENCE: 48

Arg Val Cys Ala Leu Leu Ser Cys Thr Ser His Lys Asp
1               5                  10

<210> SEQ ID NO 49
<211> LENGTH: 20
<212> TYPE: PRT
<213> ORGANISM: Homo sapiens
<220> FEATURE:
<223> OTHER INFORMATION: MTHFD1L Monofunctional C1-tetrahydrofolate
      synthase, mitochondrial; Q6UB35_C906
<220> FEATURE:
<221> NAME/KEY: MOD_RES
<222> LOCATION: (16)..(16)
<223> OTHER INFORMATION: Site of chemical conjugation

<400> SEQUENCE: 49

Lys Ile Asp Arg Tyr Thr Gln Gln Gly Phe Gly Asn Leu Pro Ile Cys
1               5                  10                  15

Met Ala Lys Thr
            20

<210> SEQ ID NO 50
<211> LENGTH: 27
<212> TYPE: PRT
<213> ORGANISM: Homo sapiens
<220> FEATURE:
<223> OTHER INFORMATION: TUBB Tubulin beta chain;
      P07437_C239
<220> FEATURE:
<221> NAME/KEY: MOD_RES
<222> LOCATION: (24)..(24)
<223> OTHER INFORMATION: Site of chemical conjugation

<400> SEQUENCE: 50

Lys Leu Thr Thr Pro Thr Tyr Gly Asp Leu Asn His Leu Val Ser Ala
1               5                  10                  15

Thr Met Ser Gly Val Thr Thr Cys Leu Arg Phe
            20                  25

<210> SEQ ID NO 51
<211> LENGTH: 25
<212> TYPE: PRT
<213> ORGANISM: Homo sapiens
```

```
<220> FEATURE:
<223> OTHER INFORMATION: PDIA6 Protein disulfide-isomerase A6;
      Q15084_C55
<220> FEATURE:
<221> NAME/KEY: MOD_RES
<222> LOCATION: (19)..(19)
<223> OTHER INFORMATION: Site of chemical conjugation

<400> SEQUENCE: 51

Arg Glu Val Ile Gln Ser Asp Ser Leu Trp Leu Val Glu Phe Tyr Ala
1               5                   10                  15

Pro Trp Cys Gly His Cys Gln Arg Leu
            20                  25

<210> SEQ ID NO 52
<211> LENGTH: 13
<212> TYPE: PRT
<213> ORGANISM: Homo sapiens
<220> FEATURE:
<223> OTHER INFORMATION: PKM Pyruvate kinase isozymes M1/M2;
      P14618_C423
<220> FEATURE:
<221> NAME/KEY: MOD_RES
<222> LOCATION: (2)..(2)
<223> OTHER INFORMATION: Site of chemical conjugation

<400> SEQUENCE: 52

Lys Cys Cys Ser Gly Ala Ile Ile Val Leu Thr Lys Ser
1               5                   10

<210> SEQ ID NO 53
<211> LENGTH: 29
<212> TYPE: PRT
<213> ORGANISM: Homo sapiens
<220> FEATURE:
<223> OTHER INFORMATION: RPS23 40S ribosomal protein S23;
      P62266_C90
<220> FEATURE:
<221> NAME/KEY: MOD_RES
<222> LOCATION: (11)..(11)
<223> OTHER INFORMATION: Site of chemical conjugation

<400> SEQUENCE: 53

Lys Ile Thr Ala Phe Val Pro Asn Asp Gly Cys Leu Asn Phe Ile Glu
1               5                   10                  15

Glu Asn Asp Glu Val Leu Val Ala Gly Phe Gly Arg Lys
            20                  25

<210> SEQ ID NO 54
<211> LENGTH: 41
<212> TYPE: PRT
<213> ORGANISM: Homo sapiens
<220> FEATURE:
<223> OTHER INFORMATION: TUBA1A Tubulin alpha-1A chain;
      Q71U36_C20
<220> FEATURE:
<221> NAME/KEY: MOD_RES
<222> LOCATION: (20)..(20)
<223> OTHER INFORMATION: Site of chemical conjugation

<400> SEQUENCE: 54

Met Arg Glu Cys Ile Ser Ile His Val Gly Gln Ala Gly Val Gln Ile
1               5                   10                  15

Gly Asn Ala Cys Trp Glu Leu Tyr Cys Leu Glu His Gly Ile Gln Pro
            20                  25                  30

Asp Gly Gln Met Pro Ser Asp Lys Thr
            35                  40
```

```
<210> SEQ ID NO 55
<211> LENGTH: 11
<212> TYPE: PRT
<213> ORGANISM: Homo sapiens
<220> FEATURE:
<223> OTHER INFORMATION: PGLS 6-phosphogluconolactonase;
      O95336_C32
<220> FEATURE:
<221> NAME/KEY: MOD_RES
<222> LOCATION: (4)..(4)
<223> OTHER INFORMATION: Site of chemical conjugation

<400> SEQUENCE: 55

Arg Ala Ala Cys Cys Leu Ala Gly Ala Arg Ala
1               5                   10

<210> SEQ ID NO 56
<211> LENGTH: 25
<212> TYPE: PRT
<213> ORGANISM: Homo sapiens
<220> FEATURE:
<223> OTHER INFORMATION: ACAT1 Acetyl-CoA acetyltransferase,
      mitochondrial; P24752_C413
<220> FEATURE:
<221> NAME/KEY: MOD_RES
<222> LOCATION: (11)..(11)
<223> OTHER INFORMATION: Site of chemical conjugation

<400> SEQUENCE: 56

Lys Gln Gly Glu Tyr Gly Leu Ala Ser Ile Cys Asn Gly Gly Gly
1               5                   10                  15

Ala Ser Ala Met Leu Ile Gln Lys Leu
            20                  25

<210> SEQ ID NO 57
<211> LENGTH: 14
<212> TYPE: PRT
<213> ORGANISM: Homo sapiens
<220> FEATURE:
<223> OTHER INFORMATION: RPS4X 40S ribosomal protein S4, X isoform;
      P62701_C41
<220> FEATURE:
<221> NAME/KEY: MOD_RES
<222> LOCATION: (5)..(5)
<223> OTHER INFORMATION: Site of chemical conjugation

<400> SEQUENCE: 57

Lys Leu Arg Glu Cys Leu Pro Leu Ile Ile Phe Leu Arg Asn
1               5                   10

<210> SEQ ID NO 58
<211> LENGTH: 22
<212> TYPE: PRT
<213> ORGANISM: Homo sapiens
<220> FEATURE:
<223> OTHER INFORMATION: RPL23 60S ribosomal protein L23;
      P62829_C28
<220> FEATURE:
<221> NAME/KEY: MOD_RES
<222> LOCATION: (14)..(14)
<223> OTHER INFORMATION: Site of chemical conjugation

<400> SEQUENCE: 58

Arg Ile Ser Leu Gly Leu Pro Val Gly Ala Val Ile Asn Cys Ala Asp
1               5                   10                  15

Asn Thr Gly Ala Lys Asn
            20
```

<210> SEQ ID NO 59
<211> LENGTH: 40
<212> TYPE: PRT
<213> ORGANISM: Homo sapiens
<220> FEATURE:
<223> OTHER INFORMATION: TUBA1A Tubulin alpha-1A chain;
     Q71U36_C25
<220> FEATURE:
<221> NAME/KEY: MOD_RES
<222> LOCATION: (24)..(24)
<223> OTHER INFORMATION: Site of chemical conjugation

<400> SEQUENCE: 59

Arg Glu Cys Ile Ser Ile His Val Gly Gln Ala Gly Val Gln Ile Gly
1               5                   10                  15

Asn Ala Cys Trp Glu Leu Tyr Cys Leu Glu His Gly Ile Gln Pro Asp
            20                  25                  30

Gly Gln Met Pro Ser Asp Lys Thr
        35                  40

<210> SEQ ID NO 60
<211> LENGTH: 32
<212> TYPE: PRT
<213> ORGANISM: Homo sapiens
<220> FEATURE:
<223> OTHER INFORMATION: ERO1L ERO1-like protein alpha;
     Q96HE7_C166
<220> FEATURE:
<221> NAME/KEY: MOD_RES
<222> LOCATION: (10)..(10)
<223> OTHER INFORMATION: Site of chemical conjugation

<400> SEQUENCE: 60

Lys His Asp Asp Ser Ser Asp Asn Phe Cys Glu Ala Asp Asp Ile Gln
1               5                   10                  15

Ser Pro Glu Ala Glu Tyr Val Asp Leu Leu Leu Asn Pro Glu Arg Tyr
            20                  25                  30

<210> SEQ ID NO 61
<211> LENGTH: 31
<212> TYPE: PRT
<213> ORGANISM: Homo sapiens
<220> FEATURE:
<223> OTHER INFORMATION: ERO1L ERO1-like protein alpha;
     Q96HE7_C241
<220> FEATURE:
<221> NAME/KEY: MOD_RES
<222> LOCATION: (27)..(27)
<223> OTHER INFORMATION: Site of chemical conjugation

<400> SEQUENCE: 61

Lys Arg Pro Leu Asn Pro Leu Ala Ser Gly Gln Gly Thr Ser Glu Glu
1               5                   10                  15

Asn Thr Phe Tyr Ser Trp Leu Glu Gly Leu Cys Val Glu Lys Arg
            20                  25                  30

<210> SEQ ID NO 62
<211> LENGTH: 16
<212> TYPE: PRT
<213> ORGANISM: Homo sapiens
<220> FEATURE:
<223> OTHER INFORMATION: TXNDC17 Thioredoxin domain-containing protein
     17; Q9BRA2_C43
<220> FEATURE:
<221> NAME/KEY: MOD_RES
<222> LOCATION: (4)..(4)
<223> OTHER INFORMATION: Site of chemical conjugation

<400> SEQUENCE: 62

```
Lys Ser Trp Cys Pro Asp Cys Val Gln Ala Glu Pro Val Val Arg Glu
1               5                   10                  15

<210> SEQ ID NO 63
<211> LENGTH: 17
<212> TYPE: PRT
<213> ORGANISM: Homo sapiens
<220> FEATURE:
<223> OTHER INFORMATION: PDIA4 Protein disulfide-isomerase A4;
      P13667_C555
<220> FEATURE:
<221> NAME/KEY: MOD_RES
<222> LOCATION: (12)..(12)
<223> OTHER INFORMATION: Site of chemical conjugation

<400> SEQUENCE: 63

Lys Asp Val Leu Ile Glu Phe Tyr Ala Pro Trp Cys Gly His Cys Lys
1               5                   10                  15

Gln

<210> SEQ ID NO 64
<211> LENGTH: 17
<212> TYPE: PRT
<213> ORGANISM: Homo sapiens
<220> FEATURE:
<223> OTHER INFORMATION: PDIA3 Protein disulfide-isomerase A3;
      P30101_C406
<220> FEATURE:
<221> NAME/KEY: MOD_RES
<222> LOCATION: (12)..(12)
<223> OTHER INFORMATION: Site of chemical conjugation

<400> SEQUENCE: 64

Lys Asp Val Leu Ile Glu Phe Tyr Ala Pro Trp Cys Gly His Cys Lys
1               5                   10                  15

Asn

<210> SEQ ID NO 65
<211> LENGTH: 11
<212> TYPE: PRT
<213> ORGANISM: Homo sapiens
<220> FEATURE:
<223> OTHER INFORMATION: TUBB Tubulin beta chain;
      P07437_C354
<220> FEATURE:
<221> NAME/KEY: MOD_RES
<222> LOCATION: (5)..(5)
<223> OTHER INFORMATION: Site of chemical conjugation

<400> SEQUENCE: 65

Lys Thr Ala Val Cys Asp Ile Pro Pro Arg Gly
1               5                   10

<210> SEQ ID NO 66
<211> LENGTH: 10
<212> TYPE: PRT
<213> ORGANISM: Homo sapiens
<220> FEATURE:
<223> OTHER INFORMATION: RPL24 60S ribosomal protein L24;
      P83731_C36
<220> FEATURE:
<221> NAME/KEY: MOD_RES
<222> LOCATION: (2)..(2)
<223> OTHER INFORMATION: Site of chemical conjugation

<400> SEQUENCE: 66

Lys Cys Glu Ser Ala Phe Leu Ser Lys Arg
1               5                   10
```

```
<210> SEQ ID NO 67
<211> LENGTH: 10
<212> TYPE: PRT
<213> ORGANISM: Homo sapiens
<220> FEATURE:
<223> OTHER INFORMATION: CORO1C Coronin-1C;
      Q9ULV4_C420
<220> FEATURE:
<221> NAME/KEY: MOD_RES
<222> LOCATION: (2)..(2)
<223> OTHER INFORMATION: Site of chemical conjugation

<400> SEQUENCE: 67

Lys Cys Asp Leu Ile Ser Ile Pro Lys Lys
1               5                   10

<210> SEQ ID NO 68
<211> LENGTH: 10
<212> TYPE: PRT
<213> ORGANISM: Homo sapiens
<220> FEATURE:
<223> OTHER INFORMATION: RPS27 40S ribosomal protein S27;
      P42677_C77
<220> FEATURE:
<221> NAME/KEY: MOD_RES
<222> LOCATION: (6)..(6)
<223> OTHER INFORMATION: Site of chemical conjugation

<400> SEQUENCE: 68

Arg Leu Thr Glu Gly Cys Ser Phe Arg Arg
1               5                   10

<210> SEQ ID NO 69
<211> LENGTH: 11
<212> TYPE: PRT
<213> ORGANISM: Homo sapiens
<220> FEATURE:
<223> OTHER INFORMATION: CLIC1 Chloride intracellular channel protein 1;
      O00299_C24
<220> FEATURE:
<221> NAME/KEY: MOD_RES
<222> LOCATION: (5)..(5)
<223> OTHER INFORMATION: Site of chemical conjugation

<400> SEQUENCE: 69

Lys Ile Gly Asn Cys Pro Phe Ser Gln Arg Leu
1               5                   10

<210> SEQ ID NO 70
<211> LENGTH: 13
<212> TYPE: PRT
<213> ORGANISM: Homo sapiens
<220> FEATURE:
<223> OTHER INFORMATION: SRP9 Signal recognition particle 9 kDa protein;
      P49458_C48
<220> FEATURE:
<221> NAME/KEY: MOD_RES
<222> LOCATION: (8)..(8)
<223> OTHER INFORMATION: Site of chemical conjugation

<400> SEQUENCE: 70

Lys Val Thr Asp Asp Leu Val Cys Leu Val Tyr Lys Thr
1               5                   10

<210> SEQ ID NO 71
<211> LENGTH: 21
<212> TYPE: PRT
<213> ORGANISM: Homo sapiens
<220> FEATURE:
```

```
<223> OTHER INFORMATION: ACAA2 3-ketoacyl-CoA thiolase, mitochondrial;
      P42765_C92
<220> FEATURE:
<221> NAME/KEY: MOD_RES
<222> LOCATION: (3)..(3)
<223> OTHER INFORMATION: Site of chemical conjugation

<400> SEQUENCE: 71

Arg Leu Cys Gly Ser Gly Phe Gln Ser Ile Val Asn Gly Cys Gln Glu
1               5                   10                  15

Ile Cys Val Lys Glu
            20

<210> SEQ ID NO 72
<211> LENGTH: 13
<212> TYPE: PRT
<213> ORGANISM: Homo sapiens
<220> FEATURE:
<223> OTHER INFORMATION: NONO Non-POU domain-containing octamer-binding
      protein; Q15233_C145
<220> FEATURE:
<221> NAME/KEY: MOD_RES
<222> LOCATION: (4)..(4)
<223> OTHER INFORMATION: Site of chemical conjugation

<400> SEQUENCE: 72

Arg Phe Ala Cys His Ser Ala Ser Leu Thr Val Arg Asn
1               5                   10

<210> SEQ ID NO 73
<211> LENGTH: 31
<212> TYPE: PRT
<213> ORGANISM: Homo sapiens
<220> FEATURE:
<223> OTHER INFORMATION: DNM2 Dynamin-2;
      P50570_C27
<220> FEATURE:
<221> NAME/KEY: MOD_RES
<222> LOCATION: (13)..(13)
<223> OTHER INFORMATION: Site of chemical conjugation

<400> SEQUENCE: 73

Lys Leu Gln Asp Ala Phe Ser Ser Ile Gly Gln Ser Cys His Leu Asp
1               5                   10                  15

Leu Pro Gln Ile Ala Val Val Gly Gly Gln Ser Ala Gly Lys Ser
            20                  25                  30

<210> SEQ ID NO 74
<211> LENGTH: 21
<212> TYPE: PRT
<213> ORGANISM: Homo sapiens
<220> FEATURE:
<223> OTHER INFORMATION: MCM3 DNA replication licensing factor MCM3;
      P25205_C119
<220> FEATURE:
<221> NAME/KEY: MOD_RES
<222> LOCATION: (6)..(6)
<223> OTHER INFORMATION: Site of chemical conjugation

<400> SEQUENCE: 74

Arg Thr Leu Thr Ser Cys Phe Leu Ser Cys Val Val Cys Val Glu Gly
1               5                   10                  15

Ile Val Thr Lys Cys
            20

<210> SEQ ID NO 75
<211> LENGTH: 13
<212> TYPE: PRT
```

```
<213> ORGANISM: Homo sapiens
<220> FEATURE:
<223> OTHER INFORMATION: NT5DC1 5-nucleotidase domain-containing protein
      1; Q5TFE4_C119
<220> FEATURE:
<221> NAME/KEY: MOD_RES
<222> LOCATION: (11)..(11)
<223> OTHER INFORMATION: Site of chemical conjugation

<400> SEQUENCE: 75

Lys His Phe Leu Ser Asp Thr Gly Met Ala Cys Arg Ser
1               5                   10

<210> SEQ ID NO 76
<211> LENGTH: 15
<212> TYPE: PRT
<213> ORGANISM: Homo sapiens
<220> FEATURE:
<223> OTHER INFORMATION: CNN2 Calponin-2;
      Q99439_C215
<220> FEATURE:
<221> NAME/KEY: MOD_RES
<222> LOCATION: (2)..(2)
<223> OTHER INFORMATION: Site of chemical conjugation

<400> SEQUENCE: 76

Lys Cys Ala Ser Gln Val Gly Met Thr Ala Pro Gly Thr Arg Arg
1               5                   10                  15

<210> SEQ ID NO 77
<211> LENGTH: 13
<212> TYPE: PRT
<213> ORGANISM: Homo sapiens
<220> FEATURE:
<223> OTHER INFORMATION: PSME1 Proteasome activator complex subunit 1;
      Q06323_C22
<220> FEATURE:
<221> NAME/KEY: MOD_RES
<222> LOCATION: (10)..(10)
<223> OTHER INFORMATION: Site of chemical conjugation

<400> SEQUENCE: 77

Lys Val Asp Val Phe Arg Glu Asp Leu Cys Thr Lys Thr
1               5                   10

<210> SEQ ID NO 78
<211> LENGTH: 15
<212> TYPE: PRT
<213> ORGANISM: Homo sapiens
<220> FEATURE:
<223> OTHER INFORMATION: SARS Serine--tRNA ligase, cytoplasmic;
      P49591_C438
<220> FEATURE:
<221> NAME/KEY: MOD_RES
<222> LOCATION: (4)..(4)
<223> OTHER INFORMATION: Site of chemical conjugation

<400> SEQUENCE: 78

Arg Thr Ile Cys Ala Ile Leu Glu Asn Tyr Gln Thr Glu Lys Gly
1               5                   10                  15

<210> SEQ ID NO 79
<211> LENGTH: 13
<212> TYPE: PRT
<213> ORGANISM: Homo sapiens
<220> FEATURE:
<223> OTHER INFORMATION: NUDCD1 NudC domain-containing protein 1;
      Q96RS6_C376
<220> FEATURE:
<221> NAME/KEY: MOD_RES
<222> LOCATION: (6)..(6)
```

<223> OTHER INFORMATION: Site of chemical conjugation

<400> SEQUENCE: 79

Arg Asp Ser Ala Gln Cys Ala Ala Ile Ala Glu Arg Leu
1               5                   10

<210> SEQ ID NO 80
<211> LENGTH: 34
<212> TYPE: PRT
<213> ORGANISM: Homo sapiens
<220> FEATURE:
<223> OTHER INFORMATION: TUBA1A Tubulin alpha-1A chain;
      Q71U36_C129
<220> FEATURE:
<221> NAME/KEY: MOD_RES
<222> LOCATION: (6)..(6)
<223> OTHER INFORMATION: Site of chemical conjugation

<400> SEQUENCE: 80

Lys Leu Ala Asp Gln Cys Thr Gly Leu Gln Gly Phe Leu Val Phe His
1               5                   10                  15

Ser Phe Gly Gly Gly Thr Gly Ser Gly Phe Thr Ser Leu Leu Met Glu
            20                  25                  30

Arg Leu

<210> SEQ ID NO 81
<211> LENGTH: 12
<212> TYPE: PRT
<213> ORGANISM: Homo sapiens
<220> FEATURE:
<223> OTHER INFORMATION: NAA15 N-alpha-acetyltransferase 15, NatA
      auxiliary subunit; Q9BXJ9_C721
<220> FEATURE:
<221> NAME/KEY: MOD_RES
<222> LOCATION: (8)..(8)
<223> OTHER INFORMATION: Site of chemical conjugation

<400> SEQUENCE: 81

Arg Leu Phe Asn Thr Ala Val Cys Glu Ser Lys Asp
1               5                   10

<210> SEQ ID NO 82
<211> LENGTH: 13
<212> TYPE: PRT
<213> ORGANISM: Homo sapiens
<220> FEATURE:
<223> OTHER INFORMATION: CSTF2 Cleavage stimulation factor subunit 2;
      P33240_C150
<220> FEATURE:
<221> NAME/KEY: MOD_RES
<222> LOCATION: (3)..(3)
<223> OTHER INFORMATION: Site of chemical conjugation

<400> SEQUENCE: 82

Lys Leu Cys Val Gln Asn Ser Pro Gln Glu Ala Arg Asn
1               5                   10

<210> SEQ ID NO 83
<211> LENGTH: 38
<212> TYPE: PRT
<213> ORGANISM: Homo sapiens
<220> FEATURE:
<223> OTHER INFORMATION: AIMP2 Aminoacyl tRNA synthase complex-
      interacting multifunctional protein 2; Q13155_C291
<220> FEATURE:
<221> NAME/KEY: MOD_RES
<222> LOCATION: (27)..(27)
<223> OTHER INFORMATION: Site of chemical conjugation

<400> SEQUENCE: 83

Lys Ser Pro Trp Leu Ala Gly Asn Glu Leu Thr Val Ala Asp Val Val
1               5                   10                  15

Leu Trp Ser Val Leu Gln Gln Ile Gly Gly Cys Ser Val Thr Val Pro
                20                  25                  30

Ala Asn Val Gln Arg Trp
            35

<210> SEQ ID NO 84
<211> LENGTH: 13
<212> TYPE: PRT
<213> ORGANISM: Homo sapiens
<220> FEATURE:
<223> OTHER INFORMATION: TIPRL TIP41-like protein;
      O75663_C87
<220> FEATURE:
<221> NAME/KEY: MOD_RES
<222> LOCATION: (4)..(4)
<223> OTHER INFORMATION: Site of chemical conjugation

<400> SEQUENCE: 84

Lys Val Ala Cys Ala Glu Glu Trp Gln Glu Ser Arg Thr
1               5                   10

<210> SEQ ID NO 85
<211> LENGTH: 10
<212> TYPE: PRT
<213> ORGANISM: Homo sapiens
<220> FEATURE:
<223> OTHER INFORMATION: GNB2L1 Guanine nucleotide-binding protein
      subunit beta-2-like 1; P63244_C182
<220> FEATURE:
<221> NAME/KEY: MOD_RES
<222> LOCATION: (8)..(8)
<223> OTHER INFORMATION: Site of chemical conjugation

<400> SEQUENCE: 85

Lys Val Trp Asn Leu Ala Asn Cys Lys Leu
1               5                   10

<210> SEQ ID NO 86
<211> LENGTH: 21
<212> TYPE: PRT
<213> ORGANISM: Homo sapiens
<220> FEATURE:
<223> OTHER INFORMATION: EIF3M Eukaryotic translation initiation factor
      3 subunit; Q7L2H7_C134
<220> FEATURE:
<221> NAME/KEY: MOD_RES
<222> LOCATION: (6)..(6)
<223> OTHER INFORMATION: Site of chemical conjugation

<400> SEQUENCE: 86

Lys Val Ala Ala Ser Cys Gly Ala Ile Gln Tyr Ile Pro Thr Glu Leu
1               5                   10                  15

Asp Gln Val Arg Lys
            20

<210> SEQ ID NO 87
<211> LENGTH: 30
<212> TYPE: PRT
<213> ORGANISM: Homo sapiens
<220> FEATURE:
<223> OTHER INFORMATION: FASN Fatty acid synthase;
      P49327_C2359
<220> FEATURE:
<221> NAME/KEY: MOD_RES
<222> LOCATION: (6)..(6)

```
<223> OTHER INFORMATION: Site of chemical conjugation

<400> SEQUENCE: 87

Lys Leu Thr Pro Gly Cys Glu Ala Glu Ala Glu Thr Glu Ala Ile Cys
1               5                   10                  15

Phe Phe Val Gln Gln Phe Thr Asp Met Glu His Asn Arg Val
            20                  25                  30

<210> SEQ ID NO 88
<211> LENGTH: 38
<212> TYPE: PRT
<213> ORGANISM: Homo sapiens
<220> FEATURE:
<223> OTHER INFORMATION: TMPO Lamina-associated polypeptide 2, isoform
      alpha; P42166_C561
<220> FEATURE:
<221> NAME/KEY: MOD_RES
<222> LOCATION: (27)..(27)
<223> OTHER INFORMATION: Site of chemical conjugation

<400> SEQUENCE: 88

Lys Val Asp Asp Glu Ile Leu Gly Phe Ile Ser Glu Ala Thr Pro Leu
1               5                   10                  15

Gly Gly Ile Gln Ala Ala Ser Thr Glu Ser Cys Asn Gln Gln Leu Asp
            20                  25                  30

Leu Ala Leu Cys Arg Ala
        35

<210> SEQ ID NO 89
<211> LENGTH: 9
<212> TYPE: PRT
<213> ORGANISM: Homo sapiens
<220> FEATURE:
<223> OTHER INFORMATION: ACAT1 Acetyl-CoA acetyltransferase,
      mitochondrial; P24752_C126
<220> FEATURE:
<221> NAME/KEY: MOD_RES
<222> LOCATION: (3)..(3)
<223> OTHER INFORMATION: Site of chemical conjugation

<400> SEQUENCE: 89

Lys Val Cys Ala Ser Gly Met Lys Ala
1               5

<210> SEQ ID NO 90
<211> LENGTH: 13
<212> TYPE: PRT
<213> ORGANISM: Homo sapiens
<220> FEATURE:
<223> OTHER INFORMATION: RPL4 60S ribosomal protein L4;
      P36578_C96
<220> FEATURE:
<221> NAME/KEY: MOD_RES
<222> LOCATION: (11)..(11)
<223> OTHER INFORMATION: Site of chemical conjugation

<400> SEQUENCE: 90

Arg Ser Gly Gln Gly Ala Phe Gly Asn Met Cys Arg Gly
1               5                   10

<210> SEQ ID NO 91
<211> LENGTH: 10
<212> TYPE: PRT
<213> ORGANISM: Homo sapiens
<220> FEATURE:
<223> OTHER INFORMATION: THUMPD1 THUMP domain-containing protein 1;
      Q9NXG2_C31
<220> FEATURE:
```

```
<221> NAME/KEY: MOD_RES
<222> LOCATION: (3)..(3)
<223> OTHER INFORMATION: Site of chemical conjugation

<400> SEQUENCE: 91

Arg Arg Cys Asp Ala Gly Gly Pro Arg Gln
1               5                   10

<210> SEQ ID NO 92
<211> LENGTH: 18
<212> TYPE: PRT
<213> ORGANISM: Homo sapiens
<220> FEATURE:
<223> OTHER INFORMATION: P4HB Protein disulfide-isomerase;
      P07237_C397
<220> FEATURE:
<221> NAME/KEY: MOD_RES
<222> LOCATION: (13)..(13)
<223> OTHER INFORMATION: Site of chemical conjugation

<400> SEQUENCE: 92

Lys Lys Asn Val Phe Val Glu Phe Tyr Ala Pro Trp Cys Gly His Cys
1               5                   10                  15

Lys Gln

<210> SEQ ID NO 93
<211> LENGTH: 15
<212> TYPE: PRT
<213> ORGANISM: Homo sapiens
<220> FEATURE:
<223> OTHER INFORMATION: DCK Deoxycytidine kinase;
      P27707_C9
<220> FEATURE:
<221> NAME/KEY: MOD_RES
<222> LOCATION: (3)..(3)
<223> OTHER INFORMATION: Site of chemical conjugation

<400> SEQUENCE: 93

Arg Ser Cys Pro Ser Phe Ser Ala Ser Ser Glu Gly Thr Arg Ile
1               5                   10                  15

<210> SEQ ID NO 94
<211> LENGTH: 9
<212> TYPE: PRT
<213> ORGANISM: Homo sapiens
<220> FEATURE:
<223> OTHER INFORMATION: EIF3F Eukaryotic translation initiation factor
      3 subunit; O00303_C256
<220> FEATURE:
<221> NAME/KEY: MOD_RES
<222> LOCATION: (3)..(3)
<223> OTHER INFORMATION: Site of chemical conjugation

<400> SEQUENCE: 94

Lys Thr Cys Phe Ser Pro Asn Arg Val
1               5

<210> SEQ ID NO 95
<211> LENGTH: 32
<212> TYPE: PRT
<213> ORGANISM: Homo sapiens
<220> FEATURE:
<223> OTHER INFORMATION: SNX6 Sorting nexin-6;
      Q9UNH7_C264
<220> FEATURE:
<221> NAME/KEY: MOD_RES
<222> LOCATION: (26)..(26)
<223> OTHER INFORMATION: Site of chemical conjugation

<400> SEQUENCE: 95
```

```
Lys Ser Ala Asp Asp Tyr Asn Arg Ile Gly Ser Ser Leu Tyr Ala
1               5                   10                  15

Leu Gly Thr Gln Asp Ser Thr Asp Ile Cys Lys Phe Phe Leu Lys Val
                20                  25                  30

<210> SEQ ID NO 96
<211> LENGTH: 36
<212> TYPE: PRT
<213> ORGANISM: Homo sapiens
<220> FEATURE:
<223> OTHER INFORMATION: PDIA6 Protein disulfide-isomerase A6;
      Q15084_C190
<220> FEATURE:
<221> NAME/KEY: MOD_RES
<222> LOCATION: (31)..(31)
<223> OTHER INFORMATION: Site of chemical conjugation

<400> SEQUENCE: 96

Lys Asp Val Ile Glu Leu Thr Asp Asp Ser Phe Asp Lys Asn Val Leu
1               5                   10                  15

Asp Ser Glu Asp Val Trp Met Val Glu Phe Tyr Ala Pro Trp Cys Gly
                20                  25                  30

His Cys Lys Asn
        35

<210> SEQ ID NO 97
<211> LENGTH: 11
<212> TYPE: PRT
<213> ORGANISM: Homo sapiens
<220> FEATURE:
<223> OTHER INFORMATION: HNRNPR Heterogeneous nuclear ribonucleoprotein
      R; O43390_C99
<220> FEATURE:
<221> NAME/KEY: MOD_RES
<222> LOCATION: (6)..(6)
<223> OTHER INFORMATION: Site of chemical conjugation

<400> SEQUENCE: 97

Lys Ser Ala Phe Leu Cys Gly Val Met Lys Thr
1               5                   10

<210> SEQ ID NO 98
<211> LENGTH: 45
<212> TYPE: PRT
<213> ORGANISM: Homo sapiens
<220> FEATURE:
<223> OTHER INFORMATION: COG3 Conserved oligomeric Golgi complex subunit
      3; Q96JB2_C65
<220> FEATURE:
<221> NAME/KEY: MOD_RES
<222> LOCATION: (19)..(19)
<223> OTHER INFORMATION: Site of chemical conjugation

<400> SEQUENCE: 98

Lys Ala Ala Ala Glu Asn Leu Pro Val Pro Ala Glu Leu Pro Ile Glu
1               5                   10                  15

Asp Leu Cys Ser Leu Thr Ser Gln Ser Leu Pro Ile Glu Leu Thr Ser
                20                  25                  30

Val Val Pro Glu Ser Thr Glu Asp Ile Leu Leu Lys Gly
        35                  40                  45

<210> SEQ ID NO 99
<211> LENGTH: 10
<212> TYPE: PRT
<213> ORGANISM: Homo sapiens
<220> FEATURE:
```

<223> OTHER INFORMATION: CRKL Crk-like protein;
      P46109_C249
<220> FEATURE:
<221> NAME/KEY: MOD_RES
<222> LOCATION: (5)..(5)
<223> OTHER INFORMATION: Site of chemical conjugation

<400> SEQUENCE: 99

Lys Arg Val Pro Cys Ala Tyr Asp Lys Thr
1               5                   10

<210> SEQ ID NO 100
<211> LENGTH: 18
<212> TYPE: PRT
<213> ORGANISM: Homo sapiens
<220> FEATURE:
<223> OTHER INFORMATION: RPL30 60S ribosomal protein L30;
      P62888_C92
<220> FEATURE:
<221> NAME/KEY: MOD_RES
<222> LOCATION: (3)..(3)
<223> OTHER INFORMATION: Site of chemical conjugation

<400> SEQUENCE: 100

Arg Val Cys Thr Leu Ala Ile Ile Asp Pro Gly Asp Ser Asp Ile Ile
1               5                   10                  15

Arg Ser

<210> SEQ ID NO 101
<211> LENGTH: 29
<212> TYPE: PRT
<213> ORGANISM: Homo sapiens
<220> FEATURE:
<223> OTHER INFORMATION: TBC1D23 TBC1 domain family member 23;
      Q9NUY8_C283
<220> FEATURE:
<221> NAME/KEY: MOD_RES
<222> LOCATION: (26)..(26)
<223> OTHER INFORMATION: Site of chemical conjugation

<400> SEQUENCE: 101

Lys Phe Leu Glu Asn Thr Pro Ser Ser Leu Asn Ile Glu Asp Ile Glu
1               5                   10                  15

Asp Leu Phe Ser Leu Ala Gln Tyr Tyr Cys Ser Lys Thr
            20                  25

<210> SEQ ID NO 102
<211> LENGTH: 26
<212> TYPE: PRT
<213> ORGANISM: Homo sapiens
<220> FEATURE:
<223> OTHER INFORMATION: NCBP1 Nuclear cap-binding protein subunit 1;
      Q09161_C44
<220> FEATURE:
<221> NAME/KEY: MOD_RES
<222> LOCATION: (4)..(4)
<223> OTHER INFORMATION: Site of chemical conjugation

<400> SEQUENCE: 102

Lys Ser Ala Cys Ser Leu Glu Ser Asn Leu Glu Gly Leu Ala Gly Val
1               5                   10                  15

Leu Glu Ala Asp Leu Pro Asn Tyr Lys Ser
            20                  25

<210> SEQ ID NO 103
<211> LENGTH: 19
<212> TYPE: PRT
<213> ORGANISM: Homo sapiens

```
<220> FEATURE:
<223> OTHER INFORMATION: DCTN4 Dynactin subunit 4;
      Q9UJW0_C258
<220> FEATURE:
<221> NAME/KEY: MOD_RES
<222> LOCATION: (11)..(11)
<223> OTHER INFORMATION: Site of chemical conjugation

<400> SEQUENCE: 103

Arg Leu Leu Gln Pro Asp Phe Gln Pro Val Cys Ala Ser Gln Leu Tyr
1               5                   10                  15

Pro Arg His

<210> SEQ ID NO 104
<211> LENGTH: 37
<212> TYPE: PRT
<213> ORGANISM: Homo sapiens
<220> FEATURE:
<223> OTHER INFORMATION: OGT UDP-N-acetylglucosamine--peptide
      N-acetylglucosamine; O15294_C758
<220> FEATURE:
<221> NAME/KEY: MOD_RES
<222> LOCATION: (2)..(2)
<223> OTHER INFORMATION: Site of chemical conjugation

<400> SEQUENCE: 104

Lys Cys Pro Asp Gly Gly Asp Asn Ala Asp Ser Ser Asn Thr Ala Leu
1               5                   10                  15

Asn Met Pro Val Ile Pro Met Asn Thr Ile Ala Glu Ala Val Ile Glu
            20                  25                  30

Met Ile Asn Arg Gly
        35

<210> SEQ ID NO 105
<211> LENGTH: 28
<212> TYPE: PRT
<213> ORGANISM: Homo sapiens
<220> FEATURE:
<223> OTHER INFORMATION: HSPA9 Stress-70 protein, mitochondrial;
      P38646_C317
<220> FEATURE:
<221> NAME/KEY: MOD_RES
<222> LOCATION: (4)..(4)
<223> OTHER INFORMATION: Site of chemical conjugation

<400> SEQUENCE: 105

Lys Ala Lys Cys Glu Leu Ser Ser Ser Val Gln Thr Asp Ile Asn Leu
1               5                   10                  15

Pro Tyr Leu Thr Met Asp Ser Ser Gly Pro Lys His
            20                  25

<210> SEQ ID NO 106
<211> LENGTH: 16
<212> TYPE: PRT
<213> ORGANISM: Homo sapiens
<220> FEATURE:
<223> OTHER INFORMATION: FN3KRP Ketosamine-3-kinase;
      Q9HA64_C24
<220> FEATURE:
<221> NAME/KEY: MOD_RES
<222> LOCATION: (10)..(10)
<223> OTHER INFORMATION: Site of chemical conjugation

<400> SEQUENCE: 106

Arg Ala Thr Gly His Ser Gly Gly Gly Cys Ile Ser Gln Gly Arg Ser
1               5                   10                  15
```

```
<210> SEQ ID NO 107
<211> LENGTH: 55
<212> TYPE: PRT
<213> ORGANISM: Homo sapiens
<220> FEATURE:
<223> OTHER INFORMATION: DYNC1LI1 Cytoplasmic dynein 1 light
      intermediate chain 1; Q9Y6G9_C51
<220> FEATURE:
<221> NAME/KEY: MOD_RES
<222> LOCATION: (46)..(46)
<223> OTHER INFORMATION: Site of chemical conjugation

<400> SEQUENCE: 107

Arg Val Gly Ser Phe Gly Ser Ser Pro Pro Gly Leu Ser Ser Thr Tyr
1               5                   10                  15

Thr Gly Gly Pro Leu Gly Asn Glu Ile Ala Ser Gly Asn Gly Gly Ala
            20                  25                  30

Ala Ala Gly Asp Asp Glu Asp Gly Gln Asn Leu Trp Ser Cys Ile Leu
        35                  40                  45

Ser Glu Val Ser Thr Arg Ser
    50                  55

<210> SEQ ID NO 108
<211> LENGTH: 15
<212> TYPE: PRT
<213> ORGANISM: Homo sapiens
<220> FEATURE:
<223> OTHER INFORMATION: HNRNPF Heterogeneous nuclear ribonucleoprotein
      F; P52597_C267
<220> FEATURE:
<221> NAME/KEY: MOD_RES
<222> LOCATION: (6)..(6)
<223> OTHER INFORMATION: Site of chemical conjugation

<400> SEQUENCE: 108

Arg Asp Leu Ser Tyr Cys Leu Ser Gly Met Tyr Asp His Arg Tyr
1               5                   10                  15

<210> SEQ ID NO 109
<211> LENGTH: 25
<212> TYPE: PRT
<213> ORGANISM: Homo sapiens
<220> FEATURE:
<223> OTHER INFORMATION: PARK7 Protein DJ-1;
      Q99497_C106
<220> FEATURE:
<221> NAME/KEY: MOD_RES
<222> LOCATION: (8)..(8)
<223> OTHER INFORMATION: Site of chemical conjugation

<400> SEQUENCE: 109

Lys Gly Leu Ile Ala Ala Ile Cys Ala Gly Pro Thr Ala Leu Leu Ala
1               5                   10                  15

His Glu Ile Gly Phe Gly Ser Lys Val
            20                  25

<210> SEQ ID NO 110
<211> LENGTH: 26
<212> TYPE: PRT
<213> ORGANISM: Homo sapiens
<220> FEATURE:
<223> OTHER INFORMATION: GSDMD Gasdermin-D;
      P57764_C268
<220> FEATURE:
<221> NAME/KEY: MOD_RES
<222> LOCATION: (2)..(2)
<223> OTHER INFORMATION: Site of chemical conjugation

<400> SEQUENCE: 110
```

-continued

```
Arg Cys Leu His Asn Phe Leu Thr Asp Gly Val Pro Ala Glu Gly Ala
1               5                   10                  15

Phe Thr Glu Asp Phe Gln Gly Leu Arg Ala
            20                  25

<210> SEQ ID NO 111
<211> LENGTH: 12
<212> TYPE: PRT
<213> ORGANISM: Homo sapiens
<220> FEATURE:
<223> OTHER INFORMATION: PGP Phosphoglycolate phosphatase;
      A6NDG6_C297
<220> FEATURE:
<221> NAME/KEY: MOD_RES
<222> LOCATION: (8)..(8)
<223> OTHER INFORMATION: Site of chemical conjugation

<400> SEQUENCE: 111

Lys Asn Asn Gln Glu Ser Asp Cys Val Ser Lys Lys
1               5                   10

<210> SEQ ID NO 112
<211> LENGTH: 16
<212> TYPE: PRT
<213> ORGANISM: Homo sapiens
<220> FEATURE:
<223> OTHER INFORMATION: MCM6 DNA replication licensing factor MCM6;
      Q14566_C301
<220> FEATURE:
<221> NAME/KEY: MOD_RES
<222> LOCATION: (7)..(7)
<223> OTHER INFORMATION: Site of chemical conjugation

<400> SEQUENCE: 112

Arg Leu Val Phe Leu Ala Cys Cys Val Ala Pro Thr Asn Pro Arg Phe
1               5                   10                  15

<210> SEQ ID NO 113
<211> LENGTH: 18
<212> TYPE: PRT
<213> ORGANISM: Homo sapiens
<220> FEATURE:
<223> OTHER INFORMATION: CLTC Clathrin heavy chain 1;
      Q00610_C870
<220> FEATURE:
<221> NAME/KEY: MOD_RES
<222> LOCATION: (6)..(6)
<223> OTHER INFORMATION: Site of chemical conjugation

<400> SEQUENCE: 113

Arg Ile His Glu Gly Cys Glu Glu Pro Ala Thr His Asn Ala Leu Ala
1               5                   10                  15

Lys Ile

<210> SEQ ID NO 114
<211> LENGTH: 33
<212> TYPE: PRT
<213> ORGANISM: Homo sapiens
<220> FEATURE:
<223> OTHER INFORMATION: MMS19 MMS19 nucleotide excision repair protein
      homolog; Q96T76_C848
<220> FEATURE:
<221> NAME/KEY: MOD_RES
<222> LOCATION: (26)..(26)
<223> OTHER INFORMATION: Site of chemical conjugation

<400> SEQUENCE: 114

Arg Leu Met Gly Leu Leu Ser Asp Pro Glu Leu Gly Pro Ala Ala Ala
```

```
                1               5                  10                  15
Asp Gly Phe Ser Leu Leu Met Ser Asp Cys Thr Asp Val Leu Thr Arg
                20                  25                  30

Ala

<210> SEQ ID NO 115
<211> LENGTH: 12
<212> TYPE: PRT
<213> ORGANISM: Homo sapiens
<220> FEATURE:
<223> OTHER INFORMATION: ACTR3 Actin-related protein 3;
      P61158_C235
<220> FEATURE:
<221> NAME/KEY: MOD_RES
<222> LOCATION: (6)..(6)
<223> OTHER INFORMATION: Site of chemical conjugation

<400> SEQUENCE: 115

Arg Tyr Ser Tyr Val Cys Pro Asp Leu Val Lys Glu
1               5                  10

<210> SEQ ID NO 116
<211> LENGTH: 10
<212> TYPE: PRT
<213> ORGANISM: Homo sapiens
<220> FEATURE:
<223> OTHER INFORMATION: CFL1 Cofilin-1;
      P23528_C80
<220> FEATURE:
<221> NAME/KEY: MOD_RES
<222> LOCATION: (8)..(8)
<223> OTHER INFORMATION: Site of chemical conjugation

<400> SEQUENCE: 116

Lys Met Leu Pro Asp Lys Asp Cys Arg Tyr
1               5                  10

<210> SEQ ID NO 117
<211> LENGTH: 31
<212> TYPE: PRT
<213> ORGANISM: Homo sapiens
<220> FEATURE:
<223> OTHER INFORMATION: TIGAR Fructose-2,6-bisphosphatase TIGAR;
      Q9NQ88_C161
<220> FEATURE:
<221> NAME/KEY: MOD_RES
<222> LOCATION: (17)..(17)
<223> OTHER INFORMATION: Site of chemical conjugation

<400> SEQUENCE: 117

Lys Glu Ala Asp Gln Lys Glu Gln Phe Ser Gln Gly Ser Pro Ser Asn
1               5                  10                  15

Cys Leu Glu Thr Ser Leu Ala Glu Ile Phe Pro Leu Gly Lys Asn
                20                  25                  30

<210> SEQ ID NO 118
<211> LENGTH: 26
<212> TYPE: PRT
<213> ORGANISM: Homo sapiens
<220> FEATURE:
<223> OTHER INFORMATION: CPSF3 Cleavage and polyadenylation specificity
      factor subunit 3; Q9UKF6_C498
<220> FEATURE:
<221> NAME/KEY: MOD_RES
<222> LOCATION: (11)..(11)
<223> OTHER INFORMATION: Site of chemical conjugation

<400> SEQUENCE: 118
```

Arg Asn Phe Asn Tyr His Ile Leu Ser Pro Cys Asp Leu Ser Asn Tyr
1               5                   10                  15

Thr Asp Leu Ala Met Ser Thr Val Lys Gln
            20                  25

<210> SEQ ID NO 119
<211> LENGTH: 14
<212> TYPE: PRT
<213> ORGANISM: Homo sapiens
<220> FEATURE:
<223> OTHER INFORMATION: SMARCC2 SWI/SNF complex subunit SMARCC2;
      Q8TAQ2_C145
<220> FEATURE:
<221> NAME/KEY: MOD_RES
<222> LOCATION: (7)..(7)
<223> OTHER INFORMATION: Site of chemical conjugation

<400> SEQUENCE: 119

Arg Pro Asn Ile Phe Leu Cys Pro Glu Ile Glu Pro Lys Leu
1               5                   10

<210> SEQ ID NO 120
<211> LENGTH: 20
<212> TYPE: PRT
<213> ORGANISM: Homo sapiens
<220> FEATURE:
<223> OTHER INFORMATION: UBE2L3 Ubiquitin-conjugating enzyme E2 L3;
      P68036_C86
<220> FEATURE:
<221> NAME/KEY: MOD_RES
<222> LOCATION: (5)..(5)
<223> OTHER INFORMATION: Site of chemical conjugation

<400> SEQUENCE: 120

Lys Gly Gln Val Cys Leu Pro Val Ile Ser Ala Glu Asn Trp Lys Pro
1               5                   10                  15

Ala Thr Lys Thr
            20

<210> SEQ ID NO 121
<211> LENGTH: 16
<212> TYPE: PRT
<213> ORGANISM: Homo sapiens
<220> FEATURE:
<223> OTHER INFORMATION: MOB4 MOB-like protein phocein;
      Q9Y3A3_C134
<220> FEATURE:
<221> NAME/KEY: MOD_RES
<222> LOCATION: (9)..(9)
<223> OTHER INFORMATION: Site of chemical conjugation

<400> SEQUENCE: 121

Arg His Thr Leu Asp Gly Ala Ala Cys Leu Leu Asn Ser Asn Lys Tyr
1               5                   10                  15

<210> SEQ ID NO 122
<211> LENGTH: 10
<212> TYPE: PRT
<213> ORGANISM: Homo sapiens
<220> FEATURE:
<223> OTHER INFORMATION: AARS Alanine--tRNA ligase, cytoplasmic;
      P49588_C773
<220> FEATURE:
<221> NAME/KEY: MOD_RES
<222> LOCATION: (2)..(2)
<223> OTHER INFORMATION: Site of chemical conjugation

<400> SEQUENCE: 122

Lys Cys Leu Ser Val Met Glu Ala Lys Val

<210> SEQ ID NO 123
<211> LENGTH: 13
<212> TYPE: PRT
<213> ORGANISM: Homo sapiens
<220> FEATURE:
<223> OTHER INFORMATION: GMPPA Mannose-1-phosphate guanyltransferase
    alpha; Q96IJ6_C389
<220> FEATURE:
<221> NAME/KEY: MOD_RES
<222> LOCATION: (11)..(11)
<223> OTHER INFORMATION: Site of chemical conjugation

<400> SEQUENCE: 123

Lys Leu Leu Pro Ala Ile Thr Ile Leu Gly Cys Arg Val
1               5                   10

<210> SEQ ID NO 124
<211> LENGTH: 11
<212> TYPE: PRT
<213> ORGANISM: Homo sapiens
<220> FEATURE:
<223> OTHER INFORMATION: RPL10 60S ribosomal protein L10;
    P27635_C105
<220> FEATURE:
<221> NAME/KEY: MOD_RES
<222> LOCATION: (5)..(5)
<223> OTHER INFORMATION: Site of chemical conjugation

<400> SEQUENCE: 124

Lys Met Leu Ser Cys Ala Gly Ala Asp Arg Leu
1               5                   10

<210> SEQ ID NO 125
<211> LENGTH: 9
<212> TYPE: PRT
<213> ORGANISM: Homo sapiens
<220> FEATURE:
<223> OTHER INFORMATION: ARPC3 Actin-related protein 2/3 complex subunit
    3; O15145_C162
<220> FEATURE:
<221> NAME/KEY: MOD_RES
<222> LOCATION: (5)..(5)
<223> OTHER INFORMATION: Site of chemical conjugation

<400> SEQUENCE: 125

Lys Trp Trp Thr Cys Phe Val Lys Arg
1               5

<210> SEQ ID NO 126
<211> LENGTH: 16
<212> TYPE: PRT
<213> ORGANISM: Homo sapiens
<220> FEATURE:
<223> OTHER INFORMATION: CCT5 T-complex protein 1 subunit epsilon;
    P48643_C253
<220> FEATURE:
<221> NAME/KEY: MOD_RES
<222> LOCATION: (7)..(7)
<223> OTHER INFORMATION: Site of chemical conjugation

<400> SEQUENCE: 126

Lys Ile Ala Ile Leu Thr Cys Pro Phe Glu Pro Pro Lys Pro Lys Thr
1               5                   10                  15

<210> SEQ ID NO 127
<211> LENGTH: 44
<212> TYPE: PRT
<213> ORGANISM: Homo sapiens

```
<220> FEATURE:
<223> OTHER INFORMATION: MTHFD1 C-1-tetrahydrofolate synthase,
      cytoplasmic; P11586_C918
<220> FEATURE:
<221> NAME/KEY: MOD_RES
<222> LOCATION: (27)..(27)
<223> OTHER INFORMATION: Site of chemical conjugation

<400> SEQUENCE: 127

Arg Ala Ser Val Gly Ala Gly Phe Leu Tyr Pro Leu Val Gly Thr Met
1               5                   10                  15

Ser Thr Met Pro Gly Leu Pro Thr Arg Pro Cys Phe Tyr Asp Ile Asp
            20                  25                  30

Leu Asp Pro Glu Thr Glu Gln Val Asn Gly Leu Phe
        35                  40

<210> SEQ ID NO 128
<211> LENGTH: 22
<212> TYPE: PRT
<213> ORGANISM: Homo sapiens
<220> FEATURE:
<223> OTHER INFORMATION: ATXN7L3B Putative ataxin-7-like protein 3B;
      Q96GX2_C75
<220> FEATURE:
<221> NAME/KEY: MOD_RES
<222> LOCATION: (5)..(5)
<223> OTHER INFORMATION: Site of chemical conjugation

<400> SEQUENCE: 128

Arg Leu Pro Leu Cys Ser Leu Pro Gly Glu Pro Gly Asn Gly Pro Asp
1               5                   10                  15

Gln Gln Leu Gln Arg Ser
            20

<210> SEQ ID NO 129
<211> LENGTH: 13
<212> TYPE: PRT
<213> ORGANISM: Homo sapiens
<220> FEATURE:
<223> OTHER INFORMATION: TCP1 T-complex protein 1 subunit alpha;
      P17987_C76
<220> FEATURE:
<221> NAME/KEY: MOD_RES
<222> LOCATION: (4)..(4)
<223> OTHER INFORMATION: Site of chemical conjugation

<400> SEQUENCE: 129

Lys Val Leu Cys Glu Leu Ala Asp Leu Gln Asp Lys Glu
1               5                   10

<210> SEQ ID NO 130
<211> LENGTH: 38
<212> TYPE: PRT
<213> ORGANISM: Homo sapiens
<220> FEATURE:
<223> OTHER INFORMATION: TMOD3 Tropomodulin-3;
      Q9NYL9_C132
<220> FEATURE:
<221> NAME/KEY: MOD_RES
<222> LOCATION: (21)..(21)
<223> OTHER INFORMATION: Site of chemical conjugation

<400> SEQUENCE: 130

Lys Val Ser Leu Asp Pro Glu Leu Glu Glu Ala Leu Thr Ser Ala Ser
1               5                   10                  15

Asp Thr Glu Leu Cys Asp Leu Ala Ala Ile Leu Gly Met His Asn Leu
            20                  25                  30
```

Ile Thr Asn Thr Lys Phe
         35

<210> SEQ ID NO 131
<211> LENGTH: 13
<212> TYPE: PRT
<213> ORGANISM: Homo sapiens
<220> FEATURE:
<223> OTHER INFORMATION: DNM1L Dynamin-1-like protein;
      O00429_C367
<220> FEATURE:
<221> NAME/KEY: MOD_RES
<222> LOCATION: (3)..(3)
<223> OTHER INFORMATION: Site of chemical conjugation

<400> SEQUENCE: 131

Arg Ile Cys Tyr Ile Phe His Glu Thr Phe Gly Arg Thr
1               5                   10

<210> SEQ ID NO 132
<211> LENGTH: 11
<212> TYPE: PRT
<213> ORGANISM: Homo sapiens
<220> FEATURE:
<223> OTHER INFORMATION: AIMP2 Aminoacyl tRNA synthase complex-
      interacting multifunctional protein 2; Q13155_C23
<220> FEATURE:
<221> NAME/KEY: MOD_RES
<222> LOCATION: (7)..(7)
<223> OTHER INFORMATION: Site of chemical conjugation

<400> SEQUENCE: 132

Arg Val Glu Leu Pro Thr Cys Met Tyr Arg Leu
1               5                   10

<210> SEQ ID NO 133
<211> LENGTH: 25
<212> TYPE: PRT
<213> ORGANISM: Homo sapiens
<220> FEATURE:
<223> OTHER INFORMATION: PDIA3 Protein disulfide-isomerase A3;
      P30101_C57
<220> FEATURE:
<221> NAME/KEY: MOD_RES
<222> LOCATION: (20)..(20)
<223> OTHER INFORMATION: Site of chemical conjugation

<400> SEQUENCE: 133

Arg Ile Ser Asp Thr Gly Ser Ala Gly Leu Met Leu Val Glu Phe Phe
1               5                   10                  15

Ala Pro Trp Cys Gly His Cys Lys Arg
            20                  25

<210> SEQ ID NO 134
<211> LENGTH: 8
<212> TYPE: PRT
<213> ORGANISM: Homo sapiens
<220> FEATURE:
<223> OTHER INFORMATION: DNPEP Aspartyl aminopeptidase;
      Q9ULA0_C144
<220> FEATURE:
<221> NAME/KEY: MOD_RES
<222> LOCATION: (2)..(2)
<223> OTHER INFORMATION: Site of chemical conjugation

<400> SEQUENCE: 134

Lys Cys Pro Thr Ser Gly Arg Leu
1               5

```
<210> SEQ ID NO 135
<211> LENGTH: 28
<212> TYPE: PRT
<213> ORGANISM: Homo sapiens
<220> FEATURE:
<223> OTHER INFORMATION: ACAT2 Acetyl-CoA acetyltransferase, cytosolic;
      Q9BWD1_C92
<220> FEATURE:
<221> NAME/KEY: MOD_RES
<222> LOCATION: (22)..(22)
<223> OTHER INFORMATION: Site of chemical conjugation

<400> SEQUENCE: 135

Arg Gln Ala Ser Val Gly Ala Gly Ile Pro Tyr Ser Val Pro Ala Trp
1               5                   10                  15

Ser Cys Gln Met Ile Cys Gly Ser Gly Leu Lys Ala
            20                  25

<210> SEQ ID NO 136
<211> LENGTH: 12
<212> TYPE: PRT
<213> ORGANISM: Homo sapiens
<220> FEATURE:
<223> OTHER INFORMATION: TXNDC5 Thioredoxin domain-containing protein 5;
      Q8NBS9_C350
<220> FEATURE:
<221> NAME/KEY: MOD_RES
<222> LOCATION: (7)..(7)
<223> OTHER INFORMATION: Site of chemical conjugation

<400> SEQUENCE: 136

Lys Phe Tyr Ala Pro Trp Cys Gly His Cys Lys Thr
1               5                   10

<210> SEQ ID NO 137
<211> LENGTH: 22
<212> TYPE: PRT
<213> ORGANISM: Homo sapiens
<220> FEATURE:
<223> OTHER INFORMATION: TUBA4A Tubulin alpha-4A chain;
      P68366_C54
<220> FEATURE:
<221> NAME/KEY: MOD_RES
<222> LOCATION: (15)..(15)
<223> OTHER INFORMATION: Site of chemical conjugation

<400> SEQUENCE: 137

Lys Thr Ile Gly Gly Gly Asp Asp Ser Phe Thr Thr Phe Phe Cys Glu
1               5                   10                  15

Thr Gly Ala Gly Lys His
            20

<210> SEQ ID NO 138
<211> LENGTH: 12
<212> TYPE: PRT
<213> ORGANISM: Homo sapiens
<220> FEATURE:
<223> OTHER INFORMATION: TK1 Thymidine kinase, cytosolic;
      P04183_C66
<220> FEATURE:
<221> NAME/KEY: MOD_RES
<222> LOCATION: (7)..(7)
<223> OTHER INFORMATION: Site of chemical conjugation

<400> SEQUENCE: 138

Arg Tyr Ser Ser Ser Phe Cys Thr His Asp Arg Asn
1               5                   10

<210> SEQ ID NO 139
```

```
<211> LENGTH: 20
<212> TYPE: PRT
<213> ORGANISM: Homo sapiens
<220> FEATURE:
<223> OTHER INFORMATION: NCAPD2 Condensin complex subunit 1;
      Q15021_C439
<220> FEATURE:
<221> NAME/KEY: MOD_RES
<222> LOCATION: (18)..(18)
<223> OTHER INFORMATION: Site of chemical conjugation

<400> SEQUENCE: 139

Lys Asn Ala Ile Gln Leu Leu Ala Ser Phe Leu Ala Asn Asn Pro Phe
1               5                   10                  15

Ser Cys Lys Leu
            20

<210> SEQ ID NO 140
<211> LENGTH: 19
<212> TYPE: PRT
<213> ORGANISM: Homo sapiens
<220> FEATURE:
<223> OTHER INFORMATION: PDCD6IP Programmed cell death 6-interacting
      protein; Q8WUM4_C250
<220> FEATURE:
<221> NAME/KEY: MOD_RES
<222> LOCATION: (3)..(3)
<223> OTHER INFORMATION: Site of chemical conjugation

<400> SEQUENCE: 140

Lys His Cys Ile Met Gln Ala Asn Ala Glu Tyr His Gln Ser Ile Leu
1               5                   10                  15

Ala Lys Gln

<210> SEQ ID NO 141
<211> LENGTH: 25
<212> TYPE: PRT
<213> ORGANISM: Homo sapiens
<220> FEATURE:
<223> OTHER INFORMATION: EDC3 Enhancer of mRNA-decapping protein 3;
      Q96F86_C413
<220> FEATURE:
<221> NAME/KEY: MOD_RES
<222> LOCATION: (17)..(17)
<223> OTHER INFORMATION: Site of chemical conjugation

<400> SEQUENCE: 141

Lys Asp Leu Pro Thr Ser Pro Val Asp Leu Val Ile Asn Cys Leu Asp
1               5                   10                  15

Cys Pro Glu Asn Val Phe Leu Arg Asp
            20                  25

<210> SEQ ID NO 142
<211> LENGTH: 15
<212> TYPE: PRT
<213> ORGANISM: Homo sapiens
<220> FEATURE:
<223> OTHER INFORMATION: GLRX Glutaredoxin-1;
      P35754_C23
<220> FEATURE:
<221> NAME/KEY: MOD_RES
<222> LOCATION: (10)..(10)
<223> OTHER INFORMATION: Site of chemical conjugation

<400> SEQUENCE: 142

Lys Val Val Val Phe Ile Lys Pro Thr Cys Pro Tyr Cys Arg Arg
1               5                   10                  15
```

-continued

```
<210> SEQ ID NO 143
<211> LENGTH: 20
<212> TYPE: PRT
<213> ORGANISM: Homo sapiens
<220> FEATURE:
<223> OTHER INFORMATION: TIGAR Fructose-2,6-bisphosphatase TIGAR;
      Q9NQ88_C114
<220> FEATURE:
<221> NAME/KEY: MOD_RES
<222> LOCATION: (4)..(4)
<223> OTHER INFORMATION: Site of chemical conjugation

<400> SEQUENCE: 143

Arg Glu Glu Cys Pro Val Phe Thr Pro Pro Gly Gly Glu Thr Leu Asp
1               5                   10                  15

Gln Val Lys Met
            20

<210> SEQ ID NO 144
<211> LENGTH: 29
<212> TYPE: PRT
<213> ORGANISM: Homo sapiens
<220> FEATURE:
<223> OTHER INFORMATION: IMPDH2 Inosine-5-monophosphate dehydrogenase 2;
      P12268_C331
<220> FEATURE:
<221> NAME/KEY: MOD_RES
<222> LOCATION: (10)..(10)
<223> OTHER INFORMATION: Site of chemical conjugation

<400> SEQUENCE: 144

Arg Val Gly Met Gly Ser Gly Ser Ile Cys Ile Thr Gln Glu Val Leu
1               5                   10                  15

Ala Cys Gly Arg Pro Gln Ala Thr Ala Val Tyr Lys Val
            20                  25

<210> SEQ ID NO 145
<211> LENGTH: 33
<212> TYPE: PRT
<213> ORGANISM: Homo sapiens
<220> FEATURE:
<223> OTHER INFORMATION: ATP5A1 ATP synthase subunit alpha,
      mitochondrial; P25705_C294
<220> FEATURE:
<221> NAME/KEY: MOD_RES
<222> LOCATION: (25)..(25)
<223> OTHER INFORMATION: Site of chemical conjugation

<400> SEQUENCE: 145

Lys Tyr Thr Ile Val Val Ser Ala Thr Ala Ser Asp Ala Ala Pro Leu
1               5                   10                  15

Gln Tyr Leu Ala Pro Tyr Ser Gly Cys Ser Met Gly Glu Tyr Phe Arg
            20                  25                  30

Asp

<210> SEQ ID NO 146
<211> LENGTH: 22
<212> TYPE: PRT
<213> ORGANISM: Homo sapiens
<220> FEATURE:
<223> OTHER INFORMATION: UCHL3 Ubiquitin carboxyl-terminal hydrolase
      isozyme L3; P15374_C95
<220> FEATURE:
<221> NAME/KEY: MOD_RES
<222> LOCATION: (8)..(8)
<223> OTHER INFORMATION: Site of chemical conjugation

<400> SEQUENCE: 146
```

```
Lys Gln Thr Ile Ser Asn Ala Cys Gly Thr Ile Gly Leu Ile His Ala
1               5                   10                  15

Ile Ala Asn Asn Lys Asp
            20

<210> SEQ ID NO 147
<211> LENGTH: 12
<212> TYPE: PRT
<213> ORGANISM: Homo sapiens
<220> FEATURE:
<223> OTHER INFORMATION: RPL24 60S ribosomal protein L24;
      P83731_C6
<220> FEATURE:
<221> NAME/KEY: MOD_RES
<222> LOCATION: (5)..(5)
<223> OTHER INFORMATION: Site of chemical conjugation

<400> SEQUENCE: 147

Lys Val Glu Leu Cys Ser Phe Ser Gly Tyr Lys Ile
1               5                   10

<210> SEQ ID NO 148
<211> LENGTH: 21
<212> TYPE: PRT
<213> ORGANISM: Homo sapiens
<220> FEATURE:
<223> OTHER INFORMATION: NHP2 H/ACA ribonucleoprotein complex subunit 2;
      Q9NX24_C18
<220> FEATURE:
<221> NAME/KEY: MOD_RES
<222> LOCATION: (16)..(16)
<223> OTHER INFORMATION: Site of chemical conjugation

<400> SEQUENCE: 148

Lys Ile Lys Ala Asp Pro Asp Gly Pro Glu Ala Gln Ala Glu Ala Cys
1               5                   10                  15

Ser Gly Glu Arg Thr
            20

<210> SEQ ID NO 149
<211> LENGTH: 10
<212> TYPE: PRT
<213> ORGANISM: Homo sapiens
<220> FEATURE:
<223> OTHER INFORMATION: ILK Integrin-linked protein kinase;
      Q13418_C346
<220> FEATURE:
<221> NAME/KEY: MOD_RES
<222> LOCATION: (6)..(6)
<223> OTHER INFORMATION: Site of chemical conjugation

<400> SEQUENCE: 149

Lys Phe Ser Phe Gln Cys Pro Gly Arg Met
1               5                   10

<210> SEQ ID NO 150
<211> LENGTH: 26
<212> TYPE: PRT
<213> ORGANISM: Homo sapiens
<220> FEATURE:
<223> OTHER INFORMATION: TCOF1 Treacle protein;
      Q13428_C38
<220> FEATURE:
<221> NAME/KEY: MOD_RES
<222> LOCATION: (2)..(2)
<223> OTHER INFORMATION: Site of chemical conjugation

<400> SEQUENCE: 150

Lys Cys Phe Leu Ala Gln Pro Val Thr Leu Leu Asp Ile Tyr Thr His
```

-continued

```
                1               5                  10                  15
Trp Gln Gln Thr Ser Glu Leu Gly Arg Lys
            20                  25

<210> SEQ ID NO 151
<211> LENGTH: 11
<212> TYPE: PRT
<213> ORGANISM: Homo sapiens
<220> FEATURE:
<223> OTHER INFORMATION: CDK2 Cyclin-dependent kinase 2;
      P24941_C177
<220> FEATURE:
<221> NAME/KEY: MOD_RES
<222> LOCATION: (9)..(9)
<223> OTHER INFORMATION: Site of chemical conjugation

<400> SEQUENCE: 151

Arg Ala Pro Glu Ile Leu Leu Gly Cys Lys Tyr
1               5                  10

<210> SEQ ID NO 152
<211> LENGTH: 14
<212> TYPE: PRT
<213> ORGANISM: Homo sapiens
<220> FEATURE:
<223> OTHER INFORMATION: PSMC4 26S protease regulatory subunit 6B;
      P43686_C210
<220> FEATURE:
<221> NAME/KEY: MOD_RES
<222> LOCATION: (11)..(11)
<223> OTHER INFORMATION: Site of chemical conjugation

<400> SEQUENCE: 152

Arg Gly Val Leu Met Tyr Gly Pro Pro Gly Cys Gly Lys Thr
1               5                  10

<210> SEQ ID NO 153
<211> LENGTH: 21
<212> TYPE: PRT
<213> ORGANISM: Homo sapiens
<220> FEATURE:
<223> OTHER INFORMATION: WAC WW domain-containing adapter protein with
      coiled-coil region; Q9BTA9_C553
<220> FEATURE:
<221> NAME/KEY: MOD_RES
<222> LOCATION: (4)..(4)
<223> OTHER INFORMATION: Site of chemical conjugation

<400> SEQUENCE: 153

Arg Ser Thr Cys Ser Leu Thr Pro Ala Leu Ala Ala His Phe Ser Glu
1               5                  10                  15

Asn Leu Ile Lys His
            20

<210> SEQ ID NO 154
<211> LENGTH: 18
<212> TYPE: PRT
<213> ORGANISM: Homo sapiens
<220> FEATURE:
<223> OTHER INFORMATION: HAT1 Histone acetyltransferase type B catalytic
      subunit; O14929_C101
<220> FEATURE:
<221> NAME/KEY: MOD_RES
<222> LOCATION: (8)..(8)
<223> OTHER INFORMATION: Site of chemical conjugation

<400> SEQUENCE: 154

Lys Val Asp Glu Asn Phe Asp Cys Val Glu Ala Asp Asp Val Glu Gly
1               5                  10                  15
```

Lys Ile

<210> SEQ ID NO 155
<211> LENGTH: 18
<212> TYPE: PRT
<213> ORGANISM: Homo sapiens
<220> FEATURE:
<223> OTHER INFORMATION: ECI2 Enoyl-CoA delta isomerase 2,
      mitochondrial; O75521_C380
<220> FEATURE:
<221> NAME/KEY: MOD_RES
<222> LOCATION: (7)..(7)
<223> OTHER INFORMATION: Site of chemical conjugation

<400> SEQUENCE: 155

Arg Trp Leu Ser Asp Glu Cys Thr Asn Ala Val Val Asn Phe Leu Ser
1               5                   10                  15

Arg Lys

<210> SEQ ID NO 156
<211> LENGTH: 14
<212> TYPE: PRT
<213> ORGANISM: Homo sapiens
<220> FEATURE:
<223> OTHER INFORMATION: MTHFD1 C-1-tetrahydrofolate synthase,
      cytoplasmic; P11586_C863
<220> FEATURE:
<221> NAME/KEY: MOD_RES
<222> LOCATION: (10)..(10)
<223> OTHER INFORMATION: Site of chemical conjugation

<400> SEQUENCE: 156

Lys Gln Gly Phe Gly Asn Leu Pro Ile Cys Met Ala Lys Thr
1               5                   10

<210> SEQ ID NO 157
<211> LENGTH: 17
<212> TYPE: PRT
<213> ORGANISM: Homo sapiens
<220> FEATURE:
<223> OTHER INFORMATION: DCK Deoxycytidine kinase;
      P27707_C45
<220> FEATURE:
<221> NAME/KEY: MOD_RES
<222> LOCATION: (4)..(4)
<223> OTHER INFORMATION: Site of chemical conjugation

<400> SEQUENCE: 157

Lys Gln Leu Cys Glu Asp Trp Glu Val Val Pro Glu Pro Val Ala Arg
1               5                   10                  15

Trp

<210> SEQ ID NO 158
<211> LENGTH: 17
<212> TYPE: PRT
<213> ORGANISM: Homo sapiens
<220> FEATURE:
<223> OTHER INFORMATION: UBA6 Ubiquitin-like modifier-activating enzyme
      6; A0AVT1_C347
<220> FEATURE:
<221> NAME/KEY: MOD_RES
<222> LOCATION: (7)..(7)
<223> OTHER INFORMATION: Site of chemical conjugation

<400> SEQUENCE: 158

Arg Lys Pro Asn Val Gly Cys Gln Gln Asp Ser Glu Glu Leu Leu Lys
1               5                   10                  15

Leu

<210> SEQ ID NO 159
<211> LENGTH: 25
<212> TYPE: PRT
<213> ORGANISM: Homo sapiens
<220> FEATURE:
<223> OTHER INFORMATION: ISOC2 Isochorismatase domain-containing protein 2, mitochondrial; Q96AB3_C114
<220> FEATURE:
<221> NAME/KEY: MOD_RES
<222> LOCATION: (13)..(13)
<223> OTHER INFORMATION: Site of chemical conjugation

<400> SEQUENCE: 159

Arg Ser Val Leu Leu Cys Gly Ile Glu Ala Gln Ala Cys Ile Leu Asn
1               5                   10                  15

Thr Thr Leu Asp Leu Leu Asp Arg Gly
            20                  25

<210> SEQ ID NO 160
<211> LENGTH: 14
<212> TYPE: PRT
<213> ORGANISM: Homo sapiens
<220> FEATURE:
<223> OTHER INFORMATION: DCTN1 Dynactin subunit 1; Q14203_C1252
<220> FEATURE:
<221> NAME/KEY: MOD_RES
<222> LOCATION: (6)..(6)
<223> OTHER INFORMATION: Site of chemical conjugation

<400> SEQUENCE: 160

Lys Val Thr Phe Ser Cys Ala Ala Gly Phe Gly Gln Arg His
1               5                   10

<210> SEQ ID NO 161
<211> LENGTH: 21
<212> TYPE: PRT
<213> ORGANISM: Homo sapiens
<220> FEATURE:
<223> OTHER INFORMATION: MCMBP Mini-chromosome maintenance complex-binding protein; Q9BTE3_C287
<220> FEATURE:
<221> NAME/KEY: MOD_RES
<222> LOCATION: (12)..(12)
<223> OTHER INFORMATION: Site of chemical conjugation

<400> SEQUENCE: 161

Arg Asp Ala Ser Ala Leu Leu Asp Pro Met Glu Cys Thr Asp Thr Ala
1               5                   10                  15

Glu Glu Gln Arg Val
            20

<210> SEQ ID NO 162
<211> LENGTH: 18
<212> TYPE: PRT
<213> ORGANISM: Homo sapiens
<220> FEATURE:
<223> OTHER INFORMATION: IPO7 Importin-7; O95373_C757
<220> FEATURE:
<221> NAME/KEY: MOD_RES
<222> LOCATION: (6)..(6)
<223> OTHER INFORMATION: Site of chemical conjugation

<400> SEQUENCE: 162

Arg Gly Ile Asp Gln Cys Ile Pro Leu Phe Val Glu Ala Ala Leu Glu
1               5                   10                  15

Arg Leu

<210> SEQ ID NO 163
<211> LENGTH: 9
<212> TYPE: PRT
<213> ORGANISM: Homo sapiens
<220> FEATURE:
<223> OTHER INFORMATION: PCMT1 Protein-L-isoaspartate(D-aspartate)
     O-methyltransferase 1; P22061_C102
<220> FEATURE:
<221> NAME/KEY: MOD_RES
<222> LOCATION: (5)..(5)
<223> OTHER INFORMATION: Site of chemical conjugation

<400> SEQUENCE: 163

Arg Met Val Gly Cys Thr Gly Lys Val
1               5

<210> SEQ ID NO 164
<211> LENGTH: 11
<212> TYPE: PRT
<213> ORGANISM: Homo sapiens
<220> FEATURE:
<223> OTHER INFORMATION: CSE1L Exportin-2;
     P55060_C842
<220> FEATURE:
<221> NAME/KEY: MOD_RES
<222> LOCATION: (4)..(4)
<223> OTHER INFORMATION: Site of chemical conjugation

<400> SEQUENCE: 164

Lys Lys Ile Cys Ala Val Gly Ile Thr Lys Leu
1               5                   10

<210> SEQ ID NO 165
<211> LENGTH: 12
<212> TYPE: PRT
<213> ORGANISM: Homo sapiens
<220> FEATURE:
<223> OTHER INFORMATION: NAA15 N-alpha-acetyltransferase 15, NatA
     auxiliary subunit; Q9BXJ9_C322
<220> FEATURE:
<221> NAME/KEY: MOD_RES
<222> LOCATION: (3)..(3)
<223> OTHER INFORMATION: Site of chemical conjugation

<400> SEQUENCE: 165

Lys Gly Cys Pro Pro Val Phe Asn Thr Leu Arg Ser
1               5                   10

<210> SEQ ID NO 166
<211> LENGTH: 14
<212> TYPE: PRT
<213> ORGANISM: Homo sapiens
<220> FEATURE:
<223> OTHER INFORMATION: PSMC6 26S protease regulatory subunit 10B;
     P62333_C170
<220> FEATURE:
<221> NAME/KEY: MOD_RES
<222> LOCATION: (3)..(3)
<223> OTHER INFORMATION: Site of chemical conjugation

<400> SEQUENCE: 166

Lys Gly Cys Leu Leu Tyr Gly Pro Pro Gly Thr Gly Lys Thr
1               5                   10

<210> SEQ ID NO 167
<211> LENGTH: 19
<212> TYPE: PRT

```
<213> ORGANISM: Homo sapiens
<220> FEATURE:
<223> OTHER INFORMATION: DLGAP5 Disks large-associated protein 5;
      Q15398_C129
<220> FEATURE:
<221> NAME/KEY: MOD_RES
<222> LOCATION: (8)..(8)
<223> OTHER INFORMATION: Site of chemical conjugation

<400> SEQUENCE: 167

Arg Tyr Arg Pro Asp Met Pro Cys Phe Leu Leu Ser Asn Gln Asn Ala
1               5                   10                  15

Val Lys Ala

<210> SEQ ID NO 168
<211> LENGTH: 28
<212> TYPE: PRT
<213> ORGANISM: Homo sapiens
<220> FEATURE:
<223> OTHER INFORMATION: C2orf49 Ashwin;
      Q9BVC5_C10
<220> FEATURE:
<221> NAME/KEY: MOD_RES
<222> LOCATION: (3)..(3)
<223> OTHER INFORMATION: Site of chemical conjugation

<400> SEQUENCE: 168

Arg Ser Cys Thr Asp Ser Glu Leu Leu Leu His Pro Glu Leu Leu Ser
1               5                   10                  15

Gln Glu Phe Leu Leu Leu Thr Leu Glu Gln Lys Asn
            20                  25

<210> SEQ ID NO 169
<211> LENGTH: 13
<212> TYPE: PRT
<213> ORGANISM: Homo sapiens
<220> FEATURE:
<223> OTHER INFORMATION: RPS11 40S ribosomal protein S11;
      P62280_C116
<220> FEATURE:
<221> NAME/KEY: MOD_RES
<222> LOCATION: (10)..(10)
<223> OTHER INFORMATION: Site of chemical conjugation

<400> SEQUENCE: 169

Lys Asn Met Ser Val His Leu Ser Pro Cys Phe Arg Asp
1               5                   10

<210> SEQ ID NO 170
<211> LENGTH: 34
<212> TYPE: PRT
<213> ORGANISM: Homo sapiens
<220> FEATURE:
<223> OTHER INFORMATION: STAT1 Signal transducer and activator of
      transcription 1; P42224_C255
<220> FEATURE:
<221> NAME/KEY: MOD_RES
<222> LOCATION: (14)..(14)
<223> OTHER INFORMATION: Site of chemical conjugation

<400> SEQUENCE: 170

Arg Gln Gln Ser Ala Cys Ile Gly Gly Pro Pro Asn Ala Cys Leu Asp
1               5                   10                  15

Gln Leu Gln Asn Trp Phe Thr Ile Val Ala Glu Ser Leu Gln Gln Val
            20                  25                  30

Arg Gln
```

```
<210> SEQ ID NO 171
<211> LENGTH: 19
<212> TYPE: PRT
<213> ORGANISM: Homo sapiens
<220> FEATURE:
<223> OTHER INFORMATION: MED15 Mediator of RNA polymerase II
      transcription subuni; Q96RN5_C618
<220> FEATURE:
<221> NAME/KEY: MOD_RES
<222> LOCATION: (6)..(6)
<223> OTHER INFORMATION: Site of chemical conjugation

<400> SEQUENCE: 171

Lys Gln Gln Tyr Leu Cys Gln Pro Leu Leu Asp Ala Val Leu Ala Asn
1               5                   10                  15

Ile Arg Ser

<210> SEQ ID NO 172
<211> LENGTH: 42
<212> TYPE: PRT
<213> ORGANISM: Homo sapiens
<220> FEATURE:
<223> OTHER INFORMATION: MTHFD1L Monofunctional C1-tetrahydrofolate
      synthase, mitochondrial; Q6UB35_C961
<220> FEATURE:
<221> NAME/KEY: MOD_RES
<222> LOCATION: (27)..(27)
<223> OTHER INFORMATION: Site of chemical conjugation

<400> SEQUENCE: 172

Arg Ala Ser Ile Gly Ala Gly Phe Ile Tyr Pro Leu Val Gly Thr Met
1               5                   10                  15

Ser Thr Met Pro Gly Leu Pro Thr Arg Pro Cys Phe Tyr Asp Ile Asp
            20                  25                  30

Leu Asp Thr Glu Thr Glu Gln Val Lys Gly
        35                  40

<210> SEQ ID NO 173
<211> LENGTH: 9
<212> TYPE: PRT
<213> ORGANISM: Homo sapiens
<223> OTHER INFORMATION: DTYMK Thymidylate kinase;
      P23919_C163
<220> FEATURE:
<221> NAME/KEY: MOD_RES
<222> LOCATION: (2)..(2)
<223> OTHER INFORMATION: Site of chemical conjugation

<400> SEQUENCE: 173

Arg Cys Phe His Gln Leu Met Lys Asp
1               5

<210> SEQ ID NO 174
<211> LENGTH: 29
<212> TYPE: PRT
<213> ORGANISM: Homo sapiens
<220> FEATURE:
<223> OTHER INFORMATION: GCN1L1 Translational activator GCN1;
      Q92616_C1692
<220> FEATURE:
<221> NAME/KEY: MOD_RES
<222> LOCATION: (7)..(7)
<223> OTHER INFORMATION: Site of chemical conjugation

<400> SEQUENCE: 174

Lys Gly Met Gly Glu Ser Cys Phe Glu Asp Leu Leu Pro Trp Leu Met
1               5                   10                  15
```

```
Glu Thr Leu Thr Tyr Glu Gln Ser Ser Val Asp Arg Ser
            20                  25
```

<210> SEQ ID NO 175
<211> LENGTH: 12
<212> TYPE: PRT
<213> ORGANISM: Homo sapiens
<220> FEATURE:
<223> OTHER INFORMATION: TMPO Lamina-associated polypeptide 2, isoform
      alpha; P42166_C341
<220> FEATURE:
<221> NAME/KEY: MOD_RES
<222> LOCATION: (8)..(8)
<223> OTHER INFORMATION: Site of chemical conjugation

<400> SEQUENCE: 175

```
Lys Ser Gly Ile Gln Pro Leu Cys Pro Glu Arg Ser
1               5                   10
```

<210> SEQ ID NO 176
<211> LENGTH: 11
<212> TYPE: PRT
<213> ORGANISM: Homo sapiens
<220> FEATURE:
<223> OTHER INFORMATION: ETHE1 Protein ETHE1, mitochondrial;
      O95571_C170
<220> FEATURE:
<221> NAME/KEY: MOD_RES
<222> LOCATION: (8)..(8)
<223> OTHER INFORMATION: Site of chemical conjugation

<400> SEQUENCE: 176

```
Arg Thr Asp Phe Gln Gln Gly Cys Ala Lys Thr
1               5                   10
```

<210> SEQ ID NO 177
<211> LENGTH: 14
<212> TYPE: PRT
<213> ORGANISM: Homo sapiens
<220> FEATURE:
<223> OTHER INFORMATION: NDC80 Kinetochore protein NDC80 homolog;
      O14777_C449
<220> FEATURE:
<221> NAME/KEY: MOD_RES
<222> LOCATION: (10)..(10)
<223> OTHER INFORMATION: Site of chemical conjugation

<400> SEQUENCE: 177

```
Lys Phe Asn Pro Glu Ala Gly Ala Asn Cys Leu Val Lys Tyr
1               5                   10
```

<210> SEQ ID NO 178
<211> LENGTH: 14
<212> TYPE: PRT
<213> ORGANISM: Homo sapiens
<220> FEATURE:
<223> OTHER INFORMATION: ATP5C1 ATP synthase subunit gamma,
      mitochondrial; P36542_C103
<220> FEATURE:
<221> NAME/KEY: MOD_RES
<222> LOCATION: (4)..(4)
<223> OTHER INFORMATION: Site of chemical conjugation

<400> SEQUENCE: 178

```
Arg Gly Leu Cys Gly Ala Ile His Ser Ser Ile Ala Lys Gln
1               5                   10
```

<210> SEQ ID NO 179
<211> LENGTH: 34
<212> TYPE: PRT

```
<213> ORGANISM: Homo sapiens
<220> FEATURE:
<223> OTHER INFORMATION: FAM96B Mitotic spindle-associated MMXD complex
      subunit MIP18; Q9Y3D0_C93
<220> FEATURE:
<221> NAME/KEY: MOD_RES
<222> LOCATION: (22)..(22)
<223> OTHER INFORMATION: Site of chemical conjugation

<400> SEQUENCE: 179

Arg Val Gln Val Ser Asp Pro Glu Ser Thr Val Ala Val Ala Phe Thr
1               5                   10                  15

Pro Thr Ile Pro His Cys Ser Met Ala Thr Leu Ile Gly Leu Ser Ile
            20                  25                  30

Lys Val

<210> SEQ ID NO 180
<211> LENGTH: 22
<212> TYPE: PRT
<213> ORGANISM: Homo sapiens
<220> FEATURE:
<223> OTHER INFORMATION: RARS Arginine--tRNA ligase, cytoplasmic;
      P54136_C34
<220> FEATURE:
<221> NAME/KEY: MOD_RES
<222> LOCATION: (5)..(5)
<223> OTHER INFORMATION: Site of chemical conjugation

<400> SEQUENCE: 180

Lys Asn Cys Gly Cys Leu Gly Ala Ser Pro Asn Leu Glu Gln Leu Gln
1               5                   10                  15

Glu Glu Asn Leu Lys Leu
            20

<210> SEQ ID NO 181
<211> LENGTH: 13
<212> TYPE: PRT
<213> ORGANISM: Homo sapiens
<220> FEATURE:
<223> OTHER INFORMATION: MMS19 MMS19 nucleotide excision repair protein
      homolog; Q96T76_C819
<220> FEATURE:
<221> NAME/KEY: MOD_RES
<222> LOCATION: (8)..(8)
<223> OTHER INFORMATION: Site of chemical conjugation

<400> SEQUENCE: 181

Arg Tyr His Pro Leu Ser Ser Cys Leu Thr Ala Arg Leu
1               5                   10

<210> SEQ ID NO 182
<211> LENGTH: 35
<212> TYPE: PRT
<213> ORGANISM: Homo sapiens
<220> FEATURE:
<223> OTHER INFORMATION: UBA3 NEDD8-activating enzyme E1 catalytic
      subunit; Q8TBC4_C237
<220> FEATURE:
<221> NAME/KEY: MOD_RES
<222> LOCATION: (27)..(27)
<223> OTHER INFORMATION: Site of chemical conjugation

<400> SEQUENCE: 182

Arg Val Ile Leu Pro Gly Met Thr Ala Cys Ile Glu Cys Thr Leu Glu
1               5                   10                  15

Leu Tyr Pro Pro Gln Val Asn Phe Pro Met Cys Thr Ile Ala Ser Met
            20                  25                  30
```

-continued

Pro Arg Leu
      35

<210> SEQ ID NO 183
<211> LENGTH: 11
<212> TYPE: PRT
<213> ORGANISM: Homo sapiens
<220> FEATURE:
<223> OTHER INFORMATION: SNW1 SNW domain-containing protein 1;
      Q13573_C250
<220> FEATURE:
<221> NAME/KEY: MOD_RES
<222> LOCATION: (5)..(5)
<223> OTHER INFORMATION: Site of chemical conjugation

<400> SEQUENCE: 183

Lys Ile Pro Pro Cys Ile Ser Asn Trp Lys Asn
1               5                   10

<210> SEQ ID NO 184
<211> LENGTH: 18
<212> TYPE: PRT
<213> ORGANISM: Homo sapiens
<220> FEATURE:
<223> OTHER INFORMATION: MAP2K3 Dual specificity mitogen-activated
      protein kinase; P46734_C207
<220> FEATURE:
<221> NAME/KEY: MOD_RES
<222> LOCATION: (3)..(3)
<223> OTHER INFORMATION: Site of chemical conjugation

<400> SEQUENCE: 184

Lys Met Cys Asp Phe Gly Ile Ser Gly Tyr Leu Val Asp Ser Val Ala
1               5                   10                  15

Lys Thr

<210> SEQ ID NO 185
<211> LENGTH: 27
<212> TYPE: PRT
<213> ORGANISM: Homo sapiens
<220> FEATURE:
<223> OTHER INFORMATION: HSPA4 Heat shock 70 kDa protein 4;
      P34932_C34
<220> FEATURE:
<221> NAME/KEY: MOD_RES
<222> LOCATION: (16)..(16)
<223> OTHER INFORMATION: Site of chemical conjugation

<400> SEQUENCE: 185

Arg Ala Gly Gly Ile Glu Thr Ile Ala Asn Glu Tyr Ser Asp Arg Cys
1               5                   10                  15

Thr Pro Ala Cys Ile Ser Phe Gly Pro Lys Asn
            20                  25

<210> SEQ ID NO 186
<211> LENGTH: 25
<212> TYPE: PRT
<213> ORGANISM: Homo sapiens
<220> FEATURE:
<223> OTHER INFORMATION: CTSZ Cathepsin Z;
      Q9UBR2_C92
<220> FEATURE:
<221> NAME/KEY: MOD_RES
<222> LOCATION: (12)..(12)
<223> OTHER INFORMATION: Site of chemical conjugation

<400> SEQUENCE: 186

Arg Asn Gln His Ile Pro Gln Tyr Cys Gly Ser Cys Trp Ala His Ala
1               5                   10                  15

Ser Thr Ser Ala Met Ala Asp Arg Ile
            20                  25

<210> SEQ ID NO 187
<211> LENGTH: 20
<212> TYPE: PRT
<213> ORGANISM: Homo sapiens
<220> FEATURE:
<223> OTHER INFORMATION: UBE2S Ubiquitin-conjugating enzyme E2 S;
      Q16763_C118
<220> FEATURE:
<221> NAME/KEY: MOD_RES
<222> LOCATION: (2)..(2)
<223> OTHER INFORMATION: Site of chemical conjugation

<400> SEQUENCE: 187

Lys Cys Leu Leu Ile His Pro Asn Pro Glu Ser Ala Leu Asn Glu Glu
1               5                   10                  15

Ala Gly Arg Leu
            20

<210> SEQ ID NO 188
<211> LENGTH: 19
<212> TYPE: PRT
<213> ORGANISM: Homo sapiens
<220> FEATURE:
<223> OTHER INFORMATION: PPAT Amidophosphoribosyltransferase;
      Q06203_C100
<220> FEATURE:
<221> NAME/KEY: MOD_RES
<222> LOCATION: (2)..(2)
<223> OTHER INFORMATION: Site of chemical conjugation

<400> SEQUENCE: 188

Lys Cys Glu Leu Glu Asn Cys Gln Pro Phe Val Val Glu Thr Leu His
1               5                   10                  15

Gly Lys Ile

<210> SEQ ID NO 189
<211> LENGTH: 18
<212> TYPE: PRT
<213> ORGANISM: Homo sapiens
<220> FEATURE:
<223> OTHER INFORMATION: ALDH5A1 Succinate-semialdehyde dehydrogenase,
      mitochondria; P51649_C340
<220> FEATURE:
<221> NAME/KEY: MOD_RES
<222> LOCATION: (7)..(7)
<223> OTHER INFORMATION: Site of chemical conjugation

<400> SEQUENCE: 189

Arg Asn Thr Gly Gln Thr Cys Val Cys Ser Asn Gln Phe Leu Val Gln
1               5                   10                  15

Arg Gly

<210> SEQ ID NO 190
<211> LENGTH: 22
<212> TYPE: PRT
<213> ORGANISM: Homo sapiens
<220> FEATURE:
<223> OTHER INFORMATION: MSH2 DNA mismatch repair protein Msh2;
      P43246_C822
<220> FEATURE:
<221> NAME/KEY: MOD_RES
<222> LOCATION: (5)..(5)
<223> OTHER INFORMATION: Site of chemical conjugation

<400> SEQUENCE: 190

```
Lys Lys Gly Val Cys Asp Gln Ser Phe Gly Ile His Val Ala Glu Leu
1               5                   10                  15

Ala Asn Phe Pro Lys His
            20

<210> SEQ ID NO 191
<211> LENGTH: 30
<212> TYPE: PRT
<213> ORGANISM: Homo sapiens
<220> FEATURE:
<223> OTHER INFORMATION: CAD CAD protein;
      P27708_C73
<220> FEATURE:
<221> NAME/KEY: MOD_RES
<222> LOCATION: (28)..(28)
<223> OTHER INFORMATION: Site of chemical conjugation

<400> SEQUENCE: 191

Lys Ala Gln Ile Leu Val Leu Thr Tyr Pro Leu Ile Gly Asn Tyr Gly
1               5                   10                  15

Ile Pro Pro Asp Glu Met Asp Glu Phe Gly Leu Cys Lys Trp
            20                  25                  30

<210> SEQ ID NO 192
<211> LENGTH: 14
<212> TYPE: PRT
<213> ORGANISM: Homo sapiens
<220> FEATURE:
<223> OTHER INFORMATION: PCK2 Phosphoenolpyruvate carboxykinase;
      Q16822_C306
<220> FEATURE:
<221> NAME/KEY: MOD_RES
<222> LOCATION: (11)..(11)
<223> OTHER INFORMATION: Site of chemical conjugation

<400> SEQUENCE: 192

Arg Tyr Val Ala Ala Ala Phe Pro Ser Ala Cys Gly Lys Thr
1               5                   10

<210> SEQ ID NO 193
<211> LENGTH: 24
<212> TYPE: PRT
<213> ORGANISM: Homo sapiens
<220> FEATURE:
<223> OTHER INFORMATION: PFKP 6-phosphofructokinase type C;
      Q01813_C641
<220> FEATURE:
<221> NAME/KEY: MOD_RES
<222> LOCATION: (5)..(5)
<223> OTHER INFORMATION: Site of chemical conjugation

<400> SEQUENCE: 193

Arg Asn Glu Ser Cys Ser Glu Asn Tyr Thr Thr Asp Phe Ile Tyr Gln
1               5                   10                  15

Leu Tyr Ser Glu Glu Gly Lys Gly
            20

<210> SEQ ID NO 194
<211> LENGTH: 19
<212> TYPE: PRT
<213> ORGANISM: Homo sapiens
<220> FEATURE:
<223> OTHER INFORMATION: ACSF2 Acyl-CoA synthetase family member 2,
      mitochondrial; Q96CM8_C64
<220> FEATURE:
<221> NAME/KEY: MOD_RES
<222> LOCATION: (16)..(16)
<223> OTHER INFORMATION: Site of chemical conjugation
```

-continued

```
<400> SEQUENCE: 194

Arg Met Val Ser Thr Pro Ile Gly Gly Leu Ser Tyr Val Gln Gly Cys
1               5                   10                  15

Thr Lys Lys

<210> SEQ ID NO 195
<211> LENGTH: 46
<212> TYPE: PRT
<213> ORGANISM: Homo sapiens
<220> FEATURE:
<223> OTHER INFORMATION: MSTO1 Protein misato homolog 1;
      Q9BUK6_C403
<220> FEATURE:
<221> NAME/KEY: MOD_RES
<222> LOCATION: (38)..(38)
<223> OTHER INFORMATION: Site of chemical conjugation

<400> SEQUENCE: 195

Lys Val Val Thr Ala Gly Ala Ile Ile Pro Phe Pro Leu Ala Pro Gly
1               5                   10                  15

Gln Ser Leu Pro Asp Ser Leu Met Gln Phe Gly Gly Ala Thr Pro Trp
                20                  25                  30

Thr Pro Leu Ser Ala Cys Gly Glu Pro Ser Gly Thr Arg Cys
        35                  40                  45

<210> SEQ ID NO 196
<211> LENGTH: 36
<212> TYPE: PRT
<213> ORGANISM: Homo sapiens
<220> FEATURE:
<223> OTHER INFORMATION: PAICS Multifunctional protein ADE2;
      P22234_C374
<220> FEATURE:
<221> NAME/KEY: MOD_RES
<222> LOCATION: (8)..(8)
<223> OTHER INFORMATION: Site of chemical conjugation

<400> SEQUENCE: 196

Arg Leu Pro Ser Gly Leu Gly Cys Ser Thr Val Leu Ser Pro Glu Gly
1               5                   10                  15

Ser Ala Gln Phe Ala Ala Gln Ile Phe Gly Leu Ser Asn His Leu Val
                20                  25                  30

Trp Ser Lys Leu
        35

<210> SEQ ID NO 197
<211> LENGTH: 27
<212> TYPE: PRT
<213> ORGANISM: Homo sapiens
<220> FEATURE:
<223> OTHER INFORMATION: DESI1 Desumoylating isopeptidase 1;
      Q6ICB0_C108
<220> FEATURE:
<221> NAME/KEY: MOD_RES
<222> LOCATION: (12)..(12)
<223> OTHER INFORMATION: Site of chemical conjugation

<400> SEQUENCE: 197

Arg Gly Glu Ala Tyr Asn Leu Phe Glu His Asn Cys Asn Thr Phe Ser
1               5                   10                  15

Asn Glu Val Ala Gln Phe Leu Thr Gly Arg Lys
                20                  25

<210> SEQ ID NO 198
```

```
<211> LENGTH: 14
<212> TYPE: PRT
<213> ORGANISM: Homo sapiens
<220> FEATURE:
<223> OTHER INFORMATION: PSMC6 26S protease regulatory subunit 10B;
      P62333_C193
<220> FEATURE:
<221> NAME/KEY: MOD_RES
<222> LOCATION: (9)..(9)
<223> OTHER INFORMATION: Site of chemical conjugation

<400> SEQUENCE: 198

Arg Ala Val Ala Ser Gln Leu Asp Cys Asn Phe Leu Lys Val
1               5                   10

<210> SEQ ID NO 199
<211> LENGTH: 29
<212> TYPE: PRT
<213> ORGANISM: Homo sapiens
<220> FEATURE:
<223> OTHER INFORMATION: TRAPPC5 Trafficking protein particle complex
      subunit 5; Q8IUR0_C139
<220> FEATURE:
<221> NAME/KEY: MOD_RES
<222> LOCATION: (8)..(8)
<223> OTHER INFORMATION: Site of chemical conjugation

<400> SEQUENCE: 199

Lys Glu Asn Ser Thr Leu Asn Cys Ala Ser Phe Thr Ala Gly Ile Val
1               5                   10                  15

Glu Ala Val Leu Thr His Ser Gly Phe Pro Ala Lys Val
            20                  25

<210> SEQ ID NO 200
<211> LENGTH: 34
<212> TYPE: PRT
<213> ORGANISM: Homo sapiens
<220> FEATURE:
<223> OTHER INFORMATION: PFKP 6-phosphofructokinase type C;
      Q01813_C179
<220> FEATURE:
<221> NAME/KEY: MOD_RES
<222> LOCATION: (19)..(19)
<223> OTHER INFORMATION: Site of chemical conjugation

<400> SEQUENCE: 200

Lys Tyr Ala Tyr Leu Asn Val Val Gly Met Val Gly Ser Ile Asp Asn
1               5                   10                  15

Asp Phe Cys Gly Thr Asp Met Thr Ile Gly Thr Asp Ser Ala Leu His
            20                  25                  30

Arg Ile

<210> SEQ ID NO 201
<211> LENGTH: 9
<212> TYPE: PRT
<213> ORGANISM: Homo sapiens
<220> FEATURE:
<223> OTHER INFORMATION: ATP6V1A V-type proton ATPase catalytic subunit
      A; P38606_C138
<220> FEATURE:
<221> NAME/KEY: MOD_RES
<222> LOCATION: (7)..(7)
<223> OTHER INFORMATION: Site of chemical conjugation

<400> SEQUENCE: 201

Lys Trp Asp Phe Thr Pro Cys Lys Asn
1               5
```

```
<210> SEQ ID NO 202
<211> LENGTH: 15
<212> TYPE: PRT
<213> ORGANISM: Homo sapiens
<220> FEATURE:
<223> OTHER INFORMATION: MRPS6 28S ribosomal protein S6, mitochondrial;
      P82932_C105
<220> FEATURE:
<221> NAME/KEY: MOD_RES
<222> LOCATION: (3)..(3)
<223> OTHER INFORMATION: Site of chemical conjugation

<400> SEQUENCE: 202

Lys Glu Cys Glu Gly Ile Val Pro Val Pro Leu Ala Glu Lys Leu
1               5                   10                  15

<210> SEQ ID NO 203
<211> LENGTH: 19
<212> TYPE: PRT
<213> ORGANISM: Homo sapiens
<220> FEATURE:
<223> OTHER INFORMATION: LANCL2 LanC-like protein 2;
      Q9NS86_C187
<220> FEATURE:
<221> NAME/KEY: MOD_RES
<222> LOCATION: (5)..(5)
<223> OTHER INFORMATION: Site of chemical conjugation

<400> SEQUENCE: 203

Arg Ser Val Val Cys Gln Glu Ser Asp Leu Pro Asp Glu Leu Leu Tyr
1               5                   10                  15

Gly Arg Ala

<210> SEQ ID NO 204
<211> LENGTH: 14
<212> TYPE: PRT
<213> ORGANISM: Homo sapiens
<220> FEATURE:
<223> OTHER INFORMATION: CORO1C Coronin-1C;
      Q9ULV4_C456
<220> FEATURE:
<221> NAME/KEY: MOD_RES
<222> LOCATION: (8)..(8)
<223> OTHER INFORMATION: Site of chemical conjugation

<400> SEQUENCE: 204

Lys Ser Ile Lys Asp Thr Ile Cys Asn Gln Asp Glu Arg Ile
1               5                   10

<210> SEQ ID NO 205
<211> LENGTH: 22
<212> TYPE: PRT
<213> ORGANISM: Homo sapiens
<220> FEATURE:
<223> OTHER INFORMATION: ACAA1 3-ketoacyl-CoA thiolase, peroxisomal;
      P09110_C381
<220> FEATURE:
<221> NAME/KEY: MOD_RES
<222> LOCATION: (17)..(17)
<223> OTHER INFORMATION: Site of chemical conjugation

<400> SEQUENCE: 205

Lys Val Asn Pro Leu Gly Gly Ala Val Ala Leu Gly His Pro Leu Gly
1               5                   10                  15

Cys Thr Gly Ala Arg Gln
            20

<210> SEQ ID NO 206
<211> LENGTH: 20
```

```
<212> TYPE: PRT
<213> ORGANISM: Homo sapiens
<220> FEATURE:
<223> OTHER INFORMATION: GRPEL1 GrpE protein homolog 1, mitochondrial;
      Q9HAV7_C124
<220> FEATURE:
<221> NAME/KEY: MOD_RES
<222> LOCATION: (5)..(5)
<223> OTHER INFORMATION: Site of chemical conjugation

<400> SEQUENCE: 206

Lys Ala Thr Gln Cys Val Pro Lys Glu Glu Ile Lys Asp Asp Asn Pro
1               5                   10                  15

His Leu Lys Asn
            20

<210> SEQ ID NO 207
<211> LENGTH: 12
<212> TYPE: PRT
<213> ORGANISM: Homo sapiens
<220> FEATURE:
<223> OTHER INFORMATION: PPP2R5D Serine/threonine-protein phosphatase 2A
      56 kDa regulatory subunit; Q14738_C17
<220> FEATURE:
<221> NAME/KEY: MOD_RES
<222> LOCATION: (2)..(2)
<223> OTHER INFORMATION: Site of chemical conjugation

<400> SEQUENCE: 207

Lys Cys Thr Ala Lys Pro Ser Ser Ser Gly Lys Asp
1               5                   10

<210> SEQ ID NO 208
<211> LENGTH: 23
<212> TYPE: PRT
<213> ORGANISM: Homo sapiens
<220> FEATURE:
<223> OTHER INFORMATION: TXN2 Thioredoxin, mitochondrial;
      Q99757_C90
<220> FEATURE:
<221> NAME/KEY: MOD_RES
<222> LOCATION: (18)..(18)
<223> OTHER INFORMATION: Site of chemical conjugation

<400> SEQUENCE: 208

Arg Val Val Asn Ser Glu Thr Pro Val Val Val Asp Phe His Ala Gln
1               5                   10                  15

Trp Cys Gly Pro Cys Lys Ile
            20

<210> SEQ ID NO 209
<211> LENGTH: 31
<212> TYPE: PRT
<213> ORGANISM: Homo sapiens
<220> FEATURE:
<223> OTHER INFORMATION: GALK1 Galactokinase;
      P51570_C182
<220> FEATURE:
<221> NAME/KEY: MOD_RES
<222> LOCATION: (17)..(17)
<223> OTHER INFORMATION: Site of chemical conjugation

<400> SEQUENCE: 209

Arg Ala Gln Val Cys Gln Gln Ala Glu His Ser Phe Ala Gly Met Pro
1               5                   10                  15

Cys Gly Ile Met Asp Gln Phe Ile Ser Leu Met Gly Gln Lys Gly
            20                  25                  30
```

```
<210> SEQ ID NO 210
<211> LENGTH: 13
<212> TYPE: PRT
<213> ORGANISM: Homo sapiens
<220> FEATURE:
<223> OTHER INFORMATION: RBPJ Recombining binding protein suppressor of
      hairless; Q06330_C313
<220> FEATURE:
<221> NAME/KEY: MOD_RES
<222> LOCATION: (10)..(10)
<223> OTHER INFORMATION: Site of chemical conjugation

<400> SEQUENCE: 210

Arg Ile Ile Gln Phe Gln Ala Thr Pro Cys Pro Lys Glu
1               5                   10

<210> SEQ ID NO 211
<211> LENGTH: 14
<212> TYPE: PRT
<213> ORGANISM: Homo sapiens
<220> FEATURE:
<223> OTHER INFORMATION: MED17 Mediator of RNA polymerase II
      transcription subunit; Q9NVC6_C649
<220> FEATURE:
<221> NAME/KEY: MOD_RES
<222> LOCATION: (12)..(12)
<223> OTHER INFORMATION: Site of chemical conjugation

<400> SEQUENCE: 211

Lys Met Glu Leu Leu Met Ser Ala Leu Ser Pro Cys Leu Leu
1               5                   10

<210> SEQ ID NO 212
<211> LENGTH: 24
<212> TYPE: PRT
<213> ORGANISM: Homo sapiens
<220> FEATURE:
<223> OTHER INFORMATION: CCT7 T-complex protein 1 subunit eta;
      Q99832_C511
<220> FEATURE:
<221> NAME/KEY: MOD_RES
<222> LOCATION: (13)..(13)
<223> OTHER INFORMATION: Site of chemical conjugation

<400> SEQUENCE: 212

Arg Ile Asn Ala Leu Thr Ala Ala Ser Glu Ala Ala Cys Leu Ile Val
1               5                   10                  15

Ser Val Asp Glu Thr Ile Lys Asn
            20

<210> SEQ ID NO 213
<211> LENGTH: 20
<212> TYPE: PRT
<213> ORGANISM: Homo sapiens
<220> FEATURE:
<223> OTHER INFORMATION: MCMBP Mini-chromosome maintenance complex-
      binding protein; Q9BTE3_C325
<220> FEATURE:
<221> NAME/KEY: MOD_RES
<222> LOCATION: (12)..(12)
<223> OTHER INFORMATION: Site of chemical conjugation

<400> SEQUENCE: 213

Lys Leu Gln His Ile Asn Pro Leu Leu Pro Ala Cys Leu Asn Lys Glu
1               5                   10                  15

Glu Ser Lys Thr
            20

<210> SEQ ID NO 214
```

-continued

```
<211> LENGTH: 16
<212> TYPE: PRT
<213> ORGANISM: Homo sapiens
<220> FEATURE:
<223> OTHER INFORMATION: TK1 Thymidine kinase, cytosolic;
      P04183_C230
<220> FEATURE:
<221> NAME/KEY: MOD_RES
<222> LOCATION: (12)..(12)
<223> OTHER INFORMATION: Site of chemical conjugation

<400> SEQUENCE: 214

Arg Lys Leu Phe Ala Pro Gln Gln Ile Leu Gln Cys Ser Pro Ala Asn
1               5                   10                  15

<210> SEQ ID NO 215
<211> LENGTH: 23
<212> TYPE: PRT
<213> ORGANISM: Homo sapiens
<220> FEATURE:
<223> OTHER INFORMATION: WRNIP1 ATPase WRNIP1;
      Q96S55_C272
<220> FEATURE:
<221> NAME/KEY: MOD_RES
<222> LOCATION: (20)..(20)
<223> OTHER INFORMATION: Site of chemical conjugation

<400> SEQUENCE: 215

Arg Ser Leu Leu Glu Thr Asn Glu Ile Pro Ser Leu Ile Leu Trp Gly
1               5                   10                  15

Pro Pro Gly Cys Gly Lys Thr
            20

<210> SEQ ID NO 216
<211> LENGTH: 45
<212> TYPE: PRT
<213> ORGANISM: Homo sapiens
<220> FEATURE:
<223> OTHER INFORMATION: C7orf59 UPF0539 protein C7orf59;
      Q0VGL1_C51
<220> FEATURE:
<221> NAME/KEY: MOD_RES
<222> LOCATION: (41)..(41)
<223> OTHER INFORMATION: Site of chemical conjugation

<400> SEQUENCE: 216

Arg Ile Pro Asp Gln Leu Gly Tyr Leu Val Leu Ser Glu Gly Ala Val
1               5                   10                  15

Leu Ala Ser Ser Gly Asp Leu Glu Asn Asp Glu Gln Ala Ala Ser Ala
            20                  25                  30

Ile Ser Glu Leu Val Ser Thr Ala Cys Gly Phe Arg Leu
        35                  40                  45

<210> SEQ ID NO 217
<211> LENGTH: 17
<212> TYPE: PRT
<213> ORGANISM: Homo sapiens
<220> FEATURE:
<223> OTHER INFORMATION: THOC6 THO complex subunit 6 homolog;
      Q86W42_C35
<220> FEATURE:
<221> NAME/KEY: MOD_RES
<222> LOCATION: (14)..(14)
<223> OTHER INFORMATION: Site of chemical conjugation

<400> SEQUENCE: 217

Arg Leu His Met Thr Ile Phe Ser Gln Ser Val Ser Pro Cys Gly Lys
1               5                   10                  15
```

Phe

```
<210> SEQ ID NO 218
<211> LENGTH: 12
<212> TYPE: PRT
<213> ORGANISM: Homo sapiens
<220> FEATURE:
<223> OTHER INFORMATION: XPO1 Exportin-1;
      O14980_C528
<220> FEATURE:
<221> NAME/KEY: MOD_RES
<222> LOCATION: (7)..(7)
<223> OTHER INFORMATION: Site of chemical conjugation

<400> SEQUENCE: 218

Lys Asp Leu Leu Gly Leu Cys Glu Gln Lys Arg Gly
1               5                   10

<210> SEQ ID NO 219
<211> LENGTH: 9
<212> TYPE: PRT
<213> ORGANISM: Homo sapiens
<220> FEATURE:
<223> OTHER INFORMATION: MSH2 DNA mismatch repair protein Msh2;
      P43246_C843
<220> FEATURE:
<221> NAME/KEY: MOD_RES
<222> LOCATION: (6)..(6)
<223> OTHER INFORMATION: Site of chemical conjugation

<400> SEQUENCE: 219

Lys His Val Ile Glu Cys Ala Lys Gln
1               5

<210> SEQ ID NO 220
<211> LENGTH: 9
<212> TYPE: PRT
<213> ORGANISM: Homo sapiens
<220> FEATURE:
<223> OTHER INFORMATION: HNRNPU Heterogeneous nuclear ribonucleoprotein
      U; Q00839_C562
<220> FEATURE:
<221> NAME/KEY: MOD_RES
<222> LOCATION: (5)..(5)
<223> OTHER INFORMATION: Site of chemical conjugation

<400> SEQUENCE: 220

Arg Ala Pro Gln Cys Leu Gly Lys Phe
1               5

<210> SEQ ID NO 221
<211> LENGTH: 20
<212> TYPE: PRT
<213> ORGANISM: Homo sapiens
<220> FEATURE:
<223> OTHER INFORMATION: TSEN15 tRNA-splicing endonuclease subunit
      Sen15; Q8WW01_C13
<220> FEATURE:
<221> NAME/KEY: MOD_RES
<222> LOCATION: (10)..(10)
<223> OTHER INFORMATION: Site of chemical conjugation

<400> SEQUENCE: 221

Arg Gly Asp Ser Glu Pro Thr Pro Gly Cys Ser Gly Leu Gly Pro Gly
1               5                   10                  15

Gly Val Arg Gly
            20

<210> SEQ ID NO 222
```

```
<211> LENGTH: 18
<212> TYPE: PRT
<213> ORGANISM: Homo sapiens
<220> FEATURE:
<223> OTHER INFORMATION: DIAPH1 Protein diaphanous homolog 1;
      O60610_C1227
<220> FEATURE:
<221> NAME/KEY: MOD_RES
<222> LOCATION: (5)..(5)
<223> OTHER INFORMATION: Site of chemical conjugation

<400> SEQUENCE: 222

Arg Lys Ala Gly Cys Ala Val Thr Ser Leu Leu Ala Ser Glu Leu Thr
1               5                   10                  15

Lys Asp

<210> SEQ ID NO 223
<211> LENGTH: 24
<212> TYPE: PRT
<213> ORGANISM: Homo sapiens
<220> FEATURE:
<223> OTHER INFORMATION: Asun Protein asunder homolog;
      Q9NVM9_C349
<220> FEATURE:
<221> NAME/KEY: MOD_RES
<222> LOCATION: (14)..(14)
<223> OTHER INFORMATION: Site of chemical conjugation

<400> SEQUENCE: 223

Arg Ile Ser Pro Val Asp Val Asn Ser Arg Pro Ser Ser Cys Leu Thr
1               5                   10                  15

Asn Phe Leu Leu Asn Gly Arg Ser
            20

<210> SEQ ID NO 224
<211> LENGTH: 13
<212> TYPE: PRT
<213> ORGANISM: Homo sapiens
<220> FEATURE:
<223> OTHER INFORMATION: PFAS Phosphoribosylformylglycinamidine
      synthase; O15067_C270
<220> FEATURE:
<221> NAME/KEY: MOD_RES
<222> LOCATION: (3)..(3)
<223> OTHER INFORMATION: Site of chemical conjugation

<400> SEQUENCE: 224

Lys Phe Cys Asp Asn Ser Ser Ala Ile Gln Gly Lys Glu
1               5                   10

<210> SEQ ID NO 225
<211> LENGTH: 26
<212> TYPE: PRT
<213> ORGANISM: Homo sapiens
<220> FEATURE:
<223> OTHER INFORMATION: ATP6V1A V-type proton ATPase catalytic subunit
      A; P38606_C254
<220> FEATURE:
<221> NAME/KEY: MOD_RES
<222> LOCATION: (23)..(23)
<223> OTHER INFORMATION: Site of chemical conjugation

<400> SEQUENCE: 225

Arg Val Leu Asp Ala Leu Phe Pro Cys Val Gln Gly Gly Thr Thr Ala
1               5                   10                  15

Ile Pro Gly Ala Phe Gly Cys Gly Lys Thr
            20                  25
```

```
<210> SEQ ID NO 226
<211> LENGTH: 12
<212> TYPE: PRT
<213> ORGANISM: Homo sapiens
<220> FEATURE:
<223> OTHER INFORMATION: TXNDC5 Thioredoxin domain-containing protein 5;
      Q8NBS9_C217
<220> FEATURE:
<221> NAME/KEY: MOD_RES
<222> LOCATION: (7)..(7)
<223> OTHER INFORMATION: Site of chemical conjugation

<400> SEQUENCE: 226

Lys Phe Phe Ala Pro Trp Cys Gly His Cys Lys Ala
1               5                   10

<210> SEQ ID NO 227
<211> LENGTH: 26
<212> TYPE: PRT
<213> ORGANISM: Homo sapiens
<220> FEATURE:
<223> OTHER INFORMATION: ADD1 Alpha-adducin;
      P35611_C68
<220> FEATURE:
<221> NAME/KEY: MOD_RES
<222> LOCATION: (12)..(12)
<223> OTHER INFORMATION: Site of chemical conjugation

<400> SEQUENCE: 227

Arg Val Ser Met Ile Leu Gln Ser Pro Ala Phe Cys Glu Glu Leu Glu
1               5                   10                  15

Ser Met Ile Gln Glu Gln Phe Lys Lys Gly
            20                  25

<210> SEQ ID NO 228
<211> LENGTH: 14
<212> TYPE: PRT
<213> ORGANISM: Homo sapiens
<220> FEATURE:
<223> OTHER INFORMATION: STAT1 Signal transducer and activator of
      transcription 1; P42224_C492
<220> FEATURE:
<221> NAME/KEY: MOD_RES
<222> LOCATION: (11)..(11)
<223> OTHER INFORMATION: Site of chemical conjugation

<400> SEQUENCE: 228

Arg Asn Leu Ser Phe Phe Leu Thr Pro Pro Cys Ala Arg Trp
1               5                   10

<210> SEQ ID NO 229
<211> LENGTH: 16
<212> TYPE: PRT
<213> ORGANISM: Homo sapiens
<220> FEATURE:
<223> OTHER INFORMATION: IQGAP1 Ras GTPase-activating-like protein
      IQGAP1; P46940_C781
<220> FEATURE:
<221> NAME/KEY: MOD_RES
<222> LOCATION: (9)..(9)
<223> OTHER INFORMATION: Site of chemical conjugation

<400> SEQUENCE: 229

Lys Lys Gln Ile Pro Ala Ile Thr Cys Ile Gln Ser Gln Trp Arg Gly
1               5                   10                  15

<210> SEQ ID NO 230
<211> LENGTH: 27
<212> TYPE: PRT
<213> ORGANISM: Homo sapiens
```

```
<220> FEATURE:
<223> OTHER INFORMATION: ZWINT ZW10 interactor;
      O95229_C54
<220> FEATURE:
<221> NAME/KEY: MOD_RES
<222> LOCATION: (6)..(6)
<223> OTHER INFORMATION: Site of chemical conjugation

<400> SEQUENCE: 230

Lys Asp Lys Leu Leu Cys Ser Gln Leu Gln Val Ala Asp Phe Leu Gln
1               5                   10                  15

Asn Ile Leu Ala Gln Glu Asp Thr Ala Lys Gly
            20                  25

<210> SEQ ID NO 231
<211> LENGTH: 12
<212> TYPE: PRT
<213> ORGANISM: Homo sapiens
<220> FEATURE:
<223> OTHER INFORMATION: RPL36AL 60S ribosomal protein L36a-like;
      Q969Q0_C88
<220> FEATURE:
<221> NAME/KEY: MOD_RES
<222> LOCATION: (2)..(2)
<223> OTHER INFORMATION: Site of chemical conjugation

<400> SEQUENCE: 231

Arg Cys Lys His Phe Glu Leu Gly Gly Asp Lys Lys
1               5                   10

<210> SEQ ID NO 232
<211> LENGTH: 23
<212> TYPE: PRT
<213> ORGANISM: Homo sapiens
<220> FEATURE:
<223> OTHER INFORMATION: PDS5A Sister chromatid cohesion protein PDS5
      homolog A; Q29RF7_C242
<220> FEATURE:
<221> NAME/KEY: MOD_RES
<222> LOCATION: (9)..(9)
<223> OTHER INFORMATION: Site of chemical conjugation

<400> SEQUENCE: 232

Arg Thr Val Gln Thr Ile Glu Ala Cys Ile Ala Asn Phe Phe Asn Gln
1               5                   10                  15

Val Leu Val Leu Gly Arg Ser
            20

<210> SEQ ID NO 233
<211> LENGTH: 24
<212> TYPE: PRT
<213> ORGANISM: Homo sapiens
<220> FEATURE:
<223> OTHER INFORMATION: TSR1 Pre-rRNA-processing protein TSR1 homolog;
      Q2NL82_C126
<220> FEATURE:
<221> NAME/KEY: MOD_RES
<222> LOCATION: (21)..(21)
<223> OTHER INFORMATION: Site of chemical conjugation

<400> SEQUENCE: 233

Arg Asp Thr Gly Thr Val His Leu Asn Glu Leu Gly Asn Thr Gln Asn
1               5                   10                  15

Phe Met Leu Leu Cys Pro Arg Leu
            20

<210> SEQ ID NO 234
<211> LENGTH: 11
```

```
<212> TYPE: PRT
<213> ORGANISM: Homo sapiens
<220> FEATURE:
<223> OTHER INFORMATION: NUP50 Nuclear pore complex protein Nup50;
      Q9UKX7_C151
<220> FEATURE:
<221> NAME/KEY: MOD_RES
<222> LOCATION: (3)..(3)
<223> OTHER INFORMATION: Site of chemical conjugation

<400> SEQUENCE: 234

Lys Ala Cys Val Gly Asn Ala Tyr His Lys Gln
1               5                   10

<210> SEQ ID NO 235
<211> LENGTH: 20
<212> TYPE: PRT
<213> ORGANISM: Homo sapiens
<220> FEATURE:
<223> OTHER INFORMATION: RPL17 60S ribosomal protein L17;
      P18621_C144
<220> FEATURE:
<221> NAME/KEY: MOD_RES
<222> LOCATION: (10)..(10)
<223> OTHER INFORMATION: Site of chemical conjugation

<400> SEQUENCE: 235

Arg Ile Asn Pro Tyr Met Ser Ser Pro Cys His Ile Glu Met Ile Leu
1               5                   10                  15

Thr Glu Lys Glu
            20

<210> SEQ ID NO 236
<211> LENGTH: 21
<212> TYPE: PRT
<213> ORGANISM: Homo sapiens
<220> FEATURE:
<223> OTHER INFORMATION: ALDH9A1 4-trimethylaminobutyraldehyde
      dehydrogenase; P49189_C288
<220> FEATURE:
<221> NAME/KEY: MOD_RES
<222> LOCATION: (15)..(15)
<223> OTHER INFORMATION: Site of chemical conjugation

<400> SEQUENCE: 236

Lys Gly Ala Leu Met Ala Asn Phe Leu Thr Gln Gly Gln Val Cys Cys
1               5                   10                  15

Asn Gly Thr Arg Val
            20

<210> SEQ ID NO 237
<211> LENGTH: 18
<212> TYPE: PRT
<213> ORGANISM: Homo sapiens
<220> FEATURE:
<223> OTHER INFORMATION: MAP2K4 Dual specificity mitogen-activated
      protein kinase; P45985_C246
<220> FEATURE:
<221> NAME/KEY: MOD_RES
<222> LOCATION: (3)..(3)
<223> OTHER INFORMATION: Site of chemical conjugation

<400> SEQUENCE: 237

Lys Leu Cys Asp Phe Gly Ile Ser Gly Gln Leu Val Asp Ser Ile Ala
1               5                   10                  15

Lys Thr

<210> SEQ ID NO 238
```

```
<211> LENGTH: 41
<212> TYPE: PRT
<213> ORGANISM: Homo sapiens
<220> FEATURE:
<223> OTHER INFORMATION: TCOF1 Treacle protein;
      Q13428_C1298
<220> FEATURE:
<221> NAME/KEY: MOD_RES
<222> LOCATION: (21)..(21)
<223> OTHER INFORMATION: Site of chemical conjugation

<400> SEQUENCE: 238

Lys Lys Gly Ala Gly Asn Pro Gln Ala Ser Thr Leu Ala Leu Gln Ser
1               5                   10                  15

Asn Ile Thr Gln Cys Leu Leu Gly Gln Pro Trp Pro Leu Asn Glu Ala
            20                  25                  30

Gln Val Gln Ala Ser Val Val Lys Val
        35                  40

<210> SEQ ID NO 239
<211> LENGTH: 21
<212> TYPE: PRT
<213> ORGANISM: Homo sapiens
<220> FEATURE:
<223> OTHER INFORMATION: CPPED1 Calcineurin-like phosphoesterase domain-
      containing; Q9BRF8_C54
<220> FEATURE:
<221> NAME/KEY: MOD_RES
<222> LOCATION: (8)..(8)
<223> OTHER INFORMATION: Site of chemical conjugation

<400> SEQUENCE: 239

Lys Ala Trp Ser Thr Gly Asp Cys Asp Asn Gly Gly Asp Glu Trp Glu
1               5                   10                  15

Gln Glu Ile Arg Leu
            20

<210> SEQ ID NO 240
<211> LENGTH: 11
<212> TYPE: PRT
<213> ORGANISM: Homo sapiens
<220> FEATURE:
<223> OTHER INFORMATION: AIP AH receptor-interacting protein;
      O00170_C122
<220> FEATURE:
<221> NAME/KEY: MOD_RES
<222> LOCATION: (4)..(4)
<223> OTHER INFORMATION: Site of chemical conjugation

<400> SEQUENCE: 240

Arg His Cys Cys Gly Val Ala Gln Met Arg Glu
1               5                   10

<210> SEQ ID NO 241
<211> LENGTH: 33
<212> TYPE: PRT
<213> ORGANISM: Homo sapiens
<220> FEATURE:
<223> OTHER INFORMATION: DUSP12 Dual specificity protein phosphatase 12;
      Q9UNI6_C265
<220> FEATURE:
<221> NAME/KEY: MOD_RES
<222> LOCATION: (5)..(5)
<223> OTHER INFORMATION: Site of chemical conjugation

<400> SEQUENCE: 241

Arg Gln Ala Gln Cys Thr Ser Tyr Phe Ile Glu Pro Val Gln Trp Met
1               5                   10                  15
```

Glu Ser Ala Leu Leu Gly Val Met Asp Gly Gln Leu Leu Cys Pro Lys
            20                  25                  30

Cys

<210> SEQ ID NO 242
<211> LENGTH: 18
<212> TYPE: PRT
<213> ORGANISM: Homo sapiens
<220> FEATURE:
<223> OTHER INFORMATION: GTF2A2 Transcription initiation factor IIA
      subunit 2; P52657_C68
<220> FEATURE:
<221> NAME/KEY: MOD_RES
<222> LOCATION: (3)..(3)
<223> OTHER INFORMATION: Site of chemical conjugation

<400> SEQUENCE: 242

Arg Phe Cys Asp Asn Val Trp Thr Phe Val Leu Asn Asp Val Glu Phe
1               5                   10                  15

Arg Glu

<210> SEQ ID NO 243
<211> LENGTH: 40
<212> TYPE: PRT
<213> ORGANISM: Homo sapiens
<220> FEATURE:
<223> OTHER INFORMATION: PFAS Phosphoribosylformylglycinamidine
      synthase; O15067_C1287
<220> FEATURE:
<221> NAME/KEY: MOD_RES
<222> LOCATION: (36)..(36)
<223> OTHER INFORMATION: Site of chemical conjugation

<400> SEQUENCE: 243

Arg Gly Leu Ala Pro Leu His Trp Ala Asp Asp Gly Asn Pro Thr
1               5                   10                  15

Glu Gln Tyr Pro Leu Asn Pro Asn Gly Ser Pro Gly Gly Val Ala Gly
            20                  25                  30

Ile Cys Ser Cys Asp Gly Arg His
            35                  40

<210> SEQ ID NO 244
<211> LENGTH: 13
<212> TYPE: PRT
<213> ORGANISM: Homo sapiens
<220> FEATURE:
<223> OTHER INFORMATION: HPCAL1 Hippocalcin-like protein 1;
      P37235_C185
<220> FEATURE:
<221> NAME/KEY: MOD_RES
<222> LOCATION: (5)..(5)
<223> OTHER INFORMATION: Site of chemical conjugation

<400> SEQUENCE: 244

Arg Leu Leu Gln Cys Asp Pro Ser Ser Ala Ser Gln Phe
1               5                   10

<210> SEQ ID NO 245
<211> LENGTH: 14
<212> TYPE: PRT
<213> ORGANISM: Homo sapiens
<220> FEATURE:
<223> OTHER INFORMATION: MVD Diphosphomevalonate decarboxylase;
      P53602_C108
<220> FEATURE:
<221> NAME/KEY: MOD_RES
<222> LOCATION: (12)..(12)
<223> OTHER INFORMATION: Site of chemical conjugation

```
<400> SEQUENCE: 245

Arg Asp Gly Asp Pro Leu Pro Ser Ser Leu Ser Cys Lys Val
1               5                   10

<210> SEQ ID NO 246
<211> LENGTH: 19
<212> TYPE: PRT
<213> ORGANISM: Homo sapiens
<220> FEATURE:
<223> OTHER INFORMATION: EFHD2 EF-hand domain-containing protein D2;
      Q96C19_C172
<220> FEATURE:
<221> NAME/KEY: MOD_RES
<222> LOCATION: (14)..(14)
<223> OTHER INFORMATION: Site of chemical conjugation

<400> SEQUENCE: 246

Lys Ala Ala Ala Gly Glu Leu Gln Glu Asp Ser Gly Leu Cys Val Leu
1               5                   10                  15
Ala Arg Leu

<210> SEQ ID NO 247
<211> LENGTH: 16
<212> TYPE: PRT
<213> ORGANISM: Homo sapiens
<220> FEATURE:
<223> OTHER INFORMATION: RTN4 Reticulon-4;
      Q9NQC3_C1101
<220> FEATURE:
<221> NAME/KEY: MOD_RES
<222> LOCATION: (12)..(12)
<223> OTHER INFORMATION: Site of chemical conjugation

<400> SEQUENCE: 247

Lys Tyr Ser Asn Ser Ala Leu Gly His Val Asn Cys Thr Ile Lys Glu
1               5                   10                  15

<210> SEQ ID NO 248
<211> LENGTH: 18
<212> TYPE: PRT
<213> ORGANISM: Homo sapiens
<220> FEATURE:
<223> OTHER INFORMATION: PHGDH D-3-phosphoglycerate dehydrogenase;
      O43175_C369
<220> FEATURE:
<221> NAME/KEY: MOD_RES
<222> LOCATION: (6)..(6)
<223> OTHER INFORMATION: Site of chemical conjugation

<400> SEQUENCE: 248

Lys Asn Ala Gly Asn Cys Leu Ser Pro Ala Val Ile Val Gly Leu Leu
1               5                   10                  15
Lys Glu

<210> SEQ ID NO 249
<211> LENGTH: 10
<212> TYPE: PRT
<213> ORGANISM: Homo sapiens
<220> FEATURE:
<223> OTHER INFORMATION: RAD9A Cell cycle checkpoint control protein
      RAD9A; Q99638_C114
<220> FEATURE:
<221> NAME/KEY: MOD_RES
<222> LOCATION: (8)..(8)
<223> OTHER INFORMATION: Site of chemical conjugation

<400> SEQUENCE: 249
```

Arg Leu Val Val Gln Leu His Cys Lys Phe
1               5                   10

<210> SEQ ID NO 250
<211> LENGTH: 26
<212> TYPE: PRT
<213> ORGANISM: Homo sapiens
<220> FEATURE:
<223> OTHER INFORMATION: PRDX1 Peroxiredoxin-1;
      Q06830_C83
<220> FEATURE:
<221> NAME/KEY: MOD_RES
<222> LOCATION: (16)..(16)
<223> OTHER INFORMATION: Site of chemical conjugation

<400> SEQUENCE: 250

Lys Leu Asn Cys Gln Val Ile Gly Ala Ser Val Asp Ser His Phe Cys
1               5                   10                  15

His Leu Ala Trp Val Asn Thr Pro Lys Lys
            20                  25

<210> SEQ ID NO 251
<211> LENGTH: 20
<212> TYPE: PRT
<213> ORGANISM: Homo sapiens
<220> FEATURE:
<223> OTHER INFORMATION: SORD Sorbitol dehydrogenase;
      Q00796_C45
<220> FEATURE:
<221> NAME/KEY: MOD_RES
<222> LOCATION: (8)..(8)
<223> OTHER INFORMATION: Site of chemical conjugation

<400> SEQUENCE: 251

Arg Met His Ser Val Gly Ile Cys Gly Ser Asp Val His Tyr Trp Glu
1               5                   10                  15

Tyr Gly Arg Ile
            20

<210> SEQ ID NO 252
<211> LENGTH: 17
<212> TYPE: PRT
<213> ORGANISM: Homo sapiens
<220> FEATURE:
<223> OTHER INFORMATION: CHRAC1 Chromatin accessibility complex protein
      1; Q9NRG0_C55
<220> FEATURE:
<221> NAME/KEY: MOD_RES
<222> LOCATION: (9)..(9)
<223> OTHER INFORMATION: Site of chemical conjugation

<400> SEQUENCE: 252

Lys Ala Thr Glu Leu Phe Val Gln Cys Leu Ala Thr Tyr Ser Tyr Arg
1               5                   10                  15

His

<210> SEQ ID NO 253
<211> LENGTH: 34
<212> TYPE: PRT
<213> ORGANISM: Homo sapiens
<220> FEATURE:
<223> OTHER INFORMATION: S100A11 Protein S100-A11;
      P31949_C91
<220> FEATURE:
<221> NAME/KEY: MOD_RES
<222> LOCATION: (27)..(27)
<223> OTHER INFORMATION: Site of chemical conjugation

<400> SEQUENCE: 253

-continued

```
Lys Lys Leu Asp Thr Asn Ser Asp Gly Gln Leu Asp Phe Ser Glu Phe
1               5                   10                  15

Leu Asn Leu Ile Gly Gly Leu Ala Met Ala Cys His Asp Ser Phe Leu
            20                  25                  30

Lys Ala

<210> SEQ ID NO 254
<211> LENGTH: 15
<212> TYPE: PRT
<213> ORGANISM: Homo sapiens
<220> FEATURE:
<223> OTHER INFORMATION: TUBA8 Tubulin alpha-8 chain;
      Q9NY65_C347
<220> FEATURE:
<221> NAME/KEY: MOD_RES
<222> LOCATION: (9)..(9)
<223> OTHER INFORMATION: Site of chemical conjugation

<400> SEQUENCE: 254

Arg Thr Ile Gln Phe Val Asp Trp Cys Pro Thr Gly Phe Lys Val
1               5                   10                  15

<210> SEQ ID NO 255
<211> LENGTH: 12
<212> TYPE: PRT
<213> ORGANISM: Homo sapiens
<220> FEATURE:
<223> OTHER INFORMATION: CDKN2AIP CDKN2A-interacting protein;
      Q9NXV6_C516
<220> FEATURE:
<221> NAME/KEY: MOD_RES
<222> LOCATION: (9)..(9)
<223> OTHER INFORMATION: Site of chemical conjugation

<400> SEQUENCE: 255

Lys Ser Val Tyr Leu Gly Thr Gly Cys Gly Lys Ser
1               5                   10

<210> SEQ ID NO 256
<211> LENGTH: 23
<212> TYPE: PRT
<213> ORGANISM: Homo sapiens
<220> FEATURE:
<223> OTHER INFORMATION: PRDX4 Peroxiredoxin-4;
      Q13162_C51
<220> FEATURE:
<221> NAME/KEY: MOD_RES
<222> LOCATION: (7)..(7)
<223> OTHER INFORMATION: Site of chemical conjugation

<400> SEQUENCE: 256

Arg Thr Arg Glu Glu Glu Cys His Phe Tyr Ala Gly Gly Gln Val Tyr
1               5                   10                  15

Pro Gly Glu Ala Ser Arg Val
            20

<210> SEQ ID NO 257
<211> LENGTH: 23
<212> TYPE: PRT
<213> ORGANISM: Homo sapiens
<220> FEATURE:
<223> OTHER INFORMATION: PSME4 Proteasome activator complex subunit 4;
      Q14997_C1840
<220> FEATURE:
<221> NAME/KEY: MOD_RES
<222> LOCATION: (20)..(20)
<223> OTHER INFORMATION: Site of chemical conjugation
```

-continued

```
<400> SEQUENCE: 257

Lys Gln Gln Phe Thr Asp Asp Gln Leu Leu Val Leu Thr Asp Leu Leu
1               5                   10                  15

Val Ser Pro Cys Tyr Tyr Ala
            20

<210> SEQ ID NO 258
<211> LENGTH: 21
<212> TYPE: PRT
<213> ORGANISM: Homo sapiens
<220> FEATURE:
<223> OTHER INFORMATION: NCAPH Condensin complex subunit 2;
      Q15003_C418
<220> FEATURE:
<221> NAME/KEY: MOD_RES
<222> LOCATION: (4)..(4)
<223> OTHER INFORMATION: Site of chemical conjugation

<400> SEQUENCE: 258

Arg Thr Met Cys Pro Leu Leu Ser Met Lys Pro Gly Glu Tyr Ser Tyr
1               5                   10                  15

Phe Ser Pro Arg Thr
            20

<210> SEQ ID NO 259
<211> LENGTH: 12
<212> TYPE: PRT
<213> ORGANISM: Homo sapiens
<220> FEATURE:
<223> OTHER INFORMATION: AMPD2 AMP deaminase 2;
      Q01433_C107
<220> FEATURE:
<221> NAME/KEY: MOD_RES
<222> LOCATION: (9)..(9)
<223> OTHER INFORMATION: Site of chemical conjugation

<400> SEQUENCE: 259

Arg Ser Leu Pro Gly Pro Ala Pro Cys Leu Lys His
1               5                   10

<210> SEQ ID NO 260
<211> LENGTH: 12
<212> TYPE: PRT
<213> ORGANISM: Homo sapiens
<220> FEATURE:
<223> OTHER INFORMATION: IDH1 Isocitrate dehydrogenase;
      O75874_C269
<220> FEATURE:
<221> NAME/KEY: MOD_RES
<222> LOCATION: (10)..(10)
<223> OTHER INFORMATION: Site of chemical conjugation

<400> SEQUENCE: 260

Lys Ser Glu Gly Gly Phe Ile Trp Ala Cys Lys Asn
1               5                   10

<210> SEQ ID NO 261
<211> LENGTH: 23
<212> TYPE: PRT
<213> ORGANISM: Homo sapiens
<220> FEATURE:
<223> OTHER INFORMATION: PDS5A Sister chromatid cohesion protein PDS5
      homolog A; Q29RF7_C532
<220> FEATURE:
<221> NAME/KEY: MOD_RES
<222> LOCATION: (16)..(16)
<223> OTHER INFORMATION: Site of chemical conjugation

<400> SEQUENCE: 261
```

-continued

Arg Glu Leu Leu Asp Leu His Lys Gln Pro Thr Ser Glu Ala Asn Cys
1               5                   10                  15

Ser Ala Met Phe Gly Lys Leu
            20

<210> SEQ ID NO 262
<211> LENGTH: 10
<212> TYPE: PRT
<213> ORGANISM: Homo sapiens
<220> FEATURE:
<223> OTHER INFORMATION: PC Pyruvate carboxylase, mitochondrial;
      P11498_C622
<220> FEATURE:
<221> NAME/KEY: MOD_RES
<222> LOCATION: (6)..(6)
<223> OTHER INFORMATION: Site of chemical conjugation

<400> SEQUENCE: 262

Arg Phe Leu Tyr Glu Cys Pro Trp Arg Arg
1               5                   10

<210> SEQ ID NO 263
<211> LENGTH: 29
<212> TYPE: PRT
<213> ORGANISM: Homo sapiens
<220> FEATURE:
<223> OTHER INFORMATION: TUFM Elongation factor Tu, mitochondrial;
      P49411_C147
<220> FEATURE:
<221> NAME/KEY: MOD_RES
<222> LOCATION: (13)..(13)
<223> OTHER INFORMATION: Site of chemical conjugation

<400> SEQUENCE: 263

Lys Asn Met Ile Thr Gly Thr Ala Pro Leu Asp Gly Cys Ile Leu Val
1               5                   10                  15

Val Ala Ala Asn Asp Gly Pro Met Pro Gln Thr Arg Glu
            20                  25

<210> SEQ ID NO 264
<211> LENGTH: 12
<212> TYPE: PRT
<213> ORGANISM: Homo sapiens
<220> FEATURE:
<223> OTHER INFORMATION: ILKAP Integrin-linked kinase-associated
      serine/threonine; Q9H0C8_C301
<220> FEATURE:
<221> NAME/KEY: MOD_RES
<222> LOCATION: (2)..(2)
<223> OTHER INFORMATION: Site of chemical conjugation

<400> SEQUENCE: 264

Arg Cys Gly Val Thr Ser Val Pro Asp Ile Arg Arg
1               5                   10

<210> SEQ ID NO 265
<211> LENGTH: 16
<212> TYPE: PRT
<213> ORGANISM: Homo sapiens
<220> FEATURE:
<223> OTHER INFORMATION: ALDH6A1 Methylmalonate-semialdehyde
      dehydrogenase; Q02252_C317
<220> FEATURE:
<221> NAME/KEY: MOD_RES
<222> LOCATION: (2)..(2)
<223> OTHER INFORMATION: Site of chemical conjugation

<400> SEQUENCE: 265

Arg Cys Met Ala Leu Ser Thr Ala Val Leu Val Gly Glu Ala Lys Lys
1               5                   10                  15

<210> SEQ ID NO 266
<211> LENGTH: 18
<212> TYPE: PRT
<213> ORGANISM: Homo sapiens
<220> FEATURE:
<223> OTHER INFORMATION: PSMD14 26S proteasome non-ATPase regulatory
      subunit 14; O00487_C238
<220> FEATURE:
<221> NAME/KEY: MOD_RES
<222> LOCATION: (16)..(16)
<223> OTHER INFORMATION: Site of chemical conjugation

<400> SEQUENCE: 266

Lys Ser Trp Met Glu Gly Leu Thr Leu Gln Asp Tyr Ser Glu His Cys
1               5                   10                  15

Lys His

<210> SEQ ID NO 267
<211> LENGTH: 11
<212> TYPE: PRT
<213> ORGANISM: Homo sapiens
<220> FEATURE:
<223> OTHER INFORMATION: DTYMK Thymidylate kinase;
      P23919_C117
<220> FEATURE:
<221> NAME/KEY: MOD_RES
<222> LOCATION: (9)..(9)
<223> OTHER INFORMATION: Site of chemical conjugation

<400> SEQUENCE: 267

Lys Glu Asn Phe Ser Leu Asp Trp Cys Lys Gln
1               5                   10

<210> SEQ ID NO 268
<211> LENGTH: 21
<212> TYPE: PRT
<213> ORGANISM: Homo sapiens
<220> FEATURE:
<223> OTHER INFORMATION: ZNF217 Zinc finger protein 217;
      O75362_C286
<220> FEATURE:
<221> NAME/KEY: MOD_RES
<222> LOCATION: (2)..(2)
<223> OTHER INFORMATION: Site of chemical conjugation

<400> SEQUENCE: 268

Arg Cys Ile Pro Gln Leu Asp Pro Phe Thr Thr Phe Gln Ala Trp Gln
1               5                   10                  15

Leu Ala Thr Lys Gly
            20

<210> SEQ ID NO 269
<211> LENGTH: 10
<212> TYPE: PRT
<213> ORGANISM: Homo sapiens
<220> FEATURE:
<223> OTHER INFORMATION: PRKAR1A cAMP-dependent protein kinase type
      I-alpha regulatory subunit; P10644_C18
<220> FEATURE:
<221> NAME/KEY: MOD_RES
<222> LOCATION: (3)..(3)
<223> OTHER INFORMATION: Site of chemical conjugation

<400> SEQUENCE: 269

Arg Glu Cys Glu Leu Tyr Val Gln Lys His
1               5                   10

<210> SEQ ID NO 270
<211> LENGTH: 11
<212> TYPE: PRT
<213> ORGANISM: Homo sapiens
<220> FEATURE:
<223> OTHER INFORMATION: HCFC1 Host cell factor 1;
      P51610_C1872
<220> FEATURE:
<221> NAME/KEY: MOD_RES
<222> LOCATION: (8)..(8)
<223> OTHER INFORMATION: Site of chemical conjugation

<400> SEQUENCE: 270

Arg Val Ala Gly Ile Asn Ala Cys Gly Arg Gly
1               5                   10

<210> SEQ ID NO 271
<211> LENGTH: 14
<212> TYPE: PRT
<213> ORGANISM: Homo sapiens
<220> FEATURE:
<223> OTHER INFORMATION: FAM203B Protein FAM203B;
      P0CB43_C51
<220> FEATURE:
<221> NAME/KEY: MOD_RES
<222> LOCATION: (9)..(9)
<223> OTHER INFORMATION: Site of chemical conjugation

<400> SEQUENCE: 271

Arg His Val Leu Ala Leu Thr Gly Cys Gly Pro Gly Arg Ala
1               5                   10

<210> SEQ ID NO 272
<211> LENGTH: 24
<212> TYPE: PRT
<213> ORGANISM: Homo sapiens
<220> FEATURE:
<223> OTHER INFORMATION: PFKFB2 6-phosphofructo-2-kinase/fructose-2,6-
      bisphosphata; O60825_C158
<220> FEATURE:
<221> NAME/KEY: MOD_RES
<222> LOCATION: (9)..(9)
<223> OTHER INFORMATION: Site of chemical conjugation

<400> SEQUENCE: 272

Lys Val Phe Phe Val Glu Ser Val Cys Asp Asp Pro Asp Val Ile Ala
1               5                   10                  15

Ala Asn Ile Leu Glu Val Lys Val
            20

<210> SEQ ID NO 273
<211> LENGTH: 12
<212> TYPE: PRT
<213> ORGANISM: Homo sapiens
<220> FEATURE:
<223> OTHER INFORMATION: TBCE Tubulin-specific chaperone E;
      Q15813_C141
<220> FEATURE:
<221> NAME/KEY: MOD_RES
<222> LOCATION: (7)..(7)
<223> OTHER INFORMATION: Site of chemical conjugation

<400> SEQUENCE: 273

Arg Asn Cys Ala Val Ser Cys Ala Gly Glu Lys Gly
1               5                   10

<210> SEQ ID NO 274
<211> LENGTH: 18

-continued

```
<212> TYPE: PRT
<213> ORGANISM: Homo sapiens
<220> FEATURE:
<223> OTHER INFORMATION: PRDX5 Peroxiredoxin-5, mitochondrial;
      P30044_C100
<220> FEATURE:
<221> NAME/KEY: MOD_RES
<222> LOCATION: (15)..(15)
<223> OTHER INFORMATION: Site of chemical conjugation

<400> SEQUENCE: 274

Lys Gly Val Leu Phe Gly Val Pro Gly Ala Phe Thr Pro Gly Cys Ser
1               5                   10                  15

Lys Thr

<210> SEQ ID NO 275
<211> LENGTH: 22
<212> TYPE: PRT
<213> ORGANISM: Homo sapiens
<220> FEATURE:
<223> OTHER INFORMATION: NUP93 Nuclear pore complex protein Nup93;
      Q8N1F7_C522
<220> FEATURE:
<221> NAME/KEY: MOD_RES
<222> LOCATION: (19)..(19)
<223> OTHER INFORMATION: Site of chemical conjugation

<400> SEQUENCE: 275

Lys Ser Ser Gly Gln Ser Ala Gln Leu Leu Ser His Glu Pro Gly Asp
1               5                   10                  15

Pro Pro Cys Leu Arg Arg
            20

<210> SEQ ID NO 276
<211> LENGTH: 24
<212> TYPE: PRT
<213> ORGANISM: Homo sapiens
<220> FEATURE:
<223> OTHER INFORMATION: PDP1;
      Q9P0J1_C149
<220> FEATURE:
<221> NAME/KEY: MOD_RES
<222> LOCATION: (14)..(14)
<223> OTHER INFORMATION: Site of chemical conjugation

<400> SEQUENCE: 276

Arg Gly Met Leu Leu Gly Val Phe Asp Gly His Ala Gly Cys Ala Cys
1               5                   10                  15

Ser Gln Ala Val Ser Glu Arg Leu
            20

<210> SEQ ID NO 277
<211> LENGTH: 19
<212> TYPE: PRT
<213> ORGANISM: Homo sapiens
<220> FEATURE:
<223> OTHER INFORMATION: CTSB Cathepsin B;
      P07858_C319
<220> FEATURE:
<221> NAME/KEY: MOD_RES
<222> LOCATION: (6)..(6)
<223> OTHER INFORMATION: Site of chemical conjugation

<400> SEQUENCE: 277

Arg Gly Gln Asp His Cys Gly Ile Glu Ser Glu Val Val Ala Gly Ile
1               5                   10                  15

Pro Arg Thr
```

```
<210> SEQ ID NO 278
<211> LENGTH: 19
<212> TYPE: PRT
<213> ORGANISM: Homo sapiens
<220> FEATURE:
<223> OTHER INFORMATION: ACTN1 Alpha-actinin-1;
      P12814_C370
<220> FEATURE:
<221> NAME/KEY: MOD_RES
<222> LOCATION: (12)..(12)
<223> OTHER INFORMATION: Site of chemical conjugation

<400> SEQUENCE: 278

Arg Met Val Ser Asp Ile Asn Asn Ala Trp Gly Cys Leu Glu Gln Val
1               5                   10                  15

Glu Lys Gly

<210> SEQ ID NO 279
<211> LENGTH: 21
<212> TYPE: PRT
<213> ORGANISM: Homo sapiens
<220> FEATURE:
<223> OTHER INFORMATION: OGT UDP-N-acetylglucosamine--peptide
      N-acetylglucosamine; O15294_C620
<220> FEATURE:
<221> NAME/KEY: MOD_RES
<222> LOCATION: (17)..(17)
<223> OTHER INFORMATION: Site of chemical conjugation

<400> SEQUENCE: 279

Lys Val Met Ala Glu Ala Asn His Phe Ile Asp Leu Ser Gln Ile Pro
1               5                   10                  15

Cys Asn Gly Lys Ala
            20

<210> SEQ ID NO 280
<211> LENGTH: 19
<212> TYPE: PRT
<213> ORGANISM: Homo sapiens
<220> FEATURE:
<223> OTHER INFORMATION: TMPRSS12 Transmembrane protease serine 12;
      Q86WS5_C64
<220> FEATURE:
<221> NAME/KEY: MOD_RES
<222> LOCATION: (12)..(12)
<223> OTHER INFORMATION: Site of chemical conjugation

<400> SEQUENCE: 280

Arg Arg Arg Glu Gly Gly Ala His Ala Glu Asp Cys Gly Thr Ala Pro
1               5                   10                  15

Leu Lys Asp

<210> SEQ ID NO 281
<211> LENGTH: 13
<212> TYPE: PRT
<213> ORGANISM: Homo sapiens
<220> FEATURE:
<223> OTHER INFORMATION: ANLN Actin-binding protein anillin;
      Q9NQW6_C712
<220> FEATURE:
<221> NAME/KEY: MOD_RES
<222> LOCATION: (7)..(7)
<223> OTHER INFORMATION: Site of chemical conjugation

<400> SEQUENCE: 281

Lys Asn Asn Ala Phe Pro Cys Gln Val Asn Ile Lys Gln
1               5                   10
```

```
<210> SEQ ID NO 282
<211> LENGTH: 17
<212> TYPE: PRT
<213> ORGANISM: Homo sapiens
<220> FEATURE:
<223> OTHER INFORMATION: PPP4R2 Serine/threonine-protein phosphatase 4
      regulatory; Q9NY27_C22
<220> FEATURE:
<221> NAME/KEY: MOD_RES
<222> LOCATION: (4)..(4)
<223> OTHER INFORMATION: Site of chemical conjugation

<400> SEQUENCE: 282

Lys Glu Val Cys Pro Val Leu Asp Gln Phe Leu Cys His Val Ala Lys
1               5                   10                  15

Thr

<210> SEQ ID NO 283
<211> LENGTH: 34
<212> TYPE: PRT
<213> ORGANISM: Homo sapiens
<220> FEATURE:
<223> OTHER INFORMATION: STAT3 Signal transducer and activator of
      transcription 3; P40763_C259
<220> FEATURE:
<221> NAME/KEY: MOD_RES
<222> LOCATION: (14)..(14)
<223> OTHER INFORMATION: Site of chemical conjugation

<400> SEQUENCE: 283

Arg Gln Gln Ile Ala Cys Ile Gly Gly Pro Pro Asn Ile Cys Leu Asp
1               5                   10                  15

Arg Leu Glu Asn Trp Ile Thr Ser Leu Ala Glu Ser Gln Leu Gln Thr
            20                  25                  30

Arg Gln

<210> SEQ ID NO 284
<211> LENGTH: 33
<212> TYPE: PRT
<213> ORGANISM: Homo sapiens
<220> FEATURE:
<223> OTHER INFORMATION: UGDH UDP-glucose 6-dehydrogenase;
      O60701_C276
<220> FEATURE:
<221> NAME/KEY: MOD_RES
<222> LOCATION: (10)..(10)
<223> OTHER INFORMATION: Site of chemical conjugation

<400> SEQUENCE: 284

Lys Ala Ser Val Gly Phe Gly Gly Ser Cys Phe Gln Lys Asp Val Leu
1               5                   10                  15

Asn Leu Val Tyr Leu Cys Glu Ala Leu Asn Leu Pro Glu Val Ala Arg
            20                  25                  30

Tyr

<210> SEQ ID NO 285
<211> LENGTH: 23
<212> TYPE: PRT
<213> ORGANISM: Homo sapiens
<220> FEATURE:
<223> OTHER INFORMATION: AHNAK Neuroblast differentiation-associated
      protein AHNAK; Q09666_C108
<220> FEATURE:
<221> NAME/KEY: MOD_RES
<222> LOCATION: (7)..(7)
<223> OTHER INFORMATION: Site of chemical conjugation
```

```
<400> SEQUENCE: 285

Arg Glu Val Phe Ser Ser Cys Ser Ser Glu Val Val Leu Ser Gly Asp
1               5                   10                  15

Asp Glu Glu Tyr Gln Arg Ile
            20

<210> SEQ ID NO 286
<211> LENGTH: 11
<212> TYPE: PRT
<213> ORGANISM: Homo sapiens
<220> FEATURE:
<223> OTHER INFORMATION: HINT1 Histidine triad nucleotide-binding
      protein 1; P49773_C84
<220> FEATURE:
<221> NAME/KEY: MOD_RES
<222> LOCATION: (2)..(2)
<223> OTHER INFORMATION: Site of chemical conjugation

<400> SEQUENCE: 286

Lys Cys Ala Ala Asp Leu Gly Leu Asn Lys Gly
1               5                   10

<210> SEQ ID NO 287
<211> LENGTH: 29
<212> TYPE: PRT
<213> ORGANISM: Homo sapiens
<220> FEATURE:
<223> OTHER INFORMATION: UBR5 E3 ubiquitin-protein ligase UBR5;
      O95071_C2314
<220> FEATURE:
<221> NAME/KEY: MOD_RES
<222> LOCATION: (22)..(22)
<223> OTHER INFORMATION: Site of chemical conjugation

<400> SEQUENCE: 287

Arg Ser Phe Tyr Thr Ala Ile Ala Gln Ala Phe Leu Ser Asn Glu Lys
1               5                   10                  15

Leu Pro Asn Leu Glu Cys Ile Gln Asn Ala Asn Lys Gly
            20                  25

<210> SEQ ID NO 288
<211> LENGTH: 13
<212> TYPE: PRT
<213> ORGANISM: Homo sapiens
<220> FEATURE:
<223> OTHER INFORMATION: SAMHD1 SAM domain and HD domain-containing
      protein 1; Q9Y3Z3_C522
<220> FEATURE:
<221> NAME/KEY: MOD_RES
<222> LOCATION: (11)..(11)
<223> OTHER INFORMATION: Site of chemical conjugation

<400> SEQUENCE: 288

Lys Asn Pro Ile Asp His Val Ser Phe Tyr Cys Lys Thr
1               5                   10

<210> SEQ ID NO 289
<211> LENGTH: 9
<212> TYPE: PRT
<213> ORGANISM: Homo sapiens
<220> FEATURE:
<223> OTHER INFORMATION: WDHD1 WD repeat and HMG-box DNA-binding protein
      1; O75717_C773
<220> FEATURE:
<221> NAME/KEY: MOD_RES
<222> LOCATION: (7)..(7)
<223> OTHER INFORMATION: Site of chemical conjugation

<400> SEQUENCE: 289
```

```
Lys Met Leu Ala Leu Ser Cys Lys Leu
1               5

<210> SEQ ID NO 290
<211> LENGTH: 23
<212> TYPE: PRT
<213> ORGANISM: Homo sapiens
<220> FEATURE:
<223> OTHER INFORMATION: OSGEP Probable tRNA threonylcarbamoyladenosine
      biosynthe; Q9NPF4_C265
<220> FEATURE:
<221> NAME/KEY: MOD_RES
<222> LOCATION: (19)..(19)
<223> OTHER INFORMATION: Site of chemical conjugation

<400> SEQUENCE: 290

Arg Ala Met Ala His Cys Gly Ser Gln Glu Ala Leu Ile Val Gly Gly
1               5                   10                  15

Val Gly Cys Asn Val Arg Leu
            20

<210> SEQ ID NO 291
<211> LENGTH: 20
<212> TYPE: PRT
<213> ORGANISM: Homo sapiens
<220> FEATURE:
<223> OTHER INFORMATION: MGMT Methylated-DNA--protein-cysteine
      methyltransferase; P16455_C150
<220> FEATURE:
<221> NAME/KEY: MOD_RES
<222> LOCATION: (4)..(4)
<223> OTHER INFORMATION: Site of chemical conjugation

<400> SEQUENCE: 291

Arg Val Val Cys Ser Ser Gly Ala Val Gly Asn Tyr Ser Gly Gly Leu
1               5                   10                  15

Ala Val Lys Glu
            20

<210> SEQ ID NO 292
<211> LENGTH: 24
<212> TYPE: PRT
<213> ORGANISM: Homo sapiens
<220> FEATURE:
<223> OTHER INFORMATION: FASN Fatty acid synthase;
      P49327_C1558
<220> FEATURE:
<221> NAME/KEY: MOD_RES
<222> LOCATION: (7)..(7)
<223> OTHER INFORMATION: Site of chemical conjugation

<400> SEQUENCE: 292

Arg His Ala Gln Pro Thr Cys Pro Gly Ala Gln Leu Cys Thr Val Tyr
1               5                   10                  15

Tyr Ala Ser Leu Asn Phe Arg Asp
            20

<210> SEQ ID NO 293
<211> LENGTH: 11
<212> TYPE: PRT
<213> ORGANISM: Homo sapiens
<220> FEATURE:
<223> OTHER INFORMATION: DCUN1D1 DCN1-like protein 1;
      Q96GG9_C115
<220> FEATURE:
<221> NAME/KEY: MOD_RES
<222> LOCATION: (6)..(6)
<223> OTHER INFORMATION: Site of chemical conjugation
```

<400> SEQUENCE: 293

Arg Ala Ala Thr Gln Cys Glu Phe Ser Lys Gln
1               5                   10

<210> SEQ ID NO 294
<211> LENGTH: 33
<212> TYPE: PRT
<213> ORGANISM: Homo sapiens
<220> FEATURE:
<223> OTHER INFORMATION: PLS3 Plastin-3;
      P13797_C33
<220> FEATURE:
<221> NAME/KEY: MOD_RES
<222> LOCATION: (23)..(23)
<223> OTHER INFORMATION: Site of chemical conjugation

<400> SEQUENCE: 294

Lys Asp Glu Leu Asp Glu Leu Lys Glu Ala Phe Ala Lys Val Asp Leu
1               5                   10                  15

Asn Ser Asn Gly Phe Ile Cys Asp Tyr Glu Leu His Glu Leu Phe Lys
            20                  25                  30

Glu

<210> SEQ ID NO 295
<211> LENGTH: 26
<212> TYPE: PRT
<213> ORGANISM: Homo sapiens
<220> FEATURE:
<223> OTHER INFORMATION: NUP62 Nuclear pore glycoprotein p62;
      P37198_C475
<220> FEATURE:
<221> NAME/KEY: MOD_RES
<222> LOCATION: (24)..(24)
<223> OTHER INFORMATION: Site of chemical conjugation

<400> SEQUENCE: 295

Lys Asp Ile Ile Glu His Leu Asn Thr Ser Gly Ala Pro Ala Asp Thr
1               5                   10                  15

Ser Asp Pro Leu Gln Gln Ile Cys Lys Ile
            20                  25

<210> SEQ ID NO 296
<211> LENGTH: 14
<212> TYPE: PRT
<213> ORGANISM: Homo sapiens
<220> FEATURE:
<223> OTHER INFORMATION: ADA Adenosine deaminase;
      P00813_C75
<220> FEATURE:
<221> NAME/KEY: MOD_RES
<222> LOCATION: (12)..(12)
<223> OTHER INFORMATION: Site of chemical conjugation

<400> SEQUENCE: 296

Lys Phe Asp Tyr Tyr Met Pro Ala Ile Ala Gly Cys Arg Glu
1               5                   10

<210> SEQ ID NO 297
<211> LENGTH: 25
<212> TYPE: PRT
<213> ORGANISM: Homo sapiens
<220> FEATURE:
<223> OTHER INFORMATION: KIAA0664 Clustered mitochondria protein
      homolog; O75153_C333
<220> FEATURE:
<221> NAME/KEY: MOD_RES
<222> LOCATION: (22)..(22)

<223> OTHER INFORMATION: Site of chemical conjugation

<400> SEQUENCE: 297

Arg Ile Ala Thr Pro Phe Gln Val Tyr Ser Trp Thr Ala Pro Gln Ala
1               5                   10                  15

Glu His Ala Met Asp Cys Val Arg Ala
            20                  25

<210> SEQ ID NO 298
<211> LENGTH: 20
<212> TYPE: PRT
<213> ORGANISM: Homo sapiens
<220> FEATURE:
<223> OTHER INFORMATION: C5orf51 UPF0600 protein C5orf51;
      A6NDU8_C179
<220> FEATURE:
<221> NAME/KEY: MOD_RES
<222> LOCATION: (2)..(2)
<223> OTHER INFORMATION: Site of chemical conjugation

<400> SEQUENCE: 298

Arg Cys Pro Ile Gln Leu Asn Glu Gly Val Ser Phe Gln Asp Leu Asp
1               5                   10                  15

Thr Ala Lys Leu
            20

<210> SEQ ID NO 299
<211> LENGTH: 34
<212> TYPE: PRT
<213> ORGANISM: Homo sapiens
<220> FEATURE:
<223> OTHER INFORMATION: CDK19 Cyclin-dependent kinase 19;
      Q9BWU1_C349
<220> FEATURE:
<221> NAME/KEY: MOD_RES
<222> LOCATION: (27)..(27)
<223> OTHER INFORMATION: Site of chemical conjugation

<400> SEQUENCE: 299

Arg Ile Thr Ser Glu Gln Ala Leu Gln Asp Pro Tyr Phe Gln Glu Asp
1               5                   10                  15

Pro Leu Pro Thr Leu Asp Val Phe Ala Gly Cys Gln Ile Pro Tyr Pro
            20                  25                  30

Lys Arg

<210> SEQ ID NO 300
<211> LENGTH: 13
<212> TYPE: PRT
<213> ORGANISM: Homo sapiens
<220> FEATURE:
<223> OTHER INFORMATION: STK38 Serine/threonine-protein kinase 38;
      Q15208_C234
<220> FEATURE:
<221> NAME/KEY: MOD_RES
<222> LOCATION: (8)..(8)
<223> OTHER INFORMATION: Site of chemical conjugation

<400> SEQUENCE: 300

Lys Leu Ser Asp Phe Gly Leu Cys Thr Gly Leu Lys Lys
1               5                   10

<210> SEQ ID NO 301
<211> LENGTH: 20
<212> TYPE: PRT
<213> ORGANISM: Homo sapiens
<220> FEATURE:
<223> OTHER INFORMATION: ACIN1 Apoptotic chromatin condensation inducer in the nucleus; Q9UKV3_C1223
<220> FEATURE:
<221> NAME/KEY: MOD_RES
<222> LOCATION: (5)..(5)
<223> OTHER INFORMATION: Site of chemical conjugation

<400> SEQUENCE: 301

Lys Ala Ala Pro Cys Ile Tyr Trp Leu Pro Leu Thr Asp Ser Gln Ile
1               5                   10                  15

Val Gln Lys Glu
            20

<210> SEQ ID NO 302
<211> LENGTH: 17
<212> TYPE: PRT
<213> ORGANISM: Homo sapiens
<220> FEATURE:
<223> OTHER INFORMATION: MAPK9 Mitogen-activated protein kinase 9;
      P45984_C177
<220> FEATURE:
<221> NAME/KEY: MOD_RES
<222> LOCATION: (4)..(4)
<223> OTHER INFORMATION: Site of chemical conjugation

<400> SEQUENCE: 302

Arg Thr Ala Cys Thr Asn Phe Met Met Thr Pro Tyr Val Val Thr Arg
1               5                   10                  15

Tyr

<210> SEQ ID NO 303
<211> LENGTH: 14
<212> TYPE: PRT
<213> ORGANISM: Homo sapiens
<220> FEATURE:
<223> OTHER INFORMATION: DYNC1H1 Cytoplasmic dynein 1 heavy chain 1;
      Q14204_C1999
<220> FEATURE:
<221> NAME/KEY: MOD_RES
<222> LOCATION: (8)..(8)
<223> OTHER INFORMATION: Site of chemical conjugation

<400> SEQUENCE: 303

Lys Thr Ser Ala Pro Ile Thr Cys Glu Leu Leu Asn Lys Gln
1               5                   10

<210> SEQ ID NO 304
<211> LENGTH: 14
<212> TYPE: PRT
<213> ORGANISM: Homo sapiens
<220> FEATURE:
<223> OTHER INFORMATION: PML Protein PML;
      P29590_C389
<220> FEATURE:
<221> NAME/KEY: MOD_RES
<222> LOCATION: (8)..(8)
<223> OTHER INFORMATION: Site of chemical conjugation

<400> SEQUENCE: 304

Arg Leu Gln Asp Leu Ser Ser Cys Ile Thr Gln Gly Lys Asp
1               5                   10

<210> SEQ ID NO 305
<211> LENGTH: 20
<212> TYPE: PRT
<213> ORGANISM: Homo sapiens
<220> FEATURE:
<223> OTHER INFORMATION: PSMC6 26S protease regulatory subunit 10B;
      P62333_C228
<220> FEATURE:

```
<221> NAME/KEY: MOD_RES
<222> LOCATION: (6)..(6)
<223> OTHER INFORMATION: Site of chemical conjugation

<400> SEQUENCE: 305

Arg Asp His Gln Pro Cys Ile Ile Phe Met Asp Glu Ile Asp Ala Ile
1               5                   10                  15

Gly Gly Arg Arg
            20

<210> SEQ ID NO 306
<211> LENGTH: 28
<212> TYPE: PRT
<213> ORGANISM: Homo sapiens
<220> FEATURE:
<223> OTHER INFORMATION: LCP1 Plastin-2;
      P13796_C101
<220> FEATURE:
<221> NAME/KEY: MOD_RES
<222> LOCATION: (5)..(5)
<223> OTHER INFORMATION: Site of chemical conjugation

<400> SEQUENCE: 306

Lys Glu Gly Ile Cys Ala Ile Gly Gly Thr Ser Glu Gln Ser Ser Val
1               5                   10                  15

Gly Thr Gln His Ser Tyr Ser Glu Glu Glu Lys Tyr
            20                  25

<210> SEQ ID NO 307
<211> LENGTH: 24
<212> TYPE: PRT
<213> ORGANISM: Homo sapiens
<220> FEATURE:
<223> OTHER INFORMATION: BABAM1 BRISC and BRCA1-A complex member 1;
      Q9NWV8_C222
<220> FEATURE:
<221> NAME/KEY: MOD_RES
<222> LOCATION: (11)..(11)
<223> OTHER INFORMATION: Site of chemical conjugation

<400> SEQUENCE: 307

Arg Thr Ile Leu Val Tyr Ser Arg Pro Pro Cys Gln Pro Gln Phe Ser
1               5                   10                  15

Leu Thr Glu Pro Met Lys Lys Met
            20

<210> SEQ ID NO 308
<211> LENGTH: 28
<212> TYPE: PRT
<213> ORGANISM: Homo sapiens
<220> FEATURE:
<223> OTHER INFORMATION: IFIT3 Interferon-induced protein with
      tetratricopeptide; O14879_C343
<220> FEATURE:
<221> NAME/KEY: MOD_RES
<222> LOCATION: (20)..(20)
<223> OTHER INFORMATION: Site of chemical conjugation

<400> SEQUENCE: 308

Lys Gly Leu Asn Pro Leu Asn Ala Tyr Ser Asp Leu Ala Glu Phe Leu
1               5                   10                  15

Glu Thr Glu Cys Tyr Gln Thr Pro Phe Asn Lys Glu
            20                  25

<210> SEQ ID NO 309
<211> LENGTH: 13
<212> TYPE: PRT
```

```
<213> ORGANISM: Homo sapiens
<220> FEATURE:
<223> OTHER INFORMATION: RASSF2 Ras association domain-containing
      protein 2; P50749_C251
<220> FEATURE:
<221> NAME/KEY: MOD_RES
<222> LOCATION: (7)..(7)
<223> OTHER INFORMATION: Site of chemical conjugation

<400> SEQUENCE: 309

Arg Ile Leu Gln Gly Pro Cys Glu Gln Ile Ser Lys Val
1               5                   10

<210> SEQ ID NO 310
<211> LENGTH: 9
<212> TYPE: PRT
<213> ORGANISM: Homo sapiens
<220> FEATURE:
<223> OTHER INFORMATION: TXNL1 Thioredoxin-like protein 1;
      O43396_C34
<220> FEATURE:
<221> NAME/KEY: MOD_RES
<222> LOCATION: (3)..(3)
<223> OTHER INFORMATION: Site of chemical conjugation

<400> SEQUENCE: 310

Arg Gly Cys Gly Pro Cys Leu Arg Ile
1               5

<210> SEQ ID NO 311
<211> LENGTH: 14
<212> TYPE: PRT
<213> ORGANISM: Homo sapiens
<220> FEATURE:
<223> OTHER INFORMATION: NUP214 Nuclear pore complex protein Nup214;
      P35658_C728
<220> FEATURE:
<221> NAME/KEY: MOD_RES
<222> LOCATION: (3)..(3)
<223> OTHER INFORMATION: Site of chemical conjugation

<400> SEQUENCE: 311

Lys Ala Cys Phe Gln Val Gly Thr Ser Glu Glu Met Lys Met
1               5                   10

<210> SEQ ID NO 312
<211> LENGTH: 13
<212> TYPE: PRT
<213> ORGANISM: Homo sapiens
<220> FEATURE:
<223> OTHER INFORMATION: TMPO Lamina-associated polypeptide 2, isoform
      alpha; P42166_C684
<220> FEATURE:
<221> NAME/KEY: MOD_RES
<222> LOCATION: (11)..(11)
<223> OTHER INFORMATION: Site of chemical conjugation

<400> SEQUENCE: 312

Lys Gly Gly Thr Leu Phe Gly Gly Glu Val Cys Lys Val
1               5                   10

<210> SEQ ID NO 313
<211> LENGTH: 15
<212> TYPE: PRT
<213> ORGANISM: Homo sapiens
<220> FEATURE:
<223> OTHER INFORMATION: TRMT61A tRNA (adenine(58)-N(1))-
      methyltransferase catalyti; Q96FX7_C209
<220> FEATURE:
<221> NAME/KEY: MOD_RES
<222> LOCATION: (8)..(8)
```

```
<223> OTHER INFORMATION: Site of chemical conjugation

<400> SEQUENCE: 313

Arg Phe Cys Ser Phe Ser Pro Cys Ile Glu Gln Val Gln Arg Thr
1               5                   10                  15

<210> SEQ ID NO 314
<211> LENGTH: 50
<212> TYPE: PRT
<213> ORGANISM: Homo sapiens
<220> FEATURE:
<223> OTHER INFORMATION: TUBA1A Tubulin alpha-1A chain;
      Q71U36_C200
<220> FEATURE:
<221> NAME/KEY: MOD_RES
<222> LOCATION: (35)..(35)
<223> OTHER INFORMATION: Site of chemical conjugation

<400> SEQUENCE: 314

Lys Leu Glu Phe Ser Ile Tyr Pro Ala Pro Gln Val Ser Thr Ala Val
1               5                   10                  15

Val Glu Pro Tyr Asn Ser Ile Leu Thr Thr His Thr Thr Leu Glu His
            20                  25                  30

Ser Asp Cys Ala Phe Met Val Asp Asn Glu Ala Ile Tyr Asp Ile Cys
        35                  40                  45

Arg Arg
    50

<210> SEQ ID NO 315
<211> LENGTH: 14
<212> TYPE: PRT
<213> ORGANISM: Homo sapiens
<220> FEATURE:
<223> OTHER INFORMATION: EIF3J Eukaryotic translation initiation factor
      3 subunit; O75822_C207
<220> FEATURE:
<221> NAME/KEY: MOD_RES
<222> LOCATION: (10)..(10)
<223> OTHER INFORMATION: Site of chemical conjugation

<400> SEQUENCE: 315

Lys Ile Thr Asn Ser Leu Thr Val Leu Cys Ser Glu Lys Gln
1               5                   10

<210> SEQ ID NO 316
<211> LENGTH: 45
<212> TYPE: PRT
<213> ORGANISM: Homo sapiens
<220> FEATURE:
<223> OTHER INFORMATION: GRHPR Glyoxylate reductase/hydroxypyruvate
      reductase; Q9UBQ7_C216
<220> FEATURE:
<221> NAME/KEY: MOD_RES
<222> LOCATION: (32)..(32)
<223> OTHER INFORMATION: Site of chemical conjugation

<400> SEQUENCE: 316

Arg Gln Pro Arg Pro Glu Glu Ala Ala Glu Phe Gln Ala Glu Phe Val
1               5                   10                  15

Ser Thr Pro Glu Leu Ala Ala Gln Ser Asp Phe Ile Val Val Ala Cys
            20                  25                  30

Ser Leu Thr Pro Ala Thr Glu Gly Leu Cys Asn Lys Asp
        35                  40                  45

<210> SEQ ID NO 317
<211> LENGTH: 16
```

```
<212> TYPE: PRT
<213> ORGANISM: Homo sapiens
<220> FEATURE:
<223> OTHER INFORMATION: CCNH Cyclin-H;
      P51946_C244
<220> FEATURE:
<221> NAME/KEY: MOD_RES
<222> LOCATION: (6)..(6)
<223> OTHER INFORMATION: Site of chemical conjugation

<400> SEQUENCE: 317

Lys Glu Asn Arg Thr Cys Leu Ser Gln Leu Leu Asp Ile Met Lys Ser
1               5                   10                  15

<210> SEQ ID NO 318
<211> LENGTH: 37
<212> TYPE: PRT
<213> ORGANISM: Homo sapiens
<220> FEATURE:
<223> OTHER INFORMATION: ALDH2 Aldehyde dehydrogenase, mitochondrial;
      P05091_C319
<220> FEATURE:
<221> NAME/KEY: MOD_RES
<222> LOCATION: (31)..(31)
<223> OTHER INFORMATION: Site of chemical conjugation

<400> SEQUENCE: 318

Lys Ser Pro Asn Ile Ile Met Ser Asp Ala Asp Met Asp Trp Ala Val
1               5                   10                  15

Glu Gln Ala His Phe Ala Leu Phe Phe Asn Gln Gly Gln Cys Cys Cys
            20                  25                  30

Ala Gly Ser Arg Thr
        35

<210> SEQ ID NO 319
<211> LENGTH: 13
<212> TYPE: PRT
<213> ORGANISM: Homo sapiens
<220> FEATURE:
<223> OTHER INFORMATION: HSPBP1 Hsp70-binding protein 1;
      Q9NZL4_C204
<220> FEATURE:
<221> NAME/KEY: MOD_RES
<222> LOCATION: (8)..(8)
<223> OTHER INFORMATION: Site of chemical conjugation

<400> SEQUENCE: 319

Arg Leu Leu Asp Arg Asp Ala Cys Asp Thr Val Arg Val
1               5                   10

<210> SEQ ID NO 320
<211> LENGTH: 13
<212> TYPE: PRT
<213> ORGANISM: Homo sapiens
<220> FEATURE:
<223> OTHER INFORMATION: PMPCB Mitochondrial-processing peptidase
      subunit beta; O75439_C265
<220> FEATURE:
<221> NAME/KEY: MOD_RES
<222> LOCATION: (9)..(9)
<223> OTHER INFORMATION: Site of chemical conjugation

<400> SEQUENCE: 320

Lys Phe His Phe Gly Asp Ser Leu Cys Thr His Lys Gly
1               5                   10

<210> SEQ ID NO 321
<211> LENGTH: 11
<212> TYPE: PRT
```

-continued

```
<213> ORGANISM: Homo sapiens
<220> FEATURE:
<223> OTHER INFORMATION: CSRP2 Cysteine and glycine-rich protein 2;
      Q16527_C33
<220> FEATURE:
<221> NAME/KEY: MOD_RES
<222> LOCATION: (2)..(2)
<223> OTHER INFORMATION: Site of chemical conjugation

<400> SEQUENCE: 321

Arg Cys Cys Phe Leu Cys Met Val Cys Arg Lys
1               5                   10

<210> SEQ ID NO 322
<211> LENGTH: 11
<212> TYPE: PRT
<213> ORGANISM: Homo sapiens
<220> FEATURE:
<223> OTHER INFORMATION: TBC1D15 TBC1 domain family member 15;
      Q8TC07_C197
<220> FEATURE:
<221> NAME/KEY: MOD_RES
<222> LOCATION: (7)..(7)
<223> OTHER INFORMATION: Site of chemical conjugation

<400> SEQUENCE: 322

Arg Thr Leu Leu Val Asn Cys Gln Asn Lys Ser
1               5                   10

<210> SEQ ID NO 323
<211> LENGTH: 13
<212> TYPE: PRT
<213> ORGANISM: Homo sapiens
<220> FEATURE:
<223> OTHER INFORMATION: CTSB Cathepsin B;
      P07858_C211
<220> FEATURE:
<221> NAME/KEY: MOD_RES
<222> LOCATION: (3)..(3)
<223> OTHER INFORMATION: Site of chemical conjugation

<400> SEQUENCE: 323

Lys Ile Cys Glu Pro Gly Tyr Ser Pro Thr Tyr Lys Gln
1               5                   10

<210> SEQ ID NO 324
<211> LENGTH: 11
<212> TYPE: PRT
<213> ORGANISM: Homo sapiens
<220> FEATURE:
<223> OTHER INFORMATION: PLEC Plectin;
      Q15149_C3110
<220> FEATURE:
<221> NAME/KEY: MOD_RES
<222> LOCATION: (5)..(5)
<223> OTHER INFORMATION: Site of chemical conjugation

<400> SEQUENCE: 324

Lys Gly Arg Leu Cys Phe Glu Gly Leu Arg Ser
1               5                   10

<210> SEQ ID NO 325
<211> LENGTH: 13
<212> TYPE: PRT
<213> ORGANISM: Homo sapiens
<220> FEATURE:
<223> OTHER INFORMATION: LIN7C Protein lin-7 homolog C;
      Q9NUP9_C47
<220> FEATURE:
<221> NAME/KEY: MOD_RES
<222> LOCATION: (8)..(8)
```

<223> OTHER INFORMATION: Site of chemical conjugation

<400> SEQUENCE: 325

Arg Val Leu Gln Ser Glu Phe Cys Asn Ala Val Arg Glu
1               5                   10

<210> SEQ ID NO 326
<211> LENGTH: 36
<212> TYPE: PRT
<213> ORGANISM: Homo sapiens
<220> FEATURE:
<223> OTHER INFORMATION: SMC1A Structural maintenance of chromosomes
      protein 1A; Q14683_C987
<220> FEATURE:
<221> NAME/KEY: MOD_RES
<222> LOCATION: (13)..(13)
<223> OTHER INFORMATION: Site of chemical conjugation

<400> SEQUENCE: 326

Arg Glu Ala Leu Ile Glu Ile Asp Tyr Gly Asp Leu Cys Glu Asp Leu
1               5                   10                  15

Lys Asp Ala Gln Ala Glu Glu Ile Lys Gln Glu Met Asn Thr Leu
            20                  25                  30

Gln Gln Lys Leu
        35

<210> SEQ ID NO 327
<211> LENGTH: 20
<212> TYPE: PRT
<213> ORGANISM: Homo sapiens
<220> FEATURE:
<223> OTHER INFORMATION: ACAA1 3-ketoacyl-CoA thiolase, peroxisomal;
      P09110_C177
<220> FEATURE:
<221> NAME/KEY: MOD_RES
<222> LOCATION: (5)..(5)
<223> OTHER INFORMATION: Site of chemical conjugation

<400> SEQUENCE: 327

Lys Ala Arg Asp Cys Leu Ile Pro Met Gly Ile Thr Ser Glu Asn Val
1               5                   10                  15

Ala Glu Arg Phe
            20

<210> SEQ ID NO 328
<211> LENGTH: 19
<212> TYPE: PRT
<213> ORGANISM: Homo sapiens
<220> FEATURE:
<223> OTHER INFORMATION: MIF4GD MIF4G domain-containing protein;
      A9UHW6_C49
<220> FEATURE:
<221> NAME/KEY: MOD_RES
<222> LOCATION: (14)..(14)
<223> OTHER INFORMATION: Site of chemical conjugation

<400> SEQUENCE: 328

Lys Val Ala Asn Val Ile Val Asp His Ser Leu Gln Asp Cys Val Phe
1               5                   10                  15

Ser Lys Glu

<210> SEQ ID NO 329
<211> LENGTH: 35
<212> TYPE: PRT
<213> ORGANISM: Homo sapiens
<220> FEATURE:
<223> OTHER INFORMATION: ACP6 Lysophosphatidic acid phosphatase type 6;

```
        Q9NPH0_C267
<220> FEATURE:
<221> NAME/KEY: MOD_RES
<222> LOCATION: (30)..(30)
<223> OTHER INFORMATION: Site of chemical conjugation

<400> SEQUENCE: 329

Arg Met Gly Ile Asp Ser Ser Asp Lys Val Asp Phe Phe Ile Leu Leu
1               5                   10                  15

Asp Asn Val Ala Ala Glu Gln Ala His Asn Leu Pro Ser Cys Pro Met
            20                  25                  30

Leu Lys Arg
        35

<210> SEQ ID NO 330
<211> LENGTH: 12
<212> TYPE: PRT
<213> ORGANISM: Homo sapiens
<220> FEATURE:
<223> OTHER INFORMATION: RAD50 DNA repair protein RAD50;
      Q92878_C1302
<220> FEATURE:
<221> NAME/KEY: MOD_RES
<222> LOCATION: (2)..(2)
<223> OTHER INFORMATION: Site of chemical conjugation

<400> SEQUENCE: 330

Lys Cys Ser Val Ser Ser Leu Gly Phe Asn Val His
1               5                   10

<210> SEQ ID NO 331
<211> LENGTH: 29
<212> TYPE: PRT
<213> ORGANISM: Homo sapiens
<220> FEATURE:
<223> OTHER INFORMATION: UBE2L6 Ubiquitin/ISG15-conjugating enzyme E2
      L6; O14933_C98
<220> FEATURE:
<221> NAME/KEY: MOD_RES
<222> LOCATION: (26)..(26)
<223> OTHER INFORMATION: Site of chemical conjugation

<400> SEQUENCE: 331

Lys Ile Tyr His Pro Asn Val Asp Glu Asn Gly Gln Ile Cys Leu Pro
1               5                   10                  15

Ile Ile Ser Ser Glu Asn Trp Lys Pro Cys Thr Lys Thr
            20                  25

<210> SEQ ID NO 332
<211> LENGTH: 13
<212> TYPE: PRT
<213> ORGANISM: Homo sapiens
<220> FEATURE:
<223> OTHER INFORMATION: RPL3 60S ribosomal protein L3;
      P39023_C253
<220> FEATURE:
<221> NAME/KEY: MOD_RES
<222> LOCATION: (4)..(4)
<223> OTHER INFORMATION: Site of chemical conjugation

<400> SEQUENCE: 332

Lys Val Ala Cys Ile Gly Ala Trp His Pro Ala Arg Val
1               5                   10

<210> SEQ ID NO 333
<211> LENGTH: 20
<212> TYPE: PRT
<213> ORGANISM: Homo sapiens
```

```
<220> FEATURE:
<223> OTHER INFORMATION: SEPT9 Septin-9;
      Q9UHD8_C531
<220> FEATURE:
<221> NAME/KEY: MOD_RES
<222> LOCATION: (13)..(13)
<223> OTHER INFORMATION: Site of chemical conjugation

<400> SEQUENCE: 333

Lys Trp Gly Thr Ile Glu Val Glu Asn Thr Thr His Cys Glu Phe Ala
1               5                  10                  15

Tyr Leu Arg Asp
            20

<210> SEQ ID NO 334
<211> LENGTH: 20
<212> TYPE: PRT
<213> ORGANISM: Homo sapiens
<220> FEATURE:
<223> OTHER INFORMATION: TMPO Lamina-associated polypeptide 2, isoforms
      beta/gam; P42167_C363
<220> FEATURE:
<221> NAME/KEY: MOD_RES
<222> LOCATION: (18)..(18)
<223> OTHER INFORMATION: Site of chemical conjugation

<400> SEQUENCE: 334

Lys Glu Met Phe Pro Tyr Glu Ala Ser Thr Pro Thr Gly Ile Ser Ala
1               5                  10                  15

Ser Cys Arg Arg
            20

<210> SEQ ID NO 335
<211> LENGTH: 16
<212> TYPE: PRT
<213> ORGANISM: Homo sapiens
<220> FEATURE:
<223> OTHER INFORMATION: CASP8 Caspase-8;
      Q14790_C360
<220> FEATURE:
<221> NAME/KEY: MOD_RES
<222> LOCATION: (8)..(8)
<223> OTHER INFORMATION: Site of chemical conjugation

<400> SEQUENCE: 335

Lys Val Phe Phe Ile Gln Ala Cys Gln Gly Asp Asn Tyr Gln Lys Gly
1               5                  10                  15

<210> SEQ ID NO 336
<211> LENGTH: 8
<212> TYPE: PRT
<213> ORGANISM: Homo sapiens
<220> FEATURE:
<223> OTHER INFORMATION: PLEC Plectin;
      Q15149_C4574
<220> FEATURE:
<221> NAME/KEY: MOD_RES
<222> LOCATION: (5)..(5)
<223> OTHER INFORMATION: Site of chemical conjugation

<400> SEQUENCE: 336

Lys Tyr Leu Thr Cys Pro Lys Thr
1               5

<210> SEQ ID NO 337
<211> LENGTH: 23
<212> TYPE: PRT
<213> ORGANISM: Homo sapiens
<220> FEATURE:
```

```
<223> OTHER INFORMATION: GGA2 ADP-ribosylation factor-binding protein
      GGA2; Q9UJY4_C429
<220> FEATURE:
<221> NAME/KEY: MOD_RES
<222> LOCATION: (14)..(14)
<223> OTHER INFORMATION: Site of chemical conjugation

<400> SEQUENCE: 337

Arg Asn Leu Leu Asp Leu Leu Ser Ala Gln Pro Ala Pro Cys Pro Leu
1               5                   10                  15

Asn Tyr Val Ser Gln Lys Ser
            20

<210> SEQ ID NO 338
<211> LENGTH: 24
<212> TYPE: PRT
<213> ORGANISM: Homo sapiens
<220> FEATURE:
<223> OTHER INFORMATION: IRF4 Interferon regulatory factor 4;
      Q15306_C194
<220> FEATURE:
<221> NAME/KEY: MOD_RES
<222> LOCATION: (16)..(16)
<223> OTHER INFORMATION: Site of chemical conjugation

<400> SEQUENCE: 338

Arg Asp Tyr Val Pro Asp Gln Pro His Pro Glu Ile Pro Tyr Gln Cys
1               5                   10                  15

Pro Met Thr Phe Gly Pro Arg Gly
            20

<210> SEQ ID NO 339
<211> LENGTH: 29
<212> TYPE: PRT
<213> ORGANISM: Homo sapiens
<220> FEATURE:
<223> OTHER INFORMATION: PDE12 2,5-phosphodiesterase 12;
      Q6L8Q7_C108
<220> FEATURE:
<221> NAME/KEY: MOD_RES
<222> LOCATION: (12)..(12)
<223> OTHER INFORMATION: Site of chemical conjugation

<400> SEQUENCE: 339

Lys Ser Arg Pro Asn Ala Ser Gly Gly Ala Ala Cys Ser Gly Pro Gly
1               5                   10                  15

Pro Glu Pro Ala Val Phe Cys Glu Pro Val Val Lys Leu
            20                  25

<210> SEQ ID NO 340
<211> LENGTH: 26
<212> TYPE: PRT
<213> ORGANISM: Homo sapiens
<220> FEATURE:
<223> OTHER INFORMATION: RNASEH2C Ribonuclease H2 subunit C;
      Q8TDP1_C34
<220> FEATURE:
<221> NAME/KEY: MOD_RES
<222> LOCATION: (13)..(13)
<223> OTHER INFORMATION: Site of chemical conjugation

<400> SEQUENCE: 340

Arg Asp Ala Val Pro Ala Thr Leu His Leu Leu Pro Cys Glu Val Ala
1               5                   10                  15

Val Asp Gly Pro Ala Pro Val Gly Arg Phe
            20                  25
```

```
<210> SEQ ID NO 341
<211> LENGTH: 17
<212> TYPE: PRT
<213> ORGANISM: Homo sapiens
<220> FEATURE:
<223> OTHER INFORMATION: FLII Protein flightless-1 homolog;
      Q13045_C46
<220> FEATURE:
<221> NAME/KEY: MOD_RES
<222> LOCATION: (5)..(5)
<223> OTHER INFORMATION: Site of chemical conjugation

<400> SEQUENCE: 341

Arg Thr Gly Leu Cys Tyr Leu Pro Glu Glu Leu Ala Ala Leu Gln Lys
1               5                  10                  15

Leu

<210> SEQ ID NO 342
<211> LENGTH: 9
<212> TYPE: PRT
<213> ORGANISM: Homo sapiens
<220> FEATURE:
<223> OTHER INFORMATION: TXNDC12 Thioredoxin domain-containing protein
      12; O95881_C66
<220> FEATURE:
<221> NAME/KEY: MOD_RES
<222> LOCATION: (4)..(4)
<223> OTHER INFORMATION: Site of chemical conjugation

<400> SEQUENCE: 342

Lys Ser Trp Cys Gly Ala Cys Lys Ala
1               5

<210> SEQ ID NO 343
<211> LENGTH: 11
<212> TYPE: PRT
<213> ORGANISM: Homo sapiens
<220> FEATURE:
<223> OTHER INFORMATION: TRAPPC4 Trafficking protein particle complex
      subunit 4; Q9Y296_C195
<220> FEATURE:
<221> NAME/KEY: MOD_RES
<222> LOCATION: (2)..(2)
<223> OTHER INFORMATION: Site of chemical conjugation

<400> SEQUENCE: 343

Arg Cys Glu Leu Phe Asp Gln Asn Leu Lys Leu
1               5                  10

<210> SEQ ID NO 344
<211> LENGTH: 11
<212> TYPE: PRT
<213> ORGANISM: Homo sapiens
<220> FEATURE:
<223> OTHER INFORMATION: REEP5 Receptor expression-enhancing protein 5;
      Q00765_C18
<220> FEATURE:
<221> NAME/KEY: MOD_RES
<222> LOCATION: (3)..(3)
<223> OTHER INFORMATION: Site of chemical conjugation

<400> SEQUENCE: 344

Lys Asn Cys Met Thr Asp Leu Leu Ala Lys Leu
1               5                  10

<210> SEQ ID NO 345
<211> LENGTH: 38
<212> TYPE: PRT
<213> ORGANISM: Homo sapiens
<220> FEATURE:
```

```
<223> OTHER INFORMATION: NIT1 Nitrilase homolog 1;
      Q86X76_C165
<220> FEATURE:
<221> NAME/KEY: MOD_RES
<222> LOCATION: (5)..(5)
<223> OTHER INFORMATION: Site of chemical conjugation

<400> SEQUENCE: 345
```

Lys Thr His Leu Cys Asp Val Glu Ile Pro Gly Gln Gly Pro Met Cys
1               5                   10                  15

Glu Ser Asn Ser Thr Met Pro Gly Pro Ser Leu Glu Ser Pro Val Ser
            20                  25                  30

Thr Pro Ala Gly Lys Ile
        35

```
<210> SEQ ID NO 346
<211> LENGTH: 10
<212> TYPE: PRT
<213> ORGANISM: Homo sapiens
<220> FEATURE:
<223> OTHER INFORMATION: HNRNPF Heterogeneous nuclear ribonucleoprotein
      F; P52597_C122
<220> FEATURE:
<221> NAME/KEY: MOD_RES
<222> LOCATION: (7)..(7)
<223> OTHER INFORMATION: Site of chemical conjugation

<400> SEQUENCE: 346
```

Arg Gly Leu Pro Phe Gly Cys Thr Lys Glu
1               5                   10

```
<210> SEQ ID NO 347
<211> LENGTH: 23
<212> TYPE: PRT
<213> ORGANISM: Homo sapiens
<220> FEATURE:
<223> OTHER INFORMATION: ERO1L ERO1-like protein alpha;
      Q96HE7_C37
<220> FEATURE:
<221> NAME/KEY: MOD_RES
<222> LOCATION: (4)..(4)
<223> OTHER INFORMATION: Site of chemical conjugation

<400> SEQUENCE: 347
```

Arg Cys Phe Cys Gln Val Ser Gly Tyr Leu Asp Asp Cys Thr Cys Asp
1               5                   10                  15

Val Glu Thr Ile Asp Arg Phe
            20

```
<210> SEQ ID NO 348
<211> LENGTH: 14
<212> TYPE: PRT
<213> ORGANISM: Homo sapiens
<220> FEATURE:
<223> OTHER INFORMATION: C9orf142 Uncharacterized protein C9orf142;
      Q9BUH6_C180
<220> FEATURE:
<221> NAME/KEY: MOD_RES
<222> LOCATION: (2)..(2)
<223> OTHER INFORMATION: Site of chemical conjugation

<400> SEQUENCE: 348
```

Arg Cys Pro Gly Glu Ser Leu Ile Asn Pro Gly Phe Lys Ser
1               5                   10

```
<210> SEQ ID NO 349
<211> LENGTH: 35
<212> TYPE: PRT
```

-continued

```
<213> ORGANISM: Homo sapiens
<220> FEATURE:
<223> OTHER INFORMATION: FADD Protein FADD;
      Q13158_C98
<220> FEATURE:
<221> NAME/KEY: MOD_RES
<222> LOCATION: (22)..(22)
<223> OTHER INFORMATION: Site of chemical conjugation

<400> SEQUENCE: 349

Arg Arg Val Asp Asp Phe Glu Ala Gly Ala Ala Ala Gly Ala Ala Pro
1               5                   10                  15

Gly Glu Glu Asp Leu Cys Ala Ala Phe Asn Val Ile Cys Asp Asn Val
            20                  25                  30

Gly Lys Asp
        35

<210> SEQ ID NO 350
<211> LENGTH: 10
<212> TYPE: PRT
<213> ORGANISM: Homo sapiens
<220> FEATURE:
<223> OTHER INFORMATION: SAE1 SUMO-activating enzyme subunit 1;
      Q9UBE0_C214
<220> FEATURE:
<221> NAME/KEY: MOD_RES
<222> LOCATION: (6)..(6)
<223> OTHER INFORMATION: Site of chemical conjugation

<400> SEQUENCE: 350

Lys Lys Val Val Phe Cys Pro Val Lys Glu
1               5                   10

<210> SEQ ID NO 351
<211> LENGTH: 12
<212> TYPE: PRT
<213> ORGANISM: Homo sapiens
<220> FEATURE:
<223> OTHER INFORMATION: LARS Leucine--tRNA ligase, cytoplasmic;
      Q9P2J5_C554
<220> FEATURE:
<221> NAME/KEY: MOD_RES
<222> LOCATION: (7)..(7)
<223> OTHER INFORMATION: Site of chemical conjugation

<400> SEQUENCE: 351

Lys Asn Leu Glu Thr Phe Cys Glu Glu Thr Arg Arg
1               5                   10

<210> SEQ ID NO 352
<211> LENGTH: 19
<212> TYPE: PRT
<213> ORGANISM: Homo sapiens
<220> FEATURE:
<223> OTHER INFORMATION: QKI Protein quaking;
      Q96PU8_C35
<220> FEATURE:
<221> NAME/KEY: MOD_RES
<222> LOCATION: (10)..(10)
<223> OTHER INFORMATION: Site of chemical conjugation

<400> SEQUENCE: 352

Lys Leu Met Ser Ser Leu Pro Asn Phe Cys Gly Ile Phe Asn His Leu
1               5                   10                  15

Glu Arg Leu

<210> SEQ ID NO 353
<211> LENGTH: 16
```

```
<212> TYPE: PRT
<213> ORGANISM: Homo sapiens
<220> FEATURE:
<223> OTHER INFORMATION: DNMBP Dynamin-binding protein;
      Q6XZF7_C691
<220> FEATURE:
<221> NAME/KEY: MOD_RES
<222> LOCATION: (9)..(9)
<223> OTHER INFORMATION: Site of chemical conjugation

<400> SEQUENCE: 353

Arg Ser Leu Asp Gln Thr Ser Pro Cys Pro Leu Val Leu Val Arg Ile
1               5                   10                  15

<210> SEQ ID NO 354
<211> LENGTH: 24
<212> TYPE: PRT
<213> ORGANISM: Homo sapiens
<220> FEATURE:
<223> OTHER INFORMATION: TELO2 Telomere length regulation protein TEL2
      homolog; Q9Y4R8_C628
<220> FEATURE:
<221> NAME/KEY: MOD_RES
<222> LOCATION: (20)..(20)
<223> OTHER INFORMATION: Site of chemical conjugation

<400> SEQUENCE: 354

Arg Met Asp Ile Leu Asp Val Leu Thr Leu Ala Ala Gln Glu Leu Ser
1               5                   10                  15

Arg Pro Gly Cys Leu Gly Arg Thr
            20

<210> SEQ ID NO 355
<211> LENGTH: 14
<212> TYPE: PRT
<213> ORGANISM: Homo sapiens
<220> FEATURE:
<223> OTHER INFORMATION: SPC25 Kinetochore protein Spc25;
      Q9HBM1_C27
<220> FEATURE:
<221> NAME/KEY: MOD_RES
<222> LOCATION: (7)..(7)
<223> OTHER INFORMATION: Site of chemical conjugation

<400> SEQUENCE: 355

Lys Ser Thr Asp Thr Ser Cys Gln Met Ala Gly Leu Arg Asp
1               5                   10

<210> SEQ ID NO 356
<211> LENGTH: 18
<212> TYPE: PRT
<213> ORGANISM: Homo sapiens
<220> FEATURE:
<223> OTHER INFORMATION: TGM2 Protein-glutamine gamma-
      glutamyltransferase 2; P21980_C277
<220> FEATURE:
<221> NAME/KEY: MOD_RES
<222> LOCATION: (5)..(5)
<223> OTHER INFORMATION: Site of chemical conjugation

<400> SEQUENCE: 356

Lys Tyr Gly Gln Cys Trp Val Phe Ala Ala Val Ala Cys Thr Val Leu
1               5                   10                  15

Arg Cys

<210> SEQ ID NO 357
<211> LENGTH: 20
<212> TYPE: PRT
<213> ORGANISM: Homo sapiens
```

```
<220> FEATURE:
<223> OTHER INFORMATION: UNC45A Protein unc-45 homolog A;
      Q9H3U1_C426
<220> FEATURE:
<221> NAME/KEY: MOD_RES
<222> LOCATION: (14)..(14)
<223> OTHER INFORMATION: Site of chemical conjugation

<400> SEQUENCE: 357

Arg Ala Ile Gln Thr Val Ser Cys Leu Leu Gln Gly Pro Cys Asp Ala
1               5                   10                  15

Gly Asn Arg Ala
            20

<210> SEQ ID NO 358
<211> LENGTH: 16
<212> TYPE: PRT
<213> ORGANISM: Homo sapiens
<220> FEATURE:
<223> OTHER INFORMATION: APOBEC3C Probable DNA dC- dU-editing enzyme
      APOBEC-3C; Q9NRW3_C130
<220> FEATURE:
<221> NAME/KEY: MOD_RES
<222> LOCATION: (9)..(9)
<223> OTHER INFORMATION: Site of chemical conjugation

<400> SEQUENCE: 358

Arg Leu Tyr Tyr Phe Gln Tyr Pro Cys Tyr Gln Glu Gly Leu Arg Ser
1               5                   10                  15

<210> SEQ ID NO 359
<211> LENGTH: 8
<212> TYPE: PRT
<213> ORGANISM: Homo sapiens
<220> FEATURE:
<223> OTHER INFORMATION: ADAR Double-stranded RNA-specific adenosine
      deaminase; P55265_C1224
<220> FEATURE:
<221> NAME/KEY: MOD_RES
<222> LOCATION: (6)..(6)
<223> OTHER INFORMATION: Site of chemical conjugation

<400> SEQUENCE: 359

Lys Asn Phe Tyr Leu Cys Pro Val
1               5

<210> SEQ ID NO 360
<211> LENGTH: 12
<212> TYPE: PRT
<213> ORGANISM: Homo sapiens
<220> FEATURE:
<223> OTHER INFORMATION: IDH2 Isocitrate dehydrogenase;
      P48735_C308
<220> FEATURE:
<221> NAME/KEY: MOD_RES
<222> LOCATION: (10)..(10)
<223> OTHER INFORMATION: Site of chemical conjugation

<400> SEQUENCE: 360

Lys Ser Ser Gly Gly Phe Val Trp Ala Cys Lys Asn
1               5                   10

<210> SEQ ID NO 361
<211> LENGTH: 24
<212> TYPE: PRT
<213> ORGANISM: Homo sapiens
<220> FEATURE:
<223> OTHER INFORMATION: PLIN3 Perilipin-3;
      O60664_C39
<220> FEATURE:
```

```
<221> NAME/KEY: MOD_RES
<222> LOCATION: (12)..(12)
<223> OTHER INFORMATION: Site of chemical conjugation

<400> SEQUENCE: 361

Arg Val Ala Ser Met Pro Leu Ile Ser Ser Thr Cys Asp Met Val Ser
1               5                   10                  15

Ala Ala Tyr Ala Ser Thr Lys Glu
            20

<210> SEQ ID NO 362
<211> LENGTH: 23
<212> TYPE: PRT
<213> ORGANISM: Homo sapiens
<220> FEATURE:
<223> OTHER INFORMATION: TMOD3 Tropomodulin-3;
      Q9NYL9_C150
<220> FEATURE:
<221> NAME/KEY: MOD_RES
<222> LOCATION: (3)..(3)
<223> OTHER INFORMATION: Site of chemical conjugation

<400> SEQUENCE: 362

Lys Phe Cys Asn Ile Met Gly Ser Ser Asn Gly Val Asp Gln Glu His
1               5                   10                  15

Phe Ser Asn Val Val Lys Gly
            20

<210> SEQ ID NO 363
<211> LENGTH: 32
<212> TYPE: PRT
<213> ORGANISM: Homo sapiens
<220> FEATURE:
<223> OTHER INFORMATION: MCCC2 Methylcrotonoyl-CoA carboxylase beta
      chain, mitoch; Q9HCC0_C216
<220> FEATURE:
<221> NAME/KEY: MOD_RES
<222> LOCATION: (13)..(13)
<223> OTHER INFORMATION: Site of chemical conjugation

<400> SEQUENCE: 363

Lys Asn Ile Ala Gln Ile Ala Val Val Met Gly Ser Cys Thr Ala Gly
1               5                   10                  15

Gly Ala Tyr Val Pro Ala Met Ala Asp Glu Asn Ile Ile Val Arg Lys
            20                  25                  30

<210> SEQ ID NO 364
<211> LENGTH: 28
<212> TYPE: PRT
<213> ORGANISM: Homo sapiens
<220> FEATURE:
<223> OTHER INFORMATION: UPP1 Uridine phosphorylase 1;
      Q16831_C162
<220> FEATURE:
<221> NAME/KEY: MOD_RES
<222> LOCATION: (25)..(25)
<223> OTHER INFORMATION: Site of chemical conjugation

<400> SEQUENCE: 364

Arg Ile Gly Thr Ser Gly Gly Ile Gly Leu Glu Pro Gly Thr Val Val
1               5                   10                  15

Ile Thr Glu Gln Ala Val Asp Thr Cys Phe Lys Ala
            20                  25

<210> SEQ ID NO 365
<211> LENGTH: 20
<212> TYPE: PRT
```

```
<213> ORGANISM: Homo sapiens
<220> FEATURE:
<223> OTHER INFORMATION: ATOX1 Copper transport protein ATOX1;
      O00244_C12
<220> FEATURE:
<221> NAME/KEY: MOD_RES
<222> LOCATION: (10)..(10)
<223> OTHER INFORMATION: Site of chemical conjugation

<400> SEQUENCE: 365

Lys His Glu Phe Ser Val Asp Met Thr Cys Gly Gly Cys Ala Glu Ala
1               5                   10                  15

Val Ser Arg Val
            20

<210> SEQ ID NO 366
<211> LENGTH: 11
<212> TYPE: PRT
<213> ORGANISM: Homo sapiens
<220> FEATURE:
<223> OTHER INFORMATION: PYGB Glycogen phosphorylase, brain form;
      P11216_C326
<220> FEATURE:
<221> NAME/KEY: MOD_RES
<222> LOCATION: (3)..(3)
<223> OTHER INFORMATION: Site of chemical conjugation

<400> SEQUENCE: 366

Arg Thr Cys Phe Glu Thr Phe Pro Asp Lys Val
1               5                   10

<210> SEQ ID NO 367
<211> LENGTH: 9
<212> TYPE: PRT
<213> ORGANISM: Homo sapiens
<220> FEATURE:
<223> OTHER INFORMATION: TMPO Lamina-associated polypeptide 2, isoform
      alpha; P42166_C280
<220> FEATURE:
<221> NAME/KEY: MOD_RES
<222> LOCATION: (7)..(7)
<223> OTHER INFORMATION: Site of chemical conjugation

<400> SEQUENCE: 367

Arg Asn Leu Phe Ile Ser Cys Lys Ser
1               5

<210> SEQ ID NO 368
<211> LENGTH: 20
<212> TYPE: PRT
<213> ORGANISM: Homo sapiens
<220> FEATURE:
<223> OTHER INFORMATION: EIF3H Eukaryotic translation initiation factor
      3 subunit; O15372_C327
<220> FEATURE:
<221> NAME/KEY: MOD_RES
<222> LOCATION: (15)..(15)
<223> OTHER INFORMATION: Site of chemical conjugation

<400> SEQUENCE: 368

Arg Met Asp Ser Leu Leu Ile Ala Gly Gln Ile Asn Thr Tyr Cys Gln
1               5                   10                  15

Asn Ile Lys Glu
            20

<210> SEQ ID NO 369
<211> LENGTH: 20
<212> TYPE: PRT
<213> ORGANISM: Homo sapiens
```

```
<220> FEATURE:
<223> OTHER INFORMATION: PDCD2L Programmed cell death protein 2-like;
      Q9BRP1_C82
<220> FEATURE:
<221> NAME/KEY: MOD_RES
<222> LOCATION: (10)..(10)
<223> OTHER INFORMATION: Site of chemical conjugation

<400> SEQUENCE: 369

Arg Leu Leu His Val Phe Ala Cys Ala Cys Pro Gly Cys Ser Thr Gly
1               5                   10                  15

Gly Ala Arg Ser
            20

<210> SEQ ID NO 370
<211> LENGTH: 10
<212> TYPE: PRT
<213> ORGANISM: Homo sapiens
<220> FEATURE:
<223> OTHER INFORMATION: NCAPD2 Condensin complex subunit 1;
      Q15021_C767
<220> FEATURE:
<221> NAME/KEY: MOD_RES
<222> LOCATION: (5)..(5)
<223> OTHER INFORMATION: Site of chemical conjugation

<400> SEQUENCE: 370

Lys Val Ala Cys Cys Pro Leu Glu Arg Cys
1               5                   10

<210> SEQ ID NO 371
<211> LENGTH: 23
<212> TYPE: PRT
<213> ORGANISM: Homo sapiens
<220> FEATURE:
<223> OTHER INFORMATION: C21orf33 ES1 protein homolog, mitochondrial;
      P30042_C177
<220> FEATURE:
<221> NAME/KEY: MOD_RES
<222> LOCATION: (14)..(14)
<223> OTHER INFORMATION: Site of chemical conjugation

<400> SEQUENCE: 371

Lys Glu Phe His Gln Ala Gly Lys Pro Ile Gly Leu Cys Cys Ile Ala
1               5                   10                  15

Pro Val Leu Ala Ala Lys Val
            20

<210> SEQ ID NO 372
<211> LENGTH: 11
<212> TYPE: PRT
<213> ORGANISM: Homo sapiens
<220> FEATURE:
<223> OTHER INFORMATION: SNTB2 Beta-2-syntrophin;
      Q13425_C391
<220> FEATURE:
<221> NAME/KEY: MOD_RES
<222> LOCATION: (9)..(9)
<223> OTHER INFORMATION: Site of chemical conjugation

<400> SEQUENCE: 372

Arg Leu Val His Ser Gly Ser Gly Cys Arg Ser
1               5                   10

<210> SEQ ID NO 373
<211> LENGTH: 14
<212> TYPE: PRT
<213> ORGANISM: Homo sapiens
<220> FEATURE:
```

<223> OTHER INFORMATION: MYO1C Unconventional myosin-Ic;
      O00159_C802
<220> FEATURE:
<221> NAME/KEY: MOD_RES
<222> LOCATION: (2)..(2)
<223> OTHER INFORMATION: Site of chemical conjugation

<400> SEQUENCE: 373

Arg Cys Pro Glu Asn Ala Phe Phe Leu Asp His Val Arg Thr
1               5                   10

<210> SEQ ID NO 374
<211> LENGTH: 12
<212> TYPE: PRT
<213> ORGANISM: Homo sapiens
<220> FEATURE:
<223> OTHER INFORMATION: UBR5 E3 ubiquitin-protein ligase UBR5;
      O95071_C2267
<220> FEATURE:
<221> NAME/KEY: MOD_RES
<222> LOCATION: (2)..(2)
<223> OTHER INFORMATION: Site of chemical conjugation

<400> SEQUENCE: 374

Arg Cys Ala Thr Thr Pro Met Ala Val His Arg Val
1               5                   10

<210> SEQ ID NO 375
<211> LENGTH: 13
<212> TYPE: PRT
<213> ORGANISM: Homo sapiens
<220> FEATURE:
<223> OTHER INFORMATION: PLOD1 Procollagen-lysine,2-oxoglutarate
      5-dioxygenase 1; Q02809_C680
<220> FEATURE:
<221> NAME/KEY: MOD_RES
<222> LOCATION: (11)..(11)
<223> OTHER INFORMATION: Site of chemical conjugation

<400> SEQUENCE: 375

Arg Val Gly Val Asp Tyr Glu Gly Gly Gly Cys Arg Phe
1               5                   10

<210> SEQ ID NO 376
<211> LENGTH: 14
<212> TYPE: PRT
<213> ORGANISM: Homo sapiens
<220> FEATURE:
<223> OTHER INFORMATION: NACC1 Nucleus accumbens-associated protein 1;
      Q96RE7_C416
<220> FEATURE:
<221> NAME/KEY: MOD_RES
<222> LOCATION: (8)..(8)
<223> OTHER INFORMATION: Site of chemical conjugation

<400> SEQUENCE: 376

Arg Asn Thr Leu Ala Asn Ser Cys Gly Thr Gly Ile Arg Ser
1               5                   10

<210> SEQ ID NO 377
<211> LENGTH: 28
<212> TYPE: PRT
<213> ORGANISM: Homo sapiens
<220> FEATURE:
<223> OTHER INFORMATION: LIMCH1 LIM and calponin homology domains-
      containing protein; Q9UPQ0_C140
<220> FEATURE:
<221> NAME/KEY: MOD_RES
<222> LOCATION: (6)..(6)
<223> OTHER INFORMATION: Site of chemical conjugation

```
<400> SEQUENCE: 377

Lys Ala Ala Asn Ser Cys Thr Ser Tyr Ser Gly Thr Thr Leu Asn Leu
1               5                   10                  15

Lys Glu Phe Glu Gly Leu Leu Ala Gln Met Arg Lys
            20                  25

<210> SEQ ID NO 378
<211> LENGTH: 13
<212> TYPE: PRT
<213> ORGANISM: Homo sapiens
<220> FEATURE:
<223> OTHER INFORMATION: TCERG1 Transcription elongation regulator 1;
      O14776_C1062
<220> FEATURE:
<221> NAME/KEY: MOD_RES
<222> LOCATION: (7)..(7)
<223> OTHER INFORMATION: Site of chemical conjugation

<400> SEQUENCE: 378

Arg Tyr Leu Val Leu Asp Cys Val Pro Glu Glu Arg Arg
1               5                   10

<210> SEQ ID NO 379
<211> LENGTH: 19
<212> TYPE: PRT
<213> ORGANISM: Homo sapiens
<220> FEATURE:
<223> OTHER INFORMATION: DSN1 Kinetochore-associated protein DSN1
      homolog; Q9H410_C287
<220> FEATURE:
<221> NAME/KEY: MOD_RES
<222> LOCATION: (5)..(5)
<223> OTHER INFORMATION: Site of chemical conjugation

<400> SEQUENCE: 379

Lys Val Phe Asp Cys Met Glu Leu Val Met Asp Glu Leu Gln Gly Ser
1               5                   10                  15

Val Lys Gln

<210> SEQ ID NO 380
<211> LENGTH: 24
<212> TYPE: PRT
<213> ORGANISM: Homo sapiens
<220> FEATURE:
<223> OTHER INFORMATION: DLG1 Disks large homolog 1;
      Q12959_C378
<220> FEATURE:
<221> NAME/KEY: MOD_RES
<222> LOCATION: (9)..(9)
<223> OTHER INFORMATION: Site of chemical conjugation

<400> SEQUENCE: 380

Lys Leu Leu Ala Val Asn Asn Val Cys Leu Glu Glu Val Thr His Glu
1               5                   10                  15

Glu Ala Val Thr Ala Leu Lys Asn
            20

<210> SEQ ID NO 381
<211> LENGTH: 10
<212> TYPE: PRT
<213> ORGANISM: Homo sapiens
<220> FEATURE:
<223> OTHER INFORMATION: USP48 Ubiquitin carboxyl-terminal hydrolase 48;
      Q86UV5_C39
<220> FEATURE:
<221> NAME/KEY: MOD_RES
<222> LOCATION: (7)..(7)
<223> OTHER INFORMATION: Site of chemical conjugation
```

```
<400> SEQUENCE: 381

Arg Ile Trp Leu Glu Pro Cys Ile Arg Gly
1               5                   10

<210> SEQ ID NO 382
<211> LENGTH: 11
<212> TYPE: PRT
<213> ORGANISM: Homo sapiens
<220> FEATURE:
<223> OTHER INFORMATION: SERPINH1 Serpin H1;
      P50454_C156
<220> FEATURE:
<221> NAME/KEY: MOD_RES
<222> LOCATION: (6)..(6)
<223> OTHER INFORMATION: Site of chemical conjugation

<400> SEQUENCE: 382

Lys Gln His Tyr Asn Cys Glu His Ser Lys Ile
1               5                   10

<210> SEQ ID NO 383
<211> LENGTH: 22
<212> TYPE: PRT
<213> ORGANISM: Homo sapiens
<220> FEATURE:
<223> OTHER INFORMATION: ACO2 Aconitate hydratase, mitochondrial;
      Q99798_C451
<220> FEATURE:
<221> NAME/KEY: MOD_RES
<222> LOCATION: (15)..(15)
<223> OTHER INFORMATION: Site of chemical conjugation

<400> SEQUENCE: 383

Arg Asp Leu Gly Gly Ile Val Leu Ala Asn Ala Cys Gly Pro Cys Ile
1               5                   10                  15

Gly Gln Trp Asp Arg Lys
            20

<210> SEQ ID NO 384
<211> LENGTH: 14
<212> TYPE: PRT
<213> ORGANISM: Homo sapiens
<220> FEATURE:
<223> OTHER INFORMATION: GMPR2 GMP reductase 2;
      Q9P2T1_C186
<220> FEATURE:
<221> NAME/KEY: MOD_RES
<222> LOCATION: (10)..(10)
<223> OTHER INFORMATION: Site of chemical conjugation

<400> SEQUENCE: 384

Lys Val Gly Ile Gly Pro Gly Ser Val Cys Thr Thr Arg Lys
1               5                   10

<210> SEQ ID NO 385
<211> LENGTH: 34
<212> TYPE: PRT
<213> ORGANISM: Homo sapiens
<220> FEATURE:
<223> OTHER INFORMATION: TBCD Tubulin-specific chaperone D;
      Q9BTW9_C850
<220> FEATURE:
<221> NAME/KEY: MOD_RES
<222> LOCATION: (19)..(19)
<223> OTHER INFORMATION: Site of chemical conjugation

<400> SEQUENCE: 385

Lys Ala Gly Ala Pro Asp Glu Ala Val Cys Gly Glu Asn Val Ser Gln
```

```
                1               5                  10                 15
Ile Tyr Cys Ala Leu Leu Gly Cys Met Asp Asp Tyr Thr Thr Asp Ser
                20                 25                 30
Arg Gly
```

<210> SEQ ID NO 386
<211> LENGTH: 17
<212> TYPE: PRT
<213> ORGANISM: Homo sapiens
<220> FEATURE:
<223> OTHER INFORMATION: NUP35 Nucleoporin NUP53;
      Q8NFH5_C255
<220> FEATURE:
<221> NAME/KEY: MOD_RES
<222> LOCATION: (2)..(2)
<223> OTHER INFORMATION: Site of chemical conjugation

<400> SEQUENCE: 386

```
Arg Cys Ala Leu Ser Ser Pro Ser Leu Ala Phe Thr Pro Pro Ile Lys
1               5                  10                 15
Thr
```

<210> SEQ ID NO 387
<211> LENGTH: 12
<212> TYPE: PRT
<213> ORGANISM: Homo sapiens
<220> FEATURE:
<223> OTHER INFORMATION: PYCR1 Pyrroline-5-carboxylate reductase 1,
      mitochondrial; P32322_C120
<220> FEATURE:
<221> NAME/KEY: MOD_RES
<222> LOCATION: (2)..(2)
<223> OTHER INFORMATION: Site of chemical conjugation

<400> SEQUENCE: 387

```
Arg Cys Met Thr Asn Thr Pro Val Val Val Arg Glu
1               5                  10
```

<210> SEQ ID NO 388
<211> LENGTH: 39
<212> TYPE: PRT
<213> ORGANISM: Homo sapiens
<220> FEATURE:
<223> OTHER INFORMATION: LRBA Lipopolysaccharide-responsive and beige-
      like ancho; P50851_C1704
<220> FEATURE:
<221> NAME/KEY: MOD_RES
<222> LOCATION: (22)..(22)
<223> OTHER INFORMATION: Site of chemical conjugation

<400> SEQUENCE: 388

```
Arg Ser Leu Val Asn Ile Pro Ala Asp Gly Val Thr Val Asp Pro Ala
1               5                  10                 15
Leu Leu Pro Pro Ala Cys Leu Gly Ala Leu Gly Asp Leu Ser Val Glu
                20                 25                 30
Gln Pro Val Gln Phe Arg Ser
                35
```

<210> SEQ ID NO 389
<211> LENGTH: 19
<212> TYPE: PRT
<213> ORGANISM: Homo sapiens
<220> FEATURE:
<223> OTHER INFORMATION: CTSZ Cathepsin Z;
      Q9UBR2_C173
<220> FEATURE:
<221> NAME/KEY: MOD_RES

```
<222> LOCATION: (14)..(14)
<223> OTHER INFORMATION: Site of chemical conjugation

<400> SEQUENCE: 389

Lys Asp Gln Glu Cys Asp Lys Phe Asn Gln Cys Gly Thr Cys Asn Glu
1               5                   10                  15

Phe Lys Glu

<210> SEQ ID NO 390
<211> LENGTH: 10
<212> TYPE: PRT
<213> ORGANISM: Homo sapiens
<220> FEATURE:
<223> OTHER INFORMATION: UBR2 E3 ubiquitin-protein ligase UBR2;
      Q8IWV8_C1717
<220> FEATURE:
<221> NAME/KEY: MOD_RES
<222> LOCATION: (8)..(8)
<223> OTHER INFORMATION: Site of chemical conjugation

<400> SEQUENCE: 390

Arg Gly Asn Pro Leu His Leu Cys Lys Glu
1               5                   10

<210> SEQ ID NO 391
<211> LENGTH: 42
<212> TYPE: PRT
<213> ORGANISM: Homo sapiens
<220> FEATURE:
<223> OTHER INFORMATION: FLNB Filamin-B;
      O75369_C1087
<220> FEATURE:
<221> NAME/KEY: MOD_RES
<222> LOCATION: (4)..(4)
<223> OTHER INFORMATION: Site of chemical conjugation

<400> SEQUENCE: 391

Lys Ile Glu Cys Ser Asp Asn Gly Asp Gly Thr Cys Ser Val Ser Tyr
1               5                   10                  15

Leu Pro Thr Lys Pro Gly Glu Tyr Phe Val Asn Ile Leu Phe Glu Glu
            20                  25                  30

Val His Ile Pro Gly Ser Pro Phe Lys Ala
            35                  40

<210> SEQ ID NO 392
<211> LENGTH: 23
<212> TYPE: PRT
<213> ORGANISM: Homo sapiens
<220> FEATURE:
<223> OTHER INFORMATION: ATG4B Cysteine protease ATG4B;
      Q9Y4P1_C74
<220> FEATURE:
<221> NAME/KEY: MOD_RES
<222> LOCATION: (19)..(19)
<223> OTHER INFORMATION: Site of chemical conjugation

<400> SEQUENCE: 392

Lys Asn Phe Pro Ala Ile Gly Gly Thr Gly Pro Thr Ser Asp Thr Gly
1               5                   10                  15

Trp Gly Cys Met Leu Arg Cys
            20

<210> SEQ ID NO 393
<211> LENGTH: 10
<212> TYPE: PRT
<213> ORGANISM: Homo sapiens
<220> FEATURE:
```

```
<223> OTHER INFORMATION: NEK9 Serine/threonine-protein kinase Nek9;
      Q8TD19_C623
<220> FEATURE:
<221> NAME/KEY: MOD_RES
<222> LOCATION: (7)..(7)
<223> OTHER INFORMATION: Site of chemical conjugation

<400> SEQUENCE: 393

Arg Leu Leu Thr Phe Gly Cys Asn Lys Cys
1               5                   10

<210> SEQ ID NO 394
<211> LENGTH: 18
<212> TYPE: PRT
<213> ORGANISM: Homo sapiens
<220> FEATURE:
<223> OTHER INFORMATION: NFU1 NFU1 iron-sulfur cluster scaffold homolog,
      mitocho; Q9UMS0_C213
<220> FEATURE:
<221> NAME/KEY: MOD_RES
<222> LOCATION: (9)..(9)
<223> OTHER INFORMATION: Site of chemical conjugation

<400> SEQUENCE: 394

Lys Leu Gln Gly Ser Cys Thr Ser Cys Pro Ser Ser Ile Ile Thr Leu
1               5                   10                  15

Lys Asn

<210> SEQ ID NO 395
<211> LENGTH: 24
<212> TYPE: PRT
<213> ORGANISM: Homo sapiens
<220> FEATURE:
<223> OTHER INFORMATION: KDM4B Lysine-specific demethylase 4B;
      O94953_C694
<220> FEATURE:
<221> NAME/KEY: MOD_RES
<222> LOCATION: (16)..(16)
<223> OTHER INFORMATION: Site of chemical conjugation

<400> SEQUENCE: 395

Arg Thr Glu Pro Tyr Cys Ala Ile Cys Thr Leu Phe Tyr Pro Tyr Cys
1               5                   10                  15

Gln Ala Leu Gln Thr Glu Lys Glu
            20

<210> SEQ ID NO 396
<211> LENGTH: 33
<212> TYPE: PRT
<213> ORGANISM: Homo sapiens
<220> FEATURE:
<223> OTHER INFORMATION: PLEC Plectin;
      Q15149_C992
<220> FEATURE:
<221> NAME/KEY: MOD_RES
<222> LOCATION: (16)..(16)
<223> OTHER INFORMATION: Site of chemical conjugation

<400> SEQUENCE: 396

Lys Val Leu Ser Ser Ser Gly Ser Glu Ala Ala Val Pro Ser Val Cys
1               5                   10                  15

Phe Leu Val Pro Pro Pro Asn Gln Glu Ala Gln Glu Ala Val Thr Arg
            20                  25                  30

Leu

<210> SEQ ID NO 397
<211> LENGTH: 41
```

```
<212> TYPE: PRT
<213> ORGANISM: Homo sapiens
<220> FEATURE:
<223> OTHER INFORMATION: IDE Insulin-degrading enzyme;
      P14735_C974
<220> FEATURE:
<221> NAME/KEY: MOD_RES
<222> LOCATION: (14)..(14)
<223> OTHER INFORMATION: Site of chemical conjugation

<400> SEQUENCE: 397

Arg Glu Met Asp Ser Cys Pro Val Val Gly Glu Phe Pro Cys Gln Asn
1               5                   10                  15

Asp Ile Asn Leu Ser Gln Ala Pro Ala Leu Pro Gln Pro Glu Val Ile
            20                  25                  30

Gln Asn Met Thr Glu Phe Lys Arg Gly
        35                  40

<210> SEQ ID NO 398
<211> LENGTH: 14
<212> TYPE: PRT
<213> ORGANISM: Homo sapiens
<220> FEATURE:
<223> OTHER INFORMATION: TBC1D13 TBC1 domain family member 13;
      Q9NVG8_C282
<220> FEATURE:
<221> NAME/KEY: MOD_RES
<222> LOCATION: (8)..(8)
<223> OTHER INFORMATION: Site of chemical conjugation

<400> SEQUENCE: 398

Lys Ser Leu Asp Asp Ser Gln Cys Gly Ile Thr Tyr Lys Met
1               5                   10

<210> SEQ ID NO 399
<211> LENGTH: 21
<212> TYPE: PRT
<213> ORGANISM: Homo sapiens
<220> FEATURE:
<223> OTHER INFORMATION: DPP9 Dipeptidyl peptidase 9;
      Q86TI2_C844
<220> FEATURE:
<221> NAME/KEY: MOD_RES
<222> LOCATION: (2)..(2)
<223> OTHER INFORMATION: Site of chemical conjugation

<400> SEQUENCE: 399

Arg Cys Pro Glu Ser Gly Glu His Tyr Glu Val Thr Leu Leu His Phe
1               5                   10                  15

Leu Gln Glu Tyr Leu
            20

<210> SEQ ID NO 400
<211> LENGTH: 38
<212> TYPE: PRT
<213> ORGANISM: Homo sapiens
<220> FEATURE:
<223> OTHER INFORMATION: HEXIM1 Protein HEXIM1;
      O94992_C84
<220> FEATURE:
<221> NAME/KEY: MOD_RES
<222> LOCATION: (35)..(35)
<223> OTHER INFORMATION: Site of chemical conjugation

<400> SEQUENCE: 400

Arg Ala Phe Pro Gln Leu Gly Gly Arg Pro Gly Pro Glu Gly Glu Gly
1               5                   10                  15

Ser Leu Glu Ser Gln Pro Pro Leu Gln Thr Gln Ala Cys Pro Glu
```

```
                 20                  25                  30

Ser Ser Cys Leu Arg Glu
        35

<210> SEQ ID NO 401
<211> LENGTH: 17
<212> TYPE: PRT
<213> ORGANISM: Homo sapiens
<220> FEATURE:
<223> OTHER INFORMATION: PDSS2 Decaprenyl-diphosphate synthase subunit
      2; Q86YH6_C71
<220> FEATURE:
<221> NAME/KEY: MOD_RES
<222> LOCATION: (2)..(2)
<223> OTHER INFORMATION: Site of chemical conjugation

<400> SEQUENCE: 401

Arg Cys Leu Leu Ser Asp Glu Leu Ser Asn Ile Ala Met Gln Val Arg
1               5                   10                  15

Lys

<210> SEQ ID NO 402
<211> LENGTH: 14
<212> TYPE: PRT
<213> ORGANISM: Homo sapiens
<220> FEATURE:
<223> OTHER INFORMATION: ERCC3 TFIIH basal transcription factor complex
      helicase; P19447_C342
<220> FEATURE:
<221> NAME/KEY: MOD_RES
<222> LOCATION: (9)..(9)
<223> OTHER INFORMATION: Site of chemical conjugation

<400> SEQUENCE: 402

Arg Ser Gly Val Ile Val Leu Pro Cys Gly Ala Gly Lys Ser
1               5                   10

<210> SEQ ID NO 403
<211> LENGTH: 30
<212> TYPE: PRT
<213> ORGANISM: Homo sapiens
<220> FEATURE:
<223> OTHER INFORMATION: MSRB2 Methionine-R-sulfoxide reductase B2,
      mitochondrial; Q9Y3D2_C105
<220> FEATURE:
<221> NAME/KEY: MOD_RES
<222> LOCATION: (3)..(3)
<223> OTHER INFORMATION: Site of chemical conjugation

<400> SEQUENCE: 403

Lys Tyr Cys Ser Gly Thr Gly Trp Pro Ser Phe Ser Glu Ala His Gly
1               5                   10                  15

Thr Ser Gly Ser Asp Glu Ser His Thr Gly Ile Leu Arg Arg
            20                  25                  30

<210> SEQ ID NO 404
<211> LENGTH: 27
<212> TYPE: PRT
<213> ORGANISM: Homo sapiens
<220> FEATURE:
<223> OTHER INFORMATION: VPS18 Vacuolar protein sorting-associated
      protein 18 hom; Q9P253_C22
<220> FEATURE:
<221> NAME/KEY: MOD_RES
<222> LOCATION: (9)..(9)
<223> OTHER INFORMATION: Site of chemical conjugation

<400> SEQUENCE: 404
```

Arg Ser Ala Val Leu Gln Pro Gly Cys Pro Ser Val Gly Ile Pro His
1               5                   10                  15

Ser Gly Tyr Val Asn Ala Gln Leu Glu Lys Glu
            20                  25

<210> SEQ ID NO 405
<211> LENGTH: 12
<212> TYPE: PRT
<213> ORGANISM: Homo sapiens
<220> FEATURE:
<223> OTHER INFORMATION: RNF40 E3 ubiquitin-protein ligase BRE1B;
      O75150_C890
<220> FEATURE:
<221> NAME/KEY: MOD_RES
<222> LOCATION: (6)..(6)
<223> OTHER INFORMATION: Site of chemical conjugation

<400> SEQUENCE: 405

Arg Glu Ile Gln Pro Cys Leu Ala Glu Ser Arg Ala
1               5                   10

<210> SEQ ID NO 406
<211> LENGTH: 32
<212> TYPE: PRT
<213> ORGANISM: Homo sapiens
<220> FEATURE:
<223> OTHER INFORMATION: TYMS Thymidylate synthase;
      P04818_C199
<220> FEATURE:
<221> NAME/KEY: MOD_RES
<222> LOCATION: (15)..(15)
<223> OTHER INFORMATION: Site of chemical conjugation

<400> SEQUENCE: 406

Arg Asp Leu Pro Leu Met Ala Leu Pro Pro Cys His Ala Leu Cys Gln
1               5                   10                  15

Phe Tyr Val Val Asn Ser Glu Leu Ser Cys Gln Leu Tyr Gln Arg Ser
            20                  25                  30

<210> SEQ ID NO 407
<211> LENGTH: 23
<212> TYPE: PRT
<213> ORGANISM: Homo sapiens
<220> FEATURE:
<223> OTHER INFORMATION: CDK5 Cyclin-dependent kinase 5;
      Q00535_C157
<220> FEATURE:
<221> NAME/KEY: MOD_RES
<222> LOCATION: (2)..(2)
<223> OTHER INFORMATION: Site of chemical conjugation

<400> SEQUENCE: 407

Arg Cys Tyr Ser Ala Glu Val Val Thr Leu Trp Tyr Arg Pro Pro Asp
1               5                   10                  15

Val Leu Phe Gly Ala Lys Leu
            20

<210> SEQ ID NO 408
<211> LENGTH: 11
<212> TYPE: PRT
<213> ORGANISM: Homo sapiens
<220> FEATURE:
<223> OTHER INFORMATION: DOCK7 Dedicator of cytokinesis protein 7;
      Q96N67_C2125
<220> FEATURE:
<221> NAME/KEY: MOD_RES
<222> LOCATION: (8)..(8)
<223> OTHER INFORMATION: Site of chemical conjugation

<400> SEQUENCE: 408

Lys Ala Val Leu Pro Val Thr Cys His Arg Asp
1               5                   10

<210> SEQ ID NO 409
<211> LENGTH: 10
<212> TYPE: PRT
<213> ORGANISM: Homo sapiens
<220> FEATURE:
<223> OTHER INFORMATION: PAPSS2 Bifunctional 3-phosphoadenosine
      5-phosphosulfate; O95340_C350
<220> FEATURE:
<221> NAME/KEY: MOD_RES
<222> LOCATION: (7)..(7)
<223> OTHER INFORMATION: Site of chemical conjugation

<400> SEQUENCE: 409

Arg Val Trp Gly Thr Thr Cys Thr Lys His
1               5                   10

<210> SEQ ID NO 410
<211> LENGTH: 29
<212> TYPE: PRT
<213> ORGANISM: Homo sapiens
<220> FEATURE:
<223> OTHER INFORMATION: EDC3 Enhancer of mRNA-decapping protein 3;
      Q96F86_C499
<220> FEATURE:
<221> NAME/KEY: MOD_RES
<222> LOCATION: (27)..(27)
<223> OTHER INFORMATION: Site of chemical conjugation

<400> SEQUENCE: 410

Arg Ile Tyr Leu Cys Asp Ile Gly Ile Pro Gln Gln Val Phe Gln Glu
1               5                   10                  15

Val Gly Ile Asn Tyr His Ser Pro Phe Gly Cys Lys Phe
            20                  25

<210> SEQ ID NO 411
<211> LENGTH: 11
<212> TYPE: PRT
<213> ORGANISM: Homo sapiens
<220> FEATURE:
<223> OTHER INFORMATION: BLOC1S3 Biogenesis of lysosome-related
      organelles complex; Q6QNY0_C168
<220> FEATURE:
<221> NAME/KEY: MOD_RES
<222> LOCATION: (5)..(5)
<223> OTHER INFORMATION: Site of chemical conjugation

<400> SEQUENCE: 411

Arg Gly Asp Leu Cys Ala Leu Ala Glu Arg Leu
1               5                   10

<210> SEQ ID NO 412
<211> LENGTH: 25
<212> TYPE: PRT
<213> ORGANISM: Homo sapiens
<220> FEATURE:
<223> OTHER INFORMATION: NUP54 Nucleoporin p54;
      Q7Z3B4_C180
<220> FEATURE:
<221> NAME/KEY: MOD_RES
<222> LOCATION: (7)..(7)
<223> OTHER INFORMATION: Site of chemical conjugation

<400> SEQUENCE: 412

Lys Ala Val Gly Tyr Ser Cys Met Pro Ser Asn Lys Asp Glu Asp Gly
1               5                   10                  15

```
Leu Val Val Leu Val Phe Asn Lys Lys
            20                  25

<210> SEQ ID NO 413
<211> LENGTH: 13
<212> TYPE: PRT
<213> ORGANISM: Homo sapiens
<220> FEATURE:
<223> OTHER INFORMATION: USP22 Ubiquitin carboxyl-terminal hydrolase 22;
      Q9UPT9_C171
<220> FEATURE:
<221> NAME/KEY: MOD_RES
<222> LOCATION: (7)..(7)
<223> OTHER INFORMATION: Site of chemical conjugation

<400> SEQUENCE: 413

Arg Lys Ile Thr Ser Asn Cys Thr Ile Gly Leu Arg Gly
1               5                   10

<210> SEQ ID NO 414
<211> LENGTH: 21
<212> TYPE: PRT
<213> ORGANISM: Homo sapiens
<220> FEATURE:
<223> OTHER INFORMATION: ACADSB Short/branched chain specific acyl-CoA
      dehydrogena; P45954_C175
<220> FEATURE:
<221> NAME/KEY: MOD_RES
<222> LOCATION: (6)..(6)
<223> OTHER INFORMATION: Site of chemical conjugation

<400> SEQUENCE: 414

Lys Val Gly Ser Phe Cys Leu Ser Glu Ala Gly Ala Gly Ser Asp Ser
1               5                   10                  15

Phe Ala Leu Lys Thr
            20

<210> SEQ ID NO 415
<211> LENGTH: 15
<212> TYPE: PRT
<213> ORGANISM: Homo sapiens
<220> FEATURE:
<223> OTHER INFORMATION: IKZF3 Zinc finger protein Aiolos;
      Q9UKT9_C434
<220> FEATURE:
<221> NAME/KEY: MOD_RES
<222> LOCATION: (12)..(12)
<223> OTHER INFORMATION: Site of chemical conjugation

<400> SEQUENCE: 415

Arg Ser Tyr Glu Leu Leu Lys Pro Pro Pro Ile Cys Pro Arg Asp
1               5                   10                  15

<210> SEQ ID NO 416
<211> LENGTH: 20
<212> TYPE: PRT
<213> ORGANISM: Homo sapiens
<220> FEATURE:
<223> OTHER INFORMATION: EIF2B3 Translation initiation factor eIF-2B
      subunit gamma; Q9NR50_C281
<220> FEATURE:
<221> NAME/KEY: MOD_RES
<222> LOCATION: (14)..(14)
<223> OTHER INFORMATION: Site of chemical conjugation

<400> SEQUENCE: 416

Lys Glu Ala Asn Thr Leu Asn Leu Ala Pro Tyr Asp Ala Cys Trp Asn
1               5                   10                  15
```

Ala Cys Arg Gly
        20

<210> SEQ ID NO 417
<211> LENGTH: 14
<212> TYPE: PRT
<213> ORGANISM: Homo sapiens
<220> FEATURE:
<223> OTHER INFORMATION: RRAGC Ras-related GTP-binding protein C;
      Q9HB90_C377
<220> FEATURE:
<221> NAME/KEY: MOD_RES
<222> LOCATION: (3)..(3)
<223> OTHER INFORMATION: Site of chemical conjugation

<400> SEQUENCE: 417

Arg Ser Cys Gly His Gln Thr Ser Ala Ser Ser Leu Lys Ala
1               5                   10

<210> SEQ ID NO 418
<211> LENGTH: 23
<212> TYPE: PRT
<213> ORGANISM: Homo sapiens
<220> FEATURE:
<223> OTHER INFORMATION: FNBP1L Formin-binding protein 1-like;
      Q5T0N5_C69
<220> FEATURE:
<221> NAME/KEY: MOD_RES
<222> LOCATION: (5)..(5)
<223> OTHER INFORMATION: Site of chemical conjugation

<400> SEQUENCE: 418

Arg Phe Thr Ser Cys Val Ala Phe Phe Asn Ile Leu Asn Glu Leu Asn
1               5                   10                  15

Asp Tyr Ala Gly Gln Arg Glu
            20

<210> SEQ ID NO 419
<211> LENGTH: 13
<212> TYPE: PRT
<213> ORGANISM: Homo sapiens
<220> FEATURE:
<223> OTHER INFORMATION: CTSD Cathepsin D;
      P07339_C117
<220> FEATURE:
<221> NAME/KEY: MOD_RES
<222> LOCATION: (7)..(7)
<223> OTHER INFORMATION: Site of chemical conjugation

<400> SEQUENCE: 419

Lys Leu Leu Asp Ile Ala Cys Trp Ile His His Lys Tyr
1               5                   10

<210> SEQ ID NO 420
<211> LENGTH: 26
<212> TYPE: PRT
<213> ORGANISM: Homo sapiens
<220> FEATURE:
<223> OTHER INFORMATION: HUWE1 E3 ubiquitin-protein ligase HUWE1;
      Q7Z6Z7_C3372
<220> FEATURE:
<221> NAME/KEY: MOD_RES
<222> LOCATION: (3)..(3)
<223> OTHER INFORMATION: Site of chemical conjugation

<400> SEQUENCE: 420

Lys Ala Cys Ser Pro Cys Ser Ser Gln Ser Ser Ser Ser Gly Ile Cys
1               5                   10                  15

Thr Asp Phe Trp Asp Leu Leu Val Lys Leu

```
            20                  25

<210> SEQ ID NO 421
<211> LENGTH: 10
<212> TYPE: PRT
<213> ORGANISM: Homo sapiens
<220> FEATURE:
<223> OTHER INFORMATION: SUPT5H Transcription elongation factor SPT5;
      O00267_C626
<220> FEATURE:
<221> NAME/KEY: MOD_RES
<222> LOCATION: (8)..(8)
<223> OTHER INFORMATION: Site of chemical conjugation

<400> SEQUENCE: 421

Arg Ser Phe Ala Phe Leu His Cys Lys Lys
1               5                   10

<210> SEQ ID NO 422
<211> LENGTH: 10
<212> TYPE: PRT
<213> ORGANISM: Homo sapiens
<220> FEATURE:
<223> OTHER INFORMATION: SMC2 Structural maintenance of chromosomes
      protein 2; O95347_C1174
<220> FEATURE:
<221> NAME/KEY: MOD_RES
<222> LOCATION: (5)..(5)
<223> OTHER INFORMATION: Site of chemical conjugation

<400> SEQUENCE: 422

Arg Phe Thr Gln Cys Gln Asn Gly Lys Ile
1               5                   10

<210> SEQ ID NO 423
<211> LENGTH: 18
<212> TYPE: PRT
<213> ORGANISM: Homo sapiens
<220> FEATURE:
<223> OTHER INFORMATION: GCN1L1 Translational activator GCN1;
      Q92616_C648
<220> FEATURE:
<221> NAME/KEY: MOD_RES
<222> LOCATION: (8)..(8)
<223> OTHER INFORMATION: Site of chemical conjugation

<400> SEQUENCE: 423

Arg Val Leu Gln Glu Ala Leu Cys Val Ile Ser Gly Val Pro Gly Leu
1               5                   10                  15

Lys Gly

<210> SEQ ID NO 424
<211> LENGTH: 26
<212> TYPE: PRT
<213> ORGANISM: Homo sapiens
<220> FEATURE:
<223> OTHER INFORMATION: FOXK1 Forkhead box protein K1;
      P85037_C254
<220> FEATURE:
<221> NAME/KEY: MOD_RES
<222> LOCATION: (20)..(20)
<223> OTHER INFORMATION: Site of chemical conjugation

<400> SEQUENCE: 424

Arg Ser Met Val Ser Pro Val Pro Ser Pro Thr Gly Thr Ile Ser Val
1               5                   10                  15

Pro Asn Ser Cys Pro Ala Ser Pro Arg Gly
            20                  25
```

<210> SEQ ID NO 425
<211> LENGTH: 14
<212> TYPE: PRT
<213> ORGANISM: Homo sapiens
<220> FEATURE:
<223> OTHER INFORMATION: CAPN2 Calpain-2 catalytic subunit;
    P17655_C640
<220> FEATURE:
<221> NAME/KEY: MOD_RES
<222> LOCATION: (4)..(4)
<223> OTHER INFORMATION: Site of chemical conjugation

<400> SEQUENCE: 425

Lys Met Pro Cys Gln Leu His Gln Val Ile Val Ala Arg Phe
1               5                   10

<210> SEQ ID NO 426
<211> LENGTH: 18
<212> TYPE: PRT
<213> ORGANISM: Homo sapiens
<220> FEATURE:
<223> OTHER INFORMATION: LRBA Lipopolysaccharide-responsive and beige-
    like ancho; P50851_C2675
<220> FEATURE:
<221> NAME/KEY: MOD_RES
<222> LOCATION: (2)..(2)
<223> OTHER INFORMATION: Site of chemical conjugation

<400> SEQUENCE: 426

Lys Cys Ser Gly Ile Gly Asp Asn Pro Gly Ser Glu Thr Ala Ala Pro
1               5                   10                  15

Arg Ala

<210> SEQ ID NO 427
<211> LENGTH: 26
<212> TYPE: PRT
<213> ORGANISM: Homo sapiens
<220> FEATURE:
<223> OTHER INFORMATION: MAP2K7 Dual specificity mitogen-activated
    protein kinase; O14733_C131
<220> FEATURE:
<221> NAME/KEY: MOD_RES
<222> LOCATION: (20)..(20)
<223> OTHER INFORMATION: Site of chemical conjugation

<400> SEQUENCE: 427

Arg Tyr Gln Ala Glu Ile Asn Asp Leu Glu Asn Leu Gly Glu Met Gly
1               5                   10                  15

Ser Gly Thr Cys Gly Gln Val Trp Lys Met
            20                  25

<210> SEQ ID NO 428
<211> LENGTH: 37
<212> TYPE: PRT
<213> ORGANISM: Homo sapiens
<220> FEATURE:
<223> OTHER INFORMATION: RCCD1 RCC1 domain-containing protein 1;
    A6NED2_C139
<220> FEATURE:
<221> NAME/KEY: MOD_RES
<222> LOCATION: (34)..(34)
<223> OTHER INFORMATION: Site of chemical conjugation

<400> SEQUENCE: 428

Arg Gly Glu Pro Leu Trp Ala Gln Asn Val Val Pro Glu Ala Glu Gly
1               5                   10                  15

Glu Asp Asp Pro Ala Gly Glu Ala Gln Ala Gly Arg Leu Pro Leu Leu
            20                  25                  30

-continued

Pro Cys Ala Arg Ala
        35

<210> SEQ ID NO 429
<211> LENGTH: 16
<212> TYPE: PRT
<213> ORGANISM: Homo sapiens
<220> FEATURE:
<223> OTHER INFORMATION: NUMA1 Nuclear mitotic apparatus protein 1;
      Q14980_C961
<220> FEATURE:
<221> NAME/KEY: MOD_RES
<222> LOCATION: (4)..(4)
<223> OTHER INFORMATION: Site of chemical conjugation

<400> SEQUENCE: 429

Arg Gln Phe Cys Ser Thr Gln Ala Ala Leu Gln Ala Met Glu Arg Glu
1               5                   10                  15

<210> SEQ ID NO 430
<211> LENGTH: 22
<212> TYPE: PRT
<213> ORGANISM: Homo sapiens
<220> FEATURE:
<223> OTHER INFORMATION: MLTK Mitogen-activated protein kinase kinase
      kinase MLTK; Q9NYL2_C22
<220> FEATURE:
<221> NAME/KEY: MOD_RES
<222> LOCATION: (11)..(11)
<223> OTHER INFORMATION: Site of chemical conjugation

<400> SEQUENCE: 430

Lys Phe Asp Asp Leu Gln Phe Phe Glu Asn Cys Gly Gly Gly Ser Phe
1               5                   10                  15

Gly Ser Val Tyr Arg Ala
            20

<210> SEQ ID NO 431
<211> LENGTH: 13
<212> TYPE: PRT
<213> ORGANISM: Homo sapiens
<220> FEATURE:
<223> OTHER INFORMATION: BLMH Bleomycin hydrolase;
      Q13867_C73
<220> FEATURE:
<221> NAME/KEY: MOD_RES
<222> LOCATION: (2)..(2)
<223> OTHER INFORMATION: Site of chemical conjugation

<400> SEQUENCE: 431

Arg Cys Trp Ile Phe Ser Cys Leu Asn Val Met Arg Leu
1               5                   10

<210> SEQ ID NO 432
<211> LENGTH: 12
<212> TYPE: PRT
<213> ORGANISM: Homo sapiens
<220> FEATURE:
<223> OTHER INFORMATION: NUDT16L1 Protein syndesmos;
      Q9BRJ7_C88
<220> FEATURE:
<221> NAME/KEY: MOD_RES
<222> LOCATION: (9)..(9)
<223> OTHER INFORMATION: Site of chemical conjugation

<400> SEQUENCE: 432

Arg Val Leu Gly Leu Gly Leu Gly Cys Leu Arg Leu
1               5                   10

```
<210> SEQ ID NO 433
<211> LENGTH: 17
<212> TYPE: PRT
<213> ORGANISM: Homo sapiens
<220> FEATURE:
<223> OTHER INFORMATION: ARAP1 Arf-GAP with Rho-GAP domain, ANK repeat
      and PH domain; Q96P48_C900
<220> FEATURE:
<221> NAME/KEY: MOD_RES
<222> LOCATION: (9)..(9)
<223> OTHER INFORMATION: Site of chemical conjugation

<400> SEQUENCE: 433

Arg Ala Val Phe Pro Glu Gly Pro Cys Glu Glu Pro Leu Gln Leu Arg
1               5                   10                  15

Lys

<210> SEQ ID NO 434
<211> LENGTH: 13
<212> TYPE: PRT
<213> ORGANISM: Homo sapiens
<220> FEATURE:
<223> OTHER INFORMATION: WDR45L WD repeat domain phosphoinositide-
      interacting protein; Q5MNZ6_C63
<220> FEATURE:
<221> NAME/KEY: MOD_RES
<222> LOCATION: (2)..(2)
<223> OTHER INFORMATION: Site of chemical conjugation

<400> SEQUENCE: 434

Arg Cys Asn Tyr Leu Ala Leu Val Gly Gly Gly Lys Lys
1               5                   10

<210> SEQ ID NO 435
<211> LENGTH: 26
<212> TYPE: PRT
<213> ORGANISM: Homo sapiens
<220> FEATURE:
<223> OTHER INFORMATION: GRAP GRB2-related adapter protein;
      Q13588_C161
<220> FEATURE:
<221> NAME/KEY: MOD_RES
<222> LOCATION: (6)..(6)
<223> OTHER INFORMATION: Site of chemical conjugation

<400> SEQUENCE: 435

Lys Ser Pro Gly Ala Cys Phe Ala Gln Ala Gln Phe Asp Phe Ser Ala
1               5                   10                  15

Gln Asp Pro Ser Gln Leu Ser Phe Arg Arg
            20                  25

<210> SEQ ID NO 436
<211> LENGTH: 17
<212> TYPE: PRT
<213> ORGANISM: Homo sapiens
<220> FEATURE:
<223> OTHER INFORMATION: Uncharacterized protein;
      H0Y2S0_C31
<220> FEATURE:
<221> NAME/KEY: MOD_RES
<222> LOCATION: (13)..(13)
<223> OTHER INFORMATION: Site of chemical conjugation

<400> SEQUENCE: 436

Arg Tyr Thr Gln Gln Gly Phe Gly Asn Leu Pro Ile Cys Met Ala Lys
1               5                   10                  15

Thr
```

<210> SEQ ID NO 437
<211> LENGTH: 14
<212> TYPE: PRT
<213> ORGANISM: Homo sapiens
<220> FEATURE:
<223> OTHER INFORMATION: TPX2 Targeting protein for Xklp2;
      Q9ULW0_C536
<220> FEATURE:
<221> NAME/KEY: MOD_RES
<222> LOCATION: (6)..(6)
<223> OTHER INFORMATION: Site of chemical conjugation

<400> SEQUENCE: 437

Arg Thr Val Glu Ile Cys Pro Phe Ser Phe Asp Ser Arg Asp
1               5                   10

<210> SEQ ID NO 438
<211> LENGTH: 17
<212> TYPE: PRT
<213> ORGANISM: Homo sapiens
<220> FEATURE:
<223> OTHER INFORMATION: XPO5 Exportin-5;
      Q9HAV4_C646
<220> FEATURE:
<221> NAME/KEY: MOD_RES
<222> LOCATION: (2)..(2)
<223> OTHER INFORMATION: Site of chemical conjugation

<400> SEQUENCE: 438

Lys Cys Ala Leu Met Glu Ala Leu Val Leu Ile Ser Asn Gln Phe Lys
1               5                   10                  15

Asn

<210> SEQ ID NO 439
<211> LENGTH: 10
<212> TYPE: PRT
<213> ORGANISM: Homo sapiens
<220> FEATURE:
<223> OTHER INFORMATION: DDX59 Probable ATP-dependent RNA helicase
      DDX59; Q5T1V6_C414
<220> FEATURE:
<221> NAME/KEY: MOD_RES
<222> LOCATION: (5)..(5)
<223> OTHER INFORMATION: Site of chemical conjugation

<400> SEQUENCE: 439

Lys Asn Leu Pro Cys Ala Asn Val Arg Gln
1               5                   10

<210> SEQ ID NO 440
<211> LENGTH: 15
<212> TYPE: PRT
<213> ORGANISM: Homo sapiens
<220> FEATURE:
<223> OTHER INFORMATION: POLA2 DNA polymerase alpha subunit B;
      Q14181_C198
<220> FEATURE:
<221> NAME/KEY: MOD_RES
<222> LOCATION: (5)..(5)
<223> OTHER INFORMATION: Site of chemical conjugation

<400> SEQUENCE: 440

Lys Val Leu Gly Cys Pro Glu Ala Leu Thr Gly Ser Tyr Lys Ser
1               5                   10                  15

<210> SEQ ID NO 441
<211> LENGTH: 26
<212> TYPE: PRT
<213> ORGANISM: Homo sapiens

```
<220> FEATURE:
<223> OTHER INFORMATION: RPUSD2 RNA pseudouridylate synthase domain-
      containing protein; Q8IZ73_C246
<220> FEATURE:
<221> NAME/KEY: MOD_RES
<222> LOCATION: (23)..(23)
<223> OTHER INFORMATION: Site of chemical conjugation

<400> SEQUENCE: 441

Arg Leu Leu Ala Glu Asn Glu Asp Val Val Val Asp Lys Pro Ser
1               5                   10                  15

Ser Ile Pro Val His Pro Cys Gly Arg Phe
            20                  25

<210> SEQ ID NO 442
<211> LENGTH: 19
<212> TYPE: PRT
<213> ORGANISM: Homo sapiens
<220> FEATURE:
<223> OTHER INFORMATION: KTN1 Kinectin;
      Q86UP2_C303
<220> FEATURE:
<221> NAME/KEY: MOD_RES
<222> LOCATION: (12)..(12)
<223> OTHER INFORMATION: Site of chemical conjugation

<400> SEQUENCE: 442

Lys Thr Met Met Phe Ser Glu Asp Glu Ala Leu Cys Val Val Asp Leu
1               5                   10                  15

Leu Lys Glu

<210> SEQ ID NO 443
<211> LENGTH: 16
<212> TYPE: PRT
<213> ORGANISM: Homo sapiens
<220> FEATURE:
<223> OTHER INFORMATION: LIMD1 LIM domain-containing protein 1;
      Q9UGP4_C305
<220> FEATURE:
<221> NAME/KEY: MOD_RES
<222> LOCATION: (13)..(13)
<223> OTHER INFORMATION: Site of chemical conjugation

<400> SEQUENCE: 443

Arg Thr Pro Ser Val Ser Ala Pro Leu Ala Leu Ser Cys Pro Arg Gln
1               5                   10                  15

<210> SEQ ID NO 444
<211> LENGTH: 25
<212> TYPE: PRT
<213> ORGANISM: Homo sapiens
<220> FEATURE:
<223> OTHER INFORMATION: CTH Cystathionine gamma-lyase;
      P32929_C229
<220> FEATURE:
<221> NAME/KEY: MOD_RES
<222> LOCATION: (18)..(18)
<223> OTHER INFORMATION: Site of chemical conjugation

<400> SEQUENCE: 444

Lys Tyr Met Asn Gly His Ser Asp Val Val Met Gly Leu Val Ser Val
1               5                   10                  15

Asn Cys Glu Ser Leu His Asn Arg Leu
            20                  25

<210> SEQ ID NO 445
<211> LENGTH: 18
<212> TYPE: PRT
```

```
<213> ORGANISM: Homo sapiens
<220> FEATURE:
<223> OTHER INFORMATION: HUWE1 E3 ubiquitin-protein ligase HUWE1;
      Q7Z6Z7_C4367
<220> FEATURE:
<221> NAME/KEY: MOD_RES
<222> LOCATION: (11)..(11)
<223> OTHER INFORMATION: Site of chemical conjugation

<400> SEQUENCE: 445

Arg His Met Leu Leu Leu Ala Ile Gln Glu Cys Ser Glu Gly Phe Gly
1               5                   10                  15

Leu Ala

<210> SEQ ID NO 446
<211> LENGTH: 22
<212> TYPE: PRT
<213> ORGANISM: Homo sapiens
<220> FEATURE:
<223> OTHER INFORMATION: MAT2A S-adenosylmethionine synthase isoform
      type-2; P31153_C214
<220> FEATURE:
<221> NAME/KEY: MOD_RES
<222> LOCATION: (16)..(16)
<223> OTHER INFORMATION: Site of chemical conjugation

<400> SEQUENCE: 446

Arg Val His Thr Ile Val Ile Ser Val Gln His Asp Glu Glu Val Cys
1               5                   10                  15

Leu Asp Glu Met Arg Asp
            20

<210> SEQ ID NO 447
<211> LENGTH: 18
<212> TYPE: PRT
<213> ORGANISM: Homo sapiens
<220> FEATURE:
<223> OTHER INFORMATION: CLIC6 Chloride intracellular channel protein 6;
      Q96NY7_C487
<220> FEATURE:
<221> NAME/KEY: MOD_RES
<222> LOCATION: (12)..(12)
<223> OTHER INFORMATION: Site of chemical conjugation

<400> SEQUENCE: 447

Arg Ala Gly Tyr Asp Gly Glu Ser Ile Gly Asn Cys Pro Phe Ser Gln
1               5                   10                  15

Arg Leu

<210> SEQ ID NO 448
<211> LENGTH: 11
<212> TYPE: PRT
<213> ORGANISM: Homo sapiens
<220> FEATURE:
<223> OTHER INFORMATION: CCNB1 G2/mitotic-specific cyclin-B1;
      P14635_C238
<220> FEATURE:
<221> NAME/KEY: MOD_RES
<222> LOCATION: (7)..(7)
<223> OTHER INFORMATION: Site of chemical conjugation

<400> SEQUENCE: 448

Arg Phe Met Gln Asn Asn Cys Val Pro Lys Lys
1               5                   10

<210> SEQ ID NO 449
<211> LENGTH: 44
<212> TYPE: PRT
```

-continued

```
<213> ORGANISM: Homo sapiens
<220> FEATURE:
<223> OTHER INFORMATION: KCNAB2 Voltage-gated potassium channel subunit
      beta-2; Q13303_C248
<220> FEATURE:
<221> NAME/KEY: MOD_RES
<222> LOCATION: (27)..(27)
<223> OTHER INFORMATION: Site of chemical conjugation

<400> SEQUENCE: 449

Arg Glu Lys Val Glu Val Gln Leu Pro Glu Leu Phe His Lys Ile Gly
1               5                   10                  15

Val Gly Ala Met Thr Trp Ser Pro Leu Ala Cys Gly Ile Val Ser Gly
            20                  25                  30

Lys Tyr Asp Ser Gly Ile Pro Pro Tyr Ser Arg Ala
        35                  40

<210> SEQ ID NO 450
<211> LENGTH: 12
<212> TYPE: PRT
<213> ORGANISM: Homo sapiens
<220> FEATURE:
<223> OTHER INFORMATION: XPO5 Exportin-5;
      Q9HAV4_C44
<220> FEATURE:
<221> NAME/KEY: MOD_RES
<222> LOCATION: (2)..(2)
<223> OTHER INFORMATION: Site of chemical conjugation

<400> SEQUENCE: 450

Lys Cys Pro Ile Cys Val Pro Cys Gly Leu Arg Leu
1               5                   10

<210> SEQ ID NO 451
<211> LENGTH: 11
<212> TYPE: PRT
<213> ORGANISM: Homo sapiens
<220> FEATURE:
<223> OTHER INFORMATION: RNF214 RING finger protein 214;
      Q8ND24_C655
<220> FEATURE:
<221> NAME/KEY: MOD_RES
<222> LOCATION: (9)..(9)
<223> OTHER INFORMATION: Site of chemical conjugation

<400> SEQUENCE: 451

Arg Ser Ser His Ala Pro Ala Thr Cys Lys Leu
1               5                   10

<210> SEQ ID NO 452
<211> LENGTH: 14
<212> TYPE: PRT
<213> ORGANISM: Homo sapiens
<220> FEATURE:
<223> OTHER INFORMATION: RRAGC Ras-related GTP-binding protein C;
      Q9HB90_C358
<220> FEATURE:
<221> NAME/KEY: MOD_RES
<222> LOCATION: (11)..(11)
<223> OTHER INFORMATION: Site of chemical conjugation

<400> SEQUENCE: 452

Arg Lys Gly Leu Ile Asp Tyr Asn Phe His Cys Phe Arg Lys
1               5                   10

<210> SEQ ID NO 453
<211> LENGTH: 12
<212> TYPE: PRT
<213> ORGANISM: Homo sapiens
```

```
<220> FEATURE:
<223> OTHER INFORMATION: RAD50 DNA repair protein RAD50;
      Q92878_C1296
<220> FEATURE:
<221> NAME/KEY: MOD_RES
<222> LOCATION: (6)..(6)
<223> OTHER INFORMATION: Site of chemical conjugation

<400> SEQUENCE: 453

Lys Asn Ile Asp Gln Cys Ser Glu Ile Val Lys Cys
1               5                   10

<210> SEQ ID NO 454
<211> LENGTH: 9
<212> TYPE: PRT
<213> ORGANISM: Homo sapiens
<220> FEATURE:
<223> OTHER INFORMATION: MORC3 MORC family CW-type zinc finger protein
      3; Q14149_C15
<220> FEATURE:
<221> NAME/KEY: MOD_RES
<222> LOCATION: (6)..(6)
<223> OTHER INFORMATION: Site of chemical conjugation

<400> SEQUENCE: 454

Arg Leu Ser Ala Leu Cys Pro Lys Phe
1               5

<210> SEQ ID NO 455
<211> LENGTH: 46
<212> TYPE: PRT
<213> ORGANISM: Homo sapiens
<220> FEATURE:
<223> OTHER INFORMATION: APEH Acylamino-acid-releasing enzyme;
      P13798_C641
<220> FEATURE:
<221> NAME/KEY: MOD_RES
<222> LOCATION: (32)..(32)
<223> OTHER INFORMATION: Site of chemical conjugation

<400> SEQUENCE: 455

Arg Asn Pro Val Ile Asn Ile Ala Ser Met Leu Gly Ser Thr Asp Ile
1               5                   10                  15

Pro Asp Trp Cys Val Val Glu Ala Gly Phe Pro Phe Ser Ser Asp Cys
            20                  25                  30

Leu Pro Asp Leu Ser Val Trp Ala Glu Met Leu Asp Lys Ser
        35                  40                  45

<210> SEQ ID NO 456
<211> LENGTH: 45
<212> TYPE: PRT
<213> ORGANISM: Homo sapiens
<220> FEATURE:
<223> OTHER INFORMATION: PFKP 6-phosphofructokinase type C;
      Q01813_C563
<220> FEATURE:
<221> NAME/KEY: MOD_RES
<222> LOCATION: (40)..(40)
<223> OTHER INFORMATION: Site of chemical conjugation

<400> SEQUENCE: 456

Lys His Glu Glu Phe Cys Val Pro Met Val Met Val Pro Ala Thr Val
1               5                   10                  15

Ser Asn Asn Val Pro Gly Ser Asp Phe Ser Ile Gly Ala Asp Thr Ala
            20                  25                  30

Leu Asn Thr Ile Thr Asp Thr Cys Asp Arg Ile Lys Gln
        35                  40                  45
```

```
<210> SEQ ID NO 457
<211> LENGTH: 19
<212> TYPE: PRT
<213> ORGANISM: Homo sapiens
<220> FEATURE:
<223> OTHER INFORMATION: MMS19 MMS19 nucleotide excision repair protein
      homolog; Q96T76_C549
<220> FEATURE:
<221> NAME/KEY: MOD_RES
<222> LOCATION: (16)..(16)
<223> OTHER INFORMATION: Site of chemical conjugation

<400> SEQUENCE: 457

Arg Val Gly Glu Ser Asn Leu Thr Asn Gly Asp Glu Pro Thr Gln Cys
1               5                   10                  15

Ser Arg His

<210> SEQ ID NO 458
<211> LENGTH: 29
<212> TYPE: PRT
<213> ORGANISM: Homo sapiens
<220> FEATURE:
<223> OTHER INFORMATION: AARSD1 Alanyl-tRNA editing protein Aarsd1;
      Q9BTE6_C209
<220> FEATURE:
<221> NAME/KEY: MOD_RES
<222> LOCATION: (13)..(13)
<223> OTHER INFORMATION: Site of chemical conjugation

<400> SEQUENCE: 458

Arg Val Val Asn Ile Glu Gly Val Asp Ser Asn Met Cys Cys Gly Thr
1               5                   10                  15

His Val Ser Asn Leu Ser Asp Leu Gln Val Ile Lys Ile
            20                  25

<210> SEQ ID NO 459
<211> LENGTH: 18
<212> TYPE: PRT
<213> ORGANISM: Homo sapiens
<220> FEATURE:
<223> OTHER INFORMATION: MTMR12 Myotubularin-related protein 12;
      Q9C0I1_C694
<220> FEATURE:
<221> NAME/KEY: MOD_RES
<222> LOCATION: (14)..(14)
<223> OTHER INFORMATION: Site of chemical conjugation

<400> SEQUENCE: 459

Arg His His Ser Gln Gln Ala Pro Gln Ala Glu Ala Pro Cys Leu Leu
1               5                   10                  15

Arg Asn

<210> SEQ ID NO 460
<211> LENGTH: 24
<212> TYPE: PRT
<213> ORGANISM: Homo sapiens
<220> FEATURE:
<223> OTHER INFORMATION: CDA Cytidine deaminase;
      P32320_C14
<220> FEATURE:
<221> NAME/KEY: MOD_RES
<222> LOCATION: (11)..(11)
<223> OTHER INFORMATION: Site of chemical conjugation

<400> SEQUENCE: 460

Lys Arg Pro Ala Cys Thr Leu Lys Pro Glu Cys Val Gln Gln Leu Leu
1               5                   10                  15
```

Val Cys Ser Gln Glu Ala Lys Lys
            20

<210> SEQ ID NO 461
<211> LENGTH: 16
<212> TYPE: PRT
<213> ORGANISM: Homo sapiens
<220> FEATURE:
<223> OTHER INFORMATION: RRBP1 Ribosome-binding protein 1;
      Q9P2E9_C1323
<220> FEATURE:
<221> NAME/KEY: MOD_RES
<222> LOCATION: (14)..(14)
<223> OTHER INFORMATION: Site of chemical conjugation

<400> SEQUENCE: 461

Lys Leu Thr Ala Glu Phe Glu Glu Ala Gln Thr Ser Ala Cys Arg Leu
1               5                   10                  15

<210> SEQ ID NO 462
<211> LENGTH: 15
<212> TYPE: PRT
<213> ORGANISM: Homo sapiens
<220> FEATURE:
<223> OTHER INFORMATION: POLR2B DNA-directed RNA polymerase II subunit
      RPB2; P30876_C1093
<220> FEATURE:
<221> NAME/KEY: MOD_RES
<222> LOCATION: (3)..(3)
<223> OTHER INFORMATION: Site of chemical conjugation

<400> SEQUENCE: 462

Arg Asp Cys Gln Ile Ala His Gly Ala Ala Gln Phe Leu Arg Glu
1               5                   10                  15

<210> SEQ ID NO 463
<211> LENGTH: 17
<212> TYPE: PRT
<213> ORGANISM: Homo sapiens
<220> FEATURE:
<223> OTHER INFORMATION: P4HB Protein disulfide-isomerase;
      P07237_C53
<220> FEATURE:
<221> NAME/KEY: MOD_RES
<222> LOCATION: (12)..(12)
<223> OTHER INFORMATION: Site of chemical conjugation

<400> SEQUENCE: 463

Lys Tyr Leu Leu Val Glu Phe Tyr Ala Pro Trp Cys Gly His Cys Lys
1               5                   10                  15

Ala

<210> SEQ ID NO 464
<211> LENGTH: 43
<212> TYPE: PRT
<213> ORGANISM: Homo sapiens
<220> FEATURE:
<223> OTHER INFORMATION: RPUSD2 RNA pseudouridylate synthase domain-
      containing protein; Q8IZ73_C431
<220> FEATURE:
<221> NAME/KEY: MOD_RES
<222> LOCATION: (10)..(10)
<223> OTHER INFORMATION: Site of chemical conjugation

<400> SEQUENCE: 464

Lys Gln Ser Leu Asp Val Leu Asp Leu Cys Glu Gly Asp Leu Ser Pro
1               5                   10                  15

Gly Leu Thr Asp Ser Thr Ala Pro Ser Ser Glu Leu Gly Lys Asp Asp
            20                  25                  30

```
Leu Glu Glu Leu Ala Ala Ala Ala Gln Lys Met
        35                  40

<210> SEQ ID NO 465
<211> LENGTH: 15
<212> TYPE: PRT
<213> ORGANISM: Homo sapiens
<220> FEATURE:
<223> OTHER INFORMATION: ZCCHC8 Zinc finger CCHC domain-containing
      protein 8; Q6NZY4_C393
<220> FEATURE:
<221> NAME/KEY: MOD_RES
<222> LOCATION: (11)..(11)
<223> OTHER INFORMATION: Site of chemical conjugation

<400> SEQUENCE: 465

Arg Ile Phe Gly Ser Ile Pro Met Gln Ala Cys Gln Gln Lys Asp
1               5                   10                  15

<210> SEQ ID NO 466
<211> LENGTH: 14
<212> TYPE: PRT
<213> ORGANISM: Homo sapiens
<220> FEATURE:
<223> OTHER INFORMATION: ELP4 Elongator complex protein 4;
      Q96EB1_C218
<220> FEATURE:
<221> NAME/KEY: MOD_RES
<222> LOCATION: (5)..(5)
<223> OTHER INFORMATION: Site of chemical conjugation

<400> SEQUENCE: 466

Lys Val Glu Pro Cys Ser Leu Thr Pro Gly Tyr Thr Lys Leu
1               5                   10

<210> SEQ ID NO 467
<211> LENGTH: 12
<212> TYPE: PRT
<213> ORGANISM: Homo sapiens
<220> FEATURE:
<223> OTHER INFORMATION: PLOD3 Procollagen-lysine,2-oxoglutarate
      5-dioxygenase 3; O60568_C691
<220> FEATURE:
<221> NAME/KEY: MOD_RES
<222> LOCATION: (10)..(10)
<223> OTHER INFORMATION: Site of chemical conjugation

<400> SEQUENCE: 467

Lys Gly Leu Asp Tyr Glu Gly Gly Gly Cys Arg Phe
1               5                   10

<210> SEQ ID NO 468
<211> LENGTH: 18
<212> TYPE: PRT
<213> ORGANISM: Homo sapiens
<220> FEATURE:
<223> OTHER INFORMATION: NUDT8 Nucleoside diphosphate-linked moiety X
      motif 8, mi; Q8WV74_C207
<220> FEATURE:
<221> NAME/KEY: MOD_RES
<222> LOCATION: (7)..(7)
<223> OTHER INFORMATION: Site of chemical conjugation

<400> SEQUENCE: 468

Arg Leu Ala Gly Leu Thr Cys Ser Gly Ala Glu Gly Leu Ala Arg Pro
1               5                   10                  15

Lys Gln
```

-continued

```
<210> SEQ ID NO 469
<211> LENGTH: 27
<212> TYPE: PRT
<213> ORGANISM: Homo sapiens
<220> FEATURE:
<223> OTHER INFORMATION: HUWE1 E3 ubiquitin-protein ligase HUWE1;
      Q7Z6Z7_C4341
<220> FEATURE:
<221> NAME/KEY: MOD_RES
<222> LOCATION: (12)..(12)
<223> OTHER INFORMATION: Site of chemical conjugation

<400> SEQUENCE: 469

Arg Ser Thr Asp Arg Leu Pro Ser Ala His Thr Cys Phe Asn Gln Leu
1               5                   10                  15

Asp Leu Pro Ala Tyr Glu Ser Phe Glu Lys Leu
            20                  25

<210> SEQ ID NO 470
<211> LENGTH: 14
<212> TYPE: PRT
<213> ORGANISM: Homo sapiens
<220> FEATURE:
<223> OTHER INFORMATION: MGMT Methylated-DNA--protein-cysteine
      methyltransferase; P16455_C145
<220> FEATURE:
<221> NAME/KEY: MOD_RES
<222> LOCATION: (11)..(11)
<223> OTHER INFORMATION: Site of chemical conjugation

<400> SEQUENCE: 470

Arg Gly Asn Pro Val Pro Ile Leu Ile Pro Cys His Arg Val
1               5                   10

<210> SEQ ID NO 471
<211> LENGTH: 12
<212> TYPE: PRT
<213> ORGANISM: Homo sapiens
<220> FEATURE:
<223> OTHER INFORMATION: NIT1 Nitrilase homolog 1;
      Q86X76_C203
<220> FEATURE:
<221> NAME/KEY: MOD_RES
<222> LOCATION: (7)..(7)
<223> OTHER INFORMATION: Site of chemical conjugation

<400> SEQUENCE: 471

Lys Ile Gly Leu Ala Val Cys Tyr Asp Met Arg Phe
1               5                   10

<210> SEQ ID NO 472
<211> LENGTH: 16
<212> TYPE: PRT
<213> ORGANISM: Homo sapiens
<220> FEATURE:
<223> OTHER INFORMATION: ACBD6 Acyl-CoA-binding domain-containing
      protein 6; Q9BR61_C267
<220> FEATURE:
<221> NAME/KEY: MOD_RES
<222> LOCATION: (14)..(14)
<223> OTHER INFORMATION: Site of chemical conjugation

<400> SEQUENCE: 472

Arg Asp Gln Asp Gly Cys Leu Pro Glu Glu Val Thr Gly Cys Lys Thr
1               5                   10                  15

<210> SEQ ID NO 473
<211> LENGTH: 32
<212> TYPE: PRT
<213> ORGANISM: Homo sapiens
```

```
<220> FEATURE:
<223> OTHER INFORMATION: IRF2BP1 Interferon regulatory factor 2-binding
      protein 1; Q8IU81_C363
<220> FEATURE:
<221> NAME/KEY: MOD_RES
<222> LOCATION: (22)..(22)
<223> OTHER INFORMATION: Site of chemical conjugation

<400> SEQUENCE: 473

Arg Glu Pro Ala Pro Ala Glu Ala Leu Pro Gln Gln Tyr Pro Glu Pro
1               5                   10                  15

Ala Pro Ala Ala Leu Cys Gly Pro Pro Pro Arg Ala Pro Ser Arg Asn
                20                  25                  30

<210> SEQ ID NO 474
<211> LENGTH: 27
<212> TYPE: PRT
<213> ORGANISM: Homo sapiens
<220> FEATURE:
<223> OTHER INFORMATION: USP16 Ubiquitin carboxyl-terminal hydrolase 16;
      Q9Y5T5_C205
<220> FEATURE:
<221> NAME/KEY: MOD_RES
<222> LOCATION: (10)..(10)
<223> OTHER INFORMATION: Site of chemical conjugation

<400> SEQUENCE: 474

Lys Gly Leu Ser Asn Leu Gly Asn Thr Cys Phe Phe Asn Ala Val Met
1               5                   10                  15

Gln Asn Leu Ser Gln Thr Pro Val Leu Arg Glu
                20                  25

<210> SEQ ID NO 475
<211> LENGTH: 15
<212> TYPE: PRT
<213> ORGANISM: Homo sapiens
<220> FEATURE:
<223> OTHER INFORMATION: ANKHD1 Ankyrin repeat and KH domain-containing
      protein 1; Q8IWZ3_C615
<220> FEATURE:
<221> NAME/KEY: MOD_RES
<222> LOCATION: (6)..(6)
<223> OTHER INFORMATION: Site of chemical conjugation

<400> SEQUENCE: 475

Arg Ala Gly His Leu Cys Thr Val Gln Phe Leu Ile Ser Lys Gly
1               5                   10                  15

<210> SEQ ID NO 476
<211> LENGTH: 39
<212> TYPE: PRT
<213> ORGANISM: Homo sapiens
<220> FEATURE:
<223> OTHER INFORMATION: FADD Protein FADD;
      Q13158_C105
<220> FEATURE:
<221> NAME/KEY: MOD_RES
<222> LOCATION: (29)..(29)
<223> OTHER INFORMATION: Site of chemical conjugation

<400> SEQUENCE: 476

Arg Arg Val Asp Asp Phe Glu Ala Gly Ala Ala Ala Gly Ala Ala Pro
1               5                   10                  15

Gly Glu Glu Asp Leu Cys Ala Ala Phe Asn Val Ile Cys Asp Asn Val
                20                  25                  30

Gly Lys Asp Trp Arg Arg Leu
        35
```

```
<210> SEQ ID NO 477
<211> LENGTH: 23
<212> TYPE: PRT
<213> ORGANISM: Homo sapiens
<220> FEATURE:
<223> OTHER INFORMATION: PML Protein PML;
      P29590_C213
<220> FEATURE:
<221> NAME/KEY: MOD_RES
<222> LOCATION: (9)..(9)
<223> OTHER INFORMATION: Site of chemical conjugation

<400> SEQUENCE: 477

Arg Gly Cys Ser Lys Pro Leu Cys Cys Ser Cys Ala Leu Leu Asp Ser
1               5                   10                  15

Ser His Ser Glu Leu Lys Cys
            20

<210> SEQ ID NO 478
<211> LENGTH: 20
<212> TYPE: PRT
<213> ORGANISM: Homo sapiens
<220> FEATURE:
<223> OTHER INFORMATION: NFKB2 Nuclear factor NF-kappa-B p100 subunit;
      Q00653_C57
<220> FEATURE:
<221> NAME/KEY: MOD_RES
<222> LOCATION: (4)..(4)
<223> OTHER INFORMATION: Site of chemical conjugation

<400> SEQUENCE: 478

Arg Tyr Gly Cys Glu Gly Pro Ser His Gly Gly Leu Pro Gly Ala Ser
1               5                   10                  15

Ser Glu Lys Gly
            20

<210> SEQ ID NO 479
<211> LENGTH: 34
<212> TYPE: PRT
<213> ORGANISM: Homo sapiens
<220> FEATURE:
<223> OTHER INFORMATION: TUBB2B Tubulin beta-2B chain;
      Q9BVA1_C129
<220> FEATURE:
<221> NAME/KEY: MOD_RES
<222> LOCATION: (8)..(8)
<223> OTHER INFORMATION: Site of chemical conjugation

<400> SEQUENCE: 479

Lys Glu Ser Glu Ser Cys Asp Cys Leu Gln Gly Phe Gln Leu Thr His
1               5                   10                  15

Ser Leu Gly Gly Gly Thr Gly Ser Gly Met Gly Thr Leu Leu Ile Ser
            20                  25                  30

Lys Ile

<210> SEQ ID NO 480
<211> LENGTH: 18
<212> TYPE: PRT
<213> ORGANISM: Homo sapiens
<220> FEATURE:
<223> OTHER INFORMATION: CLIC5 Chloride intracellular channel protein 5;
      Q9NZA1_C191
<220> FEATURE:
<221> NAME/KEY: MOD_RES
<222> LOCATION: (12)..(12)
<223> OTHER INFORMATION: Site of chemical conjugation

<400> SEQUENCE: 480
```

```
Lys Ala Gly Ile Asp Gly Glu Ser Ile Gly Asn Cys Pro Phe Ser Gln
1               5                   10                  15

Arg Leu

<210> SEQ ID NO 481
<211> LENGTH: 15
<212> TYPE: PRT
<213> ORGANISM: Homo sapiens
<220> FEATURE:
<223> OTHER INFORMATION: NMT2 Glycylpeptide N-tetradecanoyltransferase
      2; O60551_C104
<220> FEATURE:
<221> NAME/KEY: MOD_RES
<222> LOCATION: (9)..(9)
<223> OTHER INFORMATION: Site of chemical conjugation

<400> SEQUENCE: 481

Arg Ala Met Glu Leu Leu Ser Ala Cys Gln Gly Pro Ala Arg Asn
1               5                   10                  15

<210> SEQ ID NO 482
<211> LENGTH: 18
<212> TYPE: PRT
<213> ORGANISM: Homo sapiens
<220> FEATURE:
<223> OTHER INFORMATION: CDKN3 Cyclin-dependent kinase inhibitor 3;
      Q16667_C39
<220> FEATURE:
<221> NAME/KEY: MOD_RES
<222> LOCATION: (4)..(4)
<223> OTHER INFORMATION: Site of chemical conjugation

<400> SEQUENCE: 482

Arg Val Asn Cys Ser Gln Phe Leu Gly Leu Cys Ala Leu Pro Gly Cys
1               5                   10                  15

Lys Phe

<210> SEQ ID NO 483
<211> LENGTH: 14
<212> TYPE: PRT
<213> ORGANISM: Homo sapiens
<220> FEATURE:
<223> OTHER INFORMATION: SBNO1 Protein strawberry notch homolog 1;
      A3KN83_C445
<220> FEATURE:
<221> NAME/KEY: MOD_RES
<222> LOCATION: (4)..(4)
<223> OTHER INFORMATION: Site of chemical conjugation

<400> SEQUENCE: 483

Lys Asn Leu Cys Pro Val Gly Ser Ser Lys Pro Thr Lys Thr
1               5                   10

<210> SEQ ID NO 484
<211> LENGTH: 10
<212> TYPE: PRT
<213> ORGANISM: Homo sapiens
<220> FEATURE:
<223> OTHER INFORMATION: C12orf29 Uncharacterized protein C12orf29;
      Q8N999_C302
<220> FEATURE:
<221> NAME/KEY: MOD_RES
<222> LOCATION: (2)..(2)
<223> OTHER INFORMATION: Site of chemical conjugation

<400> SEQUENCE: 484

Lys Cys Leu Phe Asn His Phe Leu Lys Ile
1               5                   10
```

```
<210> SEQ ID NO 485
<211> LENGTH: 11
<212> TYPE: PRT
<213> ORGANISM: Homo sapiens
<220> FEATURE:
<223> OTHER INFORMATION: HSDL2 Hydroxysteroid dehydrogenase-like protein
      2; Q6YN16_C166
<220> FEATURE:
<221> NAME/KEY: MOD_RES
<222> LOCATION: (4)..(4)
<223> OTHER INFORMATION: Site of chemical conjugation

<400> SEQUENCE: 485

Lys Gln His Cys Ala Tyr Thr Ile Ala Lys Tyr
1               5                   10

<210> SEQ ID NO 486
<211> LENGTH: 24
<212> TYPE: PRT
<213> ORGANISM: Homo sapiens
<220> FEATURE:
<223> OTHER INFORMATION: PLEKHA2 Pleckstrin homology domain-containing
      family A mem; Q9HB19_C332
<220> FEATURE:
<221> NAME/KEY: MOD_RES
<222> LOCATION: (22)..(22)
<223> OTHER INFORMATION: Site of chemical conjugation

<400> SEQUENCE: 486

Arg Ser Ile Ser Leu Thr Arg Pro Gly Ser Ser Ser Leu Ser Ser Gly
1               5                   10                  15

Pro Asn Ser Ile Leu Cys Arg Gly
            20

<210> SEQ ID NO 487
<211> LENGTH: 28
<212> TYPE: PRT
<213> ORGANISM: Homo sapiens
<220> FEATURE:
<223> OTHER INFORMATION: HNRPLL Heterogeneous nuclear ribonucleoprotein
      L-like; Q8WVV9_C464
<220> FEATURE:
<221> NAME/KEY: MOD_RES
<222> LOCATION: (19)..(19)
<223> OTHER INFORMATION: Site of chemical conjugation

<400> SEQUENCE: 487

Lys Asn Ile Ile Gln Pro Pro Ser Cys Val Leu His Tyr Tyr Asn Val
1               5                   10                  15

Pro Leu Cys Val Thr Glu Glu Thr Phe Thr Lys Leu
            20                  25

<210> SEQ ID NO 488
<211> LENGTH: 43
<212> TYPE: PRT
<213> ORGANISM: Homo sapiens
<220> FEATURE:
<223> OTHER INFORMATION: CNOT3 CCR4-NOT transcription complex subunit 3;
      O75175_C600
<220> FEATURE:
<221> NAME/KEY: MOD_RES
<222> LOCATION: (33)..(33)
<223> OTHER INFORMATION: Site of chemical conjugation

<400> SEQUENCE: 488

Arg Asp Ile Ile Leu Ser Ser Thr Ser Ala Pro Pro Ala Ser Ala Gln
1               5                   10                  15
```

-continued

Pro Pro Leu Gln Leu Ser Glu Val Asn Ile Pro Leu Ser Leu Gly Val
            20                  25                  30
Cys Pro Leu Gly Pro Val Pro Leu Thr Lys Glu
        35                  40

<210> SEQ ID NO 489
<211> LENGTH: 10
<212> TYPE: PRT
<213> ORGANISM: Homo sapiens
<220> FEATURE:
<223> OTHER INFORMATION: MEPCE 7SK snRNA methylphosphate capping enzyme;
      Q7L2J0_C419
<220> FEATURE:
<221> NAME/KEY: MOD_RES
<222> LOCATION: (8)..(8)
<223> OTHER INFORMATION: Site of chemical conjugation

<400> SEQUENCE: 489

Lys Phe Gln Tyr Gly Asn Tyr Cys Lys Tyr
1               5                   10

<210> SEQ ID NO 490
<211> LENGTH: 26
<212> TYPE: PRT
<213> ORGANISM: Homo sapiens
<220> FEATURE:
<223> OTHER INFORMATION: ARL3 ADP-ribosylation factor-like protein 3;
      P36405_C174
<220> FEATURE:
<221> NAME/KEY: MOD_RES
<222> LOCATION: (24)..(24)
<223> OTHER INFORMATION: Site of chemical conjugation

<400> SEQUENCE: 490

Arg Val Trp Gln Ile Gln Ser Cys Ser Ala Leu Thr Gly Glu Gly Val
1               5                   10                  15
Gln Asp Gly Met Asn Trp Val Cys Lys Asn
            20                  25

<210> SEQ ID NO 491
<211> LENGTH: 18
<212> TYPE: PRT
<213> ORGANISM: Homo sapiens
<220> FEATURE:
<223> OTHER INFORMATION: AMMECR1 AMME syndrome candidate gene 1 protein;
      Q9Y4X0_C175
<220> FEATURE:
<221> NAME/KEY: MOD_RES
<222> LOCATION: (3)..(3)
<223> OTHER INFORMATION: Site of chemical conjugation

<400> SEQUENCE: 491

Arg Gly Cys Ile Gly Thr Phe Ser Ala Met Asn Leu His Ser Gly Leu
1               5                   10                  15
Arg Glu

<210> SEQ ID NO 492
<211> LENGTH: 21
<212> TYPE: PRT
<213> ORGANISM: Homo sapiens
<220> FEATURE:
<223> OTHER INFORMATION: FAM120A Constitutive coactivator of PPAR-gamma-
      like protein; Q9NZB2_C531
<220> FEATURE:
<221> NAME/KEY: MOD_RES
<222> LOCATION: (13)..(13)
<223> OTHER INFORMATION: Site of chemical conjugation

<400> SEQUENCE: 492

```
Lys Gly Ser Gln Met Gly Thr Val Gln Pro Ile Pro Cys Leu Leu Ser
1               5                   10                  15

Met Pro Thr Arg Asn
            20
```

<210> SEQ ID NO 493
<211> LENGTH: 12
<212> TYPE: PRT
<213> ORGANISM: Homo sapiens
<220> FEATURE:
<223> OTHER INFORMATION: DNMT1 DNA (cytosine-5)-methyltransferase 1;
      P26358_C1478
<220> FEATURE:
<221> NAME/KEY: MOD_RES
<222> LOCATION: (6)..(6)
<223> OTHER INFORMATION: Site of chemical conjugation

<400> SEQUENCE: 493

```
Arg Gly Val Cys Ser Cys Val Glu Ala Gly Lys Ala
1               5                   10
```

<210> SEQ ID NO 494
<211> LENGTH: 9
<212> TYPE: PRT
<213> ORGANISM: Homo sapiens
<220> FEATURE:
<223> OTHER INFORMATION: CXorf38 Uncharacterized protein CXorf38;
      Q8TB03_C12
<220> FEATURE:
<221> NAME/KEY: MOD_RES
<222> LOCATION: (4)..(4)
<223> OTHER INFORMATION: Site of chemical conjugation

<400> SEQUENCE: 494

```
Arg Leu Asn Cys Ala Glu Tyr Lys Asn
1               5
```

<210> SEQ ID NO 495
<211> LENGTH: 26
<212> TYPE: PRT
<213> ORGANISM: Homo sapiens
<220> FEATURE:
<223> OTHER INFORMATION: MRPS18B 28S ribosomal protein S18b,
      mitochondrial; Q9Y676_C128
<220> FEATURE:
<221> NAME/KEY: MOD_RES
<222> LOCATION: (8)..(8)
<223> OTHER INFORMATION: Site of chemical conjugation

<400> SEQUENCE: 495

```
Lys Leu Leu Glu Gln Phe Val Cys Ala His Thr Gly Ile Ile Phe Tyr
1               5                   10                  15

Ala Pro Tyr Thr Gly Val Cys Val Lys Gln
            20                  25
```

<210> SEQ ID NO 496
<211> LENGTH: 14
<212> TYPE: PRT
<213> ORGANISM: Homo sapiens
<220> FEATURE:
<223> OTHER INFORMATION: FHOD1 FH1/FH2 domain-containing protein 1;
      Q9Y613_C502
<220> FEATURE:
<221> NAME/KEY: MOD_RES
<222> LOCATION: (9)..(9)
<223> OTHER INFORMATION: Site of chemical conjugation

<400> SEQUENCE: 496

Arg Thr Pro Gln Ser Pro Ala Pro Cys Val Leu Leu Arg Ala
1               5                   10

<210> SEQ ID NO 497
<211> LENGTH: 35
<212> TYPE: PRT
<213> ORGANISM: Homo sapiens
<220> FEATURE:
<223> OTHER INFORMATION: VRK1 Serine/threonine-protein kinase VRK1;
      Q99986_C50
<220> FEATURE:
<221> NAME/KEY: MOD_RES
<222> LOCATION: (13)..(13)
<223> OTHER INFORMATION: Site of chemical conjugation

<400> SEQUENCE: 497

Lys Val Gly Leu Pro Ile Gly Gln Gly Gly Phe Gly Cys Ile Tyr Leu
1               5                   10                  15

Ala Asp Met Asn Ser Ser Glu Ser Val Gly Ser Asp Ala Pro Cys Val
            20                  25                  30

Val Lys Val
        35

<210> SEQ ID NO 498
<211> LENGTH: 44
<212> TYPE: PRT
<213> ORGANISM: Homo sapiens
<220> FEATURE:
<223> OTHER INFORMATION: SEC24C Protein transport protein Sec24C;
      P53992_C78
<220> FEATURE:
<221> NAME/KEY: MOD_RES
<222> LOCATION: (18)..(18)
<223> OTHER INFORMATION: Site of chemical conjugation

<400> SEQUENCE: 498

Arg Ala Pro Pro Ser Ser Gly Ala Pro Pro Ala Ser Thr Ala Gln Ala
1               5                   10                  15

Pro Cys Gly Gln Ala Ala Tyr Gly Gln Phe Gly Gln Gly Asp Val Gln
            20                  25                  30

Asn Gly Pro Ser Ser Thr Val Gln Met Gln Arg Leu
        35                  40

<210> SEQ ID NO 499
<211> LENGTH: 24
<212> TYPE: PRT
<213> ORGANISM: Homo sapiens
<220> FEATURE:
<223> OTHER INFORMATION: MED15 Mediator of RNA polymerase II
      transcription subuni; Q96RN5_C660
<220> FEATURE:
<221> NAME/KEY: MOD_RES
<222> LOCATION: (21)..(21)
<223> OTHER INFORMATION: Site of chemical conjugation

<400> SEQUENCE: 499

Arg Thr Phe Val Pro Ala Met Thr Ala Ile His Gly Pro Pro Ile Thr
1               5                   10                  15

Ala Pro Val Val Cys Thr Arg Lys
            20

<210> SEQ ID NO 500
<211> LENGTH: 20
<212> TYPE: PRT
<213> ORGANISM: Homo sapiens
<220> FEATURE:
<223> OTHER INFORMATION: INF2 Inverted formin-2  L;

```
              Q27J81_C332
<220> FEATURE:
<221> NAME/KEY: MOD_RES
<222> LOCATION: (12)..(12)
<223> OTHER INFORMATION: Site of chemical conjugation

<400> SEQUENCE: 500

Arg Ala Val Leu Leu Ala Ser Asp Ala Gln Glu Cys Thr Leu Glu Glu
1               5                   10                  15

Val Val Glu Arg
            20

<210> SEQ ID NO 501
<211> LENGTH: 17
<212> TYPE: PRT
<213> ORGANISM: Homo sapiens
<220> FEATURE:
<223> OTHER INFORMATION: INF2 Inverted formin-2;
      Q27J81_C971
<220> FEATURE:
<221> NAME/KEY: MOD_RES
<222> LOCATION: (6)..(6)
<223> OTHER INFORMATION: Site of chemical conjugation

<400> SEQUENCE: 501

Lys Gln Glu Glu Val Cys Val Ile Asp Ala Leu Leu Ala Asp Ile Arg
1               5                   10                  15

Lys

<210> SEQ ID NO 502
<211> LENGTH: 15
<212> TYPE: PRT
<213> ORGANISM: Homo sapiens
<220> FEATURE:
<223> OTHER INFORMATION: ATXN10 Ataxin-10;
      Q9UBB4_C356
<220> FEATURE:
<221> NAME/KEY: MOD_RES
<222> LOCATION: (12)..(12)
<223> OTHER INFORMATION: Site of chemical conjugation

<400> SEQUENCE: 502

Lys Glu Thr Thr Asn Ile Phe Ser Asn Cys Gly Cys Val Arg Ala
1               5                   10                  15

<210> SEQ ID NO 503
<211> LENGTH: 42
<212> TYPE: PRT
<213> ORGANISM: Homo sapiens
<220> FEATURE:
<223> OTHER INFORMATION: GOLGA3 Golgin subfamily A member 3;
      Q08378_C1403
<220> FEATURE:
<221> NAME/KEY: MOD_RES
<222> LOCATION: (18)..(18)
<223> OTHER INFORMATION: Site of chemical conjugation

<400> SEQUENCE: 503

Lys Gly Glu Ala Ser Ser Ser Asn Pro Ala Thr Pro Ile Lys Ile Pro
1               5                   10                  15

Asp Cys Pro Val Pro Ala Ser Leu Leu Glu Glu Leu Leu Arg Pro Pro
            20                  25                  30

Pro Ala Val Ser Lys Glu Pro Leu Lys Asn
            35                  40

<210> SEQ ID NO 504
<211> LENGTH: 14
```

```
<212> TYPE: PRT
<213> ORGANISM: Homo sapiens
<220> FEATURE:
<223> OTHER INFORMATION: LMO7 LIM domain only protein 7;
      Q8WWI1_C228
<220> FEATURE:
<221> NAME/KEY: MOD_RES
<222> LOCATION: (10)..(10)
<223> OTHER INFORMATION: Site of chemical conjugation

<400> SEQUENCE: 504

Arg Asp Ser Gly Tyr Gly Asp Ile Trp Cys Pro Glu Arg Gly
1               5                   10

<210> SEQ ID NO 505
<211> LENGTH: 17
<212> TYPE: PRT
<213> ORGANISM: Homo sapiens
<220> FEATURE:
<223> OTHER INFORMATION: ARAF Serine/threonine-protein kinase A-Raf;
      P10398_C597
<220> FEATURE:
<221> NAME/KEY: MOD_RES
<222> LOCATION: (10)..(10)
<223> OTHER INFORMATION: Site of chemical conjugation

<400> SEQUENCE: 505

Arg Thr Gln Ala Asp Glu Leu Pro Ala Cys Leu Leu Ser Ala Ala Arg
1               5                   10                  15

Leu

<210> SEQ ID NO 506
<211> LENGTH: 22
<212> TYPE: PRT
<213> ORGANISM: Homo sapiens
<220> FEATURE:
<223> OTHER INFORMATION: ACTR10 Actin-related protein 10;
      Q9NZ32_C388
<220> FEATURE:
<221> NAME/KEY: MOD_RES
<222> LOCATION: (6)..(6)
<223> OTHER INFORMATION: Site of chemical conjugation

<400> SEQUENCE: 506

Arg Ile Pro Asp Trp Cys Ser Leu Asn Asn Pro Pro Leu Glu Met Met
1               5                   10                  15

Phe Asp Val Gly Lys Thr
            20

<210> SEQ ID NO 507
<211> LENGTH: 18
<212> TYPE: PRT
<213> ORGANISM: Homo sapiens
<220> FEATURE:
<223> OTHER INFORMATION: NOP58 Nucleolar protein 58;
      Q9Y2X3_C106
<220> FEATURE:
<221> NAME/KEY: MOD_RES
<222> LOCATION: (6)..(6)
<223> OTHER INFORMATION: Site of chemical conjugation

<400> SEQUENCE: 507

Lys Leu Asn Leu Ser Cys Ile His Ser Pro Val Val Asn Glu Leu Met
1               5                   10                  15

Arg Gly

<210> SEQ ID NO 508
<211> LENGTH: 42
```

```
<212> TYPE: PRT
<213> ORGANISM: Homo sapiens
<220> FEATURE:
<223> OTHER INFORMATION: ACLY ATP-citrate synthase;
      P53396_C764
<220> FEATURE:
<221> NAME/KEY: MOD_RES
<222> LOCATION: (30)..(30)
<223> OTHER INFORMATION: Site of chemical conjugation

<400> SEQUENCE: 508

Arg Leu Thr Lys Pro Ile Val Cys Trp Cys Ile Gly Thr Cys Ala Thr
1               5                   10                  15

Met Phe Ser Ser Glu Val Gln Phe Gly His Ala Gly Ala Cys Ala Asn
            20                  25                  30

Gln Ala Ser Glu Thr Ala Val Ala Lys Asn
        35                  40

<210> SEQ ID NO 509
<211> LENGTH: 20
<212> TYPE: PRT
<213> ORGANISM: Homo sapiens
<220> FEATURE:
<223> OTHER INFORMATION: RPL7 60S ribosomal protein L7;
      P18124_C186
<220> FEATURE:
<221> NAME/KEY: MOD_RES
<222> LOCATION: (6)..(6)
<223> OTHER INFORMATION: Site of chemical conjugation

<400> SEQUENCE: 509

Lys Tyr Gly Ile Ile Cys Met Glu Asp Leu Ile His Glu Ile Tyr Thr
1               5                   10                  15

Val Gly Lys Arg
            20

<210> SEQ ID NO 510
<211> LENGTH: 26
<212> TYPE: PRT
<213> ORGANISM: Homo sapiens
<220> FEATURE:
<223> OTHER INFORMATION: MSTO1 Protein misato homolog 1;
      Q9BUK6_C485
<220> FEATURE:
<221> NAME/KEY: MOD_RES
<222> LOCATION: (13)..(13)
<223> OTHER INFORMATION: Site of chemical conjugation

<400> SEQUENCE: 510

Arg Val Ala Pro Pro Tyr Pro His Leu Phe Ser Ser Cys Ser Pro Pro
1               5                   10                  15

Gly Met Val Leu Asp Gly Ser Pro Lys Gly
            20                  25

<210> SEQ ID NO 511
<211> LENGTH: 18
<212> TYPE: PRT
<213> ORGANISM: Homo sapiens
<220> FEATURE:
<223> OTHER INFORMATION: PES1 Pescadillo homolog;
      O00541_C272
<220> FEATURE:
<221> NAME/KEY: MOD_RES
<222> LOCATION: (14)..(14)
<223> OTHER INFORMATION: Site of chemical conjugation

<400> SEQUENCE: 511

Lys Ala Gly Glu Gly Thr Tyr Ala Leu Asp Ser Glu Ser Cys Met Glu
```

Lys Leu

<210> SEQ ID NO 512
<211> LENGTH: 13
<212> TYPE: PRT
<213> ORGANISM: Homo sapiens
<220> FEATURE:
<223> OTHER INFORMATION: VDAC3 Voltage-dependent anion-selective channel
    protein; Q9Y277_C65
<220> FEATURE:
<221> NAME/KEY: MOD_RES
<222> LOCATION: (3)..(3)
<223> OTHER INFORMATION: Site of chemical conjugation

<400> SEQUENCE: 512

Lys Val Cys Asn Tyr Gly Leu Thr Phe Thr Gln Lys Trp
1               5                   10

<210> SEQ ID NO 513
<211> LENGTH: 13
<212> TYPE: PRT
<213> ORGANISM: Homo sapiens
<220> FEATURE:
<223> OTHER INFORMATION: IRF8 Interferon regulatory factor 8;
    Q02556_C306
<220> FEATURE:
<221> NAME/KEY: MOD_RES
<222> LOCATION: (11)..(11)
<223> OTHER INFORMATION: Site of chemical conjugation

<400> SEQUENCE: 513

Arg Val Phe Cys Ser Gly Asn Ala Val Val Cys Lys Gly
1               5                   10

<210> SEQ ID NO 514
<211> LENGTH: 11
<212> TYPE: PRT
<213> ORGANISM: Homo sapiens
<220> FEATURE:
<223> OTHER INFORMATION: SPTBN1 Spectrin beta chain, non-erythrocytic 1;
    Q01082_C112
<220> FEATURE:
<221> NAME/KEY: MOD_RES
<222> LOCATION: (4)..(4)
<223> OTHER INFORMATION: Site of chemical conjugation

<400> SEQUENCE: 514

Arg Ile His Cys Leu Glu Asn Val Asp Lys Ala
1               5                   10

<210> SEQ ID NO 515
<211> LENGTH: 26
<212> TYPE: PRT
<213> ORGANISM: Homo sapiens
<220> FEATURE:
<223> OTHER INFORMATION: ZC3H12D Probable ribonuclease ZC3H12D;
    A2A288_C367
<220> FEATURE:
<221> NAME/KEY: MOD_RES
<222> LOCATION: (20)..(20)
<223> OTHER INFORMATION: Site of chemical conjugation

<400> SEQUENCE: 515

Arg Leu Ala Phe Ser Asp Asp Leu Gly Pro Leu Gly Pro Pro Leu Pro
1               5                   10                  15

Val Pro Ala Cys Ser Leu Thr Pro Arg Leu
            20                  25

-continued

```
<210> SEQ ID NO 516
<211> LENGTH: 23
<212> TYPE: PRT
<213> ORGANISM: Homo sapiens
<220> FEATURE:
<223> OTHER INFORMATION: CASK Peripheral plasma membrane protein CASK;
      O14936_C914
<220> FEATURE:
<221> NAME/KEY: MOD_RES
<222> LOCATION: (11)..(11)
<223> OTHER INFORMATION: Site of chemical conjugation

<400> SEQUENCE: 516

Arg His Leu Glu Glu Ala Val Glu Leu Val Cys Thr Ala Pro Gln Trp
1               5                   10                  15

Val Pro Val Ser Trp Val Tyr
            20

<210> SEQ ID NO 517
<211> LENGTH: 14
<212> TYPE: PRT
<213> ORGANISM: Homo sapiens
<220> FEATURE:
<223> OTHER INFORMATION: SART1 U4/U6.U5 tri-snRNP-associated protein 1;
      O43290_C645
<220> FEATURE:
<221> NAME/KEY: MOD_RES
<222> LOCATION: (10)..(10)
<223> OTHER INFORMATION: Site of chemical conjugation

<400> SEQUENCE: 517

Arg Gly Leu Ala Ala Ala Leu Leu Leu Cys Gln Asn Lys Gly
1               5                   10

<210> SEQ ID NO 518
<211> LENGTH: 27
<212> TYPE: PRT
<213> ORGANISM: Homo sapiens
<220> FEATURE:
<223> OTHER INFORMATION: PEF1 Peflin;
      Q9UBV8_C146
<220> FEATURE:
<221> NAME/KEY: MOD_RES
<222> LOCATION: (7)..(7)
<223> OTHER INFORMATION: Site of chemical conjugation

<400> SEQUENCE: 518

Lys Gln Ala Leu Val Asn Cys Asn Trp Ser Ser Phe Asn Asp Glu Thr
1               5                   10                  15

Cys Leu Met Met Ile Asn Met Phe Asp Lys Thr
            20                  25

<210> SEQ ID NO 519
<211> LENGTH: 21
<212> TYPE: PRT
<213> ORGANISM: Homo sapiens
<220> FEATURE:
<223> OTHER INFORMATION: RSBN1L Round spermatid basic protein 1-like
      protein; Q6PCB5_C280
<220> FEATURE:
<221> NAME/KEY: MOD_RES
<222> LOCATION: (7)..(7)
<223> OTHER INFORMATION: Site of chemical conjugation

<400> SEQUENCE: 519

Lys Ser Ile Gln Thr Ile Cys Ser Gly Leu Leu Thr Asp Val Glu Asp
1               5                   10                  15

Gln Ala Ala Lys Gly
            20
```

-continued

```
<210> SEQ ID NO 520
<211> LENGTH: 18
<212> TYPE: PRT
<213> ORGANISM: Homo sapiens
<220> FEATURE:
<223> OTHER INFORMATION: LGALS3BP Galectin-3-binding protein;
      Q08380_C561
<220> FEATURE:
<221> NAME/KEY: MOD_RES
<222> LOCATION: (8)..(8)
<223> OTHER INFORMATION: Site of chemical conjugation

<400> SEQUENCE: 520

Lys Ser Thr Ser Ser Phe Pro Cys Pro Ala Gly His Phe Asn Gly Phe
1               5                   10                  15

Arg Thr

<210> SEQ ID NO 521
<211> LENGTH: 10
<212> TYPE: PRT
<213> ORGANISM: Homo sapiens
<220> FEATURE:
<223> OTHER INFORMATION: CORO7 Coronin-7;
      P57737_C34
<220> FEATURE:
<221> NAME/KEY: MOD_RES
<222> LOCATION: (8)..(8)
<223> OTHER INFORMATION: Site of chemical conjugation

<400> SEQUENCE: 521

Arg Ala Gly Thr Ala Pro Ser Cys Arg Asn
1               5                   10

<210> SEQ ID NO 522
<211> LENGTH: 11
<212> TYPE: PRT
<213> ORGANISM: Homo sapiens
<220> FEATURE:
<223> OTHER INFORMATION: GCN1L1 Translational activator GCN1;
      Q92616_C1235
<220> FEATURE:
<221> NAME/KEY: MOD_RES
<222> LOCATION: (2)..(2)
<223> OTHER INFORMATION: Site of chemical conjugation

<400> SEQUENCE: 522

Arg Cys Gly Leu Ala Leu Ala Leu Asn Lys Leu
1               5                   10

<210> SEQ ID NO 523
<211> LENGTH: 11
<212> TYPE: PRT
<213> ORGANISM: Homo sapiens
<220> FEATURE:
<223> OTHER INFORMATION: NR2F2 COUP transcription factor 2;
      P24468_C326
<220> FEATURE:
<221> NAME/KEY: MOD_RES
<222> LOCATION: (2)..(2)
<223> OTHER INFORMATION: Site of chemical conjugation

<400> SEQUENCE: 523

Arg Cys Gly Leu Ala Leu Ala Leu Asn Lys Leu
1               5                   10

<210> SEQ ID NO 524
<211> LENGTH: 26
```

```
<212> TYPE: PRT
<213> ORGANISM: Homo sapiens
<220> FEATURE:
<223> OTHER INFORMATION: GFM1 Elongation factor G, mitochondrial;
      Q96RP9_C153
<220> FEATURE:
<221> NAME/KEY: MOD_RES
<222> LOCATION: (18)..(18)
<223> OTHER INFORMATION: Site of chemical conjugation

<400> SEQUENCE: 524

Arg Val Leu Asp Gly Ala Val Leu Val Leu Cys Ala Val Gly Gly Val
1               5                   10                  15

Gln Cys Gln Thr Met Thr Val Asn Arg Gln
            20                  25

<210> SEQ ID NO 525
<211> LENGTH: 21
<212> TYPE: PRT
<213> ORGANISM: Homo sapiens
<220> FEATURE:
<223> OTHER INFORMATION: POLE3 DNA polymerase epsilon subunit 3;
      Q9NRF9_C51
<220> FEATURE:
<221> NAME/KEY: MOD_RES
<222> LOCATION: (13)..(13)
<223> OTHER INFORMATION: Site of chemical conjugation

<400> SEQUENCE: 525

Arg Ala Ala Ser Val Phe Val Leu Tyr Ala Thr Ser Cys Ala Asn Asn
1               5                   10                  15

Phe Ala Met Lys Gly
            20

<210> SEQ ID NO 526
<211> LENGTH: 25
<212> TYPE: PRT
<213> ORGANISM: Homo sapiens
<220> FEATURE:
<223> OTHER INFORMATION: ALDH1B1 Aldehyde dehydrogenase X,
      mitochondrial; P30837_C179
<220> FEATURE:
<221> NAME/KEY: MOD_RES
<222> LOCATION: (8)..(8)
<223> OTHER INFORMATION: Site of chemical conjugation

<400> SEQUENCE: 526

Arg His Glu Pro Val Gly Val Cys Gly Gln Ile Ile Pro Trp Asn Phe
1               5                   10                  15

Pro Leu Val Met Gln Gly Trp Lys Leu
            20                  25

<210> SEQ ID NO 527
<211> LENGTH: 17
<212> TYPE: PRT
<213> ORGANISM: Homo sapiens
<220> FEATURE:
<223> OTHER INFORMATION: PDCD6IP Programmed cell death 6-interacting
      protein; Q8WUM4_C90
<220> FEATURE:
<221> NAME/KEY: MOD_RES
<222> LOCATION: (10)..(10)
<223> OTHER INFORMATION: Site of chemical conjugation

<400> SEQUENCE: 527

Lys Phe Pro Phe Ser Glu Asn Gln Ile Cys Leu Thr Phe Thr Trp Lys
1               5                   10                  15

Asp
```

```
<210> SEQ ID NO 528
<211> LENGTH: 21
<212> TYPE: PRT
<213> ORGANISM: Homo sapiens
<220> FEATURE:
<223> OTHER INFORMATION: ALG13 UDP-N-acetylglucosamine transferase
      subunit ALG13; Q9NP73_C86
<220> FEATURE:
<221> NAME/KEY: MOD_RES
<222> LOCATION: (14)..(14)
<223> OTHER INFORMATION: Site of chemical conjugation

<400> SEQUENCE: 528

Lys Ala Asp Leu Val Ile Ser His Ala Gly Ala Gly Ser Cys Leu Glu
1               5                   10                  15

Thr Leu Glu Lys Gly
            20

<210> SEQ ID NO 529
<211> LENGTH: 38
<212> TYPE: PRT
<213> ORGANISM: Homo sapiens
<220> FEATURE:
<223> OTHER INFORMATION: PDIA4 Protein disulfide-isomerase A4;
      P13667_C91
<220> FEATURE:
<221> NAME/KEY: MOD_RES
<222> LOCATION: (33)..(33)
<223> OTHER INFORMATION: Site of chemical conjugation

<400> SEQUENCE: 529

Lys Glu Glu Asn Gly Val Leu Val Leu Asn Asp Ala Asn Phe Asp Asn
1               5                   10                  15

Phe Val Ala Asp Lys Asp Thr Val Leu Leu Glu Phe Tyr Ala Pro Trp
            20                  25                  30

Cys Gly His Cys Lys Gln
        35

<210> SEQ ID NO 530
<211> LENGTH: 13
<212> TYPE: PRT
<213> ORGANISM: Homo sapiens
<220> FEATURE:
<223> OTHER INFORMATION: POLA1 DNA polymerase alpha catalytic subunit;
      P09884_C1403
<220> FEATURE:
<221> NAME/KEY: MOD_RES
<222> LOCATION: (8)..(8)
<223> OTHER INFORMATION: Site of chemical conjugation

<400> SEQUENCE: 530

Arg Tyr Ile Phe Asp Ala Glu Cys Ala Leu Glu Lys Leu
1               5                   10

<210> SEQ ID NO 531
<211> LENGTH: 18
<212> TYPE: PRT
<213> ORGANISM: Homo sapiens
<220> FEATURE:
<223> OTHER INFORMATION: CLIC3 Chloride intracellular channel protein 3;
      O95833_C22
<220> FEATURE:
<221> NAME/KEY: MOD_RES
<222> LOCATION: (12)..(12)
<223> OTHER INFORMATION: Site of chemical conjugation

<400> SEQUENCE: 531
```

```
Lys Ala Ser Glu Asp Gly Glu Ser Val Gly His Cys Pro Ser Cys Gln
1               5                   10                  15

Arg Leu

<210> SEQ ID NO 532
<211> LENGTH: 23
<212> TYPE: PRT
<213> ORGANISM: Homo sapiens
<220> FEATURE:
<223> OTHER INFORMATION: ECHDC1 Ethylmalonyl-CoA decarboxylase;
      Q9NTX5_C133
<220> FEATURE:
<221> NAME/KEY: MOD_RES
<222> LOCATION: (13)..(13)
<223> OTHER INFORMATION: Site of chemical conjugation

<400> SEQUENCE: 532

Lys Ser Leu Gly Thr Pro Glu Asp Gly Met Ala Val Cys Met Phe Met
1               5                   10                  15

Gln Asn Thr Leu Thr Arg Phe
            20

<210> SEQ ID NO 533
<211> LENGTH: 18
<212> TYPE: PRT
<213> ORGANISM: Homo sapiens
<220> FEATURE:
<223> OTHER INFORMATION: PTK2B Protein-tyrosine kinase 2-beta;
      Q14289_C899
<220> FEATURE:
<221> NAME/KEY: MOD_RES
<222> LOCATION: (5)..(5)
<223> OTHER INFORMATION: Site of chemical conjugation

<400> SEQUENCE: 533

Lys Asn Glu Leu Cys Gln Leu Pro Pro Glu Gly Tyr Val Val Val Val
1               5                   10                  15

Lys Asn

<210> SEQ ID NO 534
<211> LENGTH: 13
<212> TYPE: PRT
<213> ORGANISM: Homo sapiens
<220> FEATURE:
<223> OTHER INFORMATION: RANBP2 E3 SUMO-protein ligase RanBP2;
      P49792_C815
<220> FEATURE:
<221> NAME/KEY: MOD_RES
<222> LOCATION: (4)..(4)
<223> OTHER INFORMATION: Site of chemical conjugation

<400> SEQUENCE: 534

Lys Met Ile Cys Gln Gln Val Glu Ala Ile Lys Lys Glu
1               5                   10

<210> SEQ ID NO 535
<211> LENGTH: 16
<212> TYPE: PRT
<213> ORGANISM: Homo sapiens
<220> FEATURE:
<223> OTHER INFORMATION: BOP1 Ribosome biogenesis protein BOP1;
      Q14137_C404
<220> FEATURE:
<221> NAME/KEY: MOD_RES
<222> LOCATION: (9)..(9)
<223> OTHER INFORMATION: Site of chemical conjugation

<400> SEQUENCE: 535
```

Arg Asp Leu Gln Pro Phe Pro Thr Cys Gln Ala Leu Val Tyr Arg Gly
1               5                   10                  15

<210> SEQ ID NO 536
<211> LENGTH: 11
<212> TYPE: PRT
<213> ORGANISM: Homo sapiens
<220> FEATURE:
<223> OTHER INFORMATION: LRRC41 Leucine-rich repeat-containing protein
      41; Q15345_C297
<220> FEATURE:
<221> NAME/KEY: MOD_RES
<222> LOCATION: (2)..(2)
<223> OTHER INFORMATION: Site of chemical conjugation

<400> SEQUENCE: 536

Arg Cys Ala Ala Ala Leu Met Ala Ser Arg Arg
1               5                   10

<210> SEQ ID NO 537
<211> LENGTH: 13
<212> TYPE: PRT
<213> ORGANISM: Homo sapiens
<220> FEATURE:
<223> OTHER INFORMATION: LGMN Legumain;
      Q99538_C219
<220> FEATURE:
<221> NAME/KEY: MOD_RES
<222> LOCATION: (7)..(7)
<223> OTHER INFORMATION: Site of chemical conjugation

<400> SEQUENCE: 537

Arg Glu Ser Ser Tyr Ala Cys Tyr Tyr Asp Glu Lys Arg
1               5                   10

<210> SEQ ID NO 538
<211> LENGTH: 19
<212> TYPE: PRT
<213> ORGANISM: Homo sapiens
<220> FEATURE:
<223> OTHER INFORMATION: THAP11 THAP domain-containing protein 11;
      Q96EK4_C48
<220> FEATURE:
<221> NAME/KEY: MOD_RES
<222> LOCATION: (7)..(7)
<223> OTHER INFORMATION: Site of chemical conjugation

<400> SEQUENCE: 538

Arg Ala Gly Val Ser Gly Cys Phe Ser Thr Phe Gln Pro Thr Thr Gly
1               5                   10                  15

His Arg Leu

<210> SEQ ID NO 539
<211> LENGTH: 15
<212> TYPE: PRT
<213> ORGANISM: Homo sapiens
<220> FEATURE:
<223> OTHER INFORMATION: ACSL4 Long-chain-fatty-acid--CoA ligase 4;
      O60488_C420
<220> FEATURE:
<221> NAME/KEY: MOD_RES
<222> LOCATION: (8)..(8)
<223> OTHER INFORMATION: Site of chemical conjugation

<400> SEQUENCE: 539

Lys Gly Tyr Asp Ala Pro Leu Cys Asn Leu Leu Phe Lys Lys
1               5                   10                  15

<210> SEQ ID NO 540

<211> LENGTH: 18
<212> TYPE: PRT
<213> ORGANISM: Homo sapiens
<220> FEATURE:
<223> OTHER INFORMATION: FAM125A Multivesicular body subunit 12A;
    Q96EY5_C231
<220> FEATURE:
<221> NAME/KEY: MOD_RES
<222> LOCATION: (3)..(3)
<223> OTHER INFORMATION: Site of chemical conjugation

<400> SEQUENCE: 540

Lys Ser Cys Ser Pro Leu Ala Phe Ser Ala Phe Gly Asp Leu Thr Ile
1               5                   10                  15

Lys Ser

<210> SEQ ID NO 541
<211> LENGTH: 44
<212> TYPE: PRT
<213> ORGANISM: Homo sapiens
<220> FEATURE:
<223> OTHER INFORMATION: SCP2 Non-specific lipid-transfer protein;
    P22307_C307
<220> FEATURE:
<221> NAME/KEY: MOD_RES
<222> LOCATION: (17)..(17)
<223> OTHER INFORMATION: Site of chemical conjugation

<400> SEQUENCE: 541

Lys Ser Gly Leu Thr Pro Asn Asp Ile Asp Val Ile Glu Leu His Asp
1               5                   10                  15

Cys Phe Ser Thr Asn Glu Leu Leu Thr Tyr Glu Ala Leu Gly Leu Cys
            20                  25                  30

Pro Glu Gly Gln Gly Ala Thr Leu Val Asp Arg Gly
        35                  40

<210> SEQ ID NO 542
<211> LENGTH: 24
<212> TYPE: PRT
<213> ORGANISM: Homo sapiens
<220> FEATURE:
<223> OTHER INFORMATION: TBRG4 Protein TBRG4;
    Q969Z0_C335
<220> FEATURE:
<221> NAME/KEY: MOD_RES
<222> LOCATION: (21)..(21)
<223> OTHER INFORMATION: Site of chemical conjugation

<400> SEQUENCE: 542

Arg Leu Ala Thr Asp Leu Leu Ser Leu Met Pro Ser Leu Thr Ser Gly
1               5                   10                  15

Glu Val Ala His Cys Ala Lys Ser
            20

<210> SEQ ID NO 543
<211> LENGTH: 18
<212> TYPE: PRT
<213> ORGANISM: Homo sapiens
<220> FEATURE:
<223> OTHER INFORMATION: MAP2K3 Dual specificity mitogen-activated
    protein kinase; P46734_C29
<220> FEATURE:
<221> NAME/KEY: MOD_RES
<222> LOCATION: (4)..(4)
<223> OTHER INFORMATION: Site of chemical conjugation

<400> SEQUENCE: 543

Arg Ile Ser Cys Met Ser Lys Pro Pro Ala Pro Asn Pro Thr Pro Pro

Arg Asn

<210> SEQ ID NO 544
<211> LENGTH: 24
<212> TYPE: PRT
<213> ORGANISM: Homo sapiens
<220> FEATURE:
<223> OTHER INFORMATION: C3orf38 Uncharacterized protein C3orf38;
      Q5JPI3_C308
<220> FEATURE:
<221> NAME/KEY: MOD_RES
<222> LOCATION: (17)..(17)
<223> OTHER INFORMATION: Site of chemical conjugation

<400> SEQUENCE: 544

Lys Phe Glu Gln Ser Asp Leu Glu Ala Phe Tyr Asn Val Ile Thr Val
1               5                   10                  15

Cys Gly Thr Asn Glu Val Arg His
            20

<210> SEQ ID NO 545
<211> LENGTH: 45
<212> TYPE: PRT
<213> ORGANISM: Homo sapiens
<220> FEATURE:
<223> OTHER INFORMATION: EIF4ENIF1 Eukaryotic translation initiation
      factor 4E transp; Q9NRA8_C318
<220> FEATURE:
<221> NAME/KEY: MOD_RES
<222> LOCATION: (26)..(26)
<223> OTHER INFORMATION: Site of chemical conjugation

<400> SEQUENCE: 545

Arg Asp Ala Val Leu Pro Glu Gln Ser Pro Gly Asp Phe Asp Phe Asn
1               5                   10                  15

Glu Phe Phe Asn Leu Asp Lys Val Pro Cys Leu Ala Ser Met Ile Glu
            20                  25                  30

Asp Val Leu Gly Glu Gly Ser Val Ser Ala Ser Arg Phe
        35                  40                  45

<210> SEQ ID NO 546
<211> LENGTH: 21
<212> TYPE: PRT
<213> ORGANISM: Homo sapiens
<220> FEATURE:
<223> OTHER INFORMATION: MED1 Mediator of RNA polymerase II
      transcription subuni; Q15648_C135
<220> FEATURE:
<221> NAME/KEY: MOD_RES
<222> LOCATION: (12)..(12)
<223> OTHER INFORMATION: Site of chemical conjugation

<400> SEQUENCE: 546

Lys Val Ala His His Gly Glu Asn Pro Val Ser Cys Pro Glu Leu Val
1               5                   10                  15

Gln Gln Leu Arg Glu
            20

<210> SEQ ID NO 547
<211> LENGTH: 17
<212> TYPE: PRT
<213> ORGANISM: Homo sapiens
<220> FEATURE:
<223> OTHER INFORMATION: TRMT2A tRNA (uracil-5-)-methyltransferase
      homolog A; Q8IZ69_C463
<220> FEATURE:

-continued

```
<221> NAME/KEY: MOD_RES
<222> LOCATION: (8)..(8)
<223> OTHER INFORMATION: Site of chemical conjugation

<400> SEQUENCE: 547

Arg Val Ile Gly Val Glu Leu Cys Pro Glu Ala Val Glu Asp Ala Arg
1               5                   10                  15

Val

<210> SEQ ID NO 548
<211> LENGTH: 8
<212> TYPE: PRT
<213> ORGANISM: Homo sapiens
<220> FEATURE:
<223> OTHER INFORMATION: RELA Transcription factor p65;
      Q04206_C38
<220> FEATURE:
<221> NAME/KEY: MOD_RES
<222> LOCATION: (4)..(4)
<223> OTHER INFORMATION: Site of chemical conjugation

<400> SEQUENCE: 548

Arg Tyr Lys Cys Glu Gly Arg Ser
1               5

<210> SEQ ID NO 549
<211> LENGTH: 15
<212> TYPE: PRT
<213> ORGANISM: Homo sapiens
<220> FEATURE:
<223> OTHER INFORMATION: TAPBP Tapasin;
      O15533_C115
<220> FEATURE:
<221> NAME/KEY: MOD_RES
<222> LOCATION: (12)..(12)
<223> OTHER INFORMATION: Site of chemical conjugation

<400> SEQUENCE: 549

Lys Trp Ala Ser Gly Leu Thr Pro Ala Gln Asn Cys Pro Arg Ala
1               5                   10                  15

<210> SEQ ID NO 550
<211> LENGTH: 31
<212> TYPE: PRT
<213> ORGANISM: Homo sapiens
<220> FEATURE:
<223> OTHER INFORMATION: DUSP12 Dual specificity protein phosphatase 12;
      Q9UNI6_C23
<220> FEATURE:
<221> NAME/KEY: MOD_RES
<222> LOCATION: (4)..(4)
<223> OTHER INFORMATION: Site of chemical conjugation

<400> SEQUENCE: 550

Arg Val Ser Cys Ala Gly Gln Met Leu Glu Val Gln Pro Gly Leu Tyr
1               5                   10                  15

Phe Gly Gly Ala Ala Ala Val Ala Glu Pro Asp His Leu Arg Glu
            20                  25                  30

<210> SEQ ID NO 551
<211> LENGTH: 15
<212> TYPE: PRT
<213> ORGANISM: Homo sapiens
<220> FEATURE:
<223> OTHER INFORMATION: HTATIP2 Oxidoreductase HTATIP2;
      Q9BUP3_C172
<220> FEATURE:
<221> NAME/KEY: MOD_RES
<222> LOCATION: (12)..(12)
```

```
<223> OTHER INFORMATION: Site of chemical conjugation

<400> SEQUENCE: 551

Arg Tyr Ser Val Phe Arg Pro Gly Val Leu Leu Cys Asp Arg Gln
1               5                   10                  15

<210> SEQ ID NO 552
<211> LENGTH: 19
<212> TYPE: PRT
<213> ORGANISM: Homo sapiens
<220> FEATURE:
<223> OTHER INFORMATION: NUBP1 Cytosolic Fe-S cluster assembly factor
      NUBP1; P53384_C235
<220> FEATURE:
<221> NAME/KEY: MOD_RES
<222> LOCATION: (16)..(16)
<223> OTHER INFORMATION: Site of chemical conjugation

<400> SEQUENCE: 552

Lys Leu Pro Ile Ile Gly Val Val Glu Asn Met Ser Gly Phe Ile Cys
1               5                   10                  15

Pro Lys Cys

<210> SEQ ID NO 553
<211> LENGTH: 25
<212> TYPE: PRT
<213> ORGANISM: Homo sapiens
<220> FEATURE:
<223> OTHER INFORMATION: WAPAL Wings apart-like protein homolog;
      Q7Z5K2_C293
<220> FEATURE:
<221> NAME/KEY: MOD_RES
<222> LOCATION: (23)..(23)
<223> OTHER INFORMATION: Site of chemical conjugation

<400> SEQUENCE: 553

Arg Leu Glu Asn Leu Asn Glu Ala Ile Glu Glu Asp Ile Val Gln Ser
1               5                   10                  15

Val Leu Arg Pro Thr Asn Cys Arg Thr
            20                  25

<210> SEQ ID NO 554
<211> LENGTH: 21
<212> TYPE: PRT
<213> ORGANISM: Homo sapiens
<220> FEATURE:
<223> OTHER INFORMATION: CDC42BPB Serine/threonine-protein kinase MRCK
      beta; Q9Y5S2_C1517
<220> FEATURE:
<221> NAME/KEY: MOD_RES
<222> LOCATION: (16)..(16)
<223> OTHER INFORMATION: Site of chemical conjugation

<400> SEQUENCE: 554

Arg Ile Arg Pro Leu Asn Ser Glu Gly Thr Leu Asn Leu Leu Asn Cys
1               5                   10                  15

Glu Pro Pro Arg Leu
            20

<210> SEQ ID NO 555
<211> LENGTH: 9
<212> TYPE: PRT
<213> ORGANISM: Homo sapiens
<220> FEATURE:
<223> OTHER INFORMATION: EXOSC7 Exosome complex component RRP42;
      Q15024_C238
<220> FEATURE:
<221> NAME/KEY: MOD_RES
```

-continued

```
<222> LOCATION: (6)..(6)
<223> OTHER INFORMATION: Site of chemical conjugation

<400> SEQUENCE: 555

Lys Gly Val Val Thr Cys Met Arg Lys
1               5

<210> SEQ ID NO 556
<211> LENGTH: 18
<212> TYPE: PRT
<213> ORGANISM: Homo sapiens
<220> FEATURE:
<223> OTHER INFORMATION: PEX19 Peroxisomal biogenesis factor 19;
      P40855_C128
<220> FEATURE:
<221> NAME/KEY: MOD_RES
<222> LOCATION: (15)..(15)
<223> OTHER INFORMATION: Site of chemical conjugation

<400> SEQUENCE: 556

Arg Val Gly Ser Asp Met Thr Ser Gln Gln Glu Phe Thr Ser Cys Leu
1               5                   10                  15

Lys Glu

<210> SEQ ID NO 557
<211> LENGTH: 9
<212> TYPE: PRT
<213> ORGANISM: Homo sapiens
<220> FEATURE:
<223> OTHER INFORMATION: EZH2 Histone-lysine N-methyltransferase EZH2;
      Q15910_C503
<220> FEATURE:
<221> NAME/KEY: MOD_RES
<222> LOCATION: (7)..(7)
<223> OTHER INFORMATION: Site of chemical conjugation

<400> SEQUENCE: 557

Arg Leu Trp Ala Ala His Cys Arg Lys
1               5

<210> SEQ ID NO 558
<211> LENGTH: 19
<212> TYPE: PRT
<213> ORGANISM: Homo sapiens
<220> FEATURE:
<223> OTHER INFORMATION: PLEC Plectin;
      Q15149_C4071
<220> FEATURE:
<221> NAME/KEY: MOD_RES
<222> LOCATION: (8)..(8)
<223> OTHER INFORMATION: Site of chemical conjugation

<400> SEQUENCE: 558

Lys Phe Leu Glu Gly Thr Ser Cys Ile Ala Gly Val Phe Val Asp Ala
1               5                   10                  15

Thr Lys Glu

<210> SEQ ID NO 559
<211> LENGTH: 33
<212> TYPE: PRT
<213> ORGANISM: Homo sapiens
<220> FEATURE:
<223> OTHER INFORMATION: SCP2 Non-specific lipid-transfer protein;
      P22307_C94
<220> FEATURE:
<221> NAME/KEY: MOD_RES
<222> LOCATION: (21)..(21)
<223> OTHER INFORMATION: Site of chemical conjugation
```

```
<400> SEQUENCE: 559

Arg Ala Ile Tyr His Ser Leu Gly Met Thr Gly Ile Pro Ile Ile Asn
1               5                   10                  15

Val Asn Asn Asn Cys Ala Thr Gly Ser Thr Ala Leu Phe Met Ala Arg
            20                  25                  30

Gln

<210> SEQ ID NO 560
<211> LENGTH: 20
<212> TYPE: PRT
<213> ORGANISM: Homo sapiens
<220> FEATURE:
<223> OTHER INFORMATION: GTF3C1 General transcription factor 3C
      polypeptide 1; Q12789_C42
<220> FEATURE:
<221> NAME/KEY: MOD_RES
<222> LOCATION: (12)..(12)
<223> OTHER INFORMATION: Site of chemical conjugation

<400> SEQUENCE: 560

Arg Val Pro Pro Phe Pro Leu Pro Leu Glu Pro Cys Thr Gln Glu Phe
1               5                   10                  15

Leu Trp Arg Ala
            20

<210> SEQ ID NO 561
<211> LENGTH: 38
<212> TYPE: PRT
<213> ORGANISM: Homo sapiens
<220> FEATURE:
<223> OTHER INFORMATION: SMAD2 Mothers against decapentaplegic homolog
      2; Q15796_C81
<220> FEATURE:
<221> NAME/KEY: MOD_RES
<222> LOCATION: (9)..(9)
<223> OTHER INFORMATION: Site of chemical conjugation

<400> SEQUENCE: 561

Lys Cys Val Thr Ile Pro Ser Thr Cys Ser Glu Ile Trp Gly Leu Ser
1               5                   10                  15

Thr Pro Asn Thr Ile Asp Gln Trp Asp Thr Thr Gly Leu Tyr Ser Phe
            20                  25                  30

Ser Glu Gln Thr Arg Ser
        35

<210> SEQ ID NO 562
<211> LENGTH: 24
<212> TYPE: PRT
<213> ORGANISM: Homo sapiens
<220> FEATURE:
<223> OTHER INFORMATION: BAG5 BAG family molecular chaperone regulator
      5; Q9UL15_C327
<220> FEATURE:
<221> NAME/KEY: MOD_RES
<222> LOCATION: (21)..(21)
<223> OTHER INFORMATION: Site of chemical conjugation

<400> SEQUENCE: 562

Lys Thr Glu Leu Gln Gly Leu Ile Gly Gln Leu Asp Glu Val Ser Leu
1               5                   10                  15

Glu Lys Asn Pro Cys Ile Arg Glu
            20

<210> SEQ ID NO 563
<211> LENGTH: 17
```

```
<212> TYPE: PRT
<213> ORGANISM: Homo sapiens
<220> FEATURE:
<223> OTHER INFORMATION: KRI1 Protein KRI1 homolog;
      Q8N9T8_C673
<220> FEATURE:
<221> NAME/KEY: MOD_RES
<222> LOCATION: (12)..(12)
<223> OTHER INFORMATION: Site of chemical conjugation

<400> SEQUENCE: 563

Arg Leu Leu Gly Pro Thr Val Met Leu Gly Gly Cys Glu Phe Ser Arg
1               5                   10                  15

Gln

<210> SEQ ID NO 564
<211> LENGTH: 27
<212> TYPE: PRT
<213> ORGANISM: Homo sapiens
<220> FEATURE:
<223> OTHER INFORMATION: AUP1 Ancient ubiquitous protein 1;
      Q9Y679_C391
<220> FEATURE:
<221> NAME/KEY: MOD_RES
<222> LOCATION: (4)..(4)
<223> OTHER INFORMATION: Site of chemical conjugation

<400> SEQUENCE: 564

Lys Thr Gly Cys Val Asp Leu Thr Ile Thr Asn Leu Leu Glu Gly Ala
1               5                   10                  15

Val Ala Phe Met Pro Glu Asp Ile Thr Lys Gly
            20                  25

<210> SEQ ID NO 565
<211> LENGTH: 11
<212> TYPE: PRT
<213> ORGANISM: Homo sapiens
<220> FEATURE:
<223> OTHER INFORMATION: MAP2K7 Dual specificity mitogen-activated
      protein kinase; O14733_C260
<220> FEATURE:
<221> NAME/KEY: MOD_RES
<222> LOCATION: (3)..(3)
<223> OTHER INFORMATION: Site of chemical conjugation

<400> SEQUENCE: 565

Lys Leu Cys Asp Phe Gly Ile Ser Gly Arg Leu
1               5                   10

<210> SEQ ID NO 566
<211> LENGTH: 15
<212> TYPE: PRT
<213> ORGANISM: Homo sapiens
<220> FEATURE:
<223> OTHER INFORMATION: ANKRD17 Ankyrin repeat domain-containing
      protein 17; O75179_C644
<220> FEATURE:
<221> NAME/KEY: MOD_RES
<222> LOCATION: (6)..(6)
<223> OTHER INFORMATION: Site of chemical conjugation

<400> SEQUENCE: 566

Arg Ala Gly His Val Cys Thr Val Gln Phe Leu Ile Ser Lys Gly
1               5                   10                  15

<210> SEQ ID NO 567
<211> LENGTH: 12
<212> TYPE: PRT
<213> ORGANISM: Homo sapiens
```

```
<220> FEATURE:
<223> OTHER INFORMATION: PRKAR2B cAMP-dependent protein kinase type
      II-beta regulat; P31323_C388
<220> FEATURE:
<221> NAME/KEY: MOD_RES
<222> LOCATION: (6)..(6)
<223> OTHER INFORMATION: Site of chemical conjugation

<400> SEQUENCE: 567

Arg Leu Leu Gly Pro Cys Met Glu Ile Met Lys Arg
1               5                  10

<210> SEQ ID NO 568
<211> LENGTH: 18
<212> TYPE: PRT
<213> ORGANISM: Homo sapiens
<220> FEATURE:
<223> OTHER INFORMATION: NMRAL1 NmrA-like family domain-containing
      protein 1; Q9HBL8_C154
<220> FEATURE:
<221> NAME/KEY: MOD_RES
<222> LOCATION: (4)..(4)
<223> OTHER INFORMATION: Site of chemical conjugation

<400> SEQUENCE: 568

Arg Leu Pro Cys Tyr Phe Glu Asn Leu Leu Ser His Phe Leu Pro Gln
1               5                  10                  15

Lys Ala

<210> SEQ ID NO 569
<211> LENGTH: 24
<212> TYPE: PRT
<213> ORGANISM: Homo sapiens
<220> FEATURE:
<223> OTHER INFORMATION: USP28 Ubiquitin carboxyl-terminal hydrolase 28;
      Q96RU2_C171
<220> FEATURE:
<221> NAME/KEY: MOD_RES
<222> LOCATION: (7)..(7)
<223> OTHER INFORMATION: Site of chemical conjugation

<400> SEQUENCE: 569

Lys Asn Val Gly Asn Thr Cys Trp Phe Ser Ala Val Ile Gln Ser Leu
1               5                  10                  15

Phe Gln Leu Pro Glu Phe Arg Arg
            20

<210> SEQ ID NO 570
<211> LENGTH: 22
<212> TYPE: PRT
<213> ORGANISM: Homo sapiens
<220> FEATURE:
<223> OTHER INFORMATION: MMS19 MMS19 nucleotide excision repair protein
      homolog; Q96T76_C750
<220> FEATURE:
<221> NAME/KEY: MOD_RES
<222> LOCATION: (12)..(12)
<223> OTHER INFORMATION: Site of chemical conjugation

<400> SEQUENCE: 570

Arg Glu Leu Leu Glu Leu Ser Cys Cys His Ser Cys Pro Phe Ser Ser
1               5                  10                  15

Thr Ala Ala Ala Lys Cys
            20

<210> SEQ ID NO 571
<211> LENGTH: 9
<212> TYPE: PRT
```

```
<213> ORGANISM: Homo sapiens
<220> FEATURE:
<223> OTHER INFORMATION: PFKL 6-phosphofructokinase, liver type;
      P17858_C89
<220> FEATURE:
<221> NAME/KEY: MOD_RES
<222> LOCATION: (2)..(2)
<223> OTHER INFORMATION: Site of chemical conjugation

<400> SEQUENCE: 571

Arg Cys Lys Ala Phe Thr Thr Arg Glu
1               5

<210> SEQ ID NO 572
<211> LENGTH: 16
<212> TYPE: PRT
<213> ORGANISM: Homo sapiens
<220> FEATURE:
<223> OTHER INFORMATION: CYFIP2 Cytoplasmic FMR1-interacting protein 2;
      Q96F07_C1112
<220> FEATURE:
<221> NAME/KEY: MOD_RES
<222> LOCATION: (4)..(4)
<223> OTHER INFORMATION: Site of chemical conjugation

<400> SEQUENCE: 572

Arg Leu Cys Cys Gly Leu Ser Met Phe Glu Val Ile Leu Thr Arg Ile
1               5                   10                  15

<210> SEQ ID NO 573
<211> LENGTH: 9
<212> TYPE: PRT
<213> ORGANISM: Homo sapiens
<220> FEATURE:
<223> OTHER INFORMATION: NCAPD3 Condensin-2 complex subunit D3;
      P42695_C541
<220> FEATURE:
<221> NAME/KEY: MOD_RES
<222> LOCATION: (2)..(2)
<223> OTHER INFORMATION: Site of chemical conjugation

<400> SEQUENCE: 573

Arg Cys Val Met Ala Met Leu Arg Arg
1               5

<210> SEQ ID NO 574
<211> LENGTH: 10
<212> TYPE: PRT
<213> ORGANISM: Homo sapiens
<220> FEATURE:
<223> OTHER INFORMATION: POLDIP2 Polymerase delta-interacting protein 2;
      Q9Y2S7_C143
<220> FEATURE:
<221> NAME/KEY: MOD_RES
<222> LOCATION: (3)..(3)
<223> OTHER INFORMATION: Site of chemical conjugation

<400> SEQUENCE: 574

Arg Asp Cys Pro His Ile Ser Gln Arg Ser
1               5                   10

<210> SEQ ID NO 575
<211> LENGTH: 21
<212> TYPE: PRT
<213> ORGANISM: Homo sapiens
<220> FEATURE:
<223> OTHER INFORMATION: NUP98 Nuclear pore complex protein Nup98-Nup96;
      P52948_C1312
<220> FEATURE:
<221> NAME/KEY: MOD_RES
<222> LOCATION: (5)..(5)
```

<223> OTHER INFORMATION: Site of chemical conjugation

<400> SEQUENCE: 575

Arg Trp Leu Ser Cys Thr Ala Thr Pro Gln Ile Glu Glu Glu Val Ser
1               5                   10                  15

Leu Thr Gln Lys Asn
            20

<210> SEQ ID NO 576
<211> LENGTH: 25
<212> TYPE: PRT
<213> ORGANISM: Homo sapiens
<220> FEATURE:
<223> OTHER INFORMATION: DAXX Death domain-associated protein 6;
      Q9UER7_C664
<220> FEATURE:
<221> NAME/KEY: MOD_RES
<222> LOCATION: (3)..(3)
<223> OTHER INFORMATION: Site of chemical conjugation

<400> SEQUENCE: 576

Lys Ile Cys Thr Leu Pro Ser Pro Pro Ser Pro Leu Ala Ser Leu Ala
1               5                   10                  15

Pro Val Ala Asp Ser Ser Thr Arg Val
            20                  25

<210> SEQ ID NO 577
<211> LENGTH: 14
<212> TYPE: PRT
<213> ORGANISM: Homo sapiens
<220> FEATURE:
<223> OTHER INFORMATION: SMARCAD1 SWI/SNF-related matrix-associated
      actin-dependent; Q9H4L7_C772
<220> FEATURE:
<221> NAME/KEY: MOD_RES
<222> LOCATION: (6)..(6)
<223> OTHER INFORMATION: Site of chemical conjugation

<400> SEQUENCE: 577

Lys Asn Thr Glu Met Cys Asn Val Met Met Gln Leu Arg Lys
1               5                   10

<210> SEQ ID NO 578
<211> LENGTH: 16
<212> TYPE: PRT
<213> ORGANISM: Homo sapiens
<220> FEATURE:
<223> OTHER INFORMATION: PPME1 Protein phosphatase methylesterase 1;
      Q9Y570_C381
<220> FEATURE:
<221> NAME/KEY: MOD_RES
<222> LOCATION: (11)..(11)
<223> OTHER INFORMATION: Site of chemical conjugation

<400> SEQUENCE: 578

Arg Phe Ala Glu Pro Ile Gly Gly Phe Gln Cys Val Phe Pro Gly Cys
1               5                   10                  15

<210> SEQ ID NO 579
<211> LENGTH: 27
<212> TYPE: PRT
<213> ORGANISM: Homo sapiens
<220> FEATURE:
<223> OTHER INFORMATION: MSH6 DNA mismatch repair protein Msh6;
      P52701_C1117
<220> FEATURE:
<221> NAME/KEY: MOD_RES
<222> LOCATION: (17)..(17)
<223> OTHER INFORMATION: Site of chemical conjugation

```
<400> SEQUENCE: 579

Lys Thr Phe Phe Gly Asp Asp Phe Ile Pro Asn Asp Ile Leu Ile Gly
1               5                   10                  15

Cys Glu Glu Glu Glu Gln Glu Asn Gly Lys Ala
            20                  25

<210> SEQ ID NO 580
<211> LENGTH: 15
<212> TYPE: PRT
<213> ORGANISM: Homo sapiens
<220> FEATURE:
<223> OTHER INFORMATION: MCM5 DNA replication licensing factor MCM5;
      P33992_C482
<220> FEATURE:
<221> NAME/KEY: MOD_RES
<222> LOCATION: (2)..(2)
<223> OTHER INFORMATION: Site of chemical conjugation

<400> SEQUENCE: 580

Arg Cys Ser Val Leu Ala Ala Ala Asn Ser Val Phe Gly Arg Trp
1               5                   10                  15

<210> SEQ ID NO 581
<211> LENGTH: 10
<212> TYPE: PRT
<213> ORGANISM: Homo sapiens
<220> FEATURE:
<223> OTHER INFORMATION: C15orf38-AP3S2 Protein C15orf38-AP3S2;
      E2QRD5_C183
<220> FEATURE:
<221> NAME/KEY: MOD_RES
<222> LOCATION: (2)..(2)
<223> OTHER INFORMATION: Site of chemical conjugation

<400> SEQUENCE: 581

Lys Cys Asn Phe Thr Gly Asp Gly Lys Thr
1               5                   10

<210> SEQ ID NO 582
<211> LENGTH: 24
<212> TYPE: PRT
<213> ORGANISM: Homo sapiens
<220> FEATURE:
<223> OTHER INFORMATION: PFKFB4 6-phosphofructo-2-kinase/fructose-2,6-
      bisphosphata; Q16877_C159
<220> FEATURE:
<221> NAME/KEY: MOD_RES
<222> LOCATION: (9)..(9)
<223> OTHER INFORMATION: Site of chemical conjugation

<400> SEQUENCE: 582

Lys Thr Phe Phe Val Glu Ser Ile Cys Val Asp Pro Glu Val Ile Ala
1               5                   10                  15

Ala Asn Ile Val Gln Val Lys Leu
            20

<210> SEQ ID NO 583
<211> LENGTH: 30
<212> TYPE: PRT
<213> ORGANISM: Homo sapiens
<220> FEATURE:
<223> OTHER INFORMATION: CCM2 Malcavernin;
      Q9BSQ5_C211
<220> FEATURE:
<221> NAME/KEY: MOD_RES
<222> LOCATION: (9)..(9)
<223> OTHER INFORMATION: Site of chemical conjugation
```

<400> SEQUENCE: 583

Lys Val Ala Ala Glu Glu Leu Cys Cys Leu Leu Gly Gln Val Phe Gln
1               5                   10                  15

Val Val Tyr Thr Glu Ser Thr Ile Asp Phe Leu Asp Arg Ala
            20                  25                  30

<210> SEQ ID NO 584
<211> LENGTH: 10
<212> TYPE: PRT
<213> ORGANISM: Homo sapiens
<220> FEATURE:
<223> OTHER INFORMATION: MPP1 55 kDa erythrocyte membrane protein;
      Q00013_C179
<220> FEATURE:
<221> NAME/KEY: MOD_RES
<222> LOCATION: (8)..(8)
<223> OTHER INFORMATION: Site of chemical conjugation

<400> SEQUENCE: 584

Lys Lys Asp Asn Leu Ile Pro Cys Lys Glu
1               5                   10

<210> SEQ ID NO 585
<211> LENGTH: 36
<212> TYPE: PRT
<213> ORGANISM: Homo sapiens
<220> FEATURE:
<223> OTHER INFORMATION: DHRS11 Dehydrogenase/reductase SDR family
      member 11; Q6UWP2_C226
<220> FEATURE:
<221> NAME/KEY: MOD_RES
<222> LOCATION: (2)..(2)
<223> OTHER INFORMATION: Site of chemical conjugation

<400> SEQUENCE: 585

Lys Cys Leu Lys Pro Glu Asp Val Ala Glu Ala Val Ile Tyr Val Leu
1               5                   10                  15

Ser Thr Pro Ala His Ile Gln Ile Gly Asp Ile Gln Met Arg Pro Thr
            20                  25                  30

Glu Gln Val Thr
            35

<210> SEQ ID NO 586
<211> LENGTH: 13
<212> TYPE: PRT
<213> ORGANISM: Homo sapiens
<220> FEATURE:
<223> OTHER INFORMATION: AFAP1 Actin filament-associated protein 1;
      Q8N556_C713
<220> FEATURE:
<221> NAME/KEY: MOD_RES
<222> LOCATION: (11)..(11)
<223> OTHER INFORMATION: Site of chemical conjugation

<400> SEQUENCE: 586

Lys Ser Gln Ala Ala Pro Gly Ser Ser Pro Cys Arg Gly
1               5                   10

<210> SEQ ID NO 587
<211> LENGTH: 19
<212> TYPE: PRT
<213> ORGANISM: Homo sapiens
<220> FEATURE:
<223> OTHER INFORMATION: PGPEP1 Pyroglutamyl-peptidase 1;
      Q9NXJ5_C149
<220> FEATURE:
<221> NAME/KEY: MOD_RES
<222> LOCATION: (4)..(4)

-continued

<223> OTHER INFORMATION: Site of chemical conjugation

<400> SEQUENCE: 587

Arg Tyr Leu Cys Asp Phe Thr Tyr Tyr Thr Ser Leu Tyr Gln Ser His
1               5                   10                  15

Gly Arg Ser

<210> SEQ ID NO 588
<211> LENGTH: 18
<212> TYPE: PRT
<213> ORGANISM: Homo sapiens
<220> FEATURE:
<223> OTHER INFORMATION: PM20D2 Peptidase M20 domain-containing protein
      2; Q8IYS1_C14
<220> FEATURE:
<221> NAME/KEY: MOD_RES
<222> LOCATION: (14)..(14)
<223> OTHER INFORMATION: Site of chemical conjugation

<400> SEQUENCE: 588

Met Arg Pro Gly Gly Glu Arg Pro Val Glu Gly Gly Ala Cys Asn Gly
1               5                   10                  15

Arg Ser

<210> SEQ ID NO 589
<211> LENGTH: 10
<212> TYPE: PRT
<213> ORGANISM: Homo sapiens
<220> FEATURE:
<223> OTHER INFORMATION: RAD50 DNA repair protein RAD50;
      Q92878_C48
<220> FEATURE:
<221> NAME/KEY: MOD_RES
<222> LOCATION: (7)..(7)
<223> OTHER INFORMATION: Site of chemical conjugation

<400> SEQUENCE: 589

Lys Thr Thr Ile Ile Glu Cys Leu Lys Tyr
1               5                   10

<210> SEQ ID NO 590
<211> LENGTH: 22
<212> TYPE: PRT
<213> ORGANISM: Homo sapiens
<220> FEATURE:
<223> OTHER INFORMATION: TNS3 Tensin-3;
      Q68CZ2_C888
<220> FEATURE:
<221> NAME/KEY: MOD_RES
<222> LOCATION: (3)..(3)
<223> OTHER INFORMATION: Site of chemical conjugation

<400> SEQUENCE: 590

Arg Ser Cys Pro Glu Thr Leu Thr His Ala Val Gly Met Ser Glu Ser
1               5                   10                  15

Pro Ile Gly Pro Lys Ser
            20

<210> SEQ ID NO 591
<211> LENGTH: 17
<212> TYPE: PRT
<213> ORGANISM: Homo sapiens
<220> FEATURE:
<223> OTHER INFORMATION: MYCBP2 Probable E3 ubiquitin-protein ligase
      MYCBP2; O75592_C1131
<220> FEATURE:
<221> NAME/KEY: MOD_RES
<222> LOCATION: (2)..(2)

-continued

<223> OTHER INFORMATION: Site of chemical conjugation

<400> SEQUENCE: 591

Arg Cys Ser Ile Leu Ser Pro Glu Leu Ala Leu Pro Thr Gly Ser Arg
1               5                   10                  15

Ala

<210> SEQ ID NO 592
<211> LENGTH: 12
<212> TYPE: PRT
<213> ORGANISM: Homo sapiens
<220> FEATURE:
<223> OTHER INFORMATION: ZNF318 Zinc finger protein 318;
      Q5VUA4_C1860
<220> FEATURE:
<221> NAME/KEY: MOD_RES
<222> LOCATION: (7)..(7)
<223> OTHER INFORMATION: Site of chemical conjugation

<400> SEQUENCE: 592

Lys Leu Ser Pro Gln Ala Cys Ser Phe Thr Lys Ala
1               5                   10

<210> SEQ ID NO 593
<211> LENGTH: 12
<212> TYPE: PRT
<213> ORGANISM: Homo sapiens
<220> FEATURE:
<223> OTHER INFORMATION: TXNIP Thioredoxin-interacting protein;
      Q9H3M7_C170
<220> FEATURE:
<221> NAME/KEY: MOD_RES
<222> LOCATION: (4)..(4)
<223> OTHER INFORMATION: Site of chemical conjugation

<400> SEQUENCE: 593

Lys Val Ser Cys Met Phe Ile Pro Asp Gly Arg Val
1               5                   10

<210> SEQ ID NO 594
<211> LENGTH: 15
<212> TYPE: PRT
<213> ORGANISM: Homo sapiens
<220> FEATURE:
<223> OTHER INFORMATION: HMHA1 Minor histocompatibility protein HA-1;
      Q92619_C278
<220> FEATURE:
<221> NAME/KEY: MOD_RES
<222> LOCATION: (2)..(2)
<223> OTHER INFORMATION: Site of chemical conjugation

<400> SEQUENCE: 594

Arg Cys Glu Gly Gly Val Asp Ala Ala Leu Leu Tyr Ala Lys Asn
1               5                   10                  15

<210> SEQ ID NO 595
<211> LENGTH: 16
<212> TYPE: PRT
<213> ORGANISM: Homo sapiens
<220> FEATURE:
<223> OTHER INFORMATION: MKI67 Antigen KI-67;
      P46013_C903
<220> FEATURE:
<221> NAME/KEY: MOD_RES
<222> LOCATION: (12)..(12)
<223> OTHER INFORMATION: Site of chemical conjugation

<400> SEQUENCE: 595

Lys Ser Glu Glu Thr Asn Thr Glu Ile Val Glu Cys Ile Leu Lys Arg
1               5                   10                  15

<210> SEQ ID NO 596
<211> LENGTH: 39
<212> TYPE: PRT
<213> ORGANISM: Homo sapiens
<220> FEATURE:
<223> OTHER INFORMATION: TRMT112 tRNA methyltransferase 112 homolog;
      Q9UI30_C100
<220> FEATURE:
<221> NAME/KEY: MOD_RES
<222> LOCATION: (33)..(33)
<223> OTHER INFORMATION: Site of chemical conjugation

<400> SEQUENCE: 596

Lys Gly Pro Val Glu Gly Tyr Glu Glu Asn Glu Glu Phe Leu Arg Thr
1               5                   10                  15

Met His His Leu Leu Leu Glu Val Glu Val Ile Glu Gly Thr Leu Gln
            20                  25                  30

Cys Pro Glu Ser Gly Arg Met
        35

<210> SEQ ID NO 597
<211> LENGTH: 20
<212> TYPE: PRT
<213> ORGANISM: Homo sapiens
<220> FEATURE:
<223> OTHER INFORMATION: SYMPK Symplekin;
      Q92797_C848
<220> FEATURE:
<221> NAME/KEY: MOD_RES
<222> LOCATION: (17)..(17)
<223> OTHER INFORMATION: Site of chemical conjugation

<400> SEQUENCE: 597

Arg Gly Met Gly Met Asn Ser Pro Glu Leu Leu Leu Leu Val Glu Asn
1               5                   10                  15

Cys Pro Lys Gly
            20

<210> SEQ ID NO 598
<211> LENGTH: 8
<212> TYPE: PRT
<213> ORGANISM: Homo sapiens
<220> FEATURE:
<223> OTHER INFORMATION: CCT8 T-complex protein 1 subunit theta;
      P50990_C36
<220> FEATURE:
<221> NAME/KEY: MOD_RES
<222> LOCATION: (6)..(6)
<223> OTHER INFORMATION: Site of chemical conjugation

<400> SEQUENCE: 598

Arg Asn Ile Gln Ala Cys Lys Glu
1               5

<210> SEQ ID NO 599
<211> LENGTH: 10
<212> TYPE: PRT
<213> ORGANISM: Homo sapiens
<220> FEATURE:
<223> OTHER INFORMATION: DFFB DNA fragmentation factor subunit beta;
      O76075_C194
<220> FEATURE:
<221> NAME/KEY: MOD_RES
<222> LOCATION: (7)..(7)
<223> OTHER INFORMATION: Site of chemical conjugation

<400> SEQUENCE: 599

```
Arg Val Gly Ser Met Cys Gln Arg Leu
1               5                  10

<210> SEQ ID NO 600
<211> LENGTH: 21
<212> TYPE: PRT
<213> ORGANISM: Homo sapiens
<220> FEATURE:
<223> OTHER INFORMATION: NR3C1 Glucocorticoid receptor;
      P04150_C302
<220> FEATURE:
<221> NAME/KEY: MOD_RES
<222> LOCATION: (7)..(7)
<223> OTHER INFORMATION: Site of chemical conjugation

<400> SEQUENCE: 600

Lys Leu Gly Thr Val Tyr Cys Gln Ala Ser Phe Pro Gly Ala Asn Ile
1               5                  10                  15

Ile Gly Asn Lys Met
            20

<210> SEQ ID NO 601
<211> LENGTH: 25
<212> TYPE: PRT
<213> ORGANISM: Homo sapiens
<220> FEATURE:
<223> OTHER INFORMATION: VCPIP1 Deubiquitinating protein VCIP135;
      Q96JH7_C219
<220> FEATURE:
<221> NAME/KEY: MOD_RES
<222> LOCATION: (17)..(17)
<223> OTHER INFORMATION: Site of chemical conjugation

<400> SEQUENCE: 601

Lys Ser Gln Glu Cys Leu Ile Pro Val His Val Asp Gly Asp Gly His
1               5                  10                  15

Cys Leu Val His Ala Val Ser Arg Ala
            20                  25

<210> SEQ ID NO 602
<211> LENGTH: 12
<212> TYPE: PRT
<213> ORGANISM: Homo sapiens
<220> FEATURE:
<223> OTHER INFORMATION: GSTCD Glutathione S-transferase C-terminal
      domain-contai; Q8NEC7_C140
<220> FEATURE:
<221> NAME/KEY: MOD_RES
<222> LOCATION: (3)..(3)
<223> OTHER INFORMATION: Site of chemical conjugation

<400> SEQUENCE: 602

Lys Ala Cys Ala Glu Val Ser Gln Trp Thr Arg Leu
1               5                  10

<210> SEQ ID NO 603
<211> LENGTH: 18
<212> TYPE: PRT
<213> ORGANISM: Homo sapiens
<220> FEATURE:
<223> OTHER INFORMATION: IREB2 Iron-responsive element-binding protein
      2; P48200_C137
<220> FEATURE:
<221> NAME/KEY: MOD_RES
<222> LOCATION: (2)..(2)
<223> OTHER INFORMATION: Site of chemical conjugation

<400> SEQUENCE: 603
```

```
Lys Cys Ala Ile Gln Asn Ala Pro Asn Pro Gly Gly Gly Asp Leu Gln
1               5                   10                  15

Lys Ala

<210> SEQ ID NO 604
<211> LENGTH: 20
<212> TYPE: PRT
<213> ORGANISM: Homo sapiens
<220> FEATURE:
<223> OTHER INFORMATION: COG1 Conserved oligomeric Golgi complex subunit
      1; Q8WTW3_C513
<220> FEATURE:
<221> NAME/KEY: MOD_RES
<222> LOCATION: (8)..(8)
<223> OTHER INFORMATION: Site of chemical conjugation

<400> SEQUENCE: 604

Lys Ala Gln Ala Ile Ser Pro Cys Val Gln Asn Phe Cys Ser Ala Leu
1               5                   10                  15

Asp Ser Lys Leu
            20

<210> SEQ ID NO 605
<211> LENGTH: 17
<212> TYPE: PRT
<213> ORGANISM: Homo sapiens
<220> FEATURE:
<223> OTHER INFORMATION: TBC1D2 TBC1 domain family member 2A;
      Q9BYX2_C469
<220> FEATURE:
<221> NAME/KEY: MOD_RES
<222> LOCATION: (5)..(5)
<223> OTHER INFORMATION: Site of chemical conjugation

<400> SEQUENCE: 605

Arg Thr Gln Asn Cys Phe Leu Asn Ser Glu Ile His Gln Val Thr Lys
1               5                   10                  15

Ile

<210> SEQ ID NO 606
<211> LENGTH: 22
<212> TYPE: PRT
<213> ORGANISM: Homo sapiens
<220> FEATURE:
<223> OTHER INFORMATION: HNRNPA3 Heterogeneous nuclear ribonucleoprotein
      A3; P51991_C85
<220> FEATURE:
<221> NAME/KEY: MOD_RES
<222> LOCATION: (10)..(10)
<223> OTHER INFORMATION: Site of chemical conjugation

<400> SEQUENCE: 606

Arg Gly Phe Gly Phe Val Thr Tyr Ser Cys Val Glu Glu Val Asp Ala
1               5                   10                  15

Ala Met Cys Ala Arg Pro
            20

<210> SEQ ID NO 607
<211> LENGTH: 37
<212> TYPE: PRT
<213> ORGANISM: Homo sapiens
<220> FEATURE:
<223> OTHER INFORMATION: RIF1 Telomere-associated protein RIF1;
      Q5UIP0_C2298
<220> FEATURE:
<221> NAME/KEY: MOD_RES
<222> LOCATION: (18)..(18)
<223> OTHER INFORMATION: Site of chemical conjugation
```

<400> SEQUENCE: 607

Lys Glu Ser Ile Pro Cys Pro Thr Glu Ser Val Tyr Pro Pro Leu Val
1               5                   10                  15

Asn Cys Val Ala Pro Val Asp Ile Ile Leu Pro Gln Ile Thr Ser Asn
            20                  25                  30

Met Trp Ala Arg Gly
        35

<210> SEQ ID NO 608
<211> LENGTH: 22
<212> TYPE: PRT
<213> ORGANISM: Homo sapiens
<220> FEATURE:
<223> OTHER INFORMATION: IBA57 Putative transferase CAF17,
      mitochondrial; Q5T440_C170
<220> FEATURE:
<221> NAME/KEY: MOD_RES
<222> LOCATION: (13)..(13)
<223> OTHER INFORMATION: Site of chemical conjugation

<400> SEQUENCE: 608

Arg Val Trp Ala Val Leu Pro Ser Ser Pro Glu Ala Cys Gly Ala Ala
1               5                   10                  15

Ser Leu Gln Glu Arg Ala
            20

<210> SEQ ID NO 609
<211> LENGTH: 8
<212> TYPE: PRT
<213> ORGANISM: Homo sapiens
<220> FEATURE:
<223> OTHER INFORMATION: MAP1B Microtubule-associated protein 1B;
      P46821_C293
<220> FEATURE:
<221> NAME/KEY: MOD_RES
<222> LOCATION: (4)..(4)
<223> OTHER INFORMATION: Site of chemical conjugation

<400> SEQUENCE: 609

Arg Lys Ser Cys Phe Trp Lys Leu
1               5

<210> SEQ ID NO 610
<211> LENGTH: 20
<212> TYPE: PRT
<213> ORGANISM: Homo sapiens
<220> FEATURE:
<223> OTHER INFORMATION: CNPY3 Protein canopy homolog 3;
      Q9BT09_C166
<220> FEATURE:
<221> NAME/KEY: MOD_RES
<222> LOCATION: (3)..(3)
<223> OTHER INFORMATION: Site of chemical conjugation

<400> SEQUENCE: 610

Lys Gln Cys Asp Val Leu Val Glu Glu Phe Glu Glu Val Ile Glu Asp
1               5                   10                  15

Trp Tyr Arg Asn
            20

<210> SEQ ID NO 611
<211> LENGTH: 38
<212> TYPE: PRT
<213> ORGANISM: Homo sapiens
<220> FEATURE:
<223> OTHER INFORMATION: DNAJC10 DnaJ homolog subfamily C member 10;

```
       Q8IXB1_C480
<220> FEATURE:
<221> NAME/KEY: MOD_RES
<222> LOCATION: (33)..(33)
<223> OTHER INFORMATION: Site of chemical conjugation

<400> SEQUENCE: 611

Lys Glu Ser Val Asn Ser His Val Thr Thr Leu Gly Pro Gln Asn Phe
1               5                   10                  15

Pro Ala Asn Asp Lys Glu Pro Trp Leu Val Asp Phe Phe Ala Pro Trp
            20                  25                  30

Cys Pro Pro Cys Arg Ala
        35

<210> SEQ ID NO 612
<211> LENGTH: 11
<212> TYPE: PRT
<213> ORGANISM: Homo sapiens
<220> FEATURE:
<223> OTHER INFORMATION: CYR61 Protein CYR61;
      O00622_C39
<220> FEATURE:
<221> NAME/KEY: MOD_RES
<222> LOCATION: (2)..(2)
<223> OTHER INFORMATION: Site of chemical conjugation

<400> SEQUENCE: 612

Lys Cys Ala Pro Gly Val Gly Leu Val Arg Asp
1               5                   10

<210> SEQ ID NO 613
<211> LENGTH: 22
<212> TYPE: PRT
<213> ORGANISM: Homo sapiens
<220> FEATURE:
<223> OTHER INFORMATION: CWF19L1 CWF19-like protein 1;
      Q69YN2_C288
<220> FEATURE:
<221> NAME/KEY: MOD_RES
<222> LOCATION: (12)..(12)
<223> OTHER INFORMATION: Site of chemical conjugation

<400> SEQUENCE: 613

Lys Gln Ile Leu Ala Pro Val Glu Glu Ser Ala Cys Gln Phe Phe Phe
1               5                   10                  15

Asp Leu Asn Glu Lys Gln
            20

<210> SEQ ID NO 614
<211> LENGTH: 12
<212> TYPE: PRT
<213> ORGANISM: Homo sapiens
<220> FEATURE:
<223> OTHER INFORMATION: IPO4 Importin-4;
      Q8TEX9_C708
<220> FEATURE:
<221> NAME/KEY: MOD_RES
<222> LOCATION: (5)..(5)
<223> OTHER INFORMATION: Site of chemical conjugation

<400> SEQUENCE: 614

Lys Leu Leu Glu Cys Pro His Leu Asn Val Arg Lys
1               5                   10

<210> SEQ ID NO 615
<211> LENGTH: 31
<212> TYPE: PRT
<213> ORGANISM: Homo sapiens
```

```
<220> FEATURE:
<223> OTHER INFORMATION: CAPN7 Calpain-7;
      Q9Y6W3_C197
<220> FEATURE:
<221> NAME/KEY: MOD_RES
<222> LOCATION: (24)..(24)
<223> OTHER INFORMATION: Site of chemical conjugation

<400> SEQUENCE: 615

Arg Ala His Phe Pro Leu Gly Ala Asn Pro Phe Leu Glu Arg Pro Gln
1               5                   10                  15

Ser Phe Ile Ser Pro Gln Ser Cys Asp Ala Gln Gly Gln Arg Tyr
            20                  25                  30

<210> SEQ ID NO 616
<211> LENGTH: 15
<212> TYPE: PRT
<213> ORGANISM: Homo sapiens
<220> FEATURE:
<223> OTHER INFORMATION: SEC23IP SEC23-interacting protein;
      Q9Y6Y8_C604
<220> FEATURE:
<221> NAME/KEY: MOD_RES
<222> LOCATION: (2)..(2)
<223> OTHER INFORMATION: Site of chemical conjugation

<400> SEQUENCE: 616

Lys Cys Pro Gly Pro Leu Ala Val Ala Asn Gly Val Val Lys Gln
1               5                   10                  15

<210> SEQ ID NO 617
<211> LENGTH: 11
<212> TYPE: PRT
<213> ORGANISM: Homo sapiens
<220> FEATURE:
<223> OTHER INFORMATION: AKAP8L A-kinase anchor protein 8-like;
      Q9ULX6_C211
<220> FEATURE:
<221> NAME/KEY: MOD_RES
<222> LOCATION: (4)..(4)
<223> OTHER INFORMATION: Site of chemical conjugation

<400> SEQUENCE: 617

Arg Gly Gln Cys Met Ser Gly Ala Ser Arg Leu
1               5                   10

<210> SEQ ID NO 618
<211> LENGTH: 15
<212> TYPE: PRT
<213> ORGANISM: Homo sapiens
<220> FEATURE:
<223> OTHER INFORMATION: TSTA3 GDP-L-fucose synthase;
      Q13630_C116
<220> FEATURE:
<221> NAME/KEY: MOD_RES
<222> LOCATION: (9)..(9)
<223> OTHER INFORMATION: Site of chemical conjugation

<400> SEQUENCE: 618

Lys Val Val Ser Cys Leu Ser Thr Cys Ile Phe Pro Asp Lys Thr
1               5                   10                  15

<210> SEQ ID NO 619
<211> LENGTH: 18
<212> TYPE: PRT
<213> ORGANISM: Homo sapiens
<220> FEATURE:
<223> OTHER INFORMATION: PDIA4 Protein disulfide-isomerase A4;
      P13667_C94
<220> FEATURE:
```

```
<221> NAME/KEY: MOD_RES
<222> LOCATION: (16)..(16)
<223> OTHER INFORMATION: Site of chemical conjugation

<400> SEQUENCE: 619

Lys Asp Thr Val Leu Leu Glu Phe Tyr Ala Pro Trp Cys Gly His Cys
1               5                   10                  15

Lys Gln

<210> SEQ ID NO 620
<211> LENGTH: 15
<212> TYPE: PRT
<213> ORGANISM: Homo sapiens
<220> FEATURE:
<223> OTHER INFORMATION: DDX59 Probable ATP-dependent RNA helicase
      DDX59; Q5T1V6_C453
<220> FEATURE:
<221> NAME/KEY: MOD_RES
<222> LOCATION: (13)..(13)
<223> OTHER INFORMATION: Site of chemical conjugation

<400> SEQUENCE: 620

Lys Leu Phe Lys Pro Pro Val Leu Val Phe Val Asp Cys Lys Leu
1               5                   10                  15

<210> SEQ ID NO 621
<211> LENGTH: 24
<212> TYPE: PRT
<213> ORGANISM: Homo sapiens
<220> FEATURE:
<223> OTHER INFORMATION: REXO4 RNA exonuclease 4;
      Q9GZR2_C382
<220> FEATURE:
<221> NAME/KEY: MOD_RES
<222> LOCATION: (13)..(13)
<223> OTHER INFORMATION: Site of chemical conjugation

<400> SEQUENCE: 621

Lys Ile Leu Gly Leu Gln Val Gln Gln Ala Glu His Cys Ser Ile Gln
1               5                   10                  15

Asp Ala Gln Ala Ala Met Arg Leu
            20

<210> SEQ ID NO 622
<211> LENGTH: 13
<212> TYPE: PRT
<213> ORGANISM: Homo sapiens
<220> FEATURE:
<223> OTHER INFORMATION: GEMIN6 Gem-associated protein 6;
      Q8WXD5_C91
<220> FEATURE:
<221> NAME/KEY: MOD_RES
<222> LOCATION: (11)..(11)
<223> OTHER INFORMATION: Site of chemical conjugation

<400> SEQUENCE: 622

Lys Leu Met His Leu Phe Thr Ser Gly Asp Cys Lys Ala
1               5                   10

<210> SEQ ID NO 623
<211> LENGTH: 15
<212> TYPE: PRT
<213> ORGANISM: Homo sapiens
<220> FEATURE:
<223> OTHER INFORMATION: PDK1;
      Q15118_C71
<220> FEATURE:
<221> NAME/KEY: MOD_RES
<222> LOCATION: (12)..(12)
```

<223> OTHER INFORMATION: Site of chemical conjugation

<400> SEQUENCE: 623

Lys Gln Phe Leu Asp Phe Gly Ser Val Asn Ala Cys Glu Lys Thr
1               5                   10                  15

<210> SEQ ID NO 624
<211> LENGTH: 12
<212> TYPE: PRT
<213> ORGANISM: Homo sapiens
<220> FEATURE:
<223> OTHER INFORMATION: ATRIP ATR-interacting protein;
      Q8WXE1_C585
<220> FEATURE:
<221> NAME/KEY: MOD_RES
<222> LOCATION: (4)..(4)
<223> OTHER INFORMATION: Site of chemical conjugation

<400> SEQUENCE: 624

Arg Phe Gln Cys Val Phe Gln Val Leu Pro Lys Cys
1               5                   10

<210> SEQ ID NO 625
<211> LENGTH: 11
<212> TYPE: PRT
<213> ORGANISM: Homo sapiens
<220> FEATURE:
<223> OTHER INFORMATION: PIAS4 E3 SUMO-protein ligase PIAS4;
      Q8N2W9_C326
<220> FEATURE:
<221> NAME/KEY: MOD_RES
<222> LOCATION: (6)..(6)
<223> OTHER INFORMATION: Site of chemical conjugation

<400> SEQUENCE: 625

Arg Val Ser Leu Ile Cys Pro Leu Val Lys Met
1               5                   10

<210> SEQ ID NO 626
<211> LENGTH: 21
<212> TYPE: PRT
<213> ORGANISM: Homo sapiens
<220> FEATURE:
<223> OTHER INFORMATION: SEPT6 Septin-6;
      Q14141_C269
<220> FEATURE:
<221> NAME/KEY: MOD_RES
<222> LOCATION: (16)..(16)
<223> OTHER INFORMATION: Site of chemical conjugation

<400> SEQUENCE: 626

Arg Gln Tyr Pro Trp Gly Thr Val Gln Val Glu Asn Glu Ala His Cys
1               5                   10                  15

Asp Phe Val Lys Leu
            20

<210> SEQ ID NO 627
<211> LENGTH: 25
<212> TYPE: PRT
<213> ORGANISM: Homo sapiens
<220> FEATURE:
<223> OTHER INFORMATION: DNMT1 DNA (cytosine-5)-methyltransferase 1;
      P26358_C1071
<220> FEATURE:
<221> NAME/KEY: MOD_RES
<222> LOCATION: (13)..(13)
<223> OTHER INFORMATION: Site of chemical conjugation

<400> SEQUENCE: 627

```
Arg Cys Thr Val Glu Tyr Gly Glu Asp Leu Pro Glu Cys Val Gln Val
1               5                   10                  15

Tyr Ser Met Gly Gly Pro Asn Arg Phe
            20                  25
```

<210> SEQ ID NO 628  
<211> LENGTH: 19  
<212> TYPE: PRT  
<213> ORGANISM: Homo sapiens  
<220> FEATURE:  
<223> OTHER INFORMATION: THNSL1 Threonine synthase-like 1;
     Q8IYQ7_C324  
<220> FEATURE:  
<221> NAME/KEY: MOD_RES  
<222> LOCATION: (16)..(16)  
<223> OTHER INFORMATION: Site of chemical conjugation

<400> SEQUENCE: 628

```
Arg Leu Gly Glu Met Ile Glu Thr Ala Tyr Gly Glu Asn Phe Ala Cys
1               5                   10                  15

Ser Lys Ile
```

<210> SEQ ID NO 629  
<211> LENGTH: 11  
<212> TYPE: PRT  
<213> ORGANISM: Homo sapiens  
<220> FEATURE:  
<223> OTHER INFORMATION: ALDH7A1 Alpha-aminoadipic semialdehyde
     dehydrogenase; P49419_C522  
<220> FEATURE:  
<221> NAME/KEY: MOD_RES  
<222> LOCATION: (4)..(4)  
<223> OTHER INFORMATION: Site of chemical conjugation

<400> SEQUENCE: 629

```
Arg Ser Thr Cys Thr Ile Asn Tyr Ser Lys Asp
1               5                   10
```

<210> SEQ ID NO 630  
<211> LENGTH: 14  
<212> TYPE: PRT  
<213> ORGANISM: Homo sapiens  
<220> FEATURE:  
<223> OTHER INFORMATION: ZNF295 Zinc finger protein 295;
     Q9ULJ3_C129  
<220> FEATURE:  
<221> NAME/KEY: MOD_RES  
<222> LOCATION: (10)..(10)  
<223> OTHER INFORMATION: Site of chemical conjugation

<400> SEQUENCE: 630

```
Lys Thr Pro Gln Ala Pro Phe Pro Thr Cys Pro Asn Arg Lys
1               5                   10
```

<210> SEQ ID NO 631  
<211> LENGTH: 11  
<212> TYPE: PRT  
<213> ORGANISM: Homo sapiens  
<220> FEATURE:  
<223> OTHER INFORMATION: PLEKHA2 Pleckstrin homology domain-containing
     family A mem; Q9HB19_C232  
<220> FEATURE:  
<221> NAME/KEY: MOD_RES  
<222> LOCATION: (2)..(2)  
<223> OTHER INFORMATION: Site of chemical conjugation

<400> SEQUENCE: 631

```
Lys Cys Glu Gln Asp Arg Glu Pro Leu Arg Thr
1               5                   10
```

```
<210> SEQ ID NO 632
<211> LENGTH: 13
<212> TYPE: PRT
<213> ORGANISM: Homo sapiens
<220> FEATURE:
<223> OTHER INFORMATION: CLPX ATP-dependent Clp protease ATP-binding
      subunit clp; O76031_C538
<220> FEATURE:
<221> NAME/KEY: MOD_RES
<222> LOCATION: (2)..(2)
<223> OTHER INFORMATION: Site of chemical conjugation

<400> SEQUENCE: 632

Lys Cys Glu Leu Asn Val Thr Glu Asp Ala Leu Lys Ala
1               5                   10

<210> SEQ ID NO 633
<211> LENGTH: 48
<212> TYPE: PRT
<213> ORGANISM: Homo sapiens
<220> FEATURE:
<223> OTHER INFORMATION: HMGCS1 Hydroxymethylglutaryl-CoA synthase,
      cytoplasmic; Q01581_C129
<220> FEATURE:
<221> NAME/KEY: MOD_RES
<222> LOCATION: (25)..(25)
<223> OTHER INFORMATION: Site of chemical conjugation

<400> SEQUENCE: 633

Lys Thr Asn Leu Met Gln Leu Phe Glu Glu Ser Gly Asn Thr Asp Ile
1               5                   10                  15

Glu Gly Ile Asp Thr Thr Asn Ala Cys Tyr Gly Gly Thr Ala Ala Val
            20                  25                  30

Phe Asn Ala Val Asn Trp Ile Glu Ser Ser Ser Trp Asp Gly Arg Tyr
        35                  40                  45

<210> SEQ ID NO 634
<211> LENGTH: 42
<212> TYPE: PRT
<213> ORGANISM: Homo sapiens
<220> FEATURE:
<223> OTHER INFORMATION: NUDCD1 NudC domain-containing protein 1;
      Q96RS6_C402
<220> FEATURE:
<221> NAME/KEY: MOD_RES
<222> LOCATION: (21)..(21)
<223> OTHER INFORMATION: Site of chemical conjugation

<400> SEQUENCE: 634

Arg Leu Met His Leu Thr Ser Glu Glu Leu Asn Pro Asn Pro Asp Lys
1               5                   10                  15

Glu Lys Pro Pro Cys Asn Ala Gln Glu Leu Glu Glu Cys Asp Ile Phe
            20                  25                  30

Phe Glu Glu Ser Ser Ser Leu Cys Arg Phe
        35                  40

<210> SEQ ID NO 635
<211> LENGTH: 20
<212> TYPE: PRT
<213> ORGANISM: Homo sapiens
<220> FEATURE:
<223> OTHER INFORMATION: PLDN Pallidin;
      Q9UL45_C95
<220> FEATURE:
<221> NAME/KEY: MOD_RES
<222> LOCATION: (5)..(5)
<223> OTHER INFORMATION: Site of chemical conjugation
```

-continued

<400> SEQUENCE: 635

Lys Phe Lys Glu Cys His Ser Met Leu Asp Ile Asn Ala Leu Phe Ala
1               5                   10                  15

Glu Ala Lys His
            20

<210> SEQ ID NO 636
<211> LENGTH: 18
<212> TYPE: PRT
<213> ORGANISM: Homo sapiens
<220> FEATURE:
<223> OTHER INFORMATION: SMURF2 E3 ubiquitin-protein ligase SMURF2;
      Q9HAU4_C706
<220> FEATURE:
<221> NAME/KEY: MOD_RES
<222> LOCATION: (11)..(11)
<223> OTHER INFORMATION: Site of chemical conjugation

<400> SEQUENCE: 636

Arg Leu Phe Thr Ile His Gln Ile Asp Ala Cys Thr Asn Asn Leu Pro
1               5                   10                  15

Lys Ala

<210> SEQ ID NO 637
<211> LENGTH: 12
<212> TYPE: PRT
<213> ORGANISM: Homo sapiens
<220> FEATURE:
<223> OTHER INFORMATION: KIAA1524 Protein CIP2A;
      Q8TCG1_C337
<220> FEATURE:
<221> NAME/KEY: MOD_RES
<222> LOCATION: (2)..(2)
<223> OTHER INFORMATION: Site of chemical conjugation

<400> SEQUENCE: 637

Lys Cys Leu Glu Pro Thr Val Ala Leu Leu Arg Trp
1               5                   10

<210> SEQ ID NO 638
<211> LENGTH: 9
<212> TYPE: PRT
<213> ORGANISM: Homo sapiens
<220> FEATURE:
<223> OTHER INFORMATION: RAI14 Ankycorbin;
      Q9P0K7_C973
<220> FEATURE:
<221> NAME/KEY: MOD_RES
<222> LOCATION: (7)..(7)
<223> OTHER INFORMATION: Site of chemical conjugation

<400> SEQUENCE: 638

Lys Gln Ile Leu Thr Met Cys Lys Asn
1               5

<210> SEQ ID NO 639
<211> LENGTH: 26
<212> TYPE: PRT
<213> ORGANISM: Homo sapiens
<220> FEATURE:
<223> OTHER INFORMATION: EFTUD1 Elongation factor Tu GTP-binding domain-
      containing; Q7Z2Z2_C124
<220> FEATURE:
<221> NAME/KEY: MOD_RES
<222> LOCATION: (17)..(17)
<223> OTHER INFORMATION: Site of chemical conjugation

<400> SEQUENCE: 639

```
Arg Ile Cys Asp Gly Cys Ile Ile Val Val Asp Ala Val Glu Gly Val
1               5                   10                  15

Cys Pro Gln Thr Gln Ala Val Leu Arg Gln
            20                  25

<210> SEQ ID NO 640
<211> LENGTH: 14
<212> TYPE: PRT
<213> ORGANISM: Homo sapiens
<220> FEATURE:
<223> OTHER INFORMATION: TJAP1 Tight junction-associated protein 1;
      Q5JTD0_C350
<220> FEATURE:
<221> NAME/KEY: MOD_RES
<222> LOCATION: (8)..(8)
<223> OTHER INFORMATION: Site of chemical conjugation

<400> SEQUENCE: 640

Arg Asn Ser Pro Leu Pro Asn Cys Thr Tyr Ala Thr Arg Gln
1               5                   10

<210> SEQ ID NO 641
<211> LENGTH: 24
<212> TYPE: PRT
<213> ORGANISM: Homo sapiens
<220> FEATURE:
<223> OTHER INFORMATION: SUZ12 Polycomb protein SUZ12;
      Q15022_C325
<220> FEATURE:
<221> NAME/KEY: MOD_RES
<222> LOCATION: (19)..(19)
<223> OTHER INFORMATION: Site of chemical conjugation

<400> SEQUENCE: 641

Arg Leu Gln Leu Leu Asp Gly Glu Tyr Glu Val Ala Met Gln Glu Met
1               5                   10                  15

Glu Glu Cys Pro Ile Ser Lys Lys
            20

<210> SEQ ID NO 642
<211> LENGTH: 37
<212> TYPE: PRT
<213> ORGANISM: Homo sapiens
<220> FEATURE:
<223> OTHER INFORMATION: ALDH1B1 Aldehyde dehydrogenase X,
      mitochondrial; P30837_C320
<220> FEATURE:
<221> NAME/KEY: MOD_RES
<222> LOCATION: (32)..(32)
<223> OTHER INFORMATION: Site of chemical conjugation

<400> SEQUENCE: 642

Lys Ser Pro Ser Ile Val Leu Ala Asp Ala Asp Met Glu His Ala Val
1               5                   10                  15

Glu Gln Cys His Glu Ala Leu Phe Phe Asn Met Gly Gln Cys Cys Cys
            20                  25                  30

Ala Gly Ser Arg Thr
            35

<210> SEQ ID NO 643
<211> LENGTH: 13
<212> TYPE: PRT
<213> ORGANISM: Homo sapiens
<220> FEATURE:
<223> OTHER INFORMATION: CSTF2T Cleavage stimulation factor subunit 2
      tau variant; Q9H0L4_C150
<220> FEATURE:
```

```
<221> NAME/KEY: MOD_RES
<222> LOCATION: (3)..(3)
<223> OTHER INFORMATION: Site of chemical conjugation

<400> SEQUENCE: 643

Lys Leu Cys Val Gln Asn Ser His Gln Glu Ala Arg Asn
1               5                   10

<210> SEQ ID NO 644
<211> LENGTH: 13
<212> TYPE: PRT
<213> ORGANISM: Homo sapiens
<220> FEATURE:
<223> OTHER INFORMATION: TNFAIP2 Tumor necrosis factor alpha-induced
      protein 2; Q03169_C45
<220> FEATURE:
<221> NAME/KEY: MOD_RES
<222> LOCATION: (8)..(8)
<223> OTHER INFORMATION: Site of chemical conjugation

<400> SEQUENCE: 644

Lys Gly Leu Ala Asn Val Phe Cys Val Phe Thr Lys Gly
1               5                   10

<210> SEQ ID NO 645
<211> LENGTH: 22
<212> TYPE: PRT
<213> ORGANISM: Homo sapiens
<220> FEATURE:
<223> OTHER INFORMATION: ATXN10 Ataxin-10;
      Q9UBB4_C354
<220> FEATURE:
<221> NAME/KEY: MOD_RES
<222> LOCATION: (17)..(17)
<223> OTHER INFORMATION: Site of chemical conjugation

<400> SEQUENCE: 645

Arg Val Ile His Val Ala Gly Lys Glu Thr Thr Asn Ile Phe Ser Asn
1               5                   10                  15

Cys Gly Cys Val Arg Ala
            20

<210> SEQ ID NO 646
<211> LENGTH: 23
<212> TYPE: PRT
<213> ORGANISM: Homo sapiens
<220> FEATURE:
<223> OTHER INFORMATION: BTK Tyrosine-protein kinase BTK;
      Q06187_C481
<220> FEATURE:
<221> NAME/KEY: MOD_RES
<222> LOCATION: (16)..(16)
<223> OTHER INFORMATION: Site of chemical conjugation

<400> SEQUENCE: 646

Lys Gln Arg Pro Ile Phe Ile Ile Thr Glu Tyr Met Ala Asn Gly Cys
1               5                   10                  15

Leu Leu Asn Tyr Leu Arg Glu
            20

<210> SEQ ID NO 647
<211> LENGTH: 24
<212> TYPE: PRT
<213> ORGANISM: Homo sapiens
<220> FEATURE:
<223> OTHER INFORMATION: ENTHD2 AP-4 complex accessory subunit tepsin;
      Q96N21_C302
<220> FEATURE:
<221> NAME/KEY: MOD_RES
```

```
<222> LOCATION: (4)..(4)
<223> OTHER INFORMATION: Site of chemical conjugation

<400> SEQUENCE: 647

Arg Ala Leu Cys Ala Ile Ala Ser Leu Gly Ser Ser Asp Leu Leu Pro
1               5                   10                  15

Gln Glu His Ile Leu Leu Arg Thr
            20

<210> SEQ ID NO 648
<211> LENGTH: 9
<212> TYPE: PRT
<213> ORGANISM: Homo sapiens
<220> FEATURE:
<223> OTHER INFORMATION: RAD50 DNA repair protein RAD50;
      Q92878_C102
<220> FEATURE:
<221> NAME/KEY: MOD_RES
<222> LOCATION: (5)..(5)
<223> OTHER INFORMATION: Site of chemical conjugation

<400> SEQUENCE: 648

Arg Ser Met Val Cys Thr Gln Lys Ser
1               5

<210> SEQ ID NO 649
<211> LENGTH: 29
<212> TYPE: PRT
<213> ORGANISM: Homo sapiens
<220> FEATURE:
<223> OTHER INFORMATION: DENND4A C-myc promoter-binding protein;
      Q7Z401_C117
<220> FEATURE:
<221> NAME/KEY: MOD_RES
<222> LOCATION: (6)..(6)
<223> OTHER INFORMATION: Site of chemical conjugation

<400> SEQUENCE: 649

Arg Leu Lys Gln Gly Cys Glu Ile Ile Gln Ser Thr Pro Tyr Gly Arg
1               5                   10                  15

Pro Ala Asn Ile Ser Gly Ser Thr Ser Ser Gln Arg Ile
            20                  25

<210> SEQ ID NO 650
<211> LENGTH: 9
<212> TYPE: PRT
<213> ORGANISM: Homo sapiens
<220> FEATURE:
<223> OTHER INFORMATION: PNN Pinin;
      Q9H307_C249
<220> FEATURE:
<221> NAME/KEY: MOD_RES
<222> LOCATION: (3)..(3)
<223> OTHER INFORMATION: Site of chemical conjugation

<400> SEQUENCE: 650

Arg Met Cys Pro Ala Thr Gln Lys Leu
1               5

<210> SEQ ID NO 651
<211> LENGTH: 16
<212> TYPE: PRT
<213> ORGANISM: Homo sapiens
<220> FEATURE:
<223> OTHER INFORMATION: DGCR14 Protein DGCR14;
      Q96DF8_C263
<220> FEATURE:
<221> NAME/KEY: MOD_RES
<222> LOCATION: (2)..(2)
```

-continued

<223> OTHER INFORMATION: Site of chemical conjugation

<400> SEQUENCE: 651

Arg Cys Gln Leu Gln Gln Ala Ala Ala Leu Asn Ala Gln His Lys Gln
1               5                   10                  15

<210> SEQ ID NO 652
<211> LENGTH: 16
<212> TYPE: PRT
<213> ORGANISM: Homo sapiens
<220> FEATURE:
<223> OTHER INFORMATION: ATPBD4 ATP-binding domain-containing protein 4;
      Q7L8W6_C88
<220> FEATURE:
<221> NAME/KEY: MOD_RES
<222> LOCATION: (2)..(2)
<223> OTHER INFORMATION: Site of chemical conjugation

<400> SEQUENCE: 652

Lys Cys Glu Gly Asp Glu Val Glu Asp Leu Tyr Glu Leu Leu Lys Leu
1               5                   10                  15

<210> SEQ ID NO 653
<211> LENGTH: 18
<212> TYPE: PRT
<213> ORGANISM: Homo sapiens
<220> FEATURE:
<223> OTHER INFORMATION: NME3 Nucleoside diphosphate kinase 3;
      Q13232_C158
<220> FEATURE:
<221> NAME/KEY: MOD_RES
<222> LOCATION: (7)..(7)
<223> OTHER INFORMATION: Site of chemical conjugation

<400> SEQUENCE: 653

Arg Ala Asp Glu Leu Leu Cys Trp Glu Asp Ser Ala Gly His Trp Leu
1               5                   10                  15

Tyr Glu

<210> SEQ ID NO 654
<211> LENGTH: 11
<212> TYPE: PRT
<213> ORGANISM: Homo sapiens
<220> FEATURE:
<223> OTHER INFORMATION: MED9 Mediator of RNA polymerase II
      transcription subuni; Q9NWA0_C139
<220> FEATURE:
<221> NAME/KEY: MOD_RES
<222> LOCATION: (4)..(4)
<223> OTHER INFORMATION: Site of chemical conjugation

<400> SEQUENCE: 654

Lys Ser Leu Cys Met Phe Glu Ile Pro Lys Glu
1               5                   10

<210> SEQ ID NO 655
<211> LENGTH: 19
<212> TYPE: PRT
<213> ORGANISM: Homo sapiens
<220> FEATURE:
<223> OTHER INFORMATION: FRMD8 FERM domain-containing protein 8;
      Q9BZ67_C191
<220> FEATURE:
<221> NAME/KEY: MOD_RES
<222> LOCATION: (15)..(15)
<223> OTHER INFORMATION: Site of chemical conjugation

<400> SEQUENCE: 655

Arg Val Gln Leu Gly Pro Tyr Gln Pro Gly Arg Pro Ala Ala Cys Asp
1               5                   10                  15

```
1               5                   10                  15
Leu Arg Glu

<210> SEQ ID NO 656
<211> LENGTH: 18
<212> TYPE: PRT
<213> ORGANISM: Homo sapiens
<220> FEATURE:
<223> OTHER INFORMATION: IRAK1 Interleukin-1 receptor-associated kinase
      1; P51617_C608
<220> FEATURE:
<221> NAME/KEY: MOD_RES
<222> LOCATION: (9)..(9)
<223> OTHER INFORMATION: Site of chemical conjugation

<400> SEQUENCE: 656

Arg Ser Trp His Leu Thr Pro Ser Cys Pro Leu Asp Pro Ala Pro Leu
1               5                   10                  15

Arg Glu

<210> SEQ ID NO 657
<211> LENGTH: 18
<212> TYPE: PRT
<213> ORGANISM: Homo sapiens
<220> FEATURE:
<223> OTHER INFORMATION: LAS1L Ribosomal biogenesis protein LAS1L;
      Q9Y4W2_C140
<220> FEATURE:
<221> NAME/KEY: MOD_RES
<222> LOCATION: (2)..(2)
<223> OTHER INFORMATION: Site of chemical conjugation

<400> SEQUENCE: 657

Lys Cys Leu Ala Gln Glu Val Asn Ile Pro Asp Trp Ile Val Asp Leu
1               5                   10                  15

Arg His

<210> SEQ ID NO 658
<211> LENGTH: 16
<212> TYPE: PRT
<213> ORGANISM: Homo sapiens
<220> FEATURE:
<223> OTHER INFORMATION: SDHAF2 Succinate dehydrogenase assembly factor
      2, mitocho; Q9NX18_C83
<220> FEATURE:
<221> NAME/KEY: MOD_RES
<222> LOCATION: (7)..(7)
<223> OTHER INFORMATION: Site of chemical conjugation

<400> SEQUENCE: 658

Arg Gly Met Leu Glu Asn Cys Ile Leu Leu Ser Leu Phe Ala Lys Glu
1               5                   10                  15

<210> SEQ ID NO 659
<211> LENGTH: 20
<212> TYPE: PRT
<213> ORGANISM: Homo sapiens
<220> FEATURE:
<223> OTHER INFORMATION: POP5 Ribonuclease P/MRP protein subunit POP5;
      Q969H6_C146
<220> FEATURE:
<221> NAME/KEY: MOD_RES
<222> LOCATION: (3)..(3)
<223> OTHER INFORMATION: Site of chemical conjugation

<400> SEQUENCE: 659

Arg Ser Cys Leu Leu Glu Glu Glu Glu Glu Ser Gly Glu Glu Ala Ala
1               5                   10                  15
```

```
Glu Ala Met Glu
            20

<210> SEQ ID NO 660
<211> LENGTH: 15
<212> TYPE: PRT
<213> ORGANISM: Homo sapiens
<220> FEATURE:
<223> OTHER INFORMATION: NGLY1 Peptide-N(4)-(N-acetyl-beta-
      glucosaminyl)asparagin; Q96IV0_C309
<220> FEATURE:
<221> NAME/KEY: MOD_RES
<222> LOCATION: (2)..(2)
<223> OTHER INFORMATION: Site of chemical conjugation

<400> SEQUENCE: 660

Arg Cys Gly Glu Trp Ala Asn Cys Phe Thr Leu Cys Cys Arg Ala
1               5                   10                  15

<210> SEQ ID NO 661
<211> LENGTH: 13
<212> TYPE: PRT
<213> ORGANISM: Homo sapiens
<220> FEATURE:
<223> OTHER INFORMATION: CASP2 Caspase-2;
      P42575_C370
<220> FEATURE:
<221> NAME/KEY: MOD_RES
<222> LOCATION: (10)..(10)
<223> OTHER INFORMATION: Site of chemical conjugation

<400> SEQUENCE: 661

Arg Ser Asp Met Ile Cys Gly Tyr Ala Cys Leu Lys Gly
1               5                   10

<210> SEQ ID NO 662
<211> LENGTH: 14
<212> TYPE: PRT
<213> ORGANISM: Homo sapiens
<220> FEATURE:
<223> OTHER INFORMATION: RPS6KA3 Ribosomal protein S6 kinase alpha-3;
      P51812_C436
<220> FEATURE:
<221> NAME/KEY: MOD_RES
<222> LOCATION: (12)..(12)
<223> OTHER INFORMATION: Site of chemical conjugation

<400> SEQUENCE: 662

Lys Glu Asp Ile Gly Val Gly Ser Tyr Ser Val Cys Lys Arg
1               5                   10

<210> SEQ ID NO 663
<211> LENGTH: 8
<212> TYPE: PRT
<213> ORGANISM: Homo sapiens
<220> FEATURE:
<223> OTHER INFORMATION: POU2F2 POU domain, class 2, transcription
      factor 2; P09086_C346
<220> FEATURE:
<221> NAME/KEY: MOD_RES
<222> LOCATION: (5)..(5)
<223> OTHER INFORMATION: Site of chemical conjugation

<400> SEQUENCE: 663

Arg Val Trp Phe Cys Asn Arg Arg
1               5

<210> SEQ ID NO 664
<211> LENGTH: 23
```

```
<212> TYPE: PRT
<213> ORGANISM: Homo sapiens
<220> FEATURE:
<223> OTHER INFORMATION: UBR1 E3 ubiquitin-protein ligase UBR1;
      Q8IWV7_C1603
<220> FEATURE:
<221> NAME/KEY: MOD_RES
<222> LOCATION: (13)..(13)
<223> OTHER INFORMATION: Site of chemical conjugation

<400> SEQUENCE: 664

Arg Asn Ser Leu Ile Glu Leu Pro Asp Asp Tyr Ser Cys Leu Leu Asn
1               5                   10                  15

Gln Ala Ser His Phe Arg Cys
            20

<210> SEQ ID NO 665
<211> LENGTH: 9
<212> TYPE: PRT
<213> ORGANISM: Homo sapiens
<220> FEATURE:
<223> OTHER INFORMATION: SMG9 Protein SMG9;
      Q9H0W8_C380
<220> FEATURE:
<221> NAME/KEY: MOD_RES
<222> LOCATION: (6)..(6)
<223> OTHER INFORMATION: Site of chemical conjugation

<400> SEQUENCE: 665

Arg Arg Glu Asp Phe Cys Pro Arg Lys
1               5

<210> SEQ ID NO 666
<211> LENGTH: 13
<212> TYPE: PRT
<213> ORGANISM: Homo sapiens
<220> FEATURE:
<223> OTHER INFORMATION: CHEK2 Serine/threonine-protein kinase Chk2;
      O96017_C231
<220> FEATURE:
<221> NAME/KEY: MOD_RES
<222> LOCATION: (8)..(8)
<223> OTHER INFORMATION: Site of chemical conjugation

<400> SEQUENCE: 666

Lys Thr Leu Gly Ser Gly Ala Cys Gly Glu Val Lys Leu
1               5                   10

<210> SEQ ID NO 667
<211> LENGTH: 17
<212> TYPE: PRT
<213> ORGANISM: Homo sapiens
<220> FEATURE:
<223> OTHER INFORMATION: FNBP1 Formin-binding protein 1;
      Q96RU3_C70
<220> FEATURE:
<221> NAME/KEY: MOD_RES
<222> LOCATION: (15)..(15)
<223> OTHER INFORMATION: Site of chemical conjugation

<400> SEQUENCE: 667

Lys Lys Asn Ser Lys Glu Glu Glu Glu Tyr Lys Tyr Thr Ser Cys Lys
1               5                   10                  15

Ala

<210> SEQ ID NO 668
<211> LENGTH: 11
<212> TYPE: PRT
<213> ORGANISM: Homo sapiens
```

```
<220> FEATURE:
<223> OTHER INFORMATION: SMC2 Structural maintenance of chromosomes
      protein 2; O95347_C326
<220> FEATURE:
<221> NAME/KEY: MOD_RES
<222> LOCATION: (6)..(6)
<223> OTHER INFORMATION: Site of chemical conjugation

<400> SEQUENCE: 668

Lys Lys Asn Leu Ala Cys Glu Glu Ser Lys Arg
1               5                   10

<210> SEQ ID NO 669
<211> LENGTH: 15
<212> TYPE: PRT
<213> ORGANISM: Homo sapiens
<220> FEATURE:
<223> OTHER INFORMATION: INPPL1 Phosphatidylinositol 3,4,5-trisphosphate
      5-phospha; O15357_C926
<220> FEATURE:
<221> NAME/KEY: MOD_RES
<222> LOCATION: (10)..(10)
<223> OTHER INFORMATION: Site of chemical conjugation

<400> SEQUENCE: 669

Arg Lys Pro Ala Phe Thr Glu Ala Ser Cys Pro Leu Ser Arg Leu
1               5                   10                  15

<210> SEQ ID NO 670
<211> LENGTH: 32
<212> TYPE: PRT
<213> ORGANISM: Homo sapiens
<220> FEATURE:
<223> OTHER INFORMATION: RPP25L Ribonuclease P protein subunit p25-like
      protein; Q8N5L8_C131
<220> FEATURE:
<221> NAME/KEY: MOD_RES
<222> LOCATION: (9)..(9)
<223> OTHER INFORMATION: Site of chemical conjugation

<400> SEQUENCE: 670

Arg Asp Pro Leu Asp Pro Asn Glu Cys Gly Tyr Gln Pro Pro Gly Ala
1               5                   10                  15

Pro Pro Gly Leu Gly Ser Met Pro Ser Ser Ser Cys Gly Pro Arg Ser
            20                  25                  30

<210> SEQ ID NO 671
<211> LENGTH: 9
<212> TYPE: PRT
<213> ORGANISM: Homo sapiens
<220> FEATURE:
<223> OTHER INFORMATION: MTMR12 Myotubularin-related protein 12;
      Q9C0I1_C152
<220> FEATURE:
<221> NAME/KEY: MOD_RES
<222> LOCATION: (6)..(6)
<223> OTHER INFORMATION: Site of chemical conjugation

<400> SEQUENCE: 671

Arg Val Phe Gln Phe Cys Leu Arg Tyr
1               5

<210> SEQ ID NO 672
<211> LENGTH: 17
<212> TYPE: PRT
<213> ORGANISM: Homo sapiens
<220> FEATURE:
<223> OTHER INFORMATION: EDC3 Enhancer of mRNA-decapping protein 3;
      Q96F86_C137
<220> FEATURE:
```

-continued

```
<221> NAME/KEY: MOD_RES
<222> LOCATION: (14)..(14)
<223> OTHER INFORMATION: Site of chemical conjugation

<400> SEQUENCE: 672

Lys Ser Gln Asp Val Ala Val Ser Pro Gln Gln Gln Gln Cys Ser Lys
1               5                   10                  15

Ser

<210> SEQ ID NO 673
<211> LENGTH: 10
<212> TYPE: PRT
<213> ORGANISM: Homo sapiens
<220> FEATURE:
<223> OTHER INFORMATION: DFNA5 Non-syndromic hearing impairment protein
      5; O60443_C45
<220> FEATURE:
<221> NAME/KEY: MOD_RES
<222> LOCATION: (4)..(4)
<223> OTHER INFORMATION: Site of chemical conjugation

<400> SEQUENCE: 673

Arg Phe Trp Cys Trp Gln Arg Pro Lys Tyr
1               5                   10

<210> SEQ ID NO 674
<211> LENGTH: 14
<212> TYPE: PRT
<213> ORGANISM: Homo sapiens
<220> FEATURE:
<223> OTHER INFORMATION: MDN1 Midasin;
      Q9NU22_C1011
<220> FEATURE:
<221> NAME/KEY: MOD_RES
<222> LOCATION: (4)..(4)
<223> OTHER INFORMATION: Site of chemical conjugation

<400> SEQUENCE: 674

Lys Leu Ile Cys Gln His Ile Val Pro Gly Asn Val Lys Ser
1               5                   10

<210> SEQ ID NO 675
<211> LENGTH: 21
<212> TYPE: PRT
<213> ORGANISM: Homo sapiens
<220> FEATURE:
<223> OTHER INFORMATION: DYNC1H1 Cytoplasmic dynein 1 heavy chain 1;
      Q14204_C1059
<220> FEATURE:
<221> NAME/KEY: MOD_RES
<222> LOCATION: (8)..(8)
<223> OTHER INFORMATION: Site of chemical conjugation

<400> SEQUENCE: 675

Lys Val Trp Leu Gln Tyr Gln Cys Leu Trp Asp Met Gln Ala Glu Asn
1               5                   10                  15

Ile Tyr Asn Arg Leu
            20

<210> SEQ ID NO 676
<211> LENGTH: 14
<212> TYPE: PRT
<213> ORGANISM: Homo sapiens
<220> FEATURE:
<223> OTHER INFORMATION: EP300 Histone acetyltransferase p300;
      Q09472_C1738
<220> FEATURE:
<221> NAME/KEY: MOD_RES
<222> LOCATION: (2)..(2)
```

<223> OTHER INFORMATION: Site of chemical conjugation

<400> SEQUENCE: 676

Arg Cys Ile Gln Ser Leu Val His Ala Cys Gln Cys Arg Asn
1               5                   10

<210> SEQ ID NO 677
<211> LENGTH: 18
<212> TYPE: PRT
<213> ORGANISM: Homo sapiens
<220> FEATURE:
<223> OTHER INFORMATION: CKMT1B Creatine kinase U-type, mitochondrial;
      P12532_C316
<220> FEATURE:
<221> NAME/KEY: MOD_RES
<222> LOCATION: (8)..(8)
<223> OTHER INFORMATION: Site of chemical conjugation

<400> SEQUENCE: 677

Arg Leu Gly Tyr Ile Leu Thr Cys Pro Ser Asn Leu Gly Thr Gly Leu
1               5                   10                  15

Arg Ala

<210> SEQ ID NO 678
<211> LENGTH: 16
<212> TYPE: PRT
<213> ORGANISM: Homo sapiens
<220> FEATURE:
<223> OTHER INFORMATION: IMPACT Protein IMPACT;
      Q9P2X3_C195
<220> FEATURE:
<221> NAME/KEY: MOD_RES
<222> LOCATION: (13)..(13)
<223> OTHER INFORMATION: Site of chemical conjugation

<400> SEQUENCE: 678

Arg Ser Thr Phe Gln Ala His Leu Ala Pro Val Val Cys Pro Lys Gln
1               5                   10                  15

<210> SEQ ID NO 679
<211> LENGTH: 14
<212> TYPE: PRT
<213> ORGANISM: Homo sapiens
<220> FEATURE:
<223> OTHER INFORMATION: AKAP1 A-kinase anchor protein 1, mitochondrial;
      Q92667_C147
<220> FEATURE:
<221> NAME/KEY: MOD_RES
<222> LOCATION: (7)..(7)
<223> OTHER INFORMATION: Site of chemical conjugation

<400> SEQUENCE: 679

Lys Ser Ile Pro Leu Glu Cys Pro Leu Ser Ser Pro Lys Gly
1               5                   10

<210> SEQ ID NO 680
<211> LENGTH: 22
<212> TYPE: PRT
<213> ORGANISM: Homo sapiens
<220> FEATURE:
<223> OTHER INFORMATION: IFIT3 Interferon-induced protein with
      tetratricopeptide; O14879_C283
<220> FEATURE:
<221> NAME/KEY: MOD_RES
<222> LOCATION: (18)..(18)
<223> OTHER INFORMATION: Site of chemical conjugation

<400> SEQUENCE: 680

Arg Val Leu Glu Ser Thr Pro Asn Asn Gly Tyr Leu Tyr His Gln Ile
1               5                   10                  15

```
1               5                   10                  15

Gly Cys Cys Tyr Lys Ala
                20

<210> SEQ ID NO 681
<211> LENGTH: 30
<212> TYPE: PRT
<213> ORGANISM: Homo sapiens
<220> FEATURE:
<223> OTHER INFORMATION: RELB Transcription factor RelB;
      Q01201_C109
<220> FEATURE:
<221> NAME/KEY: MOD_RES
<222> LOCATION: (25)..(25)
<223> OTHER INFORMATION: Site of chemical conjugation

<400> SEQUENCE: 681

Arg Gly Ala Ala Ser Leu Ser Thr Val Thr Leu Gly Pro Val Ala Pro
1               5                   10                  15

Pro Ala Thr Pro Pro Trp Gly Cys Pro Leu Gly Arg Leu
                20                  25                  30

<210> SEQ ID NO 682
<211> LENGTH: 16
<212> TYPE: PRT
<213> ORGANISM: Homo sapiens
<220> FEATURE:
<223> OTHER INFORMATION: TRIM33 E3 ubiquitin-protein ligase TRIM33;
      Q9UPN9_C582
<220> FEATURE:
<221> NAME/KEY: MOD_RES
<222> LOCATION: (6)..(6)
<223> OTHER INFORMATION: Site of chemical conjugation

<400> SEQUENCE: 682

Arg Gly Asn Met Asn Cys Gly Ala Phe Gln Ala His Gln Met Arg Leu
1               5                   10                  15

<210> SEQ ID NO 683
<211> LENGTH: 11
<212> TYPE: PRT
<213> ORGANISM: Homo sapiens
<220> FEATURE:
<223> OTHER INFORMATION: NTPCR Cancer-related nucleoside-triphosphatase;
      Q9BSD7_C110
<220> FEATURE:
<221> NAME/KEY: MOD_RES
<222> LOCATION: (3)..(3)
<223> OTHER INFORMATION: Site of chemical conjugation

<400> SEQUENCE: 683

Arg Val Cys Val Ile Asp Glu Ile Gly Lys Met
1               5                   10

<210> SEQ ID NO 684
<211> LENGTH: 18
<212> TYPE: PRT
<213> ORGANISM: Homo sapiens
<220> FEATURE:
<223> OTHER INFORMATION: DENND1C DENN domain-containing protein 1C;
      Q8IV53_C174
<220> FEATURE:
<221> NAME/KEY: MOD_RES
<222> LOCATION: (9)..(9)
<223> OTHER INFORMATION: Site of chemical conjugation

<400> SEQUENCE: 684

Arg Gly Asn Ser Lys Pro Leu Ser Cys Phe Val Ala Pro Asp Ser Gly
1               5                   10                  15
```

Arg Leu

<210> SEQ ID NO 685
<211> LENGTH: 19
<212> TYPE: PRT
<213> ORGANISM: Homo sapiens
<220> FEATURE:
<223> OTHER INFORMATION: ACO2 Aconitate hydratase, mitochondrial;
      Q99798_C385
<220> FEATURE:
<221> NAME/KEY: MOD_RES
<222> LOCATION: (8)..(8)
<223> OTHER INFORMATION: Site of chemical conjugation

<400> SEQUENCE: 685

Arg Val Gly Leu Ile Gly Ser Cys Thr Asn Ser Ser Tyr Glu Asp Met
1               5                   10                  15

Gly Arg Ser

<210> SEQ ID NO 686
<211> LENGTH: 26
<212> TYPE: PRT
<213> ORGANISM: Homo sapiens
<220> FEATURE:
<223> OTHER INFORMATION: DYNC1H1 Cytoplasmic dynein 1 heavy chain 1;
      Q14204_C3089
<220> FEATURE:
<221> NAME/KEY: MOD_RES
<222> LOCATION: (2)..(2)
<223> OTHER INFORMATION: Site of chemical conjugation

<400> SEQUENCE: 686

Arg Cys Val Leu Asn Trp Phe Gly Asp Trp Ser Thr Glu Ala Leu Tyr
1               5                   10                  15

Gln Val Gly Lys Glu Phe Thr Ser Lys Met
            20                  25

<210> SEQ ID NO 687
<211> LENGTH: 12
<212> TYPE: PRT
<213> ORGANISM: Homo sapiens
<220> FEATURE:
<223> OTHER INFORMATION: SEPHS1 Selenide, water dikinase 1;
      P49903_C31
<220> FEATURE:
<221> NAME/KEY: MOD_RES
<222> LOCATION: (10)..(10)
<223> OTHER INFORMATION: Site of chemical conjugation

<400> SEQUENCE: 687

Arg Phe Thr Glu Leu Lys Gly Thr Gly Cys Lys Val
1               5                   10

<210> SEQ ID NO 688
<211> LENGTH: 19
<212> TYPE: PRT
<213> ORGANISM: Homo sapiens
<220> FEATURE:
<223> OTHER INFORMATION: USP34 Ubiquitin carboxyl-terminal hydrolase 34;
      Q70CQ2_C741
<220> FEATURE:
<221> NAME/KEY: MOD_RES
<222> LOCATION: (17)..(17)
<223> OTHER INFORMATION: Site of chemical conjugation

<400> SEQUENCE: 688

Arg Thr Gly Asp Phe Leu Gly Glu Thr Ile Gly Asn Glu Leu Phe Asn
1               5                   10                  15

Cys Arg Gln

<210> SEQ ID NO 689
<211> LENGTH: 27
<212> TYPE: PRT
<213> ORGANISM: Homo sapiens
<220> FEATURE:
<223> OTHER INFORMATION: CBFA2T2 Protein CBFA2T2;
      O43439_C111
<220> FEATURE:
<221> NAME/KEY: MOD_RES
<222> LOCATION: (23)..(23)
<223> OTHER INFORMATION: Site of chemical conjugation

<400> SEQUENCE: 689

Arg Phe Ser Asn Gly Pro Ala Ser Ser Thr Ser Ser Ala Leu Thr Asn
1               5                   10                  15

Gln Gln Leu Pro Ala Thr Cys Gly Ala Arg Gln
            20                  25

<210> SEQ ID NO 690
<211> LENGTH: 20
<212> TYPE: PRT
<213> ORGANISM: Homo sapiens
<220> FEATURE:
<223> OTHER INFORMATION: RPAP1 RNA polymerase II-associated protein 1;
      Q9BWH6_C1039
<220> FEATURE:
<221> NAME/KEY: MOD_RES
<222> LOCATION: (2)..(2)
<223> OTHER INFORMATION: Site of chemical conjugation

<400> SEQUENCE: 690

Arg Cys Gly Gln Gly Thr Leu Leu Ala Gln Ala Cys Gln Asp Leu Pro
1               5                   10                  15

Ser Ile Arg Asn
            20

<210> SEQ ID NO 691
<211> LENGTH: 21
<212> TYPE: PRT
<213> ORGANISM: Homo sapiens
<220> FEATURE:
<223> OTHER INFORMATION: ANKRD40 Ankyrin repeat domain-containing
      protein 40; Q6AI12_C209
<220> FEATURE:
<221> NAME/KEY: MOD_RES
<222> LOCATION: (12)..(12)
<223> OTHER INFORMATION: Site of chemical conjugation

<400> SEQUENCE: 691

Arg Thr Pro Glu Ser Thr Lys Pro Gly Pro Val Cys Gln Pro Pro Val
1               5                   10                  15

Ser Gln Ser Arg Ser
            20

<210> SEQ ID NO 692
<211> LENGTH: 28
<212> TYPE: PRT
<213> ORGANISM: Homo sapiens
<220> FEATURE:
<223> OTHER INFORMATION: HERC4 Probable E3 ubiquitin-protein ligase
      HERC4; Q5GLZ8_C60
<220> FEATURE:
<221> NAME/KEY: MOD_RES
<222> LOCATION: (17)..(17)
<223> OTHER INFORMATION: Site of chemical conjugation

```
<400> SEQUENCE: 692

Arg His Thr Val Phe Val Leu Asp Asp Gly Thr Val Tyr Thr Cys Gly
1               5                   10                  15

Cys Asn Asp Leu Gly Gln Leu Gly His Glu Lys Ser
            20                  25

<210> SEQ ID NO 693
<211> LENGTH: 12
<212> TYPE: PRT
<213> ORGANISM: Homo sapiens
<220> FEATURE:
<223> OTHER INFORMATION: NUB1 NEDD8 ultimate buster 1;
      Q9Y5A7_C52
<220> FEATURE:
<221> NAME/KEY: MOD_RES
<222> LOCATION: (5)..(5)
<223> OTHER INFORMATION: Site of chemical conjugation

<400> SEQUENCE: 693

Arg Leu Glu Cys Cys Glu Asn Glu Val Glu Lys Val
1               5                   10

<210> SEQ ID NO 694
<211> LENGTH: 18
<212> TYPE: PRT
<213> ORGANISM: Homo sapiens
<220> FEATURE:
<223> OTHER INFORMATION: BRAT1 BRCA1-associated ATM activator 1;
      Q6PJG6_C326
<220> FEATURE:
<221> NAME/KEY: MOD_RES
<222> LOCATION: (14)..(14)
<223> OTHER INFORMATION: Site of chemical conjugation

<400> SEQUENCE: 694

Arg Thr Gln Ala Phe Gln Val Leu Leu Gln Pro Leu Ala Cys Val Leu
1               5                   10                  15

Lys Ala

<210> SEQ ID NO 695
<211> LENGTH: 25
<212> TYPE: PRT
<213> ORGANISM: Homo sapiens
<220> FEATURE:
<223> OTHER INFORMATION: BRAT1 BRCA1-associated ATM activator 1;
      Q6PJG6_C673
<220> FEATURE:
<221> NAME/KEY: MOD_RES
<222> LOCATION: (4)..(4)
<223> OTHER INFORMATION: Site of chemical conjugation

<400> SEQUENCE: 695

Arg Thr His Cys Pro Tyr Ala Val Ala Leu Pro Glu Val Ala Pro Ala
1               5                   10                  15

Gln Pro Leu Thr Glu Ala Leu Arg Ala
            20                  25

<210> SEQ ID NO 696
<211> LENGTH: 14
<212> TYPE: PRT
<213> ORGANISM: Homo sapiens
<220> FEATURE:
<223> OTHER INFORMATION: SPATA5 Spermatogenesis-associated protein 5;
      Q8NB90_C672
<220> FEATURE:
<221> NAME/KEY: MOD_RES
<222> LOCATION: (11)..(11)
<223> OTHER INFORMATION: Site of chemical conjugation
```

```
<400> SEQUENCE: 696

Lys Gly Val Leu Leu Tyr Gly Pro Pro Gly Cys Ser Lys Thr
1               5                   10

<210> SEQ ID NO 697
<211> LENGTH: 13
<212> TYPE: PRT
<213> ORGANISM: Homo sapiens
<220> FEATURE:
<223> OTHER INFORMATION: HECTD1 E3 ubiquitin-protein ligase HECTD1;
      Q9ULT8_C1855
<220> FEATURE:
<221> NAME/KEY: MOD_RES
<222> LOCATION: (7)..(7)
<223> OTHER INFORMATION: Site of chemical conjugation

<400> SEQUENCE: 697

Lys Leu Leu Gln Leu Ser Cys Asn Gly Asn Val Lys Ser
1               5                   10

<210> SEQ ID NO 698
<211> LENGTH: 11
<212> TYPE: PRT
<213> ORGANISM: Homo sapiens
<220> FEATURE:
<223> OTHER INFORMATION: DECR2 Peroxisomal 2,4-dienoyl-CoA reductase;
      Q9NUI1_C22
<220> FEATURE:
<221> NAME/KEY: MOD_RES
<222> LOCATION: (5)..(5)
<223> OTHER INFORMATION: Site of chemical conjugation

<400> SEQUENCE: 698

Arg His Leu Phe Cys Pro Asp Leu Leu Arg Asp
1               5                   10

<210> SEQ ID NO 699
<211> LENGTH: 21
<212> TYPE: PRT
<213> ORGANISM: Homo sapiens
<220> FEATURE:
<223> OTHER INFORMATION: SEPT10 Septin-10;
      Q9P0V9_C293
<220> FEATURE:
<221> NAME/KEY: MOD_RES
<222> LOCATION: (16)..(16)
<223> OTHER INFORMATION: Site of chemical conjugation

<400> SEQUENCE: 699

Arg Gln Tyr Pro Trp Gly Val Val Gln Val Glu Asn Glu Asn His Cys
1               5                   10                  15

Asp Phe Val Lys Leu
            20

<210> SEQ ID NO 700
<211> LENGTH: 9
<212> TYPE: PRT
<213> ORGANISM: Homo sapiens
<220> FEATURE:
<223> OTHER INFORMATION: PALLD Palladin;
      Q8WX93_C964
<220> FEATURE:
<221> NAME/KEY: MOD_RES
<222> LOCATION: (5)..(5)
<223> OTHER INFORMATION: Site of chemical conjugation

<400> SEQUENCE: 700

Lys Val Ser Ser Cys Glu Gln Arg Leu
```

```
<210> SEQ ID NO 701
<211> LENGTH: 15
<212> TYPE: PRT
<213> ORGANISM: Homo sapiens
<220> FEATURE:
<223> OTHER INFORMATION: RAD54L2 Helicase ARIP4;
      Q9Y4B4_C820
<220> FEATURE:
<221> NAME/KEY: MOD_RES
<222> LOCATION: (4)..(4)
<223> OTHER INFORMATION: Site of chemical conjugation

<400> SEQUENCE: 701

Arg Ala Gly Cys Leu Gly Val Asn Leu Ile Gly Ala Asn Arg Val
1               5                   10                  15

<210> SEQ ID NO 702
<211> LENGTH: 21
<212> TYPE: PRT
<213> ORGANISM: Homo sapiens
<220> FEATURE:
<223> OTHER INFORMATION: UBA7 Ubiquitin-like modifier-activating enzyme
      7; P41226_C599
<220> FEATURE:
<221> NAME/KEY: MOD_RES
<222> LOCATION: (17)..(17)
<223> OTHER INFORMATION: Site of chemical conjugation

<400> SEQUENCE: 702

Arg Ala Pro Ala Ser Ala Ala Ala Ser Glu Asp Ala Pro Tyr Pro Val
1               5                   10                  15

Cys Thr Val Arg Tyr
            20

<210> SEQ ID NO 703
<211> LENGTH: 11
<212> TYPE: PRT
<213> ORGANISM: Homo sapiens
<220> FEATURE:
<223> OTHER INFORMATION: EDEM3 ER degradation-enhancing alpha-
      mannosidase-like 3; Q9BZQ6_C441
<220> FEATURE:
<221> NAME/KEY: MOD_RES
<222> LOCATION: (4)..(4)
<223> OTHER INFORMATION: Site of chemical conjugation

<400> SEQUENCE: 703

Arg Val Pro Cys Gly Phe Ala Ala Met Lys Asp
1               5                   10

<210> SEQ ID NO 704
<211> LENGTH: 30
<212> TYPE: PRT
<213> ORGANISM: Homo sapiens
<220> FEATURE:
<223> OTHER INFORMATION: KIF11 Kinesin-like protein KIF11;
      P52732_C87
<220> FEATURE:
<221> NAME/KEY: MOD_RES
<222> LOCATION: (5)..(5)
<223> OTHER INFORMATION: Site of chemical conjugation

<400> SEQUENCE: 704

Arg Ser Val Val Cys Pro Ile Leu Asp Glu Val Ile Met Gly Tyr Asn
1               5                   10                  15

Cys Thr Ile Phe Ala Tyr Gly Gln Thr Gly Thr Gly Lys Thr
            20                  25                  30
```

```
<210> SEQ ID NO 705
<211> LENGTH: 8
<212> TYPE: PRT
<213> ORGANISM: Homo sapiens
<220> FEATURE:
<223> OTHER INFORMATION: NCF1 Neutrophil cytosol factor 1;
      P14598_C378
<220> FEATURE:
<221> NAME/KEY: MOD_RES
<222> LOCATION: (2)..(2)
<223> OTHER INFORMATION: Site of chemical conjugation

<400> SEQUENCE: 705

Arg Cys Ser Glu Ser Thr Lys Arg
1               5

<210> SEQ ID NO 706
<211> LENGTH: 13
<212> TYPE: PRT
<213> ORGANISM: Homo sapiens
<220> FEATURE:
<223> OTHER INFORMATION: ZNF346 Zinc finger protein 346;
      Q9UL40_C68
<220> FEATURE:
<221> NAME/KEY: MOD_RES
<222> LOCATION: (4)..(4)
<223> OTHER INFORMATION: Site of chemical conjugation

<400> SEQUENCE: 706

Lys Asn Gln Cys Leu Phe Thr Asn Thr Gln Cys Lys Val
1               5                   10

<210> SEQ ID NO 707
<211> LENGTH: 13
<212> TYPE: PRT
<213> ORGANISM: Homo sapiens
<220> FEATURE:
<223> OTHER INFORMATION: UBE2O Ubiquitin-conjugating enzyme E2 O;
      Q9C0C9_C375
<220> FEATURE:
<221> NAME/KEY: MOD_RES
<222> LOCATION: (3)..(3)
<223> OTHER INFORMATION: Site of chemical conjugation

<400> SEQUENCE: 707

Lys Asn Cys Ala Gln Gly Glu Gly Ser Met Ala Lys Lys
1               5                   10

<210> SEQ ID NO 708
<211> LENGTH: 14
<212> TYPE: PRT
<213> ORGANISM: Homo sapiens
<220> FEATURE:
<223> OTHER INFORMATION: MAP2K7 Dual specificity mitogen-activated
      protein kinase; O14733_C280
<220> FEATURE:
<221> NAME/KEY: MOD_RES
<222> LOCATION: (5)..(5)
<223> OTHER INFORMATION: Site of chemical conjugation

<400> SEQUENCE: 708

Arg Ser Ala Gly Cys Ala Ala Tyr Met Ala Pro Glu Arg Ile
1               5                   10

<210> SEQ ID NO 709
<211> LENGTH: 19
<212> TYPE: PRT
<213> ORGANISM: Homo sapiens
<220> FEATURE:
```

-continued

<223> OTHER INFORMATION: KIF4A Chromosome-associated kinesin KIF4A;
       O95239_C269
<220> FEATURE:
<221> NAME/KEY: MOD_RES
<222> LOCATION: (5)..(5)
<223> OTHER INFORMATION: Site of chemical conjugation

<400> SEQUENCE: 709

Arg Gly Leu Leu Cys Leu Gly Asn Val Ile Ser Ala Leu Gly Asp Asp
1               5                   10                  15

Lys Lys Gly

<210> SEQ ID NO 710
<211> LENGTH: 12
<212> TYPE: PRT
<213> ORGANISM: Homo sapiens
<220> FEATURE:
<223> OTHER INFORMATION: AHCTF1 Protein ELYS;
       Q8WYP5_C521
<220> FEATURE:
<221> NAME/KEY: MOD_RES
<222> LOCATION: (2)..(2)
<223> OTHER INFORMATION: Site of chemical conjugation

<400> SEQUENCE: 710

Arg Cys Leu Val Ala Gly Leu Leu Ser Pro Arg Phe
1               5                   10

<210> SEQ ID NO 711
<211> LENGTH: 21
<212> TYPE: PRT
<213> ORGANISM: Homo sapiens
<220> FEATURE:
<223> OTHER INFORMATION: MED12 Mediator of RNA polymerase II
       transcription subuni; Q93074_C1188
<220> FEATURE:
<221> NAME/KEY: MOD_RES
<222> LOCATION: (8)..(8)
<223> OTHER INFORMATION: Site of chemical conjugation

<400> SEQUENCE: 711

Lys Thr Pro Gln Leu Asn Pro Cys Gln Ser Asp Gly Asn Lys Pro Thr
1               5                   10                  15

Val Gly Ile Arg Ser
            20

<210> SEQ ID NO 712
<211> LENGTH: 30
<212> TYPE: PRT
<213> ORGANISM: Homo sapiens
<220> FEATURE:
<223> OTHER INFORMATION: ECM1 Extracellular matrix protein 1;
       Q16610_C284
<220> FEATURE:
<221> NAME/KEY: MOD_RES
<222> LOCATION: (3)..(3)
<223> OTHER INFORMATION: Site of chemical conjugation

<400> SEQUENCE: 712

Arg Ala Cys Pro Ser His Gln Pro Asp Ile Ser Ser Gly Leu Glu Leu
1               5                   10                  15

Pro Phe Pro Pro Gly Val Pro Thr Leu Asp Asn Ile Lys Asn
            20                  25                  30

<210> SEQ ID NO 713
<211> LENGTH: 33
<212> TYPE: PRT
<213> ORGANISM: Homo sapiens

```
<220> FEATURE:
<223> OTHER INFORMATION: CYR61 Protein CYR61;
      O00622_C134
<220> FEATURE:
<221> NAME/KEY: MOD_RES
<222> LOCATION: (17)..(17)
<223> OTHER INFORMATION: Site of chemical conjugation

<400> SEQUENCE: 713

Lys His Gln Cys Thr Cys Ile Asp Gly Ala Val Gly Cys Ile Pro Leu
1               5                   10                  15

Cys Pro Gln Glu Leu Ser Leu Pro Asn Leu Gly Cys Pro Asn Pro Arg
            20                  25                  30

Leu

<210> SEQ ID NO 714
<211> LENGTH: 18
<212> TYPE: PRT
<213> ORGANISM: Homo sapiens
<220> FEATURE:
<223> OTHER INFORMATION: CTU2 Cytoplasmic tRNA 2-thiolation protein 2;
      Q2VPK5_C433
<220> FEATURE:
<221> NAME/KEY: MOD_RES
<222> LOCATION: (7)..(7)
<223> OTHER INFORMATION: Site of chemical conjugation

<400> SEQUENCE: 714

Arg Thr Pro Pro Gly Pro Cys Cys Ser Pro Gly Val Gly Trp Ala Gln
1               5                   10                  15

Arg Cys

<210> SEQ ID NO 715
<211> LENGTH: 20
<212> TYPE: PRT
<213> ORGANISM: Homo sapiens
<220> FEATURE:
<223> OTHER INFORMATION: EIF2B4 Translation initiation factor eIF-2B
      subunit delta; Q9UI10_C444
<220> FEATURE:
<221> NAME/KEY: MOD_RES
<222> LOCATION: (17)..(17)
<223> OTHER INFORMATION: Site of chemical conjugation

<400> SEQUENCE: 715

Arg Ala His Asn Val Pro Val Leu Val Cys Cys Glu Thr Tyr Lys Phe
1               5                   10                  15

Cys Glu Arg Val
            20

<210> SEQ ID NO 716
<211> LENGTH: 28
<212> TYPE: PRT
<213> ORGANISM: Homo sapiens
<220> FEATURE:
<223> OTHER INFORMATION: AGTPBP1 Cytosolic carboxypeptidase 1;
      Q9UPW5_C1164
<220> FEATURE:
<221> NAME/KEY: MOD_RES
<222> LOCATION: (26)..(26)
<223> OTHER INFORMATION: Site of chemical conjugation

<400> SEQUENCE: 716

Arg Leu Thr Ser Pro Leu Glu Tyr Asn Leu Pro Ser Ser Leu Leu Asp
1               5                   10                  15

Phe Glu Asn Asp Leu Ile Glu Ser Ser Cys Lys Val
            20                  25
```

<210> SEQ ID NO 717
<211> LENGTH: 24
<212> TYPE: PRT
<213> ORGANISM: Homo sapiens
<220> FEATURE:
<223> OTHER INFORMATION: MTMR1 Myotubularin-related protein 1;
      Q13613_C117
<220> FEATURE:
<221> NAME/KEY: MOD_RES
<222> LOCATION: (7)..(7)
<223> OTHER INFORMATION: Site of chemical conjugation

<400> SEQUENCE: 717

Lys Asp Val Met Tyr Ile Cys Pro Phe Met Gly Ala Val Ser Gly Thr
1               5                   10                  15

Leu Thr Val Thr Asp Phe Lys Leu
            20

<210> SEQ ID NO 718
<211> LENGTH: 16
<212> TYPE: PRT
<213> ORGANISM: Homo sapiens
<220> FEATURE:
<223> OTHER INFORMATION: PES1 Pescadillo homolog;
      O00541_C361
<220> FEATURE:
<221> NAME/KEY: MOD_RES
<222> LOCATION: (4)..(4)
<223> OTHER INFORMATION: Site of chemical conjugation

<400> SEQUENCE: 718

Lys Ser Leu Cys Ile Gly Ala Thr Tyr Asp Val Thr Asp Ser Arg Ile
1               5                   10                  15

<210> SEQ ID NO 719
<211> LENGTH: 24
<212> TYPE: PRT
<213> ORGANISM: Homo sapiens
<220> FEATURE:
<223> OTHER INFORMATION: PLA2G5 Calcium-dependent phospholipase A2;
      P39877_C46
<220> FEATURE:
<221> NAME/KEY: MOD_RES
<222> LOCATION: (16)..(16)
<223> OTHER INFORMATION: Site of chemical conjugation

<400> SEQUENCE: 719

Lys Val Thr Gly Lys Asn Ala Leu Thr Asn Tyr Gly Phe Tyr Gly Cys
1               5                   10                  15

Tyr Cys Gly Trp Gly Gly Arg Gly
            20

<210> SEQ ID NO 720
<211> LENGTH: 24
<212> TYPE: PRT
<213> ORGANISM: Homo sapiens
<220> FEATURE:
<223> OTHER INFORMATION: NPAT Protein NPAT;
      Q14207_C1059
<220> FEATURE:
<221> NAME/KEY: MOD_RES
<222> LOCATION: (21)..(21)
<223> OTHER INFORMATION: Site of chemical conjugation

<400> SEQUENCE: 720

Lys Ser Glu Glu Thr Thr Val Pro Phe Pro Glu Glu Ser Ile Val Pro
1               5                   10                  15

```
Ala Ala Lys Pro Cys His Arg Arg
            20

<210> SEQ ID NO 721
<211> LENGTH: 23
<212> TYPE: PRT
<213> ORGANISM: Homo sapiens
<220> FEATURE:
<223> OTHER INFORMATION: LRPPRC Leucine-rich PPR motif-containing
      protein, mitocho; P42704_C500
<220> FEATURE:
<221> NAME/KEY: MOD_RES
<222> LOCATION: (9)..(9)
<223> OTHER INFORMATION: Site of chemical conjugation

<400> SEQUENCE: 721

Arg Ala Ile Leu Gln Glu Asn Gly Cys Leu Ser Asp Ser Asp Met Phe
1               5                   10                  15

Ser Gln Ala Gly Leu Arg Ser
            20

<210> SEQ ID NO 722
<211> LENGTH: 18
<212> TYPE: PRT
<213> ORGANISM: Homo sapiens
<220> FEATURE:
<223> OTHER INFORMATION: TRAPPC1 Trafficking protein particle complex
      subunit 1; Q9Y5R8_C115
<220> FEATURE:
<221> NAME/KEY: MOD_RES
<222> LOCATION: (5)..(5)
<223> OTHER INFORMATION: Site of chemical conjugation

<400> SEQUENCE: 722

Lys Asn Pro Leu Cys Pro Leu Gly Gln Thr Val Gln Ser Glu Leu Phe
1               5                   10                  15

Arg Ser

<210> SEQ ID NO 723
<211> LENGTH: 20
<212> TYPE: PRT
<213> ORGANISM: Homo sapiens
<220> FEATURE:
<223> OTHER INFORMATION: BUB1B Mitotic checkpoint serine/threonine-
      protein kinase; O60566_C504
<220> FEATURE:
<221> NAME/KEY: MOD_RES
<222> LOCATION: (17)..(17)
<223> OTHER INFORMATION: Site of chemical conjugation

<400> SEQUENCE: 723

Lys Ile Pro Gly Met Thr Leu Ser Ser Ser Val Cys Gln Val Asn Cys
1               5                   10                  15

Cys Ala Arg Glu
            20

<210> SEQ ID NO 724
<211> LENGTH: 13
<212> TYPE: PRT
<213> ORGANISM: Homo sapiens
<220> FEATURE:
<223> OTHER INFORMATION: IBA57 Putative transferase CAF17,
      mitochondrial; Q5T440_C259
<220> FEATURE:
<221> NAME/KEY: MOD_RES
<222> LOCATION: (3)..(3)
<223> OTHER INFORMATION: Site of chemical conjugation

<400> SEQUENCE: 724
```

```
Lys Gly Cys Tyr Ile Gly Gln Glu Leu Thr Ala Arg Thr
1               5                   10
```

```
<210> SEQ ID NO 725
<211> LENGTH: 26
<212> TYPE: PRT
<213> ORGANISM: Homo sapiens
<220> FEATURE:
<223> OTHER INFORMATION: AHDC1 AT-hook DNA-binding motif-containing
      protein 1; Q5TGY3_C1540
<220> FEATURE:
<221> NAME/KEY: MOD_RES
<222> LOCATION: (12)..(12)
<223> OTHER INFORMATION: Site of chemical conjugation

<400> SEQUENCE: 725

Arg Gly Pro Ala Ala Ala Ala Gly Tyr Gly Cys Pro Leu Leu Ser
1               5                   10                  15

Asp Leu Thr Leu Ser Pro Val Pro Arg Asp
                20                  25
```

```
<210> SEQ ID NO 726
<211> LENGTH: 17
<212> TYPE: PRT
<213> ORGANISM: Homo sapiens
<220> FEATURE:
<223> OTHER INFORMATION: ZAP70 Tyrosine-protein kinase ZAP-70;
      P43403_C117
<220> FEATURE:
<221> NAME/KEY: MOD_RES
<222> LOCATION: (14)..(14)
<223> OTHER INFORMATION: Site of chemical conjugation

<400> SEQUENCE: 726

Arg Pro Ser Gly Leu Glu Pro Gln Pro Gly Val Phe Asp Cys Leu Arg
1               5                   10                  15

Asp
```

```
<210> SEQ ID NO 727
<211> LENGTH: 15
<212> TYPE: PRT
<213> ORGANISM: Homo sapiens
<220> FEATURE:
<223> OTHER INFORMATION: PSAP Proactivator polypeptide;
      P07602_C48
<220> FEATURE:
<221> NAME/KEY: MOD_RES
<222> LOCATION: (3)..(3)
<223> OTHER INFORMATION: Site of chemical conjugation

<400> SEQUENCE: 727

Lys His Cys Leu Gln Thr Val Trp Asn Lys Pro Thr Val Lys Ser
1               5                   10                  15
```

```
<210> SEQ ID NO 728
<211> LENGTH: 14
<212> TYPE: PRT
<213> ORGANISM: Homo sapiens
<220> FEATURE:
<223> OTHER INFORMATION: MED12 Mediator of RNA polymerase II
      transcription subuni; Q93074_C444
<220> FEATURE:
<221> NAME/KEY: MOD_RES
<222> LOCATION: (2)..(2)
<223> OTHER INFORMATION: Site of chemical conjugation

<400> SEQUENCE: 728

Lys Cys Gln Glu Ala Thr Ala Gly Phe Thr Ile Gly Arg Val
```

-continued

```
<210> SEQ ID NO 729
<211> LENGTH: 25
<212> TYPE: PRT
<213> ORGANISM: Homo sapiens
<220> FEATURE:
<223> OTHER INFORMATION: PELI1 E3 ubiquitin-protein ligase pellino
      homolog 1; Q96FA3_C282
<220> FEATURE:
<221> NAME/KEY: MOD_RES
<222> LOCATION: (11)..(11)
<223> OTHER INFORMATION: Site of chemical conjugation

<400> SEQUENCE: 729

Arg Gln Glu Ile Asn Ala Ala Arg Pro Gln Cys Pro Val Gly Phe Asn
1               5                   10                  15

Thr Leu Ala Phe Pro Ser Met Lys Arg
            20                  25

<210> SEQ ID NO 730
<211> LENGTH: 10
<212> TYPE: PRT
<213> ORGANISM: Homo sapiens
<220> FEATURE:
<223> OTHER INFORMATION: PNPLA6 Neuropathy target esterase;
      Q8IY17_C1199
<220> FEATURE:
<221> NAME/KEY: MOD_RES
<222> LOCATION: (7)..(7)
<223> OTHER INFORMATION: Site of chemical conjugation

<400> SEQUENCE: 730

Arg Leu Ala Tyr Val Ser Cys Val Arg Gln
1               5                   10

<210> SEQ ID NO 731
<211> LENGTH: 22
<212> TYPE: PRT
<213> ORGANISM: Homo sapiens
<220> FEATURE:
<223> OTHER INFORMATION: SMC5 Structural maintenance of chromosomes
      protein 5; Q8IY18_C91
<220> FEATURE:
<221> NAME/KEY: MOD_RES
<222> LOCATION: (6)..(6)
<223> OTHER INFORMATION: Site of chemical conjugation

<400> SEQUENCE: 731

Lys Ser Ser Ile Val Cys Ala Ile Cys Leu Gly Leu Ala Gly Lys Pro
1               5                   10                  15

Ala Phe Met Gly Arg Ala
            20

<210> SEQ ID NO 732
<211> LENGTH: 14
<212> TYPE: PRT
<213> ORGANISM: Homo sapiens
<220> FEATURE:
<223> OTHER INFORMATION: SMC4 Structural maintenance of chromosomes
      protein 4; Q9NTJ3_C110
<220> FEATURE:
<221> NAME/KEY: MOD_RES
<222> LOCATION: (4)..(4)
<223> OTHER INFORMATION: Site of chemical conjugation

<400> SEQUENCE: 732

Arg Phe Ser Cys Ile Ile Gly Pro Asn Gly Ser Gly Lys Ser
1               5                   10
```

```
<210> SEQ ID NO 733
<211> LENGTH: 26
<212> TYPE: PRT
<213> ORGANISM: Homo sapiens
<220> FEATURE:
<223> OTHER INFORMATION: CKAP4 Cytoskeleton-associated protein 4;
      Q07065_C100
<220> FEATURE:
<221> NAME/KEY: MOD_RES
<222> LOCATION: (23)..(23)
<223> OTHER INFORMATION: Site of chemical conjugation

<400> SEQUENCE: 733

Lys Ser Ser Ser Ser Ser Ser Ala Ser Ala Ala Ala Ala Ala Ala Ala
1               5                   10                  15

Ala Ser Ser Ser Ala Ser Cys Ser Arg Arg
            20                  25

<210> SEQ ID NO 734
<211> LENGTH: 42
<212> TYPE: PRT
<213> ORGANISM: Homo sapiens
<220> FEATURE:
<223> OTHER INFORMATION: RPS6KA3 Ribosomal protein S6 kinase alpha-3;
      P51812_C599
<220> FEATURE:
<221> NAME/KEY: MOD_RES
<222> LOCATION: (8)..(8)
<223> OTHER INFORMATION: Site of chemical conjugation

<400> SEQUENCE: 734

Arg Gln Gly Tyr Asp Ala Ala Cys Asp Ile Trp Ser Leu Gly Val Leu
1               5                   10                  15

Leu Tyr Thr Met Leu Thr Gly Tyr Thr Pro Phe Ala Asn Gly Pro Asp
            20                  25                  30

Asp Thr Pro Glu Glu Ile Leu Ala Arg Ile
        35                  40

<210> SEQ ID NO 735
<211> LENGTH: 22
<212> TYPE: PRT
<213> ORGANISM: Homo sapiens
<220> FEATURE:
<223> OTHER INFORMATION: METTL3 N6-adenosine-methyltransferase 70 kDa
      subunit; Q86U44_C500
<220> FEATURE:
<221> NAME/KEY: MOD_RES
<222> LOCATION: (13)..(13)
<223> OTHER INFORMATION: Site of chemical conjugation

<400> SEQUENCE: 735

Lys Gly Asn Pro Gln Gly Phe Asn Gln Gly Leu Asp Cys Asp Val Ile
1               5                   10                  15

Val Ala Glu Val Arg Ser
            20

<210> SEQ ID NO 736
<211> LENGTH: 16
<212> TYPE: PRT
<213> ORGANISM: Homo sapiens
<220> FEATURE:
<223> OTHER INFORMATION: FN3K Fructosamine-3-kinase;
      Q9H479_C24
<220> FEATURE:
<221> NAME/KEY: MOD_RES
<222> LOCATION: (10)..(10)
<223> OTHER INFORMATION: Site of chemical conjugation
```

```
<400> SEQUENCE: 736

Arg Ala Phe Gly Gly Pro Gly Ala Gly Cys Ile Ser Glu Gly Arg Ala
1               5                   10                  15

<210> SEQ ID NO 737
<211> LENGTH: 17
<212> TYPE: PRT
<213> ORGANISM: Homo sapiens
<220> FEATURE:
<223> OTHER INFORMATION: USP22 Ubiquitin carboxyl-terminal hydrolase 22;
      Q9UPT9_C44
<220> FEATURE:
<221> NAME/KEY: MOD_RES
<222> LOCATION: (6)..(6)
<223> OTHER INFORMATION: Site of chemical conjugation

<400> SEQUENCE: 737

Arg Ala Ile Tyr Gln Cys Phe Val Trp Ser Gly Thr Ala Glu Ala Arg
1               5                   10                  15

Lys

<210> SEQ ID NO 738
<211> LENGTH: 27
<212> TYPE: PRT
<213> ORGANISM: Homo sapiens
<220> FEATURE:
<223> OTHER INFORMATION: C21orf33 ES1 protein homolog, mitochondrial;
      P30042_C244
<220> FEATURE:
<221> NAME/KEY: MOD_RES
<222> LOCATION: (10)..(10)
<223> OTHER INFORMATION: Site of chemical conjugation

<400> SEQUENCE: 738

Lys Val Val Thr Thr Pro Ala Phe Met Cys Glu Thr Ala Leu His Tyr
1               5                   10                  15

Ile His Asp Gly Ile Gly Ala Met Val Arg Lys
            20                  25

<210> SEQ ID NO 739
<211> LENGTH: 26
<212> TYPE: PRT
<213> ORGANISM: Homo sapiens
<220> FEATURE:
<223> OTHER INFORMATION: KBTBD8 Kelch repeat and BTB domain-containing
      protein 8; Q8NFY9_C490
<220> FEATURE:
<221> NAME/KEY: MOD_RES
<222> LOCATION: (20)..(20)
<223> OTHER INFORMATION: Site of chemical conjugation

<400> SEQUENCE: 739

Arg Ile Gln Gly Leu Ala Ala Val Tyr Lys Asp Ser Ile Tyr Tyr Ile
1               5                   10                  15

Ala Gly Thr Cys Gly Asn His Gln Arg Met
            20                  25

<210> SEQ ID NO 740
<211> LENGTH: 19
<212> TYPE: PRT
<213> ORGANISM: Homo sapiens
<220> FEATURE:
<223> OTHER INFORMATION: NARF Nuclear prelamin A recognition factor;
      Q9UHQ1_C99
<220> FEATURE:
<221> NAME/KEY: MOD_RES
<222> LOCATION: (8)..(8)
```

<223> OTHER INFORMATION: Site of chemical conjugation

<400> SEQUENCE: 740

Lys Val Leu Val Val Ser Val Cys Pro Gln Ser Leu Pro Tyr Phe Ala
1               5                   10                  15

Ala Lys Phe

<210> SEQ ID NO 741
<211> LENGTH: 18
<212> TYPE: PRT
<213> ORGANISM: Homo sapiens
<220> FEATURE:
<223> OTHER INFORMATION: RAB3GAP1 Rab3 GTPase-activating protein
      catalytic subunit; Q15042_C218
<220> FEATURE:
<221> NAME/KEY: MOD_RES
<222> LOCATION: (4)..(4)
<223> OTHER INFORMATION: Site of chemical conjugation

<400> SEQUENCE: 741

Lys Ile Gly Cys Pro Leu Thr Pro Leu Pro Pro Val Ser Ile Ala Ile
1               5                   10                  15

Arg Phe

<210> SEQ ID NO 742
<211> LENGTH: 11
<212> TYPE: PRT
<213> ORGANISM: Homo sapiens
<220> FEATURE:
<223> OTHER INFORMATION: BRD8 Bromodomain-containing protein 8;
      Q9H0E9_C26
<220> FEATURE:
<221> NAME/KEY: MOD_RES
<222> LOCATION: (3)..(3)
<223> OTHER INFORMATION: Site of chemical conjugation

<400> SEQUENCE: 742

Lys Leu Cys Leu Ala Ser Ser Val Met Arg Ser
1               5                   10

<210> SEQ ID NO 743
<211> LENGTH: 10
<212> TYPE: PRT
<213> ORGANISM: Homo sapiens
<220> FEATURE:
<223> OTHER INFORMATION: CASP5 Caspase-5;
      P51878_C315
<220> FEATURE:
<221> NAME/KEY: MOD_RES
<222> LOCATION: (8)..(8)
<223> OTHER INFORMATION: Site of chemical conjugation

<400> SEQUENCE: 743

Lys Val Ile Ile Val Gln Ala Cys Arg Gly
1               5                   10

<210> SEQ ID NO 744
<211> LENGTH: 21
<212> TYPE: PRT
<213> ORGANISM: Homo sapiens
<220> FEATURE:
<223> OTHER INFORMATION: TNRC6B Trinucleotide repeat-containing gene 6B
      protein; Q9UPQ9_C600
<220> FEATURE:
<221> NAME/KEY: MOD_RES
<222> LOCATION: (10)..(10)
<223> OTHER INFORMATION: Site of chemical conjugation

<400> SEQUENCE: 744

-continued

```
Arg Ser Tyr Arg Pro Thr His Pro Asp Cys Gln Ala Val Leu Gln Thr
1               5                   10                  15

Leu Leu Ser Arg Thr
            20

<210> SEQ ID NO 745
<211> LENGTH: 22
<212> TYPE: PRT
<213> ORGANISM: Homo sapiens
<220> FEATURE:
<223> OTHER INFORMATION: ARNT Aryl hydrocarbon receptor nuclear
      translocator; P27540_C119
<220> FEATURE:
<221> NAME/KEY: MOD_RES
<222> LOCATION: (16)..(16)
<223> OTHER INFORMATION: Site of chemical conjugation

<400> SEQUENCE: 745

Lys Met Thr Ala Tyr Ile Thr Glu Leu Ser Asp Met Val Pro Thr Cys
1               5                   10                  15

Ser Ala Leu Ala Arg Lys
            20

<210> SEQ ID NO 746
<211> LENGTH: 20
<212> TYPE: PRT
<213> ORGANISM: Homo sapiens
<220> FEATURE:
<223> OTHER INFORMATION: FAM136A Protein FAM136A;
      Q96C01_C57
<220> FEATURE:
<221> NAME/KEY: MOD_RES
<222> LOCATION: (2)..(2)
<223> OTHER INFORMATION: Site of chemical conjugation

<400> SEQUENCE: 746

Arg Cys His Val Pro Leu Ala Gln Ala Gln Ala Leu Val Thr Ser Glu
1               5                   10                  15

Leu Glu Lys Phe
            20

<210> SEQ ID NO 747
<211> LENGTH: 19
<212> TYPE: PRT
<213> ORGANISM: Homo sapiens
<220> FEATURE:
<223> OTHER INFORMATION: STARD7 StAR-related lipid transfer protein 7,
      mitochondri; Q9NQZ5_C302
<220> FEATURE:
<221> NAME/KEY: MOD_RES
<222> LOCATION: (3)..(3)
<223> OTHER INFORMATION: Site of chemical conjugation

<400> SEQUENCE: 747

Arg Tyr Cys Val Ser Trp Met Val Ser Ser Gly Met Pro Asp Phe Leu
1               5                   10                  15

Glu Lys Leu

<210> SEQ ID NO 748
<211> LENGTH: 11
<212> TYPE: PRT
<213> ORGANISM: Homo sapiens
<220> FEATURE:
<223> OTHER INFORMATION: L2HGDH L-2-hydroxyglutarate dehydrogenase,
      mitochondrial; Q9H9P8_C376
<220> FEATURE:
<221> NAME/KEY: MOD_RES
```

-continued

```
<222> LOCATION: (3)..(3)
<223> OTHER INFORMATION: Site of chemical conjugation

<400> SEQUENCE: 748

Lys Ala Cys Phe Leu Gly Ala Thr Val Lys Tyr
1               5                   10

<210> SEQ ID NO 749
<211> LENGTH: 9
<212> TYPE: PRT
<213> ORGANISM: Homo sapiens
<220> FEATURE:
<223> OTHER INFORMATION: SCCPDH Saccharopine dehydrogenase-like
      oxidoreductase; Q8NBX0_C238
<220> FEATURE:
<221> NAME/KEY: MOD_RES
<222> LOCATION: (7)..(7)
<223> OTHER INFORMATION: Site of chemical conjugation

<400> SEQUENCE: 749

Arg Trp Pro Ile Ser Tyr Cys Arg Glu
1               5

<210> SEQ ID NO 750
<211> LENGTH: 25
<212> TYPE: PRT
<213> ORGANISM: Homo sapiens
<220> FEATURE:
<223> OTHER INFORMATION: FLAD1 FAD synthase;
      Q8NFF5_C499
<220> FEATURE:
<221> NAME/KEY: MOD_RES
<222> LOCATION: (10)..(10)
<223> OTHER INFORMATION: Site of chemical conjugation

<400> SEQUENCE: 750

Arg Thr Asp Pro Tyr Ser Cys Ser Leu Cys Pro Phe Ser Pro Thr Asp
1               5                   10                  15

Pro Gly Trp Pro Ala Phe Met Arg Ile
            20                  25

<210> SEQ ID NO 751
<211> LENGTH: 14
<212> TYPE: PRT
<213> ORGANISM: Homo sapiens
<220> FEATURE:
<223> OTHER INFORMATION: BRAT1 BRCA1-associated ATM activator 1;
      Q6PJG6_C228
<220> FEATURE:
<221> NAME/KEY: MOD_RES
<222> LOCATION: (2)..(2)
<223> OTHER INFORMATION: Site of chemical conjugation

<400> SEQUENCE: 751

Arg Cys Gln Ser Pro Trp Thr Glu Ala Leu Trp Val Arg Leu
1               5                   10

<210> SEQ ID NO 752
<211> LENGTH: 40
<212> TYPE: PRT
<213> ORGANISM: Homo sapiens
<220> FEATURE:
<223> OTHER INFORMATION: TNKS1BP1 182 kDa tankyrase-1-binding protein;
      Q9C0C2_C749
<220> FEATURE:
<221> NAME/KEY: MOD_RES
<222> LOCATION: (24)..(24)
<223> OTHER INFORMATION: Site of chemical conjugation

<400> SEQUENCE: 752
```

```
Lys Asp Leu Gln Ser Glu Phe Gly Ile Thr Gly Asp Pro Gln Pro Ser
1               5                   10                  15

Ser Phe Ser Pro Ser Ser Trp Cys Gln Gly Ala Ser Gln Asp Tyr Gly
            20                  25                  30

Leu Gly Gly Ala Ser Pro Arg Gly
        35                  40

<210> SEQ ID NO 753
<211> LENGTH: 26
<212> TYPE: PRT
<213> ORGANISM: Homo sapiens
<220> FEATURE:
<223> OTHER INFORMATION: KDM3A Lysine-specific demethylase 3A;
      Q9Y4C1_C251
<220> FEATURE:
<221> NAME/KEY: MOD_RES
<222> LOCATION: (20)..(20)
<223> OTHER INFORMATION: Site of chemical conjugation

<400> SEQUENCE: 753

Lys Ile Val Asp Pro Ser Leu Ile His Val Glu Val Val His Asp Asn
1               5                   10                  15

Leu Val Thr Cys Gly Asn Ser Ala Arg Ile
            20                  25

<210> SEQ ID NO 754
<211> LENGTH: 29
<212> TYPE: PRT
<213> ORGANISM: Homo sapiens
<220> FEATURE:
<223> OTHER INFORMATION: DTWD1 DTW domain-containing protein 1;
      Q8N5C7_C235
<220> FEATURE:
<221> NAME/KEY: MOD_RES
<222> LOCATION: (22)..(22)
<223> OTHER INFORMATION: Site of chemical conjugation

<400> SEQUENCE: 754

Lys Ile Phe Thr Asp Glu Arg Leu Gln Gly Leu Leu Gln Val Glu Leu
1               5                   10                  15

Lys Thr Arg Lys Thr Cys Phe Trp Arg His Gln Lys Gly
            20                  25

<210> SEQ ID NO 755
<211> LENGTH: 10
<212> TYPE: PRT
<213> ORGANISM: Homo sapiens
<220> FEATURE:
<223> OTHER INFORMATION: GNL3 Guanine nucleotide-binding protein-like 3;
      Q9BVP2_C131
<220> FEATURE:
<221> NAME/KEY: MOD_RES
<222> LOCATION: (5)..(5)
<223> OTHER INFORMATION: Site of chemical conjugation

<400> SEQUENCE: 755

Lys Lys Leu Tyr Cys Gln Glu Leu Lys Lys
1               5                   10

<210> SEQ ID NO 756
<211> LENGTH: 28
<212> TYPE: PRT
<213> ORGANISM: Homo sapiens
<220> FEATURE:
<223> OTHER INFORMATION: WDFY4 WD repeat- and FYVE domain-containing
      protein 4; Q6ZS81_C1963
<220> FEATURE:
```

```
<221> NAME/KEY: MOD_RES
<222> LOCATION: (23)..(23)
<223> OTHER INFORMATION: Site of chemical conjugation

<400> SEQUENCE: 756

Arg Asp Gly Lys Glu Pro Gln Pro Ser Ala Glu Ala Ala Ala Pro
1               5                   10                  15

Ser Leu Ala Asn Ile Ser Cys Phe Thr Gln Lys Leu
            20                  25

<210> SEQ ID NO 757
<211> LENGTH: 30
<212> TYPE: PRT
<213> ORGANISM: Homo sapiens
<220> FEATURE:
<223> OTHER INFORMATION: IPO13 Importin-13;
      O94829_C217
<220> FEATURE:
<221> NAME/KEY: MOD_RES
<222> LOCATION: (27)..(27)
<223> OTHER INFORMATION: Site of chemical conjugation

<400> SEQUENCE: 757

Arg Thr Ser Leu Ala Val Glu Cys Gly Ala Val Phe Pro Leu Leu Glu
1               5                   10                  15

Gln Leu Leu Gln Gln Pro Ser Ser Pro Ser Cys Val Arg Gln
            20                  25                  30

<210> SEQ ID NO 758
<211> LENGTH: 25
<212> TYPE: PRT
<213> ORGANISM: Homo sapiens
<220> FEATURE:
<223> OTHER INFORMATION: MIEN1 Migration and invasion enhancer 1;
      Q9BRT3_C33
<220> FEATURE:
<221> NAME/KEY: MOD_RES
<222> LOCATION: (10)..(10)
<223> OTHER INFORMATION: Site of chemical conjugation

<400> SEQUENCE: 758

Arg Ile Val Val Glu Tyr Cys Glu Pro Cys Gly Phe Glu Ala Thr Tyr
1               5                   10                  15

Leu Glu Leu Ala Ser Ala Val Lys Glu
            20                  25

<210> SEQ ID NO 759
<211> LENGTH: 10
<212> TYPE: PRT
<213> ORGANISM: Homo sapiens
<220> FEATURE:
<223> OTHER INFORMATION: NUDT16L1 Protein syndesmos;
      Q9BRJ7_C171
<220> FEATURE:
<221> NAME/KEY: MOD_RES
<222> LOCATION: (2)..(2)
<223> OTHER INFORMATION: Site of chemical conjugation

<400> SEQUENCE: 759

Lys Cys Gln Leu Leu Phe Ala Leu Lys Val
1               5                   10

<210> SEQ ID NO 760
<211> LENGTH: 13
<212> TYPE: PRT
<213> ORGANISM: Homo sapiens
<220> FEATURE:
<223> OTHER INFORMATION: FRMD6 FERM domain-containing protein 6;
```

```
                Q96NE9_C306
<220> FEATURE:
<221> NAME/KEY: MOD_RES
<222> LOCATION: (9)..(9)
<223> OTHER INFORMATION: Site of chemical conjugation

<400> SEQUENCE: 760

Arg Lys Leu Ile Tyr Tyr Thr Gly Cys Pro Met Arg Ser
1               5                   10

<210> SEQ ID NO 761
<211> LENGTH: 28
<212> TYPE: PRT
<213> ORGANISM: Homo sapiens
<220> FEATURE:
<223> OTHER INFORMATION: USP34 Ubiquitin carboxyl-terminal hydrolase 34;
      Q70CQ2_C1090
<220> FEATURE:
<221> NAME/KEY: MOD_RES
<222> LOCATION: (10)..(10)
<223> OTHER INFORMATION: Site of chemical conjugation

<400> SEQUENCE: 761

Arg Leu Ala Thr Ser Ala Tyr Asp Gly Cys Ser Asn Ser Glu Leu Cys
1               5                   10                  15

Gly Met Asp Gln Phe Trp Gly Ile Ala Leu Arg Ala
            20                  25

<210> SEQ ID NO 762
<211> LENGTH: 10
<212> TYPE: PRT
<213> ORGANISM: Homo sapiens
<220> FEATURE:
<223> OTHER INFORMATION: CYR61 Protein CYR61;
      O00622_C70
<220> FEATURE:
<221> NAME/KEY: MOD_RES
<222> LOCATION: (5)..(5)
<223> OTHER INFORMATION: Site of chemical conjugation

<400> SEQUENCE: 762

Lys Thr Gln Pro Cys Asp His Thr Lys Gly
1               5                   10

<210> SEQ ID NO 763
<211> LENGTH: 13
<212> TYPE: PRT
<213> ORGANISM: Homo sapiens
<220> FEATURE:
<223> OTHER INFORMATION: ATF7IP Activating transcription factor
      7-interacting prot; Q6VMQ6_C612
<220> FEATURE:
<221> NAME/KEY: MOD_RES
<222> LOCATION: (7)..(7)
<223> OTHER INFORMATION: Site of chemical conjugation

<400> SEQUENCE: 763

Lys Leu Cys Ala Leu Gln Cys Ala Val Phe Asp Lys Thr
1               5                   10

<210> SEQ ID NO 764
<211> LENGTH: 41
<212> TYPE: PRT
<213> ORGANISM: Homo sapiens
<220> FEATURE:
<223> OTHER INFORMATION: TUBB4B Tubulin beta-4B chain;
      P68371_C213
<220> FEATURE:
<221> NAME/KEY: MOD_RES
<222> LOCATION: (28)..(28)
```

```
<223> OTHER INFORMATION: Site of chemical conjugation
<220> FEATURE:
<221> NAME/KEY: MOD_RES
<222> LOCATION: (38)..(38)
<223> OTHER INFORMATION: Site of chemical conjugation

<400> SEQUENCE: 764

Lys Val Ser Asp Thr Val Val Glu Pro Tyr Asn Ala Thr Leu Ser Val
1               5                   10                  15

His Gln Leu Val Glu Asn Thr Asp Thr Tyr Cys Ile Asp Asn Glu
            20                  25                  30

Ala Leu Tyr Asp Ile Cys Phe Arg Thr
        35                  40

<210> SEQ ID NO 765
<211> LENGTH: 21
<212> TYPE: PRT
<213> ORGANISM: Homo sapiens
<220> FEATURE:
<223> OTHER INFORMATION: NR3C1 Glucocorticoid receptor;
      P04150_C622
<220> FEATURE:
<221> NAME/KEY: MOD_RES
<222> LOCATION: (9)..(9)
<223> OTHER INFORMATION: Site of chemical conjugation

<400> SEQUENCE: 765

Arg Gln Ser Ser Ala Asn Leu Leu Cys Phe Ala Pro Asp Leu Ile Ile
1               5                   10                  15

Asn Glu Gln Arg Met
            20

<210> SEQ ID NO 766
<211> LENGTH: 38
<212> TYPE: PRT
<213> ORGANISM: Homo sapiens
<220> FEATURE:
<223> OTHER INFORMATION: CHTF18 Chromosome transmission fidelity protein
      18 homolo; Q8WVB6_C280
<220> FEATURE:
<221> NAME/KEY: MOD_RES
<222> LOCATION: (28)..(28)
<223> OTHER INFORMATION: Site of chemical conjugation

<400> SEQUENCE: 766

Arg Ser Gly Glu Glu Ala Ala Gln Pro Leu Gly Ala Pro Glu Glu
1               5                   10                  15

Glu Pro Thr Asp Gly Gln Asp Ala Ser Ser His Cys Leu Trp Val Asp
            20                  25                  30

Glu Phe Ala Pro Arg His
        35

<210> SEQ ID NO 767
<211> LENGTH: 16
<212> TYPE: PRT
<213> ORGANISM: Homo sapiens
<220> FEATURE:
<223> OTHER INFORMATION: DENND4A C-myc promoter-binding protein;
      Q7Z401_C1289
<220> FEATURE:
<221> NAME/KEY: MOD_RES
<222> LOCATION: (12)..(12)
<223> OTHER INFORMATION: Site of chemical conjugation

<400> SEQUENCE: 767

Arg Leu Trp Ser Ser Pro Ala Phe Ser Pro Thr Cys Pro Phe Arg Glu
1               5                   10                  15
```

```
<210> SEQ ID NO 768
<211> LENGTH: 38
<212> TYPE: PRT
<213> ORGANISM: Homo sapiens
<220> FEATURE:
<223> OTHER INFORMATION: HNRNPK Heterogeneous nuclear ribonucleoprotein
      K; P61978_C132
<220> FEATURE:
<221> NAME/KEY: MOD_RES
<222> LOCATION: (30)..(30)
<223> OTHER INFORMATION: Site of chemical conjugation

<400> SEQUENCE: 768

Lys Ile Ile Pro Thr Leu Glu Glu Gly Leu Gln Leu Pro Ser Pro Thr
1               5                   10                  15

Ala Thr Ser Gln Leu Pro Leu Glu Ser Asp Ala Val Glu Cys Leu Asn
            20                  25                  30

Tyr Gln His Tyr Lys Gly
        35

<210> SEQ ID NO 769
<211> LENGTH: 15
<212> TYPE: PRT
<213> ORGANISM: Homo sapiens
<220> FEATURE:
<223> OTHER INFORMATION: HNRNPH1 Heterogeneous nuclear;
      P31943_C267
<220> FEATURE:
<221> NAME/KEY: MOD_RES
<222> LOCATION: (6)..(6)
<223> OTHER INFORMATION: Site of chemical conjugation

<400> SEQUENCE: 769

Arg Asp Leu Asn Tyr Cys Phe Ser Gly Met Ser Asp His Arg Tyr
1               5                   10                  15

<210> SEQ ID NO 770
<211> LENGTH: 11
<212> TYPE: PRT
<213> ORGANISM: Homo sapiens
<220> FEATURE:
<223> OTHER INFORMATION: CORO1C Coronin-1C;
      Q9ULV4_C420
<220> FEATURE:
<221> NAME/KEY: MOD_RES
<222> LOCATION: (3)..(3)
<223> OTHER INFORMATION: Site of chemical conjugation

<400> SEQUENCE: 770

Lys Lys Cys Asp Leu Ile Ser Ile Pro Lys Lys
1               5                   10

<210> SEQ ID NO 771
<211> LENGTH: 25
<212> TYPE: PRT
<213> ORGANISM: Homo sapiens
<220> FEATURE:
<223> OTHER INFORMATION: ADD1 Alpha-adducin;
      P35611_C68
<220> FEATURE:
<221> NAME/KEY: MOD_RES
<222> LOCATION: (12)..(12)
<223> OTHER INFORMATION: Site of chemical conjugation

<400> SEQUENCE: 771

Arg Val Ser Met Ile Leu Gln Ser Pro Ala Phe Cys Glu Glu Leu Glu
1               5                   10                  15
```

```
Ser Met Ile Gln Glu Gln Phe Lys Lys
            20                  25

<210> SEQ ID NO 772
<211> LENGTH: 29
<212> TYPE: PRT
<213> ORGANISM: Homo sapiens
<220> FEATURE:
<223> OTHER INFORMATION: CECR5 Cat eye syndrome critical region protein
      5; Q9BXW7_C392
<220> FEATURE:
<221> NAME/KEY: MOD_RES
<222> LOCATION: (4)..(4)
<223> OTHER INFORMATION: Site of chemical conjugation

<400> SEQUENCE: 772

Arg Asp Leu Cys Phe Ser Pro Gly Leu Met Glu Ala Ser His Val Val
1               5                   10                  15

Asn Asp Val Asn Glu Ala Val Gln Leu Val Phe Arg Lys
            20                  25

<210> SEQ ID NO 773
<211> LENGTH: 46
<212> TYPE: PRT
<213> ORGANISM: Homo sapiens
<220> FEATURE:
<223> OTHER INFORMATION: PDIA3 Protein disulfide-isomerase A3;
      P30101_C406
<220> FEATURE:
<221> NAME/KEY: MOD_RES
<222> LOCATION: (41)..(41)
<223> OTHER INFORMATION: Site of chemical conjugation

<400> SEQUENCE: 773

Lys Ser Glu Pro Ile Pro Glu Ser Asn Asp Gly Pro Val Lys Val Val
1               5                   10                  15

Val Ala Glu Asn Phe Asp Glu Ile Val Asn Asn Glu Asn Lys Asp Val
            20                  25                  30

Leu Ile Glu Phe Tyr Ala Pro Trp Cys Gly His Cys Lys Asn
        35                  40                  45

<210> SEQ ID NO 774
<211> LENGTH: 18
<212> TYPE: PRT
<213> ORGANISM: Homo sapiens
<220> FEATURE:
<223> OTHER INFORMATION: PDIA4 Protein disulfide-isomerase A4;
      P13667_C555
<220> FEATURE:
<221> NAME/KEY: MOD_RES
<222> LOCATION: (13)..(13)
<223> OTHER INFORMATION: Site of chemical conjugation

<400> SEQUENCE: 774

Lys Lys Asp Val Leu Ile Glu Phe Tyr Ala Pro Trp Cys Gly His Cys
1               5                   10                  15

Lys Gln

<210> SEQ ID NO 775
<211> LENGTH: 24
<212> TYPE: PRT
<213> ORGANISM: Homo sapiens
<220> FEATURE:
<223> OTHER INFORMATION: SMARCC2 SWI/SNF complex subunit SMARCC2;
      Q8TAQ2_C145
<220> FEATURE:
<221> NAME/KEY: MOD_RES
<222> LOCATION: (17)..(17)
```

<223> OTHER INFORMATION: Site of chemical conjugation

<400> SEQUENCE: 775

Lys Ser Leu Val Gln Asn Asn Cys Leu Ser Arg Pro Asn Ile Phe Leu
1               5                   10                  15

Cys Pro Glu Ile Glu Pro Lys Leu
            20

<210> SEQ ID NO 776
<211> LENGTH: 20
<212> TYPE: PRT
<213> ORGANISM: Homo sapiens
<220> FEATURE:
<223> OTHER INFORMATION: ZC3HAV1 Zinc finger CCCH-type antiviral protein
      1; Q7Z2W4_C645
<220> FEATURE:
<221> NAME/KEY: MOD_RES
<222> LOCATION: (17)..(17)
<223> OTHER INFORMATION: Site of chemical conjugation

<400> SEQUENCE: 776

Lys Asn Ser Asn Val Asp Ser Ser Tyr Leu Glu Ser Leu Tyr Gln Ser
1               5                   10                  15

Cys Pro Arg Gly
            20

<210> SEQ ID NO 777
<211> LENGTH: 28
<212> TYPE: PRT
<213> ORGANISM: Homo sapiens
<220> FEATURE:
<223> OTHER INFORMATION: MACROD1 O-acetyl-ADP-ribose deacetylase
      MACROD1; Q9BQ69_C186
<220> FEATURE:
<221> NAME/KEY: MOD_RES
<222> LOCATION: (24)..(24)
<223> OTHER INFORMATION: Site of chemical conjugation

<400> SEQUENCE: 777

Lys Leu Glu Val Asp Ala Ile Val Asn Ala Ala Asn Ser Ser Leu Leu
1               5                   10                  15

Gly Gly Gly Gly Val Asp Gly Cys Ile His Arg Ala
            20                  25

<210> SEQ ID NO 778
<211> LENGTH: 13
<212> TYPE: PRT
<213> ORGANISM: Homo sapiens
<220> FEATURE:
<223> OTHER INFORMATION: CCNH Cyclin-H;
      P51946_C244
<220> FEATURE:
<221> NAME/KEY: MOD_RES
<222> LOCATION: (3)..(3)
<223> OTHER INFORMATION: Site of chemical conjugation

<400> SEQUENCE: 778

Arg Thr Cys Leu Ser Gln Leu Leu Asp Ile Met Lys Ser
1               5                   10

<210> SEQ ID NO 779
<211> LENGTH: 25
<212> TYPE: PRT
<213> ORGANISM: Homo sapiens
<220> FEATURE:
<223> OTHER INFORMATION: ZWINT ZW10 interactor;
      O95229_C54
<220> FEATURE:

```
<221> NAME/KEY: MOD_RES
<222> LOCATION: (4)..(4)
<223> OTHER INFORMATION: Site of chemical conjugation

<400> SEQUENCE: 779

Lys Leu Leu Cys Ser Gln Leu Gln Val Ala Asp Phe Leu Gln Asn Ile
1               5                   10                  15

Leu Ala Gln Glu Asp Thr Ala Lys Gly
            20                  25

<210> SEQ ID NO 780
<211> LENGTH: 17
<212> TYPE: PRT
<213> ORGANISM: Homo sapiens
<220> FEATURE:
<223> OTHER INFORMATION: DIAPH1 Protein diaphanous homolog 1;
      O60610_C1227
<220> FEATURE:
<221> NAME/KEY: MOD_RES
<222> LOCATION: (4)..(4)
<223> OTHER INFORMATION: Site of chemical conjugation

<400> SEQUENCE: 780

Lys Ala Gly Cys Ala Val Thr Ser Leu Leu Ala Ser Glu Leu Thr Lys
1               5                   10                  15

Asp

<210> SEQ ID NO 781
<211> LENGTH: 21
<212> TYPE: PRT
<213> ORGANISM: Homo sapiens
<220> FEATURE:
<223> OTHER INFORMATION: PRDX4 Peroxiredoxin-4;
      Q13162_C51
<220> FEATURE:
<221> NAME/KEY: MOD_RES
<222> LOCATION: (5)..(5)
<223> OTHER INFORMATION: Site of chemical conjugation

<400> SEQUENCE: 781

Arg Glu Glu Glu Cys His Phe Tyr Ala Gly Gly Gln Val Tyr Pro Gly
1               5                   10                  15

Glu Ala Ser Arg Val
            20

<210> SEQ ID NO 782
<211> LENGTH: 24
<212> TYPE: PRT
<213> ORGANISM: Homo sapiens
<220> FEATURE:
<223> OTHER INFORMATION: USP7 Ubiquitin carboxyl-terminal hydrolase 7;
      Q93009_C223
<220> FEATURE:
<221> NAME/KEY: MOD_RES
<222> LOCATION: (7)..(7)
<223> OTHER INFORMATION: Site of chemical conjugation

<400> SEQUENCE: 782

Lys Asn Gln Gly Ala Thr Cys Tyr Met Asn Ser Leu Leu Gln Thr Leu
1               5                   10                  15

Phe Phe Thr Asn Gln Leu Arg Lys
            20

<210> SEQ ID NO 783
<211> LENGTH: 18
<212> TYPE: PRT
<213> ORGANISM: Homo sapiens
```

```
<220> FEATURE:
<223> OTHER INFORMATION: LIMCH1 LIM and calponin homology domains-
      containing protein; Q9UPQ0_C140
<220> FEATURE:
<221> NAME/KEY: MOD_RES
<222> LOCATION: (6)..(6)
<223> OTHER INFORMATION: Site of chemical conjugation

<400> SEQUENCE: 783

Lys Ala Ala Asn Ser Cys Thr Ser Tyr Ser Gly Thr Thr Leu Asn Leu
1               5                   10                  15

Lys Glu

<210> SEQ ID NO 784
<211> LENGTH: 15
<212> TYPE: PRT
<213> ORGANISM: Homo sapiens
<220> FEATURE:
<223> OTHER INFORMATION: TK1 Thymidine kinase, cytosolic;
      P04183_C230
<220> FEATURE:
<221> NAME/KEY: MOD_RES
<222> LOCATION: (11)..(11)
<223> OTHER INFORMATION: Site of chemical conjugation

<400> SEQUENCE: 784

Lys Leu Phe Ala Pro Gln Gln Ile Leu Gln Cys Ser Pro Ala Asn
1               5                   10                  15

<210> SEQ ID NO 785
<211> LENGTH: 40
<212> TYPE: PRT
<213> ORGANISM: Homo sapiens
<220> FEATURE:
<223> OTHER INFORMATION: TCOF1 Treacle protein;
      Q13428_C1298
<220> FEATURE:
<221> NAME/KEY: MOD_RES
<222> LOCATION: (20)..(20)
<223> OTHER INFORMATION: Site of chemical conjugation

<400> SEQUENCE: 785

Lys Gly Ala Gly Asn Pro Gln Ala Ser Thr Leu Ala Leu Gln Ser Asn
1               5                   10                  15

Ile Thr Gln Cys Leu Leu Gly Gln Pro Trp Pro Leu Asn Glu Ala Gln
            20                  25                  30

Val Gln Ala Ser Val Val Lys Val
            35                  40

<210> SEQ ID NO 786
<211> LENGTH: 11
<212> TYPE: PRT
<213> ORGANISM: Homo sapiens
<220> FEATURE:
<223> OTHER INFORMATION: XPO1 Exportin-1;
      O14980_C528
<220> FEATURE:
<221> NAME/KEY: MOD_RES
<222> LOCATION: (7)..(7)
<223> OTHER INFORMATION: Site of chemical conjugation

<400> SEQUENCE: 786

Lys Asp Leu Leu Gly Leu Cys Glu Gln Lys Arg
1               5                   10

<210> SEQ ID NO 787
<211> LENGTH: 31
<212> TYPE: PRT
```

```
<213> ORGANISM: Homo sapiens
<220> FEATURE:
<223> OTHER INFORMATION: SCP2 Non-specific lipid-transfer protein;
      P22307_C71
<220> FEATURE:
<221> NAME/KEY: MOD_RES
<222> LOCATION: (27)..(27)
<223> OTHER INFORMATION: Site of chemical conjugation

<400> SEQUENCE: 787

Lys Ala Leu Ala Asp Ala Gln Ile Pro Tyr Ser Ala Val Asp Gln Ala
1               5                   10                  15

Cys Val Gly Tyr Val Phe Gly Asp Ser Thr Cys Gly Gln Arg Ala
            20                  25                  30

<210> SEQ ID NO 788
<211> LENGTH: 26
<212> TYPE: PRT
<213> ORGANISM: Homo sapiens
<220> FEATURE:
<223> OTHER INFORMATION: ECI2 Enoyl-CoA delta isomerase 2,
      mitochondrial; O75521_C312
<220> FEATURE:
<221> NAME/KEY: MOD_RES
<222> LOCATION: (9)..(9)
<223> OTHER INFORMATION: Site of chemical conjugation

<400> SEQUENCE: 788

Lys Lys Leu Thr Ala Gly Glu Ala Cys Ala Gln Gly Leu Val Thr Glu
1               5                   10                  15

Val Phe Pro Asp Ser Thr Phe Gln Lys Glu
            20                  25

<210> SEQ ID NO 789
<211> LENGTH: 11
<212> TYPE: PRT
<213> ORGANISM: Homo sapiens
<220> FEATURE:
<223> OTHER INFORMATION: NT5DC3 5-nucleotidase domain-containing protein
      3; Q86UY8_C276
<220> FEATURE:
<221> NAME/KEY: MOD_RES
<222> LOCATION: (4)..(4)
<223> OTHER INFORMATION: Site of chemical conjugation

<400> SEQUENCE: 789

Lys Tyr Ile Cys Tyr Ala Glu Gln Thr Arg Ala
1               5                   10

<210> SEQ ID NO 790
<211> LENGTH: 26
<212> TYPE: PRT
<213> ORGANISM: Homo sapiens
<220> FEATURE:
<223> OTHER INFORMATION: NR2F2 COUP transcription factor 2;
      P24468_C326
<220> FEATURE:
<221> NAME/KEY: MOD_RES
<222> LOCATION: (11)..(11)
<223> OTHER INFORMATION: Site of chemical conjugation

<400> SEQUENCE: 790

Lys Ala Ile Val Leu Phe Thr Ser Asp Ala Cys Gly Leu Ser Asp Val
1               5                   10                  15

Ala His Val Glu Ser Leu Gln Glu Lys Ser
            20                  25

<210> SEQ ID NO 791
```

```
<211> LENGTH: 38
<212> TYPE: PRT
<213> ORGANISM: Homo sapiens
<220> FEATURE:
<223> OTHER INFORMATION: NPEPL1 Probable aminopeptidase NPEPL1;
      Q8NDH3_C81
<220> FEATURE:
<221> NAME/KEY: MOD_RES
<222> LOCATION: (36)..(36)
<223> OTHER INFORMATION: Site of chemical conjugation

<400> SEQUENCE: 791

Arg Val Thr Glu Glu Leu Trp Gln Ala Ala Leu Ser Thr Leu Asn Pro
1               5                  10                  15

Asn Pro Thr Asp Ser Cys Pro Leu Tyr Leu Asn Tyr Ala Thr Val Ala
            20                  25                  30

Ala Leu Pro Cys Arg Val
        35

<210> SEQ ID NO 792
<211> LENGTH: 16
<212> TYPE: PRT
<213> ORGANISM: Homo sapiens
<220> FEATURE:
<223> OTHER INFORMATION: MCMBP Mini-chromosome maintenance complex-
      binding protein; Q9BTE3_C325
<220> FEATURE:
<221> NAME/KEY: MOD_RES
<222> LOCATION: (12)..(12)
<223> OTHER INFORMATION: Site of chemical conjugation

<400> SEQUENCE: 792

Lys Leu Gln His Ile Asn Pro Leu Leu Pro Ala Cys Leu Asn Lys Glu
1               5                  10                  15

<210> SEQ ID NO 793
<211> LENGTH: 19
<212> TYPE: PRT
<213> ORGANISM: Homo sapiens
<220> FEATURE:
<223> OTHER INFORMATION: TMPO Lamina-associated polypeptide 2, isoform
      alpha; P42166_C629
<220> FEATURE:
<221> NAME/KEY: MOD_RES
<222> LOCATION: (10)..(10)
<223> OTHER INFORMATION: Site of chemical conjugation

<400> SEQUENCE: 793

Lys Thr Tyr Asp Ala Ala Ser Tyr Ile Cys Glu Ala Ala Phe Asp Glu
1               5                  10                  15

Val Lys Met

<210> SEQ ID NO 794
<211> LENGTH: 23
<212> TYPE: PRT
<213> ORGANISM: Homo sapiens
<220> FEATURE:
<223> OTHER INFORMATION: MAD2L1BP MAD2L1-binding protein;
      Q15013_C124
<220> FEATURE:
<221> NAME/KEY: MOD_RES
<222> LOCATION: (2)..(2)
<223> OTHER INFORMATION: Site of chemical conjugation

<400> SEQUENCE: 794

Lys Cys Gln Gln Ala Leu Ala Glu Leu Glu Ser Val Leu Ser His Leu
1               5                  10                  15

Glu Asp Phe Phe Ala Arg Thr
```

```
                    20

<210> SEQ ID NO 795
<211> LENGTH: 9
<212> TYPE: PRT
<213> ORGANISM: Homo sapiens
<220> FEATURE:
<223> OTHER INFORMATION: NUBP2 Cytosolic Fe-S cluster assembly factor
      NUBP2; Q9Y5Y2_C72
<220> FEATURE:
<221> NAME/KEY: MOD_RES
<222> LOCATION: (6)..(6)
<223> OTHER INFORMATION: Site of chemical conjugation

<400> SEQUENCE: 795

Arg Ala Val His Gln Cys Asp Arg Gly
1               5

<210> SEQ ID NO 796
<211> LENGTH: 37
<212> TYPE: PRT
<213> ORGANISM: Homo sapiens
<220> FEATURE:
<223> OTHER INFORMATION: CD3EAP DNA-directed RNA polymerase I subunit
      RPA34; O15446_C86
<220> FEATURE:
<221> NAME/KEY: MOD_RES
<222> LOCATION: (6)..(6)
<223> OTHER INFORMATION: Site of chemical conjugation

<400> SEQUENCE: 796

Arg Val Leu Ser Ser Cys Pro Gln Ala Gly Glu Ala Thr Leu Leu Ala
1               5                   10                  15

Pro Ser Thr Glu Ala Gly Gly Gly Leu Thr Cys Ala Ser Ala Pro Gln
            20                  25                  30

Gly Thr Leu Arg Ile
        35

<210> SEQ ID NO 797
<211> LENGTH: 16
<212> TYPE: PRT
<213> ORGANISM: Homo sapiens
<220> FEATURE:
<223> OTHER INFORMATION: TSTA3 GDP-L-fucose synthase;
      Q13630_C116
<220> FEATURE:
<221> NAME/KEY: MOD_RES
<222> LOCATION: (10)..(10)
<223> OTHER INFORMATION: Site of chemical conjugation

<400> SEQUENCE: 797

Arg Lys Val Val Ser Cys Leu Ser Thr Cys Ile Phe Pro Asp Lys Thr
1               5                   10                  15

<210> SEQ ID NO 798
<211> LENGTH: 22
<212> TYPE: PRT
<213> ORGANISM: Homo sapiens
<220> FEATURE:
<223> OTHER INFORMATION: CTSC Dipeptidyl peptidase 1;
      P53634_C258
<220> FEATURE:
<221> NAME/KEY: MOD_RES
<222> LOCATION: (9)..(9)
<223> OTHER INFORMATION: Site of chemical conjugation

<400> SEQUENCE: 798

Arg Asn Gln Ala Ser Cys Gly Ser Cys Tyr Ser Phe Ala Ser Met Gly
1               5                   10                  15
```

Met Leu Glu Ala Arg Ile
            20

<210> SEQ ID NO 799
<211> LENGTH: 34
<212> TYPE: PRT
<213> ORGANISM: Homo sapiens
<220> FEATURE:
<223> OTHER INFORMATION: FADD Protein FADD;
      Q13158_C98
<220> FEATURE:
<221> NAME/KEY: MOD_RES
<222> LOCATION: (21)..(21)
<223> OTHER INFORMATION: Site of chemical conjugation

<400> SEQUENCE: 799

Arg Val Asp Asp Phe Glu Ala Gly Ala Ala Ala Gly Ala Ala Pro Gly
1               5                   10                  15

Glu Glu Asp Leu Cys Ala Ala Phe Asn Val Ile Cys Asp Asn Val Gly
            20                  25                  30

Lys Asp

<210> SEQ ID NO 800
<211> LENGTH: 15
<212> TYPE: PRT
<213> ORGANISM: Homo sapiens
<220> FEATURE:
<223> OTHER INFORMATION: WAPAL Wings apart-like protein homolog;
      Q7Z5K2_C160
<220> FEATURE:
<221> NAME/KEY: MOD_RES
<222> LOCATION: (12)..(12)
<223> OTHER INFORMATION: Site of chemical conjugation

<400> SEQUENCE: 800

Arg Ile Val Glu Asp Asp Ala Ser Ile Ser Ser Cys Asn Lys Leu
1               5                   10                  15

<210> SEQ ID NO 801
<211> LENGTH: 10
<212> TYPE: PRT
<213> ORGANISM: Homo sapiens
<220> FEATURE:
<223> OTHER INFORMATION: TMPO Lamina-associated polypeptide 2, isoform
      alpha; P42166_C518
<220> FEATURE:
<221> NAME/KEY: MOD_RES
<222> LOCATION: (8)..(8)
<223> OTHER INFORMATION: Site of chemical conjugation

<400> SEQUENCE: 801

Arg Gln Leu Pro Ser Leu Ala Cys Lys Tyr
1               5                   10

<210> SEQ ID NO 802
<211> LENGTH: 12
<212> TYPE: PRT
<213> ORGANISM: Homo sapiens
<220> FEATURE:
<223> OTHER INFORMATION: USP22 Ubiquitin carboxyl-terminal hydrolase 22;
      Q9UPT9_C171
<220> FEATURE:
<221> NAME/KEY: MOD_RES
<222> LOCATION: (6)..(6)
<223> OTHER INFORMATION: Site of chemical conjugation

<400> SEQUENCE: 802

Lys Ile Thr Ser Asn Cys Thr Ile Gly Leu Arg Gly

-continued

```
<210> SEQ ID NO 803
<211> LENGTH: 31
<212> TYPE: PRT
<213> ORGANISM: Homo sapiens
<220> FEATURE:
<223> OTHER INFORMATION: IRF2BP1 Interferon regulatory factor 2-binding
      protein 1; Q8IU81_C363
<220> FEATURE:
<221> NAME/KEY: MOD_RES
<222> LOCATION: (25)..(25)
<223> OTHER INFORMATION: Site of chemical conjugation

<400> SEQUENCE: 803

Arg Ser Phe Arg Glu Pro Ala Pro Ala Glu Ala Leu Pro Gln Gln Tyr
1               5                   10                  15

Pro Glu Pro Ala Pro Ala Ala Leu Cys Gly Pro Pro Arg Ala
            20                  25                  30

<210> SEQ ID NO 804
<211> LENGTH: 26
<212> TYPE: PRT
<213> ORGANISM: Homo sapiens
<220> FEATURE:
<223> OTHER INFORMATION: DENND1C DENN domain-containing protein 1C;
      Q8IV53_C174
<220> FEATURE:
<221> NAME/KEY: MOD_RES
<222> LOCATION: (9)..(9)
<223> OTHER INFORMATION: Site of chemical conjugation

<400> SEQUENCE: 804

Arg Gly Asn Ser Lys Pro Leu Ser Cys Phe Val Ala Pro Asp Ser Gly
1               5                   10                  15

Arg Leu Pro Ser Ile Pro Glu Asn Arg Asn
            20                  25

<210> SEQ ID NO 805
<211> LENGTH: 16
<212> TYPE: PRT
<213> ORGANISM: Homo sapiens
<220> FEATURE:
<223> OTHER INFORMATION: APOBEC3C Probable DNA dC- dU-editing enzyme
      APOBEC-3C; Q9NRW3_C130
<220> FEATURE:
<221> NAME/KEY: MOD_RES
<222> LOCATION: (9)..(9)
<223> OTHER INFORMATION: Site of chemical conjugation

<400> SEQUENCE: 805

Arg Leu Tyr Tyr Phe Gln Tyr Pro Cys Tyr Gln Glu Gly Leu Arg Ser
1               5                   10                  15

<210> SEQ ID NO 806
<211> LENGTH: 10
<212> TYPE: PRT
<213> ORGANISM: Homo sapiens
<220> FEATURE:
<223> OTHER INFORMATION: IRAK4 Interleukin-1 receptor-associated kinase
      4; Q9NWZ3_C13
<220> FEATURE:
<221> NAME/KEY: MOD_RES
<222> LOCATION: (2)..(2)
<223> OTHER INFORMATION: Site of chemical conjugation

<400> SEQUENCE: 806

Arg Cys Leu Asn Val Gly Leu Ile Arg Lys
1               5                   10
```

```
<210> SEQ ID NO 807
<211> LENGTH: 15
<212> TYPE: PRT
<213> ORGANISM: Homo sapiens
<220> FEATURE:
<223> OTHER INFORMATION: TDRKH Tudor and KH domain-containing protein;
      Q9Y2W6_C109
<220> FEATURE:
<221> NAME/KEY: MOD_RES
<222> LOCATION: (13)..(13)
<223> OTHER INFORMATION: Site of chemical conjugation

<400> SEQUENCE: 807

Arg Val Leu Leu Ile Ser Gly Phe Pro Val Gln Val Cys Lys Ala
1               5                   10                  15

<210> SEQ ID NO 808
<211> LENGTH: 11
<212> TYPE: PRT
<213> ORGANISM: Homo sapiens
<220> FEATURE:
<223> OTHER INFORMATION: NADSYN1 Glutamine-dependent NAD(+) synthetase;
      Q6IA69_C428
<220> FEATURE:
<221> NAME/KEY: MOD_RES
<222> LOCATION: (8)..(8)
<223> OTHER INFORMATION: Site of chemical conjugation

<400> SEQUENCE: 808

Lys Asn Ser Ser Gln Glu Thr Cys Thr Arg Ala
1               5                   10

<210> SEQ ID NO 809
<211> LENGTH: 9
<212> TYPE: PRT
<213> ORGANISM: Homo sapiens
<220> FEATURE:
<223> OTHER INFORMATION: IKBKB Inhibitor of nuclear factor kappa-B
      kinase subunit; O14920_C464
<220> FEATURE:
<221> NAME/KEY: MOD_RES
<222> LOCATION: (5)..(5)
<223> OTHER INFORMATION: Site of chemical conjugation

<400> SEQUENCE: 809

Arg Asn Asn Ser Cys Leu Ser Lys Met
1               5

<210> SEQ ID NO 810
<211> LENGTH: 14
<212> TYPE: PRT
<213> ORGANISM: Homo sapiens
<220> FEATURE:
<223> OTHER INFORMATION: ADA Adenosine deaminase;
      P00813_C75
<220> FEATURE:
<221> NAME/KEY: MOD_RES
<222> LOCATION: (12)..(12)
<223> OTHER INFORMATION: Site of chemical conjugation

<400> SEQUENCE: 810

Lys Phe Asp Tyr Tyr Met Pro Ala Ile Ala Gly Cys Arg Glu
1               5                   10

<210> SEQ ID NO 811
<211> LENGTH: 13
<212> TYPE: PRT
<213> ORGANISM: Homo sapiens
<220> FEATURE:
```

```
<223> OTHER INFORMATION: VDAC3 Voltage-dependent anion-selective channel
      protein; Q9Y277_C65
<220> FEATURE:
<221> NAME/KEY: MOD_RES
<222> LOCATION: (3)..(3)
<223> OTHER INFORMATION: Site of chemical conjugation

<400> SEQUENCE: 811

Lys Val Cys Asn Tyr Gly Leu Thr Phe Thr Gln Lys Trp
1               5                   10

<210> SEQ ID NO 812
<211> LENGTH: 10
<212> TYPE: PRT
<213> ORGANISM: Homo sapiens
<220> FEATURE:
<223> OTHER INFORMATION: AARS Alanine--tRNA ligase, cytoplasmic;
      P49588_C773
<220> FEATURE:
<221> NAME/KEY: MOD_RES
<222> LOCATION: (2)..(2)
<223> OTHER INFORMATION: Site of chemical conjugation

<400> SEQUENCE: 812

Lys Cys Leu Ser Val Met Glu Ala Lys Val
1               5                   10

<210> SEQ ID NO 813
<211> LENGTH: 29
<212> TYPE: PRT
<213> ORGANISM: Homo sapiens
<220> FEATURE:
<223> OTHER INFORMATION: UBE2L6 Ubiquitin/ISG15-conjugating enzyme E2
      L6; O14933_C98
<220> FEATURE:
<221> NAME/KEY: MOD_RES
<222> LOCATION: (26)..(26)
<223> OTHER INFORMATION: Site of chemical conjugation

<400> SEQUENCE: 813

Lys Ile Tyr His Pro Asn Val Asp Glu Asn Gly Gln Ile Cys Leu Pro
1               5                   10                  15

Ile Ile Ser Ser Glu Asn Trp Lys Pro Cys Thr Lys Thr
            20                  25

<210> SEQ ID NO 814
<211> LENGTH: 11
<212> TYPE: PRT
<213> ORGANISM: Homo sapiens
<220> FEATURE:
<223> OTHER INFORMATION: PGLS 6-phosphogluconolactonase;
      O95336_C32
<220> FEATURE:
<221> NAME/KEY: MOD_RES
<222> LOCATION: (4)..(4)
<223> OTHER INFORMATION: Site of chemical conjugation

<400> SEQUENCE: 814

Arg Ala Ala Cys Cys Leu Ala Gly Ala Arg Ala
1               5                   10

<210> SEQ ID NO 815
<211> LENGTH: 12
<212> TYPE: PRT
<213> ORGANISM: Homo sapiens
<220> FEATURE:
<223> OTHER INFORMATION: PGP Phosphoglycolate phosphatase;
      A6NDG6_C297
<220> FEATURE:
<221> NAME/KEY: MOD_RES
```

<222> LOCATION: (8)..(8)
<223> OTHER INFORMATION: Site of chemical conjugation

<400> SEQUENCE: 815

Lys Asn Asn Gln Glu Ser Asp Cys Val Ser Lys Lys
1               5                   10

<210> SEQ ID NO 816
<211> LENGTH: 26
<212> TYPE: PRT
<213> ORGANISM: Homo sapiens
<220> FEATURE:
<223> OTHER INFORMATION: HUWE1 E3 ubiquitin-protein ligase HUWE1;
      Q7Z6Z7_C3372
<220> FEATURE:
<221> NAME/KEY: MOD_RES
<222> LOCATION: (3)..(3)
<223> OTHER INFORMATION: Site of chemical conjugation

<400> SEQUENCE: 816

Lys Ala Cys Ser Pro Cys Ser Ser Gln Ser Ser Ser Ser Gly Ile Cys
1               5                   10                  15

Thr Asp Phe Trp Asp Leu Leu Val Lys Leu
            20                  25

<210> SEQ ID NO 817
<211> LENGTH: 17
<212> TYPE: PRT
<213> ORGANISM: Homo sapiens
<220> FEATURE:
<223> OTHER INFORMATION: BCL2A1 Bcl-2-related protein A1;
      Q16548_C55
<220> FEATURE:
<221> NAME/KEY: MOD_RES
<222> LOCATION: (3)..(3)
<223> OTHER INFORMATION: Site of chemical conjugation

<400> SEQUENCE: 817

Lys Ser Cys Leu Asp Asn Val Asn Val Val Ser Val Asp Thr Ala Arg
1               5                   10                  15

Thr

<210> SEQ ID NO 818
<211> LENGTH: 11
<212> TYPE: PRT
<213> ORGANISM: Homo sapiens
<220> FEATURE:
<223> OTHER INFORMATION: PYGB Glycogen phosphorylase, brain form;
      P11216_C326
<220> FEATURE:
<221> NAME/KEY: MOD_RES
<222> LOCATION: (3)..(3)
<223> OTHER INFORMATION: Site of chemical conjugation

<400> SEQUENCE: 818

Arg Thr Cys Phe Glu Thr Phe Pro Asp Lys Val
1               5                   10

<210> SEQ ID NO 819
<211> LENGTH: 13
<212> TYPE: PRT
<213> ORGANISM: Homo sapiens
<220> FEATURE:
<223> OTHER INFORMATION: AGFG2 Arf-GAP domain and FG repeat-containing
      protein 2; O95081_C39
<220> FEATURE:
<221> NAME/KEY: MOD_RES
<222> LOCATION: (6)..(6)
<223> OTHER INFORMATION: Site of chemical conjugation

```
<400> SEQUENCE: 819

Arg Glu Leu Gly Gly Cys Ser Gln Ala Gly Asn Arg His
1               5                   10

<210> SEQ ID NO 820
<211> LENGTH: 20
<212> TYPE: PRT
<213> ORGANISM: Homo sapiens
<220> FEATURE:
<223> OTHER INFORMATION: ZC3HAV1 Zinc finger CCCH-type antiviral protein
      1; Q7Z2W4_C645
<220> FEATURE:
<221> NAME/KEY: MOD_RES
<222> LOCATION: (17)..(17)
<223> OTHER INFORMATION: Site of chemical conjugation

<400> SEQUENCE: 820

Lys Asn Ser Asn Val Asp Ser Ser Tyr Leu Glu Ser Leu Tyr Gln Ser
1               5                   10                  15

Cys Pro Arg Gly
            20

<210> SEQ ID NO 821
<211> LENGTH: 11
<212> TYPE: PRT
<213> ORGANISM: Homo sapiens
<220> FEATURE:
<223> OTHER INFORMATION: AIP AH receptor-interacting protein;
      O00170_C122
<220> FEATURE:
<221> NAME/KEY: MOD_RES
<222> LOCATION: (4)..(4)
<223> OTHER INFORMATION: Site of chemical conjugation

<400> SEQUENCE: 821

Arg His Cys Cys Gly Val Ala Gln Met Arg Glu
1               5                   10

<210> SEQ ID NO 822
<211> LENGTH: 11
<212> TYPE: PRT
<213> ORGANISM: Homo sapiens
<220> FEATURE:
<223> OTHER INFORMATION: TRNT1 CCA tRNA nucleotidyltransferase 1,
      mitochondrial; Q96Q11_C373
<220> FEATURE:
<221> NAME/KEY: MOD_RES
<222> LOCATION: (7)..(7)
<223> OTHER INFORMATION: Site of chemical conjugation

<400> SEQUENCE: 822

Lys Tyr Gln Gly Glu His Cys Leu Leu Lys Glu
1               5                   10

<210> SEQ ID NO 823
<211> LENGTH: 16
<212> TYPE: PRT
<213> ORGANISM: Homo sapiens
<220> FEATURE:
<223> OTHER INFORMATION: RIN3 Ras and Rab interactor 3;
      Q8TB24_C942
<220> FEATURE:
<221> NAME/KEY: MOD_RES
<222> LOCATION: (13)..(13)
<223> OTHER INFORMATION: Site of chemical conjugation

<400> SEQUENCE: 823

Arg Cys Phe Gln Leu Ala Asp Asp Ala Leu Pro His Cys Ile Lys Gly
```

-continued

<210> SEQ ID NO 824
<211> LENGTH: 14
<212> TYPE: PRT
<213> ORGANISM: Homo sapiens
<220> FEATURE:
<223> OTHER INFORMATION: LAS1L Ribosomal biogenesis protein LAS1L;
      Q9Y4W2_C456
<220> FEATURE:
<221> NAME/KEY: MOD_RES
<222> LOCATION: (5)..(5)
<223> OTHER INFORMATION: Site of chemical conjugation

<400> SEQUENCE: 824

Arg Leu Phe Asn Cys Ser Ala Ser Leu Asp Trp Pro Arg Met
1               5                   10

<210> SEQ ID NO 825
<211> LENGTH: 13
<212> TYPE: PRT
<213> ORGANISM: Homo sapiens
<220> FEATURE:
<223> OTHER INFORMATION: IRF8 Interferon regulatory factor 8;
      Q02556_C306
<220> FEATURE:
<221> NAME/KEY: MOD_RES
<222> LOCATION: (11)..(11)
<223> OTHER INFORMATION: Site of chemical conjugation

<400> SEQUENCE: 825

Arg Val Phe Cys Ser Gly Asn Ala Val Val Cys Lys Gly
1               5                   10

<210> SEQ ID NO 826
<211> LENGTH: 29
<212> TYPE: PRT
<213> ORGANISM: Homo sapiens
<220> FEATURE:
<223> OTHER INFORMATION: MARS2 Methionine--tRNA ligase, mitochondrial;
      Q96GW9_C425
<220> FEATURE:
<221> NAME/KEY: MOD_RES
<222> LOCATION: (12)..(12)
<223> OTHER INFORMATION: Site of chemical conjugation

<400> SEQUENCE: 826

Arg Ile Asn Pro Ser Glu Thr Tyr Pro Ala Phe Cys Thr Thr Cys Phe
1               5                   10                  15

Pro Ser Glu Pro Gly Leu Val Gly Pro Ser Val Arg Ala
            20                  25

<210> SEQ ID NO 827
<211> LENGTH: 24
<212> TYPE: PRT
<213> ORGANISM: Homo sapiens
<220> FEATURE:
<223> OTHER INFORMATION: IRF4 Interferon regulatory factor 4;
      Q15306_C194
<220> FEATURE:
<221> NAME/KEY: MOD_RES
<222> LOCATION: (16)..(16)
<223> OTHER INFORMATION: Site of chemical conjugation

<400> SEQUENCE: 827

Arg Asp Tyr Val Pro Asp Gln Pro His Pro Glu Ile Pro Tyr Gln Cys
1               5                   10                  15

Pro Met Thr Phe Gly Pro Arg Gly
            20

-continued

```
<210> SEQ ID NO 828
<211> LENGTH: 24
<212> TYPE: PRT
<213> ORGANISM: Homo sapiens
<220> FEATURE:
<223> OTHER INFORMATION: SPCS2 Signal peptidase complex subunit 2;
      Q15005_C17
<220> FEATURE:
<221> NAME/KEY: MOD_RES
<222> LOCATION: (8)..(8)
<223> OTHER INFORMATION: Site of chemical conjugation

<400> SEQUENCE: 828

Arg Ser Gly Gly Ser Gly Gly Cys Ser Gly Ala Gly Gly Ala Ser Asn
1               5                   10                  15

Cys Gly Thr Gly Ser Gly Arg Ser
            20

<210> SEQ ID NO 829
<211> LENGTH: 22
<212> TYPE: PRT
<213> ORGANISM: Homo sapiens
<220> FEATURE:
<223> OTHER INFORMATION: RARS Arginine--tRNA ligase, cytoplasmic;
      P54136_C32
<220> FEATURE:
<221> NAME/KEY: MOD_RES
<222> LOCATION: (3)..(3)
<223> OTHER INFORMATION: Site of chemical conjugation

<400> SEQUENCE: 829

Lys Asn Cys Gly Cys Leu Gly Ala Ser Pro Asn Leu Glu Gln Leu Gln
1               5                   10                  15

Glu Glu Asn Leu Lys Leu
            20

<210> SEQ ID NO 830
<211> LENGTH: 52
<212> TYPE: PRT
<213> ORGANISM: Homo sapiens
<220> FEATURE:
<223> OTHER INFORMATION: TUBGCP3 Gamma-tubulin complex component 3;
      Q96CW5_C194
<220> FEATURE:
<221> NAME/KEY: MOD_RES
<222> LOCATION: (49)..(49)
<223> OTHER INFORMATION: Site of chemical conjugation

<400> SEQUENCE: 830

Arg Ser Ala Gln Ser Ala Gln Ser Ser Gly Ser Val Gly Ser Ser Gly
1               5                   10                  15

Ile Ser Ser Ile Gly Leu Cys Ala Leu Ser Gly Pro Ala Pro Ala Pro
            20                  25                  30

Gln Ser Leu Leu Pro Gly Gln Ser Asn Gln Ala Pro Gly Val Gly Asp
        35                  40                  45

Cys Leu Arg Gln
    50

<210> SEQ ID NO 831
<211> LENGTH: 10
<212> TYPE: PRT
<213> ORGANISM: Homo sapiens
<220> FEATURE:
<223> OTHER INFORMATION: CRKL Crk-like protein;
      P46109_C249
<220> FEATURE:
```

```
<221> NAME/KEY: MOD_RES
<222> LOCATION: (5)..(5)
<223> OTHER INFORMATION: Site of chemical conjugation

<400> SEQUENCE: 831

Lys Arg Val Pro Cys Ala Tyr Asp Lys Thr
1               5                   10

<210> SEQ ID NO 832
<211> LENGTH: 24
<212> TYPE: PRT
<213> ORGANISM: Homo sapiens
<220> FEATURE:
<223> OTHER INFORMATION: PUSL1 tRNA pseudouridine synthase-like 1;
      Q8N0Z8_C292
<220> FEATURE:
<221> NAME/KEY: MOD_RES
<222> LOCATION: (13)..(13)
<223> OTHER INFORMATION: Site of chemical conjugation

<400> SEQUENCE: 832

Lys Ser Val Leu Tyr Gly Asn Leu Gly Ala Ala Ser Cys Thr Leu Gln
1               5                   10                  15

Gly Pro Gln Phe Gly Ser His Gly
            20

<210> SEQ ID NO 833
<211> LENGTH: 12
<212> TYPE: PRT
<213> ORGANISM: Homo sapiens
<220> FEATURE:
<223> OTHER INFORMATION: UBR4 E3 ubiquitin-protein ligase UBR4;
      Q5T4S7_C2554
<220> FEATURE:
<221> NAME/KEY: MOD_RES
<222> LOCATION: (5)..(5)
<223> OTHER INFORMATION: Site of chemical conjugation

<400> SEQUENCE: 833

Lys Ala Val Gln Cys Leu Asn Thr Ser Ser Lys Glu
1               5                   10

<210> SEQ ID NO 834
<211> LENGTH: 13
<212> TYPE: PRT
<213> ORGANISM: Homo sapiens
<220> FEATURE:
<223> OTHER INFORMATION: ZNF346 Zinc finger protein 346;
      Q9UL40_C68
<220> FEATURE:
<221> NAME/KEY: MOD_RES
<222> LOCATION: (4)..(4)
<223> OTHER INFORMATION: Site of chemical conjugation

<400> SEQUENCE: 834

Lys Asn Gln Cys Leu Phe Thr Asn Thr Gln Cys Lys Val
1               5                   10

<210> SEQ ID NO 835
<211> LENGTH: 17
<212> TYPE: PRT
<213> ORGANISM: Homo sapiens
<220> FEATURE:
<223> OTHER INFORMATION: FLII Protein flightless-1 homolog;
      Q13045_C46
<220> FEATURE:
<221> NAME/KEY: MOD_RES
<222> LOCATION: (5)..(5)
<223> OTHER INFORMATION: Site of chemical conjugation
```

```
<400> SEQUENCE: 835

Arg Thr Gly Leu Cys Tyr Leu Pro Glu Glu Leu Ala Ala Leu Gln Lys
1               5                   10                  15

Leu

<210> SEQ ID NO 836
<211> LENGTH: 28
<212> TYPE: PRT
<213> ORGANISM: Homo sapiens
<220> FEATURE:
<223> OTHER INFORMATION: KIAA0528 Uncharacterized protein KIAA0528;
      Q86YS7_C993
<220> FEATURE:
<221> NAME/KEY: MOD_RES
<222> LOCATION: (21)..(21)
<223> OTHER INFORMATION: Site of chemical conjugation

<400> SEQUENCE: 836

Arg Glu Ser Asp Leu Glu Val Val Ser Ser Gln Gln Pro Thr Thr Asn
1               5                   10                  15

Cys Gln Ser Ser Cys Thr Glu Gly Glu Val Thr Thr
            20                  25

<210> SEQ ID NO 837
<211> LENGTH: 9
<212> TYPE: PRT
<213> ORGANISM: Homo sapiens
<220> FEATURE:
<223> OTHER INFORMATION: MTCH2 Mitochondrial carrier homolog 2;
      Q9Y6C9_C296
<220> FEATURE:
<221> NAME/KEY: MOD_RES
<222> LOCATION: (4)..(4)
<223> OTHER INFORMATION: Site of chemical conjugation

<400> SEQUENCE: 837

Lys Thr Tyr Cys Cys Asp Leu Lys Met
1               5

<210> SEQ ID NO 838
<211> LENGTH: 19
<212> TYPE: PRT
<213> ORGANISM: Homo sapiens
<220> FEATURE:
<223> OTHER INFORMATION: DCXR L-xylulose reductase;
      Q7Z4W1_C244
<220> FEATURE:
<221> NAME/KEY: MOD_RES
<222> LOCATION: (19)..(19)
<223> OTHER INFORMATION: Site of chemical conjugation

<400> SEQUENCE: 838

Arg Ser Gly Met Thr Thr Gly Ser Thr Leu Pro Val Glu Gly Gly Phe
1               5                   10                  15

Trp Ala Cys

<210> SEQ ID NO 839
<211> LENGTH: 30
<212> TYPE: PRT
<213> ORGANISM: Homo sapiens
<220> FEATURE:
<223> OTHER INFORMATION: PRKCQ Protein kinase C theta type;
      Q04759_C14
<220> FEATURE:
<221> NAME/KEY: MOD_RES
<222> LOCATION: (9)..(9)
<223> OTHER INFORMATION: Site of chemical conjugation
```

```
<400> SEQUENCE: 839

Arg Ile Gly Leu Ser Asn Phe Asp Cys Gly Ser Cys Gln Ser Cys Gln
1               5                   10                  15

Gly Glu Ala Val Asn Pro Tyr Cys Ala Val Leu Val Lys Glu
            20                  25                  30

<210> SEQ ID NO 840
<211> LENGTH: 18
<212> TYPE: PRT
<213> ORGANISM: Homo sapiens
<220> FEATURE:
<223> OTHER INFORMATION: SON Protein SON;
      P18583_C92
<220> FEATURE:
<221> NAME/KEY: MOD_RES
<222> LOCATION: (2)..(2)
<223> OTHER INFORMATION: Site of chemical conjugation

<400> SEQUENCE: 840

Arg Cys Val Ser Val Gln Thr Asp Pro Thr Asp Glu Ile Pro Thr Lys
1               5                   10                  15

Lys Ser

<210> SEQ ID NO 841
<211> LENGTH: 10
<212> TYPE: PRT
<213> ORGANISM: Homo sapiens
<220> FEATURE:
<223> OTHER INFORMATION: MAT2A S-adenosylmethionine synthase isoform
      type-2; P31153_C56
<220> FEATURE:
<221> NAME/KEY: MOD_RES
<222> LOCATION: (4)..(4)
<223> OTHER INFORMATION: Site of chemical conjugation

<400> SEQUENCE: 841

Lys Val Ala Cys Glu Thr Val Ala Lys Thr
1               5                   10

<210> SEQ ID NO 842
<211> LENGTH: 23
<212> TYPE: PRT
<213> ORGANISM: Homo sapiens
<220> FEATURE:
<223> OTHER INFORMATION: BCL2A1 Bcl-2-related protein A1;
      Q16548_C19
<220> FEATURE:
<221> NAME/KEY: MOD_RES
<222> LOCATION: (9)..(9)
<223> OTHER INFORMATION: Site of chemical conjugation

<400> SEQUENCE: 842

Arg Leu Ala Gln Asp Tyr Leu Gln Cys Val Leu Gln Ile Pro Gln Pro
1               5                   10                  15

Gly Ser Gly Pro Ser Lys Thr
            20

<210> SEQ ID NO 843
<211> LENGTH: 21
<212> TYPE: PRT
<213> ORGANISM: Homo sapiens
<220> FEATURE:
<223> OTHER INFORMATION: IL16 Pro-interleukin-16;
      Q14005_C1004
<220> FEATURE:
<221> NAME/KEY: MOD_RES
<222> LOCATION: (5)..(5)
<223> OTHER INFORMATION: Site of chemical conjugation
```

<400> SEQUENCE: 843

Lys Ser Leu Leu Cys Leu Pro Ser Ser Ile Ser Cys Ala Gln Thr Pro
1               5                   10                  15

Cys Ile Pro Lys Glu
            20

<210> SEQ ID NO 844
<211> LENGTH: 25
<212> TYPE: PRT
<213> ORGANISM: Homo sapiens
<220> FEATURE:
<223> OTHER INFORMATION: MAT2A S-adenosylmethionine synthase isoform
      type-2; P31153_C104
<220> FEATURE:
<221> NAME/KEY: MOD_RES
<222> LOCATION: (3)..(3)
<223> OTHER INFORMATION: Site of chemical conjugation

<400> SEQUENCE: 844

Lys Thr Cys Asn Val Leu Val Ala Leu Glu Gln Gln Ser Pro Asp Ile
1               5                   10                  15

Ala Gln Gly Val His Leu Asp Arg Asn
            20                  25

<210> SEQ ID NO 845
<211> LENGTH: 21
<212> TYPE: PRT
<213> ORGANISM: Homo sapiens
<220> FEATURE:
<223> OTHER INFORMATION: VDAC3 Voltage-dependent anion-selective channel
      protein; Q9Y277_C36
<220> FEATURE:
<221> NAME/KEY: MOD_RES
<222> LOCATION: (3)..(3)
<223> OTHER INFORMATION: Site of chemical conjugation

<400> SEQUENCE: 845

Lys Ser Cys Ser Gly Val Glu Phe Ser Thr Ser Gly His Ala Tyr Thr
1               5                   10                  15

Asp Thr Gly Lys Ala
            20

<210> SEQ ID NO 846
<211> LENGTH: 13
<212> TYPE: PRT
<213> ORGANISM: Homo sapiens
<220> FEATURE:
<223> OTHER INFORMATION: SYNE2 Nesprin-2;
      Q8WXH0_C553
<220> FEATURE:
<221> NAME/KEY: MOD_RES
<222> LOCATION: (7)..(7)
<223> OTHER INFORMATION: Site of chemical conjugation

<400> SEQUENCE: 846

Lys Asn Leu Ala Gly Glu Cys Gln Asn Ile Asn Lys Gln
1               5                   10

<210> SEQ ID NO 847
<211> LENGTH: 17
<212> TYPE: PRT
<213> ORGANISM: Homo sapiens
<220> FEATURE:
<223> OTHER INFORMATION: SCLY Selenocysteine lyase;
      Q96I15_C22
<220> FEATURE:
<221> NAME/KEY: MOD_RES
<222> LOCATION: (14)..(14)
<223> OTHER INFORMATION: Site of chemical conjugation

<400> SEQUENCE: 847

Arg Asp Ala Pro Ala Pro Ala Ala Ser Gln Pro Ser Gly Cys Gly Lys
1               5                   10                  15

His

<210> SEQ ID NO 848
<211> LENGTH: 10
<212> TYPE: PRT
<213> ORGANISM: Homo sapiens
<220> FEATURE:
<223> OTHER INFORMATION: PML Protein PML;
      P29590_C479
<220> FEATURE:
<221> NAME/KEY: MOD_RES
<222> LOCATION: (2)..(2)
<223> OTHER INFORMATION: Site of chemical conjugation

<400> SEQUENCE: 848

Lys Cys Ser Gln Thr Gln Cys Pro Arg Lys
1               5                   10

<210> SEQ ID NO 849
<211> LENGTH: 19
<212> TYPE: PRT
<213> ORGANISM: Homo sapiens
<220> FEATURE:
<223> OTHER INFORMATION: THNSL1 Threonine synthase-like 1;
      Q8IYQ7_C324
<220> FEATURE:
<221> NAME/KEY: MOD_RES
<222> LOCATION: (16)..(16)
<223> OTHER INFORMATION: Site of chemical conjugation

<400> SEQUENCE: 849

Arg Leu Gly Glu Met Ile Glu Thr Ala Tyr Gly Glu Asn Phe Ala Cys
1               5                   10                  15

Ser Lys Ile

<210> SEQ ID NO 850
<211> LENGTH: 12
<212> TYPE: PRT
<213> ORGANISM: Homo sapiens
<220> FEATURE:
<223> OTHER INFORMATION: USP7 Ubiquitin carboxyl-terminal hydrolase 7;
      Q93009_C315
<220> FEATURE:
<221> NAME/KEY: MOD_RES
<222> LOCATION: (4)..(4)
<223> OTHER INFORMATION: Site of chemical conjugation

<400> SEQUENCE: 850

Lys Gly Thr Cys Val Glu Gly Thr Ile Pro Lys Leu
1               5                   10

<210> SEQ ID NO 851
<211> LENGTH: 11
<212> TYPE: PRT
<213> ORGANISM: Homo sapiens
<220> FEATURE:
<223> OTHER INFORMATION: TNFAIP3 Tumor necrosis factor alpha-induced
      protein 3; P21580_C54
<220> FEATURE:
<221> NAME/KEY: MOD_RES
<222> LOCATION: (3)..(3)
<223> OTHER INFORMATION: Site of chemical conjugation

```
<400> SEQUENCE: 851

Arg Thr Cys Gln Phe Cys Pro Gln Phe Arg Glu
1               5                   10

<210> SEQ ID NO 852
<211> LENGTH: 12
<212> TYPE: PRT
<213> ORGANISM: Homo sapiens
<220> FEATURE:
<223> OTHER INFORMATION: GAK Cyclin-G-associated kinase;
      O14976_C87
<220> FEATURE:
<221> NAME/KEY: MOD_RES
<222> LOCATION: (8)..(8)
<223> OTHER INFORMATION: Site of chemical conjugation

<400> SEQUENCE: 852

Arg Ala Ile Ile Gln Glu Val Cys Phe Met Lys Lys
1               5                   10

<210> SEQ ID NO 853
<211> LENGTH: 10
<212> TYPE: PRT
<213> ORGANISM: Homo sapiens
<220> FEATURE:
<223> OTHER INFORMATION: THOC1 THO complex subunit 1;
      Q96FV9_C49
<220> FEATURE:
<221> NAME/KEY: MOD_RES
<222> LOCATION: (2)..(2)
<223> OTHER INFORMATION: Site of chemical conjugation

<400> SEQUENCE: 853

Lys Cys Thr Leu Asp Gln Ala Phe Arg Gly
1               5                   10

<210> SEQ ID NO 854
<211> LENGTH: 9
<212> TYPE: PRT
<213> ORGANISM: Homo sapiens
<220> FEATURE:
<223> OTHER INFORMATION: PRKDC DNA-dependent protein kinase catalytic
      subunit; P78527_C4045
<220> FEATURE:
<221> NAME/KEY: MOD_RES
<222> LOCATION: (5)..(5)
<223> OTHER INFORMATION: Site of chemical conjugation

<400> SEQUENCE: 854

Arg Gln Lys Ile Cys Tyr Ala Lys Arg
1               5

<210> SEQ ID NO 855
<211> LENGTH: 17
<212> TYPE: PRT
<213> ORGANISM: Homo sapiens
<220> FEATURE:
<223> OTHER INFORMATION: CHRAC1 Chromatin accessibility complex protein
      1; Q9NRG0_C55
<220> FEATURE:
<221> NAME/KEY: MOD_RES
<222> LOCATION: (9)..(9)
<223> OTHER INFORMATION: Site of chemical conjugation

<400> SEQUENCE: 855

Lys Ala Thr Glu Leu Phe Val Gln Cys Leu Ala Thr Tyr Ser Tyr Arg
1               5                   10                  15
His
```

<210> SEQ ID NO 856
<211> LENGTH: 19
<212> TYPE: PRT
<213> ORGANISM: Homo sapiens
<220> FEATURE:
<223> OTHER INFORMATION: GHDC GH3 domain-containing protein;
      Q8N2G8_C502
<220> FEATURE:
<221> NAME/KEY: MOD_RES
<222> LOCATION: (7)..(7)
<223> OTHER INFORMATION: Site of chemical conjugation

<400> SEQUENCE: 856

Arg Ala Ala Leu Ala Ala Cys Pro Ser Ser Pro Phe Pro Pro Ala Met
1               5                   10                  15

Pro Arg Val

<210> SEQ ID NO 857
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 857

Asp Glu Val Asp
1

<210> SEQ ID NO 858
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 858

Ile Glu Thr Asp
1

<210> SEQ ID NO 859
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 859

Ala Glu Val Asp
1

<210> SEQ ID NO 860
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 860

Gly Gln Phe Tyr Leu Asn Glu
1               5

<210> SEQ ID NO 861
<211> LENGTH: 6

```
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 861

His His His His His His
1               5

<210> SEQ ID NO 862
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 862

Arg Arg Arg Arg Arg Arg
1               5

<210> SEQ ID NO 863
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 863

Trp Glu His Asp
1

<210> SEQ ID NO 864
<211> LENGTH: 14
<212> TYPE: PRT
<213> ORGANISM: Homo sapiens
<220> FEATURE:
<223> OTHER INFORMATION: CASP8 C360
<220> FEATURE:
<221> NAME/KEY: MOD_RES
<222> LOCATION: (7)..(7)
<223> OTHER INFORMATION: Site of chemical conjugation

<400> SEQUENCE: 864

Val Phe Phe Ile Gln Ala Cys Gln Gly Asp Asn Tyr Gln Lys
1               5                   10

<210> SEQ ID NO 865
<211> LENGTH: 18
<212> TYPE: PRT
<213> ORGANISM: Homo sapiens

<400> SEQUENCE: 865

Ser Asn Phe Asp Cys Gly Ser Cys Gln Ser Cys Gln Gly Glu Ala Val
1               5                   10                  15

Asn Pro

<210> SEQ ID NO 866
<211> LENGTH: 18
<212> TYPE: PRT
<213> ORGANISM: Mus sp.

<400> SEQUENCE: 866

Ser Asn Phe Asp Cys Gly Thr Cys Gln Ala Cys Gln Gly Glu Ala Val
1               5                   10                  15
```

```
Asn Pro

<210> SEQ ID NO 867
<211> LENGTH: 17
<212> TYPE: PRT
<213> ORGANISM: Homo sapiens

<400> SEQUENCE: 867

Asn Ser Tyr Glu Leu Gly Ser Leu Gln Ala Glu Asp Glu Ala Asn Gln
1               5                   10                  15

Pro

<210> SEQ ID NO 868
<211> LENGTH: 26
<212> TYPE: PRT
<213> ORGANISM: Homo sapiens

<400> SEQUENCE: 868

Ala Val Ser Leu Lys Pro Thr Ala Trp Ser Leu Arg His Ala Val Gly
1               5                   10                  15

Pro Arg Pro Gln Thr Phe Leu Leu Asp Pro
            20                  25
```